US011580867B2

United States Patent
Wilson et al.

(10) Patent No.: US 11,580,867 B2
(45) Date of Patent: *Feb. 14, 2023

(54) EXERCISED-BASED WATCH FACE AND COMPLICATIONS

(71) Applicant: Apple Inc., Cupertino, CA (US)

(72) Inventors: Christopher Wilson, San Francisco, CA (US); Aled Hywel Williams, San Francisco, CA (US); Kevin Will Chen, Sunnyvale, CA (US); Chester H. Chipperfield, San Francisco, CA (US); Stanley Carl Ng, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/418,786

(22) Filed: May 21, 2019

(65) Prior Publication Data
US 2019/0279520 A1    Sep. 12, 2019

Related U.S. Application Data

(63) Continuation of application No. 15/183,663, filed on Jun. 15, 2016, now Pat. No. 10,304,347.
(Continued)

(51) Int. Cl.
*G09B 5/02*        (2006.01)
*G06F 1/16*        (2006.01)
(Continued)

(52) U.S. Cl.
CPC .................. *G09B 5/02* (2013.01); *A61B 5/11* (2013.01); *A61B 5/1118* (2013.01);
(Continued)

(58) Field of Classification Search
CPC ........ G06F 1/1626; G06F 3/048; G06F 3/016; G06F 3/011; G06F 3/0488; A61B 5/1123
See application file for complete search history.

(56) References Cited

U.S. PATENT DOCUMENTS 3,148,500 A    9/1964    Hayes
4,205,628 A    6/1980    Null
(Continued)

FOREIGN PATENT DOCUMENTS

AU    2010249319 A1    6/2012
AU    2015101019 A4    9/2015
(Continued)

OTHER PUBLICATIONS

"Fitbit App" Available online at: <http://web.archive.org/web/20180114083150/https://www.fitbit.com/au/app>, Jan. 14, 2018, 8 pages.
(Continued)

*Primary Examiner* — Cao H Nguyen
(74) *Attorney, Agent, or Firm* — Dentons US LLP

(57) ABSTRACT

Exercise-based watch faces and complications for use with a portable multifunction device are disclosed. The methods described herein for exercise-based watch faces and complications provide indications of time and affordances representing applications (e.g., a workout application or a weather application). In response to detecting a user input corresponding to a selection of the affordance (e.g., representing a workout application), a workout routine can optionally be begun. Further disclosed are non-transitory computer-readable storage media, systems, and devices configured to perform the methods described herein, as well as electronic devices related thereto.

21 Claims, 110 Drawing Sheets

Related U.S. Application Data

(60) Provisional application No. 62/207,736, filed on Aug. 20, 2015.

(51) Int. Cl.
| | | |
|---|---|---|
| *G06F 3/01* | (2006.01) | |
| *G06F 3/0482* | (2013.01) | |
| *G06F 3/0488* | (2013.01) | |
| *G09B 19/00* | (2006.01) | |
| *A61B 5/11* | (2006.01) | |
| *A61B 5/00* | (2006.01) | |
| *G06F 3/04883* | (2022.01) | |
| *A61B 5/01* | (2006.01) | |
| *A61B 5/021* | (2006.01) | |
| *A61B 5/024* | (2006.01) | |
| *A61B 5/318* | (2021.01) | |

(52) U.S. Cl.
CPC .......... *A61B 5/1123* (2013.01); *A61B 5/6898* (2013.01); *G06F 1/163* (2013.01); *G06F 3/011* (2013.01); *G06F 3/016* (2013.01); *G06F 3/0482* (2013.01); *G06F 3/0488* (2013.01); *G06F 3/04883* (2013.01); *G09B 19/003* (2013.01); *A61B 5/0002* (2013.01); *A61B 5/01* (2013.01); *A61B 5/021* (2013.01); *A61B 5/024* (2013.01); *A61B 5/318* (2021.01)

(56) References Cited

U.S. PATENT DOCUMENTS

| | | |
|---|---|---|
| 4,355,380 A | 10/1982 | Huguenin et al. |
| 4,597,674 A | 7/1986 | Thompson, III |
| 4,842,266 A | 6/1989 | Sweeney, Sr. et al. |
| 4,847,819 A | 7/1989 | Hong |
| 4,945,521 A | 7/1990 | Klaus |
| 5,124,959 A | 6/1992 | Yamazaki et al. |
| 5,208,790 A | 5/1993 | Sato |
| 5,220,541 A | 6/1993 | Vuilleumier |
| 5,423,863 A | 6/1995 | Felblinger et al. |
| 5,455,808 A | 10/1995 | Grupp et al. |
| 5,458,548 A | 10/1995 | Crossing et al. |
| 5,474,077 A | 12/1995 | Suga |
| 5,500,835 A | 3/1996 | Born |
| 5,508,979 A | 4/1996 | Eisenegger |
| 5,642,731 A | 7/1997 | Kehr |
| 5,659,693 A | 8/1997 | Hansen et al. |
| 5,685,723 A | 11/1997 | Ladin et al. |
| 5,788,655 A | 8/1998 | Yoshimura et al. |
| 5,825,353 A | 10/1998 | Will |
| 5,845,257 A | 12/1998 | Fu et al. |
| 5,892,519 A | 4/1999 | Hirai |
| 5,944,633 A | 8/1999 | Wittrock |
| 5,986,655 A | 11/1999 | Chiu et al. |
| 5,999,195 A | 12/1999 | Santangeli |
| 6,013,008 A | 1/2000 | Fukushima |
| 6,043,818 A | 3/2000 | Nakano et al. |
| 6,084,598 A | 7/2000 | Chekerylla |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,128,012 A | 10/2000 | Seidensticker, Jr. et al. |
| 6,160,767 A | 12/2000 | Ho |
| 6,244,988 B1 | 6/2001 | Delman |
| 6,279,018 B1 | 8/2001 | Kudrolli et al. |
| 6,297,795 B1 | 10/2001 | Kato et al. |
| 6,302,789 B2 | 10/2001 | Harada et al. |
| 6,323,846 B1 | 11/2001 | Westerman et al. |
| 6,359,839 B1 | 3/2002 | Schenk et al. |
| 6,416,471 B1 | 7/2002 | Kumar et al. |
| 6,441,824 B2 | 8/2002 | Hertzfeld |
| 6,449,219 B1 | 9/2002 | Hepp et al. |
| 6,452,597 B1 | 9/2002 | Goldberg et al. |
| 6,477,117 B1 | 11/2002 | Narayanaswami et al. |
| 6,496,780 B1 | 12/2002 | Harris et al. |
| 6,525,997 B1 | 2/2003 | Narayanaswami et al. |
| 6,539,243 B1 | 3/2003 | Kimura et al. |
| 6,539,343 B2 | 3/2003 | Zhao et al. |
| 6,549,218 B1 | 4/2003 | Gershony et al. |
| 6,556,222 B1 | 4/2003 | Narayanaswami |
| 6,570,557 B1 | 5/2003 | Westerman et al. |
| 6,603,477 B1 | 8/2003 | Tittle |
| 6,639,584 B1 | 10/2003 | Li |
| 6,662,023 B1 | 12/2003 | Helle |
| 6,677,932 B1 | 1/2004 | Westerman |
| 6,690,623 B1 | 2/2004 | Maano |
| 6,705,972 B1 | 3/2004 | Takano et al. |
| 6,728,533 B2 | 4/2004 | Ishii |
| 6,809,724 B1 | 10/2004 | Shiraishi et al. |
| 6,837,827 B1 | 1/2005 | Lee et al. |
| 6,866,613 B1 | 3/2005 | Brown et al. |
| 6,871,076 B2 | 3/2005 | Samn |
| 7,020,514 B1 | 3/2006 | Wiesel |
| 7,081,905 B1 | 7/2006 | Raghunath |
| 7,128,693 B2 | 10/2006 | Brown et al. |
| 7,130,664 B1 | 10/2006 | Williams |
| 7,203,380 B2 | 4/2007 | Chiu et al. |
| 7,251,454 B2 | 7/2007 | White |
| 7,257,254 B2 | 8/2007 | Tunney |
| 7,302,272 B2 | 11/2007 | Ackley |
| 7,302,650 B1 | 11/2007 | Allyn et al. |
| 7,378,954 B2 | 5/2008 | Wendt |
| 7,479,949 B2 | 1/2009 | Jobs et al. |
| 7,515,509 B2 | 4/2009 | Klein |
| 7,515,903 B1 | 4/2009 | Cast |
| 7,614,008 B2 | 11/2009 | Ording |
| 7,619,615 B1 | 11/2009 | Donoghue |
| 7,633,076 B2 | 12/2009 | Huppi et al. |
| 7,637,204 B2 | 12/2009 | Sumser et al. |
| 7,653,883 B2 | 1/2010 | Hotelling et al. |
| 7,657,849 B2 | 2/2010 | Chaudhri et al. |
| 7,662,065 B1 | 2/2010 | Kahn et al. |
| 7,663,607 B2 | 2/2010 | Hotelling et al. |
| 7,695,406 B2 | 4/2010 | Waters |
| 7,739,148 B2 | 6/2010 | Suzuki et al. |
| 7,751,285 B1 | 7/2010 | Cain |
| 7,773,460 B2 | 8/2010 | Holt |
| 7,843,769 B2 | 11/2010 | Ishida et al. |
| 7,844,914 B2 | 11/2010 | Andre et al. |
| 7,898,542 B1 | 3/2011 | Yu et al. |
| 7,907,476 B2 | 3/2011 | Lee |
| 7,957,762 B2 | 6/2011 | Herz et al. |
| 7,970,827 B1 | 6/2011 | Cumberbatch et al. |
| 8,006,002 B2 | 8/2011 | Kalayjian et al. |
| 8,060,229 B2 | 11/2011 | Gupta et al. |
| 8,105,208 B2 | 1/2012 | Oleson et al. |
| 8,238,876 B2 | 8/2012 | Teng et al. |
| 8,239,784 B2 | 8/2012 | Hotelling et al. |
| 8,245,143 B2 | 8/2012 | Yach et al. |
| 8,279,180 B2 | 10/2012 | Hotelling et al. |
| 8,321,006 B1 | 11/2012 | Snyder et al. |
| 8,341,557 B2 | 12/2012 | Pisula et al. |
| 8,364,855 B2 | 1/2013 | James et al. |
| 8,381,135 B2 | 2/2013 | Hotelling et al. |
| 8,405,663 B2 | 3/2013 | Wikkerink et al. |
| 8,462,997 B2 | 6/2013 | Pettit et al. |
| 8,475,339 B2 | 7/2013 | Hwang et al. |
| 8,479,122 B2 | 7/2013 | Hotelling et al. |
| 8,496,563 B2 | 7/2013 | Komatsu et al. |
| 8,543,081 B2 | 9/2013 | Scott et al. |
| 8,595,649 B2 | 11/2013 | Sherrard et al. |
| 8,595,798 B2 | 11/2013 | Anand et al. |
| 8,666,361 B2 | 3/2014 | Chu et al. |
| 8,676,170 B2 | 3/2014 | Porrati et al. |
| 8,700,158 B2 | 4/2014 | Mass et al. |
| 8,725,842 B1 | 5/2014 | Al-nasser |
| 8,768,648 B2 * | 7/2014 | Panther ................ A61B 5/6838 702/160 |
| 8,784,115 B1 | 7/2014 | Chuang |
| 8,784,271 B2 | 7/2014 | Brumback et al. |
| 8,825,445 B2 | 9/2014 | Hoffman et al. |
| 8,847,903 B2 | 9/2014 | Stokes et al. |

(56) References Cited

U.S. PATENT DOCUMENTS

| | | |
|---|---|---|
| 8,854,925 B1 | 10/2014 | Lee et al. |
| 8,910,299 B2 | 12/2014 | Michalske |
| 8,924,894 B1 | 12/2014 | Yaksick et al. |
| 8,934,963 B1 | 1/2015 | Farazi |
| 8,938,394 B1 | 1/2015 | Faaborg et al. |
| 8,948,819 B2 | 2/2015 | Yun et al. |
| 8,963,894 B2 | 2/2015 | Klassen et al. |
| 8,990,006 B1 | 3/2015 | Wallace et al. |
| 9,011,292 B2 | 4/2015 | Weast et al. |
| 9,020,538 B1 | 4/2015 | White et al. |
| 9,070,092 B2 | 6/2015 | Chou et al. |
| 9,082,314 B2 | 7/2015 | Tsai |
| 9,141,270 B1 | 9/2015 | Stuart et al. |
| 9,152,211 B2 | 10/2015 | Gunn et al. |
| 9,152,212 B2 | 10/2015 | Gunn |
| 9,171,268 B1 | 10/2015 | Penilla et al. |
| 9,173,052 B2 | 10/2015 | Hauser et al. |
| 9,197,738 B2 | 11/2015 | Peev et al. |
| 9,224,291 B2 | 12/2015 | Moll-Carrillo et al. |
| 9,230,076 B2 | 1/2016 | King et al. |
| 9,237,855 B2 | 1/2016 | Hong et al. |
| 9,239,605 B1 | 1/2016 | Nanda et al. |
| 9,259,615 B2 | 2/2016 | Weast et al. |
| 9,369,537 B1 | 6/2016 | Mathew et al. |
| 9,377,762 B2 | 6/2016 | Hoobler et al. |
| 9,449,365 B2 | 9/2016 | Roberts |
| 9,459,781 B2 | 10/2016 | Wilson et al. |
| 9,532,734 B2 | 1/2017 | Hoffman et al. |
| 9,547,425 B2 | 1/2017 | Wilson et al. |
| 9,557,881 B1 | 1/2017 | Jain et al. |
| 9,568,891 B2 | 2/2017 | Adams et al. |
| 9,582,165 B2 | 2/2017 | Wilson et al. |
| 9,589,445 B2 | 3/2017 | White et al. |
| 9,594,354 B1 | 3/2017 | Kahn et al. |
| 9,600,178 B2 | 3/2017 | Yun et al. |
| 9,606,695 B2 | 3/2017 | Matas |
| 9,712,629 B2 | 7/2017 | Molettiere et al. |
| 9,734,477 B2 | 8/2017 | Weast et al. |
| 9,753,436 B2 | 9/2017 | Ely et al. |
| 9,794,397 B2 | 10/2017 | Min et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,910,571 B2 | 3/2018 | Chen et al. |
| 9,940,682 B2 | 4/2018 | Hoffman et al. |
| 10,019,599 B1 | 7/2018 | Moran et al. |
| 10,056,006 B1 | 8/2018 | Hsu-Hoffman et al. |
| 10,062,133 B1 | 8/2018 | Mishra et al. |
| 10,220,258 B2 | 3/2019 | Gu et al. |
| 10,226,195 B2 | 3/2019 | Briante et al. |
| 10,268,432 B2 | 4/2019 | Kyung |
| 10,300,334 B1 | 5/2019 | Chuang |
| 10,339,830 B2 | 7/2019 | Han et al. |
| 10,356,070 B2 | 7/2019 | Cha et al. |
| 10,398,381 B1 | 9/2019 | Heneghan et al. |
| 10,500,441 B2 | 12/2019 | Lagree |
| 10,620,590 B1 | 4/2020 | Guzman et al. |
| 10,643,246 B1 | 5/2020 | Suprasadachandran Pillai |
| 10,684,592 B2 | 6/2020 | Chang et al. |
| 10,721,711 B2 | 7/2020 | Kirov et al. |
| 10,736,543 B2 | 8/2020 | Chen et al. |
| 10,777,314 B1 | 9/2020 | Williams et al. |
| 10,788,797 B1 | 9/2020 | Guzman et al. |
| 10,817,981 B1 | 10/2020 | Belkin |
| 10,852,905 B1 | 12/2020 | Guzman et al. |
| 10,878,782 B1 | 12/2020 | Guzman et al. |
| 10,908,559 B1 | 2/2021 | Guzman et al. |
| 10,936,345 B1 | 3/2021 | Guzman et al. |
| 10,978,195 B2 | 4/2021 | Blahnik et al. |
| 11,009,833 B2 | 5/2021 | Essery |
| 11,050,873 B2 | 6/2021 | Kim et al. |
| 11,061,372 B1 | 7/2021 | Chen et al. |
| 11,103,161 B2 | 8/2021 | Williams et al. |
| 11,107,569 B1 | 8/2021 | Devoto |
| 11,152,100 B2 | 10/2021 | Crowley et al. |
| 11,202,598 B2 | 12/2021 | Soli et al. |
| 11,209,957 B2 | 12/2021 | Dryer et al. |
| 11,317,833 B2 | 5/2022 | Williams et al. |
| 2001/0049470 A1 | 12/2001 | Mault et al. |
| 2002/0015024 A1 | 2/2002 | Westerman et al. |
| 2002/0045960 A1 | 4/2002 | Phillips et al. |
| 2002/0054066 A1 | 5/2002 | Kikinis et al. |
| 2002/0054157 A1 | 5/2002 | Hayashi et al. |
| 2002/0054541 A1 | 5/2002 | Hall |
| 2002/0059623 A1 | 5/2002 | Rodriguez et al. |
| 2002/0081976 A1 | 6/2002 | Fujisawa et al. |
| 2002/0086774 A1 | 7/2002 | Warner |
| 2002/0098857 A1 | 7/2002 | Ishii |
| 2002/0118121 A1 | 8/2002 | Lehrman et al. |
| 2002/0131331 A1 | 9/2002 | Molander |
| 2003/0002391 A1 | 1/2003 | Biggs |
| 2003/0023178 A1 | 1/2003 | Bischoff et al. |
| 2003/0027621 A1 | 2/2003 | Libby et al. |
| 2003/0064860 A1 | 4/2003 | Yamashita et al. |
| 2003/0067497 A1 | 4/2003 | Pichon |
| 2003/0107603 A1 | 6/2003 | Clapper |
| 2003/0134714 A1 | 7/2003 | Oishi et al. |
| 2003/0164847 A1 | 9/2003 | Zaima et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0214885 A1 | 11/2003 | Powell et al. |
| 2003/0216971 A1 | 11/2003 | Sick et al. |
| 2003/0226695 A1 | 12/2003 | Mault |
| 2003/0229900 A1 | 12/2003 | Reisman |
| 2004/0001105 A1 | 1/2004 | Chew et al. |
| 2004/0014567 A1 | 1/2004 | Mendel |
| 2004/0017733 A1 | 1/2004 | Sullivan |
| 2004/0021699 A1 | 2/2004 | Fildebrandt |
| 2004/0047244 A1 | 3/2004 | Iino et al. |
| 2004/0066710 A1 | 4/2004 | Yuen et al. |
| 2004/0075699 A1 | 4/2004 | Franchi et al. |
| 2004/0075700 A1 | 4/2004 | Liu et al. |
| 2004/0077462 A1 | 4/2004 | Brown et al. |
| 2004/0083474 A1 | 4/2004 | Mckinlay et al. |
| 2004/0128286 A1 | 7/2004 | Yasushi et al. |
| 2004/0168107 A1 | 8/2004 | Sharp et al. |
| 2004/0181771 A1 | 9/2004 | Anonsen et al. |
| 2004/0192332 A1 | 9/2004 | Samn |
| 2004/0203342 A1 | 10/2004 | Sibecas et al. |
| 2004/0218472 A1 | 11/2004 | Narayanaswami et al. |
| 2004/0225966 A1 | 11/2004 | Besharat et al. |
| 2004/0236189 A1 | 11/2004 | Hawthorne et al. |
| 2004/0243547 A1 | 12/2004 | Chhatrapati et al. |
| 2004/0266491 A1 | 12/2004 | Howard et al. |
| 2005/0041667 A1 | 2/2005 | Miller et al. |
| 2005/0052446 A1 | 3/2005 | Plut |
| 2005/0075214 A1 | 4/2005 | Brown et al. |
| 2005/0079905 A1 | 4/2005 | Martens |
| 2005/0094492 A1 | 5/2005 | Rosevear |
| 2005/0113650 A1 | 5/2005 | Pacione et al. |
| 2005/0124324 A1 | 6/2005 | Thomas et al. |
| 2005/0124389 A1 | 6/2005 | Yang |
| 2005/0139852 A1 | 6/2005 | Chen et al. |
| 2005/0156873 A1 | 7/2005 | Walter et al. |
| 2005/0165627 A1 | 7/2005 | Fotsch et al. |
| 2005/0172311 A1 | 8/2005 | Hjelt et al. |
| 2005/0188856 A1 | 9/2005 | Sumser et al. |
| 2005/0190059 A1 | 9/2005 | Wehrenberg |
| 2005/0190653 A1 | 9/2005 | Chen |
| 2005/0197063 A1 | 9/2005 | White |
| 2005/0198319 A1 | 9/2005 | Chan et al. |
| 2005/0200611 A1 | 9/2005 | Goto et al. |
| 2005/0215848 A1 | 9/2005 | Lorenzato et al. |
| 2005/0216867 A1 | 9/2005 | Marvit et al. |
| 2005/0228735 A1 | 10/2005 | Duquette |
| 2005/0261031 A1 | 11/2005 | Seo et al. |
| 2005/0272564 A1 | 12/2005 | Pyles et al. |
| 2005/0278757 A1 | 12/2005 | Grossman et al. |
| 2006/0007785 A1 | 1/2006 | Fernandez et al. |
| 2006/0017692 A1 | 1/2006 | Wehrenberg et al. |
| 2006/0020174 A1 | 1/2006 | Matsumura et al. |
| 2006/0020904 A1 | 1/2006 | Aaltonen et al. |

(56) References Cited

U.S. PATENT DOCUMENTS

| | | |
|---|---|---|
| 2006/0026536 A1 | 2/2006 | Hotelling et al. |
| 2006/0033724 A1 | 2/2006 | Chaudhri et al. |
| 2006/0035628 A1 | 2/2006 | Miller et al. |
| 2006/0052727 A1 | 3/2006 | Palestrant |
| 2006/0085765 A1 | 4/2006 | Peterson et al. |
| 2006/0092770 A1 | 5/2006 | Demas |
| 2006/0098109 A1 | 5/2006 | Ooki |
| 2006/0106741 A1 | 5/2006 | Janarthanan |
| 2006/0123362 A1 | 6/2006 | Keely |
| 2006/0155578 A1 | 7/2006 | Eisenberger et al. |
| 2006/0166708 A1 | 7/2006 | Kim et al. |
| 2006/0184800 A1 | 8/2006 | Rosenberg |
| 2006/0197753 A1 | 9/2006 | Hotelling |
| 2006/0214935 A1 | 9/2006 | Boyd et al. |
| 2006/0240959 A1 | 10/2006 | Huang |
| 2006/0250524 A1 | 11/2006 | Roche |
| 2006/0277469 A1 | 12/2006 | Scott et al. |
| 2007/0004451 A1 | 1/2007 | C. Anderson |
| 2007/0006096 A1 | 1/2007 | Kim et al. |
| 2007/0021153 A1 | 1/2007 | Novak |
| 2007/0021269 A1 | 1/2007 | Shum |
| 2007/0032733 A1 | 2/2007 | Burton |
| 2007/0033069 A1 | 2/2007 | Rao et al. |
| 2007/0052851 A1 | 3/2007 | Ochs et al. |
| 2007/0055947 A1 | 3/2007 | Ostojic et al. |
| 2007/0056727 A1 | 3/2007 | Newman |
| 2007/0057775 A1 | 3/2007 | O'reilly et al. |
| 2007/0071256 A1 | 3/2007 | Ito |
| 2007/0094330 A1 | 4/2007 | Russell |
| 2007/0101279 A1 | 5/2007 | Chaudhri et al. |
| 2007/0113181 A1 | 5/2007 | Blattner et al. |
| 2007/0113726 A1 | 5/2007 | Oliver et al. |
| 2007/0135043 A1 | 6/2007 | Hayes et al. |
| 2007/0136093 A1 | 6/2007 | Rankin et al. |
| 2007/0143433 A1 | 6/2007 | Daigle |
| 2007/0146344 A1 | 6/2007 | Martin et al. |
| 2007/0169614 A1 | 7/2007 | Sasaki et al. |
| 2007/0192718 A1 | 8/2007 | Voorhees et al. |
| 2007/0211042 A1 | 9/2007 | Kim et al. |
| 2007/0213955 A1 | 9/2007 | Ishida et al. |
| 2007/0236475 A1 | 10/2007 | Wherry |
| 2007/0239754 A1 | 10/2007 | Schnitman |
| 2007/0249949 A1 | 10/2007 | Hadley |
| 2007/0250772 A1 | 10/2007 | Milosevski |
| 2007/0261537 A1 | 11/2007 | Eronen et al. |
| 2007/0271065 A1 | 11/2007 | Gupta et al. |
| 2007/0279190 A1 | 12/2007 | Lugt et al. |
| 2007/0287140 A1 | 12/2007 | Liebowitz |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0071885 A1 | 3/2008 | Hardy et al. |
| 2008/0076637 A1 | 3/2008 | Gilley et al. |
| 2008/0082145 A1 | 4/2008 | Skwarek et al. |
| 2008/0082930 A1 | 4/2008 | Omernick et al. |
| 2008/0086318 A1 | 4/2008 | Gilley et al. |
| 2008/0095470 A1 | 4/2008 | Chao et al. |
| 2008/0096726 A1 | 4/2008 | Riley et al. |
| 2008/0127268 A1 | 5/2008 | Bergeron et al. |
| 2008/0130421 A1 | 6/2008 | Akaiwa et al. |
| 2008/0141135 A1 | 6/2008 | Mason et al. |
| 2008/0150731 A1 | 6/2008 | Laukkanen et al. |
| 2008/0150959 A1 | 6/2008 | Marui |
| 2008/0151700 A1 | 6/2008 | Inoue et al. |
| 2008/0161161 A1 | 7/2008 | Pipinich et al. |
| 2008/0161707 A1 | 7/2008 | Farringdon et al. |
| 2008/0167834 A1 | 7/2008 | Herz et al. |
| 2008/0168396 A1 | 7/2008 | Matas et al. |
| 2008/0186808 A1 | 8/2008 | Lee |
| 2008/0192021 A1 | 8/2008 | Lim et al. |
| 2008/0200312 A1 | 8/2008 | Tagliabue |
| 2008/0201438 A1 | 8/2008 | Mandre et al. |
| 2008/0201647 A1 | 8/2008 | Lagerstedt et al. |
| 2008/0215240 A1 | 9/2008 | Howard et al. |
| 2008/0229226 A1 | 9/2008 | Rowbottom et al. |
| 2008/0246778 A1 | 10/2008 | Ham et al. |
| 2008/0247519 A1 | 10/2008 | Abella et al. |
| 2008/0254767 A1 | 10/2008 | Jin |
| 2008/0262946 A1 | 10/2008 | Wren |
| 2008/0270934 A1 | 10/2008 | Firebaugh et al. |
| 2008/0300110 A1 | 12/2008 | Smith et al. |
| 2008/0320391 A1 | 12/2008 | Lemay et al. |
| 2009/0007017 A1 | 1/2009 | Anzures et al. |
| 2009/0012988 A1 | 1/2009 | Brown |
| 2009/0047645 A1 | 2/2009 | Dibenedetto et al. |
| 2009/0051327 A1 | 2/2009 | Bohne |
| 2009/0058821 A1 | 3/2009 | Chaudhri et al. |
| 2009/0059730 A1 | 3/2009 | Lyons et al. |
| 2009/0068984 A1 | 3/2009 | Burnett |
| 2009/0070675 A1 | 3/2009 | Li |
| 2009/0077497 A1 | 3/2009 | Cho et al. |
| 2009/0118100 A1 | 5/2009 | Oliver et al. |
| 2009/0143114 A1 | 6/2009 | Vargas et al. |
| 2009/0146962 A1 | 6/2009 | Ahonen et al. |
| 2009/0149299 A1 | 6/2009 | Tchao et al. |
| 2009/0158173 A1 | 6/2009 | Palahnuk et al. |
| 2009/0164567 A1 | 6/2009 | Hara |
| 2009/0164923 A1 | 6/2009 | Ovi |
| 2009/0170532 A1 | 7/2009 | Lee et al. |
| 2009/0178007 A1 | 7/2009 | Matas et al. |
| 2009/0178008 A1 | 7/2009 | Herz et al. |
| 2009/0183080 A1 | 7/2009 | Thakkar et al. |
| 2009/0192823 A1 | 7/2009 | Hawkins et al. |
| 2009/0199130 A1 | 8/2009 | Tsern et al. |
| 2009/0205041 A1 | 8/2009 | Michalske |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0249247 A1 | 10/2009 | Tseng et al. |
| 2009/0259134 A1 | 10/2009 | Levine |
| 2009/0259958 A1 | 10/2009 | Ban |
| 2009/0262088 A1* | 10/2009 | Moll-Carrillo ....... G06F 1/1643 345/173 |
| 2009/0264116 A1 | 10/2009 | Thompson |
| 2009/0268949 A1 | 10/2009 | Ueshima et al. |
| 2009/0276463 A1 | 11/2009 | Miller |
| 2009/0279392 A1 | 11/2009 | Scott et al. |
| 2009/0284389 A1 | 11/2009 | Klassen et al. |
| 2009/0287103 A1 | 11/2009 | Pillai |
| 2009/0287470 A1 | 11/2009 | Farnsworth et al. |
| 2009/0300146 A1 | 12/2009 | Park et al. |
| 2009/0300598 A1 | 12/2009 | Choi |
| 2009/0305732 A1 | 12/2009 | Marcellino et al. |
| 2009/0312059 A1 | 12/2009 | Pratt et al. |
| 2009/0319243 A1 | 12/2009 | Suarez-rivera et al. |
| 2009/0319467 A1 | 12/2009 | Berg et al. |
| 2009/0327886 A1 | 12/2009 | Whytock et al. |
| 2010/0026640 A1 | 2/2010 | Kim et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1* | 3/2010 | Rottler ............. H04M 1/72403 482/9 |
| 2010/0064255 A1 | 3/2010 | Rottler et al. |
| 2010/0069035 A1 | 3/2010 | Johnson |
| 2010/0076331 A1 | 3/2010 | Chan et al. |
| 2010/0079291 A1 | 4/2010 | Kroll et al. |
| 2010/0081473 A1 | 4/2010 | Chatterjee et al. |
| 2010/0085203 A1 | 4/2010 | Kahn et al. |
| 2010/0110082 A1 | 5/2010 | Myrick et al. |
| 2010/0121700 A1 | 5/2010 | Wigder et al. |
| 2010/0124152 A1 | 5/2010 | Lee |
| 2010/0137106 A1 | 6/2010 | Oshima et al. |
| 2010/0145209 A1 | 6/2010 | Lee et al. |
| 2010/0146437 A1 | 6/2010 | Woodcock et al. |
| 2010/0149573 A1 | 6/2010 | Pat et al. |
| 2010/0156833 A1 | 6/2010 | Kim et al. |
| 2010/0157742 A1 | 6/2010 | Relyea et al. |
| 2010/0167712 A1 | 7/2010 | Stallings et al. |

(56) References Cited

U.S. PATENT DOCUMENTS

| | | |
|---|---|---|
| 2010/0179832 A1 | 7/2010 | Van deursen et al. |
| 2010/0194692 A1 | 8/2010 | Orr et al. |
| 2010/0198453 A1 | 8/2010 | Dorogusker et al. |
| 2010/0202368 A1 | 8/2010 | Hans |
| 2010/0205563 A1 | 8/2010 | Haapsaari et al. |
| 2010/0217657 A1 | 8/2010 | Gazdzinski |
| 2010/0218089 A1 | 8/2010 | Chao et al. |
| 2010/0223563 A1 | 9/2010 | Green |
| 2010/0225495 A1 | 9/2010 | Marui |
| 2010/0226213 A1 | 9/2010 | Drugge |
| 2010/0231612 A1 | 9/2010 | Chaudhri et al. |
| 2010/0235726 A1 | 9/2010 | Ording et al. |
| 2010/0243516 A1 | 9/2010 | Martin et al. |
| 2010/0257469 A1 | 10/2010 | Kim et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0000968 A1 | 1/2011 | Phillips et al. |
| 2011/0003665 A1 | 1/2011 | Burton et al. |
| 2011/0004835 A1 | 1/2011 | Yanchar et al. |
| 2011/0010195 A1 | 1/2011 | Cohn |
| 2011/0016120 A1 | 1/2011 | Haughay et al. |
| 2011/0022294 A1 | 1/2011 | Apley |
| 2011/0025719 A1 | 2/2011 | Yanase |
| 2011/0029870 A1 | 2/2011 | May et al. |
| 2011/0032105 A1 | 2/2011 | Hoffman et al. |
| 2011/0047014 A1 | 2/2011 | De |
| 2011/0061010 A1 | 3/2011 | Wasko et al. |
| 2011/0066051 A1 | 3/2011 | Moon et al. |
| 2011/0070924 A1 | 3/2011 | Kim |
| 2011/0071818 A1 | 3/2011 | Jiang |
| 2011/0071869 A1 | 3/2011 | Obrien et al. |
| 2011/0074699 A1 | 3/2011 | Marr et al. |
| 2011/0076992 A1 | 3/2011 | Chou et al. |
| 2011/0078624 A1 | 3/2011 | Missig et al. |
| 2011/0080411 A1 | 4/2011 | Wikkerink et al. |
| 2011/0083111 A1 | 4/2011 | Forutanpour et al. |
| 2011/0088086 A1 | 4/2011 | Swink et al. |
| 2011/0098928 A1* | 4/2011 | Hoffman ............. G06F 19/3481 702/5 |
| 2011/0106553 A1 | 5/2011 | Tanaka et al. |
| 2011/0109540 A1 | 5/2011 | Milne et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0138329 A1 | 6/2011 | Wells et al. |
| 2011/0151415 A1 | 6/2011 | Darling |
| 2011/0157046 A1 | 6/2011 | Lee et al. |
| 2011/0159469 A1 | 6/2011 | Hwang et al. |
| 2011/0166777 A1 | 7/2011 | Chavakula |
| 2011/0167369 A1 | 7/2011 | Van Os |
| 2011/0173221 A1 | 7/2011 | Ahiakpor et al. |
| 2011/0179372 A1 | 7/2011 | Moore et al. |
| 2011/0181521 A1 | 7/2011 | Reid et al. |
| 2011/0182151 A1 | 7/2011 | Geyer et al. |
| 2011/0191661 A1 | 8/2011 | Phillips et al. |
| 2011/0193878 A1 | 8/2011 | Seo et al. |
| 2011/0197165 A1 | 8/2011 | Filippov et al. |
| 2011/0201911 A1 | 8/2011 | Johnson et al. |
| 2011/0202883 A1 | 8/2011 | Oh et al. |
| 2011/0205851 A1 | 8/2011 | Harris |
| 2011/0213276 A1 | 9/2011 | Sarussi et al. |
| 2011/0218765 A1 | 9/2011 | Rogers |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0234152 A1 | 9/2011 | Frossen et al. |
| 2011/0237221 A1 | 9/2011 | Prakash et al. |
| 2011/0246509 A1 | 10/2011 | Migita et al. |
| 2011/0248992 A1 | 10/2011 | Van et al. |
| 2011/0256848 A1 | 10/2011 | Bok et al. |
| 2011/0261079 A1 | 10/2011 | Ingrassia et al. |
| 2011/0275940 A1 | 11/2011 | Nims et al. |
| 2011/0281342 A1 | 11/2011 | Porsch et al. |
| 2011/0296324 A1 | 12/2011 | Goossens et al. |
| 2011/0306389 A1 | 12/2011 | Nagayama |
| 2011/0306421 A1 | 12/2011 | Nishimoto et al. |
| 2011/0307821 A1 | 12/2011 | Martens |
| 2011/0316858 A1 | 12/2011 | Shen et al. |
| 2011/0320938 A1 | 12/2011 | Schorsch |
| 2012/0001922 A1 | 1/2012 | Escher et al. |
| 2012/0013552 A1 | 1/2012 | Ahn |
| 2012/0015778 A1 | 1/2012 | Lee et al. |
| 2012/0015779 A1 | 1/2012 | Powch et al. |
| 2012/0028707 A1 | 2/2012 | Raitt et al. |
| 2012/0030623 A1 | 2/2012 | Hoellwarth |
| 2012/0034897 A1 | 2/2012 | Kreitzer et al. |
| 2012/0036220 A1 | 2/2012 | Dare et al. |
| 2012/0041767 A1 | 2/2012 | Hoffman et al. |
| 2012/0042039 A1 | 2/2012 | Mark |
| 2012/0047447 A1 | 2/2012 | Haq |
| 2012/0059664 A1 | 3/2012 | Georgiev et al. |
| 2012/0059787 A1 | 3/2012 | Brown et al. |
| 2012/0062470 A1 | 3/2012 | Chang |
| 2012/0071770 A1 | 3/2012 | Grey et al. |
| 2012/0079375 A1 | 3/2012 | Ogino et al. |
| 2012/0084729 A1 | 4/2012 | Lin |
| 2012/0092383 A1 | 4/2012 | Hysek et al. |
| 2012/0105225 A1 | 5/2012 | Valtonen |
| 2012/0110438 A1 | 5/2012 | Peraza et al. |
| 2012/0116550 A1* | 5/2012 | Hoffman ............... G06F 1/1626 700/91 |
| 2012/0117507 A1 | 5/2012 | Tseng et al. |
| 2012/0124499 A1 | 5/2012 | Tsai |
| 2012/0143094 A1 | 6/2012 | Jallon |
| 2012/0150327 A1 | 6/2012 | Altman et al. |
| 2012/0150759 A1 | 6/2012 | Tarjan |
| 2012/0154156 A1 | 6/2012 | Kuntzel |
| 2012/0159380 A1 | 6/2012 | Kocienda et al. |
| 2012/0179319 A1 | 7/2012 | Gilman et al. |
| 2012/0182226 A1 | 7/2012 | Tuli |
| 2012/0197523 A1 | 8/2012 | Kirsch |
| 2012/0209829 A1 | 8/2012 | Thomas et al. |
| 2012/0218201 A1 | 8/2012 | Tamas et al. |
| 2012/0231849 A1 | 9/2012 | Yamashita |
| 2012/0232414 A1 | 9/2012 | Mollicone et al. |
| 2012/0243735 A1 | 9/2012 | Wu |
| 2012/0253485 A1 | 10/2012 | Weast et al. |
| 2012/0254804 A1 | 10/2012 | Sheha et al. |
| 2012/0254810 A1 | 10/2012 | Heck et al. |
| 2012/0258684 A1 | 10/2012 | Franz et al. |
| 2012/0274508 A1 | 11/2012 | Brown et al. |
| 2012/0283855 A1 | 11/2012 | Hoffman et al. |
| 2012/0288139 A1 | 11/2012 | Singhar |
| 2012/0290109 A1 | 11/2012 | Engelberg et al. |
| 2012/0297346 A1 | 11/2012 | Hoffknecht et al. |
| 2012/0302840 A1 | 11/2012 | Kubo |
| 2012/0302843 A1 | 11/2012 | Otsubo et al. |
| 2012/0304084 A1 | 11/2012 | Kim et al. |
| 2012/0310674 A1 | 12/2012 | Faulkner et al. |
| 2012/0317167 A1 | 12/2012 | Rahman et al. |
| 2012/0319984 A1 | 12/2012 | Borovsky et al. |
| 2012/0324390 A1 | 12/2012 | Tao |
| 2012/0326873 A1 | 12/2012 | Utter, II |
| 2013/0007665 A1 | 1/2013 | Chaudhri et al. |
| 2013/0019175 A1 | 1/2013 | Kotler et al. |
| 2013/0021236 A1 | 1/2013 | Bender |
| 2013/0030892 A1 | 1/2013 | Liu et al. |
| 2013/0044072 A1 | 2/2013 | Kobayashi et al. |
| 2013/0050263 A1 | 2/2013 | Khoe et al. |
| 2013/0054150 A1 | 2/2013 | Sacks et al. |
| 2013/0054720 A1 | 2/2013 | Kang et al. |
| 2013/0055147 A1 | 2/2013 | Vasudev et al. |
| 2013/0057566 A1 | 3/2013 | Kriese et al. |
| 2013/0063084 A1 | 3/2013 | Tilvis et al. |
| 2013/0063383 A1 | 3/2013 | Anderssonreimer et al. |
| 2013/0067050 A1 | 3/2013 | Kotteri et al. |
| 2013/0069893 A1 | 3/2013 | Brinda et al. |
| 2013/0076757 A1 | 3/2013 | Pritting |
| 2013/0081083 A1 | 3/2013 | Yu et al. |

(56) References Cited

U.S. PATENT DOCUMENTS

| | | |
|---|---|---|
| 2013/0082965 A1 | 4/2013 | Wada et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0107674 A1 | 5/2013 | Gossweiler et al. |
| 2013/0110264 A1 | 5/2013 | Weast et al. |
| 2013/0111550 A1 | 5/2013 | Naveh et al. |
| 2013/0111579 A1 | 5/2013 | Newman et al. |
| 2013/0115583 A1 | 5/2013 | Gordon et al. |
| 2013/0116967 A1 | 5/2013 | Akcasu et al. |
| 2013/0132028 A1 | 5/2013 | Crankson et al. |
| 2013/0132888 A1 | 5/2013 | Tijssen |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0141371 A1 | 6/2013 | Hallford et al. |
| 2013/0143512 A1 | 6/2013 | Hernandez et al. |
| 2013/0147825 A1 | 6/2013 | Martin et al. |
| 2013/0151285 A1 | 6/2013 | McLaren et al. |
| 2013/0157646 A1 | 6/2013 | Ferren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0185813 A1 | 7/2013 | Shim et al. |
| 2013/0187923 A1 | 7/2013 | Yoshimoto et al. |
| 2013/0188322 A1 | 7/2013 | Lowe |
| 2013/0191785 A1 | 7/2013 | Rampson et al. |
| 2013/0197679 A1 | 8/2013 | Balakrishnan et al. |
| 2013/0198672 A1 | 8/2013 | Yoon et al. |
| 2013/0203475 A1 | 8/2013 | Kil et al. |
| 2013/0205194 A1 | 8/2013 | Decker et al. |
| 2013/0215044 A1 | 8/2013 | Ahn et al. |
| 2013/0215119 A1 | 8/2013 | Vanhoecke |
| 2013/0217979 A1 | 8/2013 | Blackadar et al. |
| 2013/0222271 A1 | 8/2013 | Alberth et al. |
| 2013/0225118 A1 | 8/2013 | Jang et al. |
| 2013/0225152 A1 | 8/2013 | Matthews et al. |
| 2013/0231575 A1 | 9/2013 | Erkkila et al. |
| 2013/0231711 A1 | 9/2013 | Kaib |
| 2013/0232443 A1 | 9/2013 | Ryu et al. |
| 2013/0233097 A1 | 9/2013 | Hayner et al. |
| 2013/0234964 A1 | 9/2013 | Kim et al. |
| 2013/0239060 A1 | 9/2013 | Kang et al. |
| 2013/0239063 A1 | 9/2013 | Ubillos et al. |
| 2013/0254705 A1 | 9/2013 | Mooring et al. |
| 2013/0262155 A1 | 10/2013 | Hinkamp |
| 2013/0263719 A1 | 10/2013 | Watterson et al. |
| 2013/0290013 A1 | 10/2013 | Forrester |
| 2013/0295872 A1 | 11/2013 | Guday et al. |
| 2013/0305189 A1 | 11/2013 | Kim |
| 2013/0314204 A1 | 11/2013 | Ho et al. |
| 2013/0316763 A1 | 11/2013 | Kader |
| 2013/0318437 A1 | 11/2013 | Jung et al. |
| 2013/0318466 A1 | 11/2013 | Estrada et al. |
| 2013/0322218 A1 | 12/2013 | Burkhardt et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0326418 A1 | 12/2013 | Utsuki et al. |
| 2013/0330694 A1 | 12/2013 | Watterson |
| 2013/0332286 A1 | 12/2013 | Medelius et al. |
| 2013/0332856 A1 | 12/2013 | Sanders et al. |
| 2013/0345978 A1* | 12/2013 | Lush .................. G01C 21/3461 701/533 |
| 2013/0345980 A1 | 12/2013 | Van Os et al. |
| 2014/0013414 A1 | 1/2014 | Bruck |
| 2014/0022183 A1 | 1/2014 | Ayoub et al. |
| 2014/0037107 A1 | 2/2014 | Marino et al. |
| 2014/0037109 A1 | 2/2014 | Ban |
| 2014/0038781 A1 | 2/2014 | Foley et al. |
| 2014/0039840 A1 | 2/2014 | Yuen et al. |
| 2014/0043367 A1 | 2/2014 | Sakaino et al. |
| 2014/0047525 A1 | 2/2014 | Bonhoff |
| 2014/0055495 A1 | 2/2014 | Kim et al. |
| 2014/0059493 A1 | 2/2014 | Kim |
| 2014/0067096 A1 | 3/2014 | Aibara |
| 2014/0068755 A1 | 3/2014 | King et al. |
| 2014/0074570 A1 | 3/2014 | Hope et al. |
| 2014/0081666 A1 | 3/2014 | Teller et al. |
| 2014/0082533 A1 | 3/2014 | Kelley |
| 2014/0089836 A1 | 3/2014 | Damani et al. |
| 2014/0094224 A1 | 4/2014 | Lozovoy |
| 2014/0101169 A1 | 4/2014 | Kurata et al. |
| 2014/0108998 A1 | 4/2014 | Chaudhri et al. |
| 2014/0126336 A1 | 5/2014 | Goeller et al. |
| 2014/0129959 A1 | 5/2014 | Battles et al. |
| 2014/0135631 A1 | 5/2014 | Brumback et al. |
| 2014/0139454 A1 | 5/2014 | Mistry et al. |
| 2014/0139637 A1 | 5/2014 | Mistry et al. |
| 2014/0143678 A1 | 5/2014 | Mistry et al. |
| 2014/0143737 A1 | 5/2014 | Mistry et al. |
| 2014/0157189 A1 | 6/2014 | Morita |
| 2014/0157321 A1 | 6/2014 | Kurita |
| 2014/0164907 A1 | 6/2014 | Jung et al. |
| 2014/0173439 A1 | 6/2014 | Gutierrez et al. |
| 2014/0176346 A1 | 6/2014 | Brumback et al. |
| 2014/0176475 A1 | 6/2014 | Myers et al. |
| 2014/0179272 A1 | 6/2014 | Zhang et al. |
| 2014/0180786 A1 | 6/2014 | Sullivan |
| 2014/0189578 A1 | 7/2014 | Shuttleworth et al. |
| 2014/0189584 A1 | 7/2014 | Weng et al. |
| 2014/0199966 A1 | 7/2014 | Schushan |
| 2014/0200691 A1 | 7/2014 | Lee et al. |
| 2014/0201655 A1 | 7/2014 | Mahaffey et al. |
| 2014/0218369 A1 | 8/2014 | Yuen et al. |
| 2014/0228647 A1 | 8/2014 | Sakamoto et al. |
| 2014/0229752 A1 | 8/2014 | Lee |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1* | 8/2014 | Mestas .................. G16H 40/63 700/91 |
| 2014/0244165 A1 | 8/2014 | Bells |
| 2014/0245161 A1 | 8/2014 | Yuen et al. |
| 2014/0245177 A1 | 8/2014 | Maklouf |
| 2014/0250374 A1 | 9/2014 | Ohki et al. |
| 2014/0250391 A1 | 9/2014 | Jong et al. |
| 2014/0253487 A1 | 9/2014 | Bezinge et al. |
| 2014/0257537 A1 | 9/2014 | Stroupe et al. |
| 2014/0258935 A1 | 9/2014 | Nishida et al. |
| 2014/0267303 A1 | 9/2014 | Larkin et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0276244 A1 | 9/2014 | Kamyar |
| 2014/0277628 A1 | 9/2014 | Nieminen et al. |
| 2014/0278229 A1 | 9/2014 | Hong et al. |
| 2014/0282103 A1 | 9/2014 | Crandall |
| 2014/0282153 A1 | 9/2014 | Christiansen et al. |
| 2014/0282254 A1 | 9/2014 | Feiereisen et al. |
| 2014/0288680 A1 | 9/2014 | Hoffman et al. |
| 2014/0289660 A1 | 9/2014 | Min |
| 2014/0293755 A1 | 10/2014 | Geiser et al. |
| 2014/0304664 A1 | 10/2014 | Lee et al. |
| 2014/0310350 A1 | 10/2014 | Borggaard et al. |
| 2014/0310598 A1 | 10/2014 | Sprague et al. |
| 2014/0310618 A1 | 10/2014 | Venkatesh |
| 2014/0310643 A1 | 10/2014 | Karmanenko et al. |
| 2014/0317543 A1 | 10/2014 | Kim |
| 2014/0325384 A1 | 10/2014 | Kobayashi |
| 2014/0325408 A1 | 10/2014 | Leppanen et al. |
| 2014/0328151 A1 | 11/2014 | Serber |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0342792 A1 | 11/2014 | Markus |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0347275 A1 | 11/2014 | Kim et al. |
| 2014/0358473 A1 | 12/2014 | Goel et al. |

(56) References Cited

U.S. PATENT DOCUMENTS

| | | |
|---|---|---|
| 2014/0358584 A1 | 12/2014 | Worden et al. |
| 2014/0359477 A1 | 12/2014 | Chen |
| 2014/0362105 A1 | 12/2014 | Kocienda et al. |
| 2014/0371887 A1* | 12/2014 | Hoffman ............. G01C 22/006 700/91 |
| 2014/0380229 A1 | 12/2014 | Volodin et al. |
| 2015/0004578 A1 | 1/2015 | Gilley et al. |
| 2015/0011204 A1 | 1/2015 | Seo et al. |
| 2015/0015500 A1 | 1/2015 | Lee et al. |
| 2015/0018632 A1 | 1/2015 | Khair |
| 2015/0019981 A1 | 1/2015 | Petitt et al. |
| 2015/0019982 A1 | 1/2015 | Petitt et al. |
| 2015/0022438 A1 | 1/2015 | Hong |
| 2015/0026615 A1 | 1/2015 | Choi et al. |
| 2015/0037545 A1 | 2/2015 | Sun |
| 2015/0043046 A1 | 2/2015 | Iwamoto |
| 2015/0046814 A1 | 2/2015 | Haughay et al. |
| 2015/0049033 A1 | 2/2015 | Kim et al. |
| 2015/0052461 A1 | 2/2015 | Sullivan et al. |
| 2015/0052618 A1 | 2/2015 | Michalske |
| 2015/0055197 A1 | 2/2015 | Romanoff et al. |
| 2015/0057942 A1 | 2/2015 | Self et al. |
| 2015/0057943 A1 | 2/2015 | Self et al. |
| 2015/0058263 A1 | 2/2015 | Landers |
| 2015/0058651 A1 | 2/2015 | Choi et al. |
| 2015/0062130 A1 | 3/2015 | Ho |
| 2015/0065095 A1 | 3/2015 | Seo et al. |
| 2015/0065302 A1 | 3/2015 | Ou et al. |
| 2015/0067513 A1 | 3/2015 | Zambetti et al. |
| 2015/0067596 A1 | 3/2015 | Brown et al. |
| 2015/0067811 A1 | 3/2015 | Agnew et al. |
| 2015/0071043 A1 | 3/2015 | Kubota |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0082193 A1 | 3/2015 | Wallace et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0100621 A1 | 4/2015 | Pan |
| 2015/0105125 A1 | 4/2015 | Min et al. |
| 2015/0106025 A1 | 4/2015 | Keller et al. |
| 2015/0106221 A1 | 4/2015 | Tapley et al. |
| 2015/0106752 A1 | 4/2015 | Yang |
| 2015/0111558 A1 | 4/2015 | Yang |
| 2015/0112700 A1* | 4/2015 | Sublett ............. G06Q 30/0201 705/2 |
| 2015/0113468 A1 | 4/2015 | Clark |
| 2015/0113553 A1 | 4/2015 | Pan |
| 2015/0117162 A1 | 4/2015 | Tsai |
| 2015/0118657 A1* | 4/2015 | Shrake ............. G09B 5/065 434/127 |
| 2015/0124067 A1 | 5/2015 | Bala et al. |
| 2015/0128078 A1 | 5/2015 | Oh et al. |
| 2015/0130830 A1 | 5/2015 | Nagasaki et al. |
| 2015/0133748 A1 | 5/2015 | Edmonds et al. |
| 2015/0142689 A1 | 5/2015 | Squires |
| 2015/0143234 A1 | 5/2015 | Norris, III |
| 2015/0153943 A1 | 6/2015 | Wang |
| 2015/0160806 A1 | 6/2015 | Fey et al. |
| 2015/0160812 A1 | 6/2015 | Yuan et al. |
| 2015/0160856 A1 | 6/2015 | Jang et al. |
| 2015/0163210 A1 | 6/2015 | Meyers et al. |
| 2015/0164349 A1 | 6/2015 | Gopalakrishnan et al. |
| 2015/0172438 A1 | 6/2015 | Yang |
| 2015/0180746 A1 | 6/2015 | Day et al. |
| 2015/0181314 A1 | 6/2015 | Swanson |
| 2015/0185703 A1 | 7/2015 | Tanaka |
| 2015/0185967 A1 | 7/2015 | Ly et al. |
| 2015/0185995 A1 | 7/2015 | Shoemaker et al. |
| 2015/0193805 A1 | 7/2015 | Filipiak |
| 2015/0194137 A1 | 7/2015 | Wyatt |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205509 A1 | 7/2015 | Scriven et al. |
| 2015/0205930 A1 | 7/2015 | Shaanan et al. |
| 2015/0207922 A1 | 7/2015 | Kobayashi et al. |
| 2015/0217163 A1 | 8/2015 | Amis et al. |
| 2015/0220883 A1 | 8/2015 | B'far et al. |
| 2015/0248235 A1 | 9/2015 | Offenberg et al. |
| 2015/0251053 A1 | 9/2015 | Hoffman et al. |
| 2015/0253736 A1 | 9/2015 | Watterson |
| 2015/0253740 A1 | 9/2015 | Nishijima et al. |
| 2015/0254875 A1 | 9/2015 | Zhang |
| 2015/0262497 A1 | 9/2015 | Landau et al. |
| 2015/0269848 A1 | 9/2015 | Yuen et al. |
| 2015/0277545 A1 | 10/2015 | Flowers et al. |
| 2015/0286372 A1 | 10/2015 | Swindell et al. |
| 2015/0286391 A1 | 10/2015 | Jacobs et al. |
| 2015/0293592 A1 | 10/2015 | Cheong et al. |
| 2015/0297134 A1 | 10/2015 | Albert et al. |
| 2015/0301506 A1 | 10/2015 | Koumaiha |
| 2015/0301608 A1 | 10/2015 | Nagaraju et al. |
| 2015/0301691 A1 | 10/2015 | Qin |
| 2015/0302624 A1 | 10/2015 | Burke |
| 2015/0317945 A1 | 11/2015 | Andress et al. |
| 2015/0324751 A1 | 11/2015 | Orenstein et al. |
| 2015/0331589 A1 | 11/2015 | Kawakita |
| 2015/0334546 A1 | 11/2015 | Diamond |
| 2015/0339261 A1 | 11/2015 | Jha et al. |
| 2015/0343709 A1 | 12/2015 | Gerstle et al. |
| 2015/0346694 A1 | 12/2015 | Hoobler et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0355830 A1 | 12/2015 | Chaudhri et al. |
| 2015/0365892 A1 | 12/2015 | Ma et al. |
| 2015/0366518 A1 | 12/2015 | Sampson |
| 2015/0370469 A1 | 12/2015 | Leong et al. |
| 2015/0374310 A1 | 12/2015 | Lee |
| 2015/0379476 A1 | 12/2015 | Chaudhri et al. |
| 2016/0000379 A1 | 1/2016 | Pougatchev et al. |
| 2016/0004393 A1 | 1/2016 | Faaborg et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0022202 A1 | 1/2016 | Peterson et al. |
| 2016/0027282 A1 | 1/2016 | Lee |
| 2016/0027420 A1 | 1/2016 | Eronen |
| 2016/0034133 A1 | 2/2016 | Wilson et al. |
| 2016/0034148 A1 | 2/2016 | Wilson et al. |
| 2016/0034152 A1 | 2/2016 | Wilson et al. |
| 2016/0034166 A1 | 2/2016 | Wilson et al. |
| 2016/0034167 A1 | 2/2016 | Wilson et al. |
| 2016/0044091 A1 | 2/2016 | Doumet |
| 2016/0048283 A1 | 2/2016 | Yang et al. |
| 2016/0048298 A1 | 2/2016 | Choi et al. |
| 2016/0054710 A1 | 2/2016 | Jo et al. |
| 2016/0054892 A1 | 2/2016 | Kim et al. |
| 2016/0058336 A1 | 3/2016 | Blahnik et al. |
| 2016/0058337 A1 | 3/2016 | Blahnik et al. |
| 2016/0062450 A1 | 3/2016 | Han et al. |
| 2016/0062540 A1 | 3/2016 | Yang et al. |
| 2016/0062570 A1 | 3/2016 | Dascola et al. |
| 2016/0062572 A1 | 3/2016 | Yang et al. |
| 2016/0062582 A1 | 3/2016 | Wilson et al. |
| 2016/0062589 A1 | 3/2016 | Wan et al. |
| 2016/0062630 A1 | 3/2016 | Anzures et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0073034 A1 | 3/2016 | Mukherjee et al. |
| 2016/0085397 A1 | 3/2016 | Jain |
| 2016/0085937 A1 | 3/2016 | Dettinger et al. |
| 2016/0089569 A1 | 3/2016 | Blahnik |
| 2016/0091867 A1 | 3/2016 | Mansour et al. |
| 2016/0098137 A1 | 4/2016 | Kim et al. |
| 2016/0107031 A1 | 4/2016 | Palatsi et al. |
| 2016/0134840 A1 | 5/2016 | Mcculloch |
| 2016/0135731 A1 | 5/2016 | Drennan |
| 2016/0140828 A1 | 5/2016 | Deforest |
| 2016/0142763 A1 | 5/2016 | Kim et al. |

(56) References Cited

U.S. PATENT DOCUMENTS

| | | |
|---|---|---|
| 2016/0156584 A1 | 6/2016 | Hum et al. |
| 2016/0165037 A1 | 6/2016 | Youn et al. |
| 2016/0170731 A1 | 6/2016 | Maddern et al. |
| 2016/0179353 A1 | 6/2016 | Iskander |
| 2016/0180568 A1 | 6/2016 | Bullivant et al. |
| 2016/0188179 A1 | 6/2016 | Roh |
| 2016/0188181 A1 | 6/2016 | Smith |
| 2016/0191511 A1 | 6/2016 | Tijerina et al. |
| 2016/0196635 A1 | 7/2016 | Cho et al. |
| 2016/0210099 A1 | 7/2016 | Hampapuram et al. |
| 2016/0217601 A1 | 7/2016 | Tsuda et al. |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0261675 A1 | 9/2016 | Block et al. |
| 2016/0263435 A1 | 9/2016 | Venkatraman et al. |
| 2016/0266548 A1 | 9/2016 | Akiyama |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0283094 A1 | 9/2016 | Choi |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0320756 A1 | 11/2016 | Lee et al. |
| 2016/0324457 A1 | 11/2016 | Dagum |
| 2016/0327911 A1 | 11/2016 | Eim et al. |
| 2016/0327915 A1 | 11/2016 | Katzer et al. |
| 2016/0328736 A1 | 11/2016 | Wang et al. |
| 2016/0332025 A1* | 11/2016 | Repka .................... A61B 5/681 |
| 2016/0342327 A1 | 11/2016 | Chi et al. |
| 2016/0346607 A1 | 12/2016 | Rapfogel |
| 2016/0357354 A1 | 12/2016 | Chen et al. |
| 2016/0357386 A1 | 12/2016 | Choi |
| 2016/0358311 A1 | 12/2016 | Chen et al. |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0011210 A1* | 1/2017 | Cheong .................... H04W 4/00 |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0039535 A1 | 2/2017 | Park et al. |
| 2017/0045993 A1 | 2/2017 | Oh et al. |
| 2017/0046024 A1 | 2/2017 | Dascola et al. |
| 2017/0046052 A1 | 2/2017 | Lee et al. |
| 2017/0053542 A1 | 2/2017 | Wilson et al. |
| 2017/0061934 A1 | 3/2017 | Shin |
| 2017/0065224 A1 | 3/2017 | Rahko et al. |
| 2017/0068407 A1 | 3/2017 | Wilson et al. |
| 2017/0075305 A1 | 3/2017 | Ryu et al. |
| 2017/0075316 A1 | 3/2017 | Berdinis et al. |
| 2017/0082983 A1 | 3/2017 | Katzer et al. |
| 2017/0095695 A1 | 4/2017 | Mangusson et al. |
| 2017/0109011 A1 | 4/2017 | Jiang |
| 2017/0123571 A1 | 5/2017 | Huang et al. |
| 2017/0123640 A1 | 5/2017 | Wilson et al. |
| 2017/0134321 A1 | 5/2017 | Ushio et al. |
| 2017/0143262 A1 | 5/2017 | Kurunmäki et al. |
| 2017/0149795 A1 | 5/2017 | Day, II |
| 2017/0153606 A1 | 6/2017 | Pitis et al. |
| 2017/0153804 A1 | 6/2017 | Kim et al. |
| 2017/0160898 A1 | 6/2017 | Lee et al. |
| 2017/0161014 A1 | 6/2017 | Kikugawa et al. |
| 2017/0176950 A1 | 6/2017 | Jung et al. |
| 2017/0186399 A1 | 6/2017 | Moritani et al. |
| 2017/0209766 A1* | 7/2017 | Riley .................... A61B 5/74 |
| 2017/0230236 A1 | 8/2017 | Kim et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0255169 A1 | 9/2017 | Lee et al. |
| 2017/0257426 A1 | 9/2017 | Wilbur et al. |
| 2017/0266494 A1* | 9/2017 | Crankson ............... G06V 40/23 |
| 2017/0269715 A1 | 9/2017 | Kim et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0277136 A1 | 9/2017 | Minami et al. |
| 2017/0281026 A1 | 10/2017 | Nick et al. |
| 2017/0281057 A1 | 10/2017 | Blahnik et al. |
| 2017/0286913 A1 | 10/2017 | Liu et al. |
| 2017/0287312 A1 | 10/2017 | Schofield et al. |
| 2017/0294174 A1* | 10/2017 | Albadawi .......... A61B 5/02055 |
| 2017/0300013 A1 | 10/2017 | Satou et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0322658 A1 | 11/2017 | Lee et al. |
| 2017/0322711 A1 | 11/2017 | Robinson et al. |
| 2017/0325196 A1 | 11/2017 | Cho et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0337554 A1 | 11/2017 | Mokhasi et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357358 A1 | 12/2017 | Teutschler et al. |
| 2017/0357426 A1 | 12/2017 | Wilson et al. |
| 2017/0357427 A1 | 12/2017 | Wilson et al. |
| 2017/0357520 A1 | 12/2017 | De vries et al. |
| 2018/0000426 A1 | 1/2018 | Li |
| 2018/0001184 A1 | 1/2018 | Tran et al. |
| 2018/0011450 A1 | 1/2018 | Stackowski |
| 2018/0024619 A1 | 1/2018 | Kasuo et al. |
| 2018/0032234 A1 | 2/2018 | Michalske |
| 2018/0033311 A1 | 2/2018 | Berggren |
| 2018/0052428 A1 | 2/2018 | Abramov |
| 2018/0053200 A1 | 2/2018 | Cronin et al. |
| 2018/0056132 A1 | 3/2018 | Foley et al. |
| 2018/0059903 A1 | 3/2018 | Lim et al. |
| 2018/0061308 A1 | 3/2018 | Bae et al. |
| 2018/0065025 A1 | 3/2018 | Toda et al. |
| 2018/0067633 A1 | 3/2018 | Wilson et al. |
| 2018/0074462 A1* | 3/2018 | Helder .................... G04B 47/06 |
| 2018/0074464 A1 | 3/2018 | Essery et al. |
| 2018/0078182 A1 | 3/2018 | Chen et al. |
| 2018/0081515 A1 | 3/2018 | Block et al. |
| 2018/0088537 A1 | 3/2018 | Murai |
| 2018/0088797 A1 | 3/2018 | Mcatee et al. |
| 2018/0097925 A1 | 4/2018 | Ryu et al. |
| 2018/0120927 A1 | 5/2018 | Ma et al. |
| 2018/0121060 A1 | 5/2018 | Jeong et al. |
| 2018/0126248 A1 | 5/2018 | Dion et al. |
| 2018/0136810 A1 | 5/2018 | Martin et al. |
| 2018/0137937 A1 | 5/2018 | Gass et al. |
| 2018/0140903 A1 | 5/2018 | Poure et al. |
| 2018/0150212 A1 | 5/2018 | Chen et al. |
| 2018/0150443 A1 | 5/2018 | Singleton |
| 2018/0150709 A1 | 5/2018 | Ha |
| 2018/0157452 A1 | 6/2018 | Nelson et al. |
| 2018/0181078 A1 | 6/2018 | Imamura |
| 2018/0181381 A1 | 6/2018 | Michaely et al. |
| 2018/0188925 A1 | 7/2018 | Na et al. |
| 2018/0189077 A1 | 7/2018 | Gupta et al. |
| 2018/0206766 A1 | 7/2018 | Blahnik et al. |
| 2018/0246635 A1 | 8/2018 | Baer et al. |
| 2018/0246639 A1 | 8/2018 | Han et al. |
| 2018/0260080 A1 | 9/2018 | Cho |
| 2018/0261183 A1 | 9/2018 | Gou et al. |
| 2018/0272190 A1 | 9/2018 | Miura et al. |
| 2018/0275739 A1 | 9/2018 | Minami et al. |
| 2018/0288560 A1 | 10/2018 | Naik et al. |
| 2018/0294053 A1 | 10/2018 | Runyon et al. |
| 2018/0316783 A1 | 11/2018 | Ye et al. |
| 2018/0318647 A1 | 11/2018 | Foley et al. |

(56) References Cited

U.S. PATENT DOCUMENTS

| | | |
|---|---|---|
| 2018/0321842 A1 | 11/2018 | Lee et al. |
| 2018/0329584 A1 | 11/2018 | Williams et al. |
| 2018/0329587 A1 | 11/2018 | Ko et al. |
| 2018/0335927 A1 | 11/2018 | Anzures et al. |
| 2018/0339195 A1 | 11/2018 | Bernotas |
| 2018/0343023 A1 | 11/2018 | Park et al. |
| 2018/0345078 A1 | 12/2018 | Blahnik et al. |
| 2018/0352435 A1 | 12/2018 | Donley et al. |
| 2018/0374429 A1 | 12/2018 | Nakamura |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0069244 A1 | 2/2019 | Jeon et al. |
| 2019/0089701 A1 | 3/2019 | Mercury et al. |
| 2019/0104951 A1 | 4/2019 | Valys et al. |
| 2019/0121300 A1 | 4/2019 | Peterson et al. |
| 2019/0139207 A1 | 5/2019 | Jeong et al. |
| 2019/0143194 A1 | 5/2019 | Evancha et al. |
| 2019/0184234 A1 | 6/2019 | Packles et al. |
| 2019/0209777 A1 | 7/2019 | O'connell et al. |
| 2019/0212707 A1 | 7/2019 | Minami et al. |
| 2019/0213037 A1 | 7/2019 | Kim et al. |
| 2019/0232110 A1 | 8/2019 | Williams et al. |
| 2019/0232111 A1 | 8/2019 | Williams et al. |
| 2019/0235748 A1 | 8/2019 | Seol et al. |
| 2019/0250813 A1 | 8/2019 | Block et al. |
| 2019/0274565 A1 | 9/2019 | Soli et al. |
| 2019/0281154 A1 | 9/2019 | Choi et al. |
| 2019/0302972 A1 | 10/2019 | Kline et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0339860 A1 | 11/2019 | Chen et al. |
| 2019/0340348 A1 | 11/2019 | Yu et al. |
| 2019/0342616 A1 | 11/2019 | Domm et al. |
| 2019/0349469 A1 | 11/2019 | Skogen et al. |
| 2019/0387982 A1 | 12/2019 | Buller |
| 2020/0014967 A1 | 1/2020 | Putnam |
| 2020/0042311 A1 | 2/2020 | Shin |
| 2020/0050332 A1 | 2/2020 | Yang et al. |
| 2020/0054931 A1 | 2/2020 | Martin et al. |
| 2020/0068095 A1 | 2/2020 | Nabetani |
| 2020/0098278 A1 | 3/2020 | Doti et al. |
| 2020/0101365 A1 | 4/2020 | Wilson et al. |
| 2020/0110814 A1 | 4/2020 | Abuelsaad et al. |
| 2020/0125037 A1 | 4/2020 | Jo et al. |
| 2020/0133206 A1 | 4/2020 | Jo et al. |
| 2020/0149921 A1 | 5/2020 | Hoffman et al. |
| 2020/0160961 A1 | 5/2020 | Wadhawan et al. |
| 2020/0249632 A1 | 8/2020 | Olwal et al. |
| 2020/0264567 A1 | 8/2020 | Ok et al. |
| 2020/0297249 A1 | 9/2020 | Williams et al. |
| 2020/0342144 A1 | 10/2020 | Alameh et al. |
| 2020/0348827 A1 | 11/2020 | Wilson et al. |
| 2020/0356063 A1 | 11/2020 | Guzman et al. |
| 2020/0356224 A1 | 11/2020 | Wilson |
| 2020/0356242 A1 | 11/2020 | Wilson et al. |
| 2020/0356252 A1 | 11/2020 | Ko et al. |
| 2020/0357522 A1 | 11/2020 | Pahwa et al. |
| 2020/0359204 A1 | 11/2020 | Hawkins et al. |
| 2020/0379413 A1 | 12/2020 | Chen et al. |
| 2020/0381100 A1 | 12/2020 | Williams et al. |
| 2020/0382613 A1 | 12/2020 | Sundstrom et al. |
| 2021/0007632 A1 | 1/2021 | Blahnik et al. |
| 2021/0007633 A1 | 1/2021 | Blahnik et al. |
| 2021/0042028 A1 | 2/2021 | Block et al. |
| 2021/0048929 A1 | 2/2021 | Agnoli et al. |
| 2021/0093919 A1 | 4/2021 | Lyke et al. |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0149694 A1 | 5/2021 | Guzman et al. |
| 2021/0191584 A1 | 6/2021 | Williams et al. |
| 2021/0193293 A1 | 6/2021 | Blahnik et al. |
| 2021/0216654 A1 | 7/2021 | Ko et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0294438 A1 | 9/2021 | Yang et al. |
| 2021/0349426 A1 | 11/2021 | Chen et al. |
| 2021/0349427 A1 | 11/2021 | Chen et al. |
| 2021/0349583 A1 | 11/2021 | Guzman et al. |
| 2021/0349611 A1 | 11/2021 | Chen et al. |
| 2021/0349741 A1 | 11/2021 | Guzman et al. |
| 2021/0350900 A1 | 11/2021 | Blahnik et al. |
| 2021/0379447 A1 | 12/2021 | Lee |
| 2022/0047918 A1 | 2/2022 | Williams et al. |
| 2022/0062707 A1 | 3/2022 | Bedekar et al. |
| 2022/0121299 A1 | 4/2022 | De Vries et al. |
| 2022/0157184 A1 | 5/2022 | Wilson et al. |
| 2022/0160258 A1 | 5/2022 | Williams et al. |
| 2022/0198984 A1 | 6/2022 | Connor et al. |
| 2022/0214785 A1 | 7/2022 | Giv |
| 2022/0221964 A1 | 7/2022 | Ko et al. |
| 2022/0229537 A1 | 7/2022 | Chen et al. |
| 2022/0236867 A1 | 7/2022 | Chen et al. |
| 2022/0262509 A1 | 8/2022 | Pahwa et al. |
| 2022/0276780 A1 | 9/2022 | Ko et al. |
| 2022/0328161 A1 | 10/2022 | Gilravi et al. |
| 2022/0342514 A1 | 10/2022 | Chao et al. |

FOREIGN PATENT DOCUMENTS

| | | |
|---|---|---|
| AU | 2015101639 A4 | 12/2015 |
| CA | 2356232 A1 | 3/2002 |
| CA | 2781636 A1 | 7/2010 |
| CA | 2815518 A1 | 5/2012 |
| CA | 2800123 C | 7/2016 |
| CA | 2986980 A1 | 5/2019 |
| CH | 707412 A2 | 6/2014 |
| CN | 1337638 A | 2/2002 |
| CN | 1397904 A | 2/2003 |
| CN | 1443427 A | 9/2003 |
| CN | 1536511 A | 10/2004 |
| CN | 1585943 A | 2/2005 |
| CN | 1610866 A | 4/2005 |
| CN | 1997050 A | 7/2007 |
| CN | 1997957 A | 7/2007 |
| CN | 101061484 A | 10/2007 |
| CN | 101150810 A | 3/2008 |
| CN | 101382438 A | 3/2009 |
| CN | 101505320 A | 8/2009 |
| CN | 101541387 A | 9/2009 |
| CN | 101627349 A | 1/2010 |
| CN | 101651870 A | 2/2010 |
| CN | 101702112 A | 5/2010 |
| CN | 101819486 A | 9/2010 |
| CN | 101836894 A | 9/2010 |
| CN | 101939740 A | 1/2011 |
| CN | 101978374 A | 2/2011 |
| CN | 101981987 A | 2/2011 |
| CN | 102339201 A | 2/2012 |
| CN | 102438521 A | 5/2012 |
| CN | 102448555 A | 5/2012 |
| CN | 102681648 A | 9/2012 |
| CN | 102687176 A | 9/2012 |
| CN | 102750070 A | 10/2012 |
| CN | 102804238 A | 11/2012 |
| CN | 102989159 A | 3/2013 |
| CN | 103154954 A | 6/2013 |
| CN | 103182175 A | 7/2013 |
| CN | 103212197 A | 7/2013 |
| CN | 103297610 A | 9/2013 |
| CN | 103370924 A | 10/2013 |
| CN | 103399480 A | 11/2013 |
| CN | 103403627 A | 11/2013 |
| CN | 103544920 A | 1/2014 |
| CN | 103562832 A | 2/2014 |

(56) References Cited

FOREIGN PATENT DOCUMENTS

| | | |
|---|---|---|
| CN | 103581456 A | 2/2014 |
| CN | 103607660 A | 2/2014 |
| CN | 103649897 A | 3/2014 |
| CN | 103701504 A | 4/2014 |
| CN | 103902165 A | 7/2014 |
| CN | 103914238 A | 7/2014 |
| CN | 103973899 A | 8/2014 |
| CN | 203773233 U | 8/2014 |
| CN | 104281405 A | 1/2015 |
| CN | 104288983 A | 1/2015 |
| CN | 104487929 A | 4/2015 |
| CN | 104501043 A | 4/2015 |
| CN | 104508426 A | 4/2015 |
| CN | 104580576 A | 4/2015 |
| CN | 104815428 A | 8/2015 |
| CN | 105204931 A | 12/2015 |
| CN | 105260049 A | 1/2016 |
| CN | 105264479 A | 1/2016 |
| CN | 105335087 A | 2/2016 |
| CN | 105388966 A | 3/2016 |
| CN | 105389078 A | 3/2016 |
| CN | 105389107 A | 3/2016 |
| CN | 105453016 A | 3/2016 |
| CN | 205608658 U | 9/2016 |
| CN | 106056848 A | 10/2016 |
| CN | 106486044 A | 3/2017 |
| CN | 106537397 A | 3/2017 |
| CN | 106605201 A | 4/2017 |
| CN | 106709235 A | 5/2017 |
| CN | 106878550 A | 6/2017 |
| CN | 107239101 A | 10/2017 |
| CN | 107643677 A | 1/2018 |
| CN | 107870560 A | 4/2018 |
| CN | 108255049 A | 7/2018 |
| CN | 109196469 A | 1/2019 |
| CN | 109313655 A | 2/2019 |
| CN | 109690445 A | 4/2019 |
| CN | 103701504 A | 8/2022 |
| CN | 103544920 A | 10/2022 |
| DE | 202017105858 U1 | 3/2018 |
| EP | 0579093 A1 | 1/1994 |
| EP | 0831629 A2 | 3/1998 |
| EP | 1659504 A2 | 5/2006 |
| EP | 1674889 A1 | 6/2006 |
| EP | 1674977 A2 | 6/2006 |
| EP | 1750242 A2 | 2/2007 |
| EP | 1832969 A2 | 9/2007 |
| EP | 1855170 A2 | 11/2007 |
| EP | 1935339 A1 | 6/2008 |
| EP | 2025368 A2 | 2/2009 |
| EP | 2120115 A2 | 11/2009 |
| EP | 2194508 A1 | 6/2010 |
| EP | 2204702 A1 | 7/2010 |
| EP | 2290922 A1 | 3/2011 |
| EP | 2312512 A1 | 4/2011 |
| EP | 2360902 A2 | 8/2011 |
| EP | 2413577 A2 | 2/2012 |
| EP | 2423810 A1 | 2/2012 |
| EP | 2426902 A1 | 3/2012 |
| EP | 2600215 A1 | 6/2013 |
| EP | 2629483 A1 | 8/2013 |
| EP | 2738640 A2 | 6/2014 |
| EP | 2942932 A1 | 11/2015 |
| EP | 2990887 A2 | 3/2016 |
| EP | 2993602 A1 | 3/2016 |
| EP | 3056949 A1 | 8/2016 |
| EP | 3101958 A1 | 12/2016 |
| EP | 3122038 A1 | 1/2017 |
| EP | 3376342 A1 | 9/2018 |
| EP | 3401770 A1 | 11/2018 |
| GB | 2475669 A | 6/2011 |
| JP | 49-134364 A | 12/1974 |
| JP | 53-31170 A | 3/1978 |
| JP | 56-621 A | 1/1981 |
| JP | 6-187118 A | 7/1994 |
| JP | 3007616 U | 2/1995 |
| JP | 8-110955 A | 4/1996 |
| JP | 9-251084 A | 9/1997 |
| JP | 10-143636 A | 5/1998 |
| JP | 11-109066 A | 4/1999 |
| JP | 11-160470 A | 6/1999 |
| JP | 11-232013 A | 8/1999 |
| JP | 3062531 B2 | 7/2000 |
| JP | 2001-76078 A | 3/2001 |
| JP | 2001-144884 A | 5/2001 |
| JP | 2001-147282 A | 5/2001 |
| JP | 2001-273064 A | 10/2001 |
| JP | 2001-313886 A | 11/2001 |
| JP | 2001-318852 A | 11/2001 |
| JP | 2002-73486 A | 3/2002 |
| JP | 2002-507718 A | 3/2002 |
| JP | 2002-190007 A | 7/2002 |
| JP | 2002-251238 A | 9/2002 |
| JP | 2002-271451 A | 9/2002 |
| JP | 2003-9404 A | 1/2003 |
| JP | 2003-102868 A | 4/2003 |
| JP | 2003-157323 A | 5/2003 |
| JP | 2003-233616 A | 8/2003 |
| JP | 2003-296246 A | 10/2003 |
| JP | 2003-319912 A | 11/2003 |
| JP | 2003-337863 A | 11/2003 |
| JP | 2004-28918 A | 1/2004 |
| JP | 2004-102609 A | 4/2004 |
| JP | 2004-113466 A | 4/2004 |
| JP | 2004-184396 A | 7/2004 |
| JP | 2005-79814 A | 3/2005 |
| JP | 2005-521890 A | 7/2005 |
| JP | 2005-339017 A | 12/2005 |
| JP | 2006-101505 A | 4/2006 |
| JP | 2006-230679 A | 9/2006 |
| JP | 2006-293340 A | 10/2006 |
| JP | 2007-260288 A | 10/2007 |
| JP | 2007-330513 A | 12/2007 |
| JP | 2008-104758 A | 5/2008 |
| JP | 2008-175800 A | 7/2008 |
| JP | 2008-183339 A | 8/2008 |
| JP | 2008-272301 A | 11/2008 |
| JP | 2009-78134 A | 4/2009 |
| JP | 2009-112731 A | 5/2009 |
| JP | 2009-147889 A | 7/2009 |
| JP | 2009-293960 A | 12/2009 |
| JP | 2010-12335 A | 1/2010 |
| JP | 2010-517725 A | 5/2010 |
| JP | 2010-122901 A | 6/2010 |
| JP | 2010-124181 A | 6/2010 |
| JP | 2010-162297 A | 7/2010 |
| JP | 2010-181280 A | 8/2010 |
| JP | 2010-257051 A | 11/2010 |
| JP | 2011-125633 A | 6/2011 |
| JP | 3168099 U | 6/2011 |
| JP | 2011-159172 A | 8/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-217000 A | 10/2011 |
| JP | 2011-259253 A | 12/2011 |
| JP | 2012-020134 A | 2/2012 |
| JP | 2012-32306 A | 2/2012 |
| JP | 2012-35071 A | 2/2012 |
| JP | 2012-53642 A | 3/2012 |
| JP | 2012-59264 A | 3/2012 |
| JP | 2012-505478 A | 3/2012 |
| JP | 2012-109778 A | 6/2012 |
| JP | 2012-147432 A | 8/2012 |
| JP | 2012-517630 A | 8/2012 |
| JP | 2012-203537 A | 10/2012 |
| JP | 2012-203832 A | 10/2012 |
| JP | 2012-524640 A | 10/2012 |
| JP | 2012-230503 A | 11/2012 |
| JP | 2012-232114 A | 11/2012 |
| JP | 2012-531607 A | 12/2012 |
| JP | 2012-533117 A | 12/2012 |
| JP | 2013-3671 A | 1/2013 |

(56) References Cited

FOREIGN PATENT DOCUMENTS

| | | |
|---|---|---|
| JP | 2013-29925 A | 2/2013 |
| JP | 2013-92989 A | 5/2013 |
| JP | 2013-103020 A | 5/2013 |
| JP | 2013-117690 A | 6/2013 |
| JP | 2013-232230 A | 11/2013 |
| JP | 5346115 B1 | 11/2013 |
| JP | 2013-544140 A | 12/2013 |
| JP | 2014-500740 A | 1/2014 |
| JP | 2014-35766 A | 2/2014 |
| JP | 2014-123197 A | 7/2014 |
| JP | 2014-143575 A | 8/2014 |
| JP | 2014-519126 A | 8/2014 |
| JP | 2014-216868 A | 11/2014 |
| JP | 5630676 B2 | 11/2014 |
| JP | 2015-507811 A | 3/2015 |
| JP | 2015-210587 A | 11/2015 |
| JP | 2015-531916 A | 11/2015 |
| JP | 2016-13151 A | 1/2016 |
| JP | 2016-17331 A | 2/2016 |
| JP | 2016-502875 A | 2/2016 |
| JP | 2016-52512 A | 4/2016 |
| JP | 2016-517329 A | 6/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-527026 A | 9/2017 |
| JP | 2017-531225 A | 10/2017 |
| JP | 2017-531230 A | 10/2017 |
| JP | 2017-211994 A | 11/2017 |
| JP | 2017-532069 A | 11/2017 |
| JP | 2018-514838 A | 6/2018 |
| JP | 2018-113544 A | 7/2018 |
| JP | 2018-116067 A | 7/2018 |
| JP | 2018-202174 A | 12/2018 |
| JP | 2019-3670 A | 1/2019 |
| JP | 49-134364 A | 5/2022 |
| JP | 2001-147282 A | 5/2022 |
| JP | 2006-101505 A | 5/2022 |
| JP | 2008-175800 A | 5/2022 |
| JP | 2009-293960 A | 5/2022 |
| JP | 2012-32306 A | 5/2022 |
| JP | 5630676 B2 | 5/2022 |
| JP | 10-143636 A | 7/2022 |
| JP | 2012-109778 A | 7/2022 |
| JP | 2003-157323 A | 8/2022 |
| JP | 2003-319912 A | 8/2022 |
| JP | 2016-17331 A | 8/2022 |
| JP | 2018-202174 A | 8/2022 |
| JP | 2019-3670 A | 8/2022 |
| JP | 5346115 B1 | 8/2022 |
| JP | 2001-144884 A | 9/2022 |
| JP | 2003-9404 A | 9/2022 |
| JP | 2006-293340 A | 10/2022 |
| JP | 102681648 A | 10/2022 |
| KR | 10-2004-0107489 A | 12/2004 |
| KR | 20-0425314 Y1 | 9/2006 |
| KR | 10-2006-0117570 A | 11/2006 |
| KR | 10-2007-0025292 A | 3/2007 |
| KR | 10-2008-0058246 A | 6/2008 |
| KR | 10-2009-0112132 A | 10/2009 |
| KR | 10-2011-0017076 A | 2/2011 |
| KR | 10-2011-0093729 A | 8/2011 |
| KR | 10-2012-0023657 A | 3/2012 |
| KR | 10-2012-0076559 A | 7/2012 |
| KR | 10-2012-0132134 A | 12/2012 |
| KR | 10-2013-0043698 A | 5/2013 |
| KR | 10-2013-0109466 A | 10/2013 |
| KR | 10-2013-0111569 A | 10/2013 |
| KR | 10-2013-0111570 A | 10/2013 |
| KR | 10-2013-0135282 A | 12/2013 |
| KR | 10-2014-0025552 A | 3/2014 |
| KR | 10-2014-0064687 A | 5/2014 |
| KR | 10-2015-0026635 A | 3/2015 |
| KR | 10-2015-0038711 A | 4/2015 |
| KR | 10-2015-0081140 A | 7/2015 |
| KR | 10-2016-0026314 A | 3/2016 |
| KR | 10-2016-0027943 A | 3/2016 |
| KR | 10-2016-0142418 A | 12/2016 |
| KR | 20-2017-0003608 A | 1/2017 |
| KR | 10-2017-0029014 A | 3/2017 |
| KR | 10-2017-0032471 A | 3/2017 |
| KR | 10-2017-0076452 A | 7/2017 |
| KR | 10-2017-0081391 A | 7/2017 |
| KR | 10-2017-0082698 A | 7/2017 |
| KR | 10-2018-0011581 A | 2/2018 |
| KR | 10-2019-0020850 A | 3/2019 |
| KR | 10-2019-0071285 A | 6/2019 |
| KR | 10-2019-0141702 A | 12/2019 |
| KR | 10-2016-0027943 A | 5/2022 |
| KR | 10-2004-0107489 A | 6/2022 |
| KR | 10-2012-0132134 A | 6/2022 |
| KR | 10-2017-0081391 A | 6/2022 |
| TW | 498240 B | 8/2002 |
| TW | 546942 B | 8/2003 |
| TW | 200512616 A | 4/2005 |
| TW | 200850058 A | 12/2008 |
| TW | 200915698 A | 4/2009 |
| TW | I348803 B | 9/2011 |
| TW | 201210368 A | 3/2012 |
| TW | 201232486 A | 8/2012 |
| TW | 201240499 A | 10/2012 |
| TW | 201419115 A | 5/2014 |
| WO | 98/40795 A1 | 9/1998 |
| WO | 1999/41682 A2 | 8/1999 |
| WO | 2001/71433 A1 | 9/2001 |
| WO | 2002/27530 A2 | 4/2002 |
| WO | 2002/054157 A1 | 7/2002 |
| WO | 2003/048872 A1 | 6/2003 |
| WO | 03/085460 A2 | 10/2003 |
| WO | 2005/070289 A1 | 8/2005 |
| WO | 2006/012343 A2 | 2/2006 |
| WO | 2006/112641 A1 | 10/2006 |
| WO | 2007/018881 A2 | 2/2007 |
| WO | 2008/114491 A1 | 9/2008 |
| WO | 2009/053775 A1 | 4/2009 |
| WO | 2009/129402 A1 | 10/2009 |
| WO | 2009/146857 A2 | 12/2009 |
| WO | 2010/017627 A1 | 2/2010 |
| WO | 2010/126825 A1 | 11/2010 |
| WO | 2011/000893 A1 | 1/2011 |
| WO | 2011/062871 A2 | 5/2011 |
| WO | 2011/099819 A2 | 8/2011 |
| WO | 2012/021507 A2 | 2/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2012/161434 A2 | 11/2012 |
| WO | 2012/170446 A2 | 12/2012 |
| WO | 2013/051048 A1 | 4/2013 |
| WO | 2013/052789 A1 | 4/2013 |
| WO | 2013/093558 A1 | 6/2013 |
| WO | 2013/109762 A1 | 7/2013 |
| WO | 2013/109777 A1 | 7/2013 |
| WO | 2013/109916 A1 | 7/2013 |
| WO | 2013/136548 A1 | 9/2013 |
| WO | 2013/169842 A2 | 11/2013 |
| WO | 2013/169846 A1 | 11/2013 |
| WO | 2013/169849 A2 | 11/2013 |
| WO | 2013/169870 A1 | 11/2013 |
| WO | 2013/169875 A2 | 11/2013 |
| WO | 2013/169882 A2 | 11/2013 |
| WO | 2013/173838 A2 | 11/2013 |
| WO | 2014/022711 A1 | 2/2014 |
| WO | 2014/078114 A1 | 5/2014 |
| WO | 2014/081181 A1 | 5/2014 |
| WO | 2014/105274 A1 | 7/2014 |
| WO | 2014/105278 A1 | 7/2014 |
| WO | 2014/189197 A1 | 11/2014 |
| WO | 2014/200730 A1 | 12/2014 |
| WO | 2014/207294 A1 | 12/2014 |
| WO | 2015/023419 A1 | 2/2015 |
| WO | 2015/027133 A1 | 2/2015 |

(56) References Cited

FOREIGN PATENT DOCUMENTS

| | | |
|---|---|---|
| WO | 2015/029313 A1 | 3/2015 |
| WO | 2015/065402 A1 | 5/2015 |
| WO | 2015/163536 A1 | 10/2015 |
| WO | 2015/179592 A1 | 11/2015 |
| WO | 2015/198488 A1 | 12/2015 |
| WO | 2016/022203 A1 | 2/2016 |
| WO | 2016/022204 A1 | 2/2016 |
| WO | 2016/022205 A1 | 2/2016 |
| WO | 2016/022496 A2 | 2/2016 |
| WO | 2016/032076 A1 | 3/2016 |
| WO | 2016/036427 A1 | 3/2016 |
| WO | 2016/036472 A1 | 3/2016 |
| WO | 2016/036522 A2 | 3/2016 |
| WO | 2016/036582 A2 | 3/2016 |
| WO | 2016/057062 A1 | 4/2016 |
| WO | 2016/099097 A1 | 6/2016 |
| WO | 2016/144385 A1 | 9/2016 |
| WO | 2016/144563 A1 | 9/2016 |
| WO | 2016/144977 A1 | 9/2016 |
| WO | 2017/037242 A1 | 3/2017 |
| WO | 2017/062621 A1 | 4/2017 |
| WO | 2017/213777 A1 | 12/2017 |
| WO | 2017/213937 A1 | 12/2017 |
| WO | 2018/048700 A1 | 3/2018 |
| WO | 2018/213066 A1 | 11/2018 |
| WO | 2018/213451 A1 | 11/2018 |
| WO | 2018/222313 A1 | 12/2018 |
| WO | 2019/017508 A1 | 1/2019 |
| WO | 2019/024603 A1 | 2/2019 |
| WO | 2019/183422 A1 | 9/2019 |
| WO | 2019/200350 A1 | 10/2019 |
| WO | 2019/217086 A2 | 11/2019 |
| WO | 2019/217249 A2 | 11/2019 |
| WO | 2019/231982 A1 | 12/2019 |
| WO | 2021/050190 A1 | 3/2021 |

OTHER PUBLICATIONS

Office Action received for Australian Patent Application No. 2019100495, dated Sep. 17, 2019, 7 pages.
Office Action received for Chinese Patent Application No. 201810105846.X, dated Aug. 27, 2019, 12 pages (5 pages of English Translation and 7 pages of Official Copy).
Summons to Attend Oral Proceedings received for European Patent Application No. 15730925.3, mailed on Oct. 2, 2019, 8 pages.
Advisory Action received for U.S. Appl. No. 14/841,606, dated Feb. 28, 2019, 3 pages.
Advisory Action received for U.S. Appl. No. 14/846,511, dated Sep. 19, 2018, 8 pages.
"AdyClock—Night Alarm Clock", App for android, Google play store page: https://web.archive.org/web/20130924223153/https://play.google.com/store/apps/details?id=com.adyclock&hl=en, Sep. 24, 2013, 2 pages.
Android Central, "BeWeather weather app for Android", Available online at: <https://www.youtube.com/watch?v=G2EY2K-XkSI>, Sep. 1, 2011, 1 page.
Android Central, "Changing the watchface on your Android Wear device", Retrieved from: https://www.youtube.com/watch?v=YYwFe2K_qil, Jul. 2, 2014, 4 pages.
Apple, "iPhone User's Guide", Available at <http://mesnotices.20minutes.fr/manuel-notice-mode-emploi/APPLE/IPHONE%2D%5FE#>, Jun. 2007, 137 pages.
Certification of Examination received for Australian Patent Application No. 2018100158, dated Oct. 23, 2018, 2 pages.
Clark, Josh, "Designing Great iPhone Apps", O'Reilly Japan Co., O'Reilly Tim, vol. 1, May 24, 2012, 5 pages (Official Copy only) (see attached 37 CFR § 1.98(a) (3)).
CNET, "Google Fit's automatic activity tracking is getting smarter on Android Wear", Available online at: https://www.youtube.com/watch?v=lttzlCid_d8, May 18, 2016, 1 page.
Codrington, Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 15/798,257, dated Jun. 12, 2019, 2 pages.
Cyr, Jim, "Apple Watch—Customize Modular Watch Face", available online at: https://www.youtube.com/watch?v=02W93HbKlK8, May 13, 2015, 2 pages.
Decision to Grant Received for Danish Patent Application No. PA201770397, dated Feb. 6, 2018, 2 pages.
Decision to Refuse received for European Patent Application No. 15730924.6, dated Mar. 15, 2019, 12 pages.
"Digital alarm clock app for Android", Goggle play store digital alarm clock description page, Mar. 25, 2015, 3 pages.
"DwProgressBar v2: Stepping and Events", davidwalsh.name/dwprogressbar-2-stepping-events-mootools-progress-bar, retrieved from the Wayback Machine, Aug. 31, 2008, 4 pages.
Ebpman Tech Reviews, "LG G3 Tips: How to customize the clock face", Available online at: https://www.youtube.com/watch?v=evraMWFb1fY, Jul. 25, 2014, 1 page.
European Search Report received for European Patent Application No. 17206177.2, dated Apr. 30, 2018, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16762356.0, dated Nov. 9, 2018, 10 pages.
Feist, Jonathan, "Android customization—how to create a custom clock widget using Zooper Widget", Available Online at: https://www.androidauthority.com/zooper-widget-clock-366476/, May 15, 2014, 10 pages.
Final Office Action received for U.S. Appl. No. 12/205,847, dated Apr. 25, 2012, 42 pages.
Final Office Action received for U.S. Appl. No. 14/815,890, dated May 14, 2019, 22 pages.
Final Office Action received for U.S. Appl. No. 14/821,667, mailed on Apr. 26, 2018, 13 pages.
Final Office Action received for U.S. Appl. No. 14/841,606, dated Sep. 7, 2018, 34 pages.
Final Office Action received for U.S. Appl. No. 14/846,511 dated May 10, 2018, 21 pages.
Final Office Action received for U.S. Appl. No. 14/846,511, dated Jun. 5, 2019, 24 pages.
Final Office Action received for U.S. Appl. No. 15/798,235, dated Oct. 9, 2018, 45 pages.
Final Office Action received for U.S. Appl. No. 15/881,544, dated Jan. 29, 2019, 14 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
"Fitbit surge Fitness Watch", Manual version 1.0, May 7, 2015, 48 pages.
Fukuda, Kazuhiro, "Xperia Z1 Perfect Manual", Sotec Co., Ltd., No. 1, Nov. 15, 2013, pp. 217-218 (Official Copy only) (see attached 37 CFR § 1.98(a) (3)).
Garmin, "Fenix 5x Owner's Manual", Online Available at :—https://web.archive.org/web/20180127170640/https://static.garmin.com/pumac/fenix5x_OM_EN.pdf, Jan. 27, 2018, 42 pages.
Gazer, "iPhone 48 Super Manual", Shuwa System Co., Saito Kazukuni, vol. 1, Jun. 6, 2013, 7 pages (Official Copy only) (see attached 37 CFR § 1.98(a) (3)).
Geary, David, "Programming HTML5 Canvas", O'Reilly Japan, Inc., No. 1, Jul. 23, 2014, pp. 327-330 (Official Copy only) (see attached 37 CFR § 1.98(a) (3)).
Geek, "How to Put the Day of the Week into the Windows Taskbar Clock", available online at: https://www.howtogeek.com/194103/how-to-put-the-day-of-the-week-into-the-windows-taskbar-clock/, 2014, 3 pages.
"Graphs and Charts", Online available at: <https://www.teachervision.com/lesson-planning/graph-chart-teacher-resources, retrieved on Dec. 12, 2018, 4 pages.

(56) References Cited

OTHER PUBLICATIONS

Intention to Grant Received for Danish Patent Application No. PA201770397, dated Aug. 18, 2017, 7 pages.
Intention to Grant received for Danish Patent Application No. PA201870379, dated May 2, 2019, 2 pages.
International Preliminary Report on Patentability received for PCT Patent Application No. PCT/US2015/044473, dated Mar. 2, 2017, 20 pages.
International Preliminary Report on Patentability received for PCT Patent Application No. PCT/US2015/044485, dated Mar. 2, 2017, 20 pages.
International Preliminary Report on Patentability received for PCT Patent Application No. PCT/US2015/053353, dated Sep. 21, 2017, 15 pages.
International Preliminary Report on Patentability received for PCT Patent Application No. PCT/US2015/054223, dated Dec. 14, 2017, 18 pages.
International Preliminary Report on Patentability received for PCT Patent Application No. PCT/US2016/021403, dated Sep. 21, 2017, 21 pages.
International Preliminary Report on Patentability received for PCT Patent Application No. PCT/US2016/035090, dated Dec. 14, 2017, 14 pages.
International Preliminary Report on Patentability received for PCT Patent Application No. PCT/US2017/034834, dated Dec. 20, 2018, 9 pages.
International Preliminary Report on Patentability received for PCT Patent Application No. PCT/US2017/035554, dated Dec. 20, 2018, 39 pages.
International Search Report and Written Opinion received for PCT Patent Application No. PCT/US2015/044473, dated Feb. 12, 2016, 24 pages.
International Search Report and Written Opinion received for PCT Patent Application No. PCT/US2015/044485, dated Feb. 9, 2016, 27 pages.
International Search Report and Written Opinion received for PCT Patent Application No. PCT/US2015/053353, dated May 9, 2016, 21 pages.
International Search Report and Written Opinion received for PCT Patent Application No. PCT/US2015/054223, dated Jul. 6, 2016, 25 pages.
International Search Report and Written Opinion received for PCT Patent Application No. PCT/US2016/021403, dated May 12, 2016, 23 pages.
International Search Report and Written Opinion received for PCT Patent Application No. PCT/US2016/035090, dated Oct. 4, 2016, 17 pages.
International Search Report and Written Opinion received for PCT Patent Application No. PCT/US2017/034834, dated Aug. 23, 2017, 10 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2018/032164, dated Oct. 18, 2018, 16 Pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No PCT/US2015/044473, dated Nov. 3, 2015, 5 pages.
Invitation to Pay Additional Fees received for PCT Patent Application No. PCT/US2015/044485, dated Nov. 3, 2015, 7 pages.
Invitation to Pay Additional fees received for PCT Patent Application No. PCT/US2015/053353, dated Jan. 21, 2016, 7 pages.
Invitation to Pay Additional fees received for PCT Patent Application No. PCT/US2015/054223, dated Mar. 9, 2016, 9 pages.
Invitation to Pay Additional Fees received for PCT Patent Application No. PCT/US2016/035090, dated Jul. 15, 2016, 2 pages.
Invitation to Pay Additional Fees received for PCT Patent Application No. PCT/US2017/035554, dated Jul. 20, 2017, 2 pages.
Invitation to Pay Additional Fees received for PCT Patent Application No. PCT/US2018/032164, dated Aug. 21, 2018, 10 pages.
Kenney, Briley, "How To Customize a Smartwatch and other Personalization Questions", Available online at: <https://smartwatches.org/learn/customize-smartwatch/>, Jan. 23, 2014, 3 pages.
Minutes of Oral Proceedings received for European Patent Application No. 15730924.6, mailed on Mar. 13, 2019, 4 pages.
"MS Excel 2013", Jan. 29, 2013, 2 pages.
"Mugs", Online Available at: https://web.archive.org/web/20151029034349/http://le-mugs.com/, Oct. 29, 2015.
"Multi-Set Bar Chart", The Data Visualization Catalogue, Available Online at: https://datavizcatalogue.com/methods/multiset_barchart.html, Feb. 8, 2014, 3 pages.
"My CalStep", available at:—http://www.surprisesoftware.com/mycalstep/, retrieved from the Wayback Machine, May 9, 2007, 2 pages.
"Night Display (Alarm Clock) App", Google Play Store Night Display (Alarm Clock) Description page, available at <https://web.archive.org/web/20141007124222/https://play.google.com/store/apps/details?id=com.srk.nighttimedisplay&hl=en>, Oct. 7, 2014, pp 1-3.
Non Final Office Action received for U.S. Appl. No. 15/881,544, dated Jun. 7, 2018, 15 pages.
Non Final Office Action Received for U.S. Appl. No. 16/144,864, dated Dec. 18, 2018, 19 pages.
Non-Final Office Action received for U.S. Appl. No. 15/421,865, dated Mar. 21, 2019, 18 pages.
Non-Final Office Action received for U.S. Appl. No. 15/554,204, dated Apr. 17, 2019, 19 pages.
Non-Final Office Action received for U.S. Appl. No. 15/608,848, dated Nov. 2, 2018, 21 pages.
Non-Final Office Action received for U.S. Appl. No. 12/205,847, dated Oct. 3, 2011, 59 pages.
Non-Final Office Action received for U.S. Appl. No. 14/732,773, dated Feb. 8, 2019, 32 pages.
Non-Final Office Action received for U.S. Appl. No. 14/821,667, dated Feb. 4, 2019, 13 pages.
Non-Final Office Action received for U.S. Appl. No. 14/821,667, dated Jul. 14, 2017, 12 pages.
Non-Final Office Action received for U.S. Appl. No. 14/839,889, dated Mar. 7, 2017, 26 pages.
Non-Final Office Action received for U.S. Appl. No. 14/841,606, dated Dec. 7, 2017, 30 pages.
Non-Final Office Action received for U.S. Appl. No. 14/841,606, dated May 8, 2019, 28 pages.
Non-Final Office Action received for U.S. Appl. No. 14/846,511 dated Oct. 27, 2017, 15 pages.
Non-Final Office Action received for U.S. Appl. No. 15/355,956, dated May 31, 2019, 32 pages.
Non-Final Office Action received for U.S. Appl. No. 15/405,122, dated May 31, 2019, 43 pages.
Non-Final Office Action received for U.S. Appl. No. 15/798,235, dated Apr. 24, 2019, 25 pages.
Non-Final Office Action received for U.S. Appl. No. 15/798,235, dated Mar. 14, 2018, 58 pages.
Non-Final Office Action received for U.S. Appl. No. 15/925,652, dated Apr. 5, 2019, 28 pages.
Non-Final Office Action received for U.S. Appl. No. 16/144,849, dated Dec. 31, 2018, 28 pages.
Non-Final Office Action received for U.S. Appl. No.14/846,511, dated Nov. 30, 2018, 22 pages.
Notice of Acceptance received for Australian Patent Application No. 2016229847, dated Sep. 12, 2018, 3 pages.
Notice of Allowance received for Chinese Patent Application No. 201510481525.6, dated May 27, 2019, 2 pages (1 page of English Translation and 1 page of Official Copy).
Notice of Allowance received for Chinese Patent Application No. 201510483305.7, dated Jan. 8, 2019, 3 pages (1 page of English Translation and 2 pages of Official Copy).

(56) References Cited

OTHER PUBLICATIONS

Notice of Allowance received for Japanese Patent Application No. 2016-557650, dated Apr. 9, 2019, 4 pages (1 page of English Translation and 3 pages of Official Copy).
Notice of Allowance received for Japanese Patent Application No. 2017-505847, dated May 20, 2019, 4 pages (1 page of English Translation and 3 pages of Official Copy).
Notice of Allowance received for Japanese Patent Application No. 2018-074971, dated Apr. 23, 2019, 4 pages (1 page of English Translation and 3 pages of Official Copy).
Notice of Allowance received for Korean Patent Application No. 10-2016-7014577, dated May 30, 2019, 5 pages (2 pages of English Translation and 3 pages of Official Copy).
Notice of Allowance received for Taiwanese Patent Application No. 104134740, dated Dec. 8, 2016, 5 pages (1 page of English Translation of Search Report and 4 pages of Official Copy) (see attached 37 CFR § 1.98(a) (3)).
Notice of Allowance received for U.S. Appl. No. 12/205,847, dated Aug. 20, 2012, 13 pages.
Notice of Allowance received for U.S. Appl. No. 14/821,667, dated Jun. 12, 2019, 9 pages.
Notice of Allowance received for U.S. Appl. No. 14/839,889, dated Oct. 30, 2017, 16 pages.
Notice of Allowance received for U.S. Appl. No. 15/616,480, dated Jan. 3, 2019, 8 pages.
Notice of Allowance received for U.S. Appl. No. 15/798,257, dated May 22, 2019, 14 pages.
Obara, YuuTA, "iPhone Application Selection for Univesity Students", Shuwa System Co., Saito Kazukuni, vol. 1, May 16, 2013, 4 pages (Official Copy only) (see attached 37 CFR § 1.98(a) (3)).
Octoba, "Just Install It—Utilizing Method for Android Application Business", ASCII Media Works Co. Takano Kiyoshi, vol. 1, Apr. 25, 2013, 6 pages (Official Copy only) (see attached 37 CFR § 1.98(a) (3)).
Office Action received for Australian Patent Application No. 2016229847, dated Jul. 3, 2018, 4 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018206770, dated Apr. 30, 2019, 4 pages.
Office Action received for Australian Patent Application No. 2018206770, dated Jul. 25, 2018, 5 pages.
Office Action received for Australian Patent Application No. 2018206770, dated Mar. 5, 2019, 3 pages.
Office Action received for Chinese Patent Application No. 201380081349.6, dated Feb. 26, 2019, 12 pages (6 pages of English Translation and 6 pages of Official Copy).
Office Action received for Chinese Patent Application No. 201510479088.4, dated May 7, 2019, 6 pages (3 pages of English Translation and 3 pages of Official Copy).
Office Action received for Chinese Patent Application No. 201510483268.X, dated Apr. 16, 2019, 6 pages (3 pages of English Translation and 3 pages of Official Copy).
Office Action received for Chinese Patent Application No. 201510484514.3, dated Dec. 24, 2018, 10 pages (5 pages of English Translation and 5 pages of Official Copy).
Office Action received for Chinese Patent Application No. 201580037927.5, dated Apr. 22, 2019, 9 pages (4 pages of English Translation and 5 pages of Official Copy).
Office Action received for Chinese Patent Application No. 201680047983.1, dated Mar. 18, 2019, 18 pages (6 pages of English Translation and 12 pages of Official Copy).
Office Action received for Chinese Patent Application No. 201810037665.8, dated Dec. 7, 2018, 10 pages (5 pages of English Translation and 5 pages of Official Copy).
Office Action received for Chinese Patent Application No. 201810105846.X, dated Feb. 25, 2019, 10 pages (5 pages of English Translation and 5 pages of Official copy).
Office Action received for Danish Patent Application No. PA201570768, dated Sep. 13, 2016, 8 pages.
Office Action received for Danish Patent Application No. PA201570770, dated Apr. 7, 2017, 7 pages.
Office Action received for Danish Patent Application No. PA201570770, dated Mar. 17, 2016, 9 pages.
Office Action received for Danish Patent Application No. PA201570770, dated Sep. 12, 2016, 6 pages.
Office Action Received for Danish Patent Application No. PA201670656, dated May 2, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201770791, dated Jan. 31, 2018, 8 pages.
Office Action received for Danish Patent Application No. PA201770791, dated Jul. 13, 2018, 2 pages.
Office Action received for Danish Patent Application No. PA201870378, dated Feb. 25, 2019, 3 pages.
Office Action received for Danish Patent Application No. PA201870379, dated Feb. 28, 2019, 3 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 15747595.5, dated Apr. 15, 2019, 4 pages.
Office Action received for European Patent Application No. 17206177.2, dated May 15, 2018, 6 pages.
Office Action received for European Patent Application No. 15730925.3, dated Feb. 27, 2019, 5 pages.
Office Action received for German Patent Application No. 112015002326.7, dated Feb. 20, 2019, 7 pages (2 pages of English Translation and 5 pages of Official Copy).
Office Action received for Japanese Patent Application No. 2017-505842, dated Feb. 22, 2019, 11 pages (6 pages of English Translation and 5 pages of Official Copy).
Office Action received for Japanese Patent Application No. 2017-505847, dated Feb. 12, 2019, 13 pages (6 pages of English Translation and 7 pages of Official Copy).
Office Action received for Japanese Patent Application No. 2017-545918, dated Sep. 14, 2018, 12 pages (7 pages of English Translation and 5 pages of Official copy).
Office Action received for Japanese Patent Application No. 2018-068846, dated Jan. 8, 2019, 6 pages (3 pages of English Translation and 3 pages of Official copy).
Office Action received for Japanese Patent Application No. 2018-074971, dated Jan. 28, 2019, 6 pages (3 pages of English Translation and 3 pages of Official Copy).
Office Action received for Korean Patent Application No. 10-2017-7024570, dated Sep. 28, 2018, 14 pages (6 pages of English Translation and 8 pages of Official copy).
Office Action received for Korean Patent Application No. 10-2018-7022101, dated Feb. 14, 2019, 15 pages (6 pages of English Translation and 9 pages of Official Copy).
Office Action received for Taiwanese Patent Application No. 104126627, dated Nov. 29, 2016, 9 pages (4 pages of English Translation and 5 pages of Official Copy).
Office Action received for Taiwanese Patent Application No. 104126627, dated Aug. 30, 2018, 22 pages (9 pages of English Translation and 13 pages of Official Copy).
Office Action received for Taiwanese Patent Application No. 104126627, dated Dec. 20, 2018, 4 pages (2 pages of English Translation and 2 pages of Official Copy).
Office Action received for Taiwanese Patent Application No. 104126627, dated Oct. 16, 2017, 7 pages (3 pages of English Translation and 4 pages of Official Copy).

(56) References Cited

OTHER PUBLICATIONS

Office Action received for Taiwanese Patent Application No. 104132636, dated Dec. 13, 2018, 26 pages (9 pages of English Translation and 17 pages of Official Copy).
Office Action received for Taiwanese Patent Application No. 104132636, dated Mar. 23, 2017, 25 pages (10 pages of English Translation and 15 pages of Official copy).
Office Action received for Taiwanese Patent Application No. 104132636, dated Oct. 31, 2017, 10 pages (4 pages of English Translation and 6 pages of Official Copy).
Omar Romero, "Sony Smartwatch 2 Custom Watchfaces Tutorial", Retrieved From: <https://www.youtube.com/watch?v=8odbxqwSQR8>, May 1, 2014, 2 pages.
"Online Alarm Clock", available at :—https://web.archive.org/web/20150505081746/http://www.online-stopwatch.com/online-alarm-clock, May 5, 2015, 2 pages.
Partial Supplementary European Search Report received for European Patent Application No. 17810749.6, dated Apr. 25, 2019, 8 pages.
Rainmaker, "Garmin Fenix3 New Auto Climb Functionality", Available online at: https://www.youtube.com/watch?v=iuavOSNpVRc, Feb. 19, 2015, 1 page.
Razykdreviews, "In Depth Review of Apple Watch Activity and Workout App", available at <URL: https://www.youtube.com/watch?v=GkKl3qlK0ow>, May 11, 2015, 1 page.
Rizknows, "Garmin Connect Mobile App—Review #2", https://www.youtube.com/watch?v=7my3wMpeRbE, Oct. 22, 2015, 1 page.
Rizknows, "TomTom Multisport Cardio Review", Online available at :—https://www.youtube.com/watch?v=WoVCzLrSN9A, Sep. 4, 2015, 1 page.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report received for Danish Patent Application No. 201570768, dated Mar. 17, 2016, 11 pages.
Shiota, Shinji, "Windows 7 Dojo", Weekly ASCII, Ascii Mediaworks Inc., vol. 798, Aug. 31, 2010, 3 pages (Official Copy only) (see attached 37 CFR § 1.98(a) (3)).
Smith, "Garmin Fenix 5 Activity/Smart Watch Review", Online Available at :—https://www.youtube.com/watch?v=6PkQxXQxpoU, Sep. 2, 2017, 1 page.
Sportstechguides, "Garmin Fenix 5: How to Add Power Data Fields", Online Available at :—https://www.youtube.com/watch?v=ZkPptnnXEiQ, Apr. 29, 2017, 2 pages.
Sportstechguides, "Garmin Fenix 5: How To Set Up Run Alerts", Online Available at :—https://www.youtube.com/watch?v=gSMwv8vlhB4, May 13, 2017, 2 pages.
Stateoftech, "Samsung Galaxy Gear Tips—Change the Clock Face", Retrieved from: https://www.youtube.com/watch?v=GOom7AZUAjY, Dec. 11, 2013, 2 pages.
Summons to Attend Oral Proceedings received for European Patent Application No. 172061772, mailed on Jun. 3, 2019, 8 pages.
Supplemental Notice of Allowance received for U.S. Appl. No. 15/616,480, dated Mar. 28, 2019, 2 pages.
"Suunto Spartan Trainer Wrist HR 1.12", Online Available at :—https://web.archive.org/web/20180127155200/https://ns.suunto.com/Manuals/Spartan_Trainer_WristHR/Userguides/Suunto_Spartan_Trainer_WristHR_UserGuide_EN.pdf ,Jan. 17, 2018, 47 pages.
Suunto, "Suunto Spartan—Heart Rate Zones", Online Available at :—https://www.youtube.com/watch?v=aixfoCnS0OU, Mar. 19, 2018, 2 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.

"The Simply Alarm app for Pebble", available online at <https://web.archive.org/web/20150517070400>/http://www.rebootsramblings.ca/n/sahhelp/https://www.youtube.com/watch?v=IVp1scQPw08, May 17, 2015, 1 page.
TomTom, "TomTom Runner & Multi-Sport Reference Guide", Online available at :—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Tweedie, Steven, "Create and Customize Your Own Emojis with 'Makemoji' for iPhone", Available online at: http://www.businessinsider.com/create-custom-emojis-with-makemoji-app-2014-8, Aug. 19, 2014, 6 pages.
"Visual Pace Alarm app", Available Online at: https://apps.garmin.com/en-US/apps/3940f3a2-4847-4078-a911-d77422966082, Oct. 19, 2016, 1 page.
Watchophilia, "Mickey Mouse Watches", Online Available at: https://web.archive.org/web/20130929065422/https://www.watchophilia.com/photogallery/mickey-mousel, Sep. 29, 2013, 16 pages.
Watchuseek, "The watch every father needs: M-I-C-K-E-Y, M-O-U-S-E. Mickey Mouse . . . ?" Online Available at: https://forums.watchuseek.com/f2/watch-every-father-needs-m-i-c-k-e-y-m-o-u-s-e-mickey-mouse-855069.html, 2013, 3 pages.
Whitwam, Ryan, "Facer is Fast Becoming the De Facto Custom Watch Face Maker for Android Wear", Available online at: http://www.androidpolice.com/2014/09/19/facer-is-fast-becoming-the-de-facto-custom-watch-face-maker-for-android-wear, Sep. 19, 2014, 11 pages.
Xperia ZL2 SOL25, "Instruction Manual", Detailed version, KDDI Corporation, No. 1, vol. 1, Jun. 2014, 4 pages (Official Copy only) (see attached 37 CFR § 1.98(a) (3)).
Zlelik, "Garmin Fenix 5 Open Water Swimming Activity Demo", Online Available at:—https://www.youtube.com/watch?v=iSVhdvw2dcs, Jun. 9, 2017, 1 page.
Corrected Notice of Allowance received for U.S. Appl. No. 15/600,243, dated Mar. 31, 2020, 5 pages.
Non-Final Office Action received for U.S. Appl. No. 16/389,722, dated Apr. 3, 2020, 15 pages.
Notice of Allowance received for Japanese Patent Application No. 2018-537840, dated Mar. 19, 2020, 4 pages (1 page of English Translation and 3 pages of Official Copy).
Notice of Allowance received for U.S. Appl. No. 15/798,235, dated Apr. 1, 2020, 8 pages.
Office Action received for Australian Patent Application No. 2017277813, dated Mar. 20, 2020, 4 pages.
Office Action received for Australian Patent Application No. 2019208225, dated Mar. 20, 2020, 3 pages.
Supplemental Notice of Allowance received for U.S. Appl. No. 16/144,849, dated Mar. 31, 2020, 2 pages.
Applicant-Initiated Interview Summary received for U.S. Appl. No. 15/627,069, dated Nov. 4, 2019, 6 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Brief Communication regarding Oral Proceedings received for European Patent Application No. 17206177.2, mailed on Nov. 21, 2019, 5 pages.
Extended European Search Report received for European Patent Application No. 17810723.1, dated Nov. 12, 2019, 9 pages.
International Preliminary Report on Patentability received for PCT Patent Application No. PCT/US2018/032164, dated Nov. 21, 2019, 11 pages.
International Search Report and Written Opinion received for PCT Patent Application No. PCT/US2019/030770, dated Oct. 31, 2019, 23 pages.
Non-Final Office Action received for U.S. Appl. No. 15/705,849, dated Nov. 12, 2019, 15 pages.
Notice of Allowance received for Chinese Patent Application No. 201510483268.X, dated Nov. 6, 2019, 2 pages (1 page of English translation and 1 page of Official copy).
Notice of Allowance received for U.S. Appl. No. 15/355,956, dated Nov. 22, 2019, 29 pages.

(56) References Cited

OTHER PUBLICATIONS

Notice of Allowance received for U.S. Appl. No. 15/881,544, dated Nov. 7, 2019, 5 pages.
Office Action received for Korean Patent Application No. 10-2019-7029673, dated Nov. 5, 2019, 10 pages (4 pages of English Translation and 6 pages of Official Copy).
Andro Dollar, "Huawei Watch GT Always on Mode Update is finally here!", Online Available at: https://www.youtube.com/Watch?v=AJw_FIAf7v4, Jun. 6, 2019, 4 pages.
Internet Blog Post, "[PC] Pre-Customization of Black Desert's Characters", Online Available at: https://blog.naver.com/hsh6051/220209813968, Dec. 14, 2014, 41 pages (21 pages of English translation and 20 pages of Official Copy).
Zephyrnix, "Steam's In-Game Home menu", Online Available at: https://www.youtube.com/watch?v=jLoRFiPkcUw, see 0;00-1;06, Feb. 15, 2011, 3 pages.
Advisory Action received for U.S. Appl. No. 14/732,773, dated Aug. 23, 2019, 6 pages.
Corrected Notice of Allowance received for U.S. Appl. No. 15/798,257, dated Aug. 26, 2019, 2 pages.
Decision on Opposition received for Australian Patent Application No. 2015298710, mailed on Aug. 9, 2019, 4 pages.
International Search Report and Written Opinion received for PCT Patent Application No. PCT/US2019/024570, dated Aug. 8, 2019, 18 pages.
Non-Final Office Action received for U.S. Appl. No. 16/144,849, dated Sep. 17, 2019, 9 pages.
Office Action received for European Patent Application No. 17810749.6, dated Aug. 20, 2019, 9 pages.
Office Action received for Korean Patent Application No. 10-2018-7018904, dated Aug. 20, 2019, 8 pages (3 pages of English Translation and 5 pages of Official Copy).
Advisory Action received for U.S. Appl. No. 15/554,204, dated Mar. 12, 2020, 3 pages.
Applicant-Initiated Interview Summary received for U.S. Appl. No. 15/705,849, dated Feb. 14, 2020, 3 pages.
Brief Communication regarding Oral Proceedings received for European Patent Application No. 15730925.3, mailed on Feb. 18, 2020, 7 pages.
Final Office Action received for U.S. Appl. No. 15/627,069, dated Mar. 2, 2020, 22 pages.
Intention to Grant received for Danish Patent Application No. PA201770791, dated Feb. 19, 2020, 2 pages.
Intention to Grant received for European Patent Application No. 15747595.5, dated Feb. 17, 2020, 8 pages.
Intention to Grant received for European Patent Application No. 17206177.2, dated Feb. 24, 2020, 8 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Notice of Allowance received for Chinese Patent Application No. 201810105846.X, dated Feb. 18, 2020, 2 pages (1 page of English Translation and 1 page of Official Copy).
Notice of Allowance received for U.S. Appl. No. 16/144,849, dated Mar. 6, 2020, 9 pages.
Office Action received for Chinese Patent Application No. 201380081349.6, dated Jan. 16, 2020, 11 pages (6 pages of English Translation and 5 pages of Official Copy).
Office Action received for Danish Patent Application No. PA201870380, dated Mar. 5, 2020, 2 pages.
Office Action received for Japanese Patent Application No. 2018-014096, dated Jan. 6, 2020, 17 pages (8 pages of English Translation and 9 pages of Official Copy).
Office Action received for Japanese Patent Application No. 2019-162293, dated Jan. 31, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Wesley, "Apple Watch Series 1", online available at:—http://toolbox.info/blog/archives/1737-unknown.html, May 28, 2015, 5 pages (Official copy only) See Communication under 37 CFR § 1.98(a) (3).
YouTube, "Apple Watch Series 3", Online available at:—https://www.youtube.com/watch?v=iBPr9gEfkK8, Nov. 21, 2017, 15 pages (Official copy only) See Communication under 37 CFR § 1.98(a) (3).
Applicant Initiated Interview Summary received for U.S. Appl. No. 16/144,849, dated Jan. 21, 2020, 6 pages.
Applicant-Initiated Interview Summary received for U.S. Appl. No. 15/421,865, dated Feb. 3, 2020, 5 pages.
Applicant-Initiated Interview Summary received for U.S. Appl. No. 15/554,204, dated Jan. 31, 2020, 3 pages.
Applicant-Initiated Interview Summary received for U.S. Appl. No. 15/798,235, dated Feb. 3, 2020, 3 pages.
Corrected Notice of Allowance received for U.S. Appl. No. 14/732,773, dated Feb. 10, 2020, 3 pages.
Corrected Notice of Allowance received for U.S. Appl. No. 15/600,243, dated Feb. 5, 2020, 3 pages.
Final Office Action received for U.S. Appl. No. 15/405,122, dated Jan. 21, 2020, 36 pages.
Non-Final Office Action received for U.S. Appl. No. 15/608,848, dated Feb. 6, 2020, 12 pages.
Non-Final Office Action received for U.S. Appl. No. 16/144,864, dated Jan. 31, 2020, 29 pages.
Notice of Allowance received for U.S. Appl. No. 16/144,671, dated Feb. 10, 2020, 17 pages.
Office Action received for Australian Patent Application No. 2018279037, dated Jan. 17, 2020, 4 pages.
Phandroid, "New Android Wear Wrist Gestures in Marshmallow", Available online at: https://www.youtube.com/watch?v=0WhKuklpQ9A, Feb. 11, 2016, 3 pages.
Wikipedia, "Emoji", Available online at: https://en.wikipedia.org/w/index.php?title=Emoji&oldid=648831795, Feb. 25, 2015, 12 pages.
Wikipedia, "Emoticon", Available online at: https://en.wikipedia.org/w/index.php?title=Emoticon&oldid=648776142, Feb. 25, 2015, 9 pages.
Corrected Notice of Allowance received for U.S. Appl. No. 14/732,773, dated Mar. 24, 2020, 3 pages.
Corrected Notice of Allowance received for U.S. Appl. No. 15/600,243, dated Mar. 13, 2020, 3 pages.
Examiner's Answer to Appeal Brief received for U.S. Appl. No. 14/815,890, dated Mar. 20, 2020, 16 pages.
Notice of Allowance received for Japanese Patent Application No. 2017-505842, dated Mar. 16, 2020, 4 pages (1 page of English Translation and 3 pages of Official Copy).
Office Action received for Australian Patent Application No. 2019100495, dated Mar. 6, 2020, 3 pages.
Office Action received for Australian Patent Application No. 2019100495, dated Mar. 16, 2020, 3 pages.
Advisory Action received for U.S. Appl. No. 16/144,864, dated Jul. 29, 2019, 6 pages.
Decision to Grant received for Danish Patent Application No. PA201870379, dated Jul. 5, 2019, 2 pages.
Office Action received for Korean Patent Application No. 10-2018-7022101, dated Jul. 9, 2019, 10 pages (5 pages of English Translation and 5 pages of Official Copy).
Notice of Allowance received for Chinese Patent Application No. 201810037665.8, dated Jul. 9, 2019, 4 pages (1 page of English Translation and 3 pages of Official Copy).
Office Action received for Australian Patent Application No. 2018206770, dated Jul. 16, 2019, 5 pages.
Office Action received for Korean Patent Application No. 10-2017-7024570, dated Jul. 10, 2019, 6 pages (3 pages of English Translation and 3 pages of Official Copy).
Cancellation of Oral Proceedings received for European Patent Application No. 17206177.2, mailed on Dec. 4, 2019, 2 pages.
Final Office Action received for U.S. Appl. No. 15/421,865, dated Dec. 2, 2019, 19 pages.

(56) References Cited

OTHER PUBLICATIONS

International Preliminary Report on Patentability received for PCT Patent Application No. PCT/US2018/031662, dated Nov. 28, 2019, 12 pages.
Notice of Allowance received for Japanese Patent Application No. 2018-068846, dated Dec. 9, 2019, 4 pages (1 page of English Translation and 3 pages of Official Copy).
Notice of Allowance received for U.S. Appl. No. 14/732,773, dated Dec. 18, 2019, 21 pages.
Notice of Allowance received for U.S. Appl. No. 15/600,243, dated Dec. 12, 2019, 7 pages.
Office Action received for Chinese Patent Application No. 201680047983.1, dated Nov. 28, 2019, 9 pages (4 pages of English Translation and 5 pages of Official Copy).
Office Action received for Korean Patent Application No. 10-2019-7025781, dated Nov. 26, 2019, 10 pages (4 pages of English Translation and 6 pages of Official Copy).
Advisory Action received for U.S. Appl. No. 16/144,849, dated Aug. 12, 2019, 5 pages.
Certificate of Examination received for Australian Patent Application No. 2018101855, dated Aug. 6, 2019, 02 pages.
Decision on Acceptance received for Australian Patent Application No. 2015298710, dated Jul. 19, 2019, 18 pages.
Final Office Action received for U.S. Appl. No. 15/925,652, dated Aug. 1, 2019, 30 Pages.
Invitation to Pay Additional Fees and Partial International Search Report received for PCT Patent Application No. PCT/US2019/030770, dated Jul. 26, 2019, 15 pages.
Notice of Acceptance received for Australian Patent Application No. 2019201583, dated Jul. 15, 2019, 3 pages.
Notice of Allowance received for Japanese Patent Application No. 2017-545918, dated Jul. 22, 2019, 4 pages (1 page of English Translation and 3 pages of Official Copy).
Office Action received for Chinese Patent Application No. 201380081349.6, dated Jul. 15, 2019, 10 pages (5 pages of English Translation and 5 pages of Official copy).
Office Action received for Japanese Patent Application No. 2018-537840, dated Jul. 8, 2019, 15 pages (8 pages of English Translation and 7 pages of Official copy).
Supplementary European Search Report received for European Patent Application No. 17810749.6, dated Aug. 6, 2019, 6 pages.
Corrected Notice of Allowance received for U.S. Appl. No. 15/798,257, dated Jul. 9, 2019, 2 pages.
Notice of Allowance received for Chinese Patent Application No. 201510484514.3, dated Jun. 6, 2019, 2 pages (1 page of English Translation and 1 page of Official Copy).
Office Action received for Japanese Patent Application No. 2018-014096, dated May 8, 2019, 14 pages (7 pages of English Translation and 7 pages of Official Copy).
Advisory Action received for U.S. Appl. No. 14/846,511, dated Oct. 22, 2019, 5 pages.
Applicant-Initiated Interview Summary received for U.S. Appl. No. 15/554,204, dated Oct. 11, 2019, 5 pages.
Final Office Action received for U.S. Appl. No. 15/554,204, dated Oct. 31, 2019, 22 pages.
Final Office Action received for U.S. Appl. No. 15/798,235, dated Oct. 18, 2019, 25 pages.
Notice of Acceptance received for Australian Patent Application No. 2015298710, dated Oct. 8, 2019, 3 pages.
Notice of Allowance received for Chinese Patent Application No. 201580037927.5, dated Oct. 17, 2019, 3 pages (1 page of English Translation and 2 pages of Official Copy).
Notice of Allowance received for Korean Patent Application No. 10-2018-7022101, dated Oct. 14, 2019, 4 pages (1 page of English Translation and 3 pages of Official Copy).
Office Action received for Australian Patent Application No. 2018201089, dated Oct. 11, 2019, 4 pages.
Office Action received for Australian Patent Application No. 2019222943, dated Oct. 3, 2019, 3 pages.
Office Action received for Danish Patent Application No. PA201770191, dated Oct. 25, 2019, 4 pages.
Office Action received for Japanese Patent Application No. 2017-505842, dated Sep. 9, 2019, 7 pages (3 pages of English Translation and 4 pages of Official Copy).
Big Phil TV, "Gear S3 Watch faces with great always on display(A O D)", Available online at: https://www.youtube.com/watch?v=2cxMnrMiGU8, Apr. 5, 2017, 3 pages.
Cengic Suad, "Samsung Gear S3—Display Always On! Cool!", Available online at: https://www.youtube.com/watch?v=ceeDinbPwOY, Mar. 10, 2017, 3 pages.
Droid Life, "How to: Use Always-on Apps with Android Wear", Available online at: https://www.youtube.com/watch?v=_-xYB9EBTaA, Jun. 26, 2015, 3 pages.
Corrected Notice of Allowance received for U.S. Appl. No. 15/355,956, dated Jan. 3, 2020, 2 pages.
Non-Final Office Action received for U.S. Appl. No. 14/846,511 dated Jan. 7, 2020, 25 pages.
Office Action received for Chinese Patent Application No. 201810105846.X, dated Nov. 28, 2019, 9 pages (5 pages of English Translation and 4 pages of Official Copy).
Office Action received for Danish Patent Application No. PA201870378, dated Jan. 6, 2020, 3 pages.
Office Action received for European Patent Application No. 16837432.0, dated Jan. 10, 2020, 7 pages.
Office Action received for European Patent Application No. 19721883.7, dated Jan. 10, 2020, 4 pages.
Final Office Action received for U.S. Appl. No. 14/732,773, dated Jun. 21, 2019, 32 pages.
Final Office Action received for U.S. Appl. No. 15/608,848, dated Jun. 26, 2019, 27 pages.
Non-Final Office Action received for U.S. Appl. No. 15/600,243, dated Jun. 27, 2019, 17 Pages.
Non-Final Office Action received for U.S. Appl. No. 15/627,069, dated Jun. 21, 2019, 22 pages.
Notice of Allowance received for U.S. Appl. No. 15/881,544, dated Jun. 26, 2019, 6 pages.
Office Action received for Australian Patent Application No. 2017277813, dated Jun. 11, 2019, 3 pages.
Office Action received for Australian Patent Application No. 2018279037, dated Jun. 18, 2019, 5 pages.
Office Action received for Danish Patent Application No. PA201770791, dated Jun. 11, 2019, 3 pages.
Applicant-Initiated Interview Summary received for U.S. Appl. No. 15/405,122, dated Dec. 22, 2020, 5 pages.
Applicant-Initiated Interview Summary received for U.S. Appl. No. 15/421,865, dated Dec. 15, 2020, 6 pages.
Applicant-Initiated Interview Summary received for U.S. Appl. No. 16/138,809, dated Dec. 16, 2020, 7 pages.
Final Office Action received for U.S. Appl. No. 16/389,722, dated Dec. 8, 2020, 18 pages.
Non-Final Office Action received for U.S. Appl. No. 16/401,934, dated Dec. 11, 2020, 26 pages.
Non-Final Office Action received for U.S. Appl. No. 16/820,383, dated Dec. 14, 2020, 11 pages.
Non-Final Office Action received for U.S. Appl. No. 16/997,588, dated Dec. 14, 2020, 21 pages.
Non-Final Office Action received for U.S. Appl. No. 17/031,859, dated Dec. 15, 2020, 13 pages.
Office Action received for Australian Patent Application No. 2020102158, dated Dec. 8, 2020, 9 pages.
Office Action received for Australian Patent Application No. 2020204506, dated Dec. 7, 2020, 6 pages.
Office Action received for Danish Patent Application No. PA202070609, dated Dec. 10, 2020, 8 pages.
Office Action received for European Patent Application No. 16762356.0, dated Dec. 11, 2020, 7 pages.
Office Action received for Korean Patent Application No. 10-2020-7026036, dated Dec. 7, 2020, 8 pages (3 pages of English Translation and 5 pages of Official Copy).
Result of Consultation received for European Patent Application No. 17810749.6, mailed on Dec. 15, 2020, 3 pages.

(56) References Cited

OTHER PUBLICATIONS

Singh Lovepreet, "Samsung Galaxy Watch: How to Change Watch Face—Tips and Tricks", Online available at: <https://www.youtube.com/watch?pp=desktop&v=IN7gPxTZ1qU>, Retrieved on Dec. 10, 2020, Dec. 4, 2018, 1 page.
Vids Tube,"Bitmoji Clockface on Fitbit Versa Sense/Versa 3/Versa 2", Available online at: <https://www.youtube.com/watch?v=4V_xDnSLeHE>, Retrieved on Dec. 3, 2020, Jun. 30, 2019, 1 page.
Woolsey Amanda, "How to Customize the Clock on the Apple Watch", Available online at: <https://www.youtube.com/watch?v=t-3Bckdd9B4>, Retrieved on Dec. 11, 2020, Apr. 25, 2015, 1 page.
Advisory Action received for U.S. Appl. No. 16/144,864, dated Jul. 6, 2020, 6 pages.
Applicant Initiated Interview Summary received for U.S. Appl. No. 16/389,722, dated Jul. 7, 2020, 5 pages.
Applicant-Initiated Interview Summary received for U.S. Appl. No. 15/705,849, dated Jun. 29, 2020, 3 pages.
Applicant-Initiated Interview Summary received for U.S. Appl. No. 16/144,864, dated Jun. 22, 2020, 3 pages.
Notice of Acceptance received for Australian Patent Application No. 2017277813, dated Jun. 16, 2020, 3 pages.
Notice of Allowance received for Japanese Patent Application No. 2019-096219, dated Jun. 26, 2020, 4 pages (1 page of English Translation and 3 pages of Official Copy).
Office Action Received for Danish Patent Application No. PA201670656, dated Jul. 1, 2020, 4 pages.
Office Action received for Japanese Patent Application No. 2019-044107, dated May 29, 2020, 6 pages (3 pages of English Translation and 3 pages of Official Copy).
Applicant-Initiated Interview Summary received for U.S. Appl. No. 15/405,122, dated May 21, 2020, 5 pages.
Final Office Action received for U.S. Appl. No. 16/144,864, dated May 28, 2020, 29 pages.
Intention to Grant received for European Patent Application No. 15730925.3, dated May 28, 2020, 10 pages.
Minutes of the Oral Proceedings received for European Patent Application No. 15730925.3, mailed on May 26, 2020, 11 pages.
Non-Final Office Action received for U.S. Appl. No. 15/627,069, dated May 26, 2020, 25 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Notice of Acceptance received for Australian Patent Application No. 2018279037, dated May 13, 2020, 3 pages.
Office Action received for Chinese Patent Application No. 201510479088.4, dated Apr. 22, 2020, 7 pages (3 pages of English Translation and 4 pages of Official Copy).
Office Action received for European Patent Application No. 19721883.7, dated May 28, 2020, 11 pages.
Applicant Initiated Interview Summary received for U.S. Appl. No. 16/582,020, dated Jul. 14, 2020, 5 pages.
Applicant-Initiated Interview Summary received for U.S. Appl. No. 15/627,069, dated Jul. 20, 2020, 5 pages.
Decision to Grant received for Danish Patent Application No. PA201770791, dated Jul. 7, 2020, 2 pages.
Decision to Grant received for European Patent Application No. 15747595.5, dated Jul. 16, 2020, 2 pages.
Notice of Allowance received for Korean Patent Application No. 10-2018-7018904, dated Jun. 26, 2020, 4 pages (1 page of English Translation and 3 pages of Official copy).
Notice of Allowance received for U.S. Appl. No. 15/554,204, dated Jul. 13, 2020, 10 pages.
Notice of Allowance received for U.S. Appl. No. 16/144,735, dated Jul. 21, 2020, 13 pages.
Notice of Allowance received for U.S. Appl. No. 16/585,399, dated Jul. 21, 2020, 9 pages.
Office Action received for Australian Patent Application No. 2018268972, dated Jul. 9, 2020, 4 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Board Decision received for Chinese Patent Application No. 201380081349.6, mailed on Nov. 23, 2020, 2 pages (1 page of English Translation and 1 page of Official Copy).
Intention to Grant Received for Danish Patent Application No. PA201970596, dated Dec. 1, 2020, 2 pages.
International Search Report and Written Opinion received for PCT Patent Application No. PCT/US2020/035199, dated Oct. 30, 2020, 20 pages.
Invitation to Pay Additional Fees received for PCT Patent Application No. PCT/US2020/035199, dated Sep. 8, 2020, 12 pages.
Non-Final Office Action received for U.S. Appl. No. 16/861,651, dated Nov. 27, 2020, 11 pages.
Notice of Allowance received for U.S. Appl. No. 16/144,753, dated Dec. 4, 2020, 22 pages.
Record of Oral Hearing received for U.S. Appl. No. 14/815,890, mailed on Nov. 20, 2020, 18 pages.
Result of Consultation received for European Patent Application No. 18154145.9, mailed on Nov. 30, 2020, 17 pages.
Result of Consultation received for European Patent Application No. 15730925.3, mailed on Nov. 24, 2020, 4 pages.
Applicant Initiated Interview Summary received for U.S. Appl. No. 16/144,735, dated Jun. 18, 2020, 3 pages.
Applicant Initiated Interview Summary received for U.S. Appl. No. 16/144,753, dated Jun. 18, 2020, 3 pages.
Applicant-Initiated Interview Summary received for U.S. Appl. No. 16/138,809, dated Jun. 9, 2020, 4 pages.
Office Action received for Australian Patent Application No. 2017277971, dated Jun. 3, 2020, 3 pages.
Applicant-Initiated Interview Summary received for U.S. Appl. No. 16/659,507, dated Nov. 17, 2020, 3 pages.
Decision on Appeal received for U.S. Appl. No. 14/815,890, mailed on Nov. 24, 2020, 13 pages.
International Preliminary Report on Patentability received for PCT Patent Application No. PCT/US2019/024570, dated Nov. 19, 2020, 10 pages.
International Preliminary Report on Patentability received for PCT Patent Application No. PCT/US2019/030770, dated Nov. 19, 2020, 14 pages.
International Search Report and Written Opinion received for PCT Patent Application No. PCT/US2020/031536, dated Sep. 23, 2020, 16 pages.
International Search Report and Written Opinion received for PCT Patent Application No. PCT/US2020/031575, dated Aug. 20, 2020, 14 pages.
Invitation to Pay Additional Fees received for PCT Patent Application No. PCT/US2020/031536, dated Jul. 31, 2020, 9 pages.
Invitation to Pay Additional Fees received for PCT Patent Application No. PCT/US2020/045814, dated Nov. 18, 2020, 11 pages.
Notice of Allowance received for U.S. Appl. No. 15/925,652, dated Nov. 20, 2020, 9 pages.
Notice of Allowance received for U.S. Appl. No. 16/584,281, dated Nov. 18, 2020, 8 pages.
Office Action received for Chinese Patent Application No. 201710439448.7, dated Oct. 10, 2020, 19 pages (8 pages of English Translation and 11 pages of Official Copy).
Office Action received for European Patent Application No. 20182116.2, dated Nov. 6, 2020, 9 pages.
Advisory Action received for U.S. Appl. No. 16/582,020, dated Aug. 3, 2020, 4 pages.
European Search Report received for European Patent Application No. 20172197.4, dated Jul. 28, 2020, 4 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Australian Patent Application No. 2018201089, dated Jul. 23, 2020, 4 pages.

(56) References Cited

OTHER PUBLICATIONS

Office Action received for Chinese Patent Application No. 201680047983.1, dated Jul. 1, 2020, 6 pages (3 pages of English Translation and 3 pages of Official Copy).
Decision to Grant received for European Patent Application No. 17206177.2, dated Aug. 6, 2020, 2 pages.
Final Office Action received for U.S. Appl. No. 14/846,511, dated Aug. 11, 2020, 25 pages.
Invitation to Pay Additional Fees received for PCT Patent Application No. PCT/US2020/030079, dated Jul. 14, 2020, 12 pages.
Non-Final Office Action received for U.S. Appl. No. 15/925,652, dated Aug. 7, 2020, 39 pages.
Corrected Notice of Allowance received for U.S. Appl. No. 15/554,204, dated Aug. 19, 2020, 3 pages.
Office Action received for Australian Patent Application No. 2019250251, dated Aug. 6, 2020, 3 pages.
Office Action received for European Patent Application No. 20172197.4, dated Aug. 5, 2020, 6 pages.
Summons to Attend Oral Proceedings received for European Patent Application No. 17810749.6, mailed on Aug. 12, 2020, 11 pages.
Advisory Action received for U.S. Appl. No. 15/421,865, dated Apr. 16, 2020, 7 pages.
Android Tips, "Create a Minimal Lock Screen with Widget Locker", Online Available at: http://appstap192.blogspot.com/2012/01/create-minimal-lock-screen-with.html, Jan. 18, 2012, 6 pages.
AOD too dim. I've answered my own question to help others, Online Available: https://forums.androidcentral.com/samsung-galaxy-s9-s9-plus/874444-aod-too-dim-ive-answered-my-own-question-help-others.html, Mar. 11, 2018, 3 pages.
Applicant Initiated Interview Summary received for U.S. Appl. No. 14/846,511, dated Apr. 20, 2020, 4 pages.
Applicant Initiated Interview Summary received for U.S. Appl. No. 16/144,864, dated Apr. 29, 2020, 4 pages.
Applicant Initiated Interview Summary received for U.S. Appl. No. 16/582,020, dated Mar. 25, 2020, 5 pages.
Applicant Initiated Interview Summary received for U.S. Appl. No. 16/585,399, dated Mar. 25, 2020, 3 pages.
Brightness on lock screen, Online Available at: https://www.reddit.com/r/galaxys10/comments/b4d5fb/brightness_on_lock_screen/, 2019, 1 page.
Dan, "Get This Look: 'Minimal' Zooper Widget", Online Available at: https://www.androidguys.com/featured/customize/get-look-minimal-zooper-widget/, Mar. 7, 2014, 2 pages.
Final Office Action received for U.S. Appl. No. 16/582,020, dated Apr. 28, 2020, 31 pages.
Looking for a launcher that changes the default home screen or widgets based on Wi-Fi, location, or other context., Online Available at: https://www.reddit.com/r/androidapps/comments/35lu90/looking_for_a_launcher_that_changes_the_default/, 2015, 2 pages.
Non-Final Office Action received for U.S. Appl. No. 16/582,020, dated Jan. 13, 2020, 39 pages.
Non-Final Office Action received for U.S. Appl. No. 16/585,399, dated Jan. 23, 2020, 28 pages.
Notice of Allowance received for U.S. Appl. No. 16/144,849, dated Apr. 17, 2020, 2 pages.
Notice of Allowance received for U.S. Appl. No. 16/585,366, dated Jan. 2, 2020, 6 pages.
Nova Launcher—Lock Screen Edit, Online Available at: https://forums.androidcentral.com/ask-question/835057-nova-launcher-lock-screen-edit.html, Sep. 2017, 2 pages.
Office Action received for Chinese Patent Application No. 201710439448.7, dated Mar. 27, 2020, 13 pages (7 pages of English Translation and 6 pages of Official Copy).
Wade Cliff, "Get the most out of Nova Launcher: Changing Icon Sizes", Online Available at: https://www.androidguys.com/tips-tools/get-nova-launcher-changing-icon-sizes/, Nov. 16, 2015, 3 pages.
Wade, Cliff, "Get the most out of Nova Launcher: Customizing the Dock (Contest Included)", Online Available at: https://www.androidguys.com/tips-tools/get-nova-launcher-customizing-dockcontest-included/, Dec. 1, 2015, 5 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
Non-Final Office Action received for U.S. Appl. No. 15/421,865, dated Oct. 7, 2020, 20 pages.
Non-Final Office Action received for U.S. Appl. No. 16/659,507, dated Oct. 7, 2020, 16 pages.
Non-Final Office Action received for U.S. Appl. No. 16/894,309, dated Oct. 15, 2020, 24 pages.
Notice of Allowance received for U.S. Appl. No. 15/705,849, dated Oct. 16, 2020, 14 pages.
Notice of Allowance received for U.S. Appl. No. 16/556,023, dated Oct. 15, 2020, 8 pages.
Office Action received for Japanese Patent Application No. 2020-074878, dated Sep. 7, 2020, 13 pages (7 pages of English Translation and 6 pages of Official Copy).
Result of Consultation received for European Patent Application No. 19721883.7, mailed on Oct. 7, 2020, 3 pages.
Barbosa Jonathan, "Weather Clock 2.1 for Android", APKPure, Online Available at: https://apkpure.com/weather-clock/com.urbandroid.wclock, Oct. 15, 2015, 3 pages.
Elecont,"Weather clock—hourly forecast description", Accurate 10-day weather forecast, NOAA radar and satellite, buoy, Elecont LLC Forums, Online Available at: https://www.tapatalk.com/groups/elecontfr/weather-clock-hourly-forecast-description-t427.html, Dec. 1, 2011, 5 pages.
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Korean Patent Application No. 10-2019-7025538, dated Aug. 15, 2020, 8 pages (4 pages of English Translation and 4 pages of Official Copy).
Supplemental Notice of Allowance received for U.S. Appl. No. 16/585,399, dated Aug. 26, 2020, 2 pages.
International Search Report and Written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2019-7029673, dated Sep. 3, 2020, 9 pages (4 pages of English Translation and 5 pages of Official Copy).
Phlam, Dev, "Clockwork Tomato Presentation", Online available at: https://www.youtube.com/watch?v=2IQDx9REn0E, Apr. 29, 2016, 6 pages.

(56) References Cited

OTHER PUBLICATIONS

Result of Consultation received for European Patent Application No. 18154145.9, mailed on Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Final Office Action received for U.S. Appl. No. 16/144,753, dated Sep. 22, 2020, 9 pages.
International Search Report and Written Opinion received for PCT Patent Application No. PCT/US2020/030079, dated Sep. 4, 2020, 18 pages.
Notice of Allowance received for U.S. Appl. No. 15/798,235, dated Sep. 22, 2020, 8 pages.
Summons to Attend Oral Proceedings received for European Patent Application No. 18154145.9, mailed on Sep. 17, 2020, 11 pages.
Non-Final Office Action received for U.S. Appl. No. 15/405,122, dated Sep. 24, 2020, 30 pages.
Notice of Allowance received for U.S. Appl. No. 16/144,864, dated Sep. 29, 2020, 2 pages.
Office Action received for Korean Patent Application No. 10-2020-7001340, dated Sep. 24, 2020, 19 pages (8 pages of English Translation and 11 pages of Official Copy).
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
Bagala et al., "Evaluation of Accelerometer-Based Fall Detection Algorithms on Real-World Falls", PloS ONE, vol. 7, No. 5, May 16, 2012, 9 pages.
Extended European Search Report received for European Patent Application No. 20185974.1, dated Oct. 28, 2020, 7 pages.
Notice of Allowance received for U.S. Appl. No. 16/585,721, dated Oct. 30, 2020, 9 pages.
Office Action received for Danish Patent Application No. PA201970597, dated Oct. 29, 2020, 4 pages.
Office Action received for Japanese Patent Application No. 2019-151358, dated Oct. 2, 2020, 5 pages (2 pages of English Translation and 3 pages of Official Copy).
Office Action received for Korean Patent Application No. 10-2019-7025781, dated Oct. 30, 2020, 10 pages (4 pages of English Translation and 6 pages of Official Copy).
Applicant Initiated Interview Summary received for U.S. Appl. No. 15/608,848, dated May 12, 2020, 5 pages.
Final Office Action received for U.S. Appl. No. 15/705,849, dated May 1, 2020, 17 pages.
Final Office Action received for U.S. Appl. No. 16/144,735, dated May 4, 2020, 12 pages.
Notice of Acceptance received for Australian Patent Application No. 2019222943, dated May 5, 2020, 3 pages.
Office Action received for Chinese Patent Application No. 201680013193.1, dated Mar. 25, 2020, 21 pages (8 pages of English Translation and 13 pages of Official Copy).
Applicant Initiated Interview Summary received for U.S. Appl. No. 15/608,848, dated Oct. 26, 2020, 3 pages.
Applicant Initiated Interview Summary received for U.S. Appl. No. 16/584,445, dated Mar. 17, 2020, 5 pages.
Applicant-Initiated Interview Summary received for U.S. Appl. No. 16/584,281, dated Mar. 9, 2020, 5 pages.
Applicant-Initiated Interview Summary received for U.S. Appl. No. 16/584,281, dated Sep. 14, 2020, 6 pages.
Applicant-Initiated Interview Summary received for U.S. Appl. No. 16/585,714, dated Jul. 20, 2020, 5 pages.
Applicant-Initiated Interview Summary received for U.S. Appl. No. 16/585,721, dated Aug. 31, 2020, 5 pages.
Applicant-Initiated Interview Summary received for U.S. Appl. No. 16/585,721, dated Mar. 13, 2020, 5 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
Final Office Action received for U.S. Appl. No. 16/584,281, dated Apr. 15, 2020, 26 pages.
Final Office Action received for U.S. Appl. No. 16/585,721, dated Apr. 1, 2020, 28 pages.
Non-Final Office Action received for U.S. Appl. No. 16/584,281, dated Dec. 10, 2019, 23 pages.
Non-Final Office Action received for U.S. Appl. No. 16/584,445, dated Dec. 26, 2019, 19 pages.
Non-Final Office Action received for U.S. Appl. No. 16/585,714, dated Apr. 16, 2020, 18 pages.
Non-Final Office Action received for U.S. Appl. No. 16/585,721, dated Dec. 27, 2019, 25 pages.
Notice of Allowance received for U.S. Appl. No. 16/144,735, dated Oct. 28, 2020, 13 pages.
Notice of Allowance received for U.S. Appl. No. 16/584,281, dated Sep. 29, 2020, 5 pages.
Notice of Allowance received for U.S. Appl. No. 16/584,445, dated Apr. 17, 2020, 9 pages.
Notice of Allowance received for U.S. Appl. No. 16/584,445, dated Jul. 23, 2020, 8 pages.
Notice of Allowance received for U.S. Appl. No. 16/584,445, dated Jun. 24, 2020, 5 pages.
Notice of Allowance received for U.S. Appl. No. 16/584,445, dated May 29, 2020, 5 pages.
Notice of Allowance received for U.S. Appl. No. 16/584,445, dated Oct. 21, 2020, 6 pages.
Notice of Allowance received for U.S. Appl. No. 16/585,714, dated Sep. 25, 2020, 15 pages.
Notice of Allowance received for U.S. Appl. No. 16/585,721, dated Sep. 30, 2020, 15 pages.
Office Action and Search Report received for Danish Patent Application No. PA201970598, dated Jan. 28, 2020, 6 pages.
Office Action received for Chinese Patent Application No. 201680013193.1, dated Sep. 7, 2020, 6 pages (3 pages of English Translation and 3 pages of Official Copy).
Office Action received for Chinese Patent Application No. 201910906898.1, dated Sep. 9, 2020, 8 pages (3 pages of English Translation and 5 pages of Official Copy).
Office Action received for Danish Patent Application No. PA201970596, dated May 6, 2020, 4 pages.
Office Action received for Danish Patent Application No. PA201970598, dated Oct. 9, 2020, 4 pages.
Office Action received for Danish Patent Application No. PA201970599, dated Jan. 23, 2020, 6 pages.
Office Action received for Danish Patent Application No. PA201970599, dated May 27, 2020, 4 pages.
Office Action received for Japanese Patent Application No. 2020-104679, dated Sep. 18, 2020, 13 pages (7 pages of English Translation and 6 pages of Official Copy).
Search Report and Opinion received for Danish Patent Application No. PA201970596, dated Dec. 4, 2019, 11 pages.
Search Report and Opinion received for Danish Patent Application No. PA201970597, dated Dec. 18, 2019, 10 pages.
Search Report and Opinion received for Danish Patent Application No. PA201970598, dated Oct. 31, 2019, 9 pages.
Search Report and Opinion received for Danish Patent Application No. PA201970599, dated Nov. 8, 2019, 12 pages.
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Applicant-Initiated Interview Summary received for U.S. Appl. No. 17/041,350, dated Aug. 18, 2021, 2 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.

(56) References Cited

OTHER PUBLICATIONS

Corrected Notice of Allowance received for U.S. Appl. No. 16/582,020, dated Aug. 11, 2021, 2 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Final Office Action received for U.S. Appl. No. 17/030,321, dated Apr. 2, 2021, 28 pages.
Final Office Action received for U.S. Appl. No. 17/192,161, dated Aug. 16, 2021, 22 pages.
"Gym Book—Strength Training Planner, Logger and Analyzer", GymBookApp, Available Online at: https://web.archive.org/web/20160401104508/https://gymbookapp.com/, Apr. 1, 2016, 10 pages.
Intention to Grant received for European Patent Application No. 15730925.3, dated Aug. 16, 2021, 10 pages.
Invitation to Pay Additional Fees received for PCT Patent Application No. PCT/US2021/017736, dated Jun. 15, 2021, 14 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Notice of Acceptance received for Australian Patent Application No. 2020256383, dated Aug. 3, 2021, 3 pages.
Notice of Allowance received for Korean Patent Application No. 10-2019-7029673, dated Aug. 3, 2021, 3 pages (1 page of English Translation and 2 pages of Official Copy).
Notice of Allowance received for Korean Patent Application No. 10-2021-7013453, dated Aug. 11, 2021, 5 pages (2 pages of English Translation and 3 pages of Official Copy).
Notice of Allowance received for Korean Patent Application No. 10-2021-7013454, dated Aug. 12, 2021, 4 pages (1 page of English Translation and 3 pages of Official Copy).
Notice of Allowance received for U.S. Appl. No. 15/608,848, dated Aug. 25, 2021, 9 pages.
Notice of Allowance received for U.S. Appl. No. 16/867,002, dated Aug. 20, 2021, 12 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for Chinese Patent Application No. 201780034203.4, dated Jul. 14, 2021, 12 pages (5 pages of English Translation and 7 pages of Official Copy).
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Applicant Initiated Interview Summary received for U.S. Appl. No. 16/582,020, dated Jul. 9, 2021, 4 pages.
Applicant-Initiated Interview Summary received for U.S. Appl. No. 15/405,122, dated Jul. 7, 2021, 4 pages.
Applicant-Initiated Interview Summary received for U.S. Appl. No. 17/031,654, dated Feb. 1, 2021, 2 pages.
European Search Report received for European Patent Application No. 21168916.1, dated Jul. 14, 2021, 5 pages.
Non-Final Office Action received for U.S. Appl. No. 17/031,654, dated Nov. 19, 2020, 12 pages.
Non-Final Office Action received for U.S. Appl. No. 17/031,671, dated Apr. 30, 2021, 27 pages.
Non-Final Office Action received for U.S. Appl. No. 17/031,765, dated Jun. 28, 2021, 32 pages.
Non-Final Office Action received for U.S. Appl. No. 17/068,386, dated Jul. 15, 2021, 16 pages.
Notice of Acceptance received for Australian Patent Application No. 2020239670, dated Jul. 2, 2021, 3 pages.
Notice of Acceptance received for Australian Patent Application No. 2020309093, dated Jul. 8, 2021, 3 pages.
Notice of Allowance received for Chinese Patent Application No. 201780033973.7, dated Jul. 7, 2021, 5 pages (1 page of English Translation and 4 pages of Official Copy).
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Notice of Allowance received for U.S. Appl. No. 17/031,654, dated Feb. 10, 2021, 9 pages.
Notice of Allowance received for U.S. Appl. No. 17/031,654, dated May 27, 2021, 8 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Office Action received for Danish Patent Application No. PA202070624, dated Jun. 16, 2021, 5 pages.
Office Action received for Danish Patent Application No. PA202070625, dated Jun. 16, 2021, 3 pages.
Office Action received for European Patent Application No. 17810723.1, dated Jul. 9, 2021, 8 pages.
Office Action received for European Patent Application No. 20172197.4, dated Jul. 8, 2021, 5 pages.
Office Action received for Korean Patent Application No. 10-2020-7028759, dated Jun. 29, 2021, 12 pages (5 pages of English Translation and 7 pages of Official Copy).
Search Report and Opinion received for Danish Patent Application No. PA202070623, dated Dec. 21, 2020, 9 pages.
Search Report and Opinion received for Danish Patent Application No. PA202070624, dated Dec. 10, 2020, 10 pages.
Search Report and Opinion received for Danish Patent Application No. PA202070625, dated Dec. 17, 2020, 9 pages.
Supplemental Notice of Allowance received for U.S. Appl. No. 15/627,069, dated Jul. 12, 2021, 2 pages.
Applicant Initiated Interview Summary received for U.S. Appl. No. 17/031,671, dated Aug. 2, 2021, 5 pages.
Applicant-Initiated Interview Summary received for U.S. Appl. No. 16/888,629, dated Aug. 4, 2021, 5 pages.
Invitation to Pay Additional Fees received for PCT Patent Application No. PCT/US2021/031212, dated Jul. 28, 2021, 19 pages.
Non-Final Office Action received for U.S. Appl. No. 16/994,352, dated Jul. 30, 2021, 11 pages.
Notice of Acceptance received for Australian Patent Application No. 2021202834, dated Jul. 15, 2021, 3 pages.
Notice of Allowance received for Japanese Patent Application No. 2020-000492, dated Jul. 16, 2021, 4 pages (1 page of English Translation and 3 pages of Official Copy).
Notice of Allowance received for Korean Patent Application No. 10-2020-7026036, dated Jul. 26, 2021, 4 pages (1 page of English Translation and 3 pages of Official Copy).
Notice of Allowance received for U.S. Appl. No. 16/582,020, dated Jul. 27, 2021, 29 pages.
Office Action received for Australian Patent Application No. 2020239749, dated Jul. 16, 2021, 5 pages.
Office Action received for Chinese Patent Application No. 201910906898.1, dated Jun. 23, 2021, 6 pages (3 pages of English Translation and 3 pages of Official Copy).

(56) References Cited

OTHER PUBLICATIONS

Office Action received for Chinese Patent Application No. 201680047983.1, dated Feb. 1, 2021, 6 pages (3 pages of English Translation and 3 pages of Official Copy).
Certificate of Examination received for Australian Patent Application No. 2020102158, dated Jun. 8, 2021, 2 pages.
Corrected Notice of Allowance received for U.S. Appl. No. 16/378,136, dated Jun. 11, 2021, 2 pages.
Examiner's Answer to Appeal Brief received for U.S. Appl. No. 14/846,511, dated Jun. 14, 2021, 15 pages.
Final Office Action received for U.S. Appl. No. 16/401,934, dated Jun. 14, 2021, 30 pages.
Jean, "Our Pact Parental Control Review", Available online at: https://www.bewebsmart.com/parental-controls/our-pact-parental-control-review/, Jun. 25, 2016, 25 pages.
Non-Final Office Action received for U.S. Appl. No. 17/041,350, dated Jun. 10, 2021, 24 pages.
Notice of Acceptance received for Australian Patent Application No. 2018201089, dated May 28, 2021, 3 pages.
Notice of Allowance received for U.S. Appl. No. 15/627,069, dated Jun. 17, 2021, 14 pages.
Office Action received for Australian Patent Application No. 2020256383, dated Jun. 4, 2021, 3 pages.
Office Action received for European Patent Application No. 19721883.7, dated Jun. 15, 2021, 9 pages.
Office Action received for Korean Patent Application No. 10-2021-7013453, dated Jun. 5, 2021, 6 pages (2 pages of English Translation and 4 pages of Official Copy).
Office Action received for Korean Patent Application No. 10-2021-7013454, dated Jun. 5, 2021, 6 pages (2 pages of English Translation and 4 pages of Official Copy).
Applicant-Initiated Interview Summary received for U.S. Appl. No. 16/935,002, dated Sep. 21, 2021, 4 pages.
Applicant-Initiated Interview Summary received for U.S. Appl. No. 17/031,765, dated Sep. 22, 2021, 5 pages.
Applicant-Initiated Interview Summary received for U.S. Appl. No. 17/068,386, dated Sep. 21, 2021, 2 pages.
Final Office Action received for U.S. Appl. No. 17/041,350, dated Sep. 17, 2021, 25 pages.
Notice of Allowance received for U.S. Appl. No. 16/377,892, dated Sep. 9, 2021, 9 pages.
Notice of Allowance received for U.S. Appl. No. 16/378,136, dated Sep. 22, 2021, 7 pages.
Office Action received for Australian Patent Application No. 2020239743, dated Sep. 3, 2021, 4 pages.
Office Action received for Japanese Patent Application No. 2019-044107, dated Jul. 30, 2021, 9 pages (5 pages of English Translation and 4 pages of Official Copy).
Office Action received for Korean Patent Application No. 10-2021-7026284, dated Aug. 31, 2021, 10 pages (4 pages of English Translation and 6 pages of Official Copy).
Supplemental Notice of Allowance received for U.S. Appl. No. 16/867,002, dated Sep. 9, 2021, 2 pages.
Applicant-Initiated Interview Summary received for U.S. Appl. No. 16/389,722, dated Sep. 7, 2021, 4 pages.
Applicant-Initiated Interview Summary received for U.S. Appl. No. 16/861,651, dated Sep. 3, 2021, 5 pages.
Applicant-Initiated Interview Summary received for U.S. Appl. No. 16/943,737, dated Sep. 7, 2021, 4 pages.
Communication of the Board of Appeal received for European Patent Application No. 15771747.1, mailed on Aug. 25, 2021, 9 pages.
Decision to Grant received for Danish Patent Application No. PA201970597, dated Aug. 19, 2021, 2 pages.
Final Office Action received for U.S. Appl. No. 17/031,671, dated Sep. 7, 2021, 27 pages.
Notice of Allowance received for Japanese Patent Application No. 2019-563407, dated Aug. 20, 2021, 4 pages (1 page of English Translation and 3 pages of Official Copy).
Notice of Allowance received for Korean Patent Application No. 10-2020-7026035, dated Aug. 23, 2021, 4 pages (2 page of English Translation and 2 pages of Official Copy).
Office Action received for Australian Patent Application No. 2020239748, dated Sep. 1, 2021, 4 pages.
Office Action received for Danish Patent Application No. PA202070623, dated Aug. 24, 2021, 3 pages.
Office Action received for European Patent Application No. 21168916.1, dated Aug. 23, 2021, 8 pages.
Applicant-Initiated Interview Summary received for U.S. Appl. No. 16/997,588, dated May 12, 2021, 2 pages.
Decision to Grant received for Danish Patent Application No. PA202070609, dated May 3, 2021, 2 pages.
Non-Final Office Action received for U.S. Appl. No. 17/192,161, dated May 13, 2021, 28 pages.
Notice of Allowance received for Chinese Patent Application No. 201680013193.1, dated May 7, 2021, 5 pages (1 page of English Translation and 4 pages of Official Copy).
Notice of Allowance received for Chinese Patent Application No. 201680047983.1, dated Apr. 28, 2021, 3 pages (1 page of English Translation and 2 pages of Official Copy).
Notice of Allowance received for Korean Patent Application No. 10-2020-7001340, dated May 10, 2021, 5 pages (2 pages of English Translation and 3 pages of Official Copy).
Office Action received for Australian Patent Application No. 2020102158, dated Apr. 27, 2021, 5 pages.
Summons to Attend Oral Proceedings received for European Patent Application No. 16762356.0, mailed on May 10, 2021, 10 pages.
Summons to Oral Proceedings received for European Patent Application No. 15771747.1, mailed on Apr. 29, 2021, 8 pages.
Office Action received for European Patent Application No. 16837432.0, dated Jan. 27, 2021, 7 pages.
2RaZ Tech&Moto, "Sony Smartwatch 2 update—new feartures and watchface creator NEW!!!", Online available on:—https://www.youtube.com/watch?v=k3jjBv7QZSk, May 8, 2014, 3 pages.
Decision on Acceptance received for Australian Patent Application No. 2018201089, dated Apr. 20, 2021, 28 pages.
Final Office Action received for U.S. Appl. No. 16/861,651, dated Apr. 20, 2021, 14 pages.
Intention to Grant received for Danish Patent Application No. PA201970597, dated Apr. 20, 2021, 2 pages.
Office Action received for Danish Patent Application No. PA201970598, dated Apr. 15, 2021, 6 pages.
Office Action received for Danish Patent Application No. PA202170113, dated Apr. 15, 2021, 2 pages.
Rowinski Dan, "Why the All-In-One Smartwatch Isn't Happening Any Time Soon", Online available at:—https://web.archive.org/web/20140123074218if_/https://readwrite.com/2014/01/20/smartwatch-wearable-fitness-remote-control/, Jan. 20, 2014, 6 pages.
StateOfTech,"Samsung Galaxy Gear Tips—Installing and Customizing Clock Faces", Online available at:—https://www.youtube.com/watch?v=p2GzpL3xlUo, Dec. 12, 2013, 3 pages.
Techcloud,"How to Create Custom Watch Face for Samsung Galaxy Gear Smartwatch just in Few Seconds", Online available at:—https://www.youtube.com/watch?v=6rO-_SREDjQ, Oct. 9, 2013, 3 pages.
Theunlockr,"How to Change the Watch Face on the Galaxy Gear", Online available at:—https://www.youtube.com/watch7v-Z7EBG5aBiZg, Jan. 3, 2014, 3 pages.
Adeniyi, Samuel, "How to connect a second PS4 controller to a PlayStation 4 console", Online available on:—https://www.youtube.com/watch?v=mOZX_SrNISE, May 28, 2017, 2 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Advisory Action received for U.S. Appl. No. 16/389,722, dated Mar. 9, 2021, 5 pages.
Allison, Conor, "Working out with Fiit's wearable-powered boutique fitness classes", Online available at:—<https://www.wareable.com/wearable-tech/fiit-fitness-classes-review-3849>, May 14, 2018, 8 pages.

(56) References Cited

OTHER PUBLICATIONS

Applicant Initiated Interview Summary received for U.S. Appl. No. 15/608,848, dated Apr. 13, 2021, 4 pages.
Applicant Initiated Interview Summary received for U.S. Appl. No. 16/894,309, dated Jan. 26, 2021, 3 pages.
Applicant-Initiated Interview Summary received for U.S. Appl. No. 15/627,069, dated Jan. 22, 2021, 4 pages.
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/389,722, dated Feb. 11, 2021, 4 pages.
Applicant-Initiated Interview Summary received for U.S. Appl. No. 16/401,934, dated Feb. 23, 2021, 8 pages.
Applicant-Initiated Interview Summary received for U.S. Appl. No. 16/820,383, dated Mar. 11, 2021, 2 pages.
Applicant-Initiated Interview Summary received for U.S. Appl. No. 16/861,651, dated Mar. 25, 2021, 6 pages.
Applicant-Initiated Interview Summary received for U.S. Appl. No. 16/997,588, dated Jan. 29, 2021, 3 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Baar, Marius, "Fitbit Ace—Unboxing, Setup and 24 Hour Test", YouTube [online] [video], Retrieved from: <https://youtu.be/ekvkfqOyrls>. See especially 4:44., Oct. 24, 2018, 3 pages.
CBS This Morning, "This smart mirror puts a personal trainer in your reflection", Available on: https://www.youtube.com/watch?v=nSmTTZcpVGg, Oct. 13, 2018, 4 pages.
Decision on Appeal received for Korean Patent Application No. 10-2019-7025538, mailed on Feb. 24, 2021, 20 pages (4 pages of English Translation and 16 pages of Official Copy).
Decision to Grant received for Danish Patent Application No. PA201970596, dated Feb. 26, 2021, 2 pages.
Decision to Refuse received for European Patent Application No. 17810749.6, dated Jan. 29, 2021, 24 pages.
Decision to Refuse received for European Patent Application No. 18154145.9, dated Feb. 17, 2021, 20 pages.
Extended European Search Report received for European Patent Application No. 20203526.7, dated Jan. 29, 2021, 13 pages.
Final Office Action received for U.S. Appl. No. 15/421,865, dated Mar. 19, 2021, 20 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Final Office Action received for U.S. Appl. No. 16/894,309, dated Feb. 24, 2021, 30 pages.
Final Office Action received for U.S. Appl. No. 16/997,588, dated Mar. 30, 2021, 23 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Hamilton, Jim, "Peloton Tips", Online available on:—<https://www.youtube.com/watch?app=desktop&v=OneXtB0kaD4>, Oct. 22, 2015, 3 pages.
Intention to Grant received for Danish Patent Application No. PA201670656, dated Jan. 18, 2021, 2 pages.
Intention to Grant received for Danish Patent Application No. PA202070609, dated Jan. 14, 2021, 2 pages.
International Search Report and Written Opinion received for PCT Patent Application No. PCT/US2020/045814, dated Jan. 20, 2021, 16 pages.
Minutes of the Oral Proceedings received for European Patent Application No. 17810749.6, mailed on Jan. 26, 2021, 8 pages.
Minutes of the Oral Proceedings received for European Patent Application No. 18154145.9, mailed on Feb. 12, 2021, 8 pages.
My Mate Vince, "Setting up the Fitbit Alta HR Activity Tracker on Apple iOS", Online available at:—<https://youtu.be/FdwRF4lfvFc, Jun. 18, 2017, 3 pages.
Non-Final Office Action received for U.S. Appl. No. 15/405,122, dated Apr. 2, 2021, 35 pages.
Non-Final Office Action received for U.S. Appl. No. 15/608,848, dated Feb. 12, 2021, 14 pages.
Non-Final Office Action received for U.S. Appl. No. 16/582,020, dated Apr. 5, 2021, 29 pages.
Non-Final Office Action received for U.S. Appl. No. 16/888,629, dated Mar. 31, 2021, 14 pages.
Notice of Acceptance received for Australian Patent Application No. 2017277971, dated Feb. 17, 2021, 3 pages.
Notice of Acceptance received for Australian Patent Application No. 2018268972, dated Dec. 18, 2020, 3 pages.
Notice of Acceptance received for Australian Patent Application No. 2019208225, dated Jan. 21, 2021, 3 pages.
Notice of Acceptance received for Australian Patent Application No. 2019250251, dated Feb. 18, 2021, 3 pages.
Notice of Acceptance received for Australian Patent Application No. 2021200787, dated Mar. 19, 2021, 3 pages.
Notice of Acceptance received for Australian Patent Application No. 2020204506, dated Apr. 8, 2021, 3 pages.
Notice of Allowance received for Chinese Patent Application No. 201510479088.4, dated Jan. 21, 2021, 2 pages (1 page of English Translation and 1 page of Official Copy).
Notice of Allowance received for Chinese Patent Application No. 201710439448.7, dated Jan. 26, 2021, 2 pages (1 page of English Translation and 1 page of Official Copy).
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2019-151358, dated Jan. 22, 2021, 4 pages (1 page of English Translation and 3 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for Japanese Patent Application No. 2019-162293, dated Apr. 9, 2021, 4 pages (1 page of English Translation and 3 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for Korean Patent Application No. 10-2021-7002597, dated Feb. 25, 2021, 5 pages (1 page of English Translation and 4 pages of Official Copy).
Notice of Allowance received for U.S. Appl. No. 14/815,890, dated Feb. 12, 2021, 8 pages.
Notice of Allowance received for U.S. Appl. No. 15/925,652, dated Mar. 9, 2021, 9 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/556,023, dated Jan. 13, 2021, 8 pages.
Notice of Allowance received for U.S. Appl. No. 16/585,714, dated Jan. 8, 2021, 8 pages.
Notice of Allowance received for U.S. Appl. No. 16/585,714, dated Jan. 27, 2021, 2 pages.
Notice of Allowance received for U.S. Appl. No. 16/659,507, dated Feb. 24, 2021, 7 pages.
Notice of Allowance received for U.S. Appl. No. 16/820,383, dated Mar. 31, 2021, 11 pages.
Notice of Allowance received for U.S. Appl. No. 16/138,809, dated Apr. 16, 2021, 11 pages.
Office Action received for Australian Patent Application No. 2019208225, dated Dec. 21, 2020, 3 pages.

(56) References Cited

OTHER PUBLICATIONS

Office Action received for Australian Patent Application No. 2020239670, dated Mar. 3, 2021, 4 pages.
Office Action received for Australian Patent Application No. 2020309093, dated Jan. 21, 2021, 3 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680013193.1, dated Feb. 1, 2021, 8 pages (3 pages of English Translation and 5 pages of Official Copy).
Office Action received for Chinese Patent Application No. 201780033973.7, dated Jan. 22, 2021, 27 pages (11 pages of English Translation and 16 pages of Official Copy).
Office Action received for Chinese Patent Application No. 202010606407.4, dated Jan. 27, 2021, 16 pages (7 pages of English Translation and 9 pages of Official Copy).
Office Action received for Danish Patent Application No. PA201970599, dated Mar. 1, 2021, 4 pages.
Office Action received for European Patent Application No. 18727543.3, dated Mar. 26, 2021, 7 pages.
Office Action received for Japanese Patent Application No. 2018-184532, dated Mar. 1, 2021, 11 pages (6 pages of English Translation and 5 pages of Official Copy).
Office Action received for Japanese Patent Application No. 2019-563407, dated Feb. 5, 2021, 5 pages (2 pages of English Translation and 3 pages of Official Copy).
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Office Action received for Korean Patent Application No. 10-2020-7001340, dated Mar. 26, 2021, 13 pages (6 pages of English Translation and 7 pages of Official Copy).
Office Action received for Korean Patent Application No. 10-2020-7026035, dated Feb. 19, 2021, 13 pages (6 pages of English Translation and 7 pages of Official Copy).
Office Action received for Korean Patent Application No. 10-2019-7029673, dated Apr. 8, 2021, 7 pages (3 pages of English Translation and 4 pages of Official Copy).
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Search Report and Opinion received for Danish Patent Application No. PA202070610, dated Jan. 8, 2021, 9 pages.
Search Report and Opinion received for Danish Patent Application No. PA202070614, dated Jan. 14, 2021, 9 pages.
Search Report and Opinion received for Danish Patent Application No. PA202070815, dated Mar. 16, 2021, 8 pages.
Supplemental Notice of Allowance received for U.S. Appl. No. 14/815,890, dated Mar. 10, 2021, 2 pages.
Supplemental Notice of Allowance received for U.S. Appl. No. 15/925,652, dated Feb. 17, 2021, 3 pages.
Supplemental Notice of Allowance received for U.S. Appl. No. 15/925,652, dated Jan. 6, 2021, 3 pages.
Supplemental Notice of Allowance received for U.S. Appl. No. 15/925,652, dated Jan. 26, 2021, 3 pages.
Supplemental Notice of Allowance received for U.S. Appl. No. 16/556,023, dated Feb. 3, 2021, 2 pages.
Vicky's Blog, "How to Log In to PS4 Automatically with Particular User?", Online available on :—https://www.youtube.com/watch?v=kqdlzXAvOkY, May 30, 2018, 3 pages.
Wearablezone, "How To Set Up Your Fitbit Profile", Online available at:—<https://youtu.be/jsWPtcDWiJM>, Jun. 6, 2016, 3 pages.
Xdream, "TickTalk Video User Manual", YouTube [online] [video], Online available at: <https://youtu.be/jYhq3DwmVzo>, Mar. 17, 2017, 3 pages.
Yoyodavid, "How To Use Multiple Accounts on the Playstation 4", Online available at:—https://www.youtube.com/watch?v=5V21obRMeKE, Jan. 9, 2014, 3 pages.
Applicant-Initiated Interview Summary received for U.S. Appl. No. 15/421,865, dated Jun. 30, 2021, 6 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21165295.3, dated Jun. 18, 2021, 4 pages.
Non-Final Office Action received for U.S. Appl. No. 16/935,002, dated Jun. 25, 2021, 20 pages.
Non-Final Office Action received for U.S. Appl. No. 16/943,737, dated Jun. 25, 2021, 18 pages.
Notice of Acceptance received for Australian Patent Application No. 2021202836, dated Jun. 25, 2021, 3 pages.
Notice of Allowance received for Japanese Patent Application No. 2020-551465, dated Jun. 28, 2021, 4 pages (1 page of English Translation and 3 pages of Official Copy).
Office Action received for Australian Patent Application No. 2019267413, dated Jun. 29, 2021, 3 pages.
Office Action received for Australian Patent Application No. 2020239774, dated Jun. 28, 2021, 8 pages.
Office Action received for Chinese Patent Application No. 202010606407.4, dated Jun. 2, 2021, 12 pages (5 pages of English Translation and 7 pages of Official Copy).
Office Action received for Danish Patent Application No. PA202070610, dated Jun. 18, 2021, 8 pages.
Office Action received for European Patent Application No. 21165295.3, dated Jul. 1, 2021, 10 pages.
Phonebuff, "Hybrid Stopwatch & Timer Android App Review", Available Online at: https://www.youtube.com/watch?v=B43oCFPiWvY, Apr. 4, 2012, 7 pages.
Rosa et al., "Stripe Generator—a Free Tool for the Web Design Community", Available online at: http://www.stripegenerator.com/, Mar. 28, 2019, 2 pages.
Wade Cliff, "Get the most out of Nova Launcher: Changing Icon Sizes", Online available at: https://www.androidguys.com/tips-tools/get-nova-launcher-changing-icon-sizes/, Nov. 16, 2015, 6 pages.
Non-Final Office Action received for U.S. Appl. No. 17/031,874, dated Dec. 28, 2020, 14 pages.
Non-Final Office Action received for U.S. Appl. No. 16/389,722, dated Jun. 3, 2021, 17 pages.
Notice of Allowance received for Japanese Patent Application No. 2020-074878, dated May 28, 2021, 4 pages (1 page of English Translation and 3 pages of Official Copy).
Notice of Allowance received for U.S. Appl. No. 16/377,892, dated May 24, 2021,9 pages.
Notice of Allowance received for U.S. Appl. No. 16/378,136, dated Jun. 3, 2021, 7 pages.
Office Action received for Australian Patent Application No. 2021202834, dated May 28, 2021, 2 pages.
Office Action received for European Patent Application No. 20182116.2, dated May 25, 2021, 9 pages.
Office Action received for Japanese Patent Application No. 2020-115940, dated May 7, 2021, 3 pages (1 page of English Translation and 2 pages of Official Copy).
Search Report received for Netherlands Patent Application No. 2015236, dated Apr. 21, 2021, 19 pages (13 pages of English Translation and 6 pages of Official Copy).
Final Office Action received for U.S. Appl. No. 17/192,161, dated Oct. 18, 2021, 22 pages.

(56) References Cited

OTHER PUBLICATIONS

Non-Final Office Action received for U.S. Appl. No. 17/030,321, dated Oct. 18, 2021, 28 pages.
Office Action received for Australian Patent Application No. 2020239774, dated Oct. 5, 2021, 3 pages.
Office Action received for Danish Patent Application No. PA202070613, dated Sep. 30, 2021, 4 pages.
Applicant Initiated Interview Summary received for U.S. Appl. No. 16/994,352, dated Nov. 2, 2021, 4 pages.
Applicant Initiated Interview Summary received for U.S. Appl. No. 17/031,671, dated Nov. 8, 2021, 5 pages.
Final Office Action received for U.S. Appl. No. 15/405,122, dated Nov. 5, 2021, 45 pages.
Final Office Action received for U.S. Appl. No. 17/031,765, dated Oct. 29, 2021, 34 pages.
International Search Report and Written Opinion received for PCT Patent Application No. PCT/US2021/031669, dated Oct. 13, 2021, 17 pages.
Invitation to Pay Additional Fees received for PCT Patent Application No. PCT/US2021/031669, dated Aug. 19, 2021, 9 pages.
Non-Final Office Action received for U.S. Appl. No. 17/317,042, dated Nov. 10, 2021, 13 pages.
Notice of Allowance received for Chinese Patent Application No. 201910906898.1, dated Oct. 28, 2021, 4 pages (1 page of English Translation and 3 pages of Official Copy).
Notice of Allowance received for Japanese Patent Application No. 2020-115940, dated Oct. 22, 2021, 4 pages (1 page of English Translation and 3 pages of Official Copy).
Notice of Allowance received for Korean Patent Application No. 10-2020-7028759, dated Oct. 19, 2021, 4 pages (1 page of English Translation and 3 pages of Official Copy).
Notice of Allowance received for U.S. Appl. No. 15/608,848, dated Oct. 29, 2021, 7 pages.
Notice of Allowance received for U.S. Appl. No. 16/401,934, dated Nov. 1, 2021, 11 pages.
Notice of Allowance received for U.S. Appl. No. 16/888,629, dated Nov. 9, 2021, 11 pages.
Notice of Allowance received for U.S. Appl. No. 16/894,309, dated Nov. 5, 2021, 12 pages.
Office Action received for Australian Patent Application No. 2020239752, dated Oct. 25, 2021, 5 pages.
Office Action received for Chinese Patent Application No. 201780034203.4, dated Sep. 24, 2021, 7 pages (3 pages of English Translation and 4 pages of Official Copy).
Office Action received for European Patent Application No. 20721342.2, dated Nov. 4, 2021, 9 pages.
Office Action received for Korean Patent Application No. 10-2021-7031939, dated Oct. 19, 2021, 11 pages (5 pages of English Translation and 6 pages of Official Copy).
Non-Final Office Action received for U.S. Appl. No. 17/068,386, dated Oct. 28, 2021, 20 pages.
Notice of Allowance received for U.S. Appl. No. 17/087,845, dated Oct. 28, 2021, 9 pages.
Office Action received for Chinese Patent Application No. 202110194015.6, dated Sep. 28, 2021, 13 pages (6 pages of English Translation and 7 pages of Official Copy).
Office Action received for Danish Patent Application No. PA202070815, dated Oct. 18, 2021, 2 pages.
Office Action received for Korean Patent Application No. 10-2021-7025301, dated Oct. 15, 2021, 5 pages (2 pages of English Translation and 3 pages of Official Copy).
Supplemental Notice of Allowance received for U.S. Appl. No. 16/997,588, dated Oct. 22, 2021, 4 pages.
Applicant-Initiated Interview Summary received for U.S. Appl. No. 17/192,161, dated Sep. 29, 2021, 3 pages.
Corrected Notice of Allowance received for U.S. Appl. No. 16/820,383, dated Oct. 5, 2021, 2 pages.
Extended European Search Report received for European Patent Application No. 21169911.1, dated Sep. 20, 2021, 9 pages.
Extended European Search Report received for European Patent Application No. 21177569.7, dated Sep. 20, 2021, 8 pages.
Final Office Action received for U.S. Appl. No. 17/030,318, dated Sep. 30, 2021, 28 pages.
International Search Report and Written Opinion received for PCT Patent Application No. PCT/US2021/017736, dated Sep. 2, 2021, 25 pages.
International Search Report and Written Opinion received for PCT Patent Application No. PCT/US2021/031212, dated Sep. 21, 2021, 21 pages.
Non-Final Office Action received for U.S. Appl. No. 16/861,651, dated Sep. 30, 2021, 16 pages.
Notice of Allowance received for U.S. Appl. No. 16/997,588, dated Sep. 30, 2021, 12 pages.
Office Action received for Danish Patent Application No. PA202070614, dated Sep. 28, 2021, 4 pages.
Office Action received for Japanese Patent Application No. 2020-124605, dated Sep. 3, 2021, 5 pages (2 pages of English Translation and 3 pages of Official Copy).
International Preliminary Report on Patentability received for PCT Patent Application No. PCT/US2020/025997, dated Nov. 18, 2021, 10 pages.
International Preliminary Report on Patentability received for PCT Patent Application No. PCT/US2020/030079, dated Nov. 18, 2021, 12 pages.
International Preliminary Report on Patentability received for PCT Patent Application No. PCT/US2020/031536, dated Nov. 18, 2021, 11 pages.
International Preliminary Report on Patentability received for PCT Patent Application No. PCT/US2020/031575, dated Nov. 18, 2021, 9 pages.
Non-Final Office Action received for U.S. Appl. No. 16/987,275, dated Nov. 23, 2021, 17 pages.
Non-Final Office Action received for U.S. Appl. No. 17/157,728, dated Nov. 26, 2021, 18 pages.
Office Action received for Danish Patent Application No. PA202070615, dated Nov. 16, 2021, 4 pages.
Office Action received for European Patent Application No. 20203526.7, dated Nov. 23, 2021, 9 pages.
Office Action received for Korean Patent Application No. 10-2021-7036016, dated Nov. 10, 2021, 13 pages (6 pages of English Translation and 7 pages of Official Copy).
Advisory Action received for U.S. Appl. No. 14/732,773, dated Nov. 9, 2018, 6 pages.
Advisory Action received for U.S. Appl. No. 14/815,898, dated Aug. 30, 2016, 3 pages.
Advisory Action received for U.S. Appl. No. 14/839,922, dated Mar. 24, 2017, 4 pages.
Airshow, "Airshow App For Mobile Devices", 2012, 4 pages.
APK Root, "Butterfly 3D Live Wallpaper 1.0 APK", Available at <http://net-suckga-ilauncher2.apk-dl.com/butterfly-3d-live-wallpaper>, Feb. 26, 2013, 7 pages.
Avdonin, Nikita, "Astroviewer 3D", Available at <:https:jjwww.youtube.comjwatch?v=zY0tslx3JHY/>, Nov. 5, 2013, 2 pages.
Bogdanov, Alexei, "SKMEI 1016", Available online at <URL:https://www.youtube.com/watch?v=E4q4Fug05Fw>, Jun. 21, 2014, 2 pages.
Castellini, Rick, "Google Earth", Retrieved from <https://www.youtube.com/watch?v=bgjMSBXsFZQ>, Feb. 12, 2013, 3 pages.
Cho, H. S., "Satisfactory Innovative Smart-watch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 6 pages.
Corrected Notice of Allowance received for U.S. Appl. No. 14/815,879, dated Jul. 13, 2017, 3 pages.
Corrected Notice of Allowance received for U.S. Appl. No. 14/815,879, dated Jul. 28, 2017, 3 pages.
Corrected Notice of Allowance received for U.S. Appl. No. 14/815,879, dated Sep. 21, 2017, 2 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.

(56) References Cited

OTHER PUBLICATIONS

Decision on Opposition received for Australian Patent Application No. 2015298710, mailed on Aug. 20, 2018, 20 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
"Deluxe Moon—Guide", available online at:—https://web.archive.org/web/20130520161057/http://www.lifewaresolutions.com/deluxe_moon_guide_ip.html. May 20, 2013, 5 pages.
Evgenyevich, "Sergey, Earth & Moon in HD Gyro 3D", Available at <https://www.youtube.com/watch?v=IRwNcaSYrls/>, Dec. 1, 2013, 2 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Feldman, Ari, "Excerpts from: Designing Arcade Computer Game Graphics", Available online at: http://www.phatcode.net/res/269/files/dacgg.pdf, Jan. 1, 2001, 35 pages.
Final Office Action received for U.S. Appl. No. 14/599,424, dated Jun. 28, 2018, 12 pages.
Final Office Action received for U.S. Appl. No. 14/599,425, dated Jun. 12, 2018, 45 pages.
Final Office Action received for U.S. Appl. No. 14/599,425, dated May 19, 2017, 24 pages.
Final Office Action received for U.S. Appl. No. 14/599,425, dated Oct. 8, 2015, 20 pages.
Final Office Action received for U.S. Appl. No. 14/732,773, dated Jul. 13, 2018, 48 pages.
Final Office Action received for U.S. Appl. No. 14/815,890, dated Feb. 26, 2018, 20 pages.
Final Office Action received for U.S. Appl. No. 14/815,890, dated Nov. 21, 2016, 18 pages.
Final Office Action received for U.S. Appl. No. 14/815,898, dated Jun. 9, 2016, 19 pages.
Final Office Action received for U.S. Appl. No. 14/839,922, dated Dec. 14, 2016, 22 pages.
Final Office Action received for U.S. Appl. No. 14/815,879, dated Mar. 24, 2016, 46 pages.
First Action Interview received for U.S. Appl. No. 14/815,890, dated Aug. 12, 2016, 3 pages.
Fuchphone Extras, "LG G Watch—Designs | Watch Faces", Available online at: https://www.youtube.com/watch?v=yqxzqdi_MSE, Jul. 27, 2014, 1 page.
Fuchphone Extras, "Samsung Gear Live—Designs | Watch Faces", Available online at: https://www.youtube.com/watch?v=fFjtVAxyimE, Jul. 26, 2014, 1 page.
"Google Earth 7.0.1.8244", retrieved from the Internet: http://dl.google.com/dl/earth/client/ge7/release_7_0_1/googleearth-win-bundle-7.0.1.8244.exe, Oct. 29, 2012, 1 page.
"Google Earth on Android—AndroidCentral.com", Available online at:—https://www.youtube.com/watch?v=1WxN1RunrE4, Feb. 22, 2010, 1 page.
Gottabemobile, "How to Change Watch Faces on Android Wear", available online at URL:https://www.youtube.com/watch?v=B8iRGkGq6a8, Jul. 9, 2014, 4 pages.
Intention to Grant received for Danish Patent Application No. PA201570496, dated Feb. 17, 2016, 6 pages.
Intention to Grant received for Danish Patent Application No. PA201570668, dated Mar. 27, 2017, 2 pages.
International Preliminary Report on Patentability received for PCT Patent Application No. PCT/US2016/037686, dated Mar. 1, 2018, 12 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/032474, dated Dec. 15, 2016, 7 pages.
International Preliminary Report on Patentability received for PCT Patent Application No. PCT/US2015/034604, dated Feb. 16, 2017, 21 pages.
International Preliminary Report on Patentability received for PCT Patent Application No. PCT/US2015/034606, dated Feb. 16, 2017, 11 pages.
International Preliminary Report on Patentability received for PCT Patent Application No. PCT/US2015/034607, dated Feb. 16, 2017, 18 pages.
International Preliminary Report on Patentability received for PCT Patent Application No. PCT/US2015/047282, dated Mar. 16, 2017, 26 pages.
International Search Report and Written Opinion received for PCT Patent Application No. PCT/US2015/034604, dated Nov. 9, 2015, 30 pages.
International Search Report and Written Opinion received for PCT Patent Application No. PCT/US2015/032474, dated Aug. 19, 2015, 8 pages.
International Search Report and Written Opinion received for PCT Patent Application No. PCT/US2015/034606, dated Dec. 2, 2015, 17 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2015/034607, dated Dec. 1, 2015, 23 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Additional Fees and Partial International Search Report received for PCT Patent Application No. PCT/US2015/034604 dated Sep. 4, 2015, 6 pages.
Invitation to Additional Fees and Partial International Search Report received for PCT Patent Application No. PCT/US2015/034606 dated Sep. 9, 2015, 6 pages.
Invitation to Pay Additional Fee received for European Patent Application No. 15747595.5, dated Feb. 9, 2018, 6 pages.
Invitation to Pay Additional Fees received for PCT Patent Application No. PCT/US2015/034607, dated Sep. 30, 2015, 4 pages.
Invitation to Pay Additional Fees received for PCT Patent Application No. PCT/US2015/047282, dated Dec. 22, 2015, 7 pages.
"iPhone User Guide For iOS 7.1 Software", available online at <https://manuals.info.apple.com/MANUALS/1000/MA1681/en_US/iphone_ios7_user_guide.pdf, Mar. 10, 2014, pp. 1-162.
ISO 9241-13:1998, "Ergonomic requirements for office work with visual display terminals (VDTs)", Part 13: User guidance, International Standard ISO, Zuerich, CH, vol. 9241-13, Jul. 15, 1998, 40 pages.
Jenbsjourney, "Wondering About a Fitbit?", Available at: https://jenbsjourney.blogspot.kr/2013/08/wondering-about-fitbit.html, Aug. 6, 2013, 12 pages.
Kamijo, Noboru, "Next Generation Mobile System—WatchPad1.5", Available at <http://researcher.ibm.com/researcher/view_group_subpage.php?id=5617>, retrieved on Jul. 4, 2015, 2 pages.
"Kidizoom Smartwatch", Available online at <URL:https://www.vtechnl.com/media/downloads/Kidizoom-Smart-Watch.pdf>, Jun. 24, 2014, 23 pages.
"Link to Wayback Machine with link to Google Play showing different layouts of complications associated with a clock face", available online at <https://play.google.com/store/apps/details?id=com.levelup.beautifulwidgets.free&hl=da >, Sep. 9, 2013, 6 pages.
"Living Earth", available at : http://www.livingearthapp.com/, 2014, 6 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.

(56) References Cited

OTHER PUBLICATIONS

Nerdtalk, "The Best Android Clock Widgets", available at: https://www.youtube.com/watch?v=E1bAprWByfU, Apr. 25, 2011, 1 page.
"New, but unsigned—Easy Stopwatch for Symbian", Available online at <http://www.allaboutsymbian.com/flow/item/19490_New_but_unsigned-Easy_StopWatc.php>, Mar. 15, 2014, 15 pages.
Non Final Office Action received for U.S. Appl. No. 14/815,890, dated Jun. 6, 2017, 19 pages.
Non Final Office Action received for U.S. Appl. No. 14/815,890, dated Oct. 19, 2015, 5 pages.
Non Final Office Action received for U.S. Appl. No. 14/839,916, dated Feb. 4, 2016, 19 pages.
Non Final Office Action received for U.S. Appl. No. 14/839,922, dated Feb. 25, 2016, 20 pages.
Non-Final Office Action received for U.S. Appl. No. 14/503,372, dated Dec. 5, 2014, 11 pages.
Non-Final Office Action received for U.S. Appl. No. 14/599,424, dated Jan. 17, 2018, 13 pages.
Non-Final Office Action received for U.S. Appl. No. 14/599,425, dated Jan. 11, 2018, 42 pages.
Non-Final Office Action received for U.S. Appl. No. 14/599,425, dated Mar. 17, 2015, 16 pages.
Non-Final Office Action received for U.S. Appl. No. 14/599,425, dated Oct. 26, 2016, 22 pages.
Non-Final Office Action received for U.S. Appl. No. 14/732,773, dated Jan. 19, 2018, 45 pages.
Non-Final Office Action received for U.S. Appl. No. 14/815,879, dated Dec. 15, 2016, 33 pages.
Non-Final Office Action received for U.S. Appl. No. 14/815,890, dated Dec. 18, 2018, 21 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 15/183,663, dated Jul. 9, 2018, 13 pages.
Non-Final Office Action received for U.S. Appl. No. 14/815,879, dated Nov. 6, 2015, 35 pages.
Non-Final Office Action received for U.S. Appl. No. 14/815,898, dated Dec. 1, 2015, 22 pages.
Non-Final Office Action received for U.S. Appl. No. 14/815,907, dated Jan. 12, 2016, 22 pages.
Non-Final Office Action received for U.S. Appl. No. 14/815,909, dated Nov. 27, 2015, 12 pages.
Notice of Acceptance received for Australian Patent Application No. 2015267240, dated Apr. 10, 2018, 3 pages.
Notice of Acceptance received for Australian Patent Application No. 2015312215, dated Oct. 9, 2017, 3 pages.
Notice of Allowance received for Chinese Patent Application No. 201520358505.5, dated Jan. 13, 2016, 3 pages.
Notice of Allowance received for Chinese Patent Application No. 201520594249.X, dated Jul. 12, 2016, 4 pages.
Notice of Allowance received for Danish Patent Application No. PA201570495, dated Feb. 22, 2017, 1 page.
Notice of Allowance received for Danish Patent Application No. PA201570496, dated Apr. 18, 2016, 2 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Japanese Patent Application No. 2017-505450, dated Mar. 9, 2018, 10 pages.
Notice of Allowance received for Korean Patent Application No. 10-2016-7033638, dated May 31, 2017, 5 pages.
Notice of Allowance received for Korean Patent Application No. 10-2017-7005939, dated Mar. 30, 2018, 5 pages.
Notice of Allowance received for Taiwanese Patent Application No. 104117509, dated Mar. 31, 2017, 3 pages.
Notice of Allowance received for Taiwanese Patent Application No. 104124962, dated Jul. 27, 2017, 3 pages.
Notice of Allowance received for Taiwanese Patent Application No. 104124963, dated Sep. 28, 2017, 5 pages.
Notice of Allowance received for Taiwanese Patent Application No. 104124995, dated Jul. 27, 2017, 3 pages.
Notice of Allowance received for Taiwanese Patent Application No. 104124997, dated Jun. 16, 2017, 5 pages.
Notice of Allowance received for Taiwanese Patent Application No. 104124998, dated Mar. 31, 2017, 3 pages.
Notice of Allowance received for Taiwanese Patent Application No. 104128685, dated May 3, 2017, 3 pages.
Notice of Allowance received for U.S. Appl. No. 14/599,424, dated Dec. 13, 2018, 6 pages.
Notice of Allowance received for U.S. Appl. No. 14/599,425, dated Dec. 19, 2018, 9 pages.
Notice of Allowance received for U.S. Appl. No. 14/815,879, dated Jun. 26, 2017, 8 pages.
Notice of Allowance received for U.S. Appl. No. 14/815,898, dated Dec. 5, 2016, 3 pages.
Notice of Allowance received for U.S. Appl. No. 14/815,898, dated Oct. 24, 2016, 14 pages.
Notice of Allowance received for U.S. Appl. No. 14/815,907, dated Jul. 28, 2016, 9 pages.
Notice of Allowance received for U.S. Appl. No. 14/815,907, dated Nov. 30, 2016, 2 pages.
Notice of Allowance received for U.S. Appl. No. 14/815,909, dated Jun. 9, 2016, 3 pages.
Notice of Allowance received for U.S. Appl. No. 14/815,909, dated May 3, 2016, 12 pages.
Notice of Allowance received for U.S. Appl. No. 14/815,909, dated May 20, 2016, 2 pages.
Notice of Allowance received for U.S. Appl. No. 14/815,909, dated Sep. 6, 2016, 2 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Nova, "Tour of the Solar System", Retrieved from <http://www.pbs.org/wgbh/nova/space/tour-solar-system.html>, May 24, 2013, 14 pages.
Office Action received for Australian Patent Application No. 2015101020, dated Oct. 26, 2015, 8 pages.
Office Action received for Danish Patent Application No. PA201570499, dated Nov. 1, 2017, 6 pages.
Office Action received for European Patent Application No. 15730924.6, dated Dec. 12, 2017, 8 pages.
Office Action received for Japanese Patent Application No. 2016-569945, dated Nov. 10, 2017, 8 pages.
Office Action received for Australian Patent Application No. 2015101019, dated Oct. 14, 2015, 3 pages.
Office Action received for Australian Patent Application No. 2015100734, dated Jul. 29, 2015, 5 pages.
Office Action received for Australian Patent Application No. 2015101019, dated Apr. 7, 2016, 4 pages.
Office Action received for Australian Patent Application No. 2015101021, dated Apr. 26, 2016, 4 pages.
Office Action received for Australian Patent Application No. 2015101021, dated Oct. 28, 2015, 10 pages.
Office Action received for Australian Patent Application No. 2015267240, dated Apr. 10, 2017, 5 pages.
Office Action received for Australian Patent Application No. 2015267240, dated Mar. 21, 2018, 5 pages.
Office Action received for Australian Patent Application No. 2015298710, dated Apr. 13, 2017, 3 pages.

(56) References Cited

OTHER PUBLICATIONS

Office Action received for Australian Patent Application No. 2015298710, dated Feb. 15, 2017, 2 pages.
Office Action received for Australian Patent Application No. 2015298710, dated Nov. 6, 2018, 4 pages.
Office Action received for Australian Patent Application No. 2015298710, dated Sep. 24, 2018, 4 pages.
Office Action received for Australian Patent Application No. 2015312215, dated Oct. 13, 2016, 3 pages.
Office Action received for Australian Patent Application No. 2016100411, dated Jun. 10, 2016, 3 pages.
Office Action received for Australian Patent Application No. 2016100476, dated Jun. 9, 2016, 4 pages.
Office Action received for Australian Patent Application No. 2016100765, dated Aug. 5, 2016, 2 pages.
Office Action received for Australian Patent Application No. 2016100765, dated Dec. 16, 2016, 3 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2015101019, dated Feb. 12, 2016, 4 pages.
Office Action received for Chinese Patent Application No. 201520595384.6, dated Mar. 25, 2016, 3 pages.
Office Action received for Chinese Patent Application No. 201510284850.3, dated Jul. 9, 2018, 11 pages.
Office Action received for Chinese Patent Application No. 201510284850.3, dated Nov. 28, 2017, 15 pages.
Office Action received for Chinese Patent Application No. 201510479088.4, dated Mar. 12, 2018, 20 pages.
Office Action received for Chinese Patent Application No. 201510481525.6, dated Aug. 29, 2018, 10 pages.
Office Action received for Chinese Patent Application No. 201510481525.6, dated Nov. 29, 2017, 9 pages.
Office Action received for Chinese Patent Application No. 201510483268.X, dated Dec. 1, 2017, 11 pages.
Office Action received for Chinese Patent Application No. 201510483268.X, dated Oct. 19, 2018, 10 pages.
Office action received for Chinese Patent Application No. 201510483305.7, dated Aug. 31, 2018, 10pages.
Office action received for Chinese Patent Application No. 201510483305.7, dated Dec. 1, 2017, 13 pages.
Office Action received for Chinese Patent Application No. 201510484514.3, dated Apr. 4, 2018, 12 pages.
Office Action received for Chinese Patent Application No. 201520594249.X, dated Mar. 25, 2016, 3 pages.
Office Action received for Chinese Patent Application No. 201520595384.6, dated Dec. 30, 2016, 2 pages.
Office Action received for Chinese Patent Application No. 201520595384.6, dated Jul. 22, 2016, 3 pages.
Office Action received for Chinese Patent Application No. 201520595385.0, dated Dec. 30, 2016, 2 pages.
Office Action received for Chinese Patent Application No. 201520595385.0, dated Jul. 22, 2016, 3 pages.
Office Action received for Chinese Patent Application No. 201520595385.0, dated Mar. 25, 2016, 3 pages.
Office Action Received for Chinese Patent Application No. 201520595408.8, dated Dec. 9, 2015, 4 pages.
Office Action Received for Chinese Patent Application No. 201520595408.8, dated Dec. 30, 2016, 2 pages.
Office Action received for Chinese Patent Application No. 201520595408.8, dated Jul. 25, 2016, 3 pages.
Office Action received for Chinese Patent Application No. 201520595408.8, dated Mar. 25, 2016, 3 pages.
Office Action received for Chinese Patent Application No. 201520595538.1, dated Dec. 30, 2016, 2 pages.
Office Action received for Chinese Patent Application No. 201520595538.1, dated Jul. 22, 2016, 3 pages.
Office Action received for Chinese Patent Application No. 201520595538.1, dated Mar. 25, 2016, 3 pages.
Office Action received for Chinese Patent Application No. 201580028677.9, dated May 25, 2018, 14 pages.
Office Action received for Chinese Patent Application No. 201580037927.5, dated Jul. 20, 2018, 21 pages.
Office Action Received for Chinese Patent Application N0.201520594249.X, dated Dec. 9, 2015, 4 pages.
Office Action Received for Chinese Patent Application No. 201520595384.6, dated Dec. 9, 2015, 4 pages.
Office Action Received for Chinese Patent Application No. 201520595385.0, dated Dec. 9, 2015, 4 pages.
Office Action Received for Chinese Patent Application No. 201520595538.1, dated Dec. 9, 2015, 4 pages.
Office Action Received for Danish Patent Application No. PA201670656, dated Nov. 3, 2016, 8 pages.
Office Action received for Danish Patent Application No. PA201570495, dated Dec. 9, 2016, 2 pages.
Office action received for Danish Patent Application No. PA201570495, dated May 4, 2016, 8 pages.
Office Action received for Danish Patent Application No. PA201570495, dated Oct. 29, 2015, 7 pages.
Office Action received for Danish Patent Application No. PA201570497, dated Feb. 21, 2017, 3 pages.
Office Action received for Danish Patent Application No. PA201570497, dated May 17, 2016, 6 pages.
Office Action received for Danish Patent Application No. PA201570497, dated Nov. 15, 2016, 2 pages.
Office Action received for Danish Patent Application No. PA201570497, dated Oct. 24, 2017, 2 pages.
Office Action received for Danish Patent Application No. PA201570498, dated Feb. 6, 2017, 2 pages.
Office Action received for Danish Patent Application No. PA201570498, dated Jun. 2, 2016, 8 pages.
Office Action received for Danish Patent Application No. PA201570498, dated Oct. 26, 2017, 5 pages.
Office Action received for Danish Patent Application No. PA201570498, dated Oct. 30, 2015, 7 pages.
Office Action received for Danish Patent Application No. PA201570499, dated Feb. 14, 2017, 2 pages.
Office Action received for Danish Patent Application No. PA201570499, dated Jun. 16, 2016, 8 pages.
Office Action received for Danish Patent Application No. PA201570499, dated Jun. 19, 2018, 4 pages.
Office Action received for Danish Patent Application No. PA201570499, dated Nov. 3, 2015, 7 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 30, 2018, 5 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201570496, dated Oct. 29, 2015, 6 pages.
Office Action received for Danish Patent Application No. PA201570497, dated Oct. 30, 2015, 6 pages.
Office Action received for European Patent Application No. 13811085.3, dated Apr. 20, 2018, 15 pages.
Office Action received for European Patent Application No. 15730890.9, dated Aug. 3, 2017, 4 pages.
Office Action received for European Patent Application No. 15730925.3, dated Apr. 12, 2018, 8 pages.

(56) References Cited

OTHER PUBLICATIONS

Office Action received for European Patent Application No. 15747595.5, dated Jun. 27, 2018, 8 pages.
Office Action received for European Patent Application No. 18154145.9, dated Apr. 3, 2018, 6 pages.
Office Action received for European Patent Application No. 15771747.1, dated Oct. 31, 2017, 7 pages.
Office Action received for German Patent Application No. 112015003083.2, dated Mar. 9, 2018, 12 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2016-557650, dated Nov. 9, 2018, 6 pages.
Office Action received for Japanese Patent Application No. 2016-569945, dated Sep. 10, 2018, 11 pages.
Office Action received for Japanese Patent Application No. 2017-505450, dated Jun. 20, 2017, 8 pages.
Office Action received for Japanese Patent Application No. 2018-014096, dated Jun. 29, 2018, 20 pages.
Office Action received for Japanese Patent Application No. 2018-014096, dated Nov. 6, 2018, 15 pages.
Office Action received for Korean Patent Application No. 10-2016-7014577, dated Dec. 26, 2017, 14 pages.
Office Action received for Korean Patent Application No. 10-2016-7014577, dated Oct. 31, 2018, 11 pages.
Office Action received for Korean Patent Application No. 10-2016-7033638, dated Jan. 31, 2017, 6 pages.
Office Action received for Korean Patent Application No. 10-2017-7005939, dated Jun. 30, 2017, 6 pages.
Office Action received for Netherlands Patent Application No. 2015245, dated Jan. 24, 2017, 11 pages.
Office Action received for Netherlands Patent Application No. 2015239, dated Oct. 28, 2016, 13 pages.
Office Action Received for Taiwanese Patent Application No. 104124962, dated Nov. 29, 2016, 6 pages.
Office Action received for Taiwanese Patent Application No. 104124998, dated Nov. 29, 2016, 6 pages.
Office Action received for Taiwanese Patent Application No. 104117509, dated Aug. 22, 2016, 6 pages.
Office Action received for Taiwanese Patent Application No. 104124963, dated Jan. 5, 2017, 11 pages.
Office Action received for Taiwanese Patent Application No. 104124995, dated Dec. 1, 2016, 6 pages.
Office Action received for Taiwanese Patent Application No. 104124997, dated Dec. 8, 2016, 12 pages.
Office Action received for Taiwanese Patent Application No. 104128685, dated Jan. 4, 2017, 40 pages.
"Pentax K20D Operating Manual", http://www.ricoh-imaging.eu/en/operating-manuals-download.html, 2008, pp. 173-174.
Pre-Interview First Office Action received for U.S. Appl. No. 14/815,890, dated May 26, 2016, 4 pages.
Rehman, A, "Install Android 4.2 Gesture-Based Keyboard & Clock App On Jelly Bean 4.1 Or Higher", Excerpts From, Available online at <http://www.addictivetips.com/android/install-android-4-2-keyboard-clock-app-apk-on-jelly-bean-4-1-x/>, Nov. 3, 2012, 4 pages.
Restriction Requirement received for U.S. Appl. No. 14/815,890, dated Feb. 22, 2016, 5 pages.
"Reuse Animations—Synfig Animation Studio", Available online at: https://wiki.synfig.org/index.php?title=Doc:Reuse_Animations&oldid=18173, May 20, 2013, 5 pages.
Search report and opinion received for Danish Patent Application No. PA201770191, dated Jun. 30, 2017, 9 pages.
Search Report and Opinion Received for Netherland Patent Application No. 2015232, dated Jan. 25, 2017, 9 pages.
Search Report and Opinion received for Netherlands Patent Application No. 2015242, dated Jul. 4, 2017, 20 pages.
Search Report and Opinion received for Netherlands Patent Application No. 2018531, dated Jul. 27, 2017, 14 pages.
Smartwatch, "App Earth Space HD Live Wallpaper APK for Smart Watch", Version 1.7, Android version 2.2, Aug. 27, 2013, 1 page.
"Solar Walk Free", Vito Technology, Jun. 19, 2014, 9 pages.
Sony, "Live View™ micro display", Extended User Guide, Aug. 2010, 27 pages.
Sony, "Sony Smartwatch, User Guide", Dec. 2011, 18 pages.
Summons to attend oral proceedings received for European Patent Application No. 13811085.3, mailed on Jan. 26, 2018, 14 pages.
Summons to Attend Oral Proceedings received for European Patent Application No. 15730890.9, mailed on Sep. 10, 2018, 11 pages.
Summons to Attend Oral Proceedings received for European Patent Application No. 15730924.6, mailed on Jun. 13, 2018, 10 pages.
Summons to Attend Oral Proceedings received for European Patent Application No. 15771747.1, mailed on May 25, 2018, 17 pages.
Sun Set, "Sun Set solar image clock", Available at <https://web.archive.orgjweb/20140719005410/http://www.sunsetclock.com/>, 2013, 5 pages.
Talkandroid, "Android Wear walkthrough", Available online at: https://www.youtube.com/watch?v=4xntpZac4sw, Jun. 30, 2014, 1 page.
"Tropical Fish 14", Available online at: https://www.turbosquid.com/3d-models/tropical-fish-3d-model/388510, Feb. 4, 2008, 2 pages.
"UIKit User Interface Catalog: Page Controls", Available online at https://web.archive.org/web/20140703123442/https://developer.apple.com/library/ios/documentation/userexperience/conceptual/UIKitUICatalog/UIPageControl.html, Dec. 16, 2013, 4 pages.
"Utilization of Galaxy S4—S Health, ChatOn and Samsung Hub", Available at: http://seeit.kr/1263, Jun. 12, 2013, 25 pages.
Viticci, Frederico, "Checking Time Zones with Living Earth—MacStories", Available at <https://www.macstories.net/reviews/checking-time-zones-with-living-earth/>, Dec. 11, 2013, pp. 1-5.
Zukerman, Erez, "6 Beautiful, Interesting & Versatile Timer Apps [Android]", available at: http://www.makeuseof.com/tag/beautiful-interesting-versatile-timer-apps-android/, May 18, 2012, 5 pages.
Applicant-Initiated Interview Summary received for U.S. Appl. No. 15/405,122, dated Mar. 1, 2022, 4 pages.
Corrected Notice of Allowance received for U.S. Appl. No. 17/041,350, dated Mar. 15, 2022, 3 pages.
Notice of Acceptance received for Australian Patent Application No. 2020250323, dated Feb. 28, 2022, 3 pages.
Notice of Allowance received for Korean Patent Application No. 10-2021-7036246, dated Mar. 2, 2022, 5 pages (1 page of English Translation and 4 pages of Official Copy).
Office Action received for Australian Patent Application No. 2021203216, dated Mar. 7, 2022, 8 pages.
Office Action received for Danish Patent Application No. PA 2020 70612, dated Mar. 1, 2022, 2 pages.
Office Action received for Japanese Patent Application No. 2021-023661, dated Feb. 25, 2022, 6 pages (3 pages of English Translation and 3 pages of Official Copy).
Summons to Attend Oral Proceedings received for European Patent Application No. 13811085.3, dated Mar. 3, 2022, 3 pages.
Jurick D., ""iPhone Hacks"", Tips & Tools for Unlocking the Power of Your iPhone & iPod touch, Online:URL:https://api.pageplace.de/preview/DT0400.9780596550974_A23629666/preview-9780596550974_A23629666.pdf >, Apr. 2009, 49 pages.
Notice of Acceptance received for Australian Patent Application No. 2020239752, dated Jan. 31, 2022, 3 pages.
Notice of Allowance received for U.S. Appl. No. 17/192,161, dated Feb. 16, 2022, 8 pages.
Office Action received for Australian Patent Application No. 2021202797, dated Feb. 4, 2022, 5 pages.
Office Action received for Danish Patent Application No. PA202070624, dated Feb. 4, 2022, 4 pages.
Office Action received for Danish Patent Application No. PA202070625, dated Feb. 8, 2022, 2 pages.
Applicant-Initiated Interview Summary received for U.S. Appl. No. 15/421,865, dated Feb. 28, 2022, 5 pages.
Applicant-Initiated Interview Summary received for U.S. Appl. No. 16/389,722, dated Feb. 18, 2022, 5 pages.

(56) References Cited

OTHER PUBLICATIONS

Applicant-Initiated Interview Summary received for U.S. Appl. No. 17/031,854, dated Feb. 25, 2022, 5 pages.
Applicant-Initiated Interview Summary received for U.S. Appl. No. 17/031,859, dated Feb. 25, 2022, 4 pages.
Applicant-Initiated Interview Summary received for U.S. Appl. No. 17/031,874, dated Feb. 25, 2022, 4 pages.
Corrected Notice of Allowance received for U.S. Appl. No. 16/401,934, dated Feb. 28, 2022, 3 pages.
Final Office Action received for U.S. Appl. No. 17/068,386, dated Mar. 3, 2022, 29 pages.
Notice of Allowance received for U.S. Appl. No. 16/867,002, dated Mar. 1, 2022, 7 pages.
Notice of Allowance received for U.S. Appl. No. 16/894,309, dated Feb. 25, 2022, 9 pages.
Notice of Allowance received for U.S. Appl. No. 16/994,352, dated Mar. 2, 2022, 14 pages.
Notice of Allowance received for U.S. Appl. No. 17/041,350, dated Feb. 24, 2022, 6 pages.
Notice of Allowance received for U.S. Appl. No. 17/087,845, dated Mar. 3, 2022, 9 pages.
Notice of Allowance received for U.S. Appl. No. 17/157,728, dated Feb. 24, 2022, 7 pages.
Office Action received for Australian Patent Application No. 2020239748, dated Feb. 11, 2022, 2 pages.
Office Action received for Chinese Patent Application No. 201910858933.7, dated Dec. 30, 2021, 9 pages (4 pages of English Translation and 5 pages of Official Copy).
Office Action received for Chinese Patent Application No. 201911401161.0, dated Jan. 24, 2022, 6 pages (3 pages of English Translation and 3 pages of Official Copy).
Supplemental Notice of Allowance received for U.S. Appl. No. 17/030,318, dated Feb. 22, 2022, 2 pages.
Applicant-Initiated Interview Summary received for U.S. Appl. No. 16/987,275, dated Feb. 3, 2022, 4 pages.
Applicant-Initiated Interview Summary received for U.S. Appl. No. 17/041,350, dated Feb. 2, 2022, 2 pages.
Applicant-Initiated Interview Summary received for U.S. Appl. No. 17/157,728, dated Feb. 3, 2022, 5 pages.
Final Office Action received for U.S. Appl. No. 16/943,737, dated Feb. 4, 2022, 24 pages.
Intention to Grant received for Danish Patent Application No. PA202070615, dated Jan. 27, 2022, 2 pages.
Notice of Allowance received for Chinese Patent Application No. 201780034203.4, dated Jan. 17, 2022, 2 pages (1 page of English Translation and 1 page of Official Copy).
Notice of Allowance received for Chinese Patent Application No. 202010606407.4, dated Jan. 24, 2022, 2 pages (1 page of English Translation and 1 page of Official Copy).
Notice of Allowance received for Korean Patent Application No. 10-2021-7034748, dated Jan. 27, 2022, 6 pages (2 pages of English Translation and 4 pages of Official Copy).
Notice of Allowance received for U.S. Appl. No. 16/401,934, dated Feb. 2, 2022, 8 pages.
Office Action received for Australian Patent Application No. 2020239749, dated Jan. 21, 2022, 4 pages.
Office Action received for Australian Patent Application No. 2021201130, dated Jan. 27, 2022, 2 pages.
Office Action received for Danish Patent Application No. PA202070616, dated Jan. 27, 2022, 2 pages.
Office Action received for Japanese Patent Application No. 2020-160053, dated Jan. 31, 2022, 8 pages (4 pages of English Translation and 4 pages of Official Copy).
Office Action received for Japanese Patent Application No. 2020-160054, dated Jan. 21, 2022, 8 pages (4 pages of English Translation and 4 pages of Official Copy).
Applicant-Initiated Interview Summary received for U.S. Appl. No. 17/068,386, dated Jan. 13, 2022, 2 pages.
Corrected Notice of Allowance received for U.S. Appl. No. 16/888,629, dated Jan. 21, 2022, 2 pages.

Corrected Notice of Allowance received for U.S. Appl. No. 17/030,318, dated Jan. 24, 2022, 2 pages.
Final Office Action received for U.S. Appl. No. 16/861,651, dated Jan. 26, 2022, 16 pages.
Ilovex, ""Stripe Generator", a tool that makes it easy to create striped materials", Online available at: https://www.ilovex.co.jp/blog/system/webconsulting/stripe-generator.html, May 2, 2012, 3 pages (Official Copy only). {See Communication under 37 CFR § 1.98(a) (3)}.
Kasai, Yoshino, "Apple Watch Absolute Basics—Season 3—The key is to customize the dial", Mynavi Corporation, Online Available at: https://news.mynavi.jp/article/20171104-apple_watch/, Nov. 4, 2017, 5 pages (Official Copy only). {See Communication under 37 CFR § 1.98(a) (3)}.
Non-Final Office Action received for U.S. Appl. No. 17/031,874, dated Jan. 24, 2022, 18 pages.
Non-Final Office Action received for U.S. Appl. No. 17/373,163, dated Jan. 27, 2022, 14 pages.
Notice of Acceptance received for Australian Patent Application No. 2020239743, dated Jan. 13, 2022, 3 pages.
Notice of Acceptance received for Australian Patent Application No. 2020239774, dated Jan. 5, 2022, 3 pages.
Notice of Allowance received for Japanese Patent Application No. 2018-184532, dated Jan. 17, 2022, 4 pages (1 page of English Translation and 3 pages of Official Copy).
Office Action received for European Patent Application No. 20729346.5, dated Jan. 17, 2022, 8 pages.
Office Action received for Japanese Patent Application No. 2020-159825 dated Dec. 10, 2021, 4 pages (2 pages of English Translation and 2 pages of Official Copy).
Office Action received for Japanese Patent Application No. 2020-562622, dated Jan. 7, 2022, 13 pages (6 pages of English Translation and 7 pages of Official Copy).
Supplemental Notice of Allowance received for U.S. Appl. No. 16/894,309, dated Jan. 25, 2022, 2 pages.
Applicant-Initiated Interview Summary received for U.S. Appl. No. 16/861,651, dated Dec. 29, 2021, 5 pages.
Applicant-Initiated Interview Summary received for U.S. Appl. No. 17/031,765, dated Dec. 15, 2021, 4 pages.
Applicant-Initiated Interview Summary received for U.S. Appl. No. 17/192,161, dated Dec. 24, 2021, 4 pages.
Corrected Notice of Allowance received for U.S. Appl. No. 16/401,934, dated Dec. 23, 2021, 3 pages.
Decision of Appeal received for European Patent Application No. 15771747.1, dated Dec. 14, 2021, 21 pages.
Decision on Appeal received for U.S. Appl. No. 14/846,511, dated Dec. 29, 2021, 20 pages.
Decision to Grant received for European Patent Application No. 15730925.3, dated Dec. 9, 2021, 2 pages.
Final Office Action received for U.S. Appl. No. 16/994,352, dated Dec. 6, 2021, 14 pages.
Final Office Action received for U.S. Appl. No. 16/389,722, dated Dec. 6, 2021, 19 pages.
Final Office Action received for U.S. Appl. No. 16/935,002, dated Jan. 5, 2022, 25 pages.
Intention to Grant received for European Patent Application No. 16762356.0, dated Dec. 23, 2021, 8 pages.
International Preliminary Report on Patentability received for PCT Patent Application No. PCT/US2020/035199, dated Dec. 16, 2021, 14 pages.
Invitation to Pay Search Fees received for European Patent Application No. 20761084.1, dated Dec. 7, 2021, 3 pages.
Minutes of Oral Proceedings received for European Patent Application No. 16762356.0, dated Dec. 17, 2021, 5 pages.
Minutes of the Oral Proceedings received for European Patent Application No. 15771747.1, dated Dec. 1, 2021, 4 pages.
Non-Final Office Action received for U.S. Appl. No. 15/421,865, dated Dec. 29, 2021, 23 pages.
Non-Final Office Action received for U.S. Appl. No. 16/820,383, dated Jan. 10, 2022, 18 pages.
Non-Final Office Action received for U.S. Appl. No. 17/031,854, dated Dec. 27, 2021, 13 pages.

(56) References Cited

OTHER PUBLICATIONS

Non-Final Office Action received for U.S. Appl. No. 17/031,859, dated Dec. 24, 2021, 16 pages.
Non-Final received for U.S. Appl. No. 17/078,896, dated Dec. 24, 2021, 17 pages.
Notice of Acceptance received for Australian Patent Application No. 2019267413, dated Nov. 23, 2021, 3 pages.
Notice of Acceptance received for Australian Patent Application No. 2020269232, dated Dec. 16, 2021, 3 pages.
Notice of Allowance received for Chinese Patent Application No. 201380081349.6, dated Dec. 17, 2021, 2 pages (1 page of English Translation and 1 page of Official Copy).
Notice of Allowance received for Korean Patent Application No. 10-2021-7038005, dated Dec. 14, 2021, 4 pages (2 pages of English Translation and 2 pages of Official Copy).
Notice of Allowance received for U.S. Appl. No. 17/030,318, dated Jan. 5, 2022, 8 pages.
Office Action received for Australian Patent Application No. 2020250323, dated Dec. 14, 2021, 2 pages.
Office Action received for Chinese Patent Application No. 202010606407.4, dated Nov. 18, 2021, 6 pages (3 pages of English Translation and 3 pages of Official Copy).
Office Action received for Chinese Patent Application No. 202110363565.6, dated Nov. 16, 2021, 16 pages (9 pages of English Translation and 7 pages of Official Copy).
Office Action received for Chinese Patent Application No. 202110453180.9, dated Nov. 8, 2021, 21 pages (11 pages of English Translation and 10 pages of Official Copy).
Office Action received for Chinese Patent Application No. 202110454541.1, dated Oct. 20, 2021, 19 pages (10 pages of English Translation and 9 pages of Official Copy).
Office Action received for Indian Patent Application No. 202014041563, dated Dec. 30, 2021, 6 pages.
Office Action received for Indian Patent Application No. 202014041571, dated Dec. 17, 2021, 5 pages.
Office Action received for Indian Patent Application No. 202017041557, dated Dec. 8, 2021, 8 pages.
Office Action received for Japanese Patent Application No. 2020-124605, dated Dec. 17, 2021, 2 pages (1 page of English Translation and 1 page of Official Copy).
Office Action received for Japanese Patent Application No. 2020-159823, dated Dec. 23, 2021, 8 pages (4 pages of English Translation and 4 pages of Official Copy).
Office Action received for Japanese Patent Application No. 2020-160052, dated Dec. 17, 2021, 10 pages (5 pages of English Translation and 5 pages of Official Copy).
Office Action received for Korean Patent Application No. 10-2021-7036246, dated Nov. 26, 2021, 5 pages (2 pages of English Translation and 3 pages of Official Copy).
Office Action received for Korean Patent Application No. 10-2021-7036678, dated Dec. 22, 2021, 6 pages (2 pages of English Translation and 4 pages of Official Copy).
Result of Consultation received for European Patent Application No. 16762356.0, dated Nov. 29, 2021, 3 pages.
Search Report and Opinion received for Danish Patent Application No. PA202170113, dated Nov. 30, 2021, 9 pages.
Summons to Attend Oral Proceedings received for European Patent Application No. 20182116.2, dated Dec. 21, 2021, 7 pages.
Supplemental Notice of Allowance received for U.S. Appl. No. 16/894,309, dated Dec. 24, 2021, 2 pages.
Advisory Action received for U.S. Appl. No. 16/935,002, dated May 6, 2022, 3 Pages.
Applicant-Initiated Interview Summary received for U.S. Appl. No. 16/820,383, dated May 10, 2022, 2 pages.
Applicant-Initiated Interview Summary received for U.S. Appl. No. 16/943,737, dated Apr. 29, 2022, 6 pages.
Applicant-Initiated Interview Summary received for U.S. Appl. No. 17/317,042, dated Apr. 29, 2022, 2 pages.
Applicant-Initiated Interview Summary received for U.S. Appl. No. 17/341,839, dated Apr. 29, 2022, 2 pages.
Decision to Grant received for European Patent Application No. 16762356.0, dated Apr. 26, 2022, 2 pages.
Intention to Grant received for European Patent Application No. 20185974.1, dated Apr. 28, 2022, 8 pages.
Non-Final Office Action received for U.S. Appl. No. 17/516,537, dated May 5, 2022, 8 pages.
Notice of Allowance received for U.S. Appl. No. 17/031,543, dated May 11, 2022, 6 pages.
Notice of Allowance received for U.S. Appl. No. 17/373,163, dated May 11, 2022, 8 pages.
Office Action received for Danish Patent Application No. PA202070614, dated Apr. 28, 2022, 4 pages.
Office Action received for Danish Patent Application No. PA202070616, dated May 5, 2022, 3 pages.
Office Action received for Danish Patent Application No. PA202170113, dated May 3, 2022, 2 pages.
Office Action received for Indian Patent Application No. 202118025047, dated Apr. 26, 2022, 6 pages.
Corrected Notice of Allowance received for U.S. Appl. No. 17/192,161, dated Mar. 23, 2022, 2 pages.
International Preliminary Report on Patentability received for PCT Patent Application No. PCT/US2020/045814, dated Mar. 17, 2022, 12 pages.
Non-Final Office Action received for U.S. Appl. No. 17/031,765, dated Mar. 29, 2022, 33 pages.
Non-Final Office Action received for U.S. Appl. No. 17/341,839, dated Mar. 17, 2022, 14 pages.
Notice of Allowance received for Australian Patent Application No. 2020239748, dated Mar. 7, 2022, 3 pages.
Notice of Allowance received for Chinese Patent Application No. 202110194015.6, dated Mar. 9, 2022, 6 pages (3 pages of English Translation and 3 pages of Official Copy).
Notice of Allowance received for Korean Patent Application No. 10-2021-7025301, dated Mar. 16, 2022, 4 pages (1 page of English Translation and 3 pages of Official Copy).
Notice of Allowance received for Korean Patent Application No. 10-2021-7036678, dated Mar. 7, 2022, 5 pages (1 page of English Translation and 4 pages of Official Copy).
Notice of Allowance received for Korean Patent Application No. 10-2022-7001721, dated Feb. 28, 2022, 5 pages (1 page of English Translation and 4 pages of Official Copy).
Notice of Allowance received for U.S. Appl. No. 16/997,588, dated Mar. 18, 2022, 9 pages.
Notice of Allowance received for U.S. Appl. No. 17/197,628, dated Mar. 23, 2022, 35 pages.
Office Action received for Danish Patent Application No. PA202070610, dated Mar. 14, 2022, 7 pages.
Office Action received for Japanese Patent Application No. 2020-159824, dated Dec. 17, 2021, 13 pages (7 pages of English Translation and 6 pages of Official Copy).
Supplemental Notice of Allowance received for U.S. Appl. No. 16/867,002, dated Mar. 16, 2022, 2 pages.
Supplemental Notice of Allowance received for U.S. Appl. No. 17/030,318, dated Mar. 16, 2022, 2 pages.
Advisory Action received for U.S. Appl. No. 15/405,122, dated Apr. 18, 2022, 5 pages.
Applicant Initiated Interview Summary received for U.S. Appl. No. 17/381,570, dated Apr. 26, 2022, 5 pages.
Applicant-Initiated Interview Summary received for U.S. Appl. No. 17/031,543, dated Apr. 21, 2022, 2 pages.
Applicant-Initiated Interview Summary received for U.S. Appl. No. 17/078,896, dated Apr. 25, 2022, 2 pages.
Brief Communication Regarding Oral Proceedings received for European Patent Application No. 20182116.2, dated Apr. 13, 2022, 3 pages.
Corrected Notice of Allowance received for U.S. Appl. No. 17/157,728, dated Apr. 14, 2022, 6 pages.
Corrected Notice of Allowance received for U.S. Appl. No. 17/192,161, dated Apr. 22, 2022, 2 pages.
Corrected Notice of Allowance received for U.S. Appl. No. 17/197,628, dated Apr. 27, 2022, 3 pages.
Notice of Acceptance received for Australian Patent Application No. 2021203636, dated Apr. 14, 2022, 3 pages.

(56) References Cited

OTHER PUBLICATIONS

Office Action received for Chinese Patent Application No. 202110783860.7, dated Mar. 10, 2022, 15 pages (5 pages of English Translation and 10 pages of Official Copy).
Supplemental Notice of Allowance received for U.S. Appl. No. 16/997,588, dated Apr. 20, 2022, 4 pages.
Supplemental Notice of Allowance received for U.S. Appl. No. 17/030,321, dated Apr. 15, 2022, 2 pages.
Applicant-Initiated Interview Summary received for U.S. Appl. No. 17/373,163, dated Apr. 11, 2022, 2 pages.
Corrected Notice of Allowance received for U.S. Appl. No. 17/041,350, dated Apr. 4, 2022, 3 pages.
Corrected Notice of Allowance received for U.S. Appl. No. 17/157,728, dated Apr. 4, 2022, 3 pages.
Non-Final Office Action received for U.S. Appl. No. 17/031,543, dated Apr. 1, 2022, 9 pages.
Non-Final Office Action received for U.S. Appl. No. 17/031,671, dated Apr. 1, 2022, 32 pages.
Non-Final Office Action received for U.S. Appl. No. 17/381,570, dated Apr. 1, 2022, 29 pages.
Notice of Acceptance received for Australian Patent Application No. 2021201130, dated Mar. 28, 2022, 3 pages.
Notice of Allowance received for Japanese Patent Application No. 2020-159825, dated Mar. 25, 2022, 5 pages (1 page of English Translation and 4 pages of Official Copy).
Notice of Allowance received for Japanese Patent Application No. 2020-160054, dated Apr. 4, 2022, 4 pages (1 page of English Translation and 3 pages of Official Copy).
Notice of Allowance received for Korean Patent Application No. 10-2021-7031939, dated Apr. 5, 2022, 4 pages (1 page of English Translation and 4 pages of Official Copy).
Notice of Allowance received for U.S. Appl. No. 17/030,321, dated Apr. 1, 2022, 8 pages.
Office Action received for Australian Patent Application No. 2021203636, dated Mar. 23, 2022, 3 pages.
Result of Consultation received for European Patent Application No. 20185974.1, dated Apr. 4, 2022, 4 pages.
Supplemental Notice of Allowance received for U.S. Appl. No. 16/894,309, dated Apr. 8, 2022, 3 pages.
Supplemental Notice of Allowance received for U.S. Appl. No. 17/030,318, dated Apr. 4, 2022, 2 pages.
Applicant-Initiated Interview Summary received for U.S. Appl. No. 17/031,765, dated May 23, 2022, 5 pages.
"Garmin Edge 520", Owner's Manual, Online available at: https://www8.garmin.com/manuals/webhelp/edge520/EN-US/Edge_520_OM_EN-US.pdf, 2015, 24 pages.
Notice of Acceptance received for Australian Patent Application No. 2021202797, dated May 9, 2022, 3 pages.
Notice of Allowance received for Japanese Patent Application No. 2021-565837, dated May 16, 2022, 4 pages (1 page of English Translation and 3 pages of Official Copy).
Notice of Allowance received for U.S. Appl. No. 16/987,275, dated May 16, 2022, 7 pages.
Notice of Allowance received for U.S. Appl. No. 17/078,896, dated May 13, 2022, 8 pages.
Office Action received for Australian Patent Application No. 2022202292, dated May 10, 2022, 2 pages.
Office Action received for Danish Patent Application No. PA202070612, dated May 10, 2022, 2 pages.
Office Action received for Danish Patent Application No. PA202070613, dated May 10, 2022, 2 pages.
Office Action received for European Patent Application No. 20761084.1, dated May 9, 2022, 9 pages.
Office Action received for Japanese Patent Application No. 2020-124605, dated May 13, 2022, 6 pages (3 pages of English Translation and 3 pages of Official Copy).
Summons to Attend Oral Proceedings received for European Patent Application No. 20721342.2, dated May 20, 2022, 11 pages.
Supplemental Notice of Allowance received for U.S. Appl. No. 17/192,161, dated May 13, 2022, 2 pages.
Applicant-Initiated Interview Summary received for U.S. Appl. No. 17/516,537, dated Jul. 5, 2022, 4 pages.
Invitation to Pay Search Fees received for European Patent Application No. 20730136.7, dated Jul. 1, 2022, 4 pages.
Office Action received for Chinese Patent Application No. 202110363565.6, dated May 7, 2022, 12 pages (7 pages of English Translation and 5 pages of Official Copy).
Advisory Action received for U.S. Appl. No. 16/943,737, dated Jun. 1, 2022, 6 pages.
Applicant Initiated Interview Summary received for U.S. Appl. No. 17/031,671, dated Jun. 13, 2022, 7 pages.
Corrected Notice of Allowance received for U.S. Appl. No. 16/987,275, dated Jun. 8, 2022, 3 pages.
Corrected Notice of Allowance received for U.S. Appl. No. 17/031,543, dated Jun. 8, 2022, 3 pages.
Corrected Notice of Allowance received for U.S. Appl. No. 17/373,163, dated Jun. 27, 2022, 5 pages.
Final Office Action received for U.S. Appl. No. 16/820,383, dated Jun. 22, 2022, 21 pages.
Final Office Action received for U.S. Appl. No. 17/031,854, dated Jun. 10, 2022, 15 pages.
Final Office Action received for U.S. Appl. No. 17/031,859, dated Jun. 10, 2022, 13 pages.
Final Office Action received for U.S. Appl. No. 17/031,874, dated Jun. 2, 2022, 19 pages.
Intention to Grant received for European Patent Application No. 20182116.2, dated Jun. 2, 2022, 8 pages.
Minutes of the Oral Proceedings received for European Patent Application No. 20182116.2, dated May 24, 2022, 7 pages.
Non-Final Office Action received for U.S. Appl. No. 17/030,318, dated Jun. 14, 2022, 9 pages.
Non-Final Office Action received for U.S. Appl. No. 17/030,337, dated Jun. 14, 2022, 13 pages.
Non-Final Office Action received for U.S. Appl. No. 17/030,340, dated Jun. 14, 2022, 15 pages.
Notice of Acceptance received for Australian Patent Application No. 2020239749, dated May 27, 2022, 3 pages.
Notice of Allowance received for Chinese Patent Application No. 202110454541.1, dated May 31, 2022, 6 pages (3 pages of English Translation and 3 pages of Official Copy).
Notice of Allowance received for Japanese Patent Application No. 2020-160052, dated Jun. 3, 2022, 4 pages (1 page of English Translation and 3 pages of Official Copy).
Notice of Allowance received for Korean Patent Application No. 10-2022-7008569, dated May 19, 2022, 5 pages (2 pages of English Translation and 3 pages of Official Copy).
Notice of Allowance received for Korean Patent Application No. 10-2022-7017918, dated Jun. 13, 2022, 6 pages (2 pages of English Translation and 4 pages of Official Copy).
Notice of Allowance received for U.S. Appl. No. 16/994,352, dated Jun. 3, 2022, 9 pages.
Notice of Allowance received for U.S. Appl. No. 17/192,161, dated May 27, 2022, 8 pages.
Notice of Allowance received for U.S. Appl. No. 17/197,628, dated Jun. 24, 2022, 8 pages.
Office Action received for Australian Patent Application No. 2021204422, dated May 31, 2022, 2 pages.
Office Action received for Danish Patent Application No. PA202070623, dated May 23, 2022, 3 pages.
Office Action received for Danish Patent Application No. PA202070815, dated Jun. 14, 2022, 3 pages.
Office Action received for European Patent Application No. 21169911.1, dated Jun. 3, 2022, 5 pages.
Office Action received for European Patent Application No. 21177569.7, dated Jun. 9, 2022, 5 pages.
Office Action received for Korean Patent Application No. 10-2020-0123815, dated May 31, 2022, 10 pages (5 pages of English Translation and 5 pages of Official Copy).
Office Action received for Korean Patent Application No. 10-2020-0123852, dated Jun. 9, 2022, 10 pages (4 pages of English Translation and 6 pages of Official Copy).

(56) References Cited

OTHER PUBLICATIONS

Office Action received for Korean Patent Application No. 10-2020-0123857, dated Jun. 9, 2022, 12 pages (5 pages of English Translation and 7 pages of Official Copy).
Office Action received for Korean Patent Application No. 10-2020-0123887, dated Jun. 9, 2022, 5 pages (2 pages of English Translation and 3 pages of Official Copy).
Office Action received for Korean Patent Application No. 10-2020-7032187, dated Jun. 10, 2022, 16 pages (7 pages of English Translation and 9 pages of Official Copy).
Summons to Attend Oral Proceedings received for European Patent Application No. 20203526.7, dated Jun. 23, 2022, 9 pages.
Supplemental Notice of Allowance received for U.S. Appl. No. 16/994,352, dated Jun. 20, 2022, 2 pages.
Supplemental Notice of Allowance received for U.S. Appl. No. 17/030,321, dated Jun. 10, 2022, 2 pages.
Supplemental Notice of Allowance received for U.S. Appl. No. 17/030,321, dated May 27, 2022, 2 pages.
Supplemental Notice of Allowance received for U.S. Appl. No. 17/192,161, dated Jun. 13, 2022, 2 pages.
Final Office Action received for U.S. Appl. No. 17/381,570, dated Jul. 20, 2022, 22 pages.
Intention to Grant received for Danish Patent Application No. PA202070623, dated Jul. 20, 2022, 2 pages.
Notice of Allowance received for Japanese Patent Application No. 2019-044107, dated Jul. 11, 2022, 31 pages (1 page of English Translation and 30 pages of Official Copy).
Corrected Notice of Allowance received for U.S. Appl. No. 17/030,337, dated Aug. 31, 2022, 2 pages.
Extended European Search Report received for European Patent Application No. 22173249.8, dated Aug. 19, 2022, 15 pages.
International Preliminary Report on Patentability received for PCT Patent Application No. PCT/US2021/017736, dated Aug. 25, 2022, 19 pages.
Non-Final Office Action received for U.S. Appl. No. 17/556,165, dated Sep. 7, 2022, 15 pages.
Notice of Allowance received for Japanese Patent Application No. 2020-562622, dated Aug. 26, 2022, 4 pages (1 page of English Translation and 3 pages of Official Copy).
Notice of Allowance received for Japanese Patent Application No. 2022-107902, dated Aug. 26, 2022, 4 pages (1 page of English Translation and 3 pages of Official Copy).
Notice of Allowance received for Korean Patent Application No. 10-2020-0123815, dated Aug. 26, 2022, 7 pages (2 pages of English Translation and 5 pages of Official Copy).
Office Action received for Australian Patent Application No. 2021245228, dated Aug. 31, 2022, 2 pages.
Office Action received for Chinese Patent Application No. 201911401161.0, dated Aug. 9, 2022, 17 pages (9 pages of English Translation and 8 pages of Official Copy).
Office Action received for Japanese Patent Application No. 2021-131726, datedn Aug. 22, 2022, 8 pages (4 pages of English Translation and 4 pages of Official Copy).
Office Action received for Korean Patent Application No. 10-2022-0061486, dated Aug. 29, 2022, 5 pages (2 pages of English Translation and 3 pages of Official Copy).
Programmatically download APK from google play store, Retrieved from the Internet: https://stackoverflow.com/questions/13703982/programmatically download-apk-from-google-play-store/13704021#13704021, Dec. 10, 2012, 2 pages.
Google, "Android User's Guide", Retrieved from the Internet: https://static.googleusercontent.com/media/www.google.com/en//help/hc/pdfs/mobile/AndroidUsersGuide-30-100.pdf, Feb. 23, 2011, 140 pages.
Advisory Action received for U.S. Appl. No. 16/861,651, dated Jul. 29, 2022, 4 pages.
Applicant-Initiated Interview Summary received for U.S. Appl. No. 17/030,337, dated Jul. 27, 2022, 2 pages.
Applicant-Initiated Interview Summary received for U.S. Appl. No. 17/031,854, dated Jul. 27, 2022, 5 pages.
Applicant-Initiated Interview Summary received for U.S. Appl. No. 17/031,859, dated Jul. 28, 2022, 3 pages.
Applicant-Initiated Interview Summary received for U.S. Appl. No. 17/031,874, dated Jul. 27, 2022, 5 pages.
Communication of the Board of Appeal received for European Patent Application No. 13811085.3, dated Jul. 28, 2022, 13 pages.
Corrected Notice of Allowance received for U.S. Appl. No. 17/197,628, dated Jul. 29, 2022, 2 pages.
Decision to Grant received for Danish Patent Application No. PA202070615, dated Jul. 29, 2022, 2 pages.
Non-Final Office Action received for U.S. Appl. No. 17/591,184, dated Aug. 4, 2022, 18 pages.
Notice of Acceptance received for Australian Patent Application No. 2021203216, dated Jul. 26, 2022, 3 pages.
Notice of Allowance received for U.S. Appl. No. 16/987,275, dated Jul. 27, 2022, 6 pages.
Notice of Allowance received for U.S. Appl. No. 17/317,042, dated Jul. 26, 2022, 12 pages.
Notice of Allowance received for U.S. Appl. No. 17/373,163, dated Jul. 27, 2022, 8 pages.
Office Action received for Chinese Patent Application No. 202110453180.9, dated Jun. 16, 2022, 14 pages (7 pages of English Translation and 7 pages of Official Copy).
Office Action received for European Patent Application No. 20729346.5, dated Jul. 28, 2022, 9 pages.
Office Action received for Japanese Patent Application No. 2020-160053, dated Aug. 1, 2022, 8 pages (4 pages of English Translation and 4 pages of Official Copy).
Supplemental Notice of Allowance received for U.S. Appl. No. 17/030,321, dated Jul. 27, 2022, 2 pages.
Corrected Notice of Allowance received for U.S. Appl. No. 17/031,543, dated Jul. 18, 2022, 2 pages.
Corrected Notice of Allowance received for U.S. Appl. No. 17/373,163, dated Jul. 15, 2022, 5 pages.
Final Office Action received for U.S. Appl. No. 15/421,865, dated Jul. 12, 2022, 27 pages.
Final Office Action received for U.S. Appl. No. 17/341,839, dated Jul. 18, 2022, 15 pages.
Non-Final Office Action received for U.S. Appl. No. 16/389,722, dated Jul. 7, 2022, 16 pages.
Notice of Acceptance received for Australian Patent Application No. 2022202292, dated Jul. 6, 2022, 3 pages.
Notice of Allowance received for Japanese Patent Application No. 2021-105941, dated Jul. 4, 2022, 4 pages (1 page of English Translation and 3 pages of Official Copy).
Summons to Attend Oral Proceedings received for European Patent Application No. 17810723.1, dated Jul. 5, 2022, 8 pages.
Applicant-Initiated Interview Summary received for U.S. Appl. No. 17/556,165, dated Oct. 28, 2022, 4 pages.
Brief Communication Regarding Oral Proceedings received for European Patent Application No. 20721342.2, dated Oct. 18, 2022, 1 page.
Corrected Notice of Allowance received for U.S. Appl. No. 17/341,839, dated Oct. 26, 2022, 2 pages.
Intention to Grant received for European Patent Application No. 21177569.7, dated Oct. 27, 2022, 8 pages.
International Search Report and Written Opinion received for PCT Patent Application No. PCT/US2022/026371, dated Oct. 12, 2022, 16 pages.
Invitation to Pay Additional Fees received for PCT Patent Application No. PCT/US2022/026371, dated Aug. 18, 2022, 9 pages.
Non-Final Office Action received for U.S. Appl. No. 17/713,016, dated Oct. 27, 2022, 25 pages.
Notice of Allowance received for Korean Patent Application No. 10-2021-7036016, dated Sep. 28, 2022, 7 pages (2 pages of English Translation and 5 pages of Official Copy).
Office Action received for European Patent Application No. 19724997.2, dated Oct. 27, 2022, 5 pages.
Result of Consultation received for European Patent Application No. 20721342.2, dated Oct. 18, 2022, 3 pages.
Summons to Attend Oral Proceedings received for European Patent Application No. 18727543.3, dated Oct. 25, 2022, 8 pages.

(56) References Cited

OTHER PUBLICATIONS

Updated Notice of Allowance received for U.S. Appl. No. 17/030,340, dated Nov. 2, 2022, 2 pages.
Applicant-Initiated Interview Summary received for U.S. Appl. No. 17/341,839, dated Sep. 16, 2022, 2 pages.
Final Office Action received for U.S. Appl. No. 17/031,765, dated Sep. 12, 2022, 37 pages.
Intention to Grant received for Danish Patent Application No. PA202070815, dated Sep. 13, 2022, 2 pages.
Non-Final Office Action received for U.S. Appl. No. 17/031,859, dated Sep. 12, 2022, 17 pages.
Notice of Allowance received for U.S. Appl. No. 17/030,343, dated Sep. 16, 2022, 11 pages.
Office Action received for Danish Patent Application No. PA202070612, dated Sep. 12, 2022, 3 pages.
Office Action received for Indian Patent Application No. 202017048447, dated Sep. 5, 2022, 6 pages.
Heinrich Peter, "More Player Engagement Potential: GameCircle Now Rewards Player Experience across Games", Available online at: https://www.developer.amazon.com/es-mx/blogs/home/tag/badges, Apr. 11, 2014, 9 pages.
Lein et al., "Patternizer", Available online at: https://patternizer.com/, Apr. 2016, 5 pages.
Venusivenus, "Nike Training Club", Available online at https://www.youtube.com/watch?v=_pe6fqJPA04, Mar. 28, 2011, 6 pages.
Corrected Notice of Allowance received for U.S. Appl. No. 17/030,337, dated Oct. 18, 2022, 2 pages.
Decision to Refuse received for Japanese Patent Application No. 2020-159824, dated Sep. 30, 2022, 6 pages (3 pages of English Translation and 3 pages of Official Copy).
Final Office Action received for U.S. Appl. No. 17/516,537, dated Oct. 11, 2022, 9 pages.
Notice of Acceptance received for Australian Patent Application No. 2021245228, dated Oct. 4, 2022, 3 pages.
Notice of Acceptance received for Australian Patent Application No. 2022220279, dated Sep. 27, 2022, 3 pages.
Notice of Allowance received for Japanese Patent Application No. 2022-512865, dated Oct. 3, 2022, 4 pages (1 page of English Translation and 3 pages of Official Copy).
Office Action received for Australian Patent Application No. 2021250863, dated Oct. 6, 2022, 6 pages.
Office Action received for Danish Patent Application No. PA202070613, dated Oct. 13, 2022, 7 pages.
Office Action received for European Patent Application No. 20730136.7, dated Oct. 6, 2022, 11 pages.
Office Action received for Japanese Patent Application No. 2021-023661, dated Oct. 3, 2022, 8 pages (4 pages of English Translation and 4 pages of Official Copy).
Applicant-Initiated Interview Summary received for U.S. Appl. No. 16/820,383, dated Aug. 12, 2022, 2 pages.
Applicant-Initiated Interview Summary received for U.S. Appl. No. 17/381,570, dated Aug. 24, 2022, 5 pages.
Corrected Notice of Allowance received for U.S. Appl. No. 17/030,321, dated Aug. 15, 2022, 3 pages.
Corrected Notice of Allowance received for U.S. Appl. No. 17/031,543, dated Aug. 22, 2022, 2 pages.
Decision to Grant received for European Patent Application No. 20185974.1, dated Aug. 19, 2022, 3 pages.
Intention to Grant received for Danish Patent Application No. PA202070614, dated Aug. 8, 2022, 2 pages.
Notice of Acceptance received for Australian Patent Application No. 2021204422, dated Aug. 15, 2022, 3 pages.
Notice of Allowance received for Japanese Patent Application No. 2021-122610, dated Aug. 5, 2022, 4 pages (1 page of English Translation and 3 pages of Official Copy).
Notice of Allowance received for Korean Patent Application No. 10-2021-7026284, dated Jul. 28, 2022, 6 pages (2 pages of English Translation and 4 pages of Official Copy).
Notice of Allowance received for U.S. Appl. No. 17/030,337, dated Aug. 22, 2022, 10 pages.
Office Action received for Chinese Patent Application No. 202111457936.3, dated Jul. 5, 2022, 18 pages (9 pages of English Translation and 9 pages of Official Copy).
Office Action received for Danish Patent Application No. PA202170113, dated Aug. 18, 2022, 2 pages.
Office Action received for Japanese Patent Application No. 2020-159823, dated Aug. 15, 2022, 6 pages (3 pages of English Translation and 3 pages of Official Copy).

\* cited by examiner

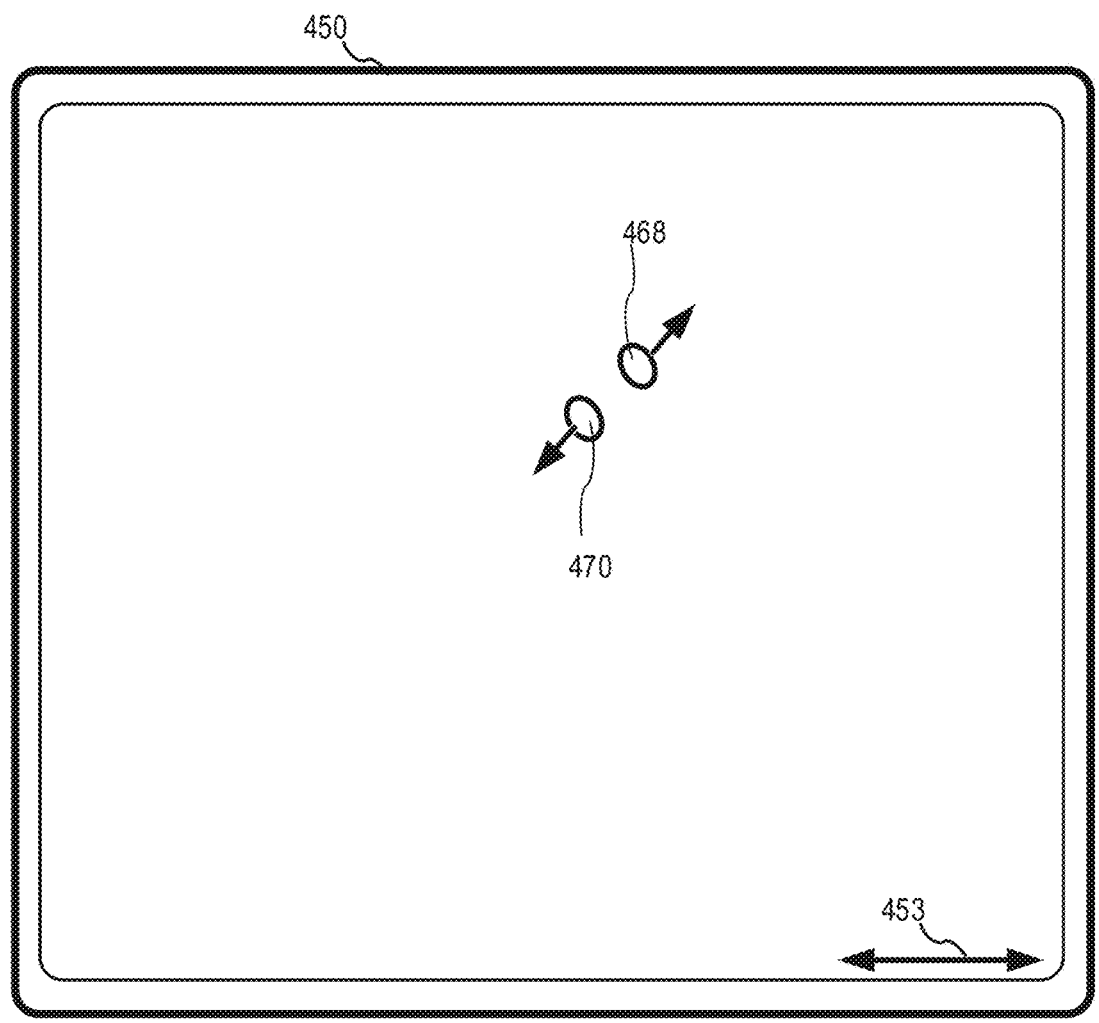
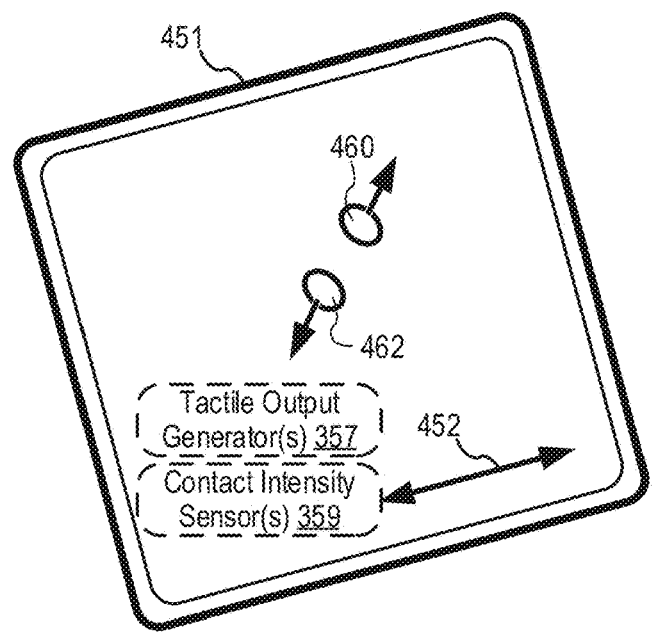
FIG. 4B

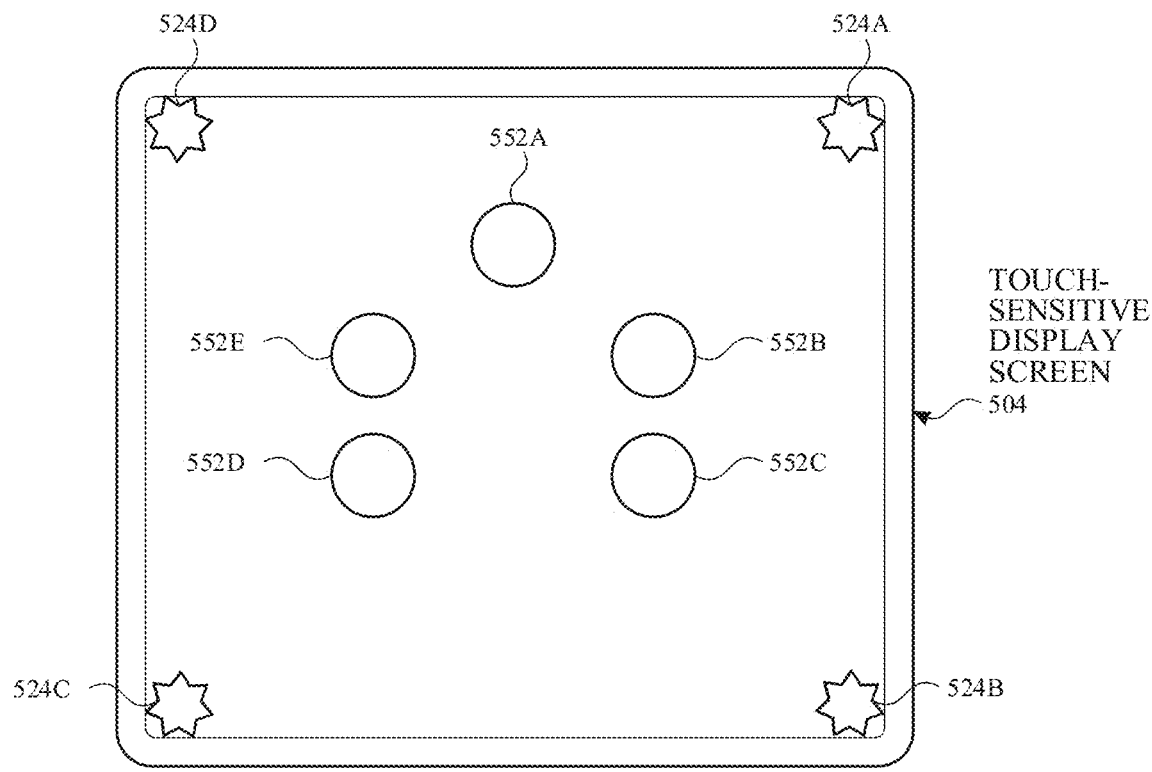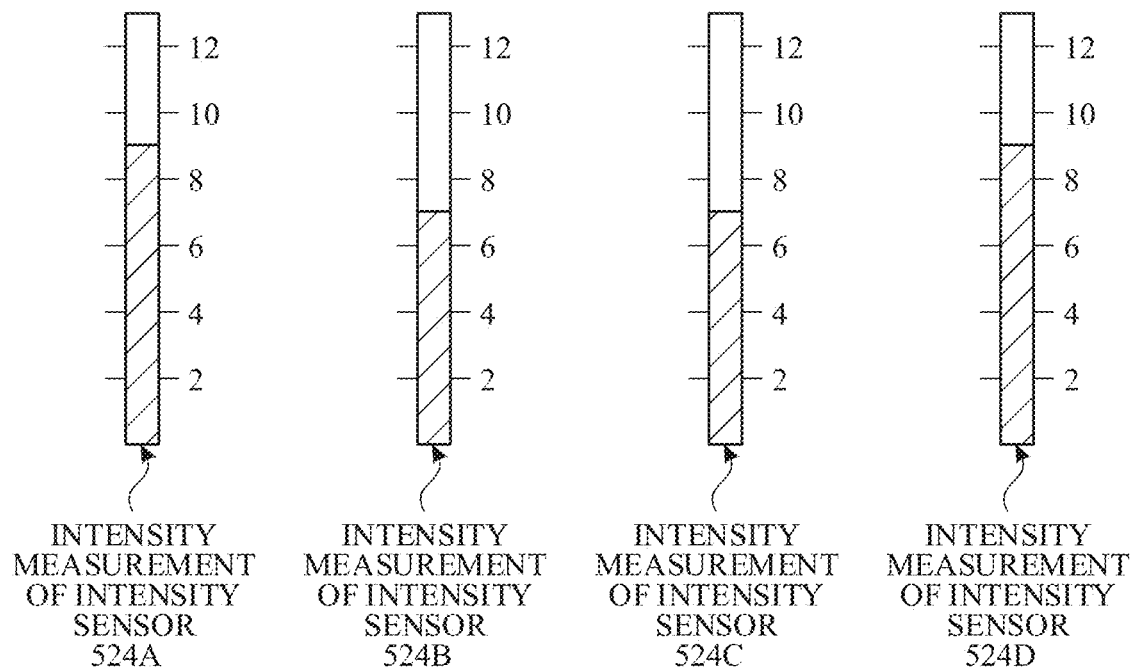
FIG. 5C

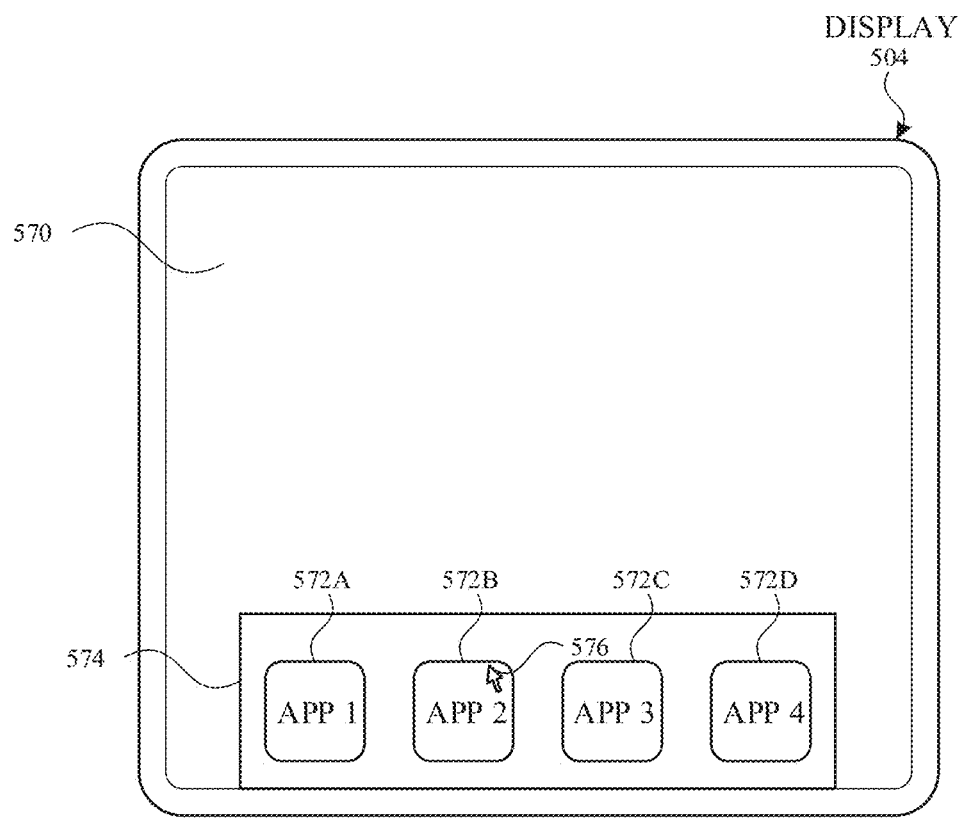
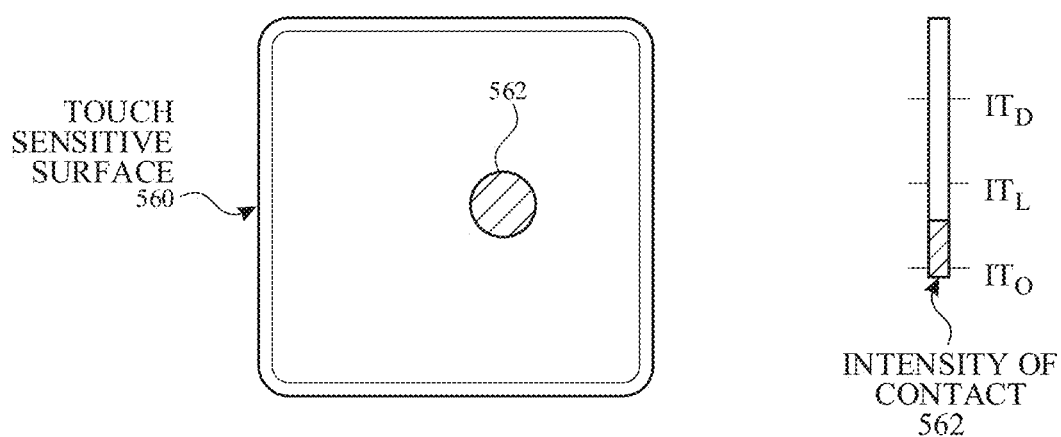
*FIG. 5E*

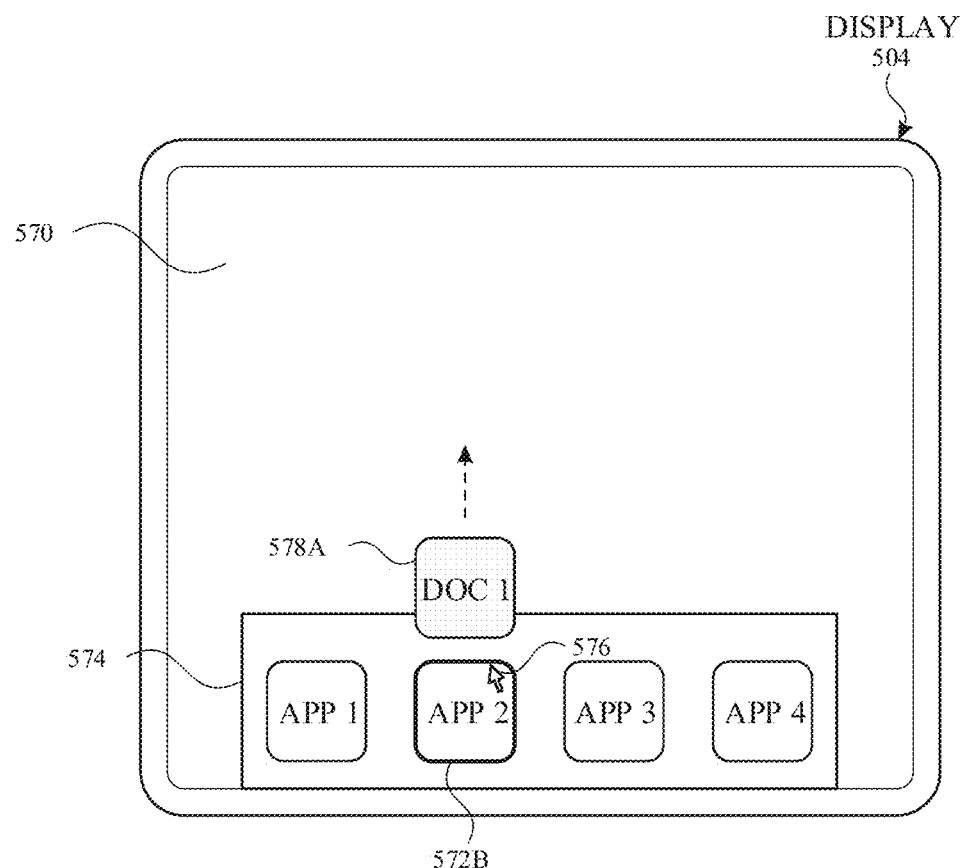
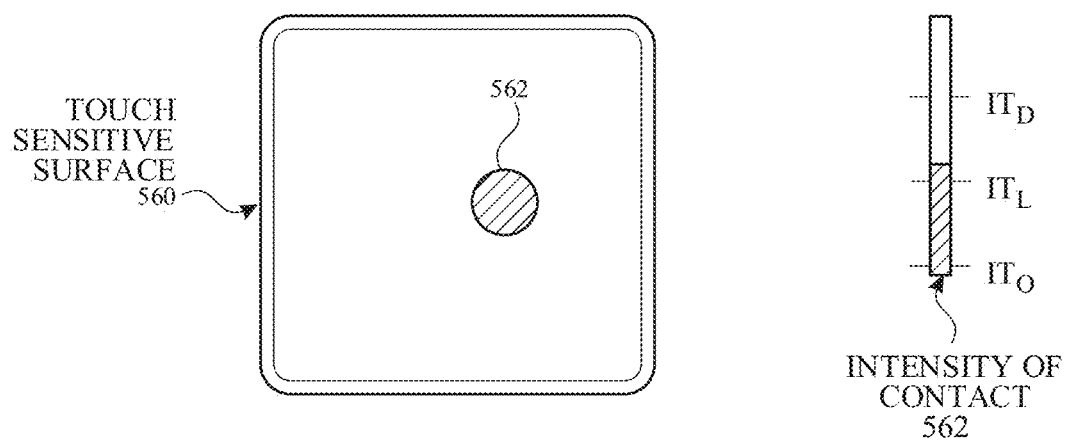
FIG. 5F

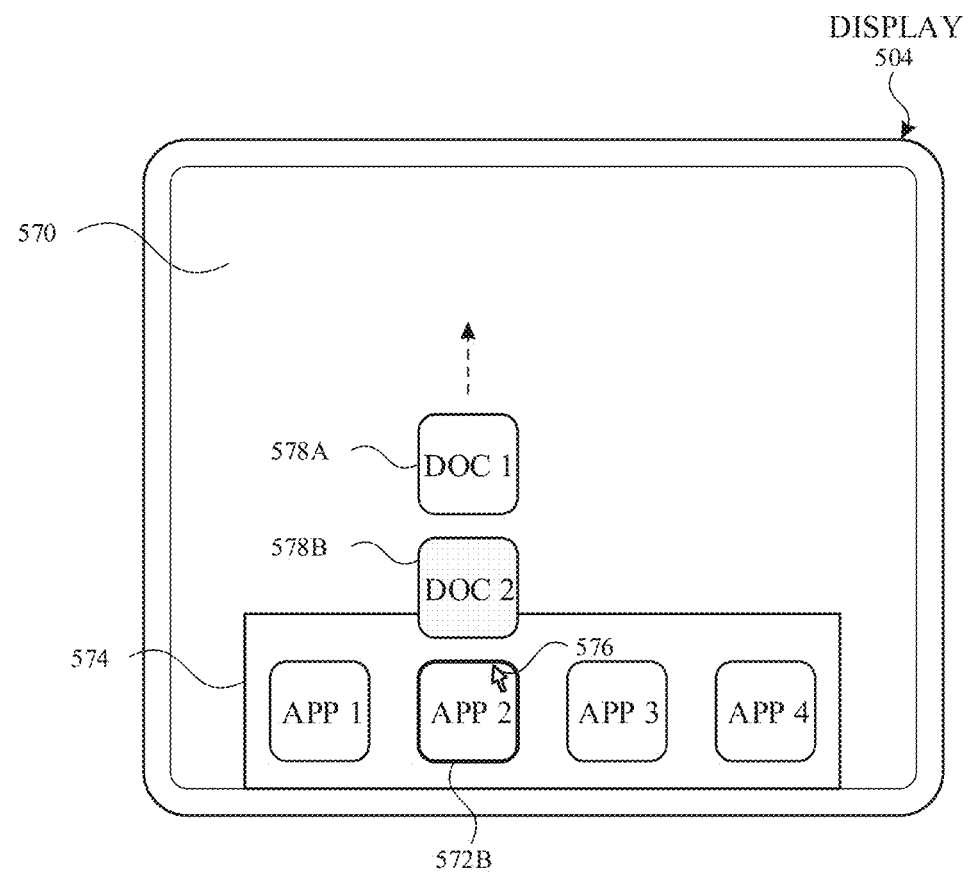
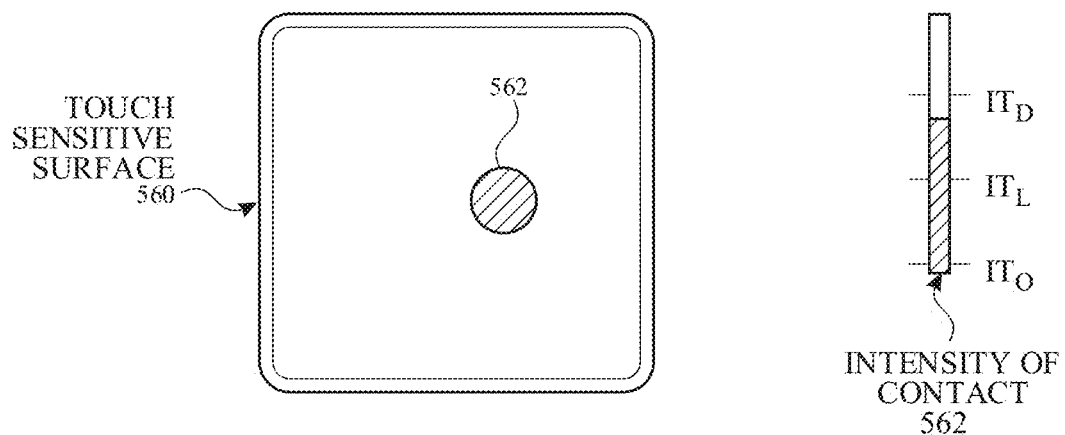
FIG. 5G

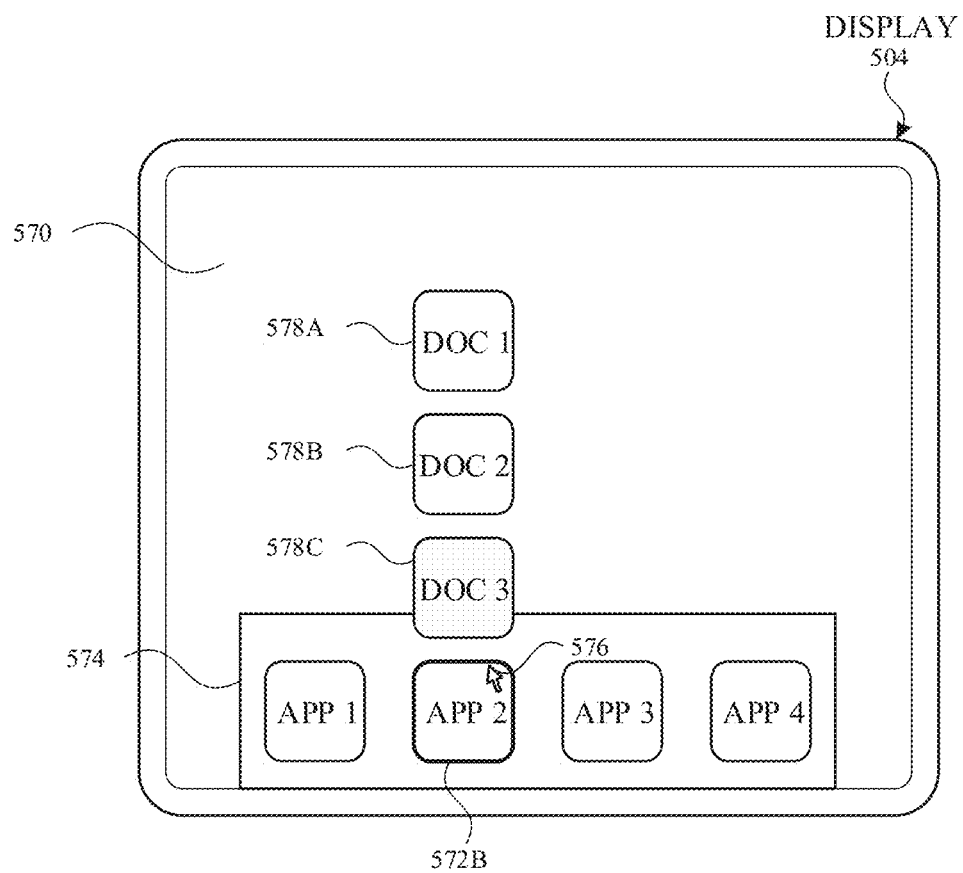
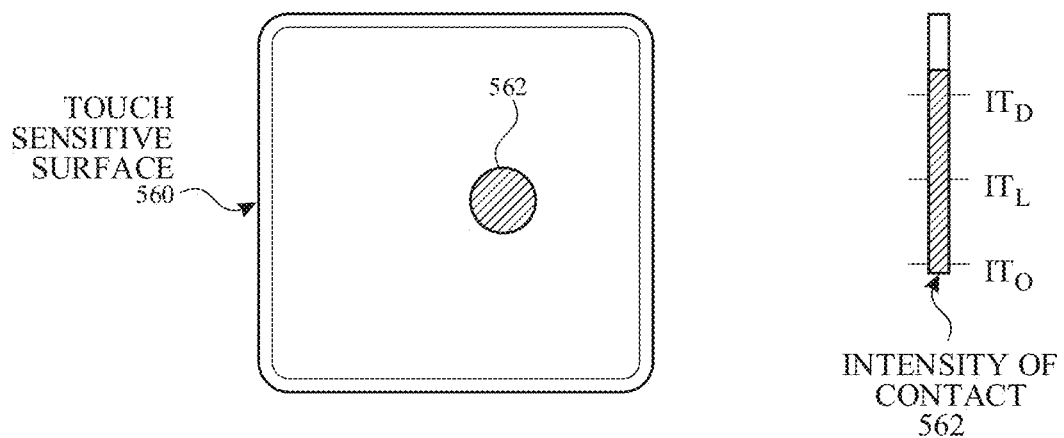
FIG. 5H

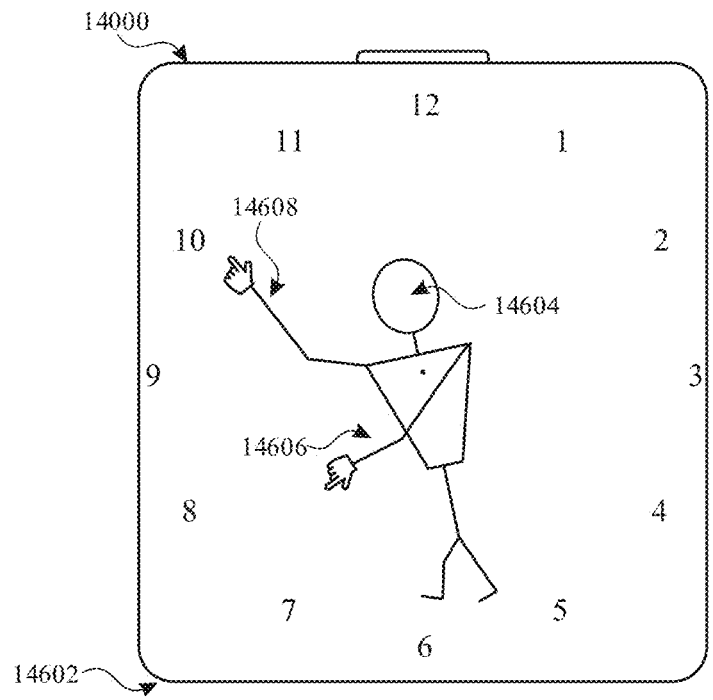
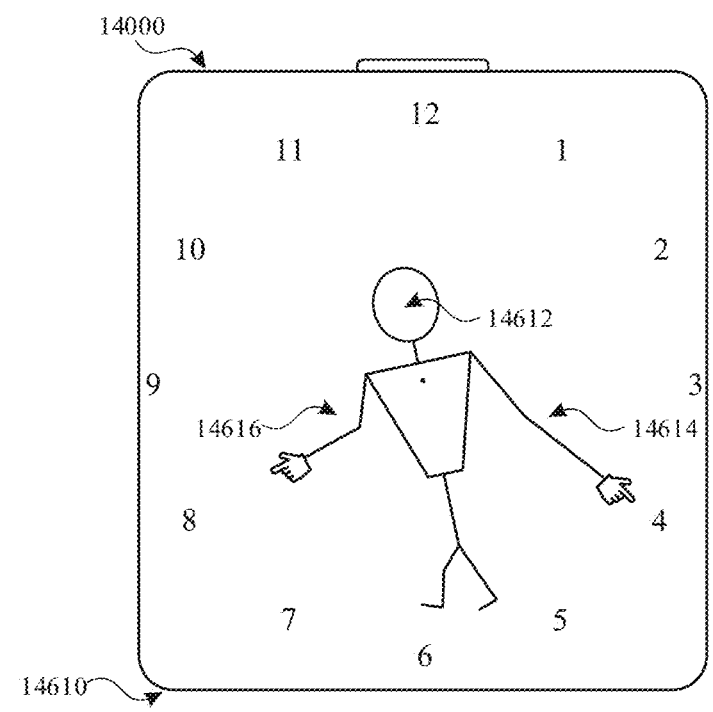
FIG. 14B

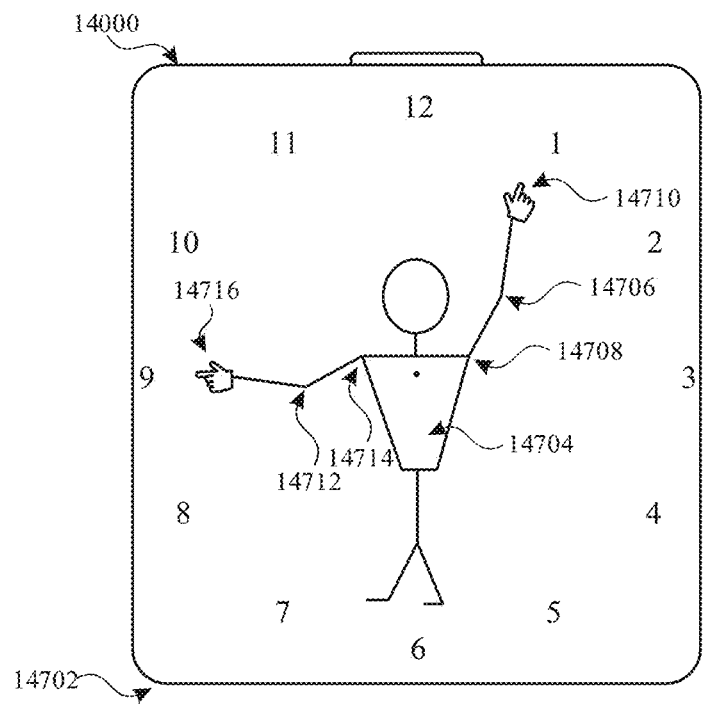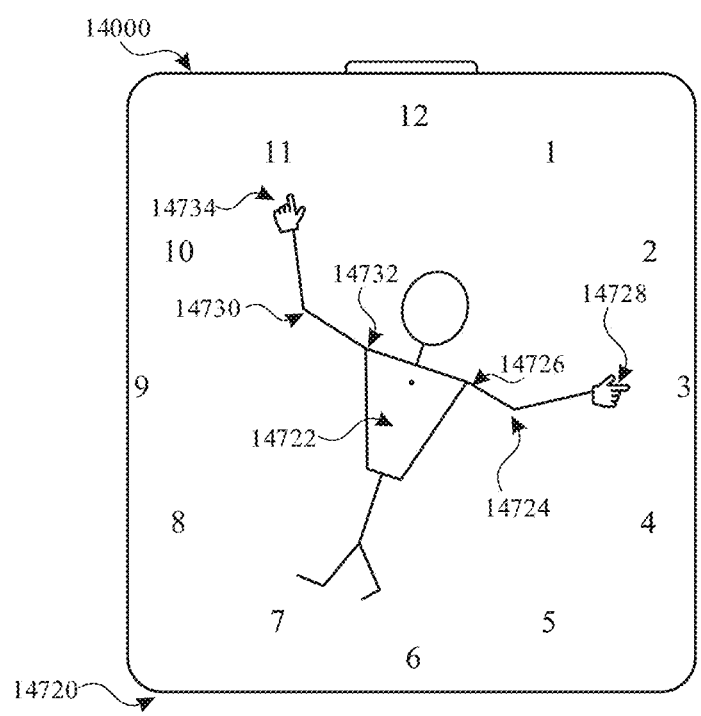
FIG. 14C

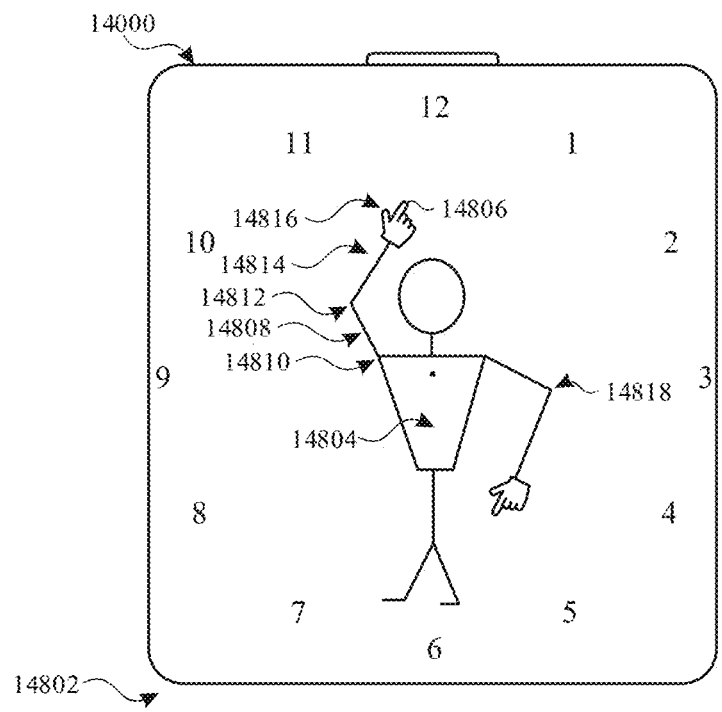
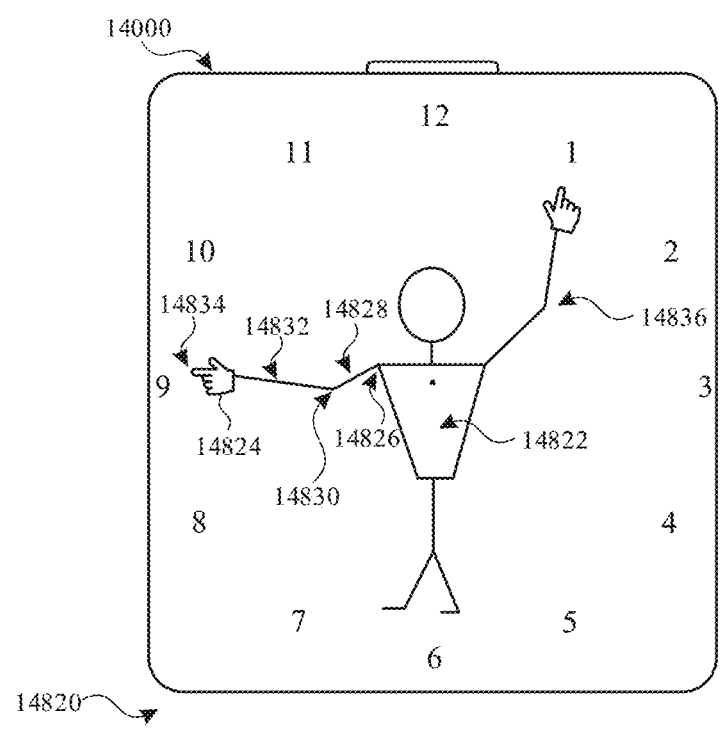
FIG. 14D

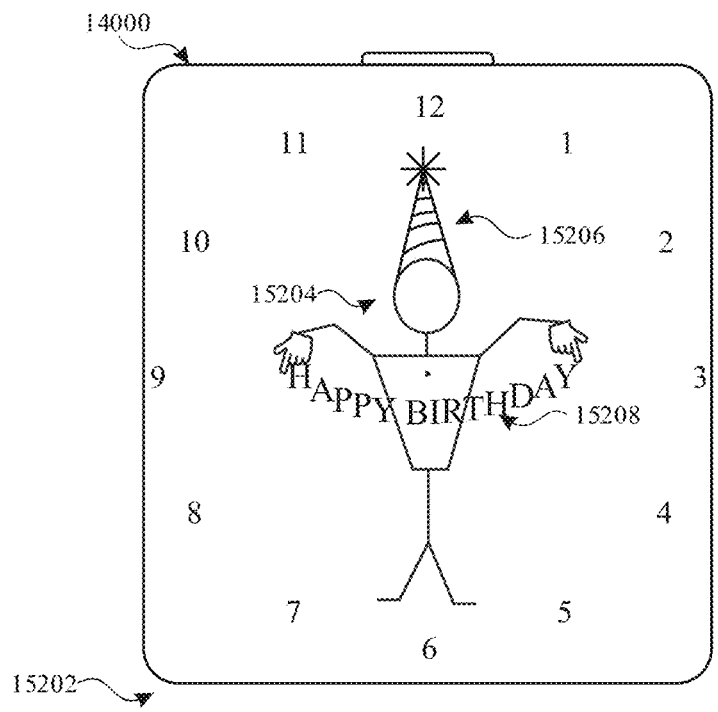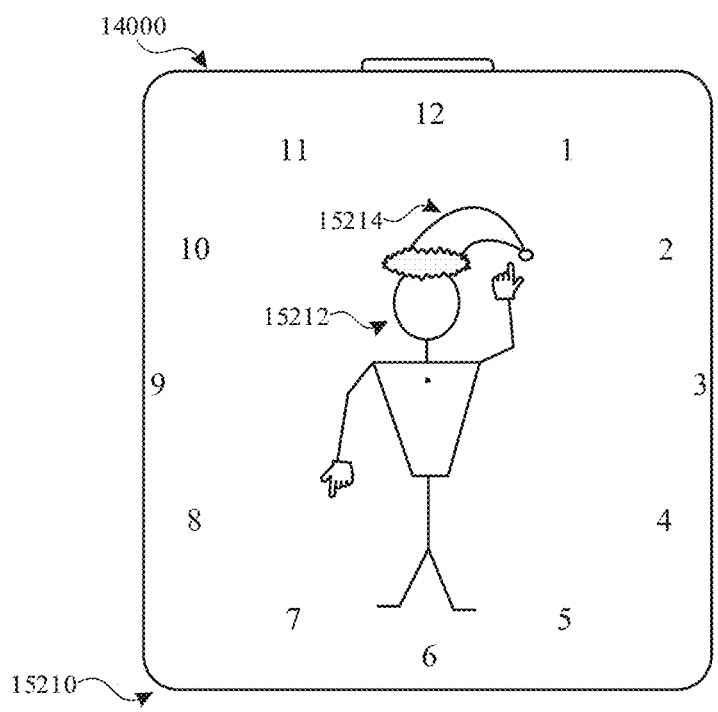
*FIG. 14H*

2100

2102

Display a clock face that indicates current time and includes a user interface object with an hour hand and a minute hand, one or more indications of an hourly timescale, and a stopwatch hand

2104

Receive data representing a user input

2106

In response to receiving the data, substitute the one or more indications of an hourly timescale with an indication of a first timescale for the stopwatch hand

2108

Animate the stopwatch hand to reflect passage of time

Display a user interface screen that includes a first affordance representing a simulation of a first region of the Earth as illuminated by the Sun at current time and a second affordance that indicates the current time

2204

Receive data representing a user input

2206

In response to receiving the data, rotate the simulation of the Earth to display a second region of the Earth as illuminated by the Sun at the current time Optionally, display a third affordance representing a moon, detect a contact on the displayed third affordance, and in response to detecting the contact, update the user interface screen by displaying a fourth affordance representing a simulation of the Moon as seen from the Earth at the current time and a fifth affordance that indicates the current time Optionally, display a sixth affordance representing a solar system, detect a contact on the displayed sixth affordance, and in response to detecting the contact, update the user interface screen by displaying a seventh affordance including representations of the Sun, the Earth, and one or more non-Earth planets at their respective positions at a current time and an eighth affordance that indicates the current time

Display a user interface screen that includes a first portion indicating daytime; a second portion indicating nighttime; a user interface object representing a sinusoidal wave with a period representing a day; a first affordance representing the Sun displayed at a first position on the sinusoidal wave indicating a current time of the day and whether the current time of the day is during daytime or nighttime; and a second affordance, the second affordance indicating the current time of day

▼

2304

Optionally, receive a contact on the touch-sensitive display at the first affordance at the first position indicating the current time

▼

2306

Optionally, while continuing to receive the user contact, detect movement of the user contact from the first position to a second position on the displayed sinusoidal wave without a break in contact of the user contact on the touch-sensitive display (second position on the sinusoidal wave indicates a non-current time)

▼

2308

Optionally, in response to detecting the contact at the second position, translate the first affordance on-screen from the first position on the sinusoidal wave to the second position on the sinusoidal wave (translation tracks the displayed sinusoidal wave)

▼

2310

Optionally, update the second affordance to indicate the non-current time

Display a user interface screen that includes a background, based on an image, with a plurality of pixels (a subset of the pixels are modified in appearance relative to the image such that the subset of pixels represents one or more of a first user interface object indicating a date and a second user interface object indicating a time of day)

Optionally, one of the first user interface object and the second user interface object is a color independent of the background

2404

Optionally, if one of the first user interface object and the second user interface object is a color independent of the background, receive data representing a background color of the background at a position of the displayed first user interface object or the displayed second user interface object (first color is different from background color at the position of the displayed first user interface object or the displayed second user interface object)

2702
Detect a user movement of the electronic device

2704
In response to detecting the movement, display an animated reveal of a clock face by displaying an hour hand and a minute hand, displaying a first hour indication, and displaying a second hour indication after the first (second hour indication is after the first hour indication on clock face in clockwise direction)

Display a character user interface object on the display. The character user interface object includes representations of a first limb and a second limb and indicates a first time by indicating a first hour with the first limb and a first minute with the second limb.

2714

Update the character user interface object to indicate a second time. The character user interface object indicates the second time by indicating a second hour with the second limb and a second minute with the first limb.

Optionally, update the character user interface object to indicate a second time by extending the first limb and retracting the second limb.

Display a character user interface object on the display. The character user interface object includes a representation of a first limb with a first endpoint and a second endpoint. The first endpoint is an axis of rotation for the limb, and the second endpoint indicates a first time value.

2724

Update the character user interface object to indicate a second time value. Updating the character user interface object includes moving the first endpoint and moving the second endpoint to indicate the second time value.

Display a character user interface object on the display. The character user interface object includes a representation of a first limb with a first segment and a second segment. The first segment of the limb connects a first endpoint to a joint. The second segment connects a second endpoint to the joint. The joint is an axis of rotation for the second segment. The position of the second endpoint indicates a first time value.

2734

Update the character user interface object to indicate a second time value. Updating the character user interface object includes moving the second endpoint along the axis of rotation to indicate the second time value.

Display a character user interface object on the display. The character user interface object indicates time.

2744

Receive first data indicative of an event.

2746

Determine whether the event meets a condition

NO

YES

2748

Update the character user interface object by changing a visual aspect of the character user interface object.

2752
Set the display to an inactive state.

2754
Receive first data indicative of an event.

2756
Set the display to an active state.

2758
Display a character user interface object on a side of the display.

2760
Animate the character user interface object towards a center of the display.

2762
Display the character user interface object at the center of the display in a position that indicates a current time.

Display a user interface screen that includes a clock face and an affordance on the clock face (affordance indicates first time of day)

3104

Detect contact on display

3106

In response to detecting the contact, enter a user interaction mode

3108

While in user interaction mode, detect a movement of the rotatable input mechanism

3110

In response to detecting the movement, update the affordance to indicate a second time of day

3112

Detect a second contact at the affordance

3114

In response to detecting the contact, set a user reminder for the second time of day

Display a user interface screen that includes a clock face and an affordance (affordance represents an application and displays a set of information from the application) as a complication

3204

Detect a contact on the affordance

3206

In response to detecting the contact, launch the application represented by the affordance

Display a user interface screen that includes a plurality of affordances (a first affordance in the plurality indicates a clock face, which includes an indication of time and an outline)

3304

Detect a contact on first affordance

3306

In response to detecting the contact, substitute the display of user interface screen with a second user interface screen (substitution includes retaining the indication of time or the outline at a larger size)

5402
At an electronic device with a display and a rotatable input mechanism:

5404
Display a first current-time indicator indicating a current time

5406
Display a first user interface object configured to display information corresponding to the current time, wherein the information corresponding to the current time pertains to a first information source and is information other than a day, time, or date of the current time

5408
Detect a first touch contact at a location corresponding to the first current-time indicator

5410
In response to detecting the first touch contact, display a non-current time indicator indicating the current time

5412
Detect a first rotation of the rotatable input mechanism

5402
At an electronic device with a display and a rotatable input mechanism:

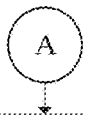

5414
In response to detecting the first rotation of the rotatable input mechanism:

5416
Display a non-current-time indicator indicating a first non-current time determined in accordance with the first rotation

5418
The first non-current time is a future time

5420
The first non-current time is a past time

5421
The non-current-time indicator is displayed at a location at which the first current-time indicator was displayed before the detection of the first rotation of the rotatable input mechanism

5422
Update the first user interface object to display information corresponding to the first non-current time, wherein the information corresponding to the first non-current time pertains to the first information source and is information other than a day, time, or date of the first non-current time

5424
The information corresponding to the first non-current time comprises a projected data

5426
The information corresponding to the first non-current time comprises a scheduled event

5428
The information corresponding to the first non-current time comprises historical data

B

5430
Update the first user interface object to indicate a lack of information corresponding to the first non-current time

5402
At an electronic device with a display and a rotatable input mechanism:

5414
In response to detecting the first rotation of the rotatable input mechanism:

5432
Display one of the first current-time indicator and a second current-time indicator

5434
Displaying the first current-time indicator comprises displaying the first current-time indicator with a modified visual appearance

5436
Displaying the first current-time indicator comprises displaying the first current-time indicator in a different position on the display than a position at which it was displayed prior to detecting the first rotation

5438
Displaying the first current-time indicator comprises animating the current-time indicator from its initial position to the different position on the display

5440
Display a time difference indicator indicating a time difference between the current time and the first non-current time

5402
At an electronic device with a display and a rotatable input mechanism:

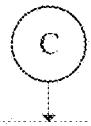 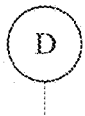 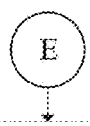

5442
In response to a passage of time, update the non-current time indicator to indicate a second non-current time in accordance with the passage of time, such that a time difference between the current time and a presently indicated non-current time remains fixed

5448
Detect a third touch contact at a location corresponding to the first current-time indicator; and in response to detecting the third touch contact: cease to display the non-current time indicator; and update the first user interface object to display information corresponding to the current time

5444
While displaying the updated first user interface object displaying information corresponding to the first non-current time, detect a second touch contact at a location corresponding to the updated first user interface object; and in response to detecting the second touch contact, display a user interface corresponding to the first user interface object

5446
The user interface corresponds to the first non-current time

5450
Detect a second rotation of the rotatable input mechanism; in response to detecting the second rotation of the rotatable input mechanism update the non-current-time indicator to indicate a third non-current time determined in accordance with the second rotation; and update the first user interface object to display information corresponding to the third non-current time, wherein the information corresponding to the third non-current time pertains to the first information source and is information other than a day, time, or date of the first non-current time; and display one of the first current-time indicator and the second current time indicator

5402
At an electronic device with a display and a rotatable input mechanism:

5452

Display a second user interface object configured to display second information corresponding to the current time, wherein the second information corresponding to the current time pertains to a second information source and is information other than a day, time, or date of the current time; and, in response to detecting the first rotation of the rotatable input mechanism: update the second user interface object to display second information corresponding to the first non-current time, wherein the second information corresponding to the first non-current time pertains to the second information source and is information other than a day, time, or date of the first non-current time.

5454

The first and second information sources are separate applications

Display a user interface screen that includes a user interface object indicating a time of day and an affordance representing a workout application, the affordance displayed as a complication associated with the user interface object > Optionally, display a second affordance representing a second application different from the workout application, the second affordance displayed as a complication associated with the user interface object

6704

Detect a user input corresponding to a selection of the first affordance

6706

In response to detecting the user input, begin a workout routine

Display a user interface screen that includes a user interface object indicating a time of day and an affordance representing an application that includes one or more weather-related data, the affordance displayed as a complication associated with the user interface object

6804

Detect a user input corresponding to a selection of the affordance

6806

In response to detecting the user input, launch the application

6808

In response to detecting the user input, display one or more workout recommendations based on weather information Optionally, obtain via wireless communication the weather information

EXERCISED-BASED WATCH FACE AND COMPLICATIONS

CROSS-REFERENCE TO RELATED APPLICATIONS

This application is a continuation of U.S. application Ser. No. 15/183,663, filed Jun. 15, 2016, entitled "EXERCISE-BASED WATCH FACE AND COMPLICATIONS" which claims priority to U.S. Provisional Application Ser. No. 62/207,736, filed Aug. 20, 2015, entitled "Exercise-Based Watch Face and Complications." These applications are incorporated by referenced herein in their entirety.

This application relates to the following applications: U.S. Provisional Application Ser. No. 62,129,828, filed Mar. 7, 2015; International Patent Application Serial No. PCT/US2013/040087, entitled "Device, Method, and Graphical User Interface for Moving a User Interface Object Based on an Intensity of a Press Input," filed May 8, 2013; International Patent Application Serial No. PCT/US2013/040072, entitled "Device, Method, and Graphical User Interface for Providing Feedback for Changing Activation States of a User Interface Object," filed May 8, 2013; International Patent Application Serial No. PCT/US2013/040070, entitled "Device, Method, and Graphical User Interface for Providing Tactile Feedback for Operations Performed in a User Interface," filed May 8, 2013; International Patent Application Serial No. PCT/US2013/040067, entitled "Device, Method, and Graphical User Interface for Facilitating User Interaction with Controls in a User Interface," filed May 8, 2013; International Patent Application Serial No. PCT/US2013/040061, entitled "Device, Method, and Graphical User Interface for Displaying User Interface Objects Corresponding to an Application," filed May 8, 2013; International Patent Application Serial No. PCT/US2013/040058, entitled "Device, Method, and Graphical User Interface for Displaying Additional Information in Response to a User Contact," filed May 8, 2013; International Patent Application Serial No. PCT/US2013/040056, entitled "Device, Method, and Graphical User Interface for Scrolling Nested Regions," filed May 8, 2013; International Patent Application Serial No. PCT/US2013/040054, entitled "Device, Method, and Graphical User Interface for Manipulating Framed Graphical Objects," filed May 8, 2013; International Patent Application Serial No. PCT/US2013/069489, entitled "Device, Method, and Graphical User Interface for Switching Between User Interfaces," filed Nov. 11, 2013; International Patent Application Serial No. PCT/US2013/069486, entitled "Device, Method, and Graphical User Interface for Determining Whether to Scroll or Select Content," filed Nov. 11, 2013; International Patent Application Serial No. PCT/US2013/069484, entitled "Device, Method, and Graphical User Interface for Moving a Cursor According to a Change in an Appearance of a Control Icon with Simulated Three-Dimensional Characteristics," filed Nov. 11, 2013; International Patent Application Serial No. PCT/US2013/069483, entitled "Device, Method, and Graphical User Interface for Transitioning Between Touch Input to Display Output Relationships," filed Nov. 11, 2013; International Patent Application Serial No. PCT/US2013/069479, entitled "Device, Method, and Graphical User Interface for Forgoing Generation of Tactile Output for a Multi-Contact Gesture," filed Nov. 11, 2013; International Patent Application Serial No. PCT/US2013/069472, entitled "Device, Method, and Graphical User Interface for Navigating User Interface Hierarchies," filed Nov. 11, 2013; International Patent Application Serial No. PCT/US2013/040108, entitled "Device, Method, and Graphical User Interface for Moving and Dropping a User Interface Object," filed May 8, 2013; International Patent Application Serial No. PCT/US2013/040101, entitled "Device, Method, and Graphical User Interface for Selecting User Interface Objects," filed May 8, 2013; International Patent Application Serial No. PCT/US2013/040098, entitled "Device, Method, and Graphical User Interface for Displaying Content Associated with a Corresponding Affordance," filed May 8, 2013; International Patent Application Serial No. PCT/US2013/040093, entitled "Device, Method, and Graphical User Interface for Transitioning Between Display States in Response to a Gesture," filed May 8, 2013; International Patent Application Serial No. PCT/US2013/040053, entitled "Device, Method, and Graphical User Interface for Selecting Object within a Group of Objects," filed May 8, 2013; U.S. Patent Application Ser. No. 61/778,211, entitled "Device, Method, and Graphical User Interface for Facilitating User Interaction with Controls in a User Interface," filed Mar. 12, 2013; U.S. Patent Application Ser. No. 61/778,191, entitled "Device, Method, and Graphical User Interface for Displaying User Interface Objects Corresponding to an Application," filed Mar. 12, 2013; U.S. Patent Application Ser. No. 61/778,171, entitled "Device, Method, and Graphical User Interface for Displaying Additional Information in Response to a User Contact," filed Mar. 12, 2013; U.S. Patent Application Ser. No. 61/778,179, entitled "Device, Method and Graphical User Interface for Scrolling Nested Regions," filed Mar. 12, 2013; U.S. Patent Application Ser. No. 61/778, 156, entitled "Device, Method, and Graphical User Interface for Manipulating Framed Graphical Objects," filed Mar. 12, 2013; U.S. Patent Application Ser. No. 61/778,125, entitled "Device, Method, And Graphical User Interface for Navigating User Interface Hierarchies," filed Mar. 12, 2013; U.S. Patent Application Ser. No. 61/778,092, entitled "Device, Method, and Graphical User Interface for Selecting Object Within a Group of Objects," filed Mar. 12, 2013; U.S. Patent Application Ser. No. 61/778,418, entitled "Device, Method, and Graphical User Interface for Switching Between User Interfaces," filed Mar. 13, 2013; U.S. Patent Application Ser. No. 61/778,416, entitled "Device, Method, and Graphical User Interface for Determining Whether to Scroll or Select Content," filed Mar. 13, 2013; U.S. Patent Application Ser. No. 61/747,278, entitled "Device, Method, and Graphical User Interface for Manipulating User Interface Objects with Visual and/or Haptic Feedback," filed Dec. 29, 2012; U.S. Patent Application Ser. No. 61/778,414, entitled "Device, Method, and Graphical User Interface for Moving and Dropping a User Interface Object," filed Mar. 13, 2013; U.S. Patent Application Ser. No. 61/778,413, entitled "Device, Method, and Graphical User Interface for Selecting User Interface Objects," filed Mar. 13, 2013; U.S. Patent Application Ser. No. 61/778,412, entitled "Device, Method, and Graphical User Interface for Displaying Content Associated with a Corresponding Affordance," filed Mar. 13, 2013; U.S. Patent Application Ser. No. 61/778,373, entitled "Device, Method, and Graphical User Interface for Managing Activation of a Control Based on Contact Intensity," filed Mar. 12, 2013; U.S. Patent Application Ser. No. 61/778,265, entitled "Device, Method, and Graphical User Interface for Transitioning Between Display States in Response to a Gesture," filed Mar. 12, 2013; U.S. Patent Application Ser. No. 61/778,367, entitled "Device, Method, and Graphical User Interface for Moving a User Interface Object Based on an Intensity of a Press Input," filed Mar. 12, 2013; U.S. Patent Application Ser. No. 61/778,363, entitled "Device, Method, and Graphical User Interface for Transitioning Between Touch Input to Display Output Relationships," filed Mar. 12, 2013; U.S. Patent Application Ser. No. 61/778, 287, entitled "Device, Method, and Graphical User Interface for Providing Feedback for Changing Activation States of a User Interface Object," filed Mar. 12, 2013; U.S. Patent Application Ser. No. 61/778,284, entitled "Device, Method, and Graphical User Interface for Providing Tactile Feedback for Operations Performed in a User Interface," filed Mar. 12, 2013; U.S. Patent Application Ser. No. 61/778,239, entitled "Device, Method, and Graphical User Interface for Forgoing Generation of Tactile Output for a Multi-Contact Gesture," filed Mar. 12, 2013; U.S. Patent Application Ser. No. 61/688, 227, entitled "Device, Method, and Graphical User Interface for Manipulating User Interface Objects with Visual and/or Haptic Feedback," filed May 9, 2012; U.S. Provisional Patent Application Ser. No. 61/645,033, filed on May 9, 2012, entitled "Adaptive Haptic Feedback for Electronic Devices;" U.S. Provisional Patent Application Ser. No. 61/665,603, filed on Jun. 28, 2012, entitled "Adaptive Haptic Feedback for Electronic Devices;" and U.S. Provisional Patent Application Ser. No. 61/681,098, filed on Aug. 8, 2012, entitled "Adaptive Haptic Feedback for Electronic Devices;" U.S. Provisional Patent Application Ser. No. 62/044,894, filed on Sep. 2, 2014, entitled "Reduced-Size Interfaces for Managing Alerts;" U.S. Provisional Patent Application Ser. No. 62/044,979, filed on Sep. 2, 2014, entitled "Stopwatch and Timer User Interfaces;" U.S. Provisional Patent Application Ser. No. 62/026,532, "Raise Gesture Detection in a Device," filed Jul. 18, 2014; and U.S. patent application Ser. No. 14/476,700, "Crown Input for a Wearable Electronic Device," filed Sep. 3, 2014. The content of these applications is hereby incorporated by reference in their entirety.

FIELD

The present disclosure relates generally to computer user interfaces, and more specifically to exercise-based watch faces and complications.

BACKGROUND

Users are increasingly relying on portable multifunction devices for day-to-day tasks. As such, a user that engages in regular workouts may require a portable multifunction device that allows them to access exercise-related information while also keeping track of time, their daily schedule, weather conditions, and the like, thereby integrating fitness with the rest of their daily routine.

SUMMARY

Some techniques for managing timekeeping and exercise-related information using portable multifunction devices, however, are generally cumbersome and inefficient. The present invention recognizes that existing techniques use a complex and time-consuming user interface, which can optionally include multiple key presses or keystrokes, or require the user to navigate through multiple screens to receive all of their fitness information. Existing techniques require more time than necessary, wasting user time and device energy. This latter consideration is particularly important in battery-operated devices. Moreover, some fitness-related devices lack important non-exercise-related functionalities, such as the ability to receive notifications, check emails, use applications, and so forth.

Accordingly, the present invention provides, inter alia, the benefit of portable electronic devices with faster, more efficient methods and interfaces for providing exercise-based watch faces and complications. Such methods and interfaces optionally complement or replace other methods for providing exercise-based watch faces and complications. Such methods and interfaces reduce the cognitive burden on a user and produce a more efficient human-machine interface. In addition, such methods and interfaces may also reduce the number of unnecessary, extraneous, repetitive, and/or redundant inputs, and may create a faster and more efficient user interface arrangement, which may reduce the number of required inputs, reduce processing power, and reduce the amount of time for which user interfaces need to be displayed in order for desired functions to be accessed and carried out. For battery-operated computing devices, such methods and interfaces conserve processor power, reduce battery usage by the display, and increase the time between battery charges.

The above deficiencies and other problems are reduced or eliminated by the disclosed devices, methods, and computer-readable media. In some embodiments, the device is a desktop computer. In some embodiments, the device is portable (e.g., a notebook computer, tablet computer, or handheld device). In some embodiments, the device has a touchpad. In some embodiments, the device has a touch-sensitive display (also known as a "touch screen" or "touch screen display"). In some embodiments, the device has hardware input mechanisms such as depressible buttons and/or rotatable input mechanisms. In some embodiments, the device has a graphical user interface (GUI), one or more processors, memory, and one or more modules, programs, or sets of instructions stored in the memory for performing multiple functions. In some embodiments, the user interacts with the GUI through finger contacts and gestures on the touch-sensitive surface and/or through rotating the rotatable input mechanism and/or through depressing hardware buttons. In some embodiments, the functions optionally include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

In some embodiments, a method of providing exercise-based watch faces and complications comprises: at an electronic device with a display: displaying a user interface screen on the display, the user interface screen including: a user interface object indicating a time of day; and an affordance representing a workout application, wherein the affordance is displayed as a complication associated with the user interface object; detecting a user input corresponding to a selection of the affordance; and in response to detecting the user input: beginning a workout routine.

In some embodiments, a non-transitory computer-readable storage medium comprises one or more programs for execution by one or more processors of a first device with a display, the one or more programs including instructions which, when executed by the one or more processors, cause the first device to: display a user interface screen on the display, the user interface screen including: a user interface object indicating a time of day; and an affordance representing a workout application, wherein the affordance is displayed as a complication associated with the user interface object; detect a user input corresponding to a selection of the affordance; and in response to detecting the user input: begin a workout routine.

In some embodiments, a transitory computer-readable storage medium comprises one or more programs for execution by one or more processors of a first device with a display, the one or more programs including instructions which, when executed by the one or more processors, cause the first device to: display a user interface screen on the display, the user interface screen including: a user interface object indicating a time of day; and an affordance representing a workout application, wherein the affordance is displayed as a complication associated with the user interface object; detect a user input corresponding to a selection of the affordance; and in response to detecting the user input: begin a workout routine.

In some embodiments, a device comprises a display; one or more processors; a memory; and one or more programs, wherein the one or more programs are stored in the memory and configured to be executed by the one or more processors, the one or more programs including instructions for: displaying a user interface screen on the display, the user interface screen including: a user interface object indicating a time of day; and an affordance representing a workout application, wherein the affordance is displayed as a complication associated with the user interface object; detecting a user input corresponding to a selection of the affordance; and in response to detecting the user input: beginning a workout routine.

In some embodiments, a device comprises means for displaying a user interface screen on a display, the user interface screen including: a user interface object indicating a time of day; and an affordance representing a workout application, wherein the affordance is displayed as a complication associated with the user interface object; means for detecting a user input corresponding to a selection of the affordance; and means responsive to detecting the user input for beginning a workout routine.

In some embodiments, an electronic device comprises a display unit; and a processing unit coupled to the display unit, the processing unit configured to: enable display, on the display unit, of a user interface screen, the user interface screen including: a user interface object indicating a time of day; and an affordance representing a workout application, wherein the affordance is displayed as a complication associated with the user interface object; detect a user input corresponding to a selection of the affordance; and in response to detecting the user input: begin a workout routine.

In some embodiments, a method of providing exercise-based watch faces and complications comprises: at an electronic device with a display: displaying a user interface screen on the display, the user interface screen including: a user interface object indicating a time of day; and an affordance representing an application that includes one or more weather-related data, wherein the affordance is displayed as a complication associated with the user interface object; detecting a user input corresponding to a selection of the affordance; in response to detecting the user input: launching the application; and displaying one or more workout recommendations based on weather information.

In some embodiments, a non-transitory computer-readable storage medium comprises one or more programs for execution by one or more processors of a first device with a display, the one or more programs including instructions which, when executed by the one or more processors, cause the first device to: display a user interface screen on the display, the user interface screen including: a user interface object indicating a time of day; and an affordance representing an application that includes one or more weather-related data, wherein the affordance is displayed as a complication associated with the user interface object; detect a user input corresponding to a selection of the affordance; and in response to detecting the user input: launch the application; and display one or more workout recommendations based on weather information.

In some embodiments, a transitory computer-readable storage medium comprises one or more programs for execution by one or more processors of a first device with a display, the one or more programs including instructions which, when executed by the one or more processors, cause the first device to: display a user interface screen on the display, the user interface screen including: a user interface object indicating a time of day; and an affordance representing an application that includes one or more weather-related data, wherein the affordance is displayed as a complication associated with the user interface object; detect a user input corresponding to a selection of the affordance; and in response to detecting the user input: launch the application; and display one or more workout recommendations based on weather information.

In some embodiments, a device comprises a display; one or more processors; a memory; and one or more programs, wherein the one or more programs are stored in the memory and configured to be executed by the one or more processors, the one or more programs including instructions for: displaying a user interface screen on the display, the user interface screen including: a user interface object indicating a time of day; and an affordance representing an application that includes one or more weather-related data, wherein the affordance is displayed as a complication associated with the user interface object; detecting a user input corresponding to a selection of the affordance; and in response to detecting the user input: launching the application; and displaying one or more workout recommendations based on weather information.

In some embodiments, a device comprises means for displaying a user interface screen on a display, the user interface screen including: a user interface object indicating a time of day; and an affordance representing an application that includes one or more weather-related data, wherein the affordance is displayed as a complication associated with the user interface object; means for detecting a user input corresponding to a selection of the affordance; and means responsive to detecting the user input for: launching the application; and displaying one or more workout recommendations based on weather information.

In some embodiments, an electronic device comprises a display unit; and a processing unit coupled to the display unit, the processing unit configured to: enable display, on the display unit, of a user interface screen, the user interface screen including: a user interface object indicating a time of day; and an affordance representing an application that includes one or more weather-related data, wherein the affordance is displayed as a complication associated with the user interface object; detect a user input corresponding to a selection of the affordance; and in response to detecting the user input: launch the application; and enable display, on the display unit, of one or more workout recommendations based on weather information.

Thus, devices are provided with faster, more efficient methods and interfaces for providing exercise-based watch faces and complications, thereby increasing the effectiveness, efficiency, and user satisfaction with such devices. Such methods and interfaces can optionally complement or replace other methods for providing exercise-based watch faces and complications.

DESCRIPTION OF THE FIGURES

FIGS. 4A and 4B illustrate an exemplary user interface for a menu of applications on a portable multifunction device in accordance with some embodiments.

FIGS. 5C-5D illustrate exemplary components of a personal electronic device having a touch-sensitive display and intensity sensors in accordance with some embodiments.

FIGS. 5E-5H illustrate exemplary components and user interfaces of a personal electronic device in accordance with some embodiments.

FIG. 21 is a flow diagram illustrating a process for context-specific user interfaces.

FIG. 22 is a flow diagram illustrating a process for context-specific user interfaces.

FIG. 23 is a flow diagram illustrating a process for context-specific user interfaces.

FIG. 24 is a flow diagram illustrating a process for context-specific user interfaces.

FIG. 27A is a flow diagram illustrating a process for context-specific user interfaces.

FIG. 27B is a flow diagram illustrating a process for context-specific user interfaces.

FIG. 27C is a flow diagram illustrating a process for context-specific user interfaces.

FIG. 27D is a flow diagram illustrating a process for context-specific user interfaces.

FIG. 27E is a flow diagram illustrating a process for context-specific user interfaces.

FIG. 27F is a flow diagram illustrating a process for context-specific user interfaces.

FIG. 31 is a flow diagram illustrating a process for context-specific user interfaces.

FIG. 32 is a flow diagram illustrating a process for context-specific user interfaces.

FIG. 33 is a flow diagram illustrating a process for context-specific user interfaces.

FIGS. 54A-54E are flow diagrams illustrating methods of activating a mode of operation in accordance with some embodiments.

FIG. 67 is a flow diagram illustrating a process for exercise-based watch faces and complications.

FIG. 68 is a flow diagram illustrating a process for exercise-based watch faces and complications.

DETAILED DESCRIPTION

The following description sets forth exemplary methods, parameters and the like. It should be recognized, however, that such description is not intended as a limitation on the scope of the present disclosure but is instead provided as a description of exemplary embodiments.

As described above, there is a need for portable multi-function devices that allow a user to keep track of time as well as access exercise-related information and functionalities. Such a device would enable users to integrate fitness goals and tracking with the rest of their daily routine. Techniques that can reduce the cognitive burden on a user who accesses timekeeping and exercise-related information may enhance productivity and user fitness. Further, such techniques can reduce processor and battery power otherwise wasted on redundant user inputs.

Figure 56A:
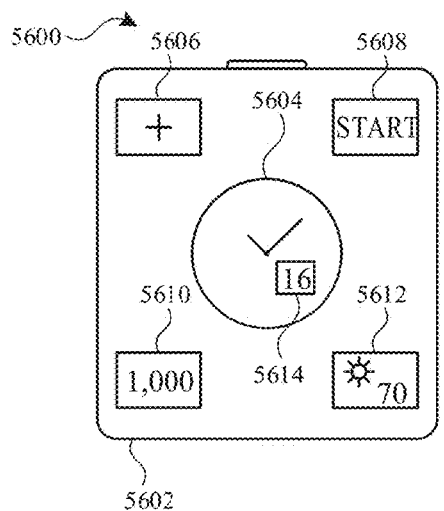
FIGS. 56A and 56B illustrate exemplary exercise-based watch faces and complications.
Figure 56B:
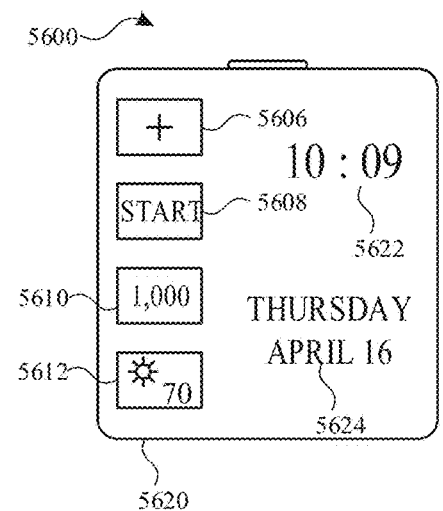

Below, FIGS. 1A-1B, 2, 3, 4A-4B, and 5A-5B provide a description of exemplary devices for performing the techniques for providing exercise-based watch faces and complications. FIGS. 56A-56B illustrate exemplary exercise-based watch faces and complications. The user interfaces in the figures are also used to illustrate the processes described below, including the processes in FIGS. 67 and 68.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
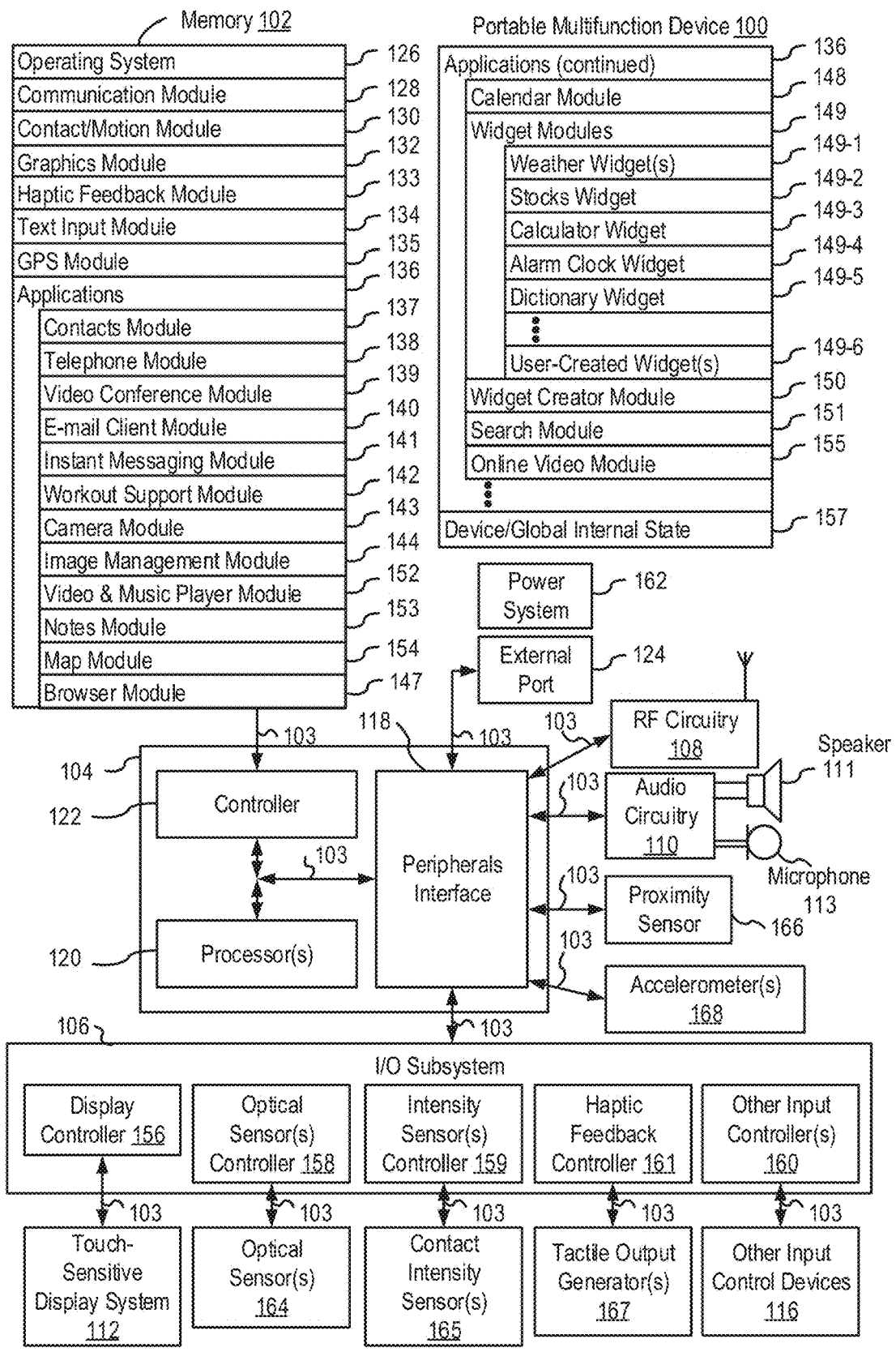
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that otherwise can optionally not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons is, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
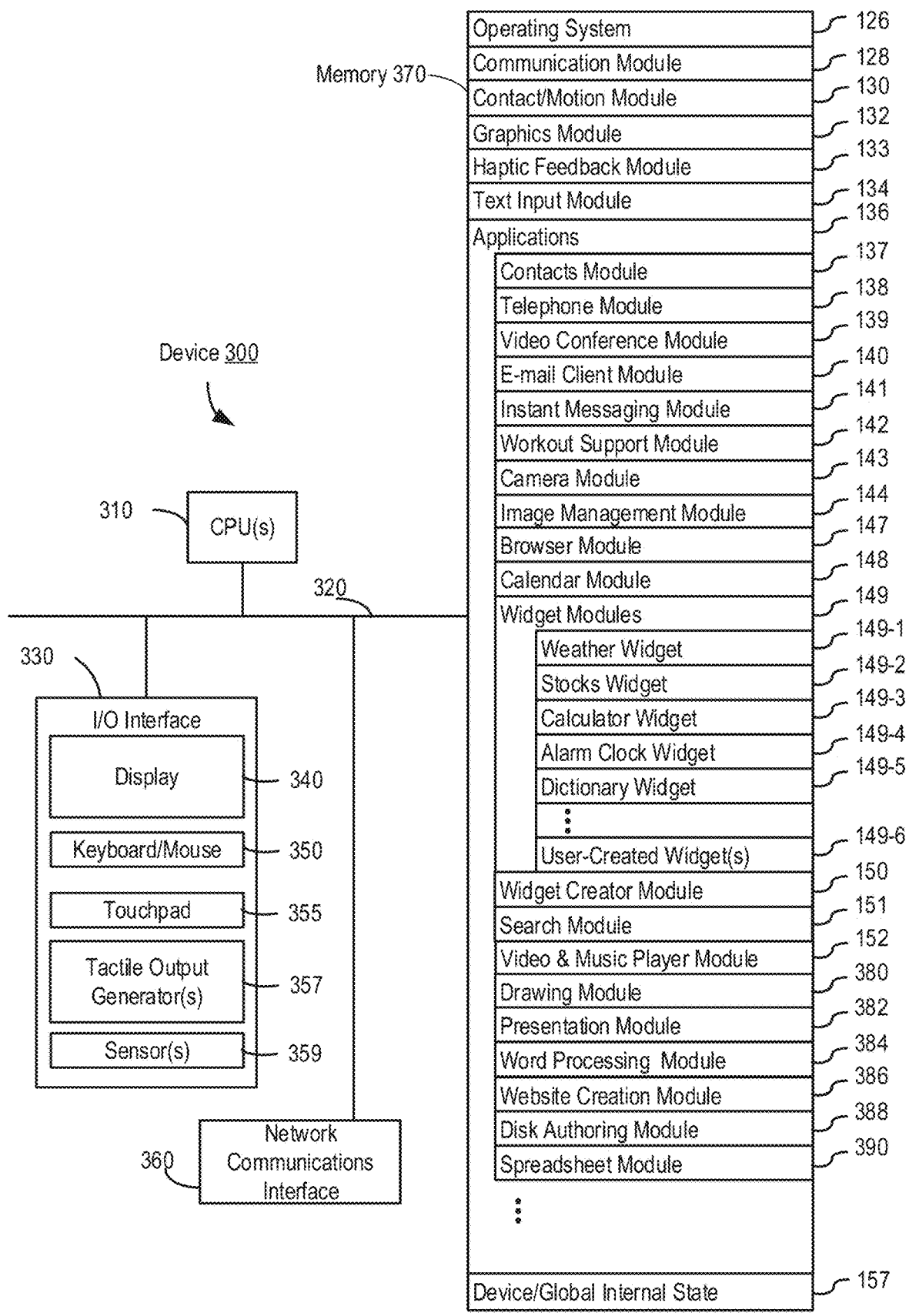
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are, optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
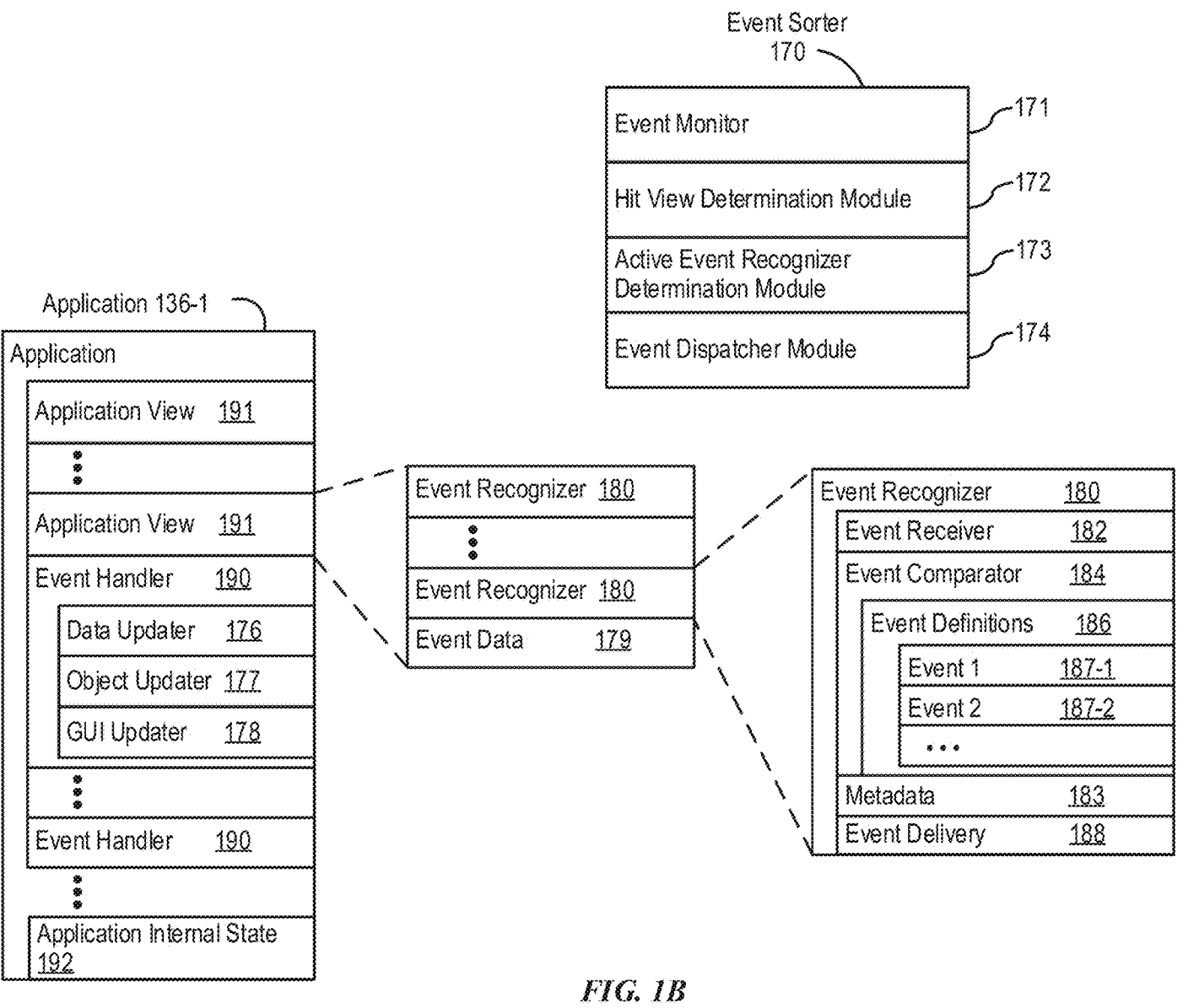
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
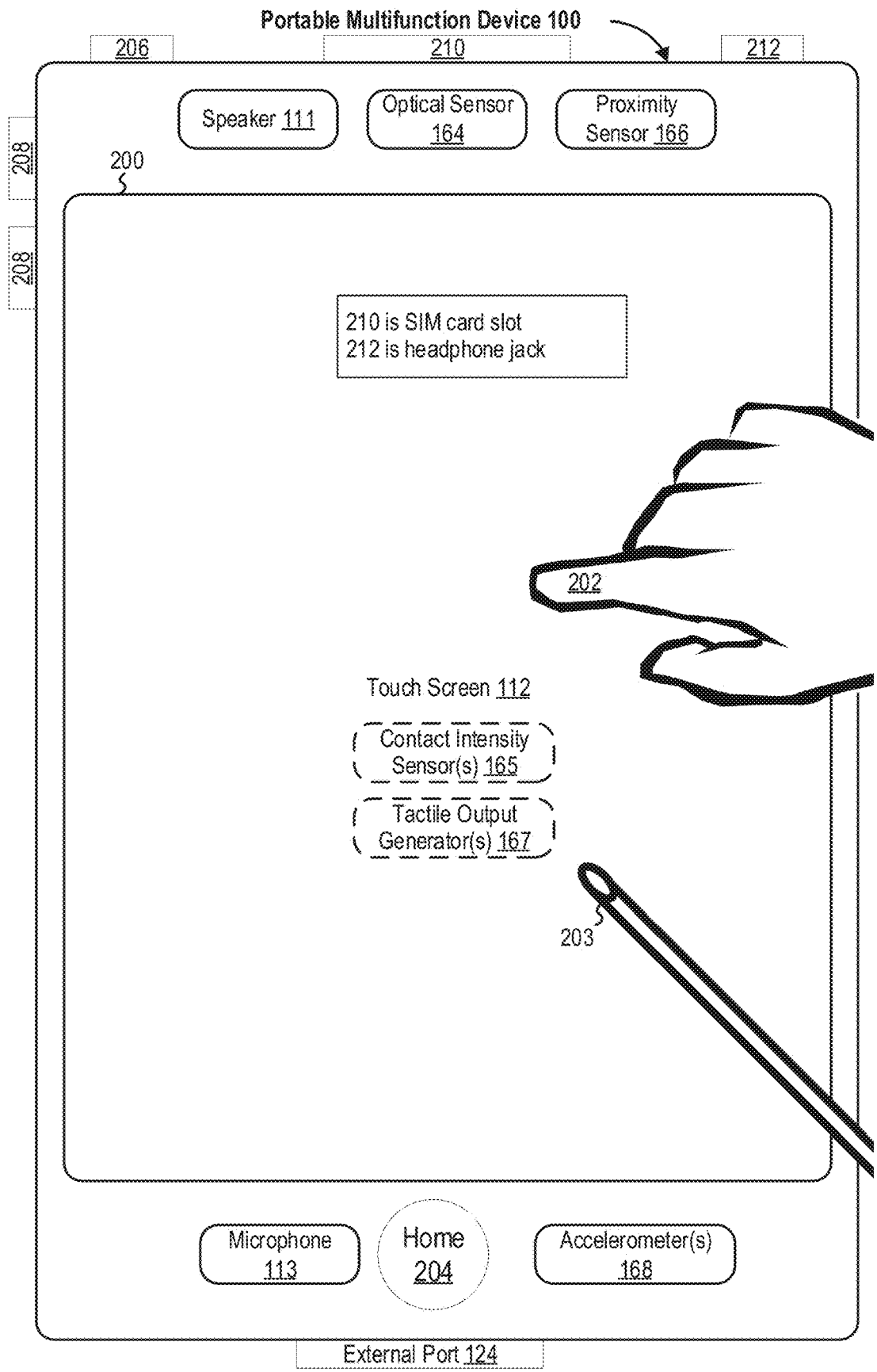
FIG. 2 illustrates a portable multifunction device having a touch-sensitive display in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
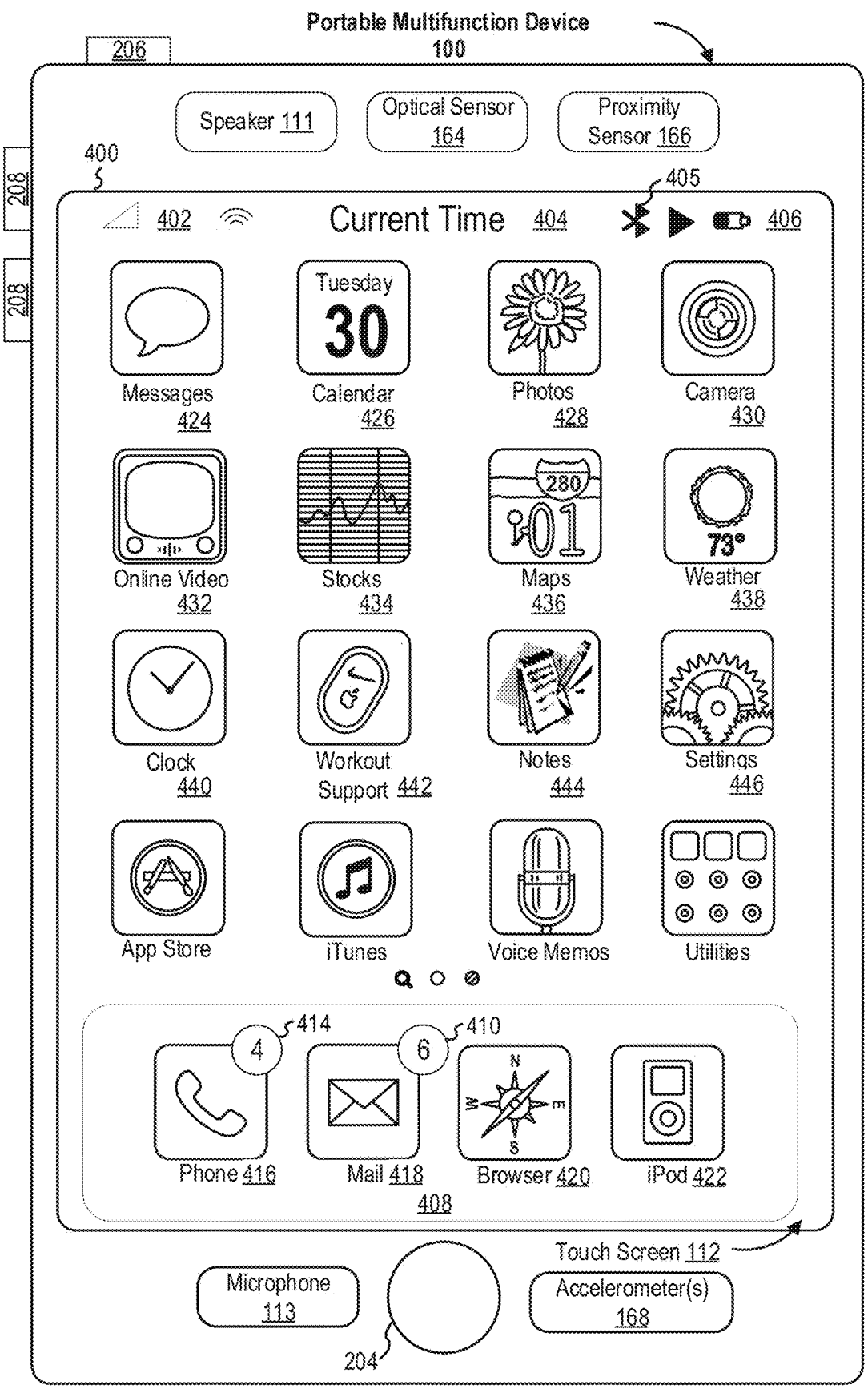

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
- Icon 416 for telephone module 138, labeled "Phone," which optionally includes an indicator 414 of the number of missed calls or voicemail messages;
- Icon 418 for e-mail client module 140, labeled "Mail," which optionally includes an indicator 410 of the number of unread e-mails;
- Icon 420 for browser module 147, labeled "Browser;" and Icon 422 for video and music player module 152, also referred to as iPod (trademark of Apple Inc.) module 152, labeled "iPod;" and Icons for other applications, such as:
- Icon 424 for IM module 141, labeled "Messages;"
- Icon 426 for calendar module 148, labeled "Calendar;"
- Icon 428 for image management module 144, labeled "Photos;"
- Icon 430 for camera module 143, labeled "Camera;"
- Icon 432 for online video module 155, labeled "Online Video;"
- Icon 434 for stocks widget 149-2, labeled "Stocks;"
- Icon 436 for map module 154, labeled "Maps;"
- Icon 438 for weather widget 149-1, labeled "Weather;"
- Icon 440 for alarm clock widget 149-4, labeled "Clock;"
- Icon 442 for workout support module 142, labeled "Workout Support;"
- Icon 444 for notes module 153, labeled "Notes;" and
- Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
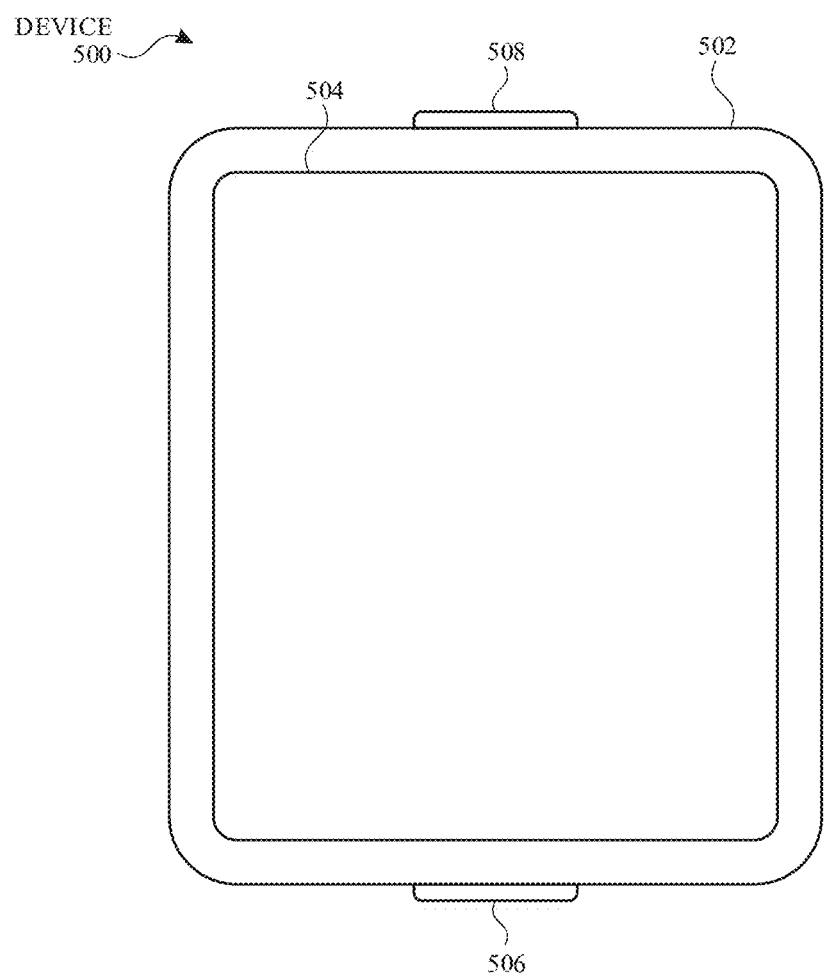
FIG. 5A is a block diagram illustrating a portable multifunction device with a touch-sensitive display and a rotatable and depressible input mechanism in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
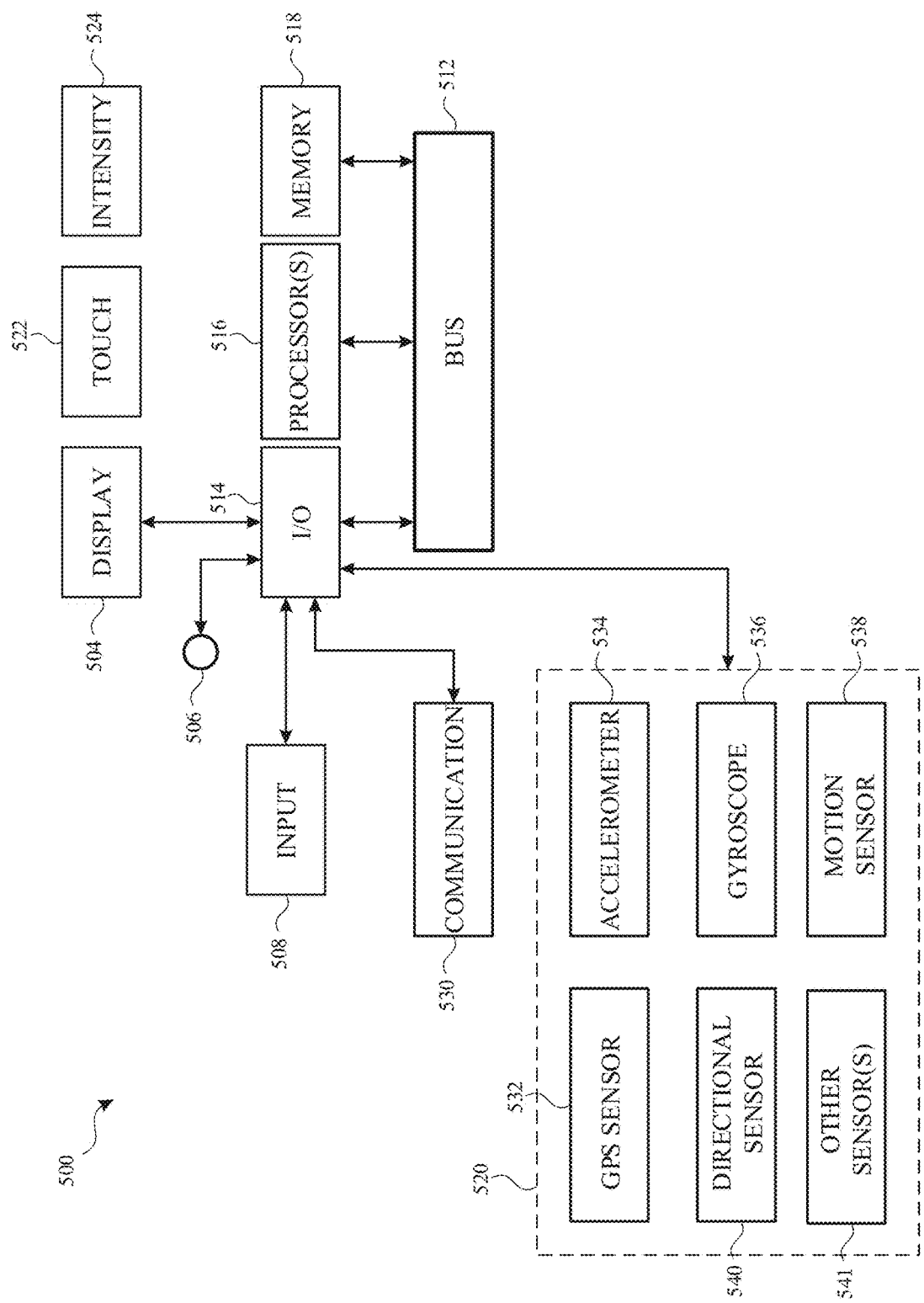
FIG. 5B illustrates a portable multifunction device having a touch-sensitive display and a rotatable and depressible input mechanism in accordance with some embodiments.
Figure 5D:
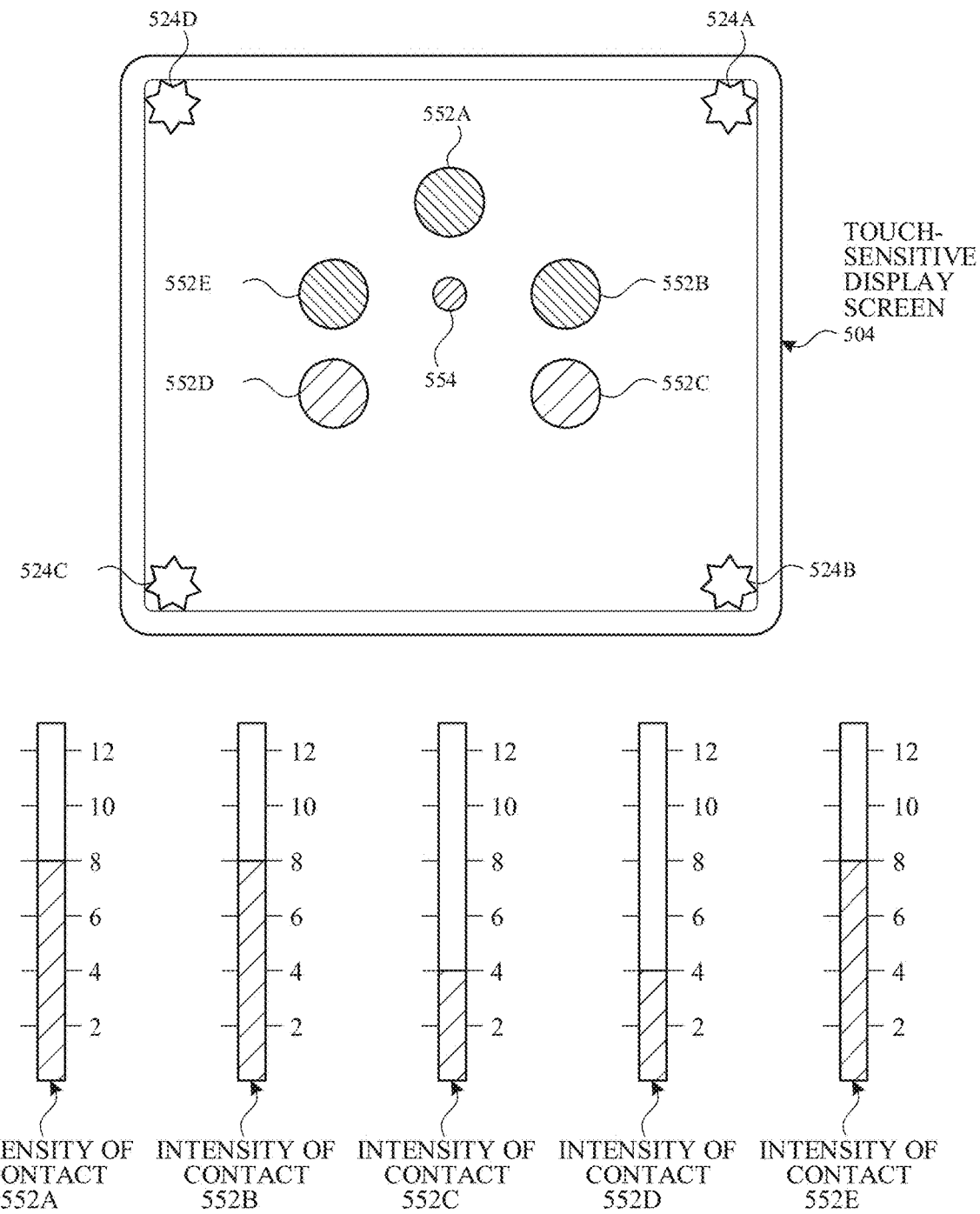

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various activity sensors 520 for detecting an activity of a user of device 500. Activity sensors 520 can include one or more of any desired type of sensor, such as GPS sensor 532, accelerometer 534, directional sensor 540 (e.g., compass), gyroscope 536, motion sensor 538, other sensor(s) 541, and/or a combination thereof, all of which can be operatively connected to I/O section 514. While not shown, other sensor(s) 541 can include any of a pedometer, a passive infrared sensor, an ultrasonic sensor, a microwave sensor, a tomographic motion detector, a camera, a biometric sensor, a light sensor, a timer, or the like.

In some examples, the biometric sensor can include one or more health-related optical sensors, capacitive sensors, thermal sensors, electric field (eField) sensors, and/or ultrasound sensors, such as photoplethysmogram (PPG) sensors, electrocardiography (ECG) sensors, and/or galvanic skin response (GSR) sensors. These sensors can generate data providing health-related information associated with the user. For example, PPG sensors can provide information regarding a user's respiratory rate, blood pressure, and/or oxygen saturation. ECG sensors can provide information regarding a user's heartbeats. GSR sensors can provide information regarding a user's skin moisture indicative of sweating and can prioritize a thermostat application to determine a user's body temperature. Using one or more of these sensors, device 500 can determine physiological characteristics of the user while performing a detected activity, such as a heart rate of a user associated with the detected activity, average body temperature of a user detected during the detected activity, any normal or abnormal physical conditions associated with the detected activity, or the like.

In some examples, GPS sensor 532 can be used to determine a user's location and movement, as well as a displacement of the user's motion. Accelerometer 534, directional sensor 540, and gyroscope 536 can further generate activity data that can be used to determine whether a user of device 500 is engaging in an activity, is inactive, or is performing a gesture. Device 500 can further include a timer that can be used, for example, to add time dimensions to various attributes of the detected physical activity, such as a duration of a user's physical activity or inactivity, time(s) of a day when the activity is detected or not detected, etc.

Activity sensors 520 can be embedded in body 502 of device 500, placed near a bottom surface of body 502 of device 500, or can be positioned at any other desirable location. In some examples, different activity sensors 520 can be placed in different locations inside or on the surfaces of device 500—e.g., some located inside body 502 and some attached to the attachment mechanism, or the like. In other examples, activity sensors 520 can be worn by a user separately from device 500. In such cases, the sensors can be configured to communicate with device 500 using a wired or wireless technology (e.g., via communication unit 531). In some examples, activity sensors 520 can be configured to communicate with each other and/or share data collected from one or more sensors. In some other examples, device 500 can be waterproof such that the sensors can detect a user's activity in water.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 2200-2500 (FIGS. 22-25). Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A-B, 3, and 5). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

5C illustrates detecting a plurality of contacts 552A-552E on touch-sensitive display screen 504 with a plurality of intensity sensors 524A-524D. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

- an active application, which is currently displayed on a display screen of the device that the application is being used on;
- a background application (or background processes), which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

1. Context-Specific User Interfaces

Attention is now directed towards embodiments of context-specific user interfaces ("UI") and associated processes that can optionally be implemented on a multifunction device with a display and a touch-sensitive surface, such as devices 100, 300, and/or 500 (FIGS. 1A, 3, and/or 5A).

The following examples illustrate exemplary embodiments of context-specific user interfaces. Described herein are overall concepts related to customizable context-specific user interfaces. It is noted that the context-specific user interfaces described herein are editable in a number of ways. A user interface can optionally display or otherwise indicate various types of information related to time, and the type(s) of information can optionally be customizable by the user. A user interface can optionally include aspects such as colors, density of display, and complications (or lack of complications) that are also customizable. As used here, consistent with its accepted meaning in art, a complication refers to any clock face feature other than those used to indicate the hours and minutes of a time (e.g., clock hands or hour/minute indications). Complications can optionally provide different types of information to a user, such as data obtained from an application, and the information conveyed to a user by a complication is also customizable, as described below.

These combinatorial features result in many thousands, if not more, of available context-specific user interfaces. Since describing each of these permutations is not practical, particular aspects are highlighted with particular context-specific user interfaces, but these exemplary descriptions are in no way intended to limit such aspects to such context-specific user interfaces, as specific aspects can optionally be used in other context-specific user interfaces, and specific context-specific user interfaces can optionally have other aspects. These embodiments are meant to illustrate the overall concepts presented, but a skilled artisan will recognize that numerous other embodiments are possible within the scope of the techniques described herein.

Figure 6A:
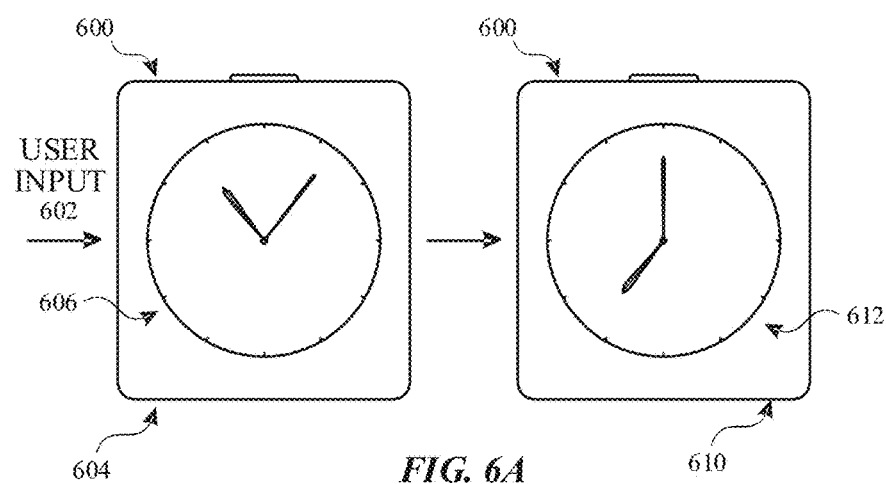
FIGS. 6A and 6B illustrate exemplary context-specific user interfaces.

FIG. 6A shows an exemplary context-specific user interface that can optionally be operated on device 600. Device 600 can optionally be device 100, 300, or 500 in some embodiments. The electronic device has a display (e.g., 504).

A user keeping track of the time of day may wish to gain some sense of how much time has elapsed since a particular event. For example, a user may wish to know how much time has elapsed since the last time the user viewed the time, or how much time has elapsed since a particular time of day, like morning. In addition to viewing a clock face, the user may wish to receive additional visual cues that reinforce the perception of elapsed time.

As shown in FIG. 6A, the device receives data representing user input 602. In response to receiving the data, the device displays user interface screen 604 on the display. Screen 604 includes clock face 606. In the example illustrated in FIG. 6A, the time is currently 7:00. Clock face 606 initially indicates a first time (10:05 as shown in FIG. 6A) that precedes the current time. Device 600 updates screen 604 by animating the clock face to transition from indicating the first time to indicating the current time. Updated screen 604 is depicted as screen 610, which displays clock face 612. Clock face 612 has been updated to indicate the current time. The animation from screens 604 to 610 represents the passage of time from the first time to the current time. In some embodiments, screen 604 and/or 610 can optionally also include an indication of the date.

As described above, the context-specific user interface exemplified in FIG. 6A first displays the clock face indicating a first time. The first time can optionally be determined based on different criteria. In some embodiments, the device receives second data representing a time of a previous user movement of the electronic device (e.g., a movement of the device such as a lowering of the user's wrist, if the device is wearable, or other movement indicative that the user is no longer actively viewing the display). The time of the previous user movement of the device can optionally be the last time the user looked at the device, or the last time the display of the device was turned off, prior to receiving the data representing user input 602. The time of the previous user movement of the electronic device is then shown as the first time indicated by the clock face. For example, in FIG. 6A, 10:05 depicted by clock face 606 can optionally be the time of a previous user movement of the device, indicating the time of a previous user interaction. In these examples, when the user interface screen updates, it provides the user an indication of how much time has elapsed since the previous user interaction (e.g., the last time the user looked at device 600).

In other embodiments, the first time can optionally be based on a predetermined interval of time. For example, the first time can optionally precede the current time by a first duration, and the first duration can optionally be a predetermined duration before the current time. That is to say, rather than being based on a user interaction, the first time indicated by the clock face can optionally be based on a predetermined or fixed duration before the current time.

In some embodiments, the predetermined duration is 5 hours. In response to user input, the clock face can optionally depict a time 5 hours before the current time, then animate the clock face to transition from indicating the first time to indicating the current time. For example, if the current time is 6:00, the device can optionally, in response to user input, display a clock face showing 1:00 that is animated to transition from 1:00 to 6:00.

In other embodiments, the first time can optionally be based on a predetermined time of day. In this case, the device can optionally begin the animation by indicating the same time of day (i.e., the first time) no matter the current time, and then animate the clock face until it reaches the current time. For example, the first time can optionally be morning (e.g., 8:00 am). In this example, if the current time is 6:00, the device can optionally, in response to user input, display a clock face showing 8:00 that is animated to transition from 8:00 to 6:00.

Regardless of how the first time is determined, in some embodiments, the clock face can optionally be animated for a period of time indicative of the duration between the first time and the current time. That is to say, the length of the animation can optionally be roughly proportional to the length of this duration. The length of animation can optionally not be precisely proportional to the first duration, but rather it can optionally convey to the user a general indication of an approximate length of the time. To illustrate using the examples described above, the clock face can optionally be animated for a longer period of time if transitioning from 8:00 to 6:00 than it is if transitioning from 3:00 to 6:00. This may be particularly useful if the duration is variable, such as if the duration is based on the time between user interactions. In this case, a user will immediately comprehend that the time elapsed between interactions is longer if the animation of the clock face is longer, or that the time between interactions is shorter if the animation of the clock face is shorter.

In other embodiments, the clock face is animated for a period of time independent of the first duration. That is to say, the length of the animation is not proportional to the duration between the first time and the current time. In some embodiments, the length of animation can optionally be the same for each animation. To illustrate using the examples described above, the clock face can optionally be animated for the same period of time regardless if transitioning from 8:00 to 6:00 or from 3:00 to 6:00. This may be helpful to reduce the time a user is viewing the transition. Alternatively, the clock face is animated for a different period of time if transitioning from 8:00 to 6:00 compared to transitioning from 3:00 to 6:00, but the periods of time can optionally not be related to the first duration.

Figure 6B:
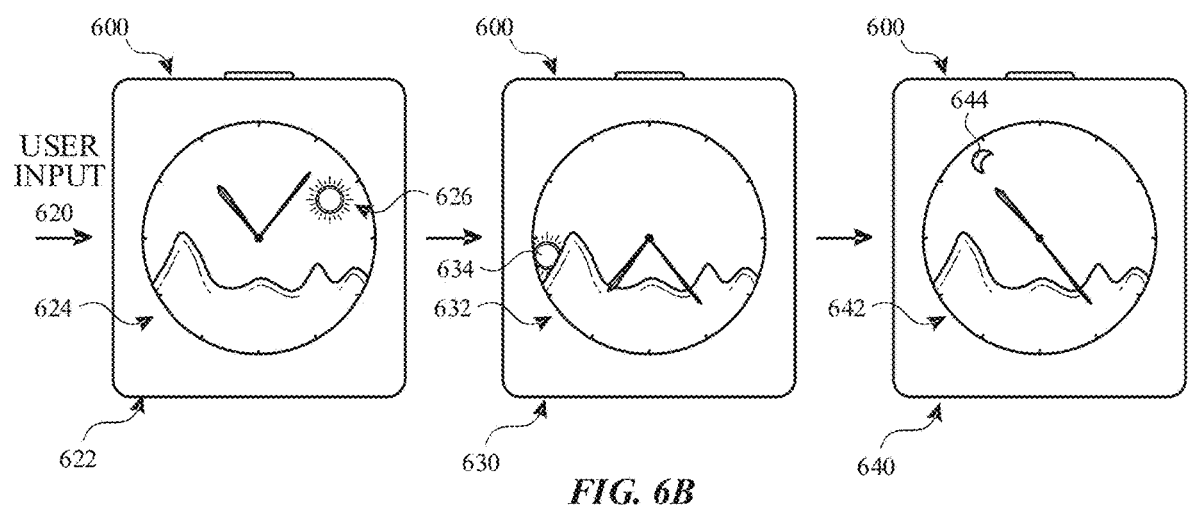

FIG. 6B illustrates optional features of this context-specific user interface. In response to data representing user input 620, device 600 displays user interface screen 622, which includes clock face 624. In this example, the current time is 10:25. Clock face 624 indicates a first time (in this example, 10:05). As a background, clock face 624 also displays an image of a mountain scene that is representative of the first time. For example, as shown in FIG. 6B, clock face 624 shows a morning view of the mountain scene (see, e.g., the position of sun 626 in the sky). Therefore, a user viewing clock face 624 understands the time based on the clock face itself and the background, which also represents the time indicated by the clock face. Note that this provides additional information to the user because the user understands that the indicated time is 10:05 am, not 10:05 pm, by the display of the scene.

In some embodiments, the device accesses an image of a scene that is representative of the time indicated by the clock face. An image of a scene that is representative of a time can optionally connote to the user a similar time of day, in conjunction with the time indicated by the clock face. The image of the scene need not connote the precise time indicated by the clock face, nor does it need to be strictly linked to the time of day at the location of the scene (this will be discussed in greater detail below). In some embodiments, the image of the scene is an image captured at substantially the same time of day as the current time (i.e., the time of day when the image was taken at the scene). In other embodiments, the image of the scene is an image captured at a different time of day, as compared to the current time.

In some embodiments, the image of the scene can optionally depict, for example, a city, beach, desert, park, lake, mountain, or valley. In some embodiments, the scene can optionally be recognizable to the user, such as a scene of Yosemite Valley or Big Ben.

Device 600 then displays screens 630 and 640. Screen 630 is optional, as described below, and includes clock face 632, which is indicating a time between the first time and the current time. This intermediate time is further represented on clock face 632 by the background (see, e.g., setting sun 634). Screen 640 includes clock face 642, which depicts the current time. Clock face 642 also displays a background that represents the current time (see, e.g., moon 644).

Therefore, in some embodiments, and in response to receiving data representing user input 620, the device accesses a first image of a scene representative of the first time (e.g., the background of clock face 624), accesses a second image of the scene representative of the current time (e.g., the background of clock face 642), and in response to receiving the data representing the user input, successively displays the first image of the scene and the second image of the scene.

The successive display indicates the passage of time from the first time to the current time. The device can optionally include a series of images for a particular scene (e.g., time lapse images), each depicting a different time of day, such that any first time or current time depicted by the clock face has a corresponding image of the scene that is representative of the depicted time. In some embodiments, the first image of the scene and the second image of the scene are displayed as backgrounds on the user interface screen.

In some embodiments, the device accesses a sequence of images of a scene that includes a first image of the scene representative of the first time (e.g., the background of clock face 624), one or more second images of the scene representative of one or more times between the first time and the current time (e.g., the background of clock face 632), and a third image of the scene representative of the current time (e.g., the background of clock face 642). In response to receiving the data representing user input 620, the device displays the sequence of images of the scene by animating the sequence of images to indicate the passage of time from the first time to the current time (e.g., like a flipbook). In some embodiments, the scene is user-designated (e.g., the device can optionally store a set of time lapse images for different scenes, and the user can optionally select the scene to be displayed).

As shown in FIG. 6B, device 600 sequentially displays screens 622, 630, and 640 to animate the displayed, respective backgrounds, thereby animating the image of the scene like a flipbook to indicate the passage of time. In some embodiments, the transition from screen 620 to 630 to 640 can optionally also be animated, e.g., by animating the hands of the clock face to rotate in a clockwise manner, and/or by animating the display of the images of the scene, as with a flipbook. If the clock face instead or additionally depicts a representation of a digital clock, the numerical indications of the hour and the minute can optionally be animated in some fashion to depict the passage of time. By displaying both the animated clock face and the animated image(s) of the scene, the device provides the user a clearer and readily distinguishable indication of the time between the first time and the current time.

In some embodiments, device 600 has a location sensor (e.g., GPS sensor 532 and/or GPS module 135), and the device obtains a current location of the device from the location sensor. The first image of the scene represents the first time at the current location, and the second image or the third image of the scene (e.g., whichever is representative of the current time) represents the current time at the current location. That is to say, the indicated passage of time reflects day/night hours at the current location. For example, if the user is at a location near the Arctic Circle, the current day may have daytime hours close to 24 hours (e.g., midnight sun). In this example, the images indicating the first time and the current time can optionally all be daytime images of the scene (e.g., Yosemite Valley), even if the first time and the current time are separated by a long period of time. Therefore, the images of the scene can optionally be representative of the depicted time(s) at the current location, but they can optionally not be representative of the depicted time(s) at the location of the scene. This concept allows the device to display a context-specific user interface for depicting the passage of time at the current location and enhances a user's interaction with the device, since the animation is grounded in the user's experience (e.g., perception of time) at the current location.

In some embodiments, the device displays a user interface object on the user interface screen at a first position based on the first time. In some embodiments, the position can optionally be based on a position along the clock face, like an hour indication (e.g., 6 o'clock position at the lower center of the display). In some embodiments, the position can optionally be based on a position across a horizon, such as a position of the Sun or the Moon. For example, in FIG. 6B, the position of sun 626 indicates the first time because it represents the sun in the scene at a position in the east just short of high noon.

In some embodiments, the device animates the user interface object by moving the user interface object from the first position to a second position on the user interface screen, where the second position is based on the current time. Moving the user interface object from the first position to a second position indicates the passage of time from the first time to the current time. As shown in FIG. 6B, sun 626 moves across the sky in the sequence of images of the scene (cf. sun 626 and sun 634). The user interface object then depicts moon 644 at a position in the night sky indicating the current time. In some embodiments, the user interface object is a graphical representation of a sun (e.g., 626 and 634). In some embodiments, the user interface object is a graphical representation of a moon (e.g., 644).

In any of the embodiments described above, the user input can optionally include a movement of the device. For example, a movement of the device could be raising of the user's wrist (if the device is wearable), or other movement indicative of the user raising the device to view the display. These movements could be detected, for example, by using an accelerometer (e.g., 534), a gyroscope (e.g., 536), a motion sensor (e.g., 538), and/or a combination thereof. In any of the context-dependent faces described herein, a movement of the device can optionally be a user input that activates the display.

Further, in any of the context-dependent faces described herein, a movement of the device such as a lowering of the user's wrist (if the device is wearable) or other movement indicative that the user is no longer actively viewing the display, or a lack of a movement of the device such as raising of the user's wrist (if the device is wearable) or other movement indicative of the user raising the device to view the display, can optionally be a user input that causes the device to turn off the display.

In other embodiments, the device can optionally have a touch-sensitive display or touch-sensitive surface (e.g., touchpad 355 in FIG. 3, touch-sensitive surface 451 in FIG. 4B, and/or touchscreen 504), and the user input can optionally be a contact on the touch-sensitive display.

Figure 7A:
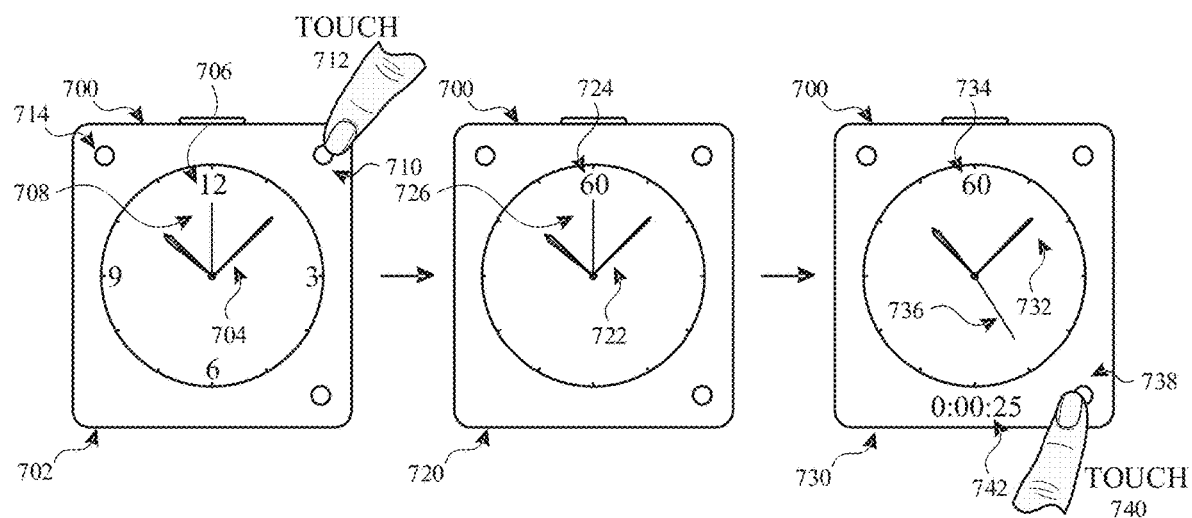
FIGS. 7A and 7B illustrate exemplary context-specific user interfaces.

Attention is now directed to the context-specific user interface shown in FIG. 7A. FIG. 7A shows exemplary context-specific user interfaces that can optionally be operated on device 700. Device 700 can optionally be device 100, 300, or 500 in some embodiments. The electronic device has a touch-sensitive display (e.g., touchscreen 504).

A user may wish to keep track of the time of day while also accessing a stopwatch function. For example, in contexts such as running or cycling, a user may wish to operate a stopwatch, record laps, and still maintain a view of the time of day.

As shown in FIG. 7A, device 700 displays a clock face that indicates current time, as depicted on user interface screen 702, on the touch-sensitive display. The clock face includes hour hand and minute hand 704. The clock face also includes one or more indications of an hourly timescale (e.g., numbers 12, 1, 2, 3, and/or tick marks or other visual indicators displayed at the corresponding positions on the clock face), such as 12 o'clock indicator 706. The clock face further includes stopwatch hand 708 (which, in some embodiments described below, also serves as a seconds hand. Note that, as used herein, the term seconds hand refers to a hand on a clock face that indicates seconds, not a second hand of two hands on a clock face).

As exemplified in FIG. 7A, device 700 receives user input, which in this case is touch 712 on start affordance 710. In response, the device replaces the 12 o'clock indicator 706 with stopwatch timescale indicator 724, as shown on screen 720. Stopwatch indicator 724 shows that the stopwatch timescale is a 60 second timescale. A timescale for the stopwatch hand can optionally refer to the amount of time needed for the stopwatch hand to complete one full revolution around the displayed clock face. Note that the clock face on screen 720 includes hour hand and minute hand 722 and stopwatch hand 726, which are the same as hour hand and minute hand 704 and stopwatch hand 708.

Further in response to touch 712, device 700 animates stopwatch hand 726 to reflect passage of time, as shown by comparing screen 720 and 730. As shown on screen 730, the stopwatch hand has moved to a second position on the clock face (note the position of stopwatch hand 736), indicating the passage of time. Given that indicator 734 shows that the stopwatch timescale is 60 seconds, the position of stopwatch hand 736 indicates that 25 seconds have passed. As shown in FIG. 7A, the user accesses this information by touch 740 on lap affordance 738, which causes the display of time 742, indicating the time elapsed since touch 712. Note that hour hand and minute hand 732 are the same as 722 and 704, and these two hands have not changed position in the last 25 seconds. In this example, the hour hand and minute hand are indicating the same time of day (e.g., 10:10) throughout screens 702, 720, and 730.

Stated another way, the device displays the time of day with the hour hand and the minute hand, and it additionally displays a stopwatch hand. In response to receiving data representing user input, the indication(s) of the hour are replaced with indication(s) of a first timescale of the stopwatch hand, but the hour hand and the minute hand continue to indicate the time of day, even though the hour indication(s) have been replaced. This allows the user to view a stopwatch and the time of day simultaneously, while showing that the stopwatch has started and indicating the timescale for the stopwatch. Also in response to receiving the data, the device animates the stopwatch hand to reflect passage of time.

In some embodiments, while animating the stopwatch hand to reflect the passage of time, the device receives second data representing a second user input, and in response to receiving the second data, the device can optionally cease the animation of the stopwatch hand. For example, this can optionally function similar to a "stop" function for the stopwatch.

In some embodiments, the device can optionally display on the touch-sensitive display a first affordance representing a start/stop function (e.g., affordance 710). The first data representing the first user input (e.g., touch 712) and the second data representing the second user input both represent contacts on the displayed first affordance. In other embodiments, the device can optionally display separate affordances for the stopwatch start and stopwatch stop functions.

In some embodiments, the device can optionally display on the touch-sensitive display a second affordance representing a lap function (e.g., affordance 738). The devices receives third data representing a contact on the displayed second affordance after receiving the first data (e.g., after invoking the start function) and before receiving the second data (e.g., before invoking the stop function). In response to receiving the third data, the device displays a third numerical indication of elapsed time between receiving the first data and receiving the third data. For example, this can optionally function similar to a "lap" function for the stopwatch that causes a display of the time elapsed since invoking the start function. As described above, this feature is illustrated on screen 730.

In some embodiments, the device can optionally display on the touch-sensitive display a third affordance representing a stopwatch application, which is depicted as affordance 714 on screen 702. The device receives fourth data representing a contact on the displayed third affordance, and in response to receiving the fourth data, the device launches the stopwatch application. This allows the user to access additional information and/or functionality related to the stopwatch feature directly from this context-specific user interface. In one embodiment, the stopwatch application is an application as described in related application: U.S. Provisional patent application entitled "Stopwatch and Timer User Interfaces", filed on Sep. 2, 2014, naming Eric Wilson et al. as inventors.

In some embodiments, the first timescale for the stopwatch hand can optionally be 60 seconds, 30 seconds, 6 seconds, or 3 seconds. In some embodiments, the movement of the stopwatch hand is animated at a rate based on the first timescale for the stopwatch hand. For example, the stopwatch hand can optionally move faster if the timescale is 3 seconds than if the timescale is 60 seconds. This allows the stopwatch hand to complete a full revolution around the clock face in the amount of time depicted by the first timescale.

In some embodiments, the device can optionally substitute the one or more indications of an hourly timescale with an indication of a first timescale for the stopwatch hand by removing the one or more indications of the hourly timescale, displaying the indication of the first timescale for the stopwatch hand, and translating the displayed indication of the first timescale for the stopwatch hand in a rotational motion in a clockwise direction. As an illustrative example, if the display includes 12 numerical indications of hourly timescale, and the first timescale for the stopwatch hand is a 6 second timescale, the device can optionally substitute the 12 numerals with a single 6 numeral. In some embodiments, this can optionally be the same 6 numeral that was previously the indicator for the 6 o'clock hour, such that the substitute and display are not perceptible to the user. The device can optionally display the 6 numerical indicating the first timescale for the stopwatch hand at the 6 o'clock position on the clock face, then translate the 6 in a clockwise motion around the clock face until it arrives at the top of the clock face (formerly the 12 o'clock position), at which point the translation stops. This improves the context-specific interface by reinforcing to the user that the clock face has transitioned from indicating hours and minutes to indicating the first timescale for the stopwatch hand.

Figure 7B:
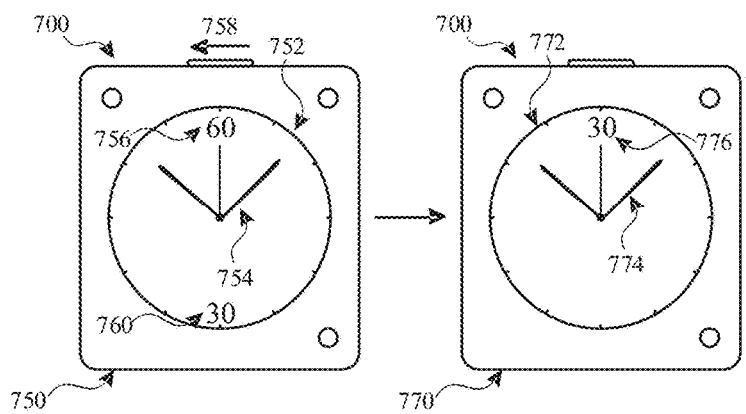

As illustrated in FIG. 7B, in some embodiments, the device has a rotatable input mechanism (e.g., 506), which can optionally be used as an optional input to change the stopwatch timescale. FIG. 7B shows screen 750 with clock face 752, which includes hour hand and minute hand 754, and stopwatch timescale indicator 756 (showing a 60 second timescale). In response to receiving fifth data representing movement of the rotatable input mechanism (e.g., movement 758), the device 700 changes the stopwatch timescale to a second timescale, as shown by stopwatch timescale indicator 776, part of clock face 772 on screen 770. Note that screen 770 continues to display hour hand and minute hand 774. The second stopwatch timescale is different from the first stopwatch timescale. This allows the user to customize the timescale for the stopwatch hand through rotating the rotatable input mechanism, allowing for a context-specific user interface depending on the user's desired stopwatch timescale.

In some embodiments, the device substitutes the indication of the first timescale for the stopwatch hand with the indication of the second timescale for the stopwatch hand by removing the indication of the first timescale for the stopwatch hand, displaying the indication of the second timescale for the stopwatch hand, and translating the displayed indication of the second timescale for the stopwatch hand in a rotational motion in a clockwise direction.

As shown in FIG. 7B, indicator of the second timescale for the stopwatch hand 760 is displayed at a position on the clock face that indicates its relative position in the first timescale For example, indicator of a 30 second timescale 760 is displayed on clock face 752 at a position based on the sixty second timescale indicated by 756. In response to receiving data representing movement 758, the device removes 756, displays 760, and translates 760 in a rotational motion in a clockwise direction until it reaches the former position of the indicator of the first timescale for the stopwatch hand (e.g., (e.g., the former position of 756, as depicted by the position of 776 on clock face 772).

In some embodiments, after receiving the first data representing the first user input, the device animates the stopwatch hand to represent a rotational motion about an origin and ceases the animation to display the stopwatch hand at a position at π/2 radians (e.g., the 12 o'clock position) relative to the rotational motion about the origin. For example, the stopwatch hand can optionally function as a seconds hand of the clock face before the first data is received. When the first data is received, the seconds hand can optionally be animated to depict a rotation around the clock face (e.g., by rotating about the center point of the clock face) until it resets at the 12 o'clock position. This signals to the user that the seconds hand has now become the stopwatch hand.

Figure 8:
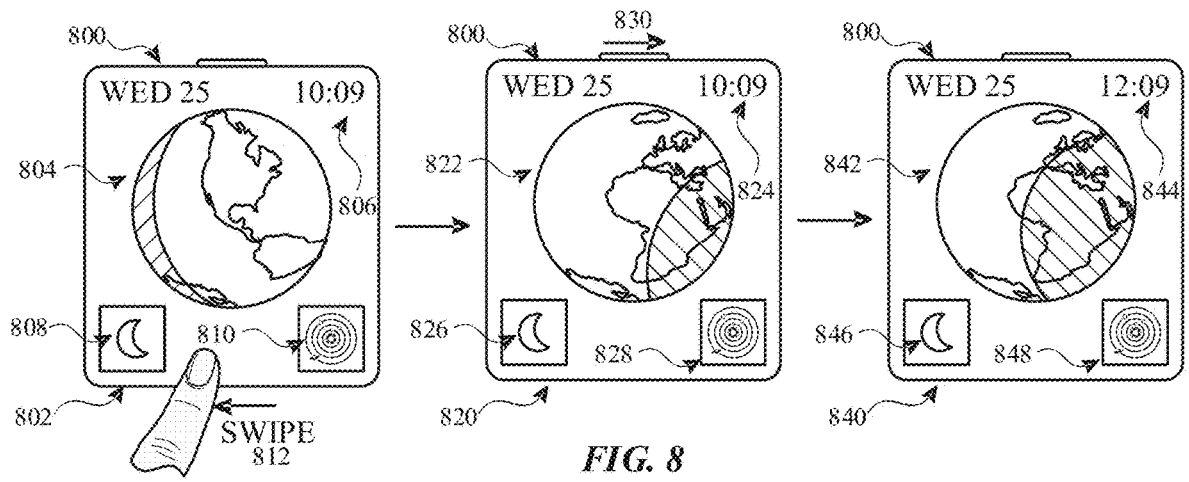
FIG. 8 illustrates exemplary context-specific user interfaces.

Attention is now directed to the context-specific user interface shown in FIG. 8. FIG. 8 shows exemplary context-specific user interfaces that can optionally be operated on device 800. Device 800 can optionally be device 100, 300, or 500 in some embodiments. The electronic device has a touch-sensitive display (e.g., touchscreen 504).

Figure 9:
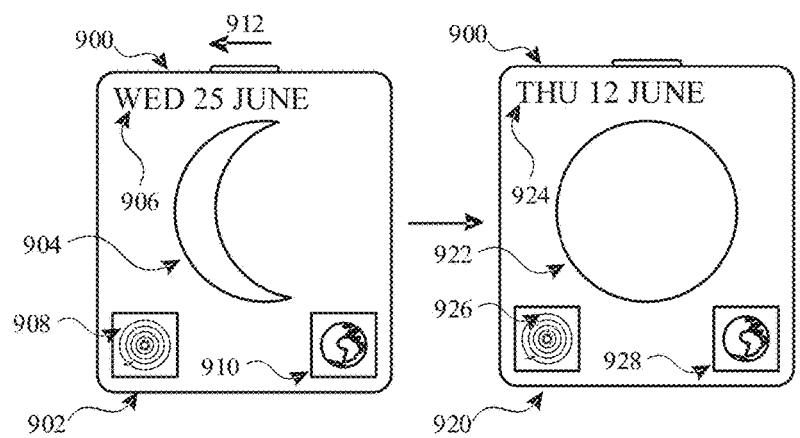
FIG. 9 illustrates exemplary context-specific user interfaces.
Figure 10:
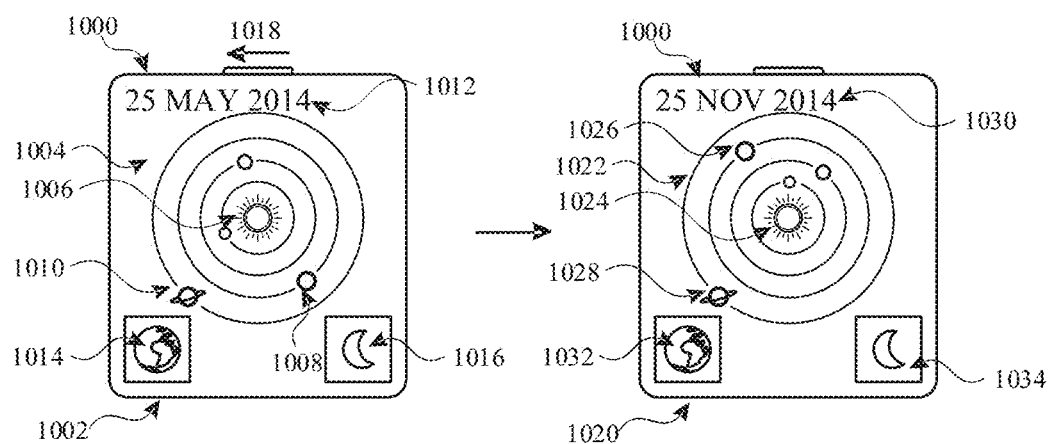
FIG. 10 illustrates exemplary context-specific user interfaces.

FIGS. 8-10 provide context-specific user interfaces that allow the user to view the passage of time while accessing a rich array of geographical, lunar, and astronomical information. For example, a user may have acquaintances all over the world and wish to know what parts of the world are in daytime or nighttime at a current time. A user may have an interest in the moon phase and wish to know what the Moon will look like tomorrow, next week, or next month. A user may have an interest in astronomy and wish to know how the planets are aligned at a particular time of interest, which could be the current day.

In FIG. 8, device 800 displays user interface screen 802 that includes first affordance 804. First affordance 804 represents a simulation of a region of the Earth, as illuminated by the Sun at the current time. For example, first affordance 804 shows that North, Central, and South America are currently in daytime, and part of the Pacific Ocean is currently in nighttime, thus simulating a region of the Earth as illuminated by the Sun at the current time.

Screen 802 also displays second affordance 806, which indicates the current time. Second affordance 806 indicates the current time (10:09) and optionally includes an indication of the day of the week (Wednesday) and the day of the month ($25^{th}$). Screen 802 further displays moon affordance 808 and solar system affordance 810, which are used to invoke additional context-specific user interfaces accessible from this screen that will be described in more detail below.

In some embodiments, the simulation of the first region of the Earth as illuminated by the Sun at the current time is a realistic rendering of the Earth at the current time. For example, the simulation of the Earth can optionally include specific geographic features. In some embodiments, the simulation of the Earth is updated to reflect weather patterns at the current time (e.g., by depicting cloud cover or other weather phenomena such as a tropical storm). The device can optionally update the Earth to reflect global-scale by obtaining data from a weather service or external server, such as The Weather Channel, Accuweather, The National Weather Service, Yahoo!™ Weather, Weather Underground, the United States Naval Observatory, or the National Oceanic and Atmospheric Administration. In some embodiments, the simulation of the first region of the Earth as illuminated by the Sun at the current time can optionally indicate other global events, such as the real-time position of the International Space Station, which can optionally be obtained from a service or external server such as from NASA.

Device 800 receives a user input (in this example, swipe 812), and in response to receiving the user input, device 800 rotates the simulation of the Earth to display a second region of the Earth as illuminated by the Sun at the current time. This is depicted on screen 820, which displays first affordance 822 depicting a second region of the Earth as illuminated by the Sun at the current time, which is indicated by second affordance 824. This feature allows the user to access additional information other than the current time from this context-specific user interface. For example, a user is able to rotate the simulation of the Earth and display which regions are currently in daytime and which regions are currently in nighttime. Tying this information to a simulation of the Earth allows the user to access complex geographical and time-related data in a manner that is instantly intuitive and comprehensible.

In some embodiments, the first affordance representing the simulation of the first region of the Earth as illuminated by the Sun at the current time includes a representation of a solar terminator (e.g., a day/night line at the current time). As illustrated by affordances 804 and 822, the simulation of the Earth can optionally include a depiction of a region of the Earth currently in daytime, a region of the Earth currently in nighttime, and/or a solar terminator dividing the two regions.

In some embodiments, the user input includes a swipe on the touch-sensitive display in a first swipe direction, as illustrated by swipe 812. This allows the user to swipe the display to rotate the simulation of the Earth. In some embodiments, the direction of rotation of the Earth is the same as the swipe direction. In some embodiments, the direction of rotation of the Earth is the opposite as the swipe direction.

In some embodiments, the user can optionally rotate the simulation of the Earth in more than one direction using swipes in different directions. For example, a swipe in one direction can optionally cause the representation of the Earth to rotate in one direction, and a swipe in an opposite or otherwise different direction can optionally cause the representation of the Earth to rotate in an opposite direction. This allows the user to swipe in different directions to direct the rotation of the simulation of the Earth.

In some embodiments, as illustrated in FIG. 8, the device has a rotatable input mechanism (e.g., 506). Device 800 receives user input representing a movement of the rotatable input mechanism (e.g., movement 830), and in response, device 800 updates first affordance 822 to represent a simulation of the first region of the Earth as illuminated by the Sun at a non-current time. This is shown on screen 840 with first affordance 842 and second affordance 844. Comparing screens 820 and 840, the simulation of the Earth has been updated (cf. 822 and 842) from indicating a region of the Earth at the current time (10:09, indicated by 824) to indicating the same region of the Earth at a non-current time (12:09, indicated by 844). This feature provides the user access to further geographic and time-related information by allowing the user to view the Earth, as illuminated by the Sun, at various times throughout the day.

In some embodiments, the device has a location sensor (e.g., GPS sensor 532 and/or GPS module 135), and before displaying the user interface screen, the device obtains a current location of the electronic device from the location sensor and displays the first region of the Earth represented by the first affordance to indicate the current location of the electronic device. This allows the device to display the Earth in such a way that the current location is part of the visible portion of the simulation of the Earth, for example as a default or user-selectable state. In some embodiments, the first affordance includes a visual marking of the current location on the representation of the Earth. This allows the user to easily identify the current location on the simulation of the Earth.

In some embodiments, the device (e.g., device 800) visually marks the current location of the device on the representation of the Earth (e.g., by displaying a symbol at the appropriate location on the representation of the Earth and/or text indicating the current location). In some embodiments, this visual marking can optionally be transitory, e.g., the visual marking can optionally be displayed briefly and then disappear or fade out. In some embodiments, while the user is at the current location, the device does not repeat the visual marking of the current location. However, if the user changes locations, the first time the user looks at the display after changing location, the device will visually mark the new current location on the representation of the Earth as set forth above. In some embodiments, the device detects a user movement of the device (e.g., a movement of the device such as raising of the user's wrist, if the device is wearable, or other movement indicative that the user is viewing the display) and in response obtains a current location of the electronic device from the location sensor. The device can optionally then determine whether the current location is the same as the location of the device at the last user movement of the device. In accordance with a determination that the current location has changed since the last user movement of the device, the device can optionally visually mark the current location on the representation of the Earth.

In some embodiments, the device visually marks a location (e.g., a current location) corresponding to the location of a contact (e.g., the location of the contact's electronic device) on the representation of the Earth (e.g., by displaying a symbol at the appropriate location on the representation of the Earth and/or text indicating the contact's location). The contact can optionally be stored, e.g., on the device or on an external device that is coupled to the device via wireless communication (e.g., Wi-Fi, Bluetooth™, near field communication ("NFC"), or any of the other cellular and/or other wireless communication techniques described herein). In some embodiments, the contact can optionally be a contact associated with a user that has agreed to provide their location data to the user of device 800, such as through a Find My Friends application, and data indicating the location of the contact's electronic device can optionally be provided through a server, which can optionally provide the location of the contacts stored on device 800. This provides the user of device 800 a quick visual reference to alert them to the current location of a contact. In some embodiments, the user can optionally further input the travel information for a contact (e.g., flight data for a contact traveling by air, train data, cruise or boat data, etc.). The device can optionally obtain data representing the current or predicted location of the contact (provided, e.g., by an airline's server in the example of flight data) and update the visual marking of the contact's location based on the obtained data.

In some embodiments, the device detects a user movement of the device (e.g., a movement of the device such as raising of the user's wrist, if the device is wearable, or other movement indicative that the user is viewing the display). In response to detecting the movement, the device animates the first affordance representing the simulation of the Earth by translating the first affordance on-screen towards the center of the displayed user interface screen. For example, upon detecting a user movement, the device animates the simulation of the Earth to rotate in from a side or edge of the display to the center of the display.

In some embodiments, the device displays on the user interface screen a third affordance representing a moon (as depicted by affordances 808, 826, and 846). In some embodiments, the third affordance can optionally be a graphical or stylized representation of a moon such as an icon, symbol, or a text indicating a moon. In some embodiments, the third affordance can optionally be a realistic rendering of the Moon as seen from the Earth at the current time with actual lunar features depicted.

The device detects a contact on the displayed third affordance, and in response to detecting the contact, the device updates the display of the user interface screen by displaying a fourth affordance representing a simulation of the Moon as seen from the Earth at the current time and a fifth affordance indicating the current time. In some embodiments, updating the display of the user interface screen includes animating the first affordance representing the simulation of the first region of the Earth as illuminated by the Sun by zooming out. This animation allows the user to recognize that the astronomical scale and/or perspective has changed.

This transitions the user interface from providing information about the current time within the current day using a simulation of the Earth to providing information about the current time within the current month using a simulation of the Moon. Whereas the context-specific user interface described in reference to FIG. 8 provides the user worldwide, customizable geographical information about day/night conditions, a context-specific user interface that provides the user customizable information about moon phases and other lunar features is illustrated in FIG. 9.

FIG. 9 shows exemplary context-specific user interfaces that can optionally be operated on device 900. Device 900 can optionally be device 100, 300, or 500 in some embodiments. The electronic device has a touch-sensitive display (e.g., touchscreen 504).

As described above, device 900 is device 800 with an updated display. Device 900 is displaying screen 902, which includes affordance 904. Affordance 904 represents a simulation of the Moon as seen from the Earth at the current time (e.g., the current moon phase). In some embodiments, fourth affordance 904 is a realistic rendering of the Moon as seen from the Earth at the current time with actual lunar features depicted. As shown by fourth affordance 904, the current moon phase is a waning crescent moon. Although FIG. 9 shows a stylized crescent moon for the representation of the Moon, this is a schematic for illustrative purposes only. Fourth affordance 904 can optionally depict a realistic rendering of the Moon, similar to how the Moon actually appears in the night sky. Screen 904 also includes fifth affordance 906, which illustrates the current time by showing the current date, day of the week, and month. In some embodiments, 906 indicates the current time of the day.

Device 900 receives a user input (e.g., movement 912 of the rotatable input mechanism), and in response to receiving the user input, the device rotates the simulation of the Moon to display the Moon as seen from the Earth at a non-current time, as shown on screen 920 by affordance 922, which represents the Moon at a non-current time, which is indicated by updated fifth affordance 924. A non-current time can optionally be within the current month or in a different month.

This is somewhat analogous to the user interaction with the simulation of the Earth described for FIG. 8. The context-specific user interface exemplified in FIG. 9 allows the user to access information about the appearance of the Moon (e.g., Moon phase, or which regions of the Moon may be visible from Earth) at various times. In some embodiments, the size of the displayed simulation of the Moon can optionally be representative of the relative distance between the Earth and the Moon at the depicted current or non-current time, or it can optionally be representative of the visual size of the Moon at the depicted current or non-current time as perceived from Earth. The device can optionally obtain such information from, e.g., a service or external server such as from NASA.

In some embodiments, a user can optionally rotate the representation of the Moon and view corresponding times by swiping the touch-sensitive display. In some embodiments, the user input can optionally include a swipe on the touch-sensitive display in a first swipe direction. In some embodiments, in response to receiving the user input, the simulation of the Moon as seen from the Earth is rotated in a first direction of rotation. In some embodiments, the first direction of rotation can optionally be based at least in part on the first swipe direction. As used herein, a rotation of the Moon can optionally include a rotation of the Moon on its axis to depict a different region of the Moon (e.g., a region of the Moon not visible from the Earth) and/or updating the appearance of the Moon as viewed from Earth at a particular time of interest, based on a rotation of the relative positions of the Moon, Earth, and Sun (e.g., updating the displayed lunar phase).

In some embodiments, the device receives a second user input, and in response to receiving the second user input, the device rotates the simulation of the Moon as seen from the Earth in a second direction of rotation that is different from the first direction. This user input could include, e.g., a swipe on the touch-sensitive display in a second swipe direction that is different from the first swipe direction.

This allows the user to direct both the direction of rotation of the Moon, and the time indicated by the fifth affordance, in response to swiping. For example, the user can optionally swipe in one direction to rotate the Moon in a specific direction and view the Moon at later times in the month, and the user can optionally swipe in another direction to rotate the Moon in an opposite direction and view the Moon at earlier times in the month.

In some embodiments, as shown in FIG. 9, a user can optionally rotate the representation of the Moon and view corresponding times by rotating a rotatable input mechanism. Thus, in some embodiments, the device has a rotatable input mechanism (e.g., 506), and the user input can optionally include a movement of the rotatable input mechanism in a first direction of rotation (e.g., rotation 912). In some embodiments, in response to receiving the user input, the simulation of the Moon as seen from the Earth is rotated in a first direction of rotation. In some embodiments, the first direction of rotation can optionally be based at least in part on the direction of movement of the rotatable input mechanism.

In some embodiments, the device receives a second user input, and in response to receiving the second user input, the device rotates the simulation of the Moon as seen from the Earth in a second direction of rotation that is different from the first direction. This user input could include, e.g., a movement of the rotatable input mechanism in a second direction of rotation that is different from the first direction of rotation.

This allows the user to direct both the direction of rotation of the Moon, and the time indicated by the fifth affordance, in response to rotating the rotatable input mechanism. For example, the user can optionally move the rotatable input mechanism in one direction to rotate the Moon in a specific direction and view the Moon at later times in the month, and the user can optionally move the rotatable input mechanism in another direction to rotate the Moon in an opposite direction and view the Moon at earlier times in the month.

In any of the embodiments described herein, the displayed simulation of the Moon can optionally indicate one or more additional lunar attributes, such as special moons (e.g., blue, black, or red moons, lunar eclipses, and so forth), the distance between the Moon and the Earth (as described above, e.g., for a supermoon), and/or moon wobble. In some embodiments, the additional lunar attribute(s) can optionally be indicated by altering the appearance of the displayed simulation of the Moon (e.g., by changing the color, size, and/or tilt of the displayed simulation of the Moon). In some embodiments, the additional lunar attribute(s) can optionally be indicated by text. In some embodiments, the additional lunar attribute(s) can optionally correspond to the current lunar attribute(s). In some embodiments, the additional lunar attribute(s) can optionally correspond to the lunar attribute(s) at the currently displayed date (e.g., if the user has rotated the Moon to view the Moon at earlier or later times in the month, as described above). For example, in some embodiments, while the simulation of the Moon is being rotated to depict the Moon at different times of the month or year, the simulation of the Moon can optionally be updated to reflect one or more additional lunar attributes at the time currently indicated by the displayed simulation of the Moon.

In some embodiments, the device can optionally display additional lunar information in response to a user input. The additional lunar information can optionally be displayed, e.g., as part of screen 902 or 920, or on a user interface screen that replaces screen 902 or 920 (such as a lunar information application). Additional lunar information can optionally include without limitation the name of the lunar phase, the distance from the Earth to the Moon, the time of moonrise and/or moonset (e.g., on the current day and/or at the user's current location), and the like. In some embodiments, the additional lunar information can optionally correspond to the current lunar information (e.g., the current lunar phase, distance to the Moon, time of moonset/moonrise, etc.). In some embodiments, the additional lunar information can optionally correspond to the lunar information of the currently displayed date, e.g., if the user has rotated the Moon to view the Moon at earlier or later times in the month, as described above.

For example, in some embodiments, the device can optionally detect a user input (e.g., a user double tap on the touch-sensitive display, including a first contact on the touch-sensitive display and a second contact on the touch-sensitive display). In the exemplary embodiment and in response to the user double tap, the device can optionally determine whether the first contact and the second contact were received within a predetermined interval. In response to detecting the user double tap, and in accordance with the determination that the first contact and the second contact were received within the predetermined interval, the device can optionally display additional lunar information.

In some embodiments, the user interface screen, after updating the display to show the simulation of the Moon, displays an affordance indicating an earth (e.g., 910 or 928). Upon contacting the earth affordance, the user can optionally return to the context-specific user interface described in reference to FIG. 8. In some embodiments, the earth affordance can optionally be a graphical or stylized representation of an earth such as an icon, symbol, or a text indicating an earth. In some embodiments, the earth affordance can optionally be a realistic rendering of the Earth.

In some embodiments, device 900 displays on the user interface screen a sixth affordance representing a solar system (as depicted by affordances 810, 828, 848, 908, and 926). In some embodiments, the sixth affordance can optionally be a graphical or stylized representation of a solar system such as an icon, symbol, or a text indicating a solar system. In some embodiments, the sixth affordance can optionally be a realistic rendering of the solar system.

Device 900 detects a contact on the displayed sixth affordance, and in response to detecting the contact, the device updates the display of the user interface screen by displaying a seventh affordance with representations of the Sun, the Earth, and one or more non-Earth planets at their respective positions at the current time and an eighth affordance indicating the current time. In some embodiments, updating the display of the user interface screen includes animating the first affordance representing the simulation of the first region of the Earth as illuminated by the Sun or animating the fourth affordance representing a simulation of the Moon as seen from the Earth by zooming out. This animation allows the user to recognize that the astronomical scale and/or perspective has changed.

This transitions the user from viewing information about the current time within the current month using a simulation of the Moon to viewing information about the current time within the current year using a simulation of the solar system. Whereas the context-specific user interface described in reference to FIG. 9 provides the user customizable information about lunar conditions, a context-specific user interface that provides the user customizable information about the solar system and relative positions of the Earth and other planet(s) is illustrated in FIG. 10.

FIG. 10 shows exemplary context-specific user interfaces that can optionally be operated on device 1000. Device 1000 can optionally be device 100, 300, or 500 in some embodiments. The electronic device has a touch-sensitive display (e.g., touchscreen 504).

As described above, device 1000 is device 800 and/or device 900 with an updated display. Device 1000 displays screen 1002, which includes seventh affordance 1004. Seventh affordance 1004 includes representation of the Sun 1006, representation of the Earth 1008, and representations of Mercury, Venus, and Saturn (e.g., Saturn is depicted by planet 1010). 1006, 1008, and 1010 are depicted at their respective positions at the current date (in this example, May 25, 2014), indicated by eighth affordance 1012. In some embodiments, eighth affordance 1012 also indicates the current time of day.

Optionally, in some embodiments, the solar system depicts all 8 planets. In some embodiments, the solar system depicts the four inner planets. In some embodiments, the solar system depicts other astronomical features, such as an asteroid or asteroid belt, one or more moons of one or more planets (e.g., the Moon), a manmade satellite or other space probe, a comet, Pluto, and so forth.

Device 1000 receives a seventh user input (e.g., movement 1018 of the rotatable input mechanism). In response, device 1000 updates the seventh affordance to depict respective positions of the Sun, the Earth, and the one or more non-Earth planets for a non-current date. This is depicted by seventh affordance 1022 on screen 1020. Seventh affordance 1022 includes representation of the Sun 1024, representation of the Earth 1026, and representations of Mercury, Venus, and Saturn (e.g., Saturn is depicted by planet 1028) at their respective positions at the non-current date, which is Nov. 25, 2014, as depicted by eighth affordance 1030. In some embodiments, eighth affordance 1030 also indicates the current time of day. 4

This context-specific user interface allows the user to access information about the relative positions of the Earth and one or more non-Earth planets at a non-current date, which can optionally be within the current year or in a different year. In some embodiments, the Sun, the Earth, and the one or more non-Earth planets are depicted as realistic renderings. In some embodiments, the Sun, the Earth, and the one or more non-Earth planets are depicted as stylized or symbolic renderings.

In some embodiments, a user can optionally rotate the representation of the solar system by swiping on the touch-sensitive display. Thus, in some embodiments, the user input can optionally include a swipe on the touch-sensitive display. In some embodiments, in response to detecting a swipe, the Earth and the one or more non-Earth planets are rotated about the Sun in a first direction of rotation. In some embodiments, the first direction of rotation can optionally be based at least in part on the first swipe direction.

In some embodiments, in response to detecting a swipe on the touch-sensitive display in a different direction, the device rotates the Earth and the one or more non-Earth planets about the Sun in a second direction of rotation that is different from the first direction. This allows the user to direct both the direction of rotation of the Earth and the one or more non-Earth planets, and the time indicated by the eighth affordance, in response to swiping. For example, the user can optionally swipe in one direction to rotate the Earth and the one or more non-Earth planets in a specific direction and view the Earth and the one or more non-Earth planets at later dates during the year (or in a different year), and the user can optionally swipe in another direction to rotate the Earth and the one or more non-Earth planets in an opposite direction and view the Earth and the one or more non-Earth planets at earlier dates during the year (or in a different year).

In some embodiments, as shown in FIG. 10, a user can optionally rotate the representation of the solar system by rotating a rotatable input mechanism (e.g., 506). In these embodiments, the user input can optionally include a movement of the rotatable input mechanism in a first direction of rotation (e.g., movement 1018). In some embodiments, in response to receiving the user input, the Earth and the one or more non-Earth planets are rotated about the Sun in a first direction of rotation. In some embodiments, the first direction of rotation can optionally be based at least in part on the direction of movement of the rotatable input mechanism.

In some embodiments, the device receives a second user input, and in response to receiving the second user input, the device rotates the Earth and the one or more non-Earth planets about the Sun in a second direction of rotation that is different from the first direction. This user input could include, e.g., a movement of the rotatable input mechanism in a second direction of rotation that is different from the first direction of rotation.

This allows the user to direct both the direction of rotation of the Earth and the one or more non-Earth planets, and the time indicated by the eighth affordance, in response to rotating the rotatable input mechanism. For example, the user can optionally move the rotatable input mechanism in one direction to rotate the Earth and the one or more non-Earth planets in a specific direction and view the Earth and the one or more non-Earth planets at later times in the year, and the user can optionally move the rotatable input mechanism in another direction to rotate the Earth and the one or more non-Earth planets in an opposite direction and view the Earth and the one or more non-Earth planets at earlier times in the year.

In some embodiments, the representation of the Earth can optionally further include a representation of the orbit of the Earth around the Sun. In some embodiments, the representation of the one or more non-Earth planets can optionally further include a representation of the orbit of the one or more non-Earth planets around the Sun. The representation of an orbit can optionally be a graphical representation, such as a line or ring. In some embodiments, the representation of the orbit can optionally be stylized. In some embodiments, the representation of the orbit can optionally be based on the actual dimensions of the planet's orbit around the Sun.

In some embodiments, the user can optionally contact the touch-sensitive display at a location associated with the representation of the Earth or the one or more non-Earth planets. For example, the contact can optionally be at or near the displayed representation of the planet itself, or the contact can optionally be at or near the displayed representation of the planet's orbit. In some embodiments, the device can optionally determine the selected planet based on a determination of the displayed representation of a planet or the displayed representation of a planet's orbit nearest to the location of the contact. In some embodiments, the contact can optionally be a press and hold-type contact on the display. Upon detecting the contact, the device can optionally visually distinguish the representation of the selected planet and/or the representation of the selected planet's orbit (e.g., by altering the color and/or brightness of the displayed planet and/or orbit, by displaying an outline or other visual demarcation of the planet and/or orbit, by animation the planet and/or orbit, etc.). In some embodiments, while continuing to receive the contact, the device can optionally determine whether the duration of the contact exceeds a predetermined threshold and, in accordance with a determination that the contact exceeds the predetermined threshold, the device can optionally visually distinguish the representation of the selected planet and/or the representation of the selected planet's orbit. When the user lets go of the contact, the device can optionally display information about the selected planet. Such information can optionally include, without limitation, the size of the planet, the distance (e.g., current distance, average distance, etc.) between the planet and the Sun, the distance (e.g., current distance, average distance, etc.) between the planet and the Earth (if the selected planet is not the Earth), a time and/or location in the sky when the planet will be visible from the Earth (if the selected planet is not the Earth), a temperature on the surface of the planet, the number of moons orbiting the planet, the number and/or identity of any spacecraft currently orbiting or near the planet, a description of the planet (e.g., whether the planet is terrestrial or gas, the date of discovery of the planet, information about the planet's name, and the like), a time (past, present, or future) of a particular alignment of the planet with another object in the solar system, and so forth.

After viewing the information about the planet, the user may wish to dismiss the information or view information about another planet. In some embodiments, the user can optionally tap to dismiss the information or swipe to select another planet. For example, a swipe in a first direction can optionally select the next planet whose orbit is farther from the Sun, relative to the previous planet, and a swipe in the opposite direction can optionally select the next planet whose orbit is nearer to the sun, relative to the previous planet. In some embodiments, after displaying the information about the Earth or the one or more non-Earth planets associated with the contact, the device can optionally receive a user input and determine whether the user input represents a tap or a swipe on the touch-sensitive display (e.g., by using contact/motion module 130 to detect the user gesture). In accordance with a determination that the user input represents a tap, the device can optionally remove the displayed information about the planet. In accordance with a determination that the user input represents a swipe, the device can optionally replace the displayed information about the planet with information about a second planet different from the first planet (e.g., a planet not associated with the user contact).

In some embodiments, the user interface screen, after updating the display to show the simulation of the solar system, displays an affordance indicating a moon (e.g., 1016 or 1034) and/or an affordance indicating an earth (e.g., 1014 or 1032). In some embodiments, the moon and/or the earth affordance can optionally be a graphical or stylized representation of an earth or moon such as an icon, symbol, or a text. In some embodiments, the moon and/or the earth affordance can optionally be a realistic rendering of the Moon or the Earth. Upon contacting the earth affordance, the user can optionally return to the context-specific user interface described in reference to FIG. 8. Upon contacting the moon affordance, the user can optionally return to the context-specific user interface described in reference to FIG. 9.

In some embodiments of any of the context specific-user interfaces illustrated in FIGS. 8-10, a user can optionally move (e.g., rotate) a rotatable input mechanism to scroll a displayed indication of time forward or backward in time. It is to be appreciated that such a feature can optionally be applied to any of the context-specific user interfaces described herein; however, for ease of explanation, this feature can optionally be described in reference to FIGS. 8-10. Any model for mapping a movement of a rotatable input mechanism to the distance or speed of scrolling can optionally be used, such as those described in U.S. patent application Ser. No. 14/476,700, "Crown Input for a Wearable Electronic Device," filed Sep. 3, 2014, which is hereby incorporated by reference in its entirety. For example, acceleration, velocity, or the like can optionally be used to determine the amount of speed of scaling of the displayed indication of time.

In some embodiments, a user can optionally move the rotatable input mechanism to scroll the indication(s) of time displayed on screen 802, 820, and/or 840. In response to detecting the movement of the rotatable input mechanism (e.g., movement 830), the device can optionally update the displayed representation of the Earth, for example by simulating a rotation of the Earth, to display the Earth as illuminated by the Sun at a different time of day (compare 822 and 842). In some embodiments, the device can optionally update the displayed indication of time to show a different time (compare 824 and 844). Similarly, as shown in FIG. 9, in response to detecting the movement of the rotatable input mechanism (e.g., movement 912), the device can optionally update the displayed simulation of the Moon to display a different moon phase at a different time of month (compare, e.g., 904 and 922), and/or update the displayed indication of time to show a different time (compare, e.g., 906 and 924). Similarly, as shown in FIG. 10, in response to detecting the movement of the rotatable input mechanism (e.g., movement 1018), the device can optionally update the displayed positions of the Earth and the one or more non-Earth planets to display different positions relative to the Sun at different times of year (compare, e.g., 1008 and 1010 to 1026 and 1028), and/or update the displayed indication of time to show a different time (compare, e.g., 1012 and 1030). In some embodiments, the representations of the Earth, the Moon, and/or the positions of the Earth and the one or more non-Earth planets can optionally be rotated in a direction based on the direction of movement of the rotatable input mechanism. In some embodiments, the representations of the Earth, the Moon, and/or the positions of the Earth and the one or more non-Earth planets can optionally be rotated at a rate based on the rate and/or amount of movement of the rotatable input mechanism, e.g., according to any of the models referenced above. It is to be appreciated that, depending on the displayed context-specific user interface, movement of the rotatable input mechanism can optionally cause the displayed indication of time to be updated at different timescales. For example, the same degree and/or rate of rotation can optionally cause the context-specific user interface shown in FIG. 8 to update by an hour, whereas the context-specific user interface shown in FIG. 9 can optionally update by a day or week, or the context-specific user interface shown in FIG. 10 can optionally update by a month or year.

In some embodiments of any of the context specific-user interfaces illustrated in FIGS. 8-10, the device can optionally indicate other global or astronomical features or objects, such as the real-time position of the International Space Station, as described above. In some embodiments, a user can optionally tap on the display (e.g., at a location corresponding to space), and in response to detecting the tap, the device can optionally provide further information on other global or astronomical features or objects, e.g., the number of people currently in space, the number and/or name(s) of spacecraft currently in space, etc.

Figure 11A:
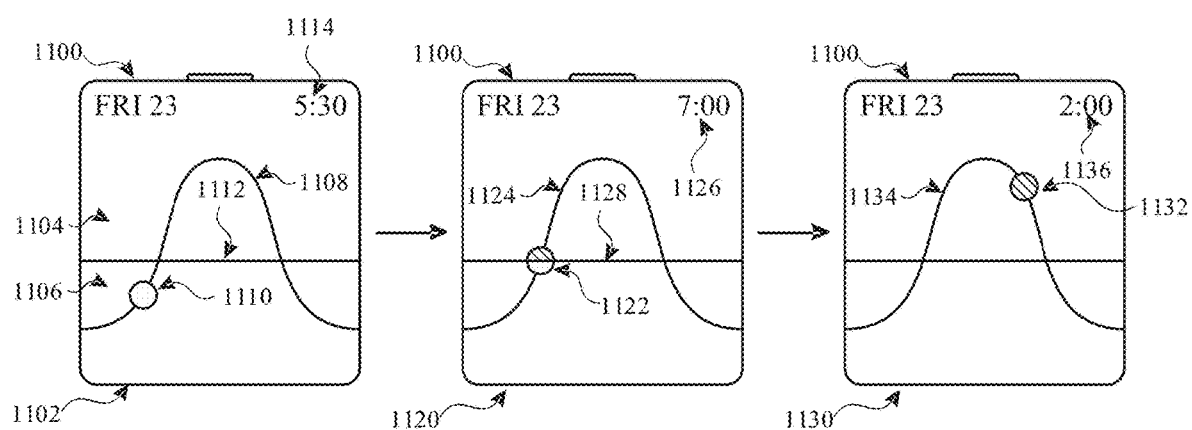
FIGS. 11A-11C illustrate exemplary context-specific user interfaces.

FIG. 11A shows exemplary context-specific user interfaces that can optionally be operated on device 1100. Device 1100 can optionally be device 100, 300, or 500 in some embodiments. The electronic device has a touch-sensitive display (e.g., touchscreen 504).

A user may wish to view the time of day in the context of daytime and nighttime hours. For example, a user may wish to know the time of dawn or dusk, or access a simple, visual indication of how much time is left before sunset.

As shown in FIG. 11A, device 1100 displays user interface screen 1102. User interface screen 1102 has two portions: first portion 1104 indicating daytime, and second portion 1106 indicating nighttime. Screen 1102 also displays a user interface object representing a sinusoidal wave 1108. Sinusoidal wave 1108 can optionally represent the general appearance of a sinusoidal wave without mathematical accuracy or precision. Importantly, however, sinusoidal wave 1108 has a period of approximately a day and indicates the path of the Sun through the day. As shown in FIG. 11A, the troughs of 1108 represent solar midnight (corresponding to two solar midnights 24 hours apart), and the peak of 1108 represents solar noon for the day. Also displayed on screen 1102 is first affordance 1110, which is displayed at a position along sinusoidal wave 1108 at a position that indicates the current time of day. Screen 1102 also displays horizon line 1112, an optional feature which divides the daytime and nighttime portions of the display. As shown, horizon line 1112 intersects sinusoidal wave 1108 at two points, representing sunrise and sunset. Finally, screen 1102 displays second affordance 1114, which indicates the current time of day.

Through the course of the day, 1114 displays the current time (in this example, 5:30 am), and first affordance 1110 tracks along the sinusoidal wave. When 1110 is in daytime portion 1104, the current time is during daytime. When 1110 is in nighttime portion 1106, the current time is in nighttime. At 5:30 am, it is just before dawn, as first affordance 1110 is still in the nighttime portion of screen 1102. The features of this context-specific user interface provide the user a simple and intuitive way to track the current time and understand how long it is until, for example, sunset, or sunrise. In some embodiments, the affordance representing the sun appears hollow (e.g., like a ring) when at a position fully within the nighttime portion (e.g., 1106) of the display, as shown by first affordance 1110. This further reinforces to the user that it is currently before dawn.

For example, screen 1120 shows a second time of day and includes first affordance 1122, sinusoidal wave 1124, and second affordance 1126. As indicated by second affordance 1126, it is now sunrise at 7:00 am. The position of first affordance 1122 along wave 1124 is between the first portion and the second portion, indicating the transition from nighttime to daytime. This is further depicted on screen 1120 by positioning affordance 1122 on line 1128, which separates the two portions of the display. This is yet further indicated by the appearance of affordance 1122 itself, which can optionally be half-filled when the affordance is at a position intersecting the first and second portions of the display.

Screen 1130 shows a third time of day and includes first affordance 1132, sinusoidal wave 1134, and second affordance 1136. As indicated by second affordance 1136, it is now 2:00 pm. The position of first affordance 1132 along wave 1134 is within the first portion of the display, indicating daytime. This is further depicted by the appearance of affordance 1132 itself, which, can optionally be filled when the affordance is at a position fully within the first portion.

In some embodiments, the color of the first and/or the second portion(s) can optionally indicate daytime (e.g., with a warm or bright color) or nighttime (e.g., with a dark or cool color). In some embodiments, the first and second portions can optionally be the same color, which can optionally be representative of the current light conditions. In these embodiments, the user may still be able to tell the current light conditions through the sinusoidal wave, optional horizon line, and/or optional appearance of the sun affordance (e.g., filled, half-filled, or hollow). In some embodiments, the sinusoidal wave can optionally include two or more colors, and these colors can optionally indicate the daytime and nighttime portions (e.g., parts of the wave in the daytime portion can optionally be one color, and parts of the wave in the nighttime portion can optionally be another). Moreover, the two portions can optionally be of any shape (not limited to rectangular). For example, the daytime portion can optionally appear as an illuminated circle that encompasses the sinusoidal wave, with the nighttime portion appearing all around the circle.

In some embodiments, device 1100 can optionally have a location sensor (e.g., GPS sensor 532 and/or GPS module 135). In these embodiments, device 1100 can optionally obtain a current location of the device from the location sensor and indicate daytime and nighttime hours at the current location at the current time through the ratio of the displayed first and second portions. That is to say, the size of the daytime and nighttime portions of the display can optionally be adjusted, relative to daytime hours at the current location and date. As an illustrative example, if the current location is near the Arctic Circle during summer, the daytime portion can optionally include all or nearly all of the screen, such that all or nearly all of the displayed sinusoidal wave is within the daytime portion. As another example, if the user were to travel latitudinally across the globe, the position of affordance 1110, 1122, or 1132 (for example) would not change, but the ratio of daytime:nighttime portions and relative amount of the sinusoidal wave within each would be adjusted to reflect the current location. This provides a more realistic depiction of the time of day to the user, thus enhancing the user interface.

In some embodiments, the amplitude of the displayed sinusoidal wave is based on the height of the Sun relative to the horizon at the current location and current time. For example, the wave can optionally flatten or otherwise decrease in amplitude to reflect the sun having a lower path through the sky at the location and current day (e.g., in locations more proximal to the poles in winter).

Figure 11B:
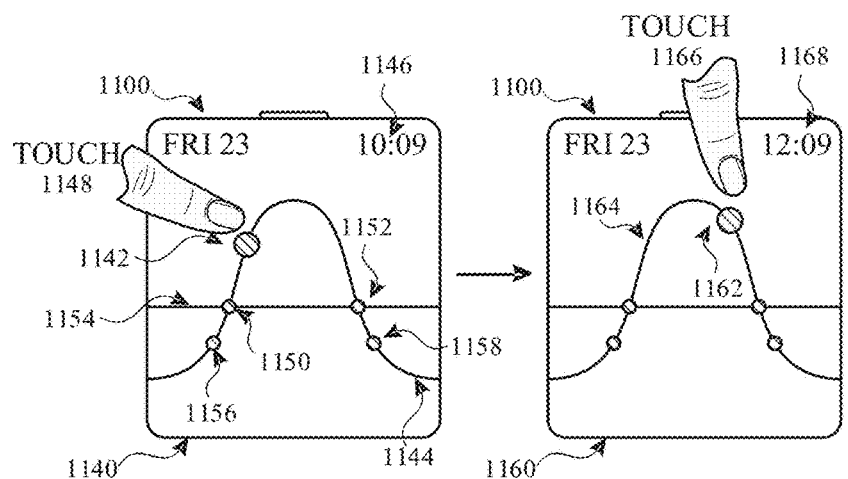

Attention is now directed to FIG. 11B, which illustrates an example of this context-specific user interface that provides a user-interactable feature to view additional day/night information. FIG. 11B shows user interface screen 1140 that can be displayed on device 1100. Screen 1140 includes first affordance 1142, which represents the position of the sun at the current time along sinusoidal wave 1144. Screen 1140 also displays second affordance 1146, which also indicates the current time (10:09 am). Device 1100 receives a user contact at displayed first affordance 1142, shown by touch 1148.

As detected by device 1100, the user touches first affordance 1142 and drags the affordance to a second position along the sinusoidal wave in a continuous gesture (as indicated by touch 1166). In response, as shown on screen 1160, device 1100 displays first affordance 1162 at the second position along sinusoidal wave 1164. Device 1100 also updates the second affordance 1168 to indicate a non-current time. This new time (12:09) corresponds to the time of day indicated by the second position of affordance 1162. Thus, the user is able to view the time of day represented by any position along the sinusoidal wave by simply moving affordance 1148 and/or 1166.

It is to be noted that the movement of the contact can optionally begin and end at positions on the sinusoidal wave, but the movement itself need not precisely track the sinusoidal wave. That is, the user is not required to track the contact precisely along the sinusoidal wave. The device can optionally simply receive a user contact at the displayed first affordance, and, while continuing to receive the user contact, detect a movement of the contact from the first position to a second position without a break in the user contact on the touch-sensitive display (e.g., the user does not lift their finger off the touch-sensitive display).

In response to detecting the contact at the second position, the device can optionally translate the first affordance on-screen to the second position while tracking the sinusoidal wave. Thus, while the user contact does not need to track the sinusoidal wave, the device nonetheless translates the first affordance from the first position to the second position by tracking the first affordance along the sinusoidal wave. In some embodiments, the device can optionally continuously update the time, as indicated by the second affordance. Alternatively, the device can optionally update the time indicated by the second affordance when the continuous contact has come to rest at the second position. In alternative embodiment, after detecting the contact at the first position, the device can optionally translate the first affordance on-screen to the second position on the sinusoidal wave in response to a rotation of a rotatable input mechanism.

FIG. 11B illustrates optional features of this context-specific user interface. As shown on screen 1140, in response to receiving user touch 1148 at affordance 1142, device 1100 displays affordances 1150 and 1152, which depict sunrise and sunset, respectively. Affordances 1150 and 1152 are displayed along wave 1144 at the two points where the wave intersects the boundary between the first portion indicating daytime and the second portion indicating nighttime. This boundary is demarcated on screen 1140 with optional horizon line 1154. When horizon line 1154 is displayed, affordances 1150 and 1152 are displayed at the two points where line 1154 intersects wave 1144. In some embodiments, affordances 1150 and 1152 can optionally further include a numerical display of sunrise and sunset times, respectively, for the current day. In some embodiments, these affordances are also displayed while device 1100 receives user contact at the second position.

Also displayed on screen 1140 in response to receiving user touch 1148 at affordance 1142 are affordances 1156 and 1158. Affordances 1156 and 1158 are displayed along wave 1144 at positions corresponding to dawn and dusk, respectively. In some embodiments, these affordances are also displayed while device 1100 receives user contact at the second position. These displayed affordances indicate to the user when first and last light will occur, allowing the user to visually gauge when they will occur, or how long ago they occurred, by the distance from affordance 1142. In some embodiments, the time of dawn can optionally be astronomical dawn, nautical dawn, or civil dawn. In some embodiments, the time of dusk can optionally be astronomical dusk, nautical dusk, or civil dusk.

In some embodiments, device 1100 detects a contact at the displayed first affordance, a movement of the contact, and a break in contact. In response to detecting the break in contact, the device can optionally translate the first affordance back to the position indicating the current time and update the second affordance to indicate the current time. This allows the user to drag the affordance to a position of interest, view the indicated time for that position, and by releasing the contact, "snap back" to the current position.

Figure 11C:
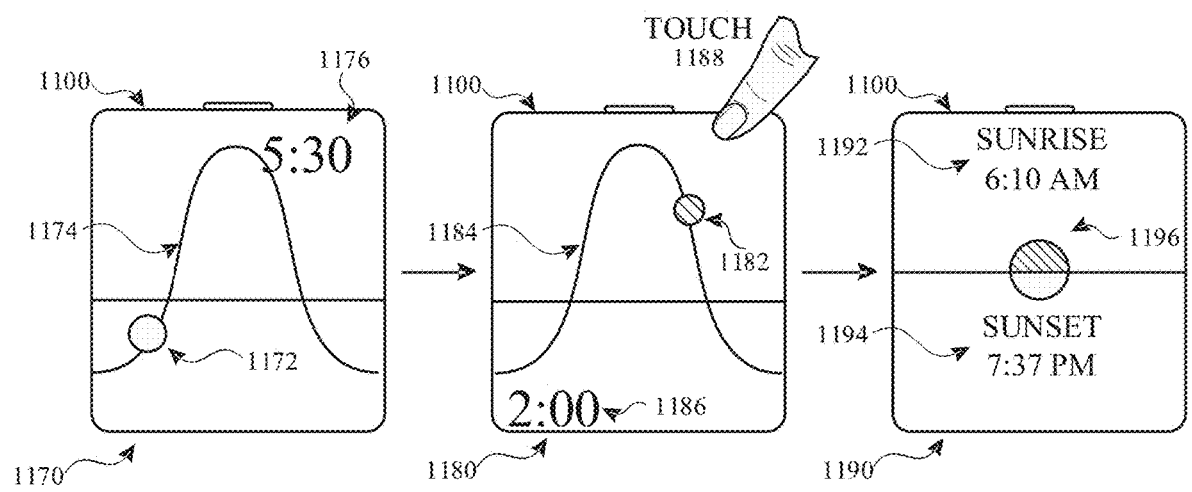

FIG. 11C illustrates further optional features of this context-specific user interface. In some embodiments, particularly when the user interface screen is displayed on a reduced-size display, it may be desirable to display each of the elements as large as possible for visibility. Screen 1170 displays first affordance 1172, sinusoidal wave 1174, and second affordance 1176. As shown, affordance 1176 intersects wave 1174. When the current time reaches 2:00, as shown on screen 1180, the position of affordance 1182 indicating 2:00 along wave 1184 intersects with the position of the second affordance. Device 1100 can optionally determine whether the position of the first affordance intersects with the second affordance (e.g., a position that would overlap with, be obscured by, or otherwise appear close to the second affordance). In response to a determination that the affordances intersect, the device can optionally display the second affordance at another position on the display that does not intersect. As illustrated on screen 1180, the position of affordance 1186 is different from that of 1176, because the relative position of 1176 on the screen would intersect with first affordance 1182. This accommodation allows the device to display a richly informative screen without visual interference between displayed elements.

The user can optionally also contact the touch-sensitive display with touch 1188 on screen 1180. This contact can optionally be, for example, at any position on the display besides the position of the first affordance representing the sun at the current time. In response to detecting the contact, device 1100 displays screen 1190, which includes sunrise time 1192, sunset time 1194, and affordance 1196, which provides a non-textual indication of daytime and nighttime. This allows the user to access sunrise and sunset times from any user interface screen.

The user can optionally also set a reminder for a time of day through this context-specific user interface. For example, if the device has a rotatable input mechanism (e.g., 506), the user can optionally rotate the rotatable input mechanism to set the reminder. In response to detecting a movement of the rotatable input mechanism, the device can optionally translate the first affordance to a third position indicating a non-current time of day. The user can optionally contact the first affordance displayed at the third position, and in response to detecting the contact, the device can optionally set a user reminder for the indicated time of day.

For example, the device can optionally display another affordance representing a user prompt to set an alert for the indicated time of day. The reminder could be a visual alert. In this example, the device can optionally display a visual alert that is displayed when the time of day is approaching. Alternatively, the device can optionally display at any time a visual affordance that shows the third position along the sinusoidal wave to help the user understand how far the indicated time of day is from the current time. In some embodiments, the user reminder could include an audio alert that audibly notifies the user when the indicated time of day has arrived or will arrive shortly. In some embodiments, the user reminder could include a haptic alert. The device can optionally create a haptic signal to the user when the indicated time of day is approaching (e.g., using haptic feedback module 133 and tactile output generator 167).

These features allow the user to further customize this context-specific user interface. It is to be appreciated that this feature does not create a specific alert at a time and date; rather, it allows the user to set a generic alert for a time of day that is not tied to a specific date. For example, a user may notice a certain lighting effect, such as sunlight through a window in their house, and wish to set a reminder so that they can view this effect at the time of day when it occurs. Within the context of daytime/nighttime information, this allows the user to customize the user interface to include not only sunrise, sunset, dawn, dusk, and so forth, but also a time of day that they wish to designate.

Figure 12:
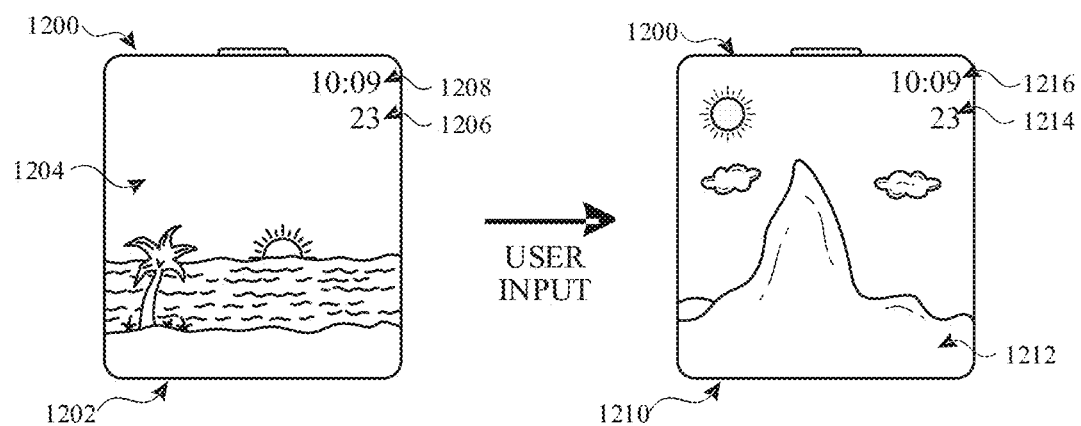
FIG. 12 illustrates exemplary context-specific user interfaces.

FIG. 12 shows exemplary context-specific user interfaces that can optionally be operated on device 1200. Device 1200 can optionally be device 100, 300, or 500 in some embodiments. In some embodiments, the electronic device has a touch-sensitive display (e.g., touchscreen 504).

A user may wish to view a certain background image on the user interface screen while retaining as much of the original image as possible. Therefore, it may be advantageous to provide a context-specific user interface that displays the time and/or date not simply as interface objects displayed over the image, but rather interface objects that appear to arise from the image itself, thereby maximizing the user's view of the image while still providing visible indications of the time and date. This may be particularly true if the user interface is displayed on a reduced-size display.

As shown in FIG. 12, device 1200 is displaying user interface screen 1202, which includes background 1204. Background 1204 is based on an image of a beach. In some embodiments, the image can optionally be a photo.

As used here, consistent with its accepted meaning in the art, the phrase "background" refers to the background of a user interface screen that is visually distinguishable from text and user interface objects also displayed in the user interface screen. Basing a background on an image simply means displaying the image as a background of a displayed screen. In some cases, the image and the background can optionally be identical. In other cases, displaying the image as a background can optionally involve modifying one or more aspects of the image to fit on the display, such as image size, image cropping, image resolution, and so forth.

Screen 1202 also includes user interface objects 1206 and 1208. 1206 indicates a date (the 23$^{rd}$), whereas 1208 indicates a time of day (10:09). In some embodiments, the device can optionally indicate the current date and/or the current time of day.

Displayed background 1204 includes a plurality of pixels. A subset of these pixels is modified in appearance relative to the image such that the subset comes to represent one or more of user interface object 1206 and user interface object 1208. That is to say, at least one of these user interface objects is displayed by modifying the background. For example, the subset of pixels can optionally be modified by changing color and/or intensity.

In some embodiments, the subset of the pixels can optionally be modified by color blending. In some embodiments, the subset of the pixels can optionally be modified by color blurring. In some embodiments, the subset of the pixels can optionally be modified by applying a gradient. Importantly, these examples illustrate that the appearance of the subset of the pixels can optionally be influenced by both the background image at the position of the user interface object(s) and the user interface object(s) themselves. This allows the user to view the image more clearly (since the user interface object(s) are not simply displayed on top of and obstructing the image), while also maintaining the legibility of the user interface object(s).

In some embodiments, one of user interface objects 1206 and 1208 is displayed by modifying the background, and the other is displayed independent of the background (e.g., a set color and/or intensity not produced by modifying the background pixel subset). In these embodiments, the device can optionally receive data representing a background color at the position of the displayed user interface object (e.g., 1206 or 1208), and the color of the displayed user interface object can optionally be different from this background color (e.g., a different color and/or intensity). For example, a background color at the position of the displayed user interface object can optionally include the most prevalent color at that position. This feature ensures that, if one of the user interface objects is a preset color, it will be displayed legibly on the background, no matter the appearance of the background.

In some embodiments, the image on which the background is based can optionally be stored on device 1200.

In other embodiments, the image on which the background is based can optionally be stored on an external device that is coupled to device 1200 via wireless communication (e.g., Wi-Fi, Bluetooth™, near field communication ("NFC"), or any of the other cellular and/or other wireless communication techniques described herein). In these embodiments, before displaying screen 1202, device 1200 can optionally receive (via wireless communication) data representing the background from the external device. Using these data, device 1200 can optionally then display the background.

Optionally, when the image is stored on an external device, device 1200 can optionally display a background based on the current background of the external device. For example, the device can optionally receive (via wireless communication) data representing a current background from the external device and display a user interface screen that includes a background corresponding with the current background of the external devices. The device then modifies a subset of the pixels of the background from the external device to represent one or more of a user interface object indicating a date and a user interface object indicating a time of day. In some embodiments, device 1200 can optionally further alter the background from the external device, for example, by changing one or more of the image size, image cropping, image resolution, and the like, particularly if the external device and device 1200 have different display dimensions and/or resolutions.

Returning to FIG. 12, a user may wish to select an image from a folder of images to serve as the background. Thus, device 1200 can optionally access a folder that includes two or more images (e.g., the images shown on screens 1202 and 1210), select a first image, and display a user interface screen that includes a background based on the first image (e.g., background 1204). As described above, this background includes a subset of pixels that are modified in appearance relative to the image to represent one or more of a user interface object indicating a date (e.g., 1206) and a user interface object indicating a time (e.g., 1208).

Optionally, as shown in FIG. 12, after displaying screen 1202, device 1200 can optionally receive data representing a user input. In response, device 1200 obtains data representing background 1204, select a second image from the folder that is different from the first image, and display screen 1210, which includes background 1212 based on the second image. As shown in FIG. 12, backgrounds 1204 and 1212 are based on different images: a beach scene and a mountain scene, respectively. This feature ensures that, when the user decides to change the displayed background, the device displays a different image, compared to the image displayed before the user input.

As shown on FIG. 12, screen 1210 also includes user interface object 1214 indicating a date and user interface object 1216 indicating a time of day. At least one of these user interface objects is displayed by modifying a subset of pixels of background 1212 at the position of the displayed user interface object(s), as described above. This subset can optionally be modified in any of the ways described above, such as color blending, blurring, gradient, etc. In some embodiments, one of the user interface objects can optionally be a color independent of the background, and device 1200 can optionally modify this color to adapt to the background, as set forth above. The image on which the background is based can optionally be stored on device 1200 or on an external device, as described above.

A variety of user inputs can optionally serve as the user input to change the background. In some embodiments, the user input can optionally be a touch on the display, a rotation of a rotatable input mechanism, a depression of a depressible and rotatable input mechanism, or a swipe on the display. In some embodiments, the user input can optionally be a user movement of the electronic device (e.g., a movement of the device such as raising of the user's wrist, if the device is wearable, or other movement indicative that the user is viewing the display). Advantageously, this feature enables the device to display a different image each time the display is viewed, thereby providing the user with a customized display at each viewing and enhancing the user interaction with the device. As described above, a user movement of the device could be detected, for example, by using an accelerometer (e.g., 534), a gyroscope (e.g., 536), a motion sensor (e.g., 538), and/or a combination thereof.

In some embodiments, the user can optionally choose to exclude an image from the folder so that it is no longer selected as a background. In these examples, the device can optionally receive data representing a user prohibition of an image from the folder. Such a prohibition can optionally be received through the user interface shown in FIG. 12, or it can optionally be received through the folder containing the two or more images (e.g., the folder can optionally include a feature that allows the user to select more images, drag images into the folder, delete images from the folder, and/or prohibit an image for use as a background). In response to receiving the data, the device can optionally prevent the display of the image as a background in response to future user input.

Figure 13A:
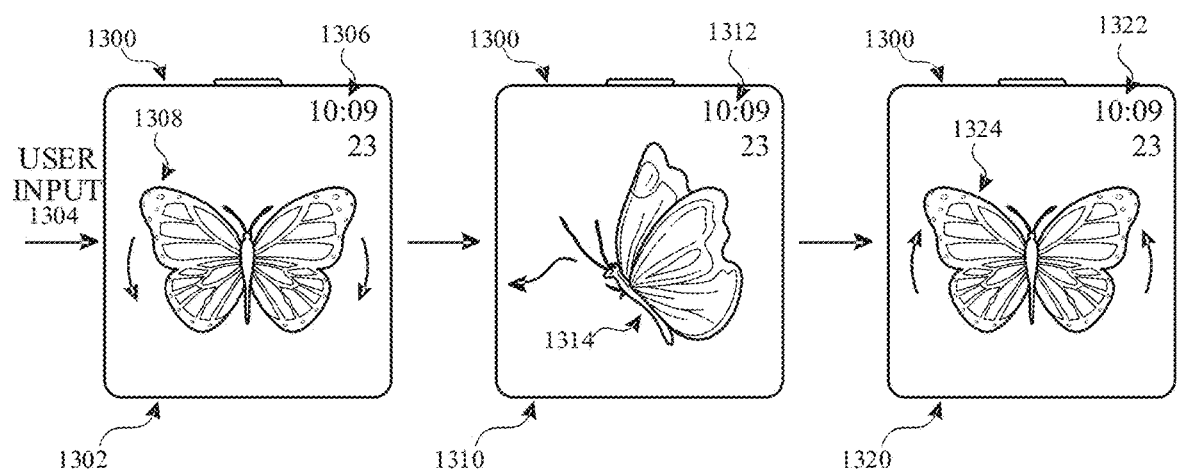
FIGS. 13A and 13B illustrate exemplary context-specific user interfaces.

FIG. 13A shows exemplary context-specific user interfaces that can optionally be operated on device 1300. Device 1300 can optionally be device 100, 300, or 500 in some embodiments. The electronic device has a touch-sensitive display (e.g., touchscreen 504).

A user may wish to view a displayed animation on an electronic device in response to an input. Because a user may look at an electronic device many times per day, particularly if the user relies on the device for timekeeping, it may be advantageous to provide the user a different experience each time the display is viewed. This keeps the user interested and engaged with the electronic device.

As shown in FIG. 13A, device 1300 displays user interface screen 1302 in response to detecting user input 1304 at 10:09. Screen 1302 includes user interface object 1306, which indicates the time, as well as user interface object 1308, which depicts a butterfly. After displaying screen 1302, device 1300 animates butterfly 1308 by sequentially displaying three animated sequences that are all different from each other. The first animated sequence is shown by butterfly 1308, which depicts the butterfly opening its wings. Next, screen 1310 displays the second animated sequence, which depicts butterfly 1314 flying from right to left on the display. Note that screen 1310 also displays user interface object 1312, which indicates the time. Finally, screen 1320 displays the third animated sequence, which depicts butterfly 1324 closing its wings. Screen 1320 again displays user interface object 1322 indicating the time.

Figure 13B:
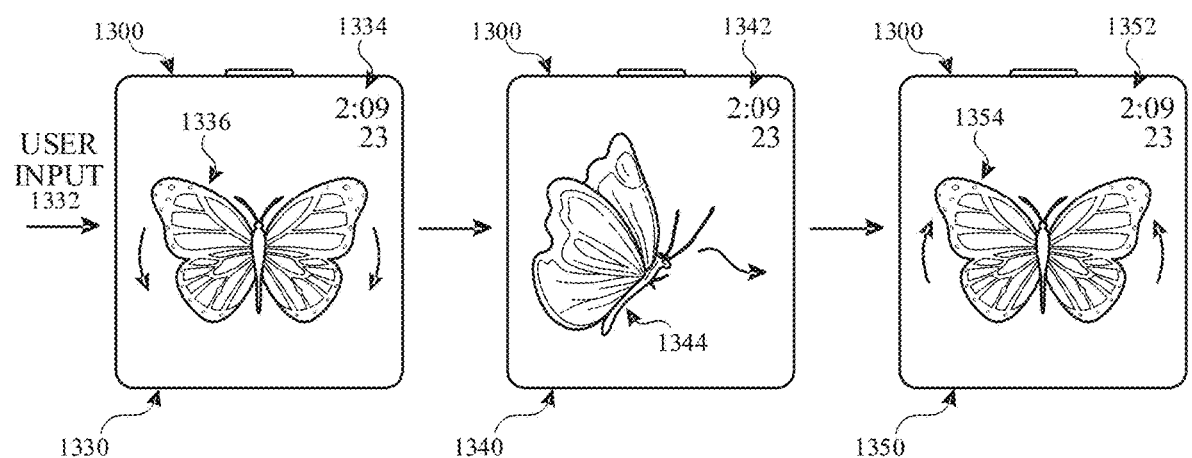

Later in the day, as shown in FIG. 13B, device 1330 detects a second user input 1332. In response, device 1300 accesses data representing the previously displayed animated sequence (i.e., the sequence shown by butterfly 1314). Device 1300 displays screen 1330. Screen 1330 includes user interface object 1334, which indicates the time is now 2:09, and user interface object 1336, which depicts a butterfly.

Device 1300 then animates butterfly 1336 by sequentially displaying three animated sequences. Butterfly 1336 on screen 1330 is animated using the same sequence as butterfly 1308 on screen 1302, showing the butterfly opening its wings. Next, screen 1340 shows butterfly 1334, which is animated to fly from left to right on the display. The animated sequence of butterfly 1334 is different from the animated sequence of butterfly 1314 on screen 1310 (data representing the sequence of butterfly 1314 had previously been accessed). This ensures that the user will view a different animation, as compared to the last user input. This makes the animation appear more realistic and/or engaging to the user, as this variation imparts a more random, lifelike quality to the animated user interface object.

Finally, screen 1350 shows butterfly 1354, which is animated using the same sequence (a butterfly closing its wings) as butterfly 1324 on screen 1320. Screens 1340 and 1350 also include user interface objects 1342 and 1342, respectively, which indicate the time.

FIGS. 13A and 13B show two butterflies (1336 and 1308) that are displayed in response to user inputs. Butterfly 1336 is related to 1308, but it need not be identical. In some embodiments, user interface object 1336 can optionally be the same as user interface object 1308. In other embodiments, user interface object 1336 can optionally be an object related, but not identical, user interface object 1308. For example, these user interface objects can optionally be animals of the same general type but with different appearances (e.g., different colors, different postures, different species, and so forth).

The animated user interface object can optionally be an animal, such as a butterfly or jellyfish, or it can optionally be a plant, like a flower. In some embodiments, it can optionally be a non-living object, single-celled organism, cartoon, human, and so forth. This context-specific user interface is not limited by the particular animated user interface object. The animated sequences can optionally be specific to the displayed objects. For example, a jellyfish can optionally swim across the screen in various directions, a flower can optionally open, close, or be blown about the wind, and so on.

As illustrated by comparing butterfly 1308 to butterfly 1324, or butterfly 1336 to butterfly 1354, the third animated sequence can optionally be based on a reverse of the first animated sequence. For example, if the first sequence depicts a butterfly opening its wings, the third sequence can optionally depict a butterfly closing its wings. Since these sequences bookend the full animated sequence, this feature imparts a cohesive feel to the entire sequence. In some embodiments, the state of the user interface object at the beginning of the first animated sequence (e.g., butterfly 1308 has closed wings, which are then animated to open) corresponds with the state of the user interface object at the end of the third animated sequence (e.g., butterfly 1324 is animated to end on closed wings), thereby providing the user with the impression of one seamless animation.

A variety of user inputs can optionally serve as the user input to display the screens exemplified in FIG. 13A-B. In some embodiments, the user input can optionally be a touch on the display, a rotation of a rotatable input mechanism, a depression of a depressible and rotatable input mechanism, or a swipe on the display. In some embodiments, the user input can optionally be a user movement of the electronic device (e.g., a movement of the device such as raising of the user's wrist, if the device is wearable, or other movement indicative that the user is viewing the display). Advantageously, this feature enables the device to seemingly display a different animation each time the display is viewed.

In some embodiments, the user interface object displayed in response to user input can optionally be the same after each input. In some embodiments, the user interface object could be different each time. For example, a user interface object can optionally be reflected (e.g., about a horizontal and/or a vertical axis), flipped, and/or rotated to create a new user interface object. This is a source of variety for the displayed user interface object and the animated sequences. For example, rotating a single object horizontally, vertically, and horizontally and vertically creates four new objects, which when coupled with an animation that directs the movement of the object creates even more variations. These aspects add combinatorial possibilities which greatly increase the number of available animations for a single object, thus reducing the number of pre-programmed animated sequences. It also helps animate objects with fewer intrinsic features and/or movements, such as a jellyfish.

The user can optionally also change the displayed user interface object. For example, device 1300 can optionally detect a contact on the touch-sensitive display, and in response, device 1300 can optionally substitute the displayed user interface object with a second user interface object. This second user interface object can optionally be related to the first (e.g., the user could select an orange butterfly if the previous one was blue).

In some embodiments, as shown in FIGS. 13A and 13B, the user interface object indicating time can optionally be a representation of a digital clock with numerical indications of an hour and a minute (see, e.g., objects 1306, 1312, 1322, 1334, 1342, and 1352). In some embodiments, the user interface object can optionally display the current time in response to user input.

Figure 14A:
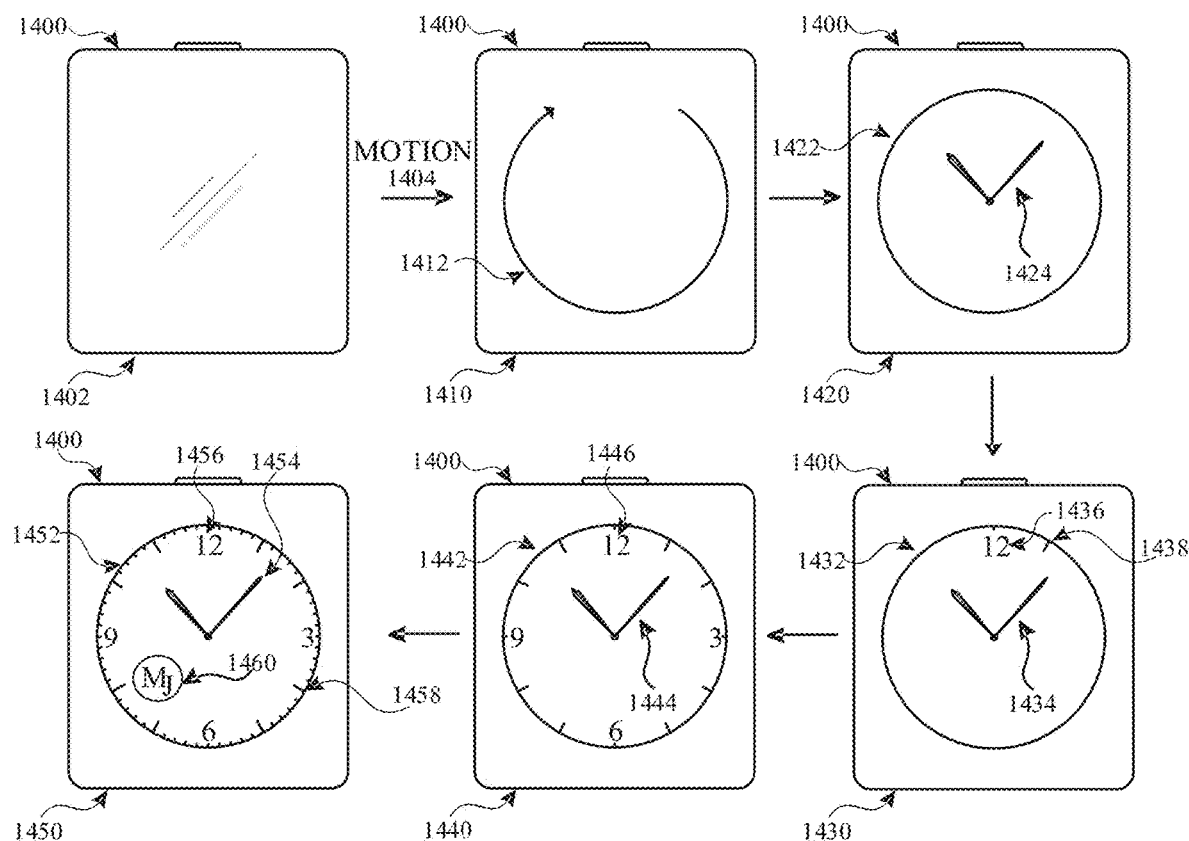
FIG. 14A illustrates exemplary context-specific user interfaces.

FIG. 14A shows exemplary context-specific user interfaces that can optionally be operated on device 1400. Device 1400 can optionally be device 100, 300, or 500 in some embodiments. The electronic device has a touch-sensitive display (e.g., touchscreen 504).

A user may wish to keep time with an interactive clock face. For example, a user may wish to view an animation with each viewing of the display, or view a clock face that changes color, to keep the interaction with the device interesting. A user may wish to customize the clock face with a personalized complication, like a monogram, or a personalized widget for displaying application data.

As shown in FIG. 14A, device 1400 has display 1402 turned off. In response to detecting a user movement of device 1400 (e.g., motion 1404), device 1400 displays an animated reveal of a clock face. On screen 1410, device 1400 displays clock face outline 1412, which is animated as if being filled in or drawn in a clockwise manner. On screen 1420, device 1400 displays full clock face outline 1422 and hour hand and minute hand 1424. On screen 1430, device 1400 displays full clock face outline 1432, hour hand and minute hand 1434, and hour indications 1436 and 1438 (indicating the 12 o'clock and 1 o'clock hours, respectively). These hour indications are progressively displayed in a clockwise direction, as shown by comparing screens 1430 and 1440.

On screen 1440, device 1400 displays clock face outline 1442, hour and minute hand 1444, and twelve hour indications, as represented by 12 o'clock indication 1446. On screen 1450, device 1400 displays clock face outline 1452, hour and minute hand 1454, twelve hour indications (as represented by 12 o'clock indication 1456), minute indications 1458, and monogram 1460, which is described in greater detail below. Therefore, as exemplified in FIG. 14A, the clock face is animated to progressively reveal its features.

Two types of hour indications are depicted in FIG. 14A: numerical hour indications (e.g., 3, 6, 9, and 12, as indicated by hour indications 1436, 1446, and 1456) and symbolic hour indications (e.g., the tick marks displayed between the numerical indications on screens 1440 and 1450). Either type of indication can optionally be used, alone or in combination. Any type of symbol can optionally be used as an hour indications; the position around the clock face, rather than the symbol itself, conveys to the user which hour is indicated. The numbers of hour indications and/or minute indications (or lack thereof) can optionally further be customized by the user, which will be explained in greater detail below.

FIG. 14A shows that one or more hour indications can optionally be progressively displayed in a clockwise manner (e.g., they can optionally appear sequentially in a clockwise direction, as depicted on screens 1430 and 1440). Similarly, the clock outline can optionally appear in a clockwise direction. This helps to orient the user. Optionally, the minute indications can optionally appear progressively in a clockwise manner. The hour hand and the minute hand (and, optionally, a seconds hand) can optionally be animated as well, such as radially (e.g., starting from the center of the clock face and appearing to extend outward towards the outline). In some embodiments, the hour and minute hand appear first, followed by the hour indications, then the minute indications. In some embodiments, the clock face shows current time.

In some embodiments, the clock face can optionally include a color. Features such as the background of the clock face, clock face outline, seconds hand, hour indication(s), minute indication(s), hour hand, minute hand, and so forth can optionally be displayed in any color. In some embodiments, device 1400 updates a color displayed on the clock face over time by continuously changing the color, so that the user perceives time passing through color change. This color can optionally be, e.g., a background color, the color of the clock face itself, and/or the color of the seconds hand (e.g., the entire seconds hand, or a portion of the seconds hand, such as a pointer, dot, or other optional feature). As an illustrative example, the color can optionally cycle through a gradient of colors, with the full cycle lasting a minute, an hour, a day, etc.

In some embodiments, device 1400 can optionally detect a user movement of the device. As described above, a user movement of the device could be detected, for example, by using an accelerometer (e.g., 534), a gyroscope (e.g., 536), a motion sensor (e.g., 538), and/or a combination thereof. A user movement of the electronic device could include movements such as a movement of the device such as raising of the user's wrist, if the device is wearable, or other movement indicative that the user is viewing the display. In response to detecting the user movement, device 1400 can optionally display a different color (e.g., a background color, the color of the clock face itself, and/or the color of the seconds hand). In some embodiments, this feature can optionally be used to allow the user to change a static color displayed on the clock face. In other embodiments, this feature can optionally be used to allow the user to change a continuously changing color, as exemplified above.

In some embodiments, device 1400 can optionally display a complication on the clock face (e.g., within the clock face itself, or adjacent to the clock face on the display). As used here, consistent with its accepted meaning in art, a complication refers to any clock face feature other than those used to indicate the hours and minutes of a time (e.g., clock hands or hour/minute indications). For example, an affordance can optionally be displayed as a clock face. As will be described in greater detail below, the affordance can optionally represent an application, and in response to detecting a contact on the affordance, device 1400 can optionally launch the application represented by the affordance.

Returning now to FIG. 14A, in some embodiments, a monogram can optionally be displayed as a complication. Screen 1450 shows monogram affordance 1460 displayed as a clock face complication. Device 1400 can optionally receive data representing a name, and in response to receiving the data, generate a monogram and display the monogram as affordance 1460 (in this example, "MJ"). Device 1400 can optionally receive this data from one or more sources, such as a saved contact entry, a V-card, an image containing a monogram (e.g., an image taken or uploaded by a user), and so forth. In some embodiments, device 1400 has a user interface for monogram editing, which can optionally be a feature of the user interface described in FIG. 14A, a separate user interface on device 1400, or a user interface on an external device in wireless communication with device 1400. It is to be appreciated that these aspects (e.g., complications, monograms, and/or colors) can optionally also be applied to any of the other context-specific user interfaces described herein. These features provide customizable elements a user may wish to include to personalize one or more clock faces, thereby improving the user interface by enhancing user interactability.

FIG. 14B shows exemplary user interface screen 14602 that device 14000 can display on its display. In some embodiments, device 14000 can optionally be one or more of devices 100 (FIG. 1A-B), 300 (FIG. 3), and/or 500 (FIG. 5A-H). The electronic device has a touch-sensitive display (e.g., touchscreen 504).

Users rely on personal electronic devices to keep time throughout the day. It is becoming increasingly desirable to present the user with interactive user interfaces that promote user interaction with a personal electronic device. Indicating the time through a character-based user interface may enhance a user's interaction with the device. Increasing the level of interactivity of a character and improving the impression of natural motion displayed by a character improve the character's lifelike appearance, thereby enhancing and prolonging user interactions with the device. Enabling the character-based interface to not only keep time, but also provide information related to other events, further enhances user interactions with the device by conveying a more lifelike and interactive character-based user interface.

Accordingly, provided herein are context-specific user interfaces that include a character user interface object. A user may wish for such character-based user interface objects to adopt a more natural and lifelike appearance. Further, a user may wish for the character-based user interface object to act in a more dynamic manner, to interact with the user, and/or to provide event-related information to a user.

Device 14000 can optionally display a character user interface object such as character user interface object 14604 on the display. Character user interface object 14604 has representations of limbs 14606 and 14608. As shown on user interface screen 14602, character user interface object 14604 can optionally indicate a time, for example 7:50, through the positions of limbs 14606 and 14608.

A character user interface object can optionally include any representation of a character, for example a human or anthropomorphized character. In some embodiments, a character can optionally be a cartoon figure. In some embodiments, a character can optionally be a realistic figure. In some embodiments, a character can optionally be a human, animal, plant, other organism, or other object. In some embodiments a character can optionally be a popularized character, such as a cartoon character.

Character user interface object 14604 can optionally indicate time by indicating an hour with a first limb (e.g., limb 14606) and by indicating a minute with a second limb (e.g., limb 14608). In some embodiments, the character user interface object can optionally be a static image that is updatable for different times. In some embodiments, the character user interface object can optionally be animated and can optionally depict movement. For example, the character user interface object can optionally be animated to represent blinking of eyes, shifting its weight, and/or changing an expression (e.g., facial expression).

As described herein, a character user interface object can optionally indicate a time through varying degrees of precision. As shown in FIG. 14B, a user interface screen can optionally include one or more numerical indications of time values, i.e., numbers that indicate hour, minute, or second values on a clock face. However, since users are accustomed to perceiving clock faces, numerical indications of time values are optional, since the relative positioning of two objects resembling the hands of a clock can optionally indicate an approximate time even without such numerical indications.

Any of the user interface screens described herein can optionally further include one or more complications, such as indications of a date, a stopwatch, a chronograph, an alarm, and the like.

In addition, limbs of a character user interface object can optionally indicate time to a user in various ways. For example, a limb (e.g., an arm or a leg) can optionally indicate a time by its relative position on the display, or by "pointing" to a position on the display along a vector. A limb can optionally also indicate a time by displaying an indicator of direction, such as a representation of a finger that indicates a position on the display corresponding to a time, either through its relative position or by pointing along a vector, as described above. A limb need not be precise in indicating a time.

Device 14000 can optionally update the character user interface object to indicate a second time by reversing the roles of the first and second limbs, i.e., by indicating a second hour with the second limb and a second minute with the first limb. For example, FIG. 14B shows user interface screen 14610 that device 14000 can optionally display. User interface screen 14610 includes character user interface object 14612. Character user interface object 14612 can optionally be the same character user interface object as character user interface object 14604 but representing a different time.

As shown on user interface screen 14610, character user interface object 14612 is indicating a time, for example 8:20, through the positions of limbs 14614 and 14616. Comparing character user interface object 14604 and 14612, both have a first limb (limb 14606 and limb 14614, respectively) and a second limb (limb 14608 and limb 14616, respectively). However, character user interface object 14604's first limb (limb 14606) is indicating an hour, whereas character user interface object 14612's first limb (limb 14614) is indicating a minute. Similarly, character user interface object 14604's second limb (limb 14608) is indicating a minute, whereas character user interface object 14612's second limb (limb 14616) is indicating an hour.

In some embodiments, device 14000 can optionally update the user interface object to indicate a second time by extending the first limb and retracting the second limb. As a user can optionally be accustomed to a standard clock face, wherein the hour hand is shorter than the minute hand, altering the extension and/or retraction of the limbs when reversing their roles may make it easier for the user to keep track of the indicated times.

Allowing a character user interface object to indicate time using limbs with reversible roles increases the flexibility for displaying the character user interface object by allowing the character to maintain a natural appearance at all times. Otherwise, if the roles of the limbs were fixed, the character might contort in an awkward way at certain times of day, for example, between 12:30 and 12:40. Enabling the character to switch roles of the limbs affords more options for character postures and positions that can optionally represent a more natural appearance, thereby enhancing the user's interactions with the device by portraying a more lifelike character user interface object.

Turning now to FIG. 14C, a user may wish to interact with a more natural-looking character user interface object. If a character user interface object indicates time with a limb that is always moving from a fixed position or role, this diminishes the natural appearance of the character because the range of motions and/or postures for the character is restricted. This can lead awkward postures and/or monotonous character appearance. A limb can optionally indicate time via animations representing free movement from both endpoints of the limb, rather than a representation of rotation about an axis whereby one endpoint is always fixed, making the character user interface object appear more natural at different times of day.

It is understood that descriptions of mechanical motions (e.g., limb motion) used herein encompass displaying representations or simulations of mechanical motion.

FIG. 14C shows exemplary user interface screen 14702 that device 14000 can display on its display. In some embodiments, device 14000 can optionally be one or more of devices 100 (FIG. 1A-B), 300 (FIG. 3), and/or 500 (FIG. 5A-H).

Device 14000 can optionally display a character user interface object such as character user interface object 14704 on the display. Character user interface object 14704 has a representation of a limb 14706. As shown on user interface screen 14702, character user interface object 14704 can optionally indicate a time, for example an hour such as 12, through the position of limb 14706. In some embodiments, the character user interface object can optionally be a static image that is updatable for different times. In some embodiments, the character user interface object can optionally be animated and can optionally depict movement.

Limb 14706 has a first endpoint 14708 at a first position that serves as a representation of an axis of rotation for limb 14706. That is, the position of limb 14706 can optionally be displayed or animated so as to represent rotation about endpoint 14708 to display different times of day. Limb 14706 also has a second endpoint 14710 at a second position that indicates a time value. In some embodiments, a time value can optionally be an hour, a minute, and/or a second.

Device 14000 can optionally update character user interface object 14704 to indicate a second time value by moving first endpoint 14708 to a third position, and moving second endpoint 14710 to a fourth position to indicate a second time value. Importantly, while first endpoint 14708 serves as an axis of rotation for limb 14706, first endpoint 14708 itself can optionally also move to indicate time. Therefore, limb 14706 is able to adopt more natural postures because its positioning is afforded more flexibility. This enhances the lifelike appearance of the character.

As an example, user interface screen 14720 shows character user interface object 14722 with limb 14724 having first endpoint 14726 and second endpoint 14728. Character user interface object 14722 can optionally be an updated display of character user interface object 14704. Comparing user interface screens 14702 and 14720, in particular limb 14706 and limb 14724, the position of the first endpoint has been updated, as reflected by the positions of first endpoints 14708 and 14726. First endpoint 14726 is at the third position, and second endpoint 14728 is at a fourth position to indicate the second time. As shown on user interface screens 14702 and 14720, limb 14706 has been updated to limb 14724 by (i) moving the position of first endpoint and (ii) rotating the limb at the axis of rotation.

In some embodiments, a character user interface object can optionally include a representation of a second limb, such as second limb 14712. Like the first limb, second limb 14712 also has a first endpoint 14714 that is an axis of rotation for second limb 14712 and a second endpoint 14716. The position of second endpoint 14716 can optionally indicate a third time value. For example, limb 14706 can optionally indicate an hour value and limb 14712 can optionally indicate a minute value. Device 14000 can optionally update character user interface object 14704 to indicate a fourth time value by moving first endpoint 14714 of the second limb 14712 to a third position, and by moving second endpoint 14716 to a fourth position to indicate a second time value. This is depicted on user interface screen 14720, which depicts second limb 14730 with first endpoint 14732 at the third position and second endpoint 14734 at the fourth position.

As described above, first and second limbs of a character user interface object can optionally each have two endpoints that can optionally each change their position. In some embodiments, the first limb is connected to a torso at a first shoulder, and the second limb is connected to the torso at a second shoulder. In some embodiments, the torso connects the movements of each limb by each shoulder, such that a position of one shoulder can optionally affect a position of the other shoulder. This feature adds to the lifelike and natural appearance of the character by coordinating or otherwise inter-relating the movements of both limbs, as with a living body.

FIG. 14D shows exemplary user interface screen 14802 that device 14000 can display on its display. In some embodiments, device 14000 can optionally be one or more of devices 100 (FIG. 1A-B), 300 (FIG. 3), and/or 500 (FIG. 5A-H).

Device 14000 can optionally display a character user interface object such as character user interface object 14804 on the display. Character user interface object 14804 has a representation of a limb 14806. As shown on user interface screen 14802, character user interface object 14804 can optionally indicate a time, for example an hour such as 12, through the position of limb 14806.

Limb 14806 has a first segment 14808 with a first endpoint 14810 at one end and a joint 14812 at the other. First endpoint 14810 has a first position. Limb 14806 also has a second segment 14814 with a second endpoint 14816 at one end and joint 14812 at the other. Therefore, first segment 14808 and second segment 14814 connect at joint 14812, which is an axis of rotation for second segment 14814. Second endpoint 14816 at the end of second segment 14814 (and hence, at one end of limb 14806) has a second position and indicates a first time value, for example an hour such as 12.

Device 14000 can optionally update character user interface object 14804 to indicate a second time value by moving second endpoint 14814 along the axis of rotation to a third position to indicate the second time. Described in anthropomorphic terms, limb 14806 has representations of an upper arm 14808 and a forearm 14814 joined at an elbow 14812. Forearm 14814 can optionally rotate at the elbow 14812 to indicate a different time. Adding a joint to a limb that indicates time is analogous to a hand of a clock, except that the arm is more natural looking than a clock hand because it includes a joint. Further, the joint enhances the potential range of motions that can optionally be depicted by the limb.

User interface screen 14820 illustrates this by displaying character user interface object 14822 with limb 14824. In some embodiments, character user interface object can optionally be the same object as character user interface object 14804 but in a different posture. Limb 14824 has a first endpoint 14826, first segment 14828, and joint 14830. Joint 14830 is connected to second segment 14832, which has second endpoint 14824. As demonstrated by comparing the features of character user interface objects 14804 and 14822, second endpoint 14834 is at a different position than second endpoint 14816, thus indicating a different time. This change in position is accomplished by rotating the second segment at the joint.

In some embodiments, moving the second endpoint can optionally include depicting static images of the second endpoint at the first and third positions. In some embodiments, moving the second endpoint can optionally include animating the character user interface object to translate the motion of the second endpoint on-screen.

In some embodiments, updating the character user interface object can optionally include moving the first endpoint. As shown by user interface screen 14802 to user interface screen 14820, first endpoint 14810 can optionally be moved to change the display of time, e.g., as shown by first endpoint 14826. Therefore, the character user interface object can optionally have a limb that, in the arm analogy above, can optionally rotate the upper arm at the shoulder, can optionally move the shoulder itself, and can optionally rotate the forearm at the elbow.

These features allow the character user interface object to assume a wider range of natural and lifelike postures with which to indicate time. If these features are animated on-screen, this allows the character to simulate the motion of a moving figure such as a person. This greatly improves user interaction with and connection to the device by more accurately simulating a moving figure like a person. It allows for both subtle and dynamic movements, giving the character a wider range of expressions that help simulate a personality of the character. Therefore, the character ceases to be a simple aggregation of two character-like clock hands that can only tell time and becomes more like an actual character that can express a personality, thereby enhancing the user's experiences with the device.

In some embodiments, the character user interface object (e.g., character user interface object 14804 and/or 14822) also includes a representation of a second limb, such as second limb 14818 as shown on user interface screen 14802 or second limb 14836 as shown on user interface screen 14820. As described above in reference to the first limb, a second limb can optionally include a first segment connecting a first endpoint of the second limb to a joint and a second segment connecting a second segment to the joint. The first endpoint of the second limb can optionally be at a first position, and the second endpoint of the second segment can optionally be at a second position. The joint can optionally serve as an axis of rotation for the second segment, which can optionally indicate a third time value. Device 14000 can optionally update the character user interface object by moving the second endpoint of the second limb along the axis of rotation at the joint to indicate a fourth time value.

In some embodiments, the first limb indicates an hour and the second limb indicates a minute. In some embodiments, the first limb indicates a minute and the second limb indicates an hour. The first limb and the second limb can optionally be distinguished, for example, by length, as with traditional clock hands. The first limb and the second limb can optionally be distinguished, for example, by the distance between the first and second endpoints. For example, one limb can optionally be bent or the shoulder can optionally be positioned such that, even though it can optionally not be shorter than another limb, it appears shorter or otherwise distinct from another limb. The first limb and the second limb can optionally be distinguished, for example, by the distance between the second endpoint and another object on the display, such as a numerical indication of time.

In some embodiments, updating the character user interface object to indicate the second time can optionally include animating the character user interface object by translating the first endpoint on-screen. For example, the character can optionally appear to move one or both shoulders. In some embodiments, the movement or position of one shoulder can optionally affect the movement or position of another shoulder, simulating the connected motion of an actual figure such as a human.

In some embodiments, updating the character user interface object to indicate the second time can optionally include animating the character user interface object by rotating the second segment at the joint on-screen. For example, the second segment can optionally rotate at the joint like a forearm.

In some embodiments, the character user interface object can optionally also translate on-screen, for example towards a center of the display.

Figure 14E:
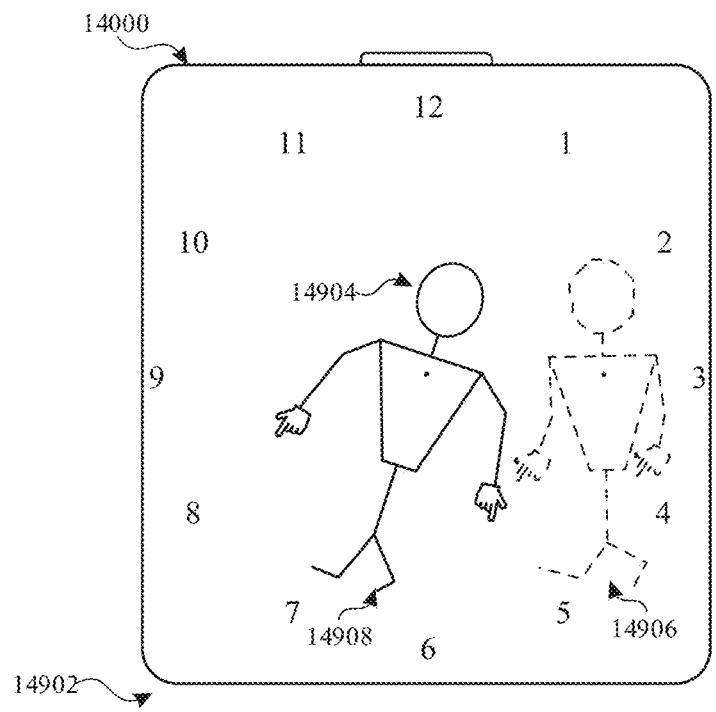
FIGS. 14B-14U illustrate exemplary context-specific user interfaces.

FIG. 14E shows exemplary user interface screen 14902 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 14904 on the display. User interface screen 14902 shows the translation of the character by sequential displays of character user interface object 14904 at two different locations, first at location 14906 and then at location 14908. Character user interface object 14904 is closer to the center of the display at location 14908, thus simulating motion in the right-to-left direction as shown in FIG. 14E. Motion such as this can optionally be used, for example, when the user initiates an interaction with the device or looks at the device, which prompts the character to move to the center of the display and indicate a time.

In some embodiments, translating the character user interface object can optionally include animating the character user interface object to represent walking, for example to the center of the display. Character user interface object 14904 illustrates this by depicting a character with legs and a torso. The different positions and postures represented by the legs and the torso of character user interface object 14904 at locations 14906 and 14908 represent walking. For example, in response to the user interacting with the device, the character can optionally be animated to walk naturally onto the screen and then assume a position corresponding to the current time. The user interaction can optionally include activating the screen, raising the device into a viewing position, pressing a button on the device that corresponds to activating a watch face, etc.

Figure 14F:
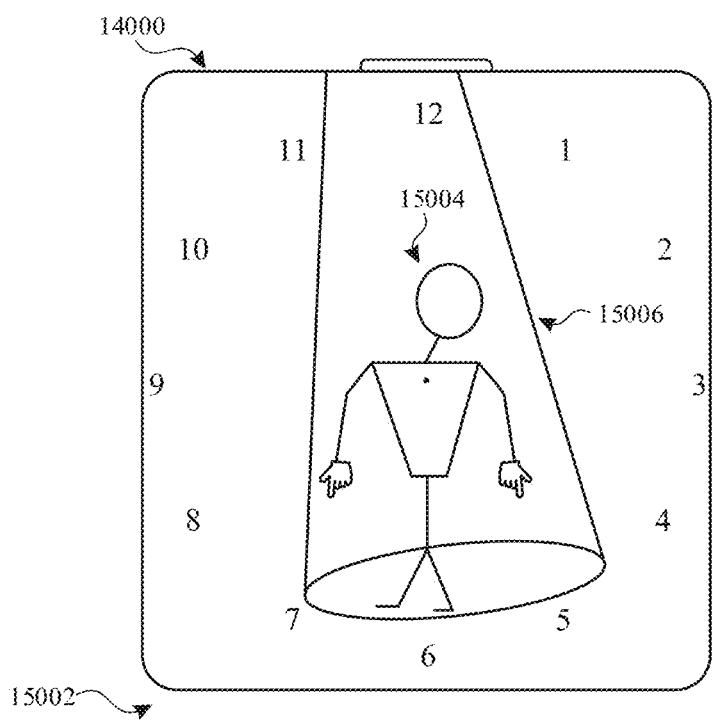

FIG. 14F shows exemplary user interface screen 15002 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15004 on the display. Device 14000 can optionally change a visual aspect of the displayed user interface screen to highlight the character user interface object. FIG. 14F illustrates an exemplary embodiment of this concept. User interface screen 15002 includes a spotlight 15006 that highlights character user interface object 15004.

In some embodiments, changing a visual aspect of the display could include one or more of changing the color and/or brightness of the user interface screen around the character user interface object, displaying a user interface object such as a spotlight, and so forth.

In some embodiments, device 14000 can optionally animate the character user interface object to represent a response by the character user interface object to the changing of the visual aspect. As shown in the exemplary embodiment of FIG. 14F, character user interface object 15004 can optionally be animated to simulate looking at spotlight 15006.

Figure 14G:
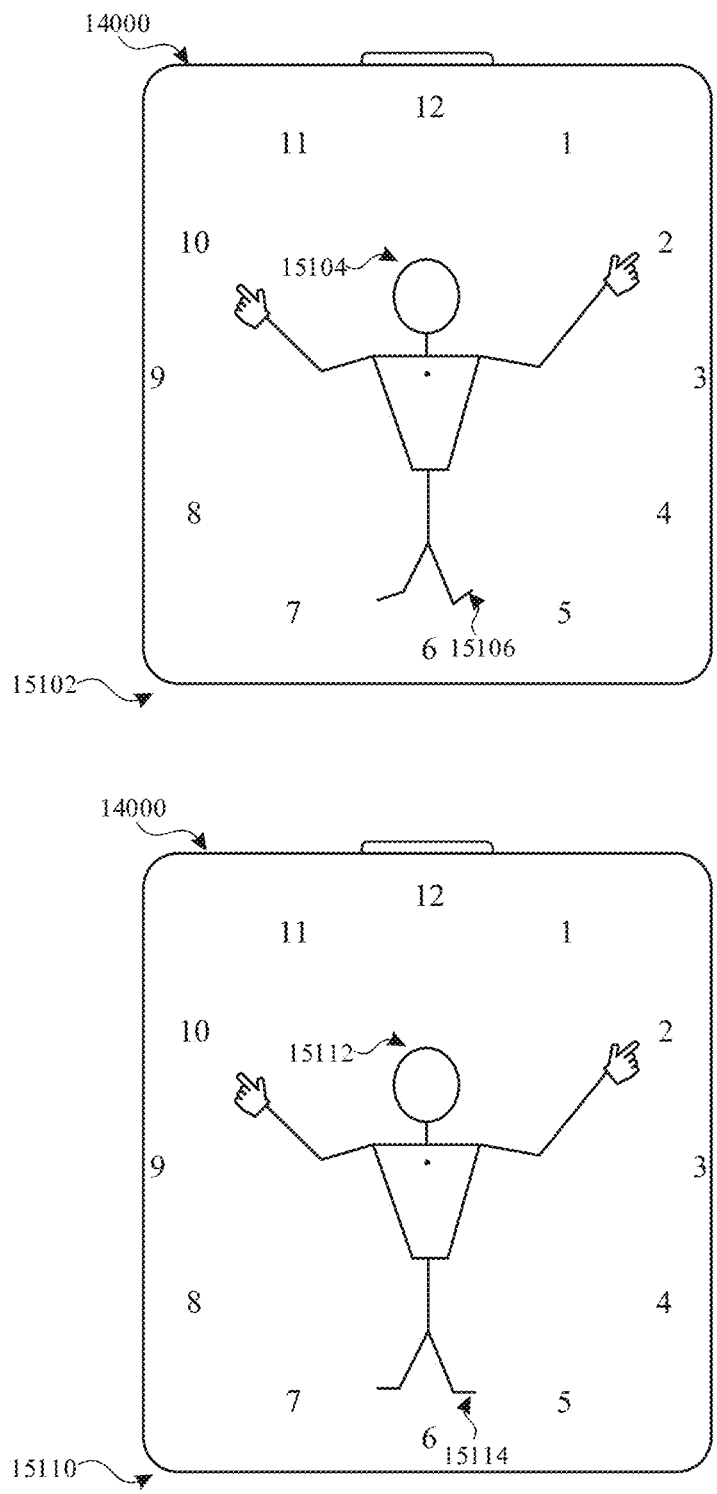

FIG. 14G shows exemplary user interface screen 15102 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15104 on the display. Character user interface object 15104 can optionally include a representation of a foot 15106. In some embodiments, character user interface object 15104 includes two limbs that indicate time values and two legs, at least one of which can optionally include a foot.

In some embodiments, device 14000 can optionally animate the foot to indicate passage of time. As shown on user interface screens 15102 and 15110, character user interface objects 15104 and 15112 include a foot (15106 and 15114, respectively). The different positions of feet 15106 and 15114 (different with respect to the position on the display and/or their posture within the character user interface object) depict this animation. For example, the character can optionally be animated to simulate a motion of the foot, such as tapping. This can optionally have a regular or irregular timing. In some embodiments, the foot is animated to move at a regular interval, such as once every second. When coupled with two limbs, this allows the character user interface object to depict, for example, hour, minute, and second time values.

In some embodiments, the first time and the second time depicted by the character user interface object are the same. In other words, the character user interface object can optionally move by shifting a limb or any endpoint of a limb without depicting a different time. This allows the character to shift posture without changing the indicated time.

In some embodiments, the display can optionally include one or more numerical indications of time. For example, the display can optionally include a representation of a circular clock face with a character user interface object in the center encircled by numerical indicators, as with a clock.

The features described above allow a character user interface object to appear more natural and lifelike by adopting a wider range of natural motions while indicating a time. A user may wish to view representations of other events by the character user interface object. Allowing the character user interface object to react to external stimuli or internal system events portrays a more interactive character, thus depicting a closer representation of a personality. The enhanced interactivity of the character further improves the user's interactions with the device by providing additional notification that an event has occurred, the occurrence of which may not have been as apparent otherwise. A character user interface object can optionally serve to supply notifications, reminders, and/or other information a user may wish to access from a personal electronic device, but the use of a character provides an interactive personality that the device can optionally use to supply these items. Further, making the character responsive to internal system events (e.g., calendar events and the like) means the character is not strictly limited to responding to external user input. Put another way, the character appears to have a more lifelike personality because it responds to events not directly prompted by the immediate actions of the user.

FIG. 14H shows exemplary user interface screen 15202 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15204 on the display. Character user interface object 15204 indicates time as described above.

Device 14000 can optionally receive first data indicative of an event. Device 14000 can optionally determine whether the event meets a condition. In accordance with the determination that the event meets the condition, device 14000 can optionally update character user interface object 15204 by changing a visual aspect of the character user interface object.

In some embodiments, after updating the displayed character user interface object, the character user interface object still indicates time. For example, the appearance or posture of the character can optionally be altered, but the character still indicates time.

In some embodiments, after updating the displayed character user interface object, the character user interface object no longer only indicates time. For example, the character can optionally adopt a posture, assume a facial expression, or use its limbs for a function other than indicating time, such as conveying a meaning related to the event and/or the condition.

In some embodiments, the first data indicates a calendar event. Device 14000 can optionally receive data indicating a calendar event, for example, by obtaining data representing the event from a calendar application on device 14000. In this example, the condition can optionally correspond to a duration of the calendar event. Determining whether the event meets the condition can optionally include determining whether a current time is within the duration of the calendar event. For example, device 14000 can optionally obtain a current time and determine whether the current time is within a duration of the calendar event (e.g., during the calendar event, or substantially contemporaneous with the calendar event but slightly preceding or slightly delayed after it).

An exemplary embodiment is shown on user interface screen 15202. In some embodiments, the calendar event is a birthday. In some embodiments, the birthday is a user's birthday. In some embodiments, updating the displayed character user interface object can optionally include animating the character user interface object to display a birthday greeting. Character user interface object 15204 is animated to display festive hat 15206 and birthday banner 15208. This animation serves to notify the user of a birthday while making the character more interactive. Importantly, the character can optionally change a visual aspect, such as by displaying a birthday greeting, without immediate input by the user, thus giving the impression that the character is able to act more autonomously, as with a personality. In some embodiments, the modification of the character is an indication of some important event related to one of the user's contacts, such as their birthday, anniversary, etc.

An exemplary embodiment is shown on user interface screen 15210. In some embodiments, the calendar event is a holiday. In some embodiments, updating the displayed character user interface object can optionally include changing a visual aspect of the character user interface object to reflect the holiday. In this example, character user interface object 15212 depicts this through Santa Claus hat 15214. This animation serves to notify the user of the holiday while making the character more interactive and decreasing the monotony of character appearance. Other examples of holidays besides Christmas may include New Year's Eve or New Year's Day, Thanksgiving, Hanukkah, the 4$^{th}$ of July, St. Patrick's Day, Valentine's Day, and the like.

In some embodiments, device 14000 can optionally receive data indicating a user preference, such as a user's favorite sports team. In accordance with receiving the data, device 14000 can optionally update character user interface object 15204 by changing a visual aspect of the character user interface object to reflect the sports team. For example, the appearance of the character user interface object can optionally be updated to portray the character user interface object wearing a uniform or other paraphernalia representing the sports team (e.g., a hat, jersey, uniform, or other representation include a logo, icon, or text representing the sports team). The display can optionally also be updated to include with the character user interface object a second user interface object representing a sports object associated with the team's sport (e.g., a baseball bat and/or baseball, football, basketball, soccer ball, hockey stick and/or hockey puck, checkered flag, and so forth). The character can optionally be updated in accordance with a determination that the team is playing that day or at that time, or in accordance with a determination that the user is going to attend an event featuring the team. The determination that the user is going to attend an event featuring the team can optionally be made through an analysis of the user's calendar events or through a determination that an electronic ticket for an event is present on the electronic device or a paired electronic device. It is understood that a user's favorite sports team is merely an exemplary user preference, and other user preferences such as a representation of a flag or country are also contemplated.

Figure 14I:
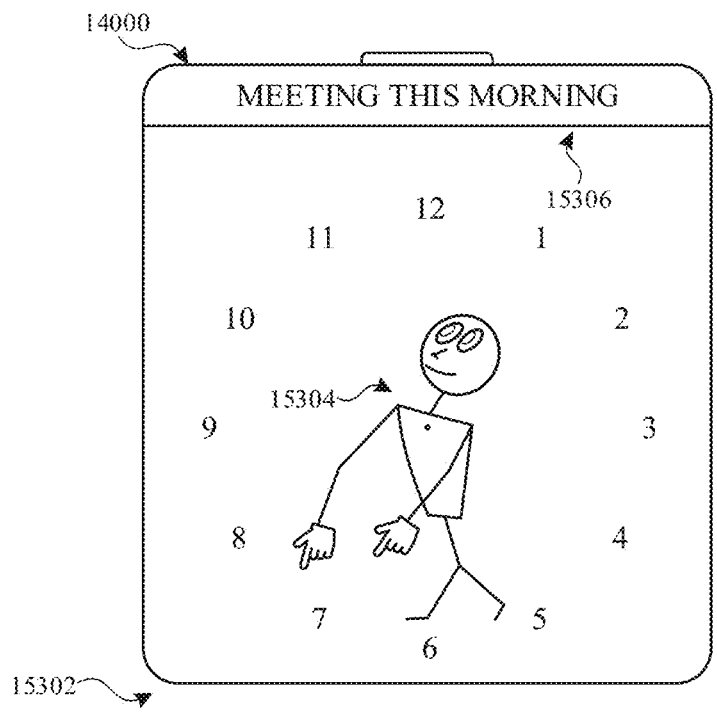

FIG. 14I shows exemplary user interface screen 15302 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15304 on the display. Character user interface object 15304 indicates time as described above.

Device 14000 can optionally receive data indicating a notification. A notification can optionally include, for example, an email, text message, reminder, virtual assistant request, or other such notification. Device 14000 can optionally further display the notification, or an affordance or user interface object representing receipt and/or a content of the notification, on user interface screen 15302, as depicted by notification 15306. Device 14000 can optionally animate character user interface object 15304 to react to notification 15306. For example, as shown on user interface screen 15302, character user interface screen 15304 can optionally appear to look at notification 15306. This can optionally include, for example, a change in posture such that the character faces the notification, or a change in the appearance of the character, such as a face, to indicate looking in the direction of the notification. Again, by providing this change in posture or change in the character's focus, the user can optionally be notified of an incoming alert or event that can optionally otherwise have been less apparent.

Figure 14J:
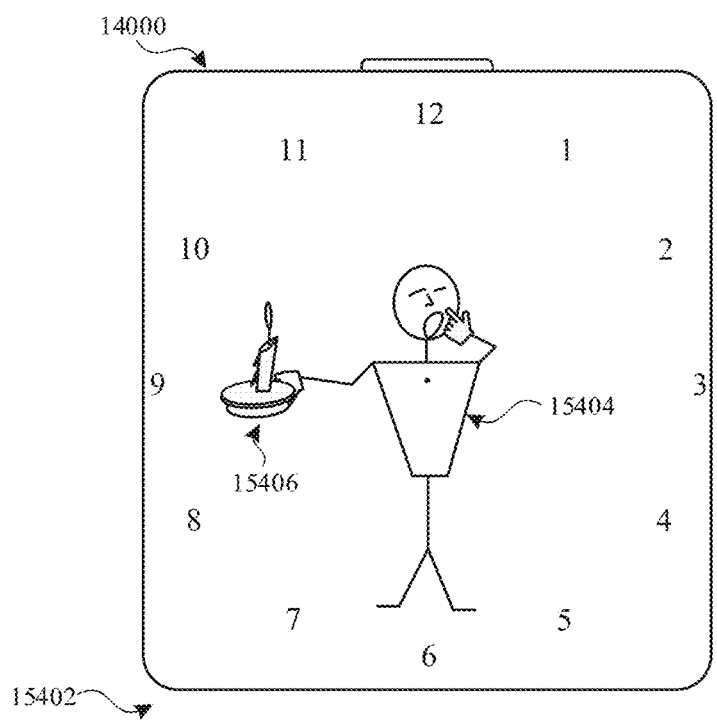

FIG. 14J shows exemplary user interface screen 15402 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15404 on the display. Character user interface object 15404 indicates time as described above.

Device 14000 can optionally receive first data indicating a time of day. A time of day could include a current time. Device 14000 can optionally determine that the time of day meets a condition, such as by determining whether the time of day is within the nighttime portion of the day. Device 14000 can optionally change a visual aspect of character user interface object 15404 to represent nighttime. As shown in user interface screen 15402, character user interface object 15404 represents nighttime by depicting a yawn and holding candle 15406. In some embodiments, character user interface object 15404 can optionally be altered to depict wearing clothing associated with nighttime, such as pajamas. In some embodiments, the character interface object is modified to yawn or wear pajamas in accordance with a determination that the user should go to sleep. The determination can optionally be based on, for example, any of a preset time, recognition of a pattern of the user's sleep, indication of an early event on the next day's calendar, recognition that the user has been active for longer than a predetermined time, etc.

Figure 14K:
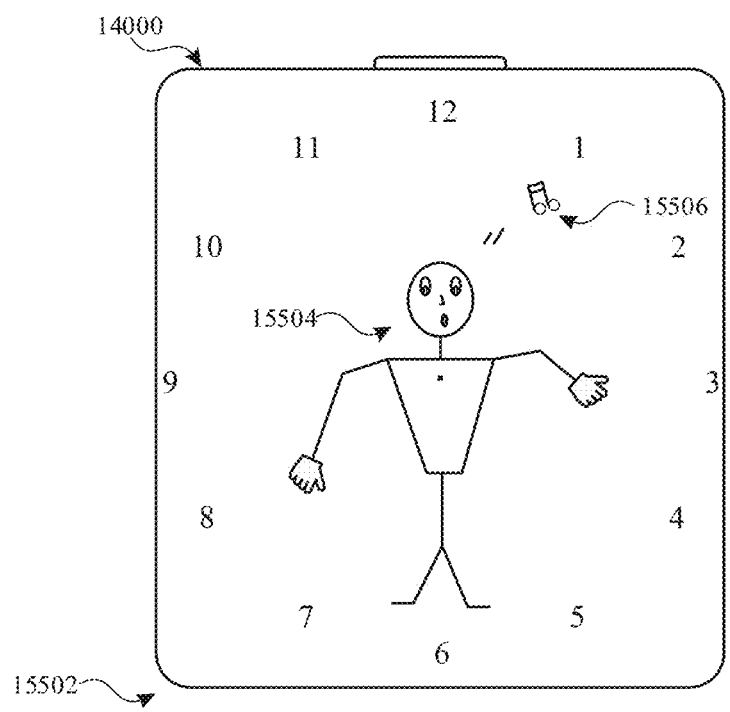

FIG. 14K shows exemplary user interface screen 15502 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15504 on the display. Character user interface object 15504 indicates time as described above.

Device 14000 can optionally receive data indicating a current time. Device 14000 can optionally determine whether the current time corresponds to an hour on the hour (for example, 1:00, 2:00, and so forth). Device 14000 can optionally determine whether the current time is an hour on the hour and if so, animate the character user interface object to announce the hour on the hour for one or more hours. As shown in user interface screen 15502, character user interface object 15504 announces the current hour by depicting musical note 15506. In some embodiments, the announcement of the hour could include a visual depiction of an announcement, such as by displaying a user interface object. In some embodiments, the announcement of an hour could include a sound such as a whistle, chime, one or more spoken words, or a bell toll.

Figure 14L:
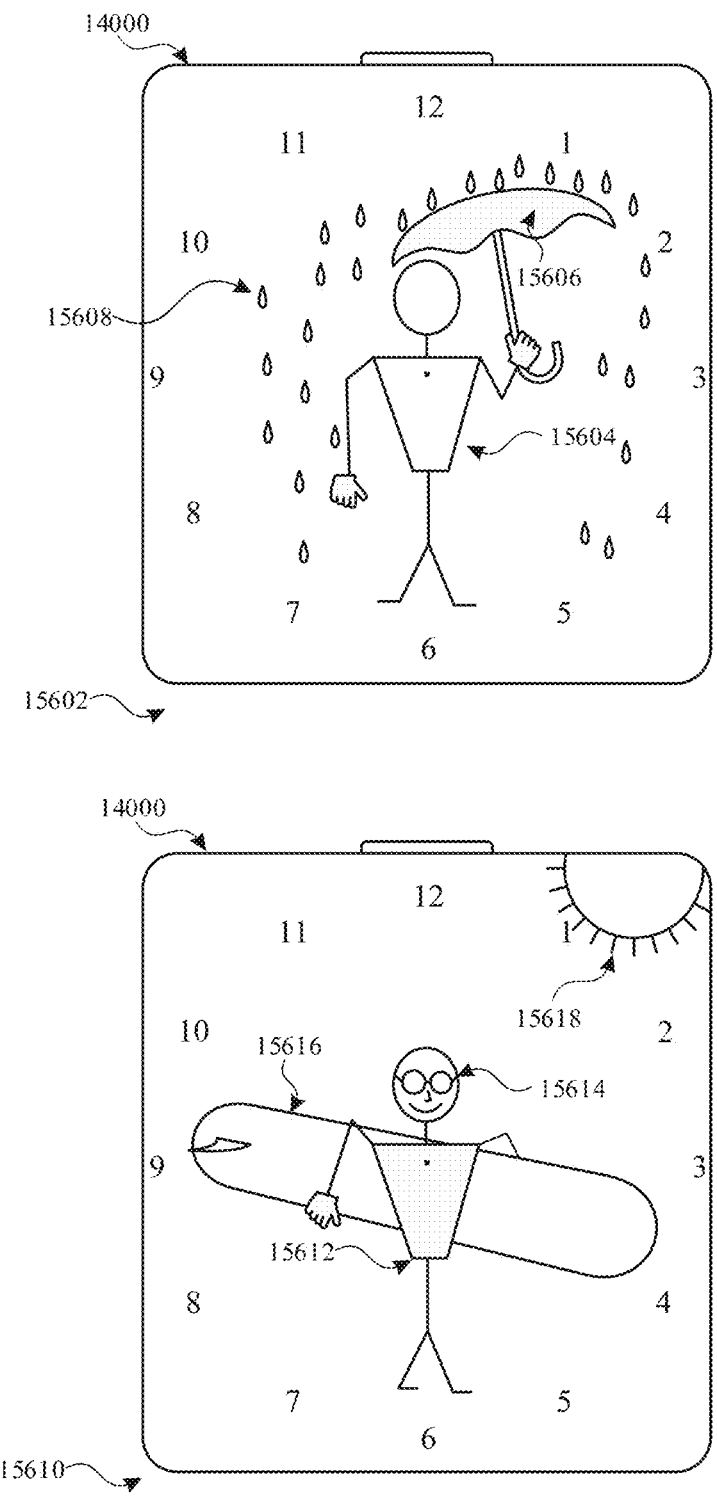

FIG. 14L shows exemplary user interface screen 15602 that device 14000 can display on its display. In some embodiments, device 14000 can optionally be one or more of devices 100 (FIG. 1A), 300 (FIG. 3), and/or 500 (FIG. 5A-H). Device 14000 can optionally display a character user interface object such as character user interface object 15604 on the display. Character user interface object 15604 indicates time as described above.

Device 14000 can optionally receive data indicating current or forecasted weather. To receive data indicating current or forecasted weather, device 14000 can optionally retrieve weather information from an external server. In some embodiments, device 14000 can optionally retrieve weather information from a weather service, such as The Weather Channel, Accuweather, The National Weather Service, Yahoo!™ Weather, Weather Underground, and the like.

Device 14000 can optionally determine whether the current or forecasted weather corresponds to one or more designated weather conditions. Designated weather conditions can optionally be system-designated and can optionally include favorable weather conditions such as sunshine or inclement weather conditions such as rain, thunderstorms, wind, snow, and so forth. If device 14000 determines that the current or forecasted weather corresponds to one or more designated weather conditions, device 14000 can optionally update the character user interface object to reflect the current or forecasted weather. For example, as shown in FIG. 14L, user interface screen 15602 includes character user interface object 15604 with umbrella 15606, as well as raindrops 15608. In some embodiments, device 14000 can optionally display a user interface object to reflect the designated weather condition. In some embodiments, the character user interface object can optionally be animated to react to the user interface object reflective of a designated weather condition. As another example, user interface screen 15610 displays character user interface object 15612 with sunglasses 15614 and surfboard 15616, as well as sun 15618.

Figure 14M:
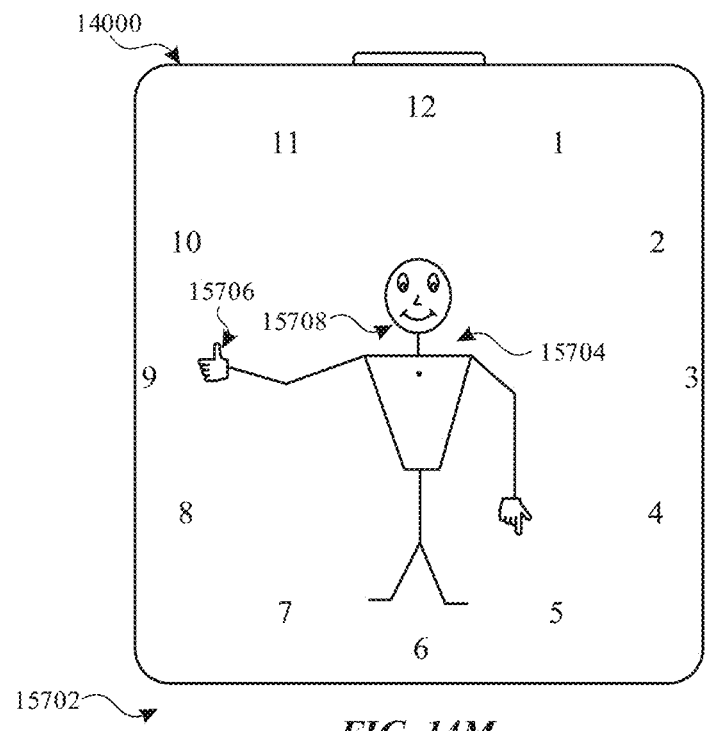

FIG. 14M shows exemplary user interface screen 15702 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15704 on the display. Character user interface object 15704 indicates time as described above.

Device 14000 can optionally receive data indicating a second electronic device. Device 14000 can optionally determine whether the data corresponds to a threshold proximity of the second electronic device to device 14000. If so, device 14000 can optionally update character user interface object 15704 by animating the character user interface object to react to the second electronic device. As shown in user interface screen 15702, character user interface object 15704 can optionally depict thumbs up 15706 or smile 15708. In some embodiments, the posture of the character user interface object can optionally be updated to reflect the proximity and/or direction of the second device. For example, the character user interface object can optionally react in the direction of the device or be reflected on the display. In some embodiments, data indicating a second electronic device can optionally be provided through a server, which can optionally provide the location of the user's contacts that have agreed to provide their location data, such as Find My Friends. Data indicating a second electronic device can optionally also be provided through a local network, for example, a recognition that one of the user's contacts has joined the same WiFi network. Data indicating a second electronic device can optionally also be provided by the second electronic device itself, such as the second electronic device announcing itself through Bluetooth, Near Field Communication, etc.

In some embodiments, a device (such as device 14000) displaying a character user interface object indicating time can optionally receive data indicating user activity. For example, the device can optionally include a user activity monitor (such as a workout monitor), an accelerometer, a gyroscope, a motion sensor, and/or a combination thereof. The device can optionally determine whether the data indicating user activity is received outside of a threshold interval after a previous user activity. For example, the device can optionally determine whether a threshold period of time has elapsed since the last data indicating user activity (e.g., the last user workout). If the device determines that the data indicating user activity is received outside of the threshold interval after a previous user activity, the device can optionally animate the character user interface object to reflect inactivity. For example, the character can optionally change an expression and/or posture to represent boredom, a sedentary or recumbent posture, a sullen or apathetic appearance, and so forth.

Figure 14N:
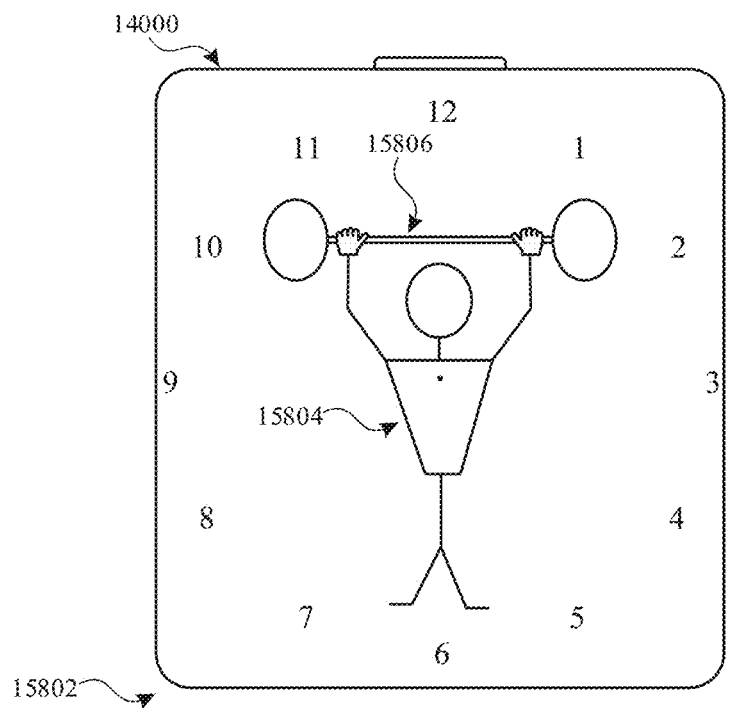

FIG. 14N shows exemplary user interface screen 15802 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15804 on the display. Character user interface object 15804 indicates time as described above.

Device 14000 can optionally receive data indicating user activity. For example, the device can optionally include a user activity monitor (such as a workout monitor), an accelerometer, a gyroscope, a motion sensor, and/or a combination thereof. Device 14000 can optionally determine whether the user activity is current user activity, and, if so, animate character user interface object 15804 to represent exercise. For example, user interface screen 15802 includes character user interface object 15804 and barbell 15806. In some embodiments, device 14000 can optionally animate the character user interface object to depict an activity related to exercise, such as motion, running, weight lifting, swimming, bicycling, pushups, and/or sweat, heavy breathing, or any other signs of physical exertion. In some embodiments, the activity monitor can optionally include options for the user to indicate which activity they are going to begin. In these cases the character appearance can optionally be changed to reflect the selected activity option.

Figure 14O:
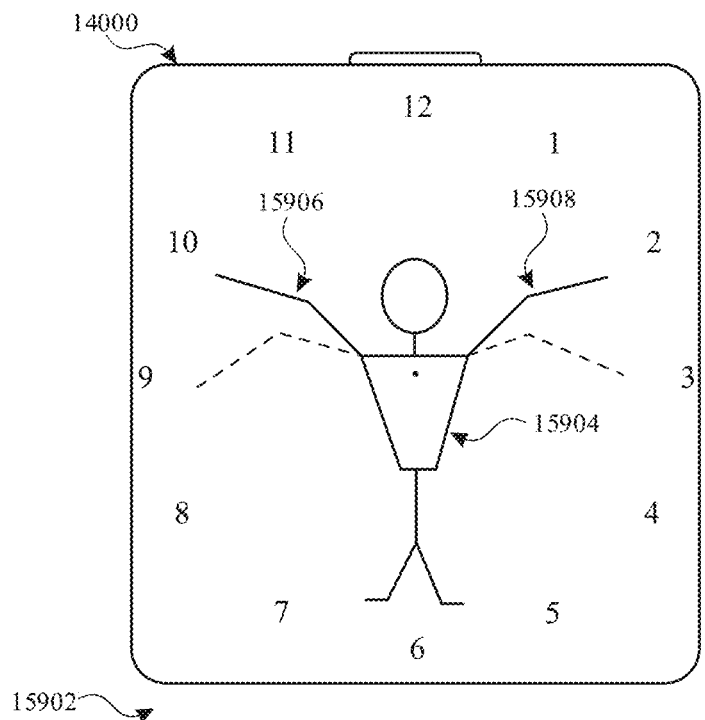

FIG. 14O shows exemplary user interface screen 15902 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 15904 on the display. Character user interface object 15904 indicates time as described above.

Device 14000 can optionally receive data indicating user movement of the device, for example by using an accelerometer, directional sensor (e.g., compass), gyroscope, motion sensor, and/or a combination thereof, and so forth. Device 14000 can optionally determine whether the data indicating user movement is received outside of a threshold interval after a previous user movement. For example, device 14000 can optionally determine whether a threshold period of time has elapsed since the last data indicating user movement (e.g., picking up the device, a motion indicative of a user wrist movement, and so forth). If device 14000 determines that the data indicating user movement is received outside of the threshold interval after a previous user movement, device 14000 can optionally animate the character user interface object to indicate fatigue. For example, user interface object 15904 includes limbs 15906 and 15908. Device 14000 can optionally animate character user interface object 15904 to droop one or more of limbs 15906 and 15908. In some embodiments, device 14000 can optionally animate character user interface object 15904 to shift position, portray physical effort, and the like.

Figure 14P:
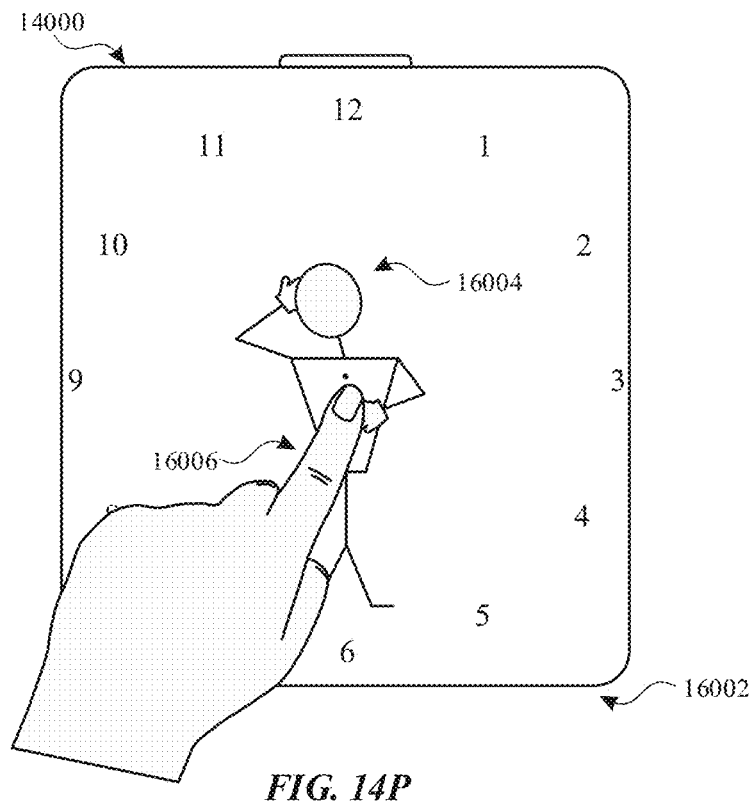

FIG. 14P shows exemplary user interface screen 16002 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object such as character user interface object 16004 on the display. Character user interface object 16004 indicates time as described above.

Device 14000 can optionally receive data indicating a user contact on the touch-sensitive surface (e.g., a touchscreen). Device 14000 can optionally determine whether the user contact corresponds to a user contact on character user interface object 16004. In some embodiments, the user contact can optionally be on a touchscreen at the position of the character user interface object. In some embodiments, the user can optionally input information to manipulate a cursor or other indicator to contact the displayed character user interface object. For example, as shown on user interface screen 16002, a user can optionally contact character user interface object 16004 with touch 16006.

If device 14000 determines that the user contact corresponds to a user contact on character user interface object 16004, device 14000 can optionally animate character user interface object 16004 to react to the contact. In some embodiments, the reaction can optionally be a specific to the location of the contact on the character user interface object. In some embodiments, the reaction can optionally be a general reaction. In some embodiments, the reaction can optionally include, for example, reacting as to tickling, hugging, or other forms of friendly contact. In some embodiments, character user interface object 16004 can optionally display a second animation distinct from the first animation in response to a second user contact.

Figure 14Q:
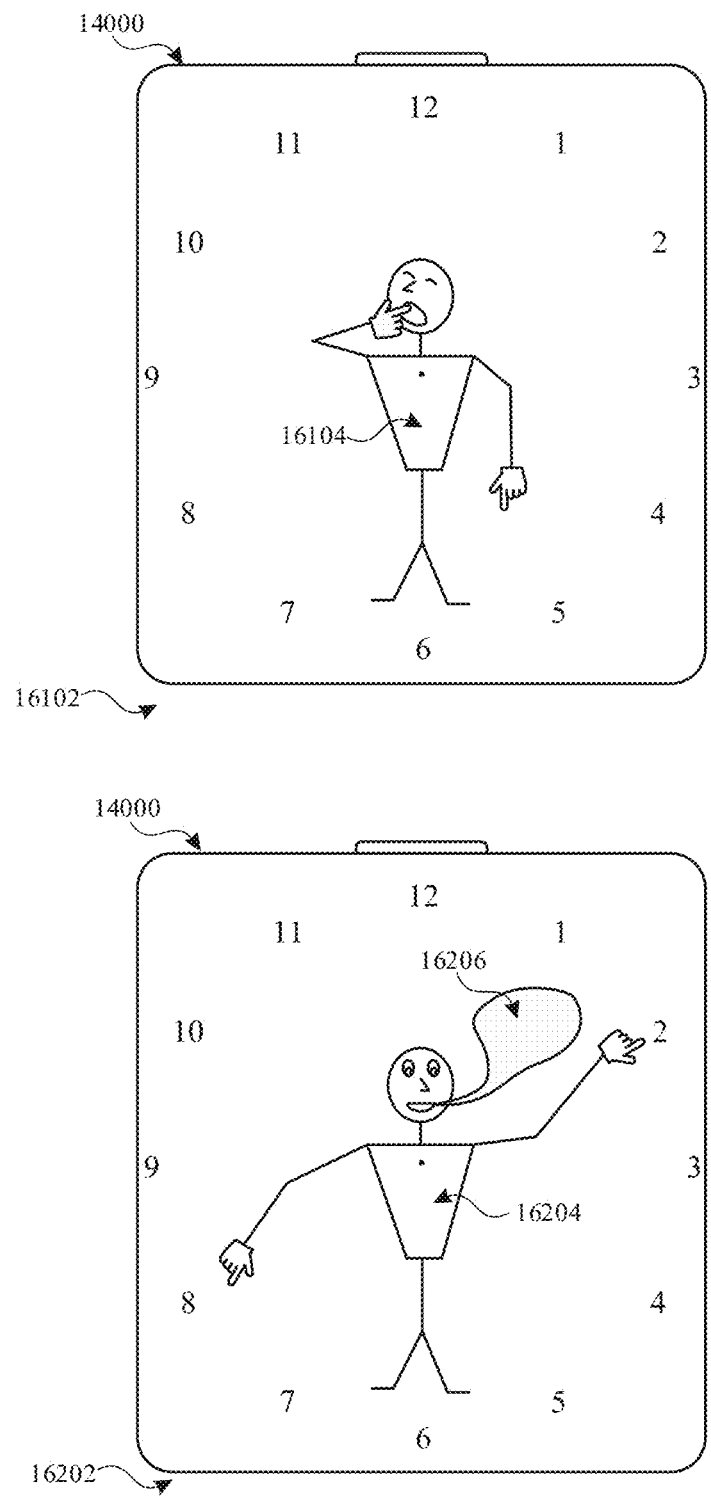

FIG. 14Q shows exemplary user interface screens 16102 and 16202 that device 14000 can display on its display. In some embodiments, device 14000 can optionally be one or more of devices 100 (FIG. 1A-B), 300 (FIG. 3), and/or 500 (FIG. 5A-H). Device 14000 can optionally display character user interface object 16104 on the display. Character user interface object 16104 indicates time as described above. As shown in FIG. 14Q, in some embodiments, character user interface object 16104 can optionally depict a facial expression, such as a yawn. In some embodiments, character user interface object 16204 can optionally depict speech, such as by presenting text in a displayed user interface object or affordance representing speech balloon 16206 or a thought balloon. Speech can optionally be depicted to visually present an announcement made by a character user interface object, such as an announcement of the hour as described above with reference to character user interface object 15504 in FIG. 14K.

Figure 14R:
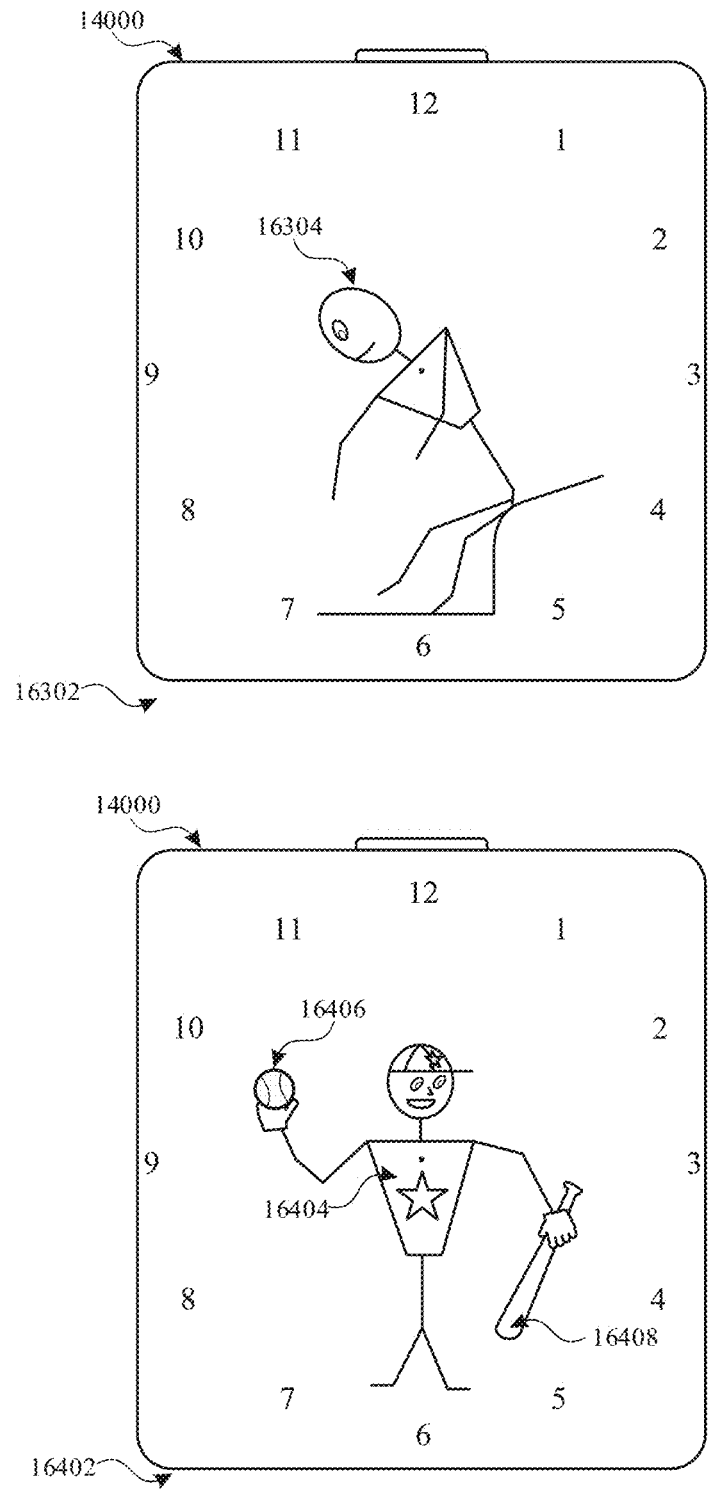

FIG. 14R shows exemplary user interface screens 16302 and 16402 that device 14000 can display on its display. In some embodiments, device 14000 can optionally be one or more of devices 100 (FIG. 1A-B), 300 (FIG. 3), and/or 500 (FIG. 5A-H). Device 14000 can optionally display character user interface object 16304. Character user interface object 16304 indicates time as described above. As shown in FIG. 14R, in some embodiments, character user interface object 16304 can optionally depict boredom or fatigue, as described above. In some embodiments, the character user interface object can optionally depict attire. For example, character user interface object 16404 can optionally depict a sports team or a sports object (e.g., baseball 16406 and bat 16408), such as those representing the user's favorite sports team, as described above.

Figure 14S:
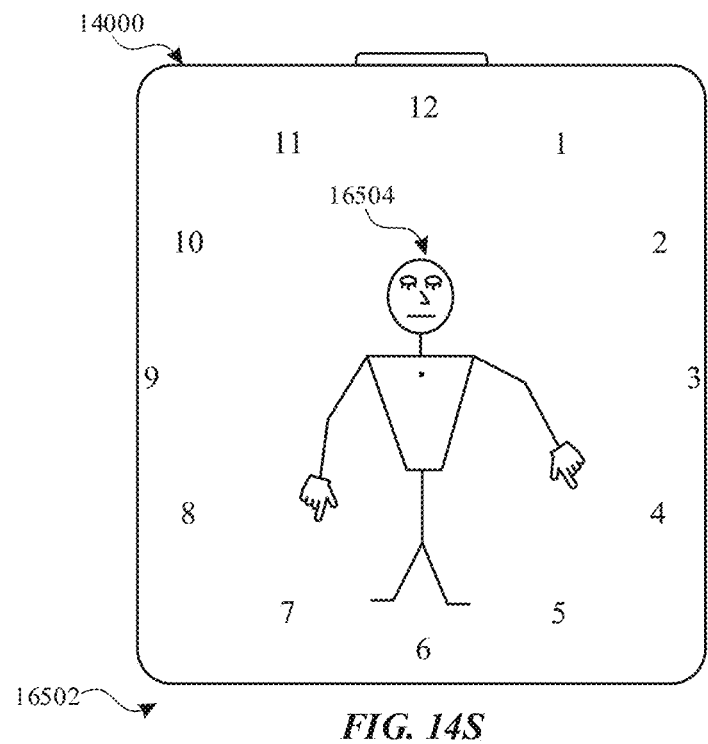

FIG. 14S shows exemplary user interface screen 16502 that device 14000 can display on its display. In some embodiments, device 14000 can optionally be one or more of devices 100 (FIG. 1A-B), 300 (FIG. 3), and/or 500 (FIG. 5A-H). Device 14000 can optionally display character user interface object 16504. Character user interface object 16504 indicates time as described above. As shown in FIG. 14S, in some embodiments, character user interface object 16504 can optionally depict a facial expression, such as blinking, closing, or winking one or more the eyes. The character interface object can optionally change facial expression at predetermined or random intervals to provide an indication to the user that the interface is still active.

Figure 14T:
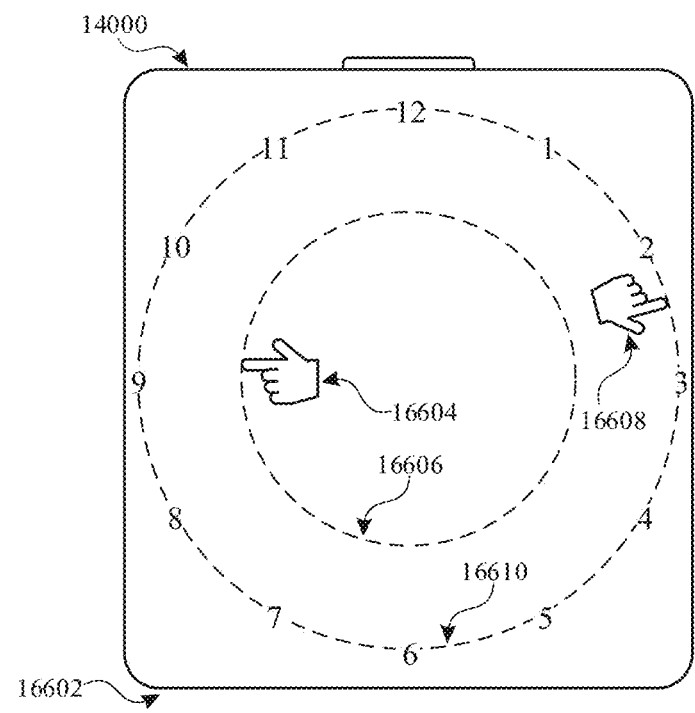
Figure 14U:
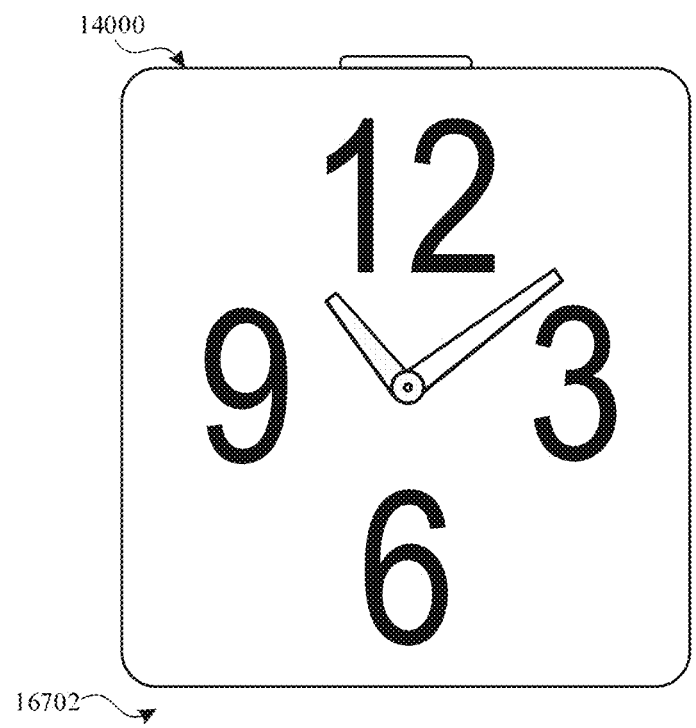

FIG. 14T shows exemplary user interface screen 16602 that device 14000 can display on its display. In some embodiments, device 14000 can optionally be one or more of devices 100 (FIG. 1A-B), 300 (FIG. 3), and/or 500 (FIG. 5A-H). Device 14000 can optionally display a character user interface object on the display. The displayed character user interface object indicates time as described above. As shown in FIG. 14T, in some embodiments, the character user interface object includes one or more second endpoints, such as a second endpoint of a limb and a second endpoint of a second limb, as described above. In some embodiments, the second endpoint 16604 of a first limb can optionally indicate an hour and be positioned along the circumference of a first circle 16606. The second endpoint 16608 of a second limb can optionally indicate a minute and be positioned along the circumference of a second circle 16610 that encircles the first circle 16606 and has a larger circumference than the first circle 16606. In this way, the user can optionally distinguish which limb indicates an hour and which limb indicates a minute by the relative closeness to an edge of the display or to one or more displayed numerical indications of time.

In some embodiments, a device (such as device 14000) can optionally detect a user input and, in response to detecting the user input, display a character user interface object. For example, the display of the device can optionally show another display or be dark, then display the user interface object on the screen in response to the user input. In some embodiments, the user input can optionally be a movement of the device (e.g., picking up the device, a motion indicative of a user wrist movement, and so forth). In some embodiments, the user input can optionally be a touch on the touch-sensitive surface (e.g., a touchscreen).

2. Editing Context-Specific User Interfaces

The context-specific user interfaces described and illustrated herein provide numerous elements and features that a user can optionally customize, depending upon a particular context. As described, these customizable elements enhance the user interfaces, making them more personal and interactive to the user.

At the same time, a user also wants a device that is easy and intuitive to use. Providing a multitude of features only serves to frustrate the user if the user interface does not provide comprehensible ways to edit these features. Described below are user interfaces for editing context-specific user interfaces that provide easy and intuitive methods that facilitate user customization.

Importantly, it is to be appreciated that, while particular embodiments such as clock faces can optionally be described with respect to particular editing features, these editing features can optionally also apply to one or more of the other user interfaces described herein. For example, a method for customizing a color of a clock face can optionally be used to change the color of a seconds hand, change an animated object (e.g., a butterfly), or change a clock face background (e.g., a photo or image of a scene). Similarly, methods for customizing complications can optionally be used to add and/or edit various complications on any clock face, regardless of whether an embodiment of that clock face bearing a particular complication was described herein. A skilled artisan will recognize that the methods described below provide user interface functionalities that can optionally be applied to elements and aspects of various context-specific user interfaces in numerous combinations, such that each possible combination would be impossible to elaborate individually.

It is to be further appreciated that references to a "clock face" with respect to clock face editing and/or selection as described herein are not in any way limited to a traditional notion of a "clock face," e.g., a circular display with hour indications and one or more hands to indicate time, or a representation of a digital clock. Any context-specific user interface with an indication of time described herein can optionally properly be termed a clock face.

Figure 15:
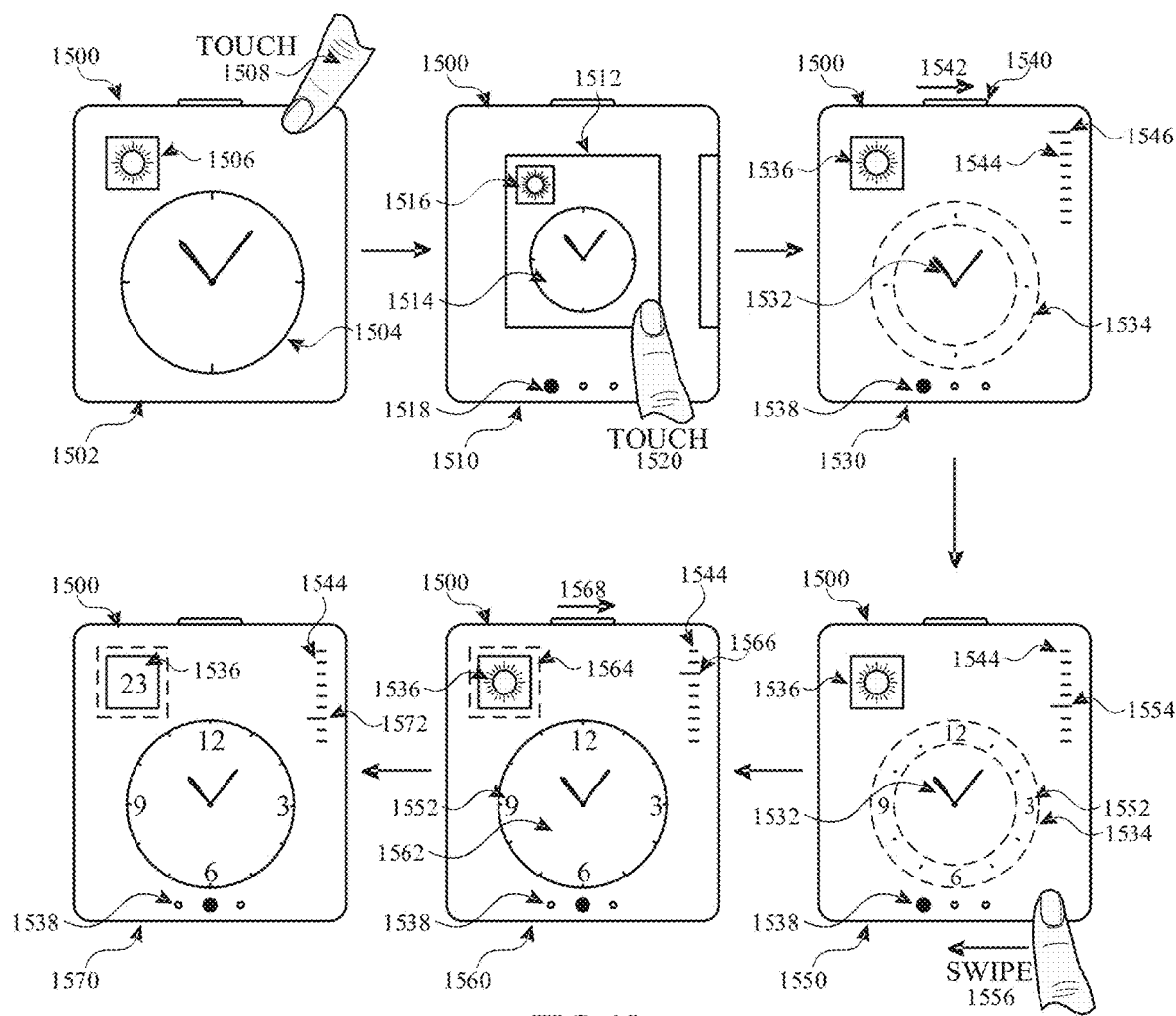
FIG. 15 illustrates exemplary context-specific user interfaces.

Attention is now directed to FIG. 15. FIG. 15 shows exemplary context-specific user interfaces that can optionally be operated on device 1500. Device 1500 can optionally be device 100, 300, or 500 in some embodiments. The electronic device has a touch-sensitive display (e.g., touchscreen 504) configured to detect the intensity of contacts. Exemplary components for detecting the intensity of contacts, as well as techniques for their detection, have been referenced and described in greater detail above.

Device 1500 displays user interface screen 1502, which includes clock face 1504. Clock face 1504 also includes complication 1506 that displays a set of information from a weather application (e.g., current weather conditions). In this example, the user wishes to change multiple aspects of clock face 1504. Specifically, the user decides to change the hour indications on clock face 1504 and complication 1506.

The user contacts the touch-sensitive display of device 1500 with touch 1508. Touch 1508 has a characteristic intensity above an intensity threshold, which prompts device 1500 to enter a clock face edit mode, shown on screen 1510. Clock face edit mode allows the user to edit one or more aspects of a clock face. Device 1500 indicates that the user has entered clock face edit mode by visually distinguishing the clock face. In this example, screen 1510 shows a smaller version of the display of screen 1502 (e.g., 1512), which includes reduced size clock face 1514 based on clock face 1504. Reduced size complication 1516, which is based on complication 1506, is also displayed. This display indicates to the user that the user is in clock face edit mode while giving the user an indication of what the edited clock face will look like on the display. In some embodiments, a user can optionally be able to select a different clock face by swiping displayed screen 1510, as described in greater detail below in reference to FIGS. 16A-C.

Screen 1510 also displays paging affordance 1518. Paging affordances can optionally indicate where the user is within a sequence of options, as well as how many options are available in the sequence. In clock face edit mode, paging affordances can optionally indicate which editable aspect of the clock face a user is editing, where this aspect falls within a sequence of editable aspects, and the total number of editable aspects in the sequence (if clock face selection is available on this screen, paging affordance 1518 can optionally depict the currently selected clock face within a sequence of selectable clock faces and/or clock face options, as described below). A paging affordance may be advantageous in clock face edit mode to help the user navigate the interface and explore all of the editable options available within each type of clock face.

The user selects the displayed clock face for editing by contacting 1512 through touch 1520. In response to detecting touch 1520, device 1500 visually indicates an element of the clock face for editing. As shown on screen 1530, the hour indications have been selected for editing, as indicated by outline 1534 around the position of the hour indications. The other elements of the clock face are still retained, as shown by hour hand and minute hand 1532 and complication 1536.

In this example, three aspects of the clock face are available for user editing. This is depicted by paging affordance 1538. The first editable aspect is the hour indications (e.g., their number and/or appearance). This is relayed to the user by paging affordance 1538. By viewing outline 1534 in combination with paging affordance 1538, the user recognizes that the hour indications are the first of three editable aspects of this clock face.

Device 1500 also has rotatable input mechanism 1540. The user can optionally move rotatable input mechanism 1540 to cycle through different options for editing different aspects of the clock face. On screen 1530, the user can optionally select different options for the hour indications (which are currently editable, as depicted by outline 1534) through movement 1542. Advantageously, using a rotatable input mechanism to cycle through editing options (rather than using, e.g., a touch interaction) frees up touch interactions with the screen to instead provide other functionalities, thus expanding the interactability of the device. Using a rotatable input mechanism is also helpful in cases where smaller elements of the display are being edited, as finerscale touch gestures can optionally be difficult on a reduced-size display for users with large fingers.

Also displayed on screen 1530 is positional indicator 1544, shown as a column of 9 lines. Positional indicator 1544 is an indicator of a current position along a series of positions. This can optionally be used, for example, in combination with rotatable input mechanism 1540. On screen 1530, positional indicator 1544 indicates to the user the position of the currently selected option (e.g., by line 1546) within a series of all selectable options.

Upon detecting movement 1542, device 1500 displays screen 1550. In response to detecting movement 1542, device 1500 edits the hour indications, in this case by increasing the number of indications and adding numerals. This is shown by indications 1552, still highlighted by outline 1534. The other elements of the clock face, hour hand and minute hand 1532 and complication 1536, remain the same. Positional indicator 1544 has been updated to indicate the position of this hour indication option, highlighted by line 1554, within a series of positions of hour indication options.

As indicated by paging affordance 1538, the hour indications are the first editable aspect of this clock face within a sequence of editable aspects. The user can optionally select a second editable aspect by swiping the touch-sensitive display (e.g., swipe 1556). In response to detecting the swipe, device 1500 displays screen 1560. Screen 1560 includes clock face 1562, which now has 12 hour indications, including 4 numerical indications, as depicted by hour indications 1552. Note that these hour indications are the hour indications that were selected by the user on the previous screen (see indications 1552). Paging affordance 1538 has now been updated to indicate that editing complications is the second editable aspect within the sequence of editable aspects in this clock face.

On screen 1560, complication 1536 is currently editable, as indicated to the user by outline 1564. Currently, complication 1536 is displaying current weather conditions using information from a weather application. This option is option 3 in a series of options, as indicated by updated positional indicator 1544 and line 1566. Positional indicator 1544 lets the user know that the currently selected feature (i.e., complication 1536) is editable by the rotatable input mechanism.

While screen 1560 depicts a single complication, it should be understood that multiple complications can optionally be displayed. When multiple complications are displayed, a user can optionally select a particular complication for editing by contacting the corresponding position of the complication. Outline 1564 then transitions from the previously selected complication or element to the currently selected complication or element and rotatable input mechanism can optionally then be used to edit the complication or element at the selected location. This concept is described in greater detail below in reference to FIG. 18C.

It is to be noted that positional indicator 1544 is displayed on screens 1530, 1550, and 1560, even though the available options depicted by the indicators are different. A positional indicator can optionally be a universal indicator of options available through a particular type of user input, such as a movement of the rotatable input mechanism. Rather than displaying positions within a particular context, such as editing a certain feature or displaying data from a particular application, a positional indicator shows the user positions available through a type of user input, no matter the particular context in which the user input is being used. This better indicates to the user which user input should be used for this functionality. In some embodiments, a positional indicator is displayed on the display at a position adjacent to the user input for which it is used (e.g., next to the rotatable input mechanism to indicate positions accessible by moving the rotatable input mechanism).

A positional indicator (e.g., positional indicator 1544) can optionally be responsive to one or more inputs. For example, as shown in FIG. 15, the positional indicator 1544 can optionally indicate options available through a movement of the rotatable input mechanism. As described above, the user can optionally scroll through the available options using movement of the rotatable input mechanism. However, a user may also wish to scroll through the available options using a second type of input, such as a contact (e.g., a swipe) on the touch-sensitive display. In some embodiments, a user viewing screen 1530 can optionally swipe the touch-sensitive display in a different direction than the swipe used for removing a visual indication of a first element of the clock face for editing and visually indicating a second element of the clock face for editing (e.g., a downward swipe on the display). For example, to scroll through the available options shown in FIG. 15, the user can optionally swipe in a substantially horizontal direction (e.g., swipe 1556) to scroll through editable aspects (e.g., with swipes moving left-to-right resulting in scrolling through the sequence of editable aspects in one direction, and swipes moving right-to-left resulting in scrolling through the sequence of editable aspects in a different direction, as depicted by updating the paging affordance 1538). In this example, the user can optionally swipe in a substantially vertical direction (e.g., perpendicular to swipe 1556) to scroll through available options (e.g., with swipes moving downwards resulting in scrolling through the sequence of available options in one direction, and swipes moving upwards resulting in scrolling through the sequence of available options in a different direction, as depicted by updating the positional indicator 1544). In some embodiments, the user can optionally swipe the display at or near the location of the displayed positional indicator to scroll through the sequence of available options.

In some embodiments, upon detecting the swipe, the device can optionally update an indicator of position (e.g., an indicator of position along a series of positions that indicates a position of a currently selected option for the editable aspect along a series of selectable options for the editable aspect of the visually indicated element of the clock face) to indicate a second position along the series. In some embodiments, upon detecting the swipe, the device can optionally edit an aspect of the visually indicated element of the clock face. In some embodiments, the device can optionally visually distinguish the positional indicator (e.g., by changing a color, size, shape, animation, or other visual aspect) based on the type of input used to scroll the indicator. For example, in some embodiments, in response to detecting a movement of the rotatable input mechanism, the device can optionally display the positional indicator in a first color (e.g., green), and in some embodiments, in response to detecting a swipe, the device can optionally display the positional indicator in a second color different from the first color (e.g., white).

In clock face edit mode depicted on screen 1560, the user can optionally be able to cycle through different types of information from the weather application, or change the application from which the information is drawn. In this case, the user moves rotatable input mechanism using movement 1568, which causes device 1500 to display screen 1570. This updates complication 1536 to display the current date, which is obtained from a calendar application. This option is indicated within positional indicator 1544 by line 1572. Note that paging affordance 1538 still indicates the second position because the user is still engaged in editing complications, the second editable aspect of this clock face. A determination that the contact has a characteristic intensity above a predetermined threshold can optionally be used to distinguish the contact from other gestures, such as a tap or the beginning of a swipe.

Having finished editing the clock face, the user can optionally now exit clock face selection mode and display the edited clock face on the display. In some embodiments, this can optionally be done by detecting a user contact with a characteristic intensity above an intensity threshold. In accordance with a determination that the characteristic intensity is above the intensity threshold, the device can optionally exit clock face edit mode and cease to visually distinguish the displayed clock face for editing (e.g., by increasing the size of the displayed clock face). In some embodiments, in accordance with a determination that the characteristic intensity is above the intensity threshold, the device can optionally save this edited clock face as a new clock face that is accessible through clock face selection mode (described below). In accordance with a determination that the characteristic intensity is not above the intensity threshold (where the clock face includes an affordance representing an application, and where the contact is on the affordance representing the application), the device can optionally launch the application represented by the affordance.

In some embodiments, the device can optionally have a rotatable and depressible input mechanism (e.g., 506), and in response to detecting a depression of the rotatable and depressible input mechanism, the device can optionally exit clock face edit mode, display the currently edited clock face, and/or save the currently edited clock face for later user selection, as described above.

FIG. 15 illustrates an exemplary embodiment of clock face edit mode, but a number of other potential embodiments are possible within the scope of the techniques described herein. For example, in FIG. 15, an element was indicated for editing by visibly distinguishing an outline around the element (e.g., by displaying a visible outline, or by distinguishing a pre-existing outline already visible around the element), as illustrated by outlines 1534 and 1564. In some embodiments, the outline can optionally be animated to depict a rhythmic expansion and contraction (e.g., animation similar to pulsing or breathing). In some embodiments, the element indicated for editing itself can optionally be animated to depict a rhythmic expansion and contraction. In some embodiments, the element can optionally be animated to depict flashing. In some embodiments, a color of the element can optionally be changed (e.g., a change in color and/or intensity). Any or all of these indications can optionally be used to visually indicate the element that is currently editable.

As shown in FIG. 15, movement of a rotatable input mechanism can optionally be employed as the user input for editing an aspect of the element indicated for editing. In some embodiments, if an outline is used to indicate the currently editable element, the outline can optionally disappear when the rotatable input mechanism is being moved, and reappear when the movement stops. In this way, the user is able to see what the edited element will look like on the clock face as a whole, without any possible obstruction or distraction from the outline.

In some embodiments, in response to detecting the movement, the device can optionally change a color of the element. This could include, e.g., changing a color of a clock face background (e.g., substituting a color if the clock face background is a particular color, or selecting a different image if the clock face background includes an image), changing a color of part or all of a seconds hand (if included on the clock face), changing a color of an hour and/or minute indication, and/or changing a color of a number or colon in the display of a representation of a digital clock. Since a seconds hand is a smaller element than a background (and therefore may be more difficult for the user to perceive), changing the color of the seconds hand can optionally include an animated color change. For example, the seconds hand could first change a color of a particular point (e.g., a dot depicted along the seconds hand), then propagate this color change in either direction along the seconds hand. Alternatively, the color change could begin at the origin of the clock face and propagate outward. Animating a color change, particularly a change of a smaller element of the clock face, may be helpful to draw the user's attention to the color change.

In other embodiments, in response to detecting movement of the rotatable input mechanism, the device may change an aspect of a complication. For example, this could be used to change application data displayed by an application complication. In some embodiments, the complication may indicate a first set of information obtained by an application (e.g., application data. For example, if the application is a weather application, a set of information could be a forecasted weather condition, a current temperature, etc.), and upon editing, the complication could be updated to indicate a second set of information from the same application (e.g., if the application is a weather application, the display could be edited from showing a current temperature to showing current precipitation). In other embodiments, upon editing, the complication could be updated to indicate a set of information from a different application (e.g., if the application is a weather application, the display could be edited from showing weather to showing data from a calendar application, as illustrated by complication 1536).

In other embodiments, in response to detecting movement of the rotatable input mechanism, the device can optionally change an aspect of display density. For example, as illustrated in FIG. 15, this could be used to edit the number of visible divisions of time (e.g., the number of displayed hour and/or minute indications, such as numbers 1-12 or other marks/symbols positioned along the clock face at the hour positions). In response to detecting movement of the rotatable input mechanism, the device can optionally increase or decrease the number of visible divisions of time. As illustrated on screens 1530, 1550, and 1560, this could involve changing the number of visible divisions (e.g., from 4 to 12) and/or changing the number of numerical/symbolic hour indications (e.g., from 0 to 4).

In some embodiments, as illustrated in FIG. 15, an indicator of positions along a series of positions can optionally be displayed (e.g., positional indicator 1544). In response to detecting movement of the rotatable input mechanism, the device can optionally update the indicator from indicating a first to indicating a second position along the series of positions. In some embodiments, the indicated position can optionally reflect a currently selected option for the currently editable aspect along a series of selectable options for the currently editable aspect. As described above, in some embodiments, the indicator is displayed on the display at a position adjacent to the rotatable input mechanism, thereby strengthening the user's association between the indicator and the input. In some embodiments, if the currently editable aspect is color, the device can optionally display a positional indicator that includes a series of colors, such that the currently selected color option matches the color of the position currently indicated by the positional indicator (e.g., the color could be a similar or identical color). In some embodiments, the number of positions displayed in a position indicator increases or decreases depending on the number of options for the currently selected editable aspect.

In some embodiments, upon reaching the last position indicated by the positional indicator, the device can optionally provide an indication to the user that the last option has been displayed. For example, the device can optionally depict a dimming of one or more of the selected element, an outline around the selected element, and the positional indicator. In some embodiments, the device can optionally animate one or more of the selected element, an outline around the selected element, and the positional indicator to expand and contract (e.g., like a rubber band). In some embodiments, the device can optionally animate one or more of the selected element, an outline around the selected element, and the positional indicator to move on the display (e.g., by bouncing). These features may be advantageous to provide an indication to the user that the last option in the series of options has been reached.

In some embodiments, a user can optionally select the element on the clock face for editing by contacting the touch-sensitive display at the position of the displayed element. In other embodiments, the element can optionally be selected by swiping the touch-sensitive display, or rotating the rotatable input mechanism. Regardless of the input, selecting a second element for editing can optionally involve removing a visual indication from the previous element and visually indicating a second element for editing (visually indicating can optionally include any or all of the techniques described above).

In some embodiments, if the element selected for editing is indicated by an outline around the element, changing an element for editing could involve translating the outline on-screen away from the first element and/or translating a visible on-screen in a continuous on-screen movement towards the second element until the outline is displayed around the second element.

As illustrated in FIG. 15, clock face edit mode allows the user to alter multiple editable aspects of the clock faces described herein. In some embodiments, in response to detecting a swipe on the touch-sensitive display (e.g., swipe 1556), the device can optionally select a second element of the clock face for editing, which in response to detecting another user input (e.g., a movement of the rotatable input mechanism), can optionally be edited. This allows the user to cycle through different editable aspects of the displayed clock face, such as colors, number and/or type of complications, and display density.

A user may wish to match a color of a displayed clock face to an image. In some embodiments, the device can optionally receive a user input, and in response to receiving the user input, the device can optionally enter a color selection mode. While in the color selection mode, the device can optionally receive data representing an image, and in response to receiving the data, the device can optionally select a color of the image and update a displayed clock face by changing a color on the clock face (e.g., a clock face background, hour and/or minute indication, and/or seconds hand) to match the color of the image. In some embodiments, the color selected can optionally have the greatest prevalence of the colors in the image. This allows the user to further customize a clock face to display a designated color. For example, if the user is wearing a blue shirt, the user could take an image of the blue shirt and match the color of the clock face to the shirt. In some embodiments, the data representing the image can optionally be obtained from an image stored on the device, an image stored on an external device in wireless communication with the device (e.g., Wi-Fi, Bluetooth™, near field communication ("NFC"), or any of the other cellular and/or other wireless communication techniques described herein), or an image taken using a camera on the device, such as camera module 143 or optical sensor 164.

Figure 16A:
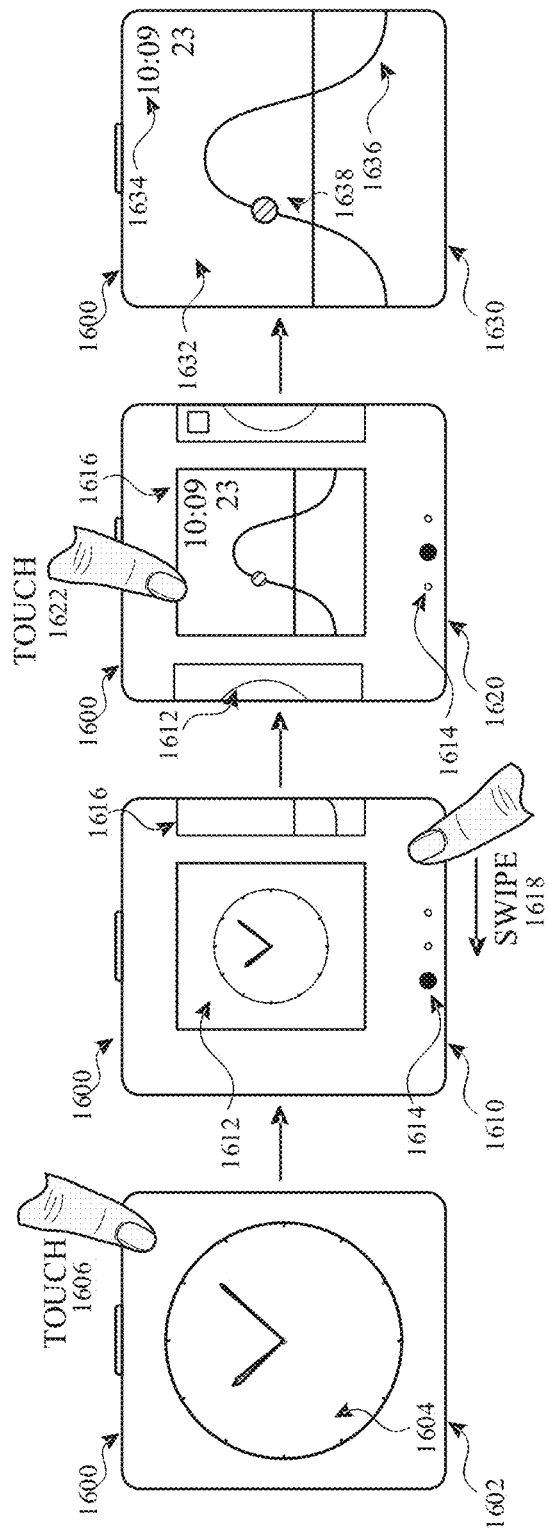
FIGS. 16A-16G illustrate exemplary context-specific user interfaces.
Figure 16B:
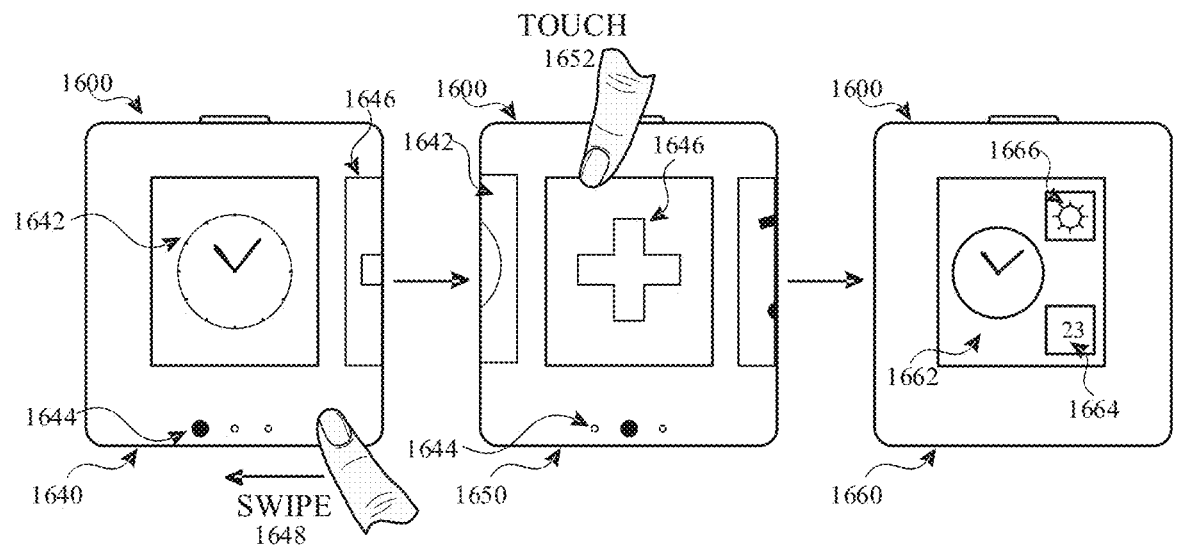
Figure 16C:
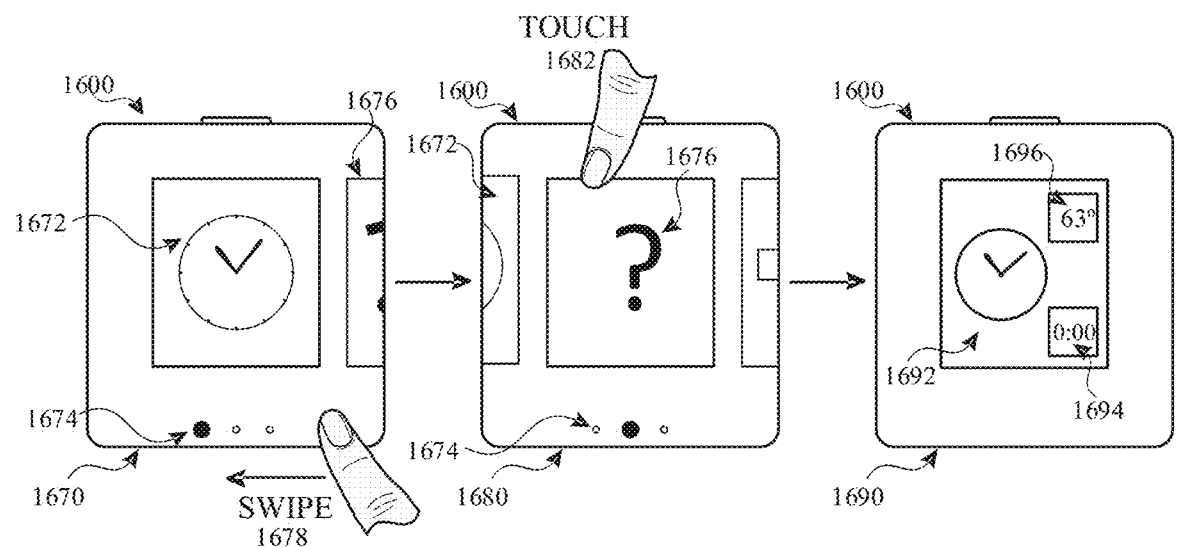
Figure 16D:
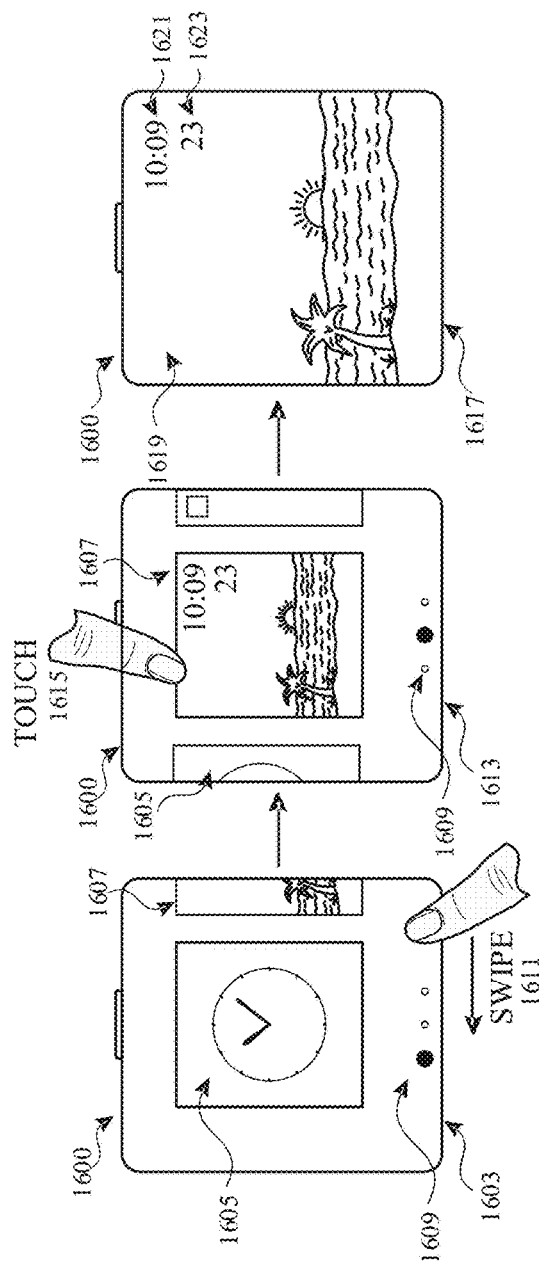
Figure 16E:
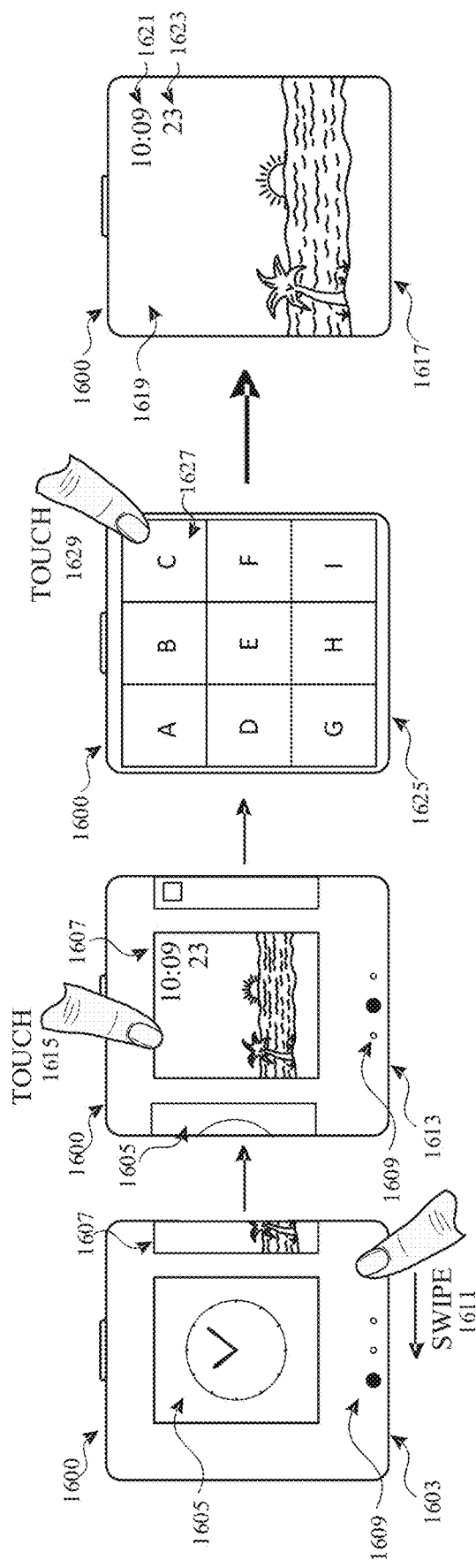
Figure 16F:
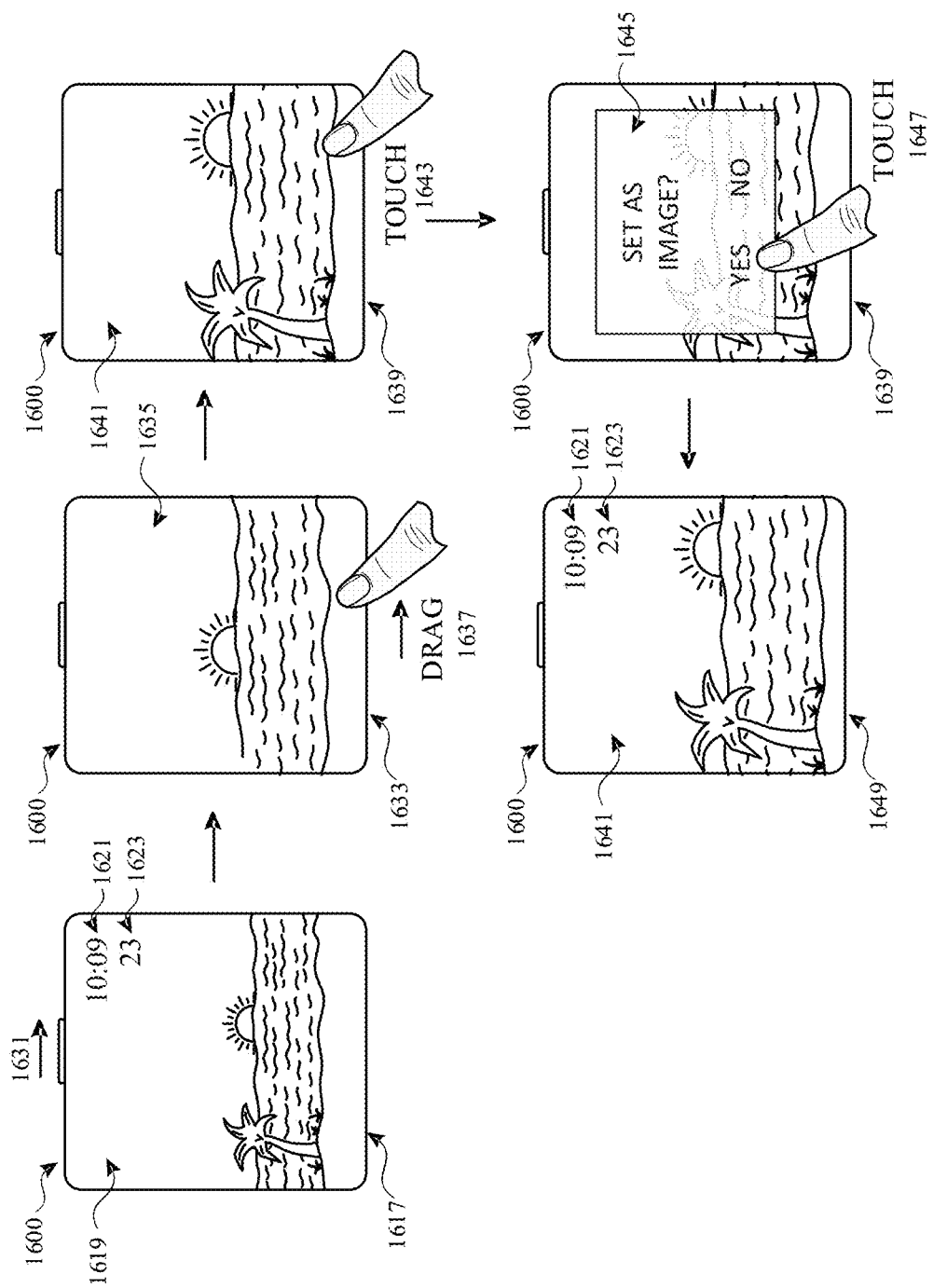
Figure 16G:
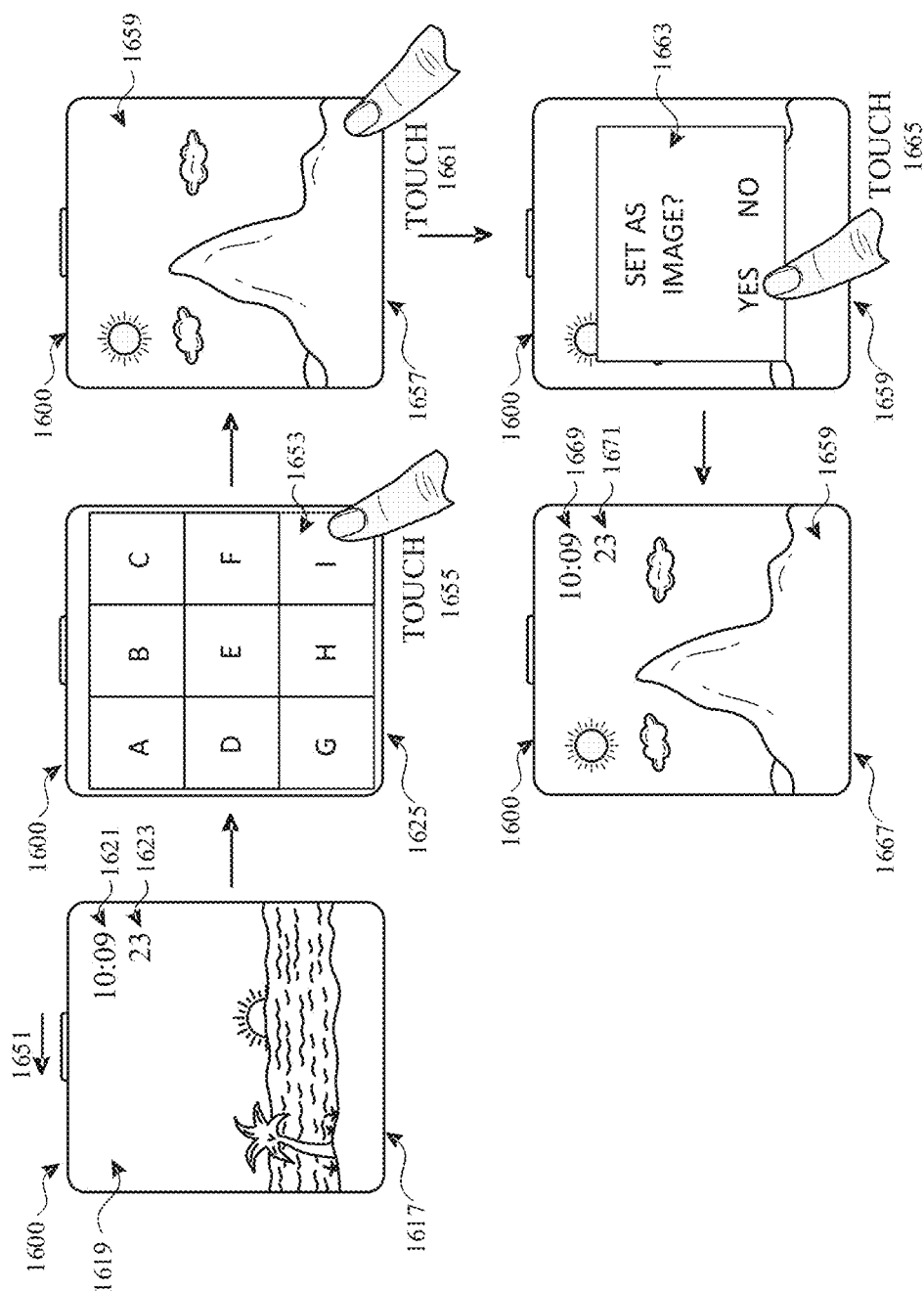

Having described various context-specific user interfaces and methods of user editing thereof, attention is now directed to methods of selecting a context-specific user interface shown in FIGS. 16A-C. Numerous individual context-specific user interfaces are possible using the techniques described here. A user may wish to select a particular clock face (e.g., from a saved library of clock faces) or make a new one, depending on a particular context. For example, a user may wish to display a particular clock face during working hours to project a professional appearance, but change the clock face during the weekend to reflect an interest (such as astronomy, exercise, or photography). A user may wish for quick access to a stopwatch in one context, while desiring an indication of daytime hours in another.

FIG. 16A shows exemplary context-specific user interfaces that can optionally be operated on device 1600. Device 1600 can optionally be device 100, 300, or 500 in some embodiments. The electronic device has a touch-sensitive display (e.g., touchscreen 504) configured to detect the intensity of contacts. Exemplary components for detecting the intensity of contacts, as well as techniques for their detection, have been referenced and described in greater detail above.

Device 1600 displays user interface screen 1602, which includes clock face 1604. In this example, the user wishes to switch from clock face 1604 to a different clock face. The user contacts the touch-sensitive display of device 1600 with touch 1606. Touch 1606 has a characteristic intensity above an intensity threshold, which prompts device 1600 to enter a clock face selection mode, shown on screen 1610. Clock face selection mode allows the user to select a clock face.

Device 1600 indicates that the user has entered clock face selection mode by visually distinguishing the clock face. This is shown on screen 1610. Screen 1610 visually distinguishes that the user has entered clock face selection mode by centering reduced size clock face 1612 on the display (reduced size clock face 1612 is based on clock face 1604). This indicates to the user that the user is in clock face selection mode while giving the user an indication of what the clock face will look like when displayed at full size.

Screen 1610 also includes paging affordance 1614. As described above, paging affordances can optionally indicate where the user is within a sequence of options, as well as how many options are available in the sequence. Paging affordance 1614 indicates to the user that clock face 1612 is the first in a series of three selectable clock faces and/or clock face options (e.g., an option to add a new clock face or randomly generate a clock face, as described below). In clock face selection mode, a paging affordance can optionally indicate a currently centered clock face and/or clock face option, a position of the currently centered clock face and/or clock face option within a sequence of clock faces and/or clock face options, and a total number of available clock faces and/or clock face options. This helps the user navigate the clock faces and clock face options.

Screen 1610 also includes a partial view of a second clock face, as shown by a partial view of second clock face 1616. In some embodiments, when the device is in clock face selection mode, the device can optionally include a display a partial view of another clock face, or clock face option, particularly the clock face or clock face option next in the sequence (e.g., as indicated by the paging affordance). This further helps the user understand that additional options are available. In other embodiments, only one clock face is displayed at any time.

Clock face selection mode can optionally be used to select a clock face for display as a context-specific user interface, or to select a clock face for editing. Therefore, in some embodiments, when a clock face such as clock face 1612 and/or clock face 1616 is centered on the display, a user can optionally contact the displayed clock face on the touch-sensitive display to select the centered clock face for editing and enter into clock face editing mode (as described above in reference to FIG. 15). In some embodiments, clock face editing mode is entered when the contact has a characteristic intensity above an intensity threshold. Coupling clock face edit and selection modes in a single interface allows the user to select different clock faces and edit them quickly and easily.

A user can optionally select a different clock face (for editing or for display as a context-specific user interface) by swiping. Device 1600 detects a swipe on the touch-sensitive display (e.g., swipe 1618). In response to detecting swipe 1618, device 1600 displays screen 1620. Screen 1620 includes second clock face 1616 centered on the display (part of second clock face 1616 was depicted on screen 1610). Screen 1620 also shows paging affordance 1614, which has been updated to indicate that the currently centered clock face 1616 is second within the sequence of clock faces and/or clock face options. Also shown is a partial view clock face 1612. This helps the user understand the sequence of clock faces, similar to a paging affordance but with the added benefit of displaying a partial view of the clock faces for user recognition.

To select clock face 1616, the user contacts the touch-sensitive display on clock face 1616 (e.g., touch 1622). In response to detecting touch 1622, device 1600 exits the clock face selection mode and displays screen 1630. Screen 1630 includes full-sized clock face 1632, which is based on clock face 1616. In this example, clock face 1632 is a context-specific user interface similar to those described in reference to FIGS. 11A-C and includes affordance 1634 indicating the time of day, user interface object 1636 (a sinusoidal wave indicating a path of the Sun through the day), and affordance 1638 representing the Sun.

As described above and illustrated in FIG. 16A, a user can optionally select a clock face from a plurality of clock faces in the device's clock face selection mode. In some embodiments, at least a first and a second clock face are shown when the device is in clock face selection mode. These clock faces can optionally be shown in sequence, but at a reduced size. In some embodiments, one clock face is centered on the display at any time, and the one or more additional clock faces on the display are shown in partial view, as depicted by partial views of clock faces 1612 and 1616. Centering a clock face can optionally include includes translating the prior clock face in the sequence on-screen and displaying the prior clock face in partial view. In other embodiments, only a single clock face is displayed on the device at any one time (i.e., no partial views).

In some embodiments, centering a clock face on the display includes simulating a movement of the clock face towards the user on the display, as if it is approaching the user. This helps draw the user's attention to the clock face while conveying to the user a sense of the clock face sequence.

As depicted by screen 1620, device 1600 can optionally display multiple available clock faces and/or clock face options in a sequence for selection by the user. A user may wish to re-order one or more clock faces within the sequence. Therefore, device 1600 can optionally provide a clock face rearrangement mode to allow the user to select a particular clock face and change its order within the sequence of available clock faces and/or clock face options. In some embodiments, a user can optionally contact the touch-sensitive display on a clock face (e.g., clock face 1616) and maintain the contact beyond a threshold interval (e.g., a "press and hold"-type user input). In response to detecting the contact, and in accordance with a determination that the contact exceeds a predetermined threshold, device 1600 can optionally enter a clock face rearrangement mode. Device 1600 can optionally highlight, outline, animate, or otherwise visually distinguish the clock face to indicate to the user that device 1600 has entered clock face rearrangement mode, and that the clock face has been selected for rearrangement. In some embodiments, while continuing to receive the user contact, device 1600 can optionally detect movement of the user contact from a first position within the sequence of displayed clock faces and/or clock face options to a second position, which is different from the first position, without a break in contact of the user contact on the touch-sensitive display. In other embodiments, the contact comprising the movement from a first position within the sequence of displayed clock faces and/or clock face options to a second position, which is different from the first position, without a break in contact of the user contact on the touch-sensitive display can optionally be a separate contact subsequent to entry into clock face rearrangement mode. In response to detecting the contact at the second position, device 1600 can optionally translate the clock face on-screen from the first position to the second position. Optionally, other partial or complete clock faces and/or clock face options on the display can optionally be moved accordingly to accommodate the new position of the user-selected clock face. A user can optionally then cease the contact to select the second position as the new position for the clock face within the sequence of displayed clock faces and/or clock face options. In some embodiments, device 1600 can optionally exit clock face rearrangement mode in response to detecting the break in contact on the touch-sensitive display after the position of at least one clock face has been rearranged. In other embodiments, in response to detecting a user input subsequent to the break in contact on the touch-sensitive display (e.g., a depression of a rotatable and depressible input mechanism such as 506), device 1600 can optionally exit clock face rearrangement mode. In some embodiments, upon exiting clock face rearrangement mode, device 1600 can optionally re-enter clock face selection mode.

In addition to selecting an existing context-specific user interface, a user may also wish to add a new one. FIG. 16B illustrates an exemplary user interface for generating a new clock face. Shown on FIG. 16B is device 1600, which displays screen 1640. Screen 1640 displays clock face 1642 and paging affordance 1644, which indicates to the user that the currently centered clock face is the first in a sequence of three selectable clock faces and/or clock face options.

Screen 1640 also displays a partial view of a clock face generation affordance (e.g., 1646).

In this example, the user swipes the display (e.g., swipe 1648), and in response to detecting the swipe, device 1600 displays a full view of clock face generation affordance 1646 centered on screen 1650. In some embodiments, as depicted by affordance 1646, a clock face generation affordance can optionally include a plus sign (or other text and/or symbol) to convey to the user that, upon activation of affordance 1646, device 1600 will generate a new clock face.

Note that screen 1650 also displays a partial view of previously displayed clock face 1642. This partial view of 1642 and updated paging affordance 1644 (updated to indicate that clock face generation is the second available user interface in the sequence) help orient the user within the sequence of available clock faces and/or clock face options. Further note that the partial view of clock face generation affordance 1646 on screen 1640 indicates to the user that a swipe will center affordance 1646 on the display (e.g., as displayed on screen 1650) for user activation.

A user can optionally activate affordance 1646, for example by contacting affordance 1646 on the touch-sensitive display (e.g., touch 1652). In response to detecting the contact, device 1600 displays screen 1660, which includes newly generated clock face 1662 centered on the display. As shown on screen 1660, new clock face 1662 includes affordance 1664, which displays the current date (e.g., obtained from a calendar application), and affordance 1666, which displays the current weather conditions (e.g., obtained from a weather application).

In response to detecting an activation of affordance 1646, in some embodiments, the device remains in clock face selection mode after centering the displayed new clock face. In other embodiments, upon centering the newly generated clock face on the display, the device enters into clock face edit mode, as described above. This allows the user to edit one or more aspects of the newly generated clock face. In some embodiments, the device exits clock face selection mode and centers the new clock face as a full-size clock face on the display.

It is to be appreciated that, while new clock face 1662 depicts a representation of an analog clock, any of the context-specific user interfaces described herein (with any of the optional features described herein) can optionally be a new clock face generated in response to activating the clock face generation affordance. In some embodiments, a new clock face can optionally have a different customizable aspect, as compared to existing clock faces on the device. For example, if the user already has a clock face that includes a blue seconds hand, the device can optionally generate a new clock face that includes a red seconds hand. This helps the user explore the options available for context-specific user interfaces described herein, thus enhancing the user interface by increasing variety.

In addition to selecting an existing context-specific user interface or generating a new context-specific user interface, a user may also wish to create a random context-specific user interface. FIG. 16C illustrates an exemplary user interface for generating a random clock face. Shown on FIG. 16C is device 1600, which displays screen 1670. Screen 1670 displays clock face 1672 and paging affordance 1674, which indicates to the user that the currently centered clock face is the first in a sequence of three selectable clock faces and/or clock face options. Screen 1670 also displays a partial view of a random clock face generation affordance (e.g., 1676).

In this example, the user swipes the display (e.g., swipe 1678), and in response to detecting the swipe, device 1600 displays a full view of random clock face generation affordance 1676 centered on screen 1680. In some embodiments, as depicted by affordance 1676, a random clock face generation affordance can optionally include a question mark (or other text and/or symbol, such as the letter "R") to convey to the user that, upon activation of affordance 1676, device 1600 will generate a random clock face.

Note that screen 1680 also displays a partial view of previously displayed clock face 1672. The partial view of 1672, along with updated paging affordance 1674 (updated to indicate that random clock face generation is the second available user interface in the sequence), helps orient the user to the sequence of clock faces and/or options available in the sequence. Further note that the partial view of random clock face generation affordance 1676 on screen 1670 indicates to the user that a swipe will center affordance 1676 on the display (e.g., as displayed on screen 1680) for user activation.

A user can optionally activate affordance 1676, for example by contacting affordance 1676 on the touch-sensitive display (e.g., touch 1682). In response to detecting the contact, device 1600 displays screen 1690, which includes randomly generated clock face 1692 centered on the display. As shown on screen 1690, new clock face 1692 includes affordance 1694, which represents an affordance for launching a stopwatch application, and affordance 1696, which displays the current temperature (e.g., obtained from a weather application).

In response to detecting an activation of affordance 1676, in some embodiments, the device remains in clock face selection mode after centering the displayed random clock face. In other embodiments, upon centering the randomly generated clock face on the display, the device enters into clock face edit mode, as described above. This allows the user to edit one or more aspects of the randomly generated clock face. In some embodiments, the device exits clock face selection mode and centers the random clock face as a full-size clock face on the display.

It is to be appreciated that, while random clock face 1692 depicts a representation of an analog clock, any of the context-specific user interfaces described herein (with any of the optional features described herein) can optionally be a random clock face generated in response to activating the random clock face generation affordance.

In some embodiments, the random clock face can optionally be different from any of the other clock faces available in clock face selection mode. The device can optionally accomplish this in multiple ways. In some embodiments, the device can optionally randomly generate a random clock face, and then check the random clock face against the other stored clock faces to ensure that it is different. In other embodiments, the device can optionally generate a random clock face and rely on the inherent probability that it will be different from the stored clock faces, given the sheer number of potential clock faces made available by the techniques described herein.

In some embodiments, upon displaying the random clock face, the device can optionally display a user prompt for generating a second random clock face. This allows the user to randomly generate another clock face if the user does not like the particular type of context-specific user interface and/or customized features of the random clock face. In some embodiments, the random clock face generation affordance can optionally depict, e.g., a slot machine or other indication of a user prompt for generating a second random clock face, to provide this feature.

In addition to centering a clock face on the display for selection, the device can optionally also highlight the centered clock face in one or more ways. For example, in some embodiments, the centered clock face can optionally be displayed by visibly distinguishing an outline around the centered clock face (e.g., by displaying a visible outline, or by distinguishing a pre-existing outline already visible around the clock face), as illustrated by 1612, 1622, 1642, and 1672. In some embodiments, the outline can optionally be animated to depict a rhythmic expansion and contraction (e.g., animation similar to pulsing or breathing). In some embodiments, the centered clock face itself can optionally be animated to depict a rhythmic expansion and contraction. In some embodiments, the centered clock face can optionally be animated to depict flashing. In some embodiments, a color of the centered clock face can optionally be changed (e.g., a change in color and/or intensity). Any or all of these indications can optionally be used to visually indicate that the centered clock face is currently selectable.

In some embodiments, the user can optionally access clock face edit mode and clock face selection mode through a shared interface. For example, a contact with a characteristic intensity above the intensity threshold can optionally cause the device to enter clock face selection mode. In this example, screen 1510 in FIG. 15 can optionally represent clock face selection mode, with a paging affordance that indicates the currently selected clock face within a sequence of selectable clock faces and/or clock face options. Upon entering clock face selection mode, in some embodiments, a second contact with a characteristic intensity above the intensity threshold can optionally cause the device to enter into the clock face edit mode and select the currently centered clock face for editing. In other embodiments, upon entering clock face selection mode, the device can optionally display an affordance representing clock face edit mode. Upon detecting a contact on the displayed affordance, the device can optionally enter into the clock face edit mode and select the currently centered clock face for editing. These features help tie the context-specific user interface selection and editing functionalities into a single interface that is user-friendly and intuitive.

3. Additional Functionalities for Context-Specific User Interfaces

A user may wish for additional functionalities in a context-specific user interface that can optionally be applied to the user interfaces described above. For example, a user may wish to set reminders, launch applications, and view the time at a designated location. Such functionalities are not limited to particular user interfaces described herein, but rather can optionally be generally applied to any or all of them. The following functionalities are generalizable features that can optionally be incorporated into any of the context-specific user interfaces described herein. While a specific functionality can optionally be described in reference to a particular context-specific user interface below, this is in no way intended to be limiting.

Figure 17A:
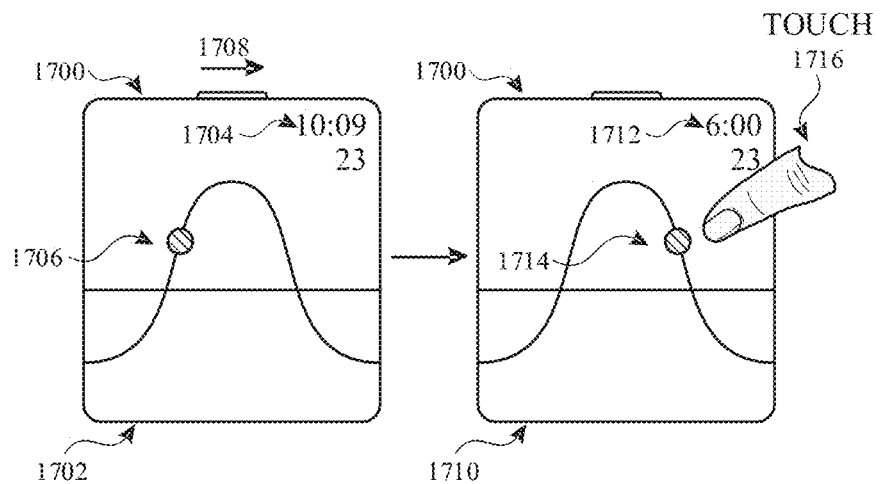
FIGS. 17A and 17B illustrate exemplary context-specific user interfaces.

FIG. 17A shows exemplary context-specific user interfaces that can optionally be operated on device 1700. Device 1700 can optionally be device 100, 300, or 500 in some embodiments. In some embodiments, the electronic device has a touch-sensitive display (e.g., touchscreen 504) and a rotatable input mechanism (e.g., 506 or 1540).

In this example, a user wants to set a reminder for 6:00 (this can optionally be a reminder for 6:00 at a specific day or a general reminder for 6:00 every day). Device 1700 displays user interface screen 1702. Screen 1702 depicts a clock face similar to those described in reference to FIGS. 11A-C and includes affordance 1704, which indicates the time of day, and a sinusoidal wave indicating a path of the Sun through the day. Screen 1702 further includes affordance 1708, which as described in FIG. 11A indicates a current time of day by its position along the sinusoidal wave (10:09).

A user can optionally contact the display, which then prompts the device to enter into a user interaction mode. User interaction mode provides the user additional interactions available within the user interface, such as setting a user reminder. Once in user interaction mode, a user moves the rotatable input mechanism (e.g., movement 1708), and in response to detecting the movement, device 1700 displays screen 1710. Screen 1710 displays a non-current time of day (6:00), as indicated by affordance 1712 and the position of affordance 1714 along the sinusoidal wave. The user can optionally use movement 1708 to scroll through times of day until a designated time is displayed (in this case 6:00) so the user can set a reminder for the designated time of day.

The user contacts the display at affordance 1714 (e.g., touch 1716), and in response to detecting the contact, device 1700 sets a reminder for the indicated time of day (6:00). This allows the user to set a designate a time of day for a user reminder.

Figure 17B:
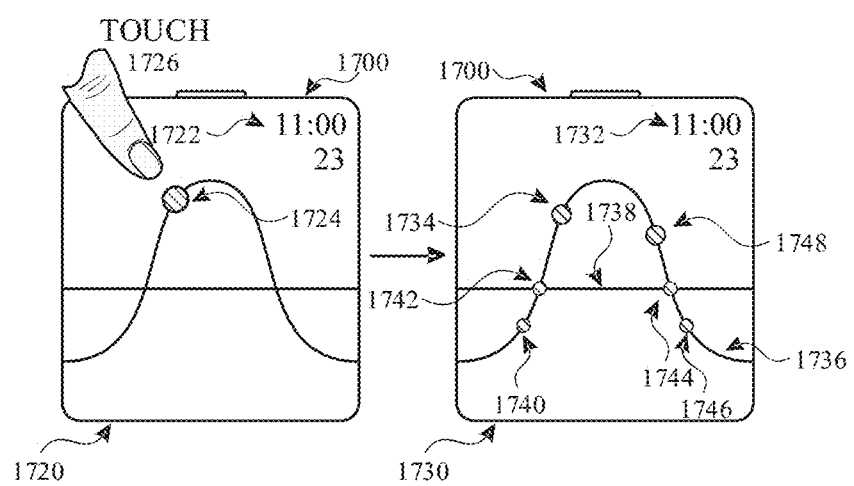

FIG. 17B shows device 1700 at a later time of day (11:00). Device 1700 displays screen 1720. Screen 1720 includes affordance 1722, which indicates the current time, and affordance 1724, which indicates a current time of day by its position along the sinusoidal wave. As shown in FIG. 11B, in this context-specific user interface, a user can optionally contact affordance 1724 (e.g., touch 1726) to view user interface objects representing dawn, dusk, sunrise, and sunset.

In response to detecting the contact, device 1700 displays screen 1730. Screen 1730 includes affordance 1732, which indicates the current time of day, and affordance 1734, which also indicates the current time of day by its position along sinusoidal wave 1736. Line 1738 depicts the boundary between the daytime and nighttime portions of the display. As described above, screen 1730 includes user interface objects 1740 (representing a time of dawn), 1742 (representing a time of sunrise), 1744 (representing a time of sunset), and 1746 (representing a time of dusk).

Importantly, screen 1730 also displays affordance 1748. Affordance 1748 is a visual reminder of the time of day designated by the user (6:00) in FIG. 17A. Thus, the device now displays a user reminder for this time of day, in this case in response to a user contact on affordance 1724.

In some embodiments, setting the user reminder can optionally include displaying an affordance representing a user prompt to set an alert for the designated time of day. This affordance can optionally include a user interface for setting one or more properties of the alert.

In some embodiments, a user reminder can optionally include a calendar event. For example, instead of a user setting the user reminder as described above, the device can optionally import a calendar event from a calendar application. Using the example illustrated in FIG. 17B, affordance 1748 can optionally represent a calendar event imported from a calendar application. Importing a calendar event from a calendar application allows the user to track the time of the calendar event compared with the current time and/or other times of interest (e.g., sunrise, sunset, dawn, or dusk). For example, the user can optionally be able to view the time of a tennis match (stored as a calendar event) as part of screen 1730 and thereby gauge how much time is left before the match is scheduled, or how much time is available between the start of the match and sunset. In some embodiments, the user can optionally move the rotatable input mechanism (e.g., movement 1708), and in response to detecting the movement, the device can optionally snap to the user reminder by visually distinguishing affordance 1748 and/or by updating a displayed indication of time to indicate the time associated with the user reminder represented by affordance 1748.

In some embodiments, the user reminder represents a recurring event. In some embodiments, the time of the user reminder is based on a fixed chronological time. To use FIG. 17B as an example, if the user reminder is a tennis match, it can optionally recur at the same chronological time throughout the year, but the position of affordance 1748 relative to line 1738 can optionally change throughout the year. This would allow the user to determine whether sufficient daylight will be present throughout the match on a given date simply by viewing the position of affordance 1748. In other embodiments, the time of the user reminder is based on a solar condition (e.g., the amount of daylight or lack thereof). For example, a user reminder can optionally reflect the time of a solar condition, such as a particular time before sunset, or the time that the sun is at a particular angle above the horizon. Therefore, if such a user reminder is recurring, the chronological time of the user reminder can optionally vary over time while still representing the same solar condition, allowing the user to plan for viewing this solar condition at any time of the year.

The user reminder for the designated time of day can optionally include one or more optional features. In some embodiments, the reminder can optionally include a visual alert for the designated time of day. For example, the device can optionally display a visual alert on or before the designated time of day. Alternatively, the device can optionally display at any time a visual affordance that shows the designated time of day within the context of the current user interface. In the example of FIG. 17B, visual affordance 1748 is displayed along the sinusoidal wave to help the user understand how far the designated time of day is from the current time of day.

In some embodiments, the user reminder can optionally include an audio alert for the designated time of day. For example, the device can optionally play a sound on or before the designated time of day. In some embodiments, the user reminder can optionally include a haptic alert generated on or before the designated time of day (e.g., using haptic feedback module 133 and tactile output generator 167). This haptic signal lets the user know when the designated time of day is approaching.

Figure 18A:
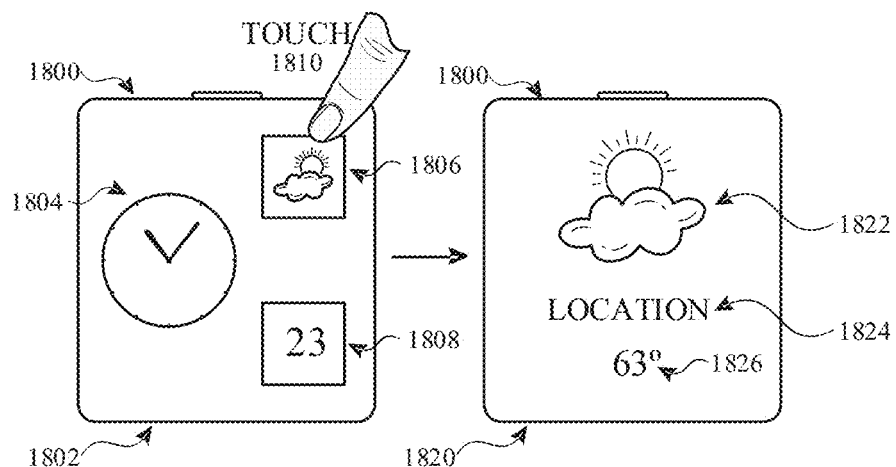
FIGS. 18A-18C illustrate exemplary context-specific user interfaces.

Turning now to FIG. 18A, any or all of the context-specific user interfaces described herein can optionally include one or more complications. One type of complication a user may wish to use is a complication for launching an application. For example, the affordance representing the complication on the clock face can optionally display a set of information from the corresponding application. However, a user may wish to view additional information from the application, or launch the full application itself.

FIG. 18A shows exemplary context-specific user interfaces that can optionally be operated on device 1800. Device 1800 can optionally be device 100, 300, or 500 in some embodiments. In some embodiments, the electronic device has a touch-sensitive display (e.g., touchscreen 504).

Device 1800 displays user interface screen 1802. Screen 1802 includes clock face 1804 and affordances 1806 and 1808, which are displayed as complications. Affordances 1806 and 1808 represent applications and include a set of information obtained from the corresponding application. In this example, affordance 1806 represents a weather application and displays weather conditions obtained from the weather application. Affordance 1808 represents a calendar application and displays the current date obtained from the calendar application. Affordance 1806 and affordance 1808 are updated in accordance with data from the corresponding application. For example, affordance 1806 is updated to display current weather conditions obtained from the weather application. Affordance 1808 is updated to display the current date obtained from the calendar application. For example, these complications can optionally be application widgets updated based on application data.

To launch the weather application, a user contacts the display at affordance 1806 (e.g., touch 1810). In response, device 1800 launches the weather application, which is depicted on screen 1820. Screen 1820 shows further weather information, including current weather conditions (e.g., user interface object 1822), an indication of the current location (e.g., user interface object 1824), and an indication of the current temperature (e.g., user interface object 1826).

Figure 18B:
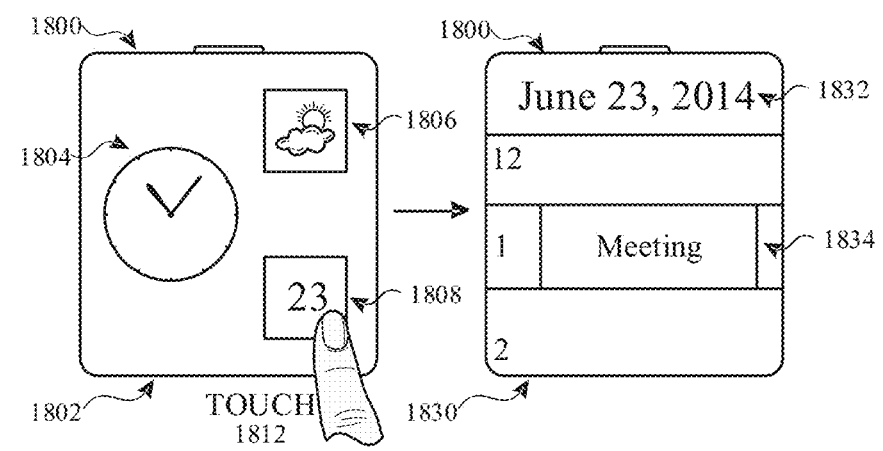

FIG. 18B also depicts device 1800 displaying screen 1802. As depicted in FIG. 18A, screen 1802 includes clock face 1804 and affordances 1806 and 1808, which are displayed as complications.

If a user wishes to launch the calendar application instead of the weather application, the user contacts the display at affordance 1808 (e.g., touch 1812). In response, device 1800 launches the calendar application, which is depicted on screen 1830. Screen 1830 shows further calendar information, including user interface object 1832, which depicts the full date, and user interface object 1834, which represents a calendar event (in this case, a meeting at 1).

In some embodiments, a user interface screen can optionally display a complication that represents an application and includes a set of information obtained from the corresponding application. In some embodiments, as illustrated by FIGS. 18A and 18B, a user interface screen can optionally display a plurality of complications that represent applications and include sets of information obtained from a plurality of applications, or a plurality of sets of information obtained from a single application.

In some embodiments, as described above, a user can optionally move a rotatable input mechanism to scroll a displayed indication of time forward or backward. In some embodiments, the device can optionally display two or more indications of time, and in response to detecting a movement of the rotatable input mechanism, the device can optionally update one or more of the displayed indications of time and keep another indication of time constant. To illustrate using screen 1802 in FIGS. 18A and B as an example, if affordance 1808 represents an indication of current time (e.g., a digital display), the device can optionally update the displayed clock face in response to detecting the movement of the rotatable input mechanism while continuing to display the current time with affordance 1808. The displayed clock face can optionally be updated, for example, by animating a clockwise or counter-clockwise movement of one or more clock hands, depending on whether the displayed time is scrolled forward or backward.

In some embodiments, the device can optionally update other displayed complications (e.g., those that do not indicate a time per se) in response to detecting the movement of the rotatable input mechanism. For example, in addition to updating the time displayed by clock face 1804, the device can optionally also update the forecasted or historical weather condition displayed by affordance 1806 to correspond with the time indicated by clock face 1804. In these embodiments, the device can optionally forego updating another displayed complication in response to scrolling the displayed time. For example, a displayed stopwatch complication can optionally remain the same while the displayed clock face is updated. In some embodiments, a displayed complication that is not updated in response to detecting the movement of the rotatable input mechanism can optionally be visually distinguished, such as by changing a hue, saturation, and/or lightness of the displayed complication. This allows the user to distinguish which complications are updated and which remain constant.

Advantageously, these context-specific user interface methods, which can optionally be applied to any of the context-user interfaces described herein simply by including an application complication, allow the user to view updated information from a particular application while also presenting a quick way to launch the corresponding application in the same user interface object. Moreover, the application and/or application information depicted by the complication can optionally further be customized using the editing methods described in reference to FIG. 15 (see, e.g., screen 1560 and 1570).

A user can optionally navigate screens on, e.g., a portable multifunction device, that include many affordances. These affordances can optionally represent, for example, applications that can optionally be launched on the device. One such affordance may activate a context-specific user interface, such as those described herein. In order to help the user recognize that a particular affordance corresponds to launching a context-specific user interface, an animation that visually connects the affordance to the interface can optionally be desirable.

Figure 18C:
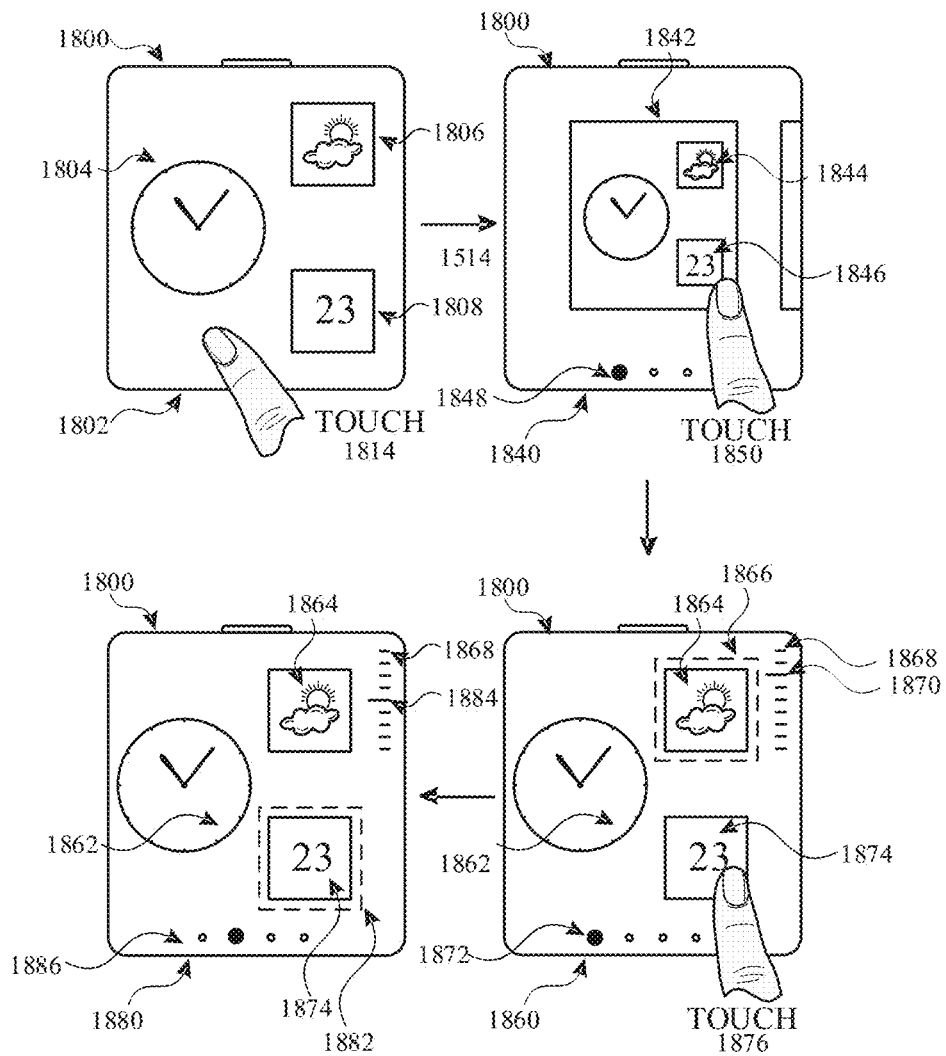

FIG. 18C shows an exemplary user interface for editing a clock face that contains more than one complication, such as the ones depicted in FIGS. 18A and 18B. FIG. 18C again depicts device 1800 displaying screen 1802, which includes clock face 1804, affordance 1806 representing a weather application, and affordance 1808 representing a calendar application.

As discussed above in reference to FIG. 15, a user can optionally customize the complications displayed on screen 1802 by entering clock face edit mode. The user contacts the touch-sensitive display of device 1800 with touch 1814. Touch 1814 has a characteristic intensity above an intensity threshold, which prompts device 1800 to enter a clock face edit mode, shown on screen 1840. Device 1800 indicates that the user has entered clock face edit mode by visually distinguishing the clock face. In this example, screen 1840 shows a smaller version of the display of screen 1802 (e.g., 1842), which includes a reduced size clock face, reduced size complication 1844, which is based on complication 1806, and reduced size complication 1846, which is based on complication 1808.

A user selects this clock face for editing by contacting displayed clock face 1842 (e.g., touch 1850). In some embodiments, touch 1850 is a contact on the touch-sensitive display. In some embodiments, touch 1850 is a contact on the touch-sensitive display with a characteristic intensity above an intensity threshold. This causes device 1800 to enter into clock face edit mode and display screen 1860. Screen 1860 displays clock face 1862 for editing. Currently, affordance 1864 representing the weather application is selected for editing, as highlighted by outline 1866. Also displayed is positional indicator 1868, which indicates the position of the displayed complication in a series of complication options using line 1870. Positional indicator 1868 further indicates to the user that a rotatable input mechanism can optionally be used to cycle through options available for editing affordance 1864 (e.g., which set of information from the weather application to display, or another application from which a set of information can optionally be displayed). Paging affordance 1872 also displays the position of the aspect of clock face 1862 currently selected for editing (i.e., complication 1864) in a series of editable aspects.

Screen 1860 also displays affordance 1874, which represents the calendar application. To select this complication for editing, the user contacts displayed affordance 1874 (e.g., touch 1876). In response, device 1800 displays screen 1880. Like screen 1860, screen 1880 displays clock face 1862, affordance 1864 (which represents the weather application), positional indicator 1868, and affordance 1874 (which represents the weather application). Affordance 1874 is now highlighted for editing, as shown by outline 1882. The position of this complication option is depicted by line 1884 in positional indicator 1868. Finally, paging affordance 1886 has been updated to display the position of affordance complication 1874 in a series of editable aspects of clock face 1862. The user can optionally now edit the set of information displayed by affordance 1874 using the rotatable input mechanism (e.g., which set of information from the calendar application to display, or another application from which a set of information can optionally be displayed). In summary, while in clock face edit mode, a user can optionally select a complication for editing when more than one complication is displayed by contacting the displayed complication. In some embodiments, this causes the affordance to be highlighted (e.g., by a visible outline or other means for visibly distinguishing the affordance described herein).

Figure 19:
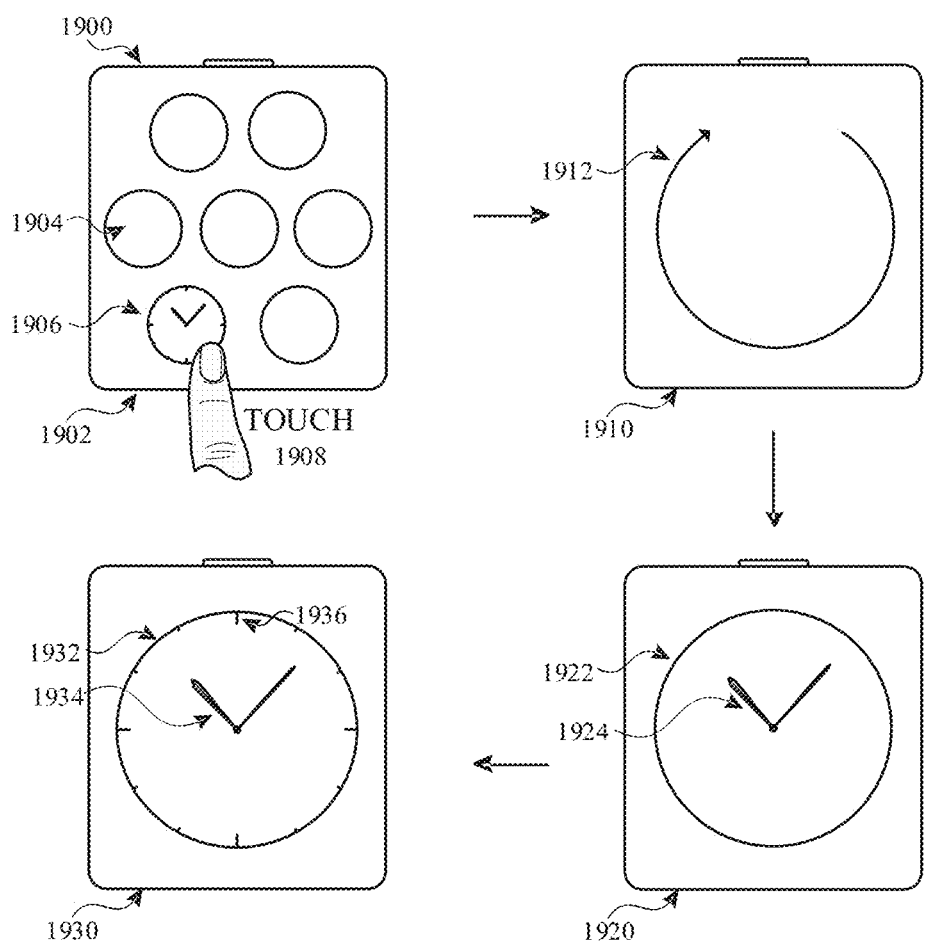
FIG. 19 illustrates exemplary context-specific user interfaces.

FIG. 19 shows exemplary context-specific user interfaces that can optionally be operated on device 1900. Device 1900 can optionally be device 100, 300, or 500 in some embodiments. In some embodiments, the electronic device has a touch-sensitive display (e.g., touchscreen 504).

Device 1900 displays user interface screen 1902, which includes a plurality of affordances (e.g., affordances 1904 and 1906). Affordance 1906 represents a clock face that includes an indication of time (e.g., the hour hand, minute hand, and tick marks) and an outline (e.g., a circle or a polygon such as a square with rounded corners). In some embodiments, the clock face can optionally indicate the current time. The user contacts the touch-sensitive display (e.g., touch 1908) at affordance 1906, and in response, device 1900 displays, sequentially, screens 1910, 1920, and 1930 in continuous on-screen animation.

Screen 1910 shows outline 1912 being animated by progressively displaying the element in a rotational motion (e.g., as if it is being filled in or drawn in a clockwise manner) Next, screen 1920 shows full outline 1922 and hour hand and minute hand 1924. Finally, screen 1930 shows full outline 1932, hour hand and minute hand 1934, and hour indication 1936. Like the outline, the hour indications can optionally also be progressively filled in sequentially (e.g., in a clockwise manner) Importantly, at least one of the elements from affordance 1906 is maintained on screen 1930 (e.g., an outline, or the hour and minute hands), but at a larger display size.

While FIG. 19 depicts an analog clock face with an hour hand and a minute hand, the techniques described in reference to FIG. 19 can optionally apply to many context-specific user interfaces. For example, if the user interface displays a representation of the Earth (as shown in FIG. 8), the affordance in the plurality of affordances can optionally depict an Earth, and the outline of the Earth can optionally be retained and/or drawn in using a clockwise motion.

A user may also wish to receive an indication from a portable multifunction device that a missed or unread notification is available. Thus, in any of the embodiments described herein, a device can optionally receive a notification, determine whether the notification has been missed (e.g., not viewed or marked as not read), and in accordance with a determination that the notification has been missed, display an affordance indicating a missed notification. In accordance with a determination that the notification has not been missed, the device can optionally forego displaying the affordance indicating a missed notification. In some embodiments, an aspect of the displayed affordance represents a number of missed notifications received by the electronic device. For example, the displayed affordance can optionally change color, change size, or be animated (e.g., to depict pulsing) to represent a number of missed notifications. In some embodiments, in response to receiving data representing user viewing of the missed notification, the device can optionally remove the displayed affordance. This provides the user a quick visual reminder that a notification can optionally be viewed.

A user may also wish to launch an application, such as a stopwatch application, from any of the context-specific user interfaces described herein. Thus, in any of the embodiments described herein, a device can optionally display a stopwatch progress affordance that indicates a currently running stopwatch application. For example, the stopwatch progress affordance can optionally depict a representation of a digital stopwatch (e.g., similar to affordance 1694 in FIG. 16C). This representation can optionally be continuously updated to indicate a stopwatch time generated by the currently running stopwatch application. A user can optionally contact the stopwatch progress affordance, and in response to detecting the contact, the device can optionally launch the stopwatch application. This provides a functional reminder that a stopwatch is currently running from any context-specific user interface.

When traveling, a user may wish to quickly access the time at home, or another designated location. Thus, in any of the embodiments described herein, a device can optionally include a location sensor (e.g., GPS sensor 532 and/or GPS module 135). While any clock face is displayed on the display, a user can optionally contact the display, and in response to detecting the contact, the device can optionally access a designated home location (e.g., a home time zone). The device can optionally obtain a current time zone (i.e., at the current location of the device), determine whether the current time zone is different from the home time zone, and in accordance with a determination that the current time zone is different from the home time zone, update the displayed clock face to indicate current time at the home time zone. In accordance with a determination that the current time zone is not different from the home time zone, the device can optionally continue to display the same clock face to indicate current time at both the home time zone and the current time zone.

In some embodiments, a user can optionally designate the home time zone. For example, the device can optionally provide a user interface for designating the home time zone.

In other embodiments, the device can optionally designate the home time zone. For example, the device could base this designation on data representing amount of time spent at a location, which times of day are spent at the location, and/or a number of contact entries associated with the location. In this way, the device can optionally automatically be able to designate a home time zone.

A user may wish to display different context-specific user interfaces, such as those described herein, depending on a particular context. For example, a user may wish to display a specific context-specific user interface or specific content (e.g., information provided by a displayed complication) while at work, then display a different context-specific user interface or different content while at home. In some embodiments, a user can optionally designate a time of day to change the displayed context-specific user interface. In some embodiments, a user can optionally designate an interval during the day wherein a particular context-specific user interface is displayed. In other embodiments, the device can optionally include a location sensor, and a user can optionally designate a context-specific user interface to be displayed at a particular location (e.g., a home or office). In some embodiments, the device can optionally employ a heuristic method to track previous user interactions, such as a time of day and/or location whereupon a user has changed context-specific user interfaces, a particular context-specific user interface that has been selected or de-selected, and the like. For example, if a user has changed context-specific user interfaces at an approximately regular time after returning home from work, the device can optionally display a prompt asking if the user would like to change context-specific user interfaces at the same time on the following day. In some embodiments, the device automatically changes the context-specific user interface based on a previous user interaction. In other embodiments, the device prompts the user to change the context-specific user interface based on a previous user interaction.

It can optionally be desirable to vary the display of any of the devices described herein. Thus, in any of the embodiments described herein, a device can optionally display a clock face that includes a plurality of pixels, detect a movement of the device (as described above), and in response to detecting the movement, move the displayed clock face on the display. Moving can optionally include modifying a subset of the pixels in the plurality (e.g., by changing color and/or intensity of one or more pixels).

A user may wish to use a virtual tachymeter (e.g., a tachymeter that is not based on a physical tachymeter dial built onto the device) on any of the devices described herein. A virtual tachymeter can optionally be provided, for example, by a tachymeter user interface object that can optionally be displayed on a dedicated tachymeter user interface screen, or on any of the user interface screens described herein (e.g., as a tachymeter complication). The user can optionally provide a user input to start the virtual tachymeter and, subsequently the user can optionally stop the virtual tachymeter by providing a second user input. For example, the tachymeter user interface object can optionally include a start affordance, a stop affordance, or a combined start/stop affordance. The user can optionally start the virtual tachymeter by contacting the start affordance or the start/stop affordance and stop the virtual tachymeter by contacting the stop affordance or the start/stop affordance. In another example, one or both user inputs can optionally be an input on a mechanical button (e.g., a rotation and/or depression of the rotatable and depressible input mechanism 506, and/or a press on button 508) to start and/or stop the virtual tachymeter. In some embodiments, one or both user inputs can optionally be an audio (e.g., verbal) input.

After the user has stopped the virtual tachymeter, the device can optionally display a time value based on the time elapsed between start and stop. This time value can optionally be based on, for example, a number of units of time in a predetermined interval (e.g., the number of seconds in an hour). In some embodiments, the displayed time value can optionally be based on the number of units of time in the predetermined interval (e.g., the number of seconds in an hour) divided by the time elapsed between start and stop. In some embodiments, the user can optionally customize the units of time used by the tachymeter, the units of time in the predetermined interval, and/or the predetermined interval. In some embodiments, while the virtual tachymeter is running, the tachymeter user interface object can optionally include an updating display to indicate the passage of time, such as a running or continuously updated countdown of the time value, a rotating shape, and the like. Advantageously, since the tachymeter is virtual, it can optionally measure any increment or interval of time because it is not constrained or fixed like a traditional tachymeter, such as a watch tachymeter. For example, a watch tachymeter is typically limited to measuring times less than or equal to 60 seconds, because the displayed time values are fixed (e.g., painted or etched onto a tachymeter dial) and only apply to values within one full rotation of the second hand.

A user may wish to use a virtual telemeter (e.g., a telemeter that is not based on a physical telemeter dial built onto the device) on any of the devices described herein. A virtual telemeter can optionally be provided, for example, by a telemeter user interface object that can optionally be displayed on a dedicated telemeter user interface screen, or on any of the user interface screens described herein (e.g., as a telemeter complication).

The user can optionally provide a user input to start the virtual telemeter and, subsequently the user can optionally stop the virtual telemeter by providing a second user input. For example, the telemeter user interface object can optionally include a start affordance, a stop affordance, or a combined start/stop affordance. The user can optionally start the virtual telemeter by contacting the start affordance or the start/stop affordance and stop the virtual telemeter by contacting the stop affordance or the start/stop affordance. In another example, one or both user inputs can optionally be an input on a mechanical button (e.g., a rotation and/or depression of the rotatable and depressible input mechanism 506, and/or a press on button 508) to start and/or stop the virtual telemeter. In some embodiments, one or both user inputs can optionally be an audio (e.g., verbal) input. After the user has stopped the virtual telemeter, the device can optionally display a distance based on the time elapsed between start and stop. This distance can optionally be based on the speed of sound. For example, the user can optionally see lightning, start the telemeter, and stop the telemeter when the user hears thunder. In this case, the distance reported by the telemeter will indicate the distance between the user and the lightning, based on the time interval between when the light reaches the user and when the sound reaches the user. In some embodiments, the user can optionally designate the units for reporting the distance (e.g., kilometers, miles, etc.). In some embodiments, while the virtual telemeter is running, the telemeter user interface object can optionally include an updating display to indicate the passage of time, such as a running or continuously updated distance, a rotating shape, and the like. Advantageously, since the telemeter is virtual, it can optionally measure any increment or interval of time because it is not constrained or fixed like a traditional telemeter, such as a watch telemeter. For example, a watch telemeter is typically limited to measuring times less than or equal to 60 seconds, because the displayed time values are fixed (e.g., painted or etched onto a telemeter dial) and only apply to values within one full rotation of the second hand.

A user may wish to use a repeated interval timer on any of the devices described herein, e.g., a timer that provides a user alert that is repeated at a certain interval. For example, if the user is exercising (e.g., interval training), they may wish to receive an alert every 30 seconds to change their mode of exercise or take a break. In another example, a user taking medication may wish to receive an alert to take their medication every hour, 4 hours, 6 hours, 12 hours, 24 hours, and so forth. Any suitable interval or duration of time can optionally be used. In some embodiments, the device can optionally display a repeated interval timer user interface. The repeated interval timer user interface can optionally include, for example, an affordance for the user to designate the interval, the timescale for the interval (e.g., seconds, minutes, hours, days, weeks, months, years, etc.), and the like. In response to receiving data representing a user-designated time interval, the device can optionally provide a user alert that is repeated at times based on the user-designated time interval. In some embodiments, the alert can optionally include a visual alert, an audio alert, and/or a haptic alert (e.g., using haptic feedback module 133 and tactile output generator 167), or any combination thereof. Rather than being based on a designated end point (e.g., a reminder for a particular day or time), the repeated interval timer is based on providing the user a demarcation of a particular interval of time. In some embodiments, the repeated interval timer runs until the user ends the timer. In some embodiments, the device can optionally further display an affordance for ending the repeated interval timer (e.g., as part of the repeated interval timer user interface, or at the time of the user alert).

In some embodiments, any of the devices described herein can optionally further generate or receive a user alert including information and display a user notification based on the alert on any of the user interface screens described herein. The user notification can optionally be, for example, a notification banner displayed across a portion of the display. The notification banner can optionally include a portion of the information of the alert. An example of a user alert can optionally include without limitation a determination that the user has crossed the boundary of a time zone. In some embodiments, the device has a location sensor (e.g., GPS sensor 532 and/or GPS module 135), and the device obtains a current location of the device from the location sensor. Using the location sensor, the device can optionally determine whether the current location of the device is in a different time zone, as compared to a previous location of the device, for example the location of the device at the time of a previous user interaction (e.g., the last time the user looked at the display, or the last time the device detected a user movement of the device, such as a wrist raise). In accordance with the determination that the current location is in a different time zone than the previous location, the device can optionally display a notification banner across a portion of the display. In some embodiments, the notification banner can optionally include an alert indicating that the user has crossed a time zone, a notification of the current time in the new time zone, and so forth. In some embodiments, the device may prompt the user whether to accept the time change (e.g., the device can optionally display an affordance for accepting the time change and/or an affordance for rejecting the time change). The user prompt can optionally be displayed as part of the notification banner, or the user prompt can optionally be displayed in response to detecting a user contact on the displayed notification banner. In response to receiving data indicating a user acceptance of the time change (e.g., a contact on the displayed affordance for accepting the time change), the device can optionally update the displayed time based on the new time zone. In response to receiving data indicating a user rejection of the time change (e.g., a contact on the displayed affordance for rejecting the time change), the device can optionally forego updating the displayed time based on the new time zone.

Figure 20:
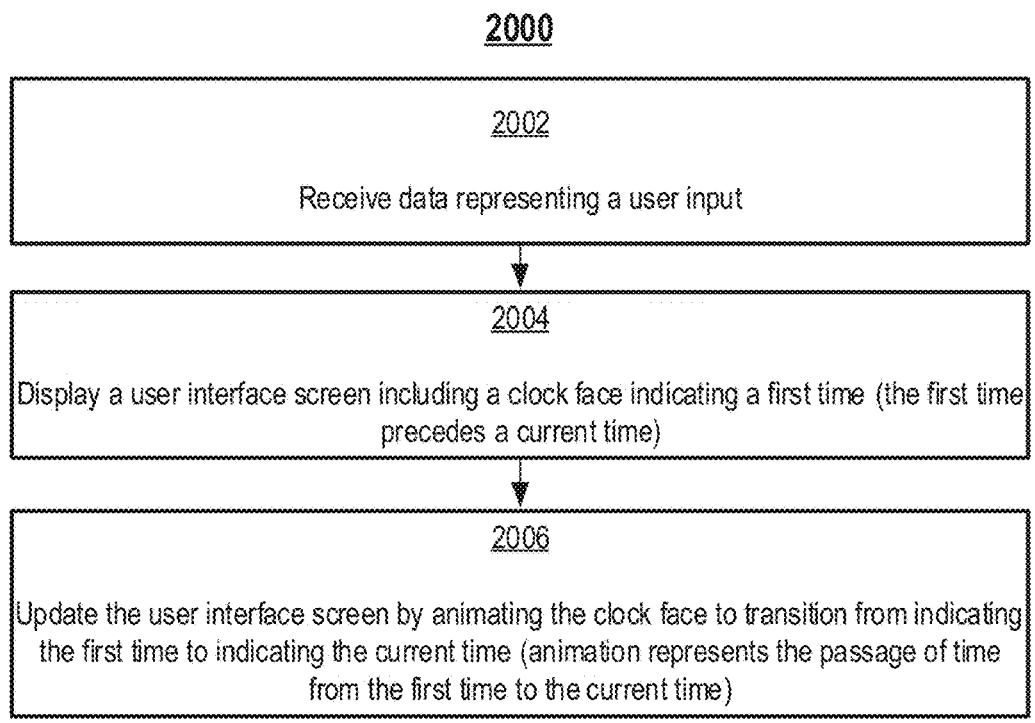
FIG. 20 is a flow diagram illustrating a process for context-specific user interfaces.

FIG. 20 is a flow diagram illustrating process 2000 for providing context-specific user interfaces. In some embodiments, process 2000 can optionally be performed at an electronic device with a touch-sensitive display, such as device 100 (FIG. 1A), 300 (FIG. 3), 500 (FIG. 5) or 600 (FIGS. 6A and 6B). Some operations in process 2000 can optionally be combined, the order of some operations can optionally be changed, and some operations can optionally be omitted. Process 2000 provides context-specific user interfaces that give the user an immediate indication of elapsed time before viewing, making these interfaces less confusing and, thus, conserving power and increasing battery life.

At block 2002, the device receives data representing a user input (e.g., 602). At block 2004, responsive at least in part to receiving the data, the device displays a user interface screen including a clock face (e.g., 606) indicating a first time (the first time precedes a current time). At block 2006, the device updates the user interface screen by animating the clock face to transition from indicating the first time to indicating the current time (animation represents the passage of time from the first time to the current time; see, e.g., 612).

Note that details of the processes described above with respect to process 2000 (FIG. 20) are also applicable in an analogous manner to the methods described below. For example, process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2000. For brevity, these details are not repeated below.

It should be understood that the particular order in which the operations in FIG. 20 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2000 can optionally be relevant to process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 21 is a flow diagram illustrating process 2100 for providing context-specific user interfaces. In some embodiments, process 2100 can optionally be performed at an electronic device with a touch-sensitive display, such as device 100 (FIG. 1A), 300 (FIG. 3), 500 (FIG. 5) or 700 (FIGS. 7A and 7B). Some operations in process 2100 can optionally be combined, the order of some operations can optionally be changed, and some operations can optionally be omitted. Process 2100 provides context-specific user interfaces that combine a stopwatch function and a timekeeping function, making these interfaces at once multifunctional and less confusing to the user, thus conserving power and increasing battery life.

At block 2102, the device displays a clock face that indicates current time and includes a user interface object with an hour hand and a minute hand, one or more indications of an hourly timescale, and a stopwatch hand (e.g., as on screen 702). At block 2104, the device receives data representing a user input (e.g., touch 712). At block 2106, responsive at least in part to receiving the data, the device substitutes the one or more indications of an hourly timescale with an indication of a first timescale for the stopwatch hand (e.g., 724). At block 2108, the device animates the stopwatch hand to reflect passage of time (e.g., cf. 726 and 736).

Note that details of the processes described above with respect to process 2100 (FIG. 21) are also applicable in an analogous manner to the methods described below. For example, process 2000 (FIG. 20), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2100. For brevity, these details are not repeated below.

It should be understood that the particular order in which the operations in FIG. 21 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2100 may be relevant to process 2000 (FIG. 20), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 22 is a flow diagram illustrating process 2200 for providing context-specific user interfaces. In some embodiments, process 2200 can optionally be performed at an electronic device with a touch-sensitive display, such as device 100 (FIG. 1A), 300 (FIG. 3), 500 (FIG. 5), 800 (FIG. 8), 900 (FIG. 9), or 1000 (FIG. 10). Some operations in process 2200 can optionally be combined, the order of some operations can optionally be changed, and some operations can optionally be omitted. Process 2200 provides context-specific user interfaces that provide timekeeping and geographical/astronomical information, making these interfaces at once multifunctional and less confusing to the user, thus conserving power and increasing battery life.

At block 2202, the device displays a user interface screen that includes a first affordance representing a simulation of a first region of the Earth as illuminated by the Sun at current time (e.g., 804) and a second affordance that indicates the current time (e.g., 806). At block 2204, the device receives data representing a user input (e.g., swipe 812). At block 2206, responsive at least in part to receiving the data, the device rotates the simulation of the Earth to display a second region of the Earth as illuminated by the Sun at the current time (e.g., 822). Optionally, at block 2206, the device displays a third affordance representing a moon (e.g., 808, 826, 846, 1016, and 1034), detects a contact on the displayed third affordance, and responsive at least in part to detecting the contact, updates the user interface screen by displaying a fourth affordance representing a simulation of the Moon as seen from the Earth at the current time (e.g., 904) and a fifth affordance that indicates the current time (e.g., 906). Optionally, at block 2206, the device displays a sixth affordance representing a solar system (e.g., 810, 828, and 848), detects a contact on the displayed sixth affordance, and responsive at least in part to detecting the contact, updates the user interface screen by displaying a seventh affordance including representations of the Sun, the Earth, and one or more non-Earth planets at their respective positions at a current time (e.g., 1004) and an eighth affordance that indicates the current time (e.g., 1012).

Note that details of the processes described above with respect to process 2200 (FIG. 22) are also applicable in an analogous manner to the methods described below. For example, process 2000 (FIG. 20), process 2100 (FIG. 21), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2200. For brevity, these details are not repeated below.

It should be understood that the particular order in which the operations in FIG. 22 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2200 may be relevant to process 2000 (FIG. 20), process 2100 (FIG. 21), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 23 is a flow diagram illustrating process 2300 for providing context-specific user interfaces. In some embodiments, process 2300 can optionally be performed at an electronic device with a touch-sensitive display, such as device 100 (FIG. 1A), 300 (FIG. 3), 500 (FIG. 5) or 1100 (FIGS. 11A-C). Some operations in process 2300 can optionally be combined, the order of some operations can optionally be changed, and some operations can optionally be omitted. Process 2300 provides context-specific user interfaces that allow the user to view current time of day with respect to daylight/nighttime conditions, making these interfaces at once multifunctional and less confusing to the user, thus conserving power and increasing battery life.

At block 2302, the device displays a user interface screen that includes a first portion indicating daytime (e.g., 1104); a second portion indicating nighttime (e.g., 1106); a user interface object representing a sinusoidal wave with a period representing a day (e.g., 1108); a first affordance representing the Sun displayed at a first position on the sinusoidal wave indicating a current time of the day and whether the current time of the day is during daytime or nighttime (e.g., 1110); and a second affordance, the second affordance indicating the current time of day (e.g., 1114). Optionally, at block 2304, the device receives a contact on the touch-sensitive display at the first affordance at the first position indicating the current time (e.g., 1148). Optionally, at block 2306, while continuing to receive the user contact, the device detects movement of the user contact from the first position to a second position on the displayed sinusoidal wave without a break in contact of the user contact on the touch-sensitive display (second position on the sinusoidal wave indicates a non-current time; see, e.g., touch 1166). Optionally, at block 2308, responsive at least in part to detecting the contact at the second position, the device translates the first affordance on-screen from the first position on the sinusoidal wave to the second position on the sinusoidal wave (translation tracks the displayed sinusoidal wave; see, e.g., 1162). Optionally, at block 2310, the device updates the second affordance to indicate the non-current time (e.g., 1168).

Note that details of the processes described above with respect to process 2300 (FIG. 23) are also applicable in an analogous manner to the methods described below. For example, process 2000 (FIG. 20), process 2100 (FIG. 21), process 2200 (FIG. 22), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2300. For brevity, these details are not repeated below.

It should be understood that the particular order in which the operations in FIG. 23 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2300 may be relevant to process 2000 (FIG. 20), process 2100 (FIG. 21), process 2200 (FIG. 22), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 24 is a flow diagram illustrating process 2400 for providing context-specific user interfaces. In some embodiments, process 2400 can optionally be performed at an electronic device with a touch-sensitive display, such as device 100 (FIG. 1A), 300 (FIG. 3), 500 (FIG. 5) or 1200 (FIG. 12). Some operations in process 2400 can optionally be combined, the order of some operations can optionally be changed, and some operations can optionally be omitted. Process 2400 provides context-specific user interfaces that provide an easily distinguishable background image and indications of date and/or time created out of the background, making these interfaces easier for the user to view, thus conserving power and increasing battery life.

At block 2402, the device displays a user interface screen that includes a background, based on an image (e.g., 1204 and 1212), with a plurality of pixels (a subset of the pixels are modified in appearance relative to the image such that the subset of pixels represents one or more of a first user interface object indicating a date and a second user interface object indicating a time of day; see, e.g., 1206 and/or 1208). Optionally, at block 2402, one of the first user interface object and the second user interface object is a color independent of the background. Optionally, at block 2404, if one of the first user interface object and the second user interface object is a color independent of the background, the device receives data representing a background color of the background at a position of the displayed first user interface object or the displayed second user interface object (first color is different from background color at the position of the displayed first user interface object or the displayed second user interface object).

Note that details of the processes described above with respect to process 2400 (FIG. 24) are also applicable in an analogous manner to the methods described below. For example, process 2000 (FIG. 20), process 2100 (FIG. 21), process 2200 (FIG. 22), process 2300 (FIG. 23), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2400. For brevity, these details are not repeated below.

It should be understood that the particular order in which the operations in FIG. 24 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2400 may be relevant to process 2000 (FIG. 20), process 2100 (FIG. 21), process 2200 (FIG. 22), process 2300 (FIG. 23), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

Figure 25:
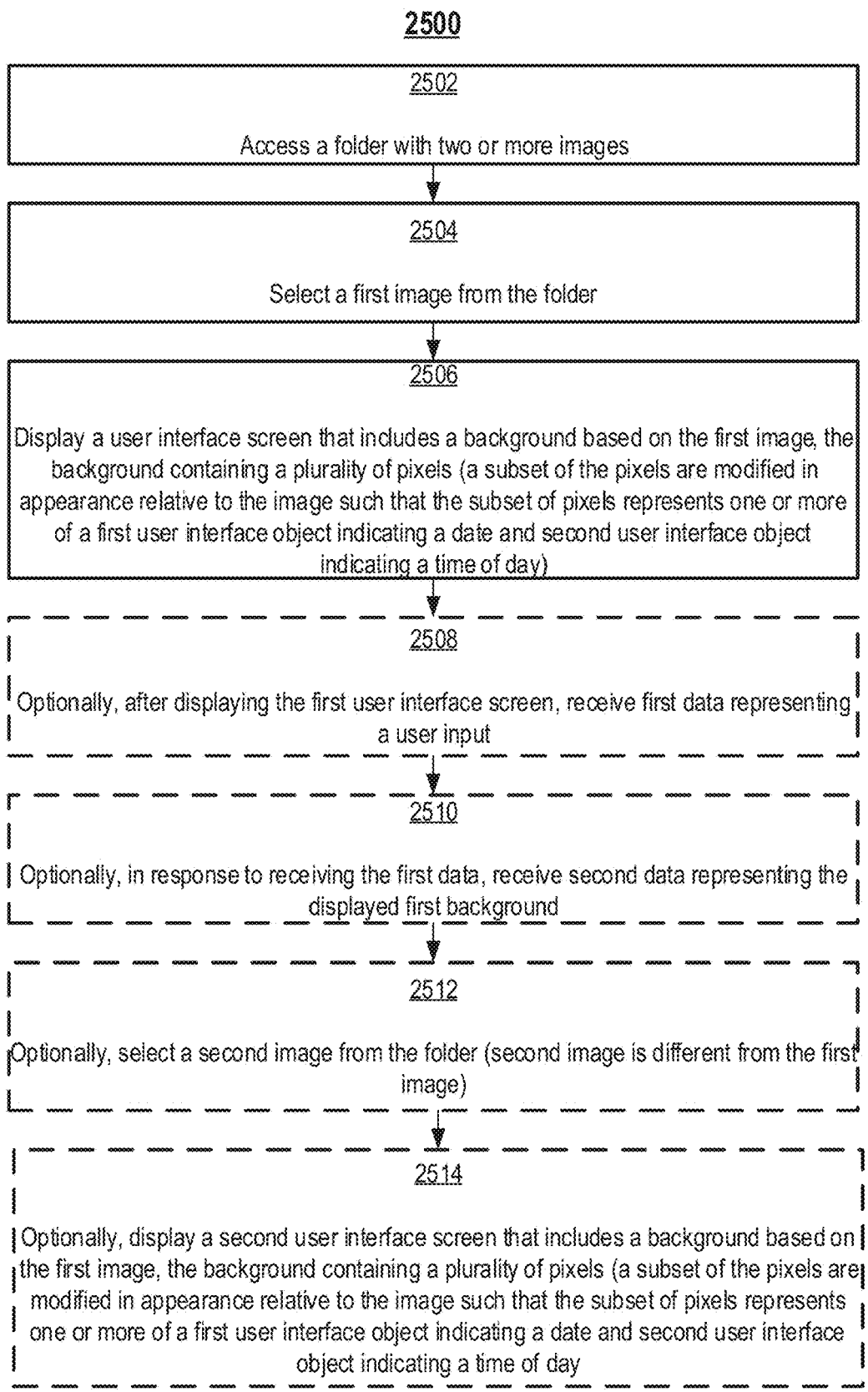
FIG. 25 is a flow diagram illustrating a process for context-specific user interfaces.

FIG. 25 is a flow diagram illustrating process 2500 for providing context-specific user interfaces. In some embodiments, process 2500 can optionally be performed at an electronic device with a touch-sensitive display, such as device 100 (FIG. 1A), 300 (FIG. 3), 500 (FIG. 5) or 1200 (FIG. 12). Some operations in process 2500 can optionally be combined, the order of some operations can optionally be changed, and some operations can optionally be omitted. Process 2500 provides context-specific user interfaces that provide an easily distinguishable background image and indications of date and/or time created out of the background, making these interfaces easier for the user to view, thus conserving power and increasing battery life.

At block 2502, the device accesses a folder with two or more images. At block 2504, the device selects a first image from the folder. At block 2506, the device displays a user interface screen (e.g., 1202) that includes a background based on the first image, the background containing a plurality of pixels (a subset of the pixels are modified in appearance relative to the image such that the subset of pixels represents one or more of a first user interface object indicating a date and second user interface object indicating a time of day; see, e.g., 1204). Optionally, at block 2508, after displaying the first user interface screen, the device receives first data representing a user input. Optionally, at block 2510, responsive at least in part to receiving the first data, the device receives second data representing the displayed first background. Optionally, at block 2512, the device selects a second image from the folder (second image is different from the first image; see, e.g., 1212). Optionally, at block 2514, the device displays a second user interface screen (e.g., 1210) that includes a background based on the first image, the background containing a plurality of pixels (a subset of the pixels are modified in appearance relative to the image such that the subset of pixels represents one or more of a first user interface object indicating a date and second user interface object indicating a time of day.

Note that details of the processes described above with respect to process 2500 (FIG. 25) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2500. For brevity, these details are not repeated below.

It should be understood that the particular order in which the operations in FIG. 25 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2500 may be relevant to process 2000 (FIG. 20), process 2100 (FIG. 21), process 2200 (FIG. 22), process 2300 (FIG. 23), process 2400 (FIG. 24), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

Figure 26:
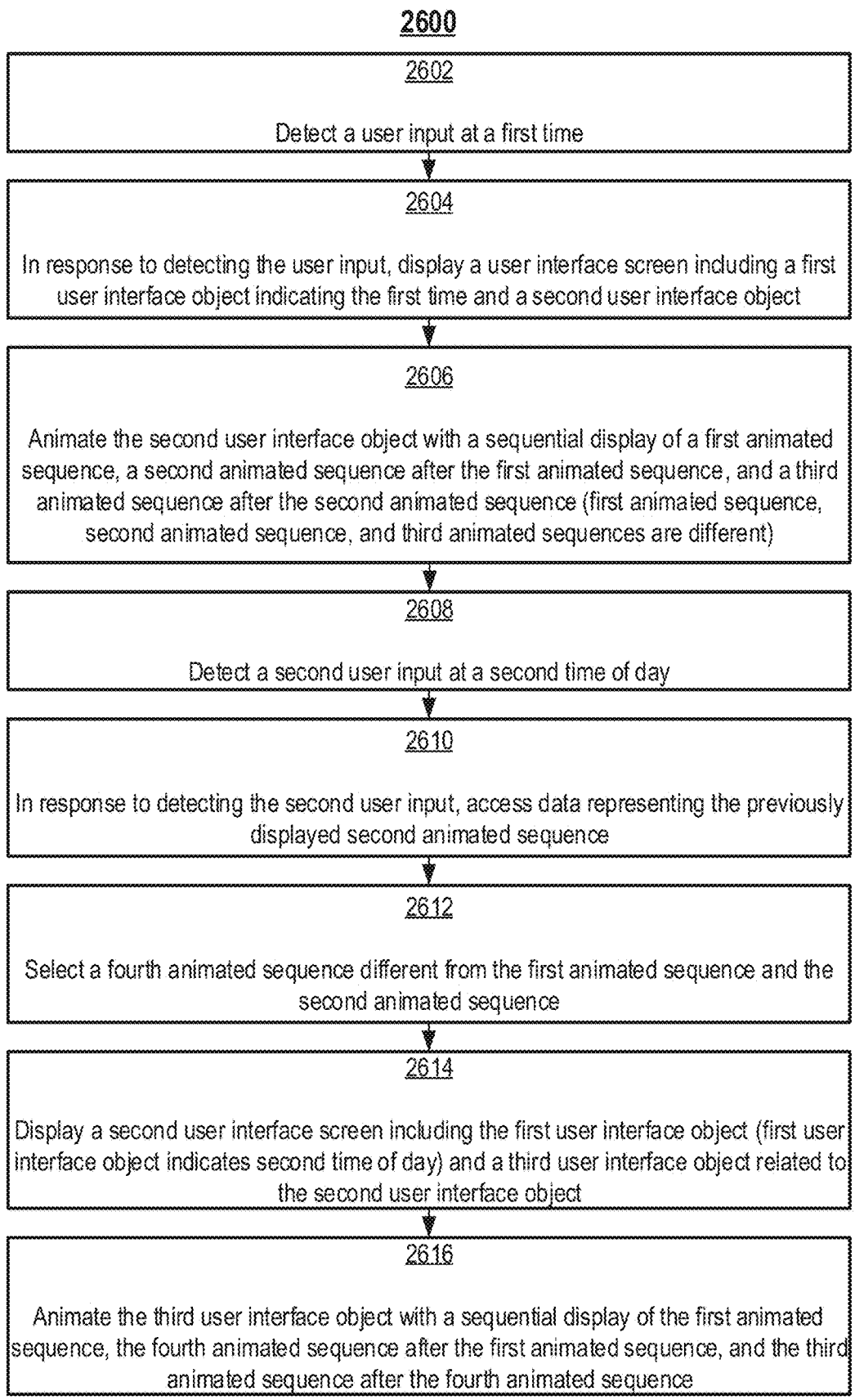
FIG. 26 is a flow diagram illustrating a process for context-specific user interfaces.

FIG. 26 is a flow diagram illustrating process 2600 for providing context-specific user interfaces. In some embodiments, process 2600 can optionally be performed at an electronic device with a touch-sensitive display, such as device 100 (FIG. 1A), 300 (FIG. 3), 500 (FIG. 5) or 1300 (FIGS. 13A and 13B). Some operations in process 2600 can optionally be combined, the order of some operations can optionally be changed, and some operations can optionally be omitted. Process 2600 provides context-specific user interfaces that provide timekeeping and a variable animated sequence, making these interfaces more interactive and engaging to the user, thus improving the interface while conserving power and increasing battery life.

At block 2602, the device detects a user input at a first time (e.g., 1304). At block 2604, responsive at least in part to detecting the user input, the device displays a user interface screen including a first user interface object indicating the first time (e.g., 1306) and a second user interface object (e.g., 1308). At block 2606, the device animates the second user interface object with a sequential display of a first animated sequence, a second animated sequence after the first animated sequence, and a third animated sequence after the second animated sequence (first animated sequence, second animated sequence, and third animated sequences are different; see, e.g., screens 1302, 1310, and 1320). At block 2608, the device detects a second user input at a second time of day (e.g., 1332). At block 2610, responsive at least in part to detecting the second user input, the device accesses data representing the previously displayed second animated sequence. At block 2612, the device selects a fourth animated sequence different from the first animated sequence and the second animated sequence. At block 2614, the device displays a second user interface screen including the first user interface object (first user interface object indicates second time of day; see, e.g., 1334) and a third user interface object related to the second user interface object (e.g., 1336). At block 2616, the device animates the third user interface object with a sequential display of the first animated sequence, the fourth animated sequence after the first animated sequence, and the third animated sequence after the fourth animated sequence (see, e.g., screens 1330, 1340, and 1350).

Note that details of the processes described above with respect to process 2600 (FIG. 26) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2600. For brevity, these details are not repeated below.

It should be understood that the particular order in which the operations in FIG. 26 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and 3300 (FIG. 33) can optionally be incorporated with one another. Thus, the techniques described with respect to process 2600 may be relevant to process 2000 (FIG. 20), process 2100 (FIG. 21), process 2200 (FIG. 22), process 2300 (FIG. 23), process 2400 (FIG. 24), process 2500 (FIG. 25), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27A is a flow diagram illustrating process 2700 for providing context-specific user interfaces. In some embodiments, process 2700 can optionally be performed at an electronic device with a touch-sensitive display, such as device 100 (FIG. 1A), 300 (FIG. 3), 500 (FIG. 5) or 1400 (FIG. 14A). Some operations in process 2700 can optionally be combined, the order of some operations can optionally be changed, and some operations can optionally be omitted.

Process 2700 provides context-specific user interfaces that are less confusing to the user, thus conserving power and increasing battery life.

At block 2702, the device detects a user movement of the device (e.g., 1404). At block 2704, responsive at least in part to detecting the movement, the device displays an animated reveal of a clock face by displaying an hour hand and a minute hand (e.g., 1424), displaying a first hour indication (e.g., 1436), and displaying a second hour indication after the first (second hour indication is after the first hour indication on clock face in clockwise direction; see, e.g., 1438).

Note that details of the processes described above with respect to process 2700 (FIG. 27A) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2700. For brevity, these details are not repeated below.

It should be understood that the particular order in which the operations in FIG. 27A have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2700 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27B is a flow diagram illustrating process 2710 for indicating time using a character-based user interface. In some embodiments, process 2710 can optionally be performed at an electronic device with a display and a touch-sensitive surface, such as device 100 (FIG. 1), 300 (FIG. 3), 500 (FIG. 5), and/or 14000 (FIGS. 14B-T). Some operations in process 2710 can optionally be combined, the order of some operations can optionally be changed, and some operations can optionally be omitted. Process 2710 provides character-based user interfaces that are less confusing, more interactive, and more engaging to the user, thus improving the interface while conserving power and increasing battery life.

At block 2712, a character user interface object that indicates a first time is displayed. The character user interface object includes representations of a first limb and a second limb and indicates a first time by indicating a first hour with the first limb and a first minute with the second limb. At block 2714, the character user interface object is updated to indicate a second time by indicating a second hour with the first limb and a second minute with the second limb. Optionally, at block 2714, updating the character user interface object to indicate a second time includes an extension of the first limb and a retraction of the second limb.

Note that details of the processes described above with respect to process 2710 (FIG. 27B) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2710. For brevity, these details are not repeated below.

It should be understood that the particular order in which the operations in FIG. 27B have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2710 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27C is a flow diagram illustrating process 2720 for indicating time using a character-based user interface. In some embodiments, process 2720 can optionally be performed at an electronic device with a display and a touch-sensitive surface, such as device 100 (FIG. 1), 300 (FIG. 3), 500 (FIG. 5), and/or 14000 (FIGS. 14B-T). Some operations in process 2720 can optionally be combined, the order of some operations can optionally be changed, and some operations can optionally be omitted. Process 2720 provides character-based user interfaces that are less confusing, more interactive, and more engaging to the user, thus improving the interface while conserving power and increasing battery life.

At block 2722, a character user interface object that indicates a first time value is displayed. The character user interface object includes a representation of a first limb with a first endpoint and a second endpoint. The first endpoint is an axis of rotation for the limb, and the second endpoint indicates a first time value. At block 2724, the character user interface object is updated to indicate a second time value. Updating the character user interface object includes moving the first endpoint and moving the second endpoint to indicate the second time value.

Note that details of the processes described above with respect to process 2720 (FIG. 27C) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2720. For brevity, these details are not repeated below.

It should be understood that the particular order in which the operations in FIG. 27C have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2720 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27D is a flow diagram illustrating process 2730 for indicating time using a character-based user interface. In some embodiments, process 2730 can optionally be performed at an electronic device with a display and a touch-sensitive surface, such as device 100 (FIG. 1), 300 (FIG. 3), 500 (FIG. 5), and/or 14000 (FIGS. 14B-T). Some operations in process 2730 can optionally be combined, the order of some operations can optionally be changed, and some operations can optionally be omitted. Process 2730 provides character-based user interfaces that are less confusing, more interactive, and more engaging to the user, thus improving the interface while conserving power and increasing battery life.

At block 2732, a character user interface object that indicates a first time value is displayed. The character user interface object includes a representation of a first limb with a first segment and a second segment. The first segment of the limb connects a first endpoint to a joint. The second segment connects a second endpoint to the joint. The joint is an axis of rotation for the second segment. The position of the second endpoint indicates a first time value. At block 2734, the character user interface object is updated to indicate a second time value. Updating the character user interface object includes moving the second endpoint along the axis of rotation to indicate the second time value.

Note that details of the processes described above with respect to process 2730 (FIG. 27D) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2730. For brevity, these details are not repeated below.

It should be understood that the particular order in which the operations in FIG. 27D have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2730 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27E is a flow diagram illustrating process 2740 for indicating time using a character-based user interface. In some embodiments, process 2740 can optionally be performed at an electronic device with a display and a touch-sensitive surface, such as device 100 (FIG. 1), 300 (FIG. 3), 500 (FIG. 5), and/or 14000 (FIGS. 14B-T). Some operations in process 2740 can optionally be combined, the order of some operations can optionally be changed, and some operations can optionally be omitted. Process 2740 provides character-based user interfaces that are less confusing, more interactive, and more engaging to the user, thus improving the interface while conserving power and increasing battery life.

At block 2742, a character user interface object that indicates time is displayed. At block 2744, first data indicative of an event is received. At block 2746, a determination is made as to whether the event meets a condition. At block 2748, in accordance with the determination that the event meets the condition, the character user interface object is updated by changing a visual aspect of the character user interface object.

Note that details of the processes described above with respect to process 2740 (FIG. 27E) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2740. For brevity, these details are not repeated below.

It should be understood that the particular order in which the operations in FIG. 27E have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2750 (FIG. 27F), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2740 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2750 (FIG. 27F), process 2800 (FIG. 28), process 2900 (FIG. 29), process 3000 (FIG. 30), process 3100 (FIG. 31), process 3200 (FIG. 32), and/or process 3300 (FIG. 33).

FIG. 27F is a flow diagram illustrating process 2750 for indicating time using a character-based user interface. In some embodiments, process 2750 can optionally be performed at an electronic device with a display and a touch-sensitive surface, such as device 100 (FIG. 1), 300 (FIG. 3), 500 (FIG. 5), and/or 14000 (FIGS. 14B-T). Some operations in process 2750 can optionally be combined, the order of some operations can optionally be changed, and some operations can optionally be omitted. Process 2750 provides character-based user interfaces that are less confusing, more interactive, and more engaging to the user, thus improving the interface while conserving power and increasing battery life.

At block 2752, the display is set to an inactive state. At block 2754, first data indicative of an event is received. At block 2756, in response to receiving the first data, the display is set to an active state. At block 2758, a character user interface object is displayed on a side of the display. At block 2760, the character user interface object is animated towards a center of the display. At block 2762, the character user interface object is displayed at the center of the display in a position that indicates a current time.

Note that details of the processes described above with respect to process 2750 (FIG. 27F) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2800 (FIG. 28), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2750. For brevity, these details are not repeated below.

It should be understood that the particular order in which the operations in FIG. 27F have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2800 (FIG. 28), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2750 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2800 (FIG. 28), process 2900 (FIG. 29), process 3000 (FIG. 30), process 3100 (FIG. 31), process 3200 (FIG. 32), and/or process 3300 (FIG. 33).

Figure 28:
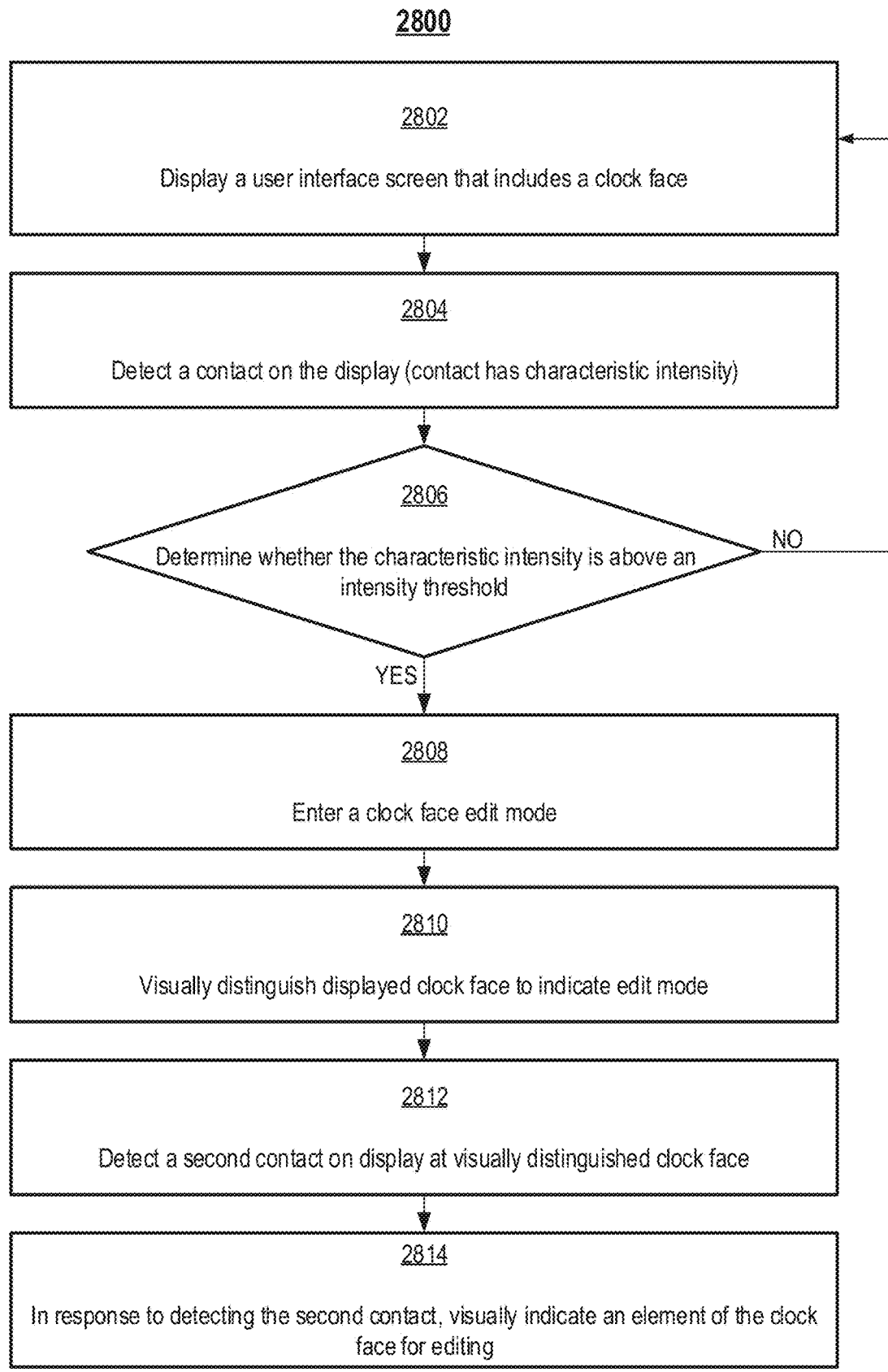
FIG. 28 is a flow diagram illustrating a process for context-specific user interfaces.

FIG. 28 is a flow diagram illustrating process 2800 for providing context-specific user interfaces. In some embodiments, process 2800 can optionally be performed at an electronic device with a touch-sensitive display configured to detect intensity of contacts, such as 500 (FIG. 5) or 1500 (FIG. 15). Some operations in process 2800 can optionally be combined, the order of some operations can optionally be changed, and some operations can optionally be omitted. Process 2800 provides for editing multiple aspects of various context-specific user interfaces in a comprehensive yet easy-to-use manner, thus conserving power and increasing battery life.

At block 2802, the device displays a user interface screen that includes a clock face (e.g., 1504). At block 2804, the device detects a contact on the display (contact has characteristic intensity; see, e.g., touch 1508). At block 2806, a determination is made as to whether the characteristic intensity is above an intensity threshold. At block 2808, in accordance with a determination that the characteristic intensity is above the intensity threshold, the device enters a clock face edit mode (see, e.g., screen 1510). In accordance with a determination that the characteristic intensity is not above the intensity threshold (where the clock face includes an affordance representing an application, and where the contact is on the affordance representing the application), the device can optionally launch the application represented by the affordance. At block 2810, the device visually distinguishes the displayed clock face to indicate edit mode (e.g., 1512). At block 2812, the device detects a second contact on the display at the visually distinguished clock face (e.g., 1520). At block 2814, responsive at least in part to detecting the second contact, the device visually indicates an element of the clock face for editing (e.g., 1534).

Note that details of the processes described above with respect to process 2800 (FIG. 28) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2900 (FIG. 29), process 3000 (FIG. 30), process 3100 (FIG. 31), process 3200 (FIG. 32), and/or process 3300 (FIG. 33) can optionally include one or more of the characteristics of the various methods described above with reference to process 2800. For brevity, these details are not repeated below.

It should be understood that the particular order in which the operations in FIG. 28 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2900 (FIG. 29), process 3000 (FIG. 30), process 3100 (FIG. 31), process 3200 (FIG. 32), and process 3300 (FIG. 33) can optionally be incorporated with one another. Thus, the techniques described with respect to process 2800 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2900 (FIG. 29), process 3000 (FIG. 30), process 3100 (FIG. 31), process 3200 (FIG. 32), and/or process 3300 (FIG. 33).

Figure 29:
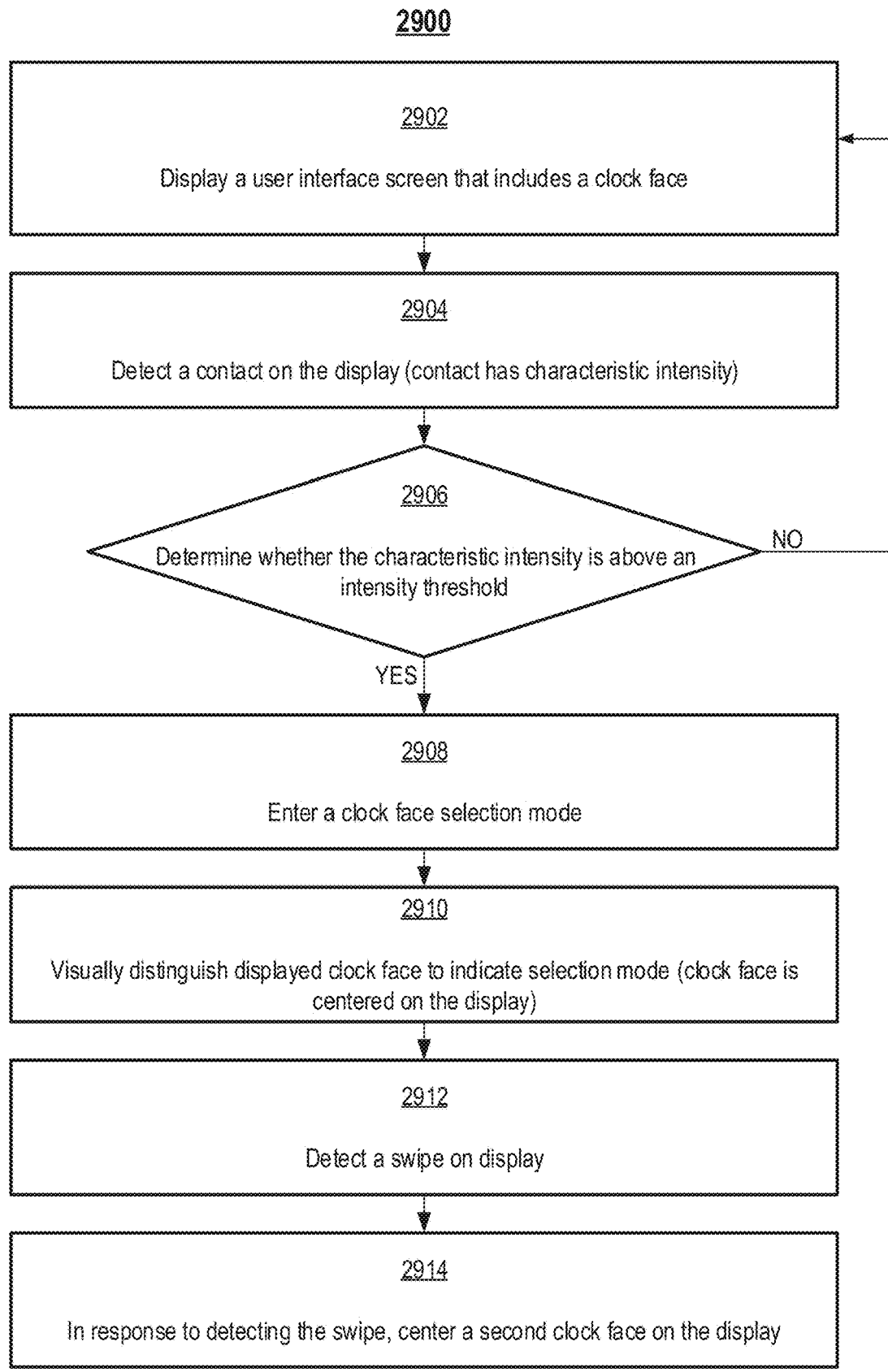
FIG. 29 is a flow diagram illustrating a process for context-specific user interfaces.

FIG. 29 is a flow diagram illustrating process 2900 for providing context-specific user interfaces. In some embodiments, process 2900 can optionally be performed at an electronic device with a touch-sensitive display configured to detect intensity of contacts, such as 500 (FIG. 5) or 1600 (FIGS. 16A-C). Some operations in process 2900 can optionally be combined, the order of some operations can optionally be changed, and some operations can optionally be omitted. Process 2900 provides for selecting context-specific user interfaces in a comprehensive yet easy-to-use manner, thus conserving power and increasing battery life.

At block 2902, the device displays a user interface screen that includes a clock face (e.g., 1604). At block 2904, the device detects a contact on the display (contact has characteristic intensity (e.g., 1606). At block 2906, a determination is made as to whether the characteristic intensity is above an intensity threshold. At block 2908, in accordance with a determination that the characteristic intensity is above the intensity threshold, the device enters a clock face selection mode (see, e.g., screen 1610). In accordance with a determination that the characteristic intensity is not above the intensity threshold (where the clock face includes an affordance representing an application, and where the contact is on the affordance representing the application), the device can optionally launch the application represented by the affordance. At block 2910, the device visually distinguishes the displayed clock face to indicate selection mode (the clock face is centered on the display; see, e.g., 1612). At block 2912, the device detects a swipe on the display at the visually distinguished clock face (e.g., 1618). At block 2914, responsive at least in part to detecting the swipe, the device centers a second clock face on the display (e.g., 1616 on screen 1620).

Note that details of the processes described above with respect to process 2900 (FIG. 29) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 3000 (FIG. 30), process 3100 (FIG. 31), process 3200 (FIG. 32), and/or process 3300 (FIG. 33) can optionally include one or more of the characteristics of the various methods described above with reference to process 2900. For brevity, these details are not repeated below.

It should be understood that the particular order in which the operations in FIG. 29 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 3000 (FIG. 30), process 3100 (FIG. 31), process 3200 (FIG. 32), and process 3300 (FIG. 33) can optionally be incorporated with one another. Thus, the techniques described with respect to process 2900 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 3000 (FIG. 30), process 3100 (FIG. 31), process 3200 (FIG. 32), and/or process 3300 (FIG. 33).

Figure 30:
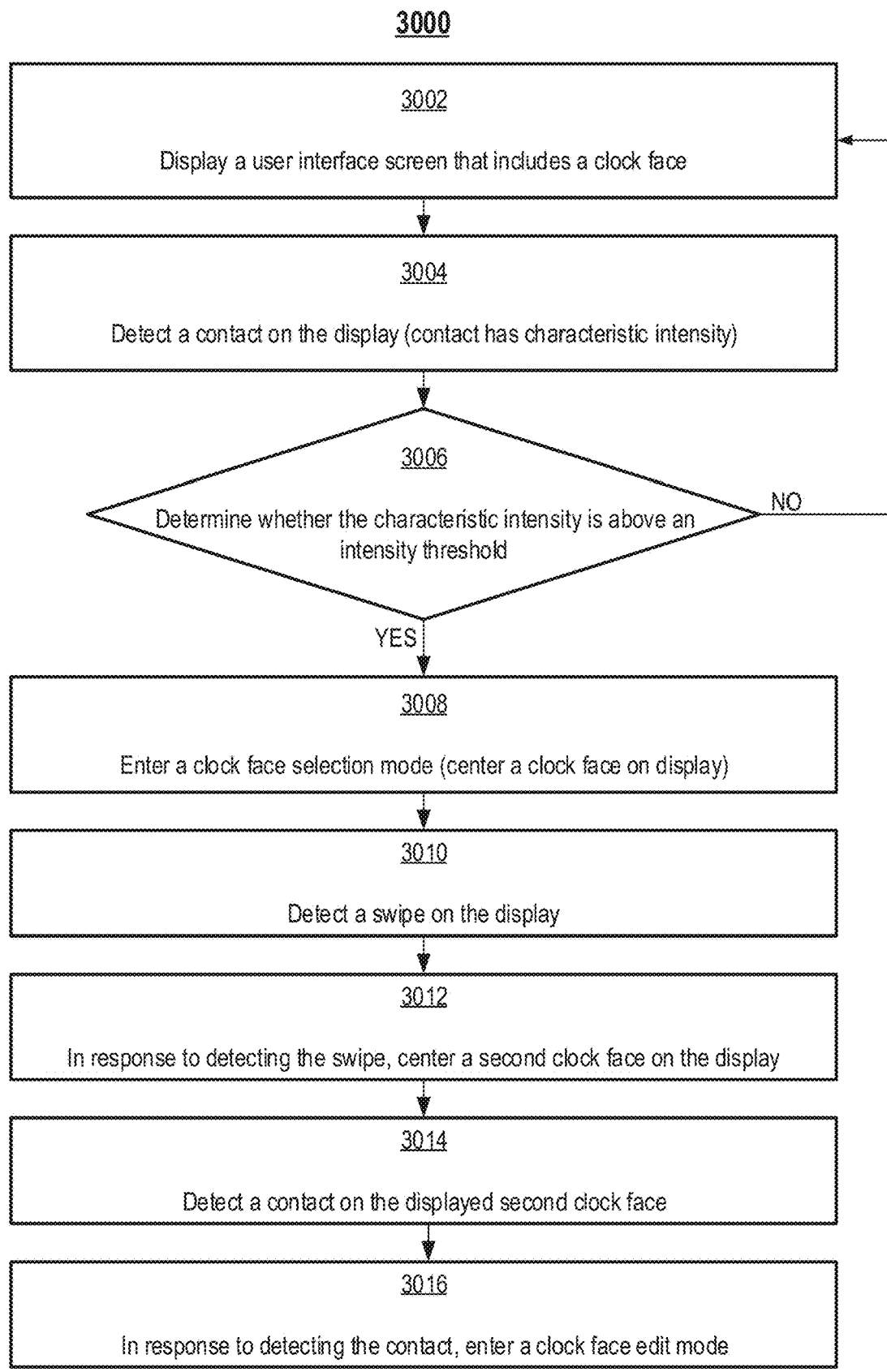
FIG. 30 is a flow diagram illustrating a process for context-specific user interfaces.

FIG. 30 is a flow diagram illustrating process 3000 for providing context-specific user interfaces. In some embodiments, process 3000 can optionally be performed at an electronic device with a touch-sensitive display configured to detect intensity of contacts, such as 500 (FIG. 5), 1500 (FIG. 15), or 1600 (FIGS. 16A-C). Some operations in process 3000 can optionally be combined, the order of some operations can optionally be changed, and some operations can optionally be omitted. For example, FIG. 30 illustrates an exemplary embodiment for accessing clock face selection and edit modes from a single interface, but other orders of operation are possible. Process 3000 provides for selecting and editing context-specific user interfaces in a comprehensive yet easy-to-use manner, thus conserving power and increasing battery life.

At block 3002, the device displays a user interface screen that includes a clock face (e.g., 1502 and/or 1602). At block 3004, the device detects a contact on the display (contact has characteristic intensity; see, e.g., 1508 and/or 1606). At block 3006, a determination is made as to whether the characteristic intensity is above an intensity threshold. At block 3008, in accordance with a determination that the characteristic intensity is above the intensity threshold, the device enters a clock face selection mode and visually distinguishes the displayed clock face to indicate selection mode (the clock face is centered on the display; see, e.g., 1512 and/or 1612). In accordance with a determination that the characteristic intensity is not above the intensity threshold (where the clock face includes an affordance representing an application, and where the contact is on the affordance representing the application), the device can optionally launch the application represented by the affordance. At block 3010, the device detects a swipe on the display at the visually distinguished clock face (e.g., 1618). At block 3012, responsive at least in part to detecting the swipe, the device centers a second clock face on the display (e.g., 1616 on screen 1620). At block 3014, the device detects a contact on the touch-sensitive display at the displayed second clock face (e.g., 1520). At block 3016, responsive at least in part to detecting the contact, the device enters a clock face edit mode for editing the second clock face (see, e.g., screen 1530).

Note that details of the processes described above with respect to process 3000 (FIG. 30) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3100 (FIG. 31), process 3200 (FIG. 32), and/or process 3300 (FIG. 33) can optionally include one or more of the characteristics of the various methods described above with reference to process 3000. For brevity, these details are not repeated below.

It should be understood that the particular order in which the operations in FIG. 30 have been described is exemplary and not intended to indicate that the described order is the only order in which the operations could be performed. One of ordinary skill in the art would recognize various ways to reorder the operations described herein, as well as excluding certain operations. For example, the device could detect a contact on the displayed first clock face before detecting the swipe. In this case, the device can optionally enter clock face edit mode to edit the first clock face. For brevity, all of these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3100 (FIG. 31), process 3200 (FIG. 32), and process 3300 (FIG. 33) can optionally be incorporated with one another. Thus, the techniques described with respect to process 2900 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3100 (FIG. 31), process 3200 (FIG. 32), and/or process 3300 (FIG. 33).

FIG. 31 is a flow diagram illustrating process 3100 for providing context-specific user interfaces. In some embodiments, process 3100 can optionally be performed at an electronic device with a touch-sensitive display and a rotatable input mechanism, such as 500 (FIG. 5) or 1600 (FIGS. 17A and 17B). Some operations in process 3100 can optionally be combined, the order of some operations can optionally be changed, and some operations can optionally be omitted. Process 3100 provides for setting a user reminder in various context-specific user interfaces in a less confusing and easy-to-access manner, thus conserving power and increasing battery life.

At block 3102, the device displays a user interface screen that includes a clock face (e.g., screen 1702) and an affordance on the clock face (affordance indicates first time of day; see, e.g., 1706). At block 3104, the device detects a contact on the display. At block 3106, responsive at least in part to detecting the contact, the device enters a user interaction mode. At block 3108, while in user interaction mode, the device detects a movement of the rotatable input mechanism (e.g., 1708). At block 3110, responsive at least in part to detecting the movement, the device updates the affordance to indicate a second time of day (e.g., 1714). At block 3112, the device detects a second contact at the affordance (e.g., 1716). At block 3114, responsive at least in part to detecting the contact, the device sets a user reminder for the second time of day (e.g., 1748).

Note that details of the processes described above with respect to process 3100 (FIG. 31) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3200 (FIG. 32), and/or process 3300 (FIG. 33) can optionally include one or more of the characteristics of the various methods described above with reference to process 3100. For brevity, these details are not repeated below.

It should be understood that the particular order in which the operations in FIG. 31 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3200 (FIG. 32), and process 3300 (FIG. 33) can optionally be incorporated with one another. Thus, the techniques described with respect to process 3100 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3200 (FIG. 32), and/or process 3300 (FIG. 33).

FIG. 32 is a flow diagram illustrating process 3200 for providing context-specific user interfaces. In some embodiments, process 3200 can optionally be performed at an electronic device with a touch-sensitive display, such as device 100 (FIG. 1A), 300 (FIG. 3), 500 (FIG. 5) or 1800 (FIGS. 18A-18C). Some operations in process 3200 can optionally be combined, the order of some operations can optionally be changed, and some operations can optionally be omitted. Process 3200 provides for launching an application directly from an application complication (which also provides application information) through various context-specific user interfaces, thus conserving power and increasing battery life by easily linking various user applications and a timekeeping clock face.

At block 3202, the device displays a user interface screen that includes a clock face (e.g., 1804) and an affordance (affordance represents an application and displays a set of information from the application) as a complication (e.g., 1806 and/or 1808). At block 3204, the device detects a contact on the affordance (e.g., 1810 and/or 1812). At block 3206, responsive at least in part to detecting the contact, the device launches the application represented by the affordance (see, e.g., screen 1820 and/or 1830).

Note that details of the processes described above with respect to process 3200 (FIG. 32) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and/or process 3300 (FIG. 33) can optionally include one or more of the characteristics of the various methods described above with reference to process 3100. For brevity, these details are not repeated below.

It should be understood that the particular order in which the operations in FIG. 32 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and process 3300 (FIG. 33) can optionally be incorporated with one another. Thus, the techniques described with respect to process 3200 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and/or process 3300 (FIG. 33).

FIG. 33 is a flow diagram illustrating process 3300 for providing context-specific user interfaces. In some embodiments, process 3300 can optionally be performed at an electronic device with a touch-sensitive display, such as device 100 (FIG. 1A), 300 (FIG. 3), 500 (FIG. 5) or 1900 (FIG. 19). Some operations in process 3300 can optionally be combined, the order of some operations can optionally be changed, and some operations can optionally be omitted. Process 3300 provides a simple means by which to access various context-specific user interfaces, thus conserving power and increasing battery life.

At block 3302, the device displays a user interface screen that includes a plurality of affordances (a first affordance in the plurality indicates a clock face, which includes an indication of time and an outline; see, e.g., screen 1902 and affordance 1906). At block 3304, the device detects a contact on first affordance (e.g., 1908). At block 3306, responsive at least in part to detecting the contact, the device substitutes the display of user interface screen with a second user interface screen (substitution includes retaining the indication of time or the outline at a larger size; see, e.g., screen 1930 with outline 1932 and/or hour hand and minute hand 1934).

Note that details of the processes described above with respect to process 3300 (FIG. 33) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and/or process 3200 (FIG. 32) can optionally include one or more of the characteristics of the various methods described above with reference to process 3300. For brevity, these details are not repeated below.

It should be understood that the particular order in which the operations in FIG. 33 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and process 3200 (FIG. 32) can optionally be incorporated with one another. Thus, the techniques described with respect to process 3300 may be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), and/or process 3200 (FIG. 32).

The operations in the information processing methods described above can optionally be implemented by running one or more functional modules in information processing apparatus such as general purpose processors or application specific chips. These modules, combinations of these modules, and/or their combination with general hardware (e.g., as described above with respect to FIGS. 1A, 1B, 3, 5A, and 5B) are all included within the scope of the techniques described herein.

Figure 34:
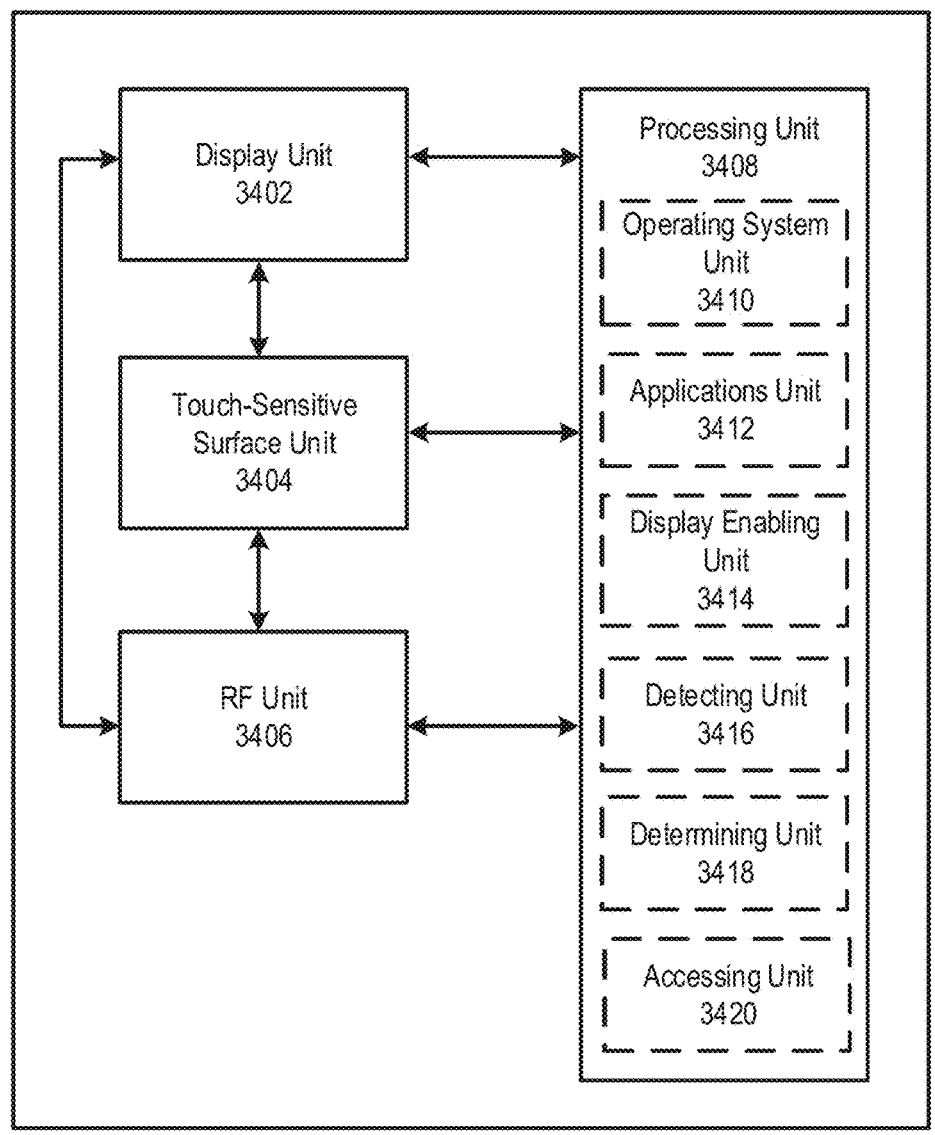
FIG. 34 is a functional block diagram of an electronic device in accordance with some embodiments.

FIG. 34 shows exemplary functional blocks of an electronic device 3400 that, in some embodiments, performs the features described above. As shown in FIG. 34, an electronic device 3400 includes a display unit 3402 configured to display graphical objects; a touch-sensitive surface unit 3404 configured to receive user gestures; one or more RF units 3406 configured to detect and communicate with external electronic devices; and a processing unit 3408 coupled to display unit 3402, touch-sensitive surface unit 3404, and RF unit(s) 3406. In some embodiments, processing unit 3408 is configured to support an operating system 3410 and an applications unit 3412. In some embodiments, operating system 3410 is configured to launch applications with applications unit 3412 or enter a device mode. In some embodiments, operating system 3410 is configured to launch an application, enter a clock face edit mode of the electronic device, enter a clock face selection mode of the electronic device, or enter a user interaction mode of the electronic device. In some embodiments, applications unit 3412 is configured to launch or run applications with applications unit 3412. For example, applications unit 3412 can optionally be used for launching an application, running a launched application, or setting a user reminder.

In some embodiments, the processing unit 3408 includes a display enabling unit 3414, a detecting unit 3416, a determining unit 3418, and an accessing unit 3420. In some embodiments, the display enabling unit 3414 is configured to cause a display of a user interface (or portions of a user interface) in conjunction with the display unit 3402. For example, the display enabling unit 3414 can optionally be used for displaying a user interface screen, updating a user interface screen, displaying a clock face, substituting one or more indications of an hourly timescale with an indication of a first timescale for a stopwatch hand, animating a stopwatch hand, rotating a simulation of the Earth (or Moon, or solar system), animating a user interface object, displaying an animated reveal of a clock face, displaying a character user interface object, updating a displayed character user interface object (e.g., updating a displayed character user interface object to indicate a second time or updating a displayed character user interface object by changing a visual aspect of the displayed character user interface object), visually distinguishing a displayed clock face to indicate a clock face edit mode, visually indicating an element of a clock face for editing, visually distinguishing a displayed clock face to indicate a clock face selection mode, centering a clock face on the display, updating an affordance to indicate a time of day, or substituting the display of a first user interface screen with a second user interface screen. In some embodiments, the detecting unit 3416 is configured to detect and/or receive user input, e.g., through the use of touch-sensitive surface unit 3404 or a rotatable input mechanism (e.g., 506 or 1540). For example, the detecting 3416 can optionally be used for detecting a user input, receiving data representing a user input, receiving a user input, detecting a user movement of the device, detecting a contact on the touch-sensitive display, detecting a swipe on the touch-sensitive display, or detecting a movement of the rotatable input mechanism. In some embodiments, the determining unit 3418 is configured to make determinations. For example, determining unit 3418 can optionally be used for determining whether characteristic intensity of a contact on the touch-sensitive display is above an intensity threshold or determining whether an event meets a condition. In some embodiments, the accessing unit 3420 is configured to access and/or select information. For example, accessing unit 3420 can optionally be used for accessing a folder, selecting an image from the folder, accessing data representing a previously displayed animated sequence, or selecting an animated sequence. The units of FIG. 34 can optionally be used to implement the various techniques and methods described above with respect to FIGS. 6A-19.

The functional blocks of the device 3400 are, optionally, implemented by hardware, software, or a combination of hardware and software to carry out the principles of the various described examples. It is understood by persons of skill in the art that the functional blocks described in FIG. 34 are, optionally, combined or separated into sub-blocks to implement the principles of the various described examples. Therefore, the description herein optionally supports any possible combination or separation or further definition of the functional blocks described herein.

Figure 35:
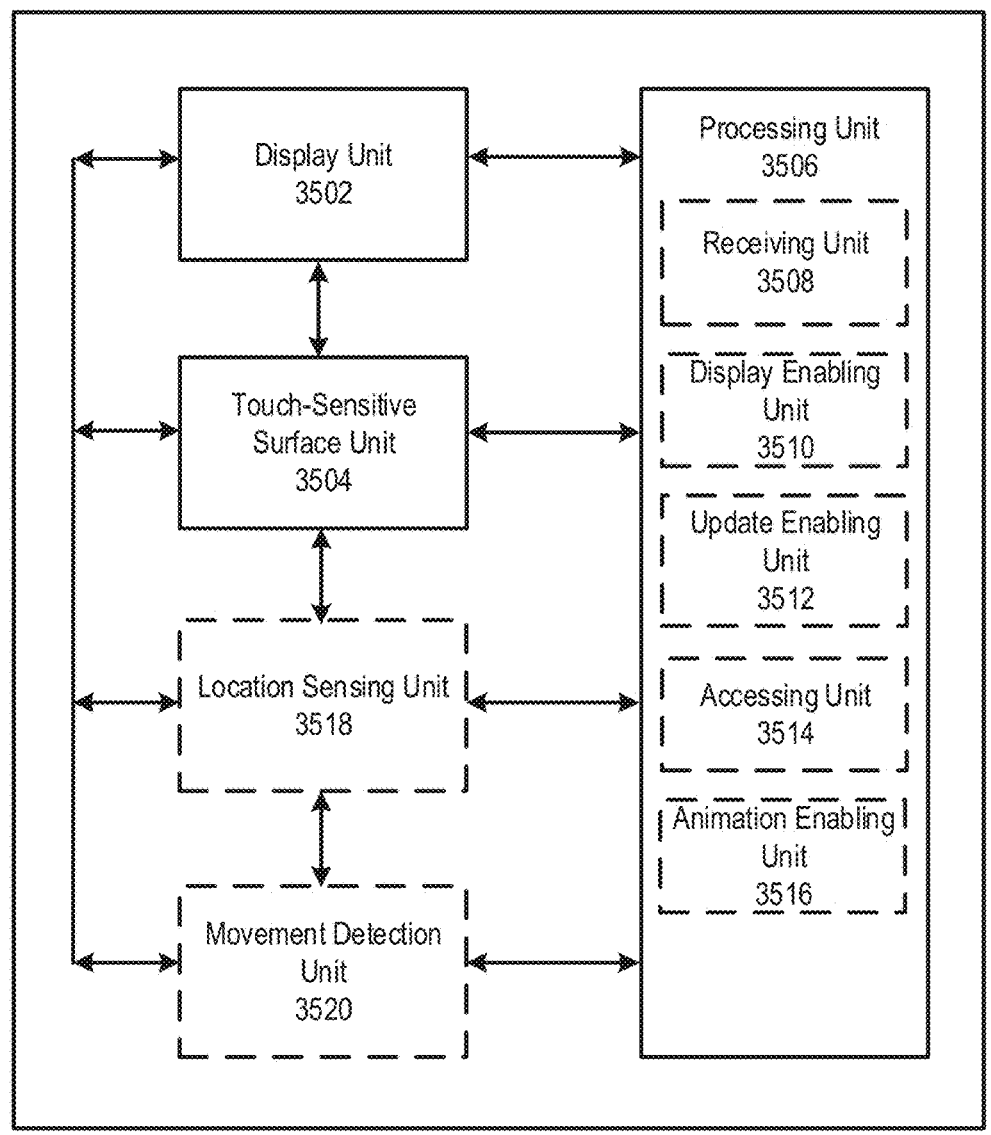
FIG. 35 is a functional block diagram of an electronic device in accordance with some embodiments.

In accordance with some embodiments, FIG. 35 shows an exemplary functional block diagram of an electronic device 3500 configured in accordance with the principles of the various described embodiments. In accordance with some embodiments, the functional blocks of electronic device 3500 are configured to perform the techniques described above. The functional blocks of the device 3500 are, optionally, implemented by hardware, software, or a combination of hardware and software to carry out the principles of the various described examples. It is understood by persons of skill in the art that the functional blocks described in FIG. 35 are, optionally, combined or separated into sub-blocks to implement the principles of the various described examples. Therefore, the description herein optionally supports any possible combination or separation or further definition of the functional blocks described herein.

As shown in FIG. 35, an electronic device 3500 includes a display unit 3502 configured to display a graphic user interface, optionally, a touch-sensitive surface unit 3504 configured to receive contacts, optionally, a location sensing unit 3518 configured to sense location, optionally, a movement detection unit 3520, and a processing unit 3506 coupled to the display unit 3502, optionally, the touch-sensitive surface unit 3504, optionally, the location sensing unit 3518, and optionally, the movement detection unit 3520. In some embodiments, the processing unit 3506 includes a receiving unit 3508, a display enabling unit 3510, an update enabling unit 3512, an accessing unit 3514, and an animation enabling unit 3516.

The processing unit 3506 is configured to receive (e.g., with receiving unit 3508) data representing a user input, and in response to receiving the data: enable display (e.g., with display enabling unit 3510), on the display unit (e.g., display unit 3502), of a user interface screen, the user interface screen including a clock face indicating a first time, wherein the first time precedes a current time; and enable update (e.g., with update enabling unit 3512), on the display unit (e.g., display unit 3502), of the user interface screen by enabling animation (e.g., with animation enabling unit 3516), on the display unit (e.g., display unit 3502), of the clock face to transition from indicating the first time to indicating the current time, wherein the animation represents the passage of time from the first time to the current time.

In some embodiments, the processing unit 3506 is further configured to receive (e.g., with receiving unit 3508) second data representing a time of a previous user movement of electronic device 3500, wherein the previous user movement of electronic device 3500 is before receipt of the data representing the user input, and wherein the time of the previous user movement of electronic device 3500 is the first time indicated by the clock face. In some embodiments, the first time precedes the current time by a first duration, and wherein the first duration is a predetermined duration before the current time. In some embodiments, the predetermined duration is 5 hours. In some embodiments, the first time is a predetermined time of day. In some embodiments, the clock face is animated for a period of time indicative of the first duration. In some embodiments, the clock face is animated for a period of time independent of the first duration. In some embodiments, the clock face comprises a representation of a digital clock including a numerical indication of an hour and a numerical indication of a minute. In some embodiments, the clock face comprises a representation of an analog clock including an hour hand and a minute hand. In some embodiments, enabling animation (e.g., with animation enabling unit 3516) of the first user interface object (e.g., on the user interface screen displayed on display unit 3502) comprises rotating one or more of the hour hand and the minute hand in a clockwise motion on-screen. In some embodiments, the processing unit 3506 is further configured to access (e.g., with accessing unit 3514) an image of a scene, wherein the image of the scene is representative of the time indicated by the clock face; and enable display (e.g., with display enabling unit 3510), on the display unit (e.g., display unit 3502), of the image as a background on the user interface screen. In some embodiments, the image of the scene is an image captured at substantially the same time of day as the time indicated by the clock face. In some embodiments, the processing unit 3506 is further configured to access (e.g., with accessing unit 3514) a first image of a scene, wherein the first image is representative of the first time; and access (e.g., with accessing unit 3514) a second image of the scene, wherein the second image is representative of the current time; and in response to receiving (e.g., with receiving unit 3508) the data representing the user input: enable successive display (e.g., with display enabling unit 3510), on the display unit (e.g., display unit 3502), of the first image of the scene and the second image of the scene, the successive display indicating the passage of time from the first time to the current time. In some embodiments, the first image of the scene and the second image of the scene are displayed as backgrounds on the user interface screen. In some embodiments, the processing unit 3506 is further configured to access (e.g., with accessing unit 3514) a sequence of images of a scene, the sequence of images including: a first image of the scene, wherein the first image of the scene is representative of the first time; one or more second images of the scene, wherein the one or more second images are representative of one or more times between the first time and the current time, and wherein the one or more second images are after the first image of the scene within the sequence of images; and a third image of the scene, wherein the third image of the scene is representative of the current time, and wherein the third image of the scene is after the one or more second images of the scene within the sequence of images; and in response to receiving (e.g., with receiving unit 3508) the data representing the user input: enable display (e.g., with display enabling unit 3510), on the display unit (e.g., display unit 3502), of the sequence of images of the scene as an animated sequence, wherein displaying the sequence of images comprises enabling animation (e.g., with animation enabling unit 3516) of the sequence of images to indicate the passage of time from the first time to the current time. In some embodiments, the sequence of images of the scene is displayed as an animated background on the user interface screen. In some embodiments, the scene is user-designated. In some embodiments, electronic device 3500 further comprises a location sensing unit (e.g., location sensing unit 3730), processing unit 3506 is coupled to the location sensing unit (e.g., location sensing unit 3730), and the processing unit 3506 is further configured to enable obtaining a current location of electronic device 3500 from the location sensor (e.g., location sensing unit 3518), wherein the first image represents the first time at the current location, and wherein the second image or the third image represents the current time at the current location. In some embodiments, the processing unit 3506 is further configured to enable display (e.g., with display enabling unit 3510), on the display unit (e.g., display unit 3502), of a user interface object on the user interface screen at a first position, wherein the first position of the user interface object is based on the first time. In some embodiments, the processing unit 3506 is further configured to enable animation (e.g., with animation enabling unit 3516), on the display unit (e.g., display unit 3502), of the user interface object by moving the user interface object from the first position to a second position on the user interface screen, wherein the second position is based on the current time, and wherein moving the user interface object from the first position to a second position indicates the passage of time from the first time to the current time. In some embodiments, the user interface object is a graphical representation of a sun. In some embodiments, the user interface object is a graphical representation of a moon. In some embodiments, the electronic device 3500 further includes a movement detection unit (e.g., movement detection unit 3520), the processing unit 3506 is coupled to the movement detection unit, and the processing unit 3506 is further configured to: detect a movement of the electronic device (e.g., with movement detection unit 3520), wherein the user input comprises the movement of the electronic device 3500. In some embodiments, the user input is a contact on the touch-sensitive surface unit (e.g., touch-sensitive surface unit 3504).

The operations described above with reference to FIG. 20 are, optionally, implemented by components depicted in FIGS. 1A-1B or FIG. 35. For example, receiving operation 2002, displaying operation 2004, and updating operation 2006 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 36:
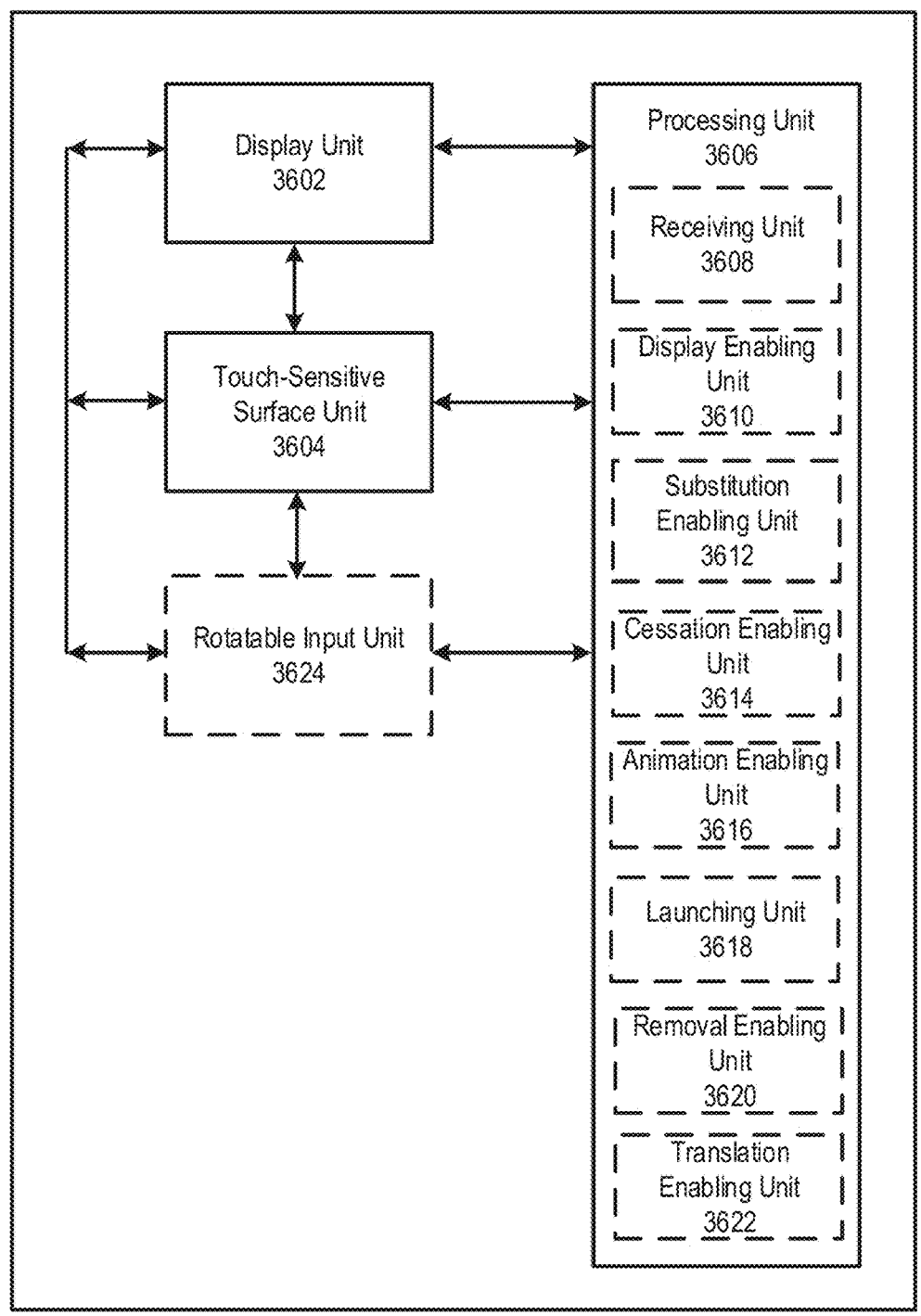
FIG. 36 is a functional block diagram of an electronic device in accordance with some embodiments.

In accordance with some embodiments, FIG. 36 shows an exemplary functional block diagram of an electronic device 3600 configured in accordance with the principles of the various described embodiments. In accordance with some embodiments, the functional blocks of electronic device 3600 are configured to perform the techniques described above. The functional blocks of the device 3600 are, optionally, implemented by hardware, software, or a combination of hardware and software to carry out the principles of the various described examples. It is understood by persons of skill in the art that the functional blocks described in FIG. 36 are, optionally, combined or separated into sub-blocks to implement the principles of the various described examples. Therefore, the description herein optionally supports any possible combination or separation or further definition of the functional blocks described herein.

As shown in FIG. 36, an electronic device 3600 includes a display unit 3602 configured to display a graphic user interface, optionally, a touch-sensitive surface unit 3604 configured to receive contacts, optionally, a rotatable input unit 3624 configured to receive rotatable input (e.g., from a rotatable input mechanism), and a processing unit 3606 coupled to the display unit 3602, optionally, the touch-sensitive surface unit 3604, and optionally, the rotatable input unit 3624. In some embodiments, the processing unit 3606 includes a receiving unit 3608, a display enabling unit 3610, a substitution enabling unit 3612, a cessation enabling unit 3614, an animation enabling unit 3616, a launching unit 3618, a removal enabling unit 3620, and a translation enabling unit 3622.

The processing unit 3606 is configured to enable display (e.g., with display enabling unit 3610), on the display unit (e.g., display unit 3602), of a clock face that indicates current time, the clock face including: a user interface object comprising an hour hand and a minute hand, wherein the user interface object indicates the current time; one or more indications of an hourly timescale; and a stopwatch hand; receive data (e.g., with receiving unit 3608) representing a user input; and enable substitution (e.g., with substitution enabling unit 3612), on the display unit (e.g., display unit 3602), of the one or more indications of an hourly timescale with an indication of a first timescale for the stopwatch hand; and enable animation (e.g., with animation enabling unit 3616), on the display unit (e.g., display unit 3602), of the stopwatch hand to reflect passage of time.

In some embodiments, the processing unit 3606 is further configured to, while enabling animation (e.g., with animation enabling unit 3616), on the display unit (e.g., display unit 3602), of the stopwatch hand to reflect the passage of time, receive second data (e.g., with receiving unit 3608) representing a second user input; and in response to receiving the second data: enable cessation (e.g., with cessation enabling unit 3614), on the display unit (e.g., display unit 3602) of the animation of the stopwatch hand. In some embodiments, the processing unit 3606 is further configured to enable display (e.g., with display enabling unit 3610), on the display unit (e.g., display unit 3602), of a first affordance, the first affordance representing a start/stop function, wherein the first data representing the first user input and the second data representing the second user input both represent contacts on the displayed first affordance. In some embodiments, the processing unit 3606 is further configured to enable display (e.g., with display enabling unit 3610), on the display unit (e.g., display unit 3602), of a second affordance, the second affordance representing a lap function; receive third data (e.g., with receiving unit 3608) representing a contact on the displayed second affordance, wherein the third data is received after receiving the first data and before receiving the second data; and enable display (e.g., with display enabling unit 3610), on the display unit (e.g., display unit 3602), of a third numerical indication of elapsed time between receiving the first data and receiving the third data. In some embodiments, the processing unit 3606 is further configured to enable display (e.g., with display enabling unit 3610), on the display unit (e.g., display unit 3602), of a third affordance, the third affordance representing a stopwatch application; receive fourth data (e.g., with receiving unit 3608) representing a contact on the displayed third affordance; and in response to receiving the fourth data: launch (e.g., with launching unit 3618) the stopwatch application. In some embodiments, the first timescale for the stopwatch hand is 60 seconds. In some embodiments, the first timescale for the stopwatch hand is 30 seconds. In some embodiments, the first timescale for the stopwatch hand is 6 seconds. In some embodiments, the first timescale for the stopwatch hand is 3 seconds. In some embodiments, movement of the stopwatch hand is animated at a rate based on the first timescale for the stopwatch hand. In some embodiments, enabling substitution (e.g., with substitution enabling unit 3612), on the display unit (e.g., display unit 3602), of the one or more indications of an hourly timescale with an indication of a first timescale for the stopwatch hand comprises: enabling removal (e.g., with removal enabling unit 3620), on the display unit (e.g., display unit 3602), of the one or more indications of the hourly timescale; enabling display (e.g., with display enabling unit 3610), on the display unit (e.g., display unit 3602), of the indication of the first timescale for the stopwatch hand; and enabling translation (e.g., with translation enabling unit 3622), on the display unit (e.g., display unit 3602), of the displayed indication of the first timescale for the stopwatch hand in a rotational motion, wherein the rotational motion is in a clockwise direction. In some embodiments, electronic device 3600 further comprises a rotatable input unit (e.g., rotatable input unit 3624), wherein the processing unit is coupled to the rotatable input unit (e.g., rotatable input unit 3624), and processing unit 3606 is further configured to receive fifth data representing a rotatable input from the rotatable input unit (e.g., with rotatable input unit 3624); and enable substitution (e.g., with substitution enabling unit 3612), on the display unit (e.g., display unit 3602) of the indication of the first timescale for the stopwatch hand with an indication of a second timescale for the stopwatch hand, wherein the second timescale is different from the first timescale. In some embodiments, enabling substitution (e.g., with substitution enabling unit 3612), on the display unit (e.g., display unit 3602) of the indication of the first timescale for the stopwatch hand with the indication of the second timescale for the stopwatch hand comprises: enabling removal (e.g., with removal enabling unit 3620), on the display unit (e.g., display unit 3602), of the indication of the first timescale for the stopwatch hand; enabling display (e.g., with display enabling unit 3610), on the display unit (e.g., display unit 3602) of the indication of the second timescale for the stopwatch hand; and enabling translation (e.g., with translation enabling unit 3622), on the display unit (e.g., display unit 3602), of the displayed indication of the second timescale for the stopwatch hand in a rotational motion, wherein the rotational motion is in a clockwise direction. In some embodiments, the processing unit 3606 is further configured to after receiving the first data representing the first user input: enable animation (e.g., with animation enabling unit 3616), on the display unit (e.g., display unit 3602), of the stopwatch hand to represent a rotational motion about an origin; and enable cessation (e.g., with cessation enabling unit 3614), on the display unit (e.g., display unit 3602), of the animation to display the stopwatch hand at a position at $\pi/2$ radians relative to the rotational motion about the origin.

The operations described above with reference to FIG. 21 are, optionally, implemented by components depicted in FIGS. 1A-1B or FIG. 36. For example, displaying operation 2102, receiving operation 2104, and substituting operation 2106 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 37:
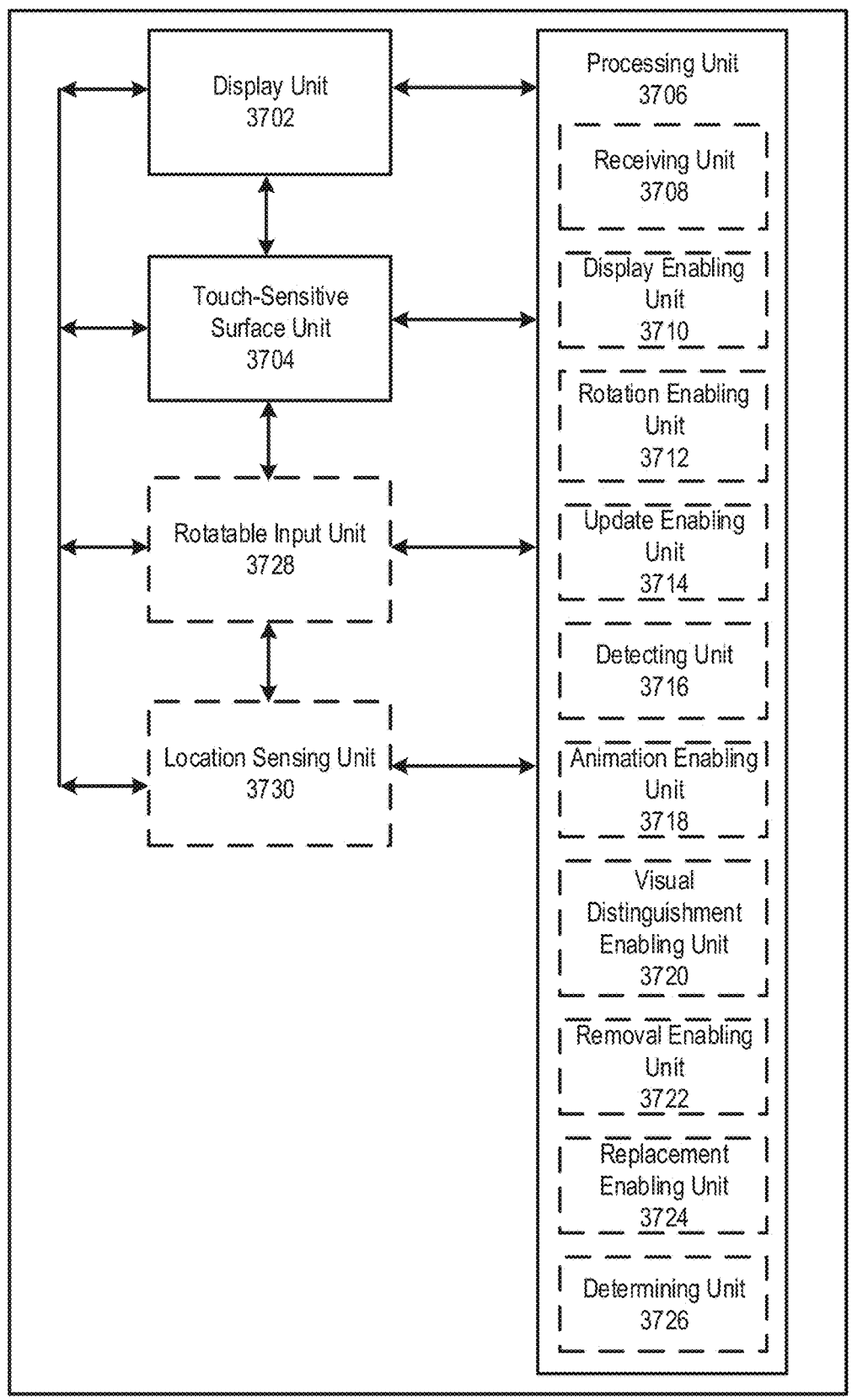
FIG. 37 is a functional block diagram of an electronic device in accordance with some embodiments.

In accordance with some embodiments, FIG. 37 shows an exemplary functional block diagram of an electronic device 3700 configured in accordance with the principles of the various described embodiments. In accordance with some embodiments, the functional blocks of electronic device 3700 are configured to perform the techniques described above. The functional blocks of the device 3700 are, optionally, implemented by hardware, software, or a combination of hardware and software to carry out the principles of the various described examples. It is understood by persons of skill in the art that the functional blocks described in FIG. 37 are, optionally, combined or separated into sub-blocks to implement the principles of the various described examples. Therefore, the description herein optionally supports any possible combination or separation or further definition of the functional blocks described herein.

As shown in FIG. 37, an electronic device 3700 includes a display unit 3702 configured to display a graphic user interface, optionally, a touch-sensitive surface unit 3704 configured to receive contacts, optionally, a rotatable input unit 3728 configured to receive rotatable input (e.g., from a rotatable input mechanism), optionally, a location sensing unit 3730 configured to sense location, and a processing unit 3706 coupled to the display unit 3702, optionally, the touch-sensitive surface unit 3704, optionally, the rotatable input unit 3728, and optionally, the location sensing unit 3730. In some embodiments, the processing unit 3706 includes a receiving unit 3708, a display enabling unit 3710, a rotation enabling unit 3712, an update enabling unit 3714, a detecting unit 3716, an animation enabling unit 3718, a visual distinguishment enabling unit 3720, a removal enabling unit 3722, a replacement enabling unit 3724, and a determining unit 3726.

The processing unit 3706 is configured to enable display (e.g., with display enabling unit 3710), on the display unit (e.g., display unit 3702), of a user interface screen, the user interface screen including: a first affordance representing a simulation of a first region of the Earth as illuminated by the Sun at a current time; and a second affordance indicating the current time; receive (e.g., with receiving unit 3708) a user input; and in response to receiving the user input: enable rotation (e.g., with rotation enabling unit 3712), on the display unit (e.g., display unit 3702), of the simulation of the Earth to display a second region of the Earth as illuminated by the Sun at the current time.

In some embodiments, the first affordance representing the simulation of the first region of the Earth as illuminated by the Sun at the current time comprises a representation of a solar terminator. In some embodiments, the user input comprises a swipe on the touch-sensitive surface unit (e.g., touch-sensitive surface unit 3704) in a first swipe direction. In some embodiments, the simulation of the first region of the Earth is rotated in a first direction of rotation, and the processing unit 3706 is further configured to: receive (e.g., with receiving unit 3708) a second user input; and in response to receiving the second user input: enable rotation (e.g., with rotation enabling unit 3712), on the display unit (e.g., display unit 3702), of the simulation of the first region of the Earth in a second direction of rotation, wherein the second direction of rotation and the first direction of rotation are different. In some embodiments, the second user input comprises a swipe on the touch-sensitive surface unit (e.g., touch-sensitive surface unit 3704) in a second swipe direction, and the first swipe direction and the second swipe direction are different. In some embodiments, electronic device 3700 further comprises a rotatable input unit (e.g., rotatable input unit 3728), wherein the processing unit 3706 is coupled to the rotatable input unit, and wherein the processing unit 3706 is further configured to: receive a third user input representing a rotatable input from the rotatable input unit (e.g., rotatable input unit 3728) and in response to receiving the third user input: enable update (e.g., with update enabling unit 3714), on the display unit (e.g., display unit 3702), of the first affordance to represent a simulation of the first region of the Earth as illuminated by the Sun at a non-current time. In some embodiments, the processing unit 3706 is further configured to: enable update (e.g., with update enabling unit 3714), on the display unit (e.g., display unit 3702), of the second affordance to indicate the non-current time. In some embodiments, electronic device 3700 further comprises a location sensing unit (e.g., location sensing unit 3730), wherein the processing unit 3706 is coupled to the location sensing unit, and wherein the processing unit 3706 is further configured to: before displaying the user interface screen, obtain a current location of electronic device 3700 from the location sensing unit (e.g., location sensing unit 3730), wherein the displayed first region of the Earth represented by the first affordance indicates the current location of electronic device 3700. In some embodiments, the processing unit 3706 is further configured to: detect (e.g., with detecting unit 3716) a user movement of electronic device 3700; and in response to detecting the user movement: enable animation (e.g., with animation enabling unit 3718), on the display unit (e.g., display unit 3702), of the first affordance representing the simulation of the Earth by translating the first affordance on-screen towards the center of the displayed user interface screen. In some embodiments, the processing unit 3706 is further configured to: enable display (e.g., with display enabling unit 3710), on the display unit (e.g., display unit 3702), of a third affordance, the third affordance representing a moon; detect (e.g., with detecting unit 3716) a contact on the displayed third affordance on the touch-sensitive surface unit (e.g., touch-sensitive surface unit 3704), and in response to detecting the contact: enable update (e.g., with update enabling unit 3714), on the display unit (e.g., display unit 3702), of the user interface screen, wherein enabling update of the display of the user interface screen comprises: enabling display (e.g., with display enabling unit 3710), on the display unit (e.g., display unit 3702), of a fourth affordance representing a simulation of the Moon, the fourth affordance representing a simulation of the Moon as seen from the Earth at the current time; and enabling display (e.g., with display enabling unit 3710), on the display unit (e.g., display unit 3702), of a fifth affordance indicating the current time. In some embodiments, enabling update (e.g., with update enabling unit 3714), on the display unit (e.g., display unit 3702), of the user interface screen comprises enabling animation (e.g., with animation enabling unit 3718), on the display unit (e.g., display unit 3702), of the first affordance representing the simulation of the first region of the Earth as illuminated by the Sun by zooming out. In some embodiments, the processing unit 3706 is further configured to: receive (e.g., with receiving unit 3708) a fourth user input; and in response to receiving the fourth user input: enable rotation (e.g., with rotation enabling unit 3712), on the display unit (e.g., display unit 3702), of the simulation of the Moon to display the Moon as seen from the Earth at a non-current time; and enable update (e.g., with update enabling unit 3714), on the display unit (e.g., display unit 3702), of the fifth affordance to indicate the non-current time. In some embodiments, the fourth user input comprises a swipe on the touch-sensitive surface unit (e.g., touch-sensitive surface unit 3704) in a first swipe direction. In some embodiments, the simulation of the Moon as seen from the Earth is rotated in a first direction of rotation, and the processing unit 3706 is further configured to: receive (e.g., with receiving unit 3708) a fifth user input; and in response to receiving the fifth user input: enable rotation (e.g., with rotation enabling unit 3712), on the display unit (e.g., display unit 3702), of the simulation of the Moon as seen from the Earth in a second direction of rotation, wherein the second direction of rotation and the first direction of rotation are different. In some embodiments, the fifth user input comprises a swipe on the touch-sensitive surface unit (e.g., touch-sensitive surface unit 3704) in a second swipe direction, and the first swipe direction and the second swipe direction are different. In some embodiments, electronic device 3700 further comprises a rotatable input unit (e.g., rotatable input unit 3728), the processing unit 3706 is coupled to the rotatable input unit, and receiving the fourth user input comprises receiving a rotatable input from the rotatable input unit (e.g., rotatable input unit 3728) in a first direction of rotation. In some embodiments, electronic device 3700 further comprises a rotatable input unit (e.g., rotatable input unit 3728), the processing unit 3706 is coupled to the rotatable input unit, and the simulation of the Moon as seen from the Earth is rotated in a first direction of rotation, wherein the processing unit is further configured to: receive (e.g., with receiving unit 3708) a sixth user input; and in response to receiving the sixth user input: enable rotation (e.g., with rotation enabling unit 3712), on the display unit (e.g., display unit 3702), of the simulation of the Moon as seen from the Earth in a second direction of rotation, wherein the second direction of rotation and the first direction of rotation are different. In some embodiments, the sixth user input comprises a rotatable input from the rotatable input unit (e.g., rotatable input unit 3728) in a second direction of rotation, and wherein the first direction of rotation and the second direction of rotation are different. In some embodiments, the processing unit 3706 is further configured to: detect (e.g., with detecting unit 3716) a user double tap on the touch-sensitive surface unit (e.g., touch-sensitive surface unit 3704), the user double tap comprising a first contact on the touch-sensitive surface unit and a second contact on the touch-sensitive surface unit; determine (e.g., with determining unit 3726) whether the first contact and the second contact were received within a predetermined interval; and in response to detecting the user double tap, and in accordance with a determination that the first contact and the second contact were received within the predetermined interval: enable display (e.g., with display enabling unit 3710), on the display unit (e.g., display unit 3702), of additional lunar information. In some embodiments, the processing unit 3706 is further configured to: enable display (e.g., with display enabling unit 3710), on the display unit (e.g., display unit 3702), of a sixth affordance on the touch-sensitive surface unit (e.g., touch-sensitive surface unit 3704), the sixth affordance representing a solar system; detect (e.g., with detecting unit 3716) a contact on the displayed sixth affordance, and in response to detecting the contact: enable update (e.g., with update enabling unit 3714), on the display unit (e.g., display unit 3702), of the user interface screen, wherein enabling update (e.g., with update enabling unit 3714), on the display unit (e.g., display unit 3702), of the user interface screen comprises: enabling display (e.g., with display enabling unit 3710), on the display unit (e.g., display unit 3702), of a seventh affordance representing a solar system, the seventh affordance comprising representations of the Sun, the Earth, and one or more non-Earth planets at their respective positions at a current time; and enabling display (e.g., with display enabling unit 3710), on the display unit (e.g., display unit 3702), of an eighth affordance indicating the current time. In some embodiments, enabling update (e.g., with update enabling unit 3714), on the display unit (e.g., display unit 3702), of the user interface screen comprises enabling animation (e.g., with animation enabling unit 3718), on the display unit (e.g., display unit 3702), of the first affordance representing the simulation of the first region of the Earth as illuminated by the Sun or enabling animation (e.g., with animation enabling unit 3718), on the display unit (e.g., display unit 3702), of the fourth affordance representing a simulation of the Moon as seen from the Earth by zooming out. In some embodiments, the processing unit 3706 is further configured to: receive (e.g., with receiving unit 3708) a seventh user input; and in response to receiving the seventh user input: enable update (e.g., with update enabling unit 3714), on the display unit (e.g., display unit 3702), of the seventh affordance to depict respective positions of the Sun, the Earth, and the one or more non-Earth planets for a non-current time, wherein updating the seventh affordance comprises rotating the Earth and the one or more non-Earth planets about the Sun; and enable update (e.g., with update enabling unit 3714), on the display unit (e.g., display unit 3702), of the eighth affordance to indicate the non-current time. In some embodiments, the seventh user input comprises a swipe on the touch-sensitive surface unit (e.g., touch-sensitive surface unit 3704) in a first swipe direction. In some embodiments, the Earth and the one or more non-Earth planets are rotated about the Sun in a first direction of rotation, and the processing unit 3706 is further configured to: receive (e.g., with receiving unit 3708) an eighth user input; and in response to receiving the eighth user input: enable rotation (e.g., with rotation enabling unit 3712), on the display unit (e.g., display unit 3702), of the Earth and the one or more non-Earth planets about the Sun in a second direction of rotation, wherein the second direction of rotation and the first direction of rotation are different. In some embodiments, the eighth user input comprises a swipe on the touch-sensitive surface unit (e.g., touch-sensitive surface unit 3704) in a second swipe direction, and wherein the first swipe direction and the second swipe direction are different. In some embodiments, electronic device 3700 further comprises a rotatable input unit (e.g., rotatable input unit 3728), the processing unit 3706 is coupled to the rotatable input unit (e.g., rotatable input unit 3728), and receiving the seventh user input comprises receiving a rotatable input from the rotatable input unit (e.g., rotatable input unit 3728) in a first direction of rotation. In some embodiments, electronic device 3700 further comprises a rotatable input unit (e.g., rotatable input unit 3728), the processing unit 3706 is coupled to the rotatable input unit, wherein the Earth and the one or more non-Earth planets are rotated about the Sun in a first direction of rotation, and the processing unit 3706 is further configured to: receive (e.g., with receiving unit 3708) a ninth user input; and in response to receiving the ninth user input: enable rotation (e.g., with rotation enabling unit 3712), on the display unit (e.g., display unit 3702), of the Earth and the one or more non-Earth planets about the Sun in a second direction of rotation, wherein the second direction of rotation and the first direction of rotation are different. In some embodiments, the ninth user input comprises a rotatable input from the rotatable input unit (e.g., rotatable input unit 3728) in a second direction of rotation, and wherein the first direction of rotation and the second direction of rotation are different. In some embodiments, the representation of the Earth further comprises a representation of the orbit of the Earth around the Sun, and wherein the representation of the one or more non-Earth planets further comprises a representation of the orbit of the one or more non-Earth planets around the Sun. In some embodiments, the processing unit 3706 is further configured to: receive (e.g., with receiving unit 3708) a tenth user input comprising a contact on the touch-sensitive surface unit (e.g., touch-sensitive surface unit 3704), wherein the contact is associated with the representation of the Earth or the representation of the one or more non-Earth planets, the contact on the touch-sensitive surface unit having an associated duration; while continuing to receive the contact, determine (e.g., with determining unit 3726) whether the duration of the contact exceeds a predetermined threshold; in response to receiving the tenth user input, and in accordance with a determination that the duration of the contact exceeds the predetermined threshold: enable visual distinguishment (e.g., with visual distinguishment enabling unit 3720), on the display unit (e.g., display unit 3702), of the representation of the Earth or the representation of the one or more non-Earth planets associated with the contact; detect (e.g., with detecting unit 3716) a break in the contact; and in response to detecting the break in the contact: enable display (e.g., with display enabling unit 3710), on the display unit (e.g., display unit 3702), of information about the Earth or the one or more non-Earth planets associated with the contact. In some embodiments, the processing unit 3706 is further configured to: after enabling display, on the display unit, of the information about the Earth or the one or more non-Earth planets associated with the contact, receive (e.g., with receiving unit 3708) an eleventh user input; determine (e.g., with determining unit 3732) whether the eleventh user input represents a tap or a swipe on the touch-sensitive surface unit (e.g., touch-sensitive surface unit 3704); in accordance with a determination that the eleventh user input represents a tap: enable removal (e.g., with removal enabling unit 3724), on the display unit (e.g., display unit 3702), of the displayed information about the Earth or the one or more non-Earth planets; and in accordance with a determination that the eleventh user input represents a swipe: enable replacement (e.g, with replacement enabling unit 3724), on the display unit (e.g., display unit 3702), of the displayed information about the Earth or the one or more non-Earth planets with information about a second planet selected from the group consisting of the Earth and the one or more non-Earth planets, wherein the second planet is not the planet associated with the contact.

The operations described above with reference to FIG. 22 are, optionally, implemented by components depicted in FIGS. 1A-1B or FIG. 37. For example, displaying operation 2202, receiving operation 2204, and rotating operation 2206 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 38:
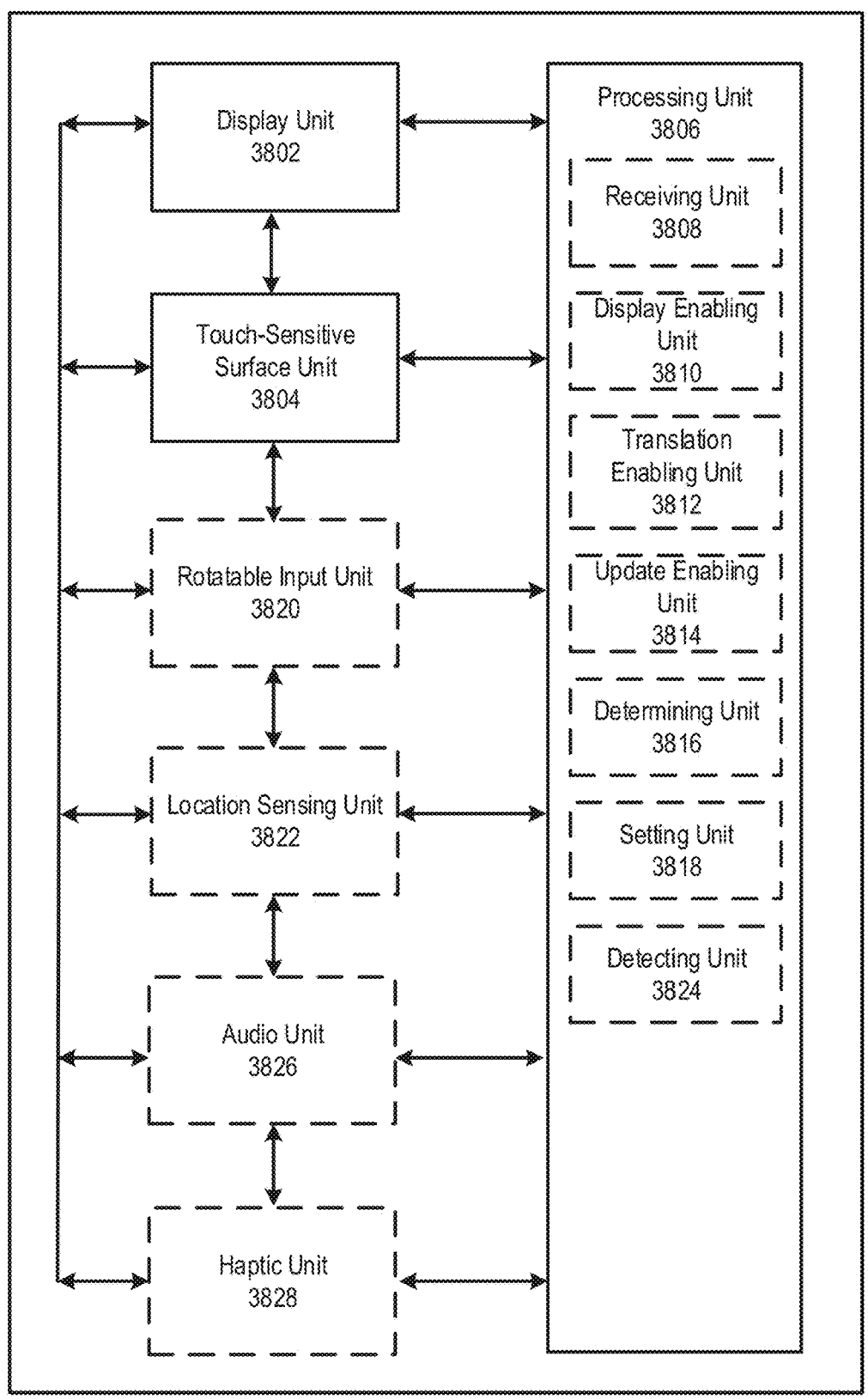
FIG. 38 is a functional block diagram of an electronic device in accordance with some embodiments.

In accordance with some embodiments, FIG. 38 shows an exemplary functional block diagram of an electronic device 3800 configured in accordance with the principles of the various described embodiments. In accordance with some embodiments, the functional blocks of electronic device 3800 are configured to perform the techniques described above. The functional blocks of the device 3800 are, optionally, implemented by hardware, software, or a combination of hardware and software to carry out the principles of the various described examples. It is understood by persons of skill in the art that the functional blocks described in FIG. 38 are, optionally, combined or separated into sub-blocks to implement the principles of the various described examples. Therefore, the description herein optionally supports any possible combination or separation or further definition of the functional blocks described herein.

As shown in FIG. 38, an electronic device 3800 includes a display unit 3802 configured to display a graphic user interface, optionally, a touch-sensitive surface unit 3804 configured to receive contacts, optionally, a rotatable input unit 3820 configured to receive rotatable input (e.g., from a rotatable input mechanism), optionally, a location sensing unit 3822 configured to sense location, optionally, an audio unit 3826, optionally, a haptic unit 3828, and a processing unit 3806 coupled to the display unit 3802, optionally, the touch-sensitive surface unit 3804, optionally, the rotatable input unit 3820, optionally, the location sensing unit 3822, optionally, the audio unit 3826, and optionally, the haptic unit 3828. In some embodiments, the processing unit 3806 includes a receiving unit 3808, a display enabling unit 3810, a translation enabling unit 3812, an update enabling unit 3814, a determining unit 3816, a setting unit 3818, and a detecting unit 3824.

The processing unit 3806 is configured to enable display (e.g., with display enabling unit 3810), on the display unit (e.g., display unit 3802), of a user interface screen, the user interface screen comprising: a first portion of the user interface screen, the first portion indicating daytime; a second portion of the user interface screen, the second portion indicating nighttime; a user interface object, the user interface object representing a sinusoidal wave with a period representing a day, wherein the sinusoidal wave indicates a path of the Sun through the day, and wherein the sinusoidal wave is displayed in one or more of the first portion and the second portion; a first affordance representing the Sun, wherein the first affordance is displayed at a first position on the displayed sinusoidal wave, the first position indicating a current time of the day and whether the current time of the day is during daytime or nighttime; and a second affordance, the second affordance indicating the current time of day.

In some embodiments, electronic device 3800 further comprises a location sensing unit (e.g., location sensing unit 3822), processing unit 3806 is coupled to the location sensing unit (e.g., location sensing unit 3822), and processing unit 3806 is further configured to: obtain a current location of the electronic device from the location sensing unit (e.g., with location sensing unit 3822), wherein the ratio of the displayed first portion indicating daytime relative to the second portion indicating nighttime indicates daylight hours at the current location at the current time. In some embodiments, amplitude of the sinusoidal wave is based on height of the Sun relative to horizon at the current location and at the current time. In some embodiments, the processing unit 3806 is further configured to: enable display (e.g., with display enabling unit 3810), on the display unit (e.g., display unit 3802), of a line on the user interface screen, wherein the line divides the first portion of the user interface screen indicating daytime and the second portion of the user interface screen indicating nighttime, wherein the line intersects the sinusoidal wave at a first point representing sunrise and at a second point representing sunset. In some embodiments, the processing unit 3806 is further configured to: receive (e.g., with receiving unit 3808) a user contact on the touch-sensitive surface unit (e.g., touch-sensitive surface unit 3804) at the first affordance, the first affordance displayed at the first position on the displayed sinusoidal wave, the first position indicating the current time; while continuing to receive the user contact, detect (e.g., with detecting unit 3824) movement (e.g., on touch-sensitive surface unit 3804) of the user contact from the first position to a second position on the displayed sinusoidal wave without a break in contact of the user contact on the touch-sensitive surface unit, the second position on the displayed sinusoidal wave indicating a non-current time; and in response to detecting the contact at the second position: enable translation (e.g., with translation enabling unit 3812), on the display unit (e.g., display unit 3802), of the first affordance on-screen from the first position on the displayed sinusoidal wave to the second position on the displayed sinusoidal wave, wherein the translation tracks the displayed sinusoidal wave; and enable update (e.g., with update enabling unit 3814), on the display unit (e.g., display unit 3802), of the second affordance to indicate the non-current time. In some embodiments, the processing unit 3806 is further configured to: in response to detecting the contact at the first affordance: enable display (e.g., with display enabling unit 3810), on the display unit (e.g., display unit 3802), of, on the user interface screen: a third user interface object, wherein the third user interface object is displayed at the first point along the sinusoidal wave representing sunrise; and a fourth user interface object, wherein the fourth user interface object is displayed at the second point along the sinusoidal wave representing sunset. In some embodiments, the processing unit 3806 is further configured to: in response to detecting (e.g., with detecting unit 3824) the contact at the first affordance (e.g., on touch-sensitive surface unit 3804): enable display (e.g., with display enabling unit 3810), on the display unit (e.g., display unit 3802), of, on the user interface screen: a fifth user interface object, wherein the fifth user interface object is displayed along the sinusoidal wave at a third point representing dawn; and a sixth user interface object, wherein the sixth user interface object is displayed along the sinusoidal wave at a fourth point representing dusk. In some embodiments, the processing unit 3806 is further configured to: detect (e.g., with detecting unit 3824) a break in contact of the user contact on the touch-sensitive surface unit (e.g., touch-sensitive surface unit 3804), and in response to detecting the break in contact of the user contact on the touch-sensitive surface unit: enable translation (e.g., with translation enabling unit 3812), on the display unit (e.g., display unit 3802), of the first affordance on-screen from the second position to the first position, wherein the translation tracks the displayed sinusoidal wave; and enable update (e.g., with update enabling unit 3814), on the display unit (e.g., display unit 3802), of the second affordance to indicate the current time of day. In some embodiments, the first affordance representing the sun appears filled when the first affordance is displayed at a position fully within the first portion of the user interface screen. In some embodiments, the first affordance representing the sun appears hollow when the first affordance is displayed at a position fully within the second portion of the user interface screen. In some embodiments, the first affordance representing the sun appears half-filled when the first affordance is displayed at a position intersecting both the first portion and the second portion of the user interface screen. In some embodiments, the processing unit 3806 is further configured to: determine (e.g., with determining unit 3816) whether the position of the first affordance on the displayed sinusoidal wave intersects with a position of the second affordance indicating the current time of day; and in accordance with a determination that the position of the first affordance on the displayed sinusoidal wave intersects with a position of the second affordance indicating the current time of day: enable display (e.g., with display enabling unit 3810), on the display unit (e.g., display unit 3802), of the second affordance at a second position that does not intersect the position of the displayed sinusoidal wave. In some embodiments, the processing unit 3806 is further configured to: detect (e.g., with detecting unit 3824) a user input; and in response to detecting the user input: enable display (e.g., with display enabling unit 3810), on the display unit (e.g., display unit 3802), of a second user interface screen, the second user interface screen comprising an indication of a time of sunrise and an indication of a time of sunset. In some embodiments, the electronic device 3800 further comprises a rotatable input unit (e.g., rotatable input unit 3820), the processing unit 3806 is coupled to the rotatable input unit, and the processing unit 3806 is further configured to: detect (e.g., with detecting unit 3824) a movement corresponding to a rotatable input from the rotatable input unit (e.g., rotatable input unit 3820); and in response to detecting the movement: enable translation (e.g., with translation enabling unit 3812), on the display unit (e.g., display unit 3802), of the first affordance representing the Sun to a third position on the displayed sinusoidal wave, wherein the third position indicates a third time of day, wherein the third time of day is not the current time of day; detect (e.g., with detecting unit 3824) a contact on the touch-sensitive surface unit (e.g., with touch-sensitive surface unit 3804) on the displayed first affordance at the third position; and in response to detecting the contact: set (e.g., with setting unit 3818) a user reminder for the third time of day. In some embodiments, setting the user reminder for the third time of day comprises: enabling display, on the display unit (e.g., display unit 3802), of a third affordance on the display, the third affordance representing a user prompt to set an alert for the third time of day.

In some embodiments, the processing unit 3806 is further configured to enable display (e.g., with display enabling unit 3810), on the display unit (e.g., display unit 3802), of a visual alert for the third time of day, and the user reminder for the third time of day comprises the visual alert for the third time of day. In some embodiments, the electronic device 3800 further comprises an audio unit (e.g., audio unit 3826), the processing unit 3806 is coupled to the audio unit, the processing unit 3806 is further configured to enable an audio alert for the third time of day via the audio unit (e.g., with audio unit 3826), and the user reminder for the third time of day comprises the audio alert for the third time of day. In some embodiments, the electronic device 3800 further comprises a haptic unit (e.g., haptic unit 3828), the processing unit 3806 is coupled to the haptic unit, the processing unit 3806 is further configured to enable a haptic alert for the third time of day via the haptic unit (e.g., with haptic unit 3828), and the user reminder for the third time of day comprises the haptic alert for the third time of day.

The operations described above with reference to FIG. 23 are, optionally, implemented by components depicted in FIGS. 1A-1B or FIG. 38. For example, displaying operation 2302, optional receiving operation 2304, and optional detecting operation 2306 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or subevent is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 39:
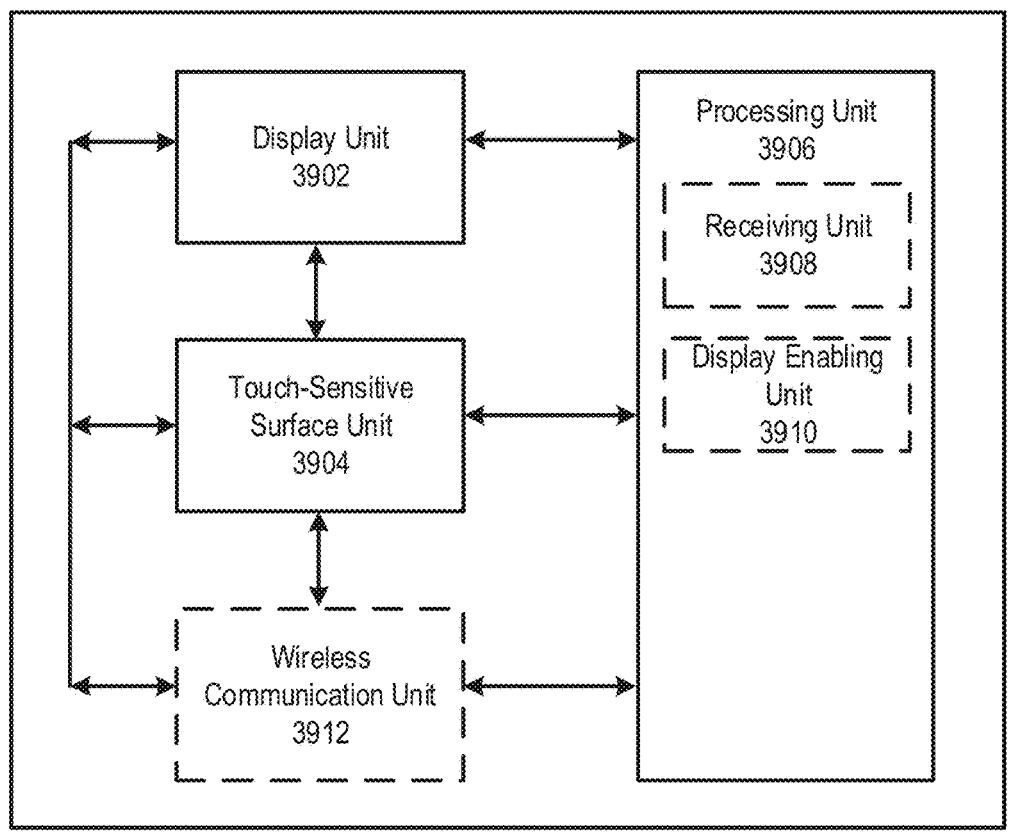
FIG. 39 is a functional block diagram of an electronic device in accordance with some embodiments.

In accordance with some embodiments, FIG. 39 shows an exemplary functional block diagram of an electronic device 3900 configured in accordance with the principles of the various described embodiments. In accordance with some embodiments, the functional blocks of electronic device 3900 are configured to perform the techniques described above. The functional blocks of the device 3900 are, optionally, implemented by hardware, software, or a combination of hardware and software to carry out the principles of the various described examples. It is understood by persons of skill in the art that the functional blocks described in FIG. 39 are, optionally, combined or separated into sub-blocks to implement the principles of the various described examples. Therefore, the description herein optionally supports any possible combination or separation or further definition of the functional blocks described herein.

As shown in FIG. 39, an electronic device 3900 includes a display unit 3902 configured to display a graphic user interface, optionally, a touch-sensitive surface unit 3904 configured to receive contacts, optionally, a wireless communication unit 3912 configured to send and/or receive wireless communication, and a processing unit 3906 coupled to the display unit 3902, optionally, the touch-sensitive surface unit 3904, and, optionally, the wireless communication unit 3912. In some embodiments, the processing unit 3906 includes a receiving unit 3908 and a display enabling unit 3910.

The processing unit 3906 is configured to enable display (e.g., with display enabling unit 3910), on the display unit (e.g., display unit 3902), of a user interface screen, the user interface screen including: a background based on an image, the background comprising a plurality of pixels, wherein a subset of the pixels are modified in appearance relative to the image such that the subset of pixels represents one or more of: a first user interface object indicating a date; and a second user interface object indicating a time of day.

In some embodiments, the subset of the pixels is modified by color blending. In some embodiments, the subset of the pixels is modified by color blurring. In some embodiments, the subset of the pixels is modified in appearance relative to the image such that the subset of pixels represents the first user interface object indicating the date. In some embodiments, the subset of the pixels is modified in appearance relative to the image such that the subset of pixels represents the second user interface object indicating the time of day. In some embodiments, one of the first user interface object indicating the date and the second user interface object indicating the time of day is a first color independent of the background. In some embodiments, the processing unit 3906 is further configured to: receive (e.g., with receiving unit 3908) data representing a background color of the background at a position of the displayed first user interface object or the displayed second user interface object, wherein the first color is different from the background color at the position of the displayed first user interface object or the displayed second user interface object. In some embodiments, the image is a photo. In some embodiments, the image is stored on the electronic device. In some embodiments, wherein the electronic device 3900 further comprises a wireless communication unit (e.g., wireless communication unit 3912), wherein the processing unit 3906 is coupled to the wireless communication unit, and the image is stored on an external device coupled to electronic device 3900 via the wireless communication unit (e.g., wireless communication unit 3912). In some embodiments, the processing unit 3906 is further configured to: before enabling display (e.g., with display enabling unit 3910), on the display unit (e.g., display unit 3902), of the user interface screen: enable receipt (e.g., with receiving unit 3908), via the wireless communication unit (e.g., wireless communication unit 3912) of data representing the background from the external device. In some embodiments, the processing unit 3906 is further configured to: enable receipt (e.g., with receiving unit 3908), via the wireless communication unit (e.g., wireless communication unit 3912) of data representing a current background of the external device, and enable display (e.g., with display enabling unit 3910), on the display unit (e.g., display unit 3902), of a second user interface screen on the display, the second user interface screen including: a second background, wherein the second background corresponds with the current background of the external device, the second background comprising a second plurality of pixels, wherein a second subset of the pixels are modified in appearance relative to the current background of the external device such that the second subset of pixels represents one or more of: a third user interface object indicating the date; and a fourth user interface object indicating the time of day.

The operations described above with reference to FIG. 24 are, optionally, implemented by components depicted in FIGS. 1A-1B or FIG. 39. For example, displaying operation 2402 and optional receiving operation 2404 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 40:
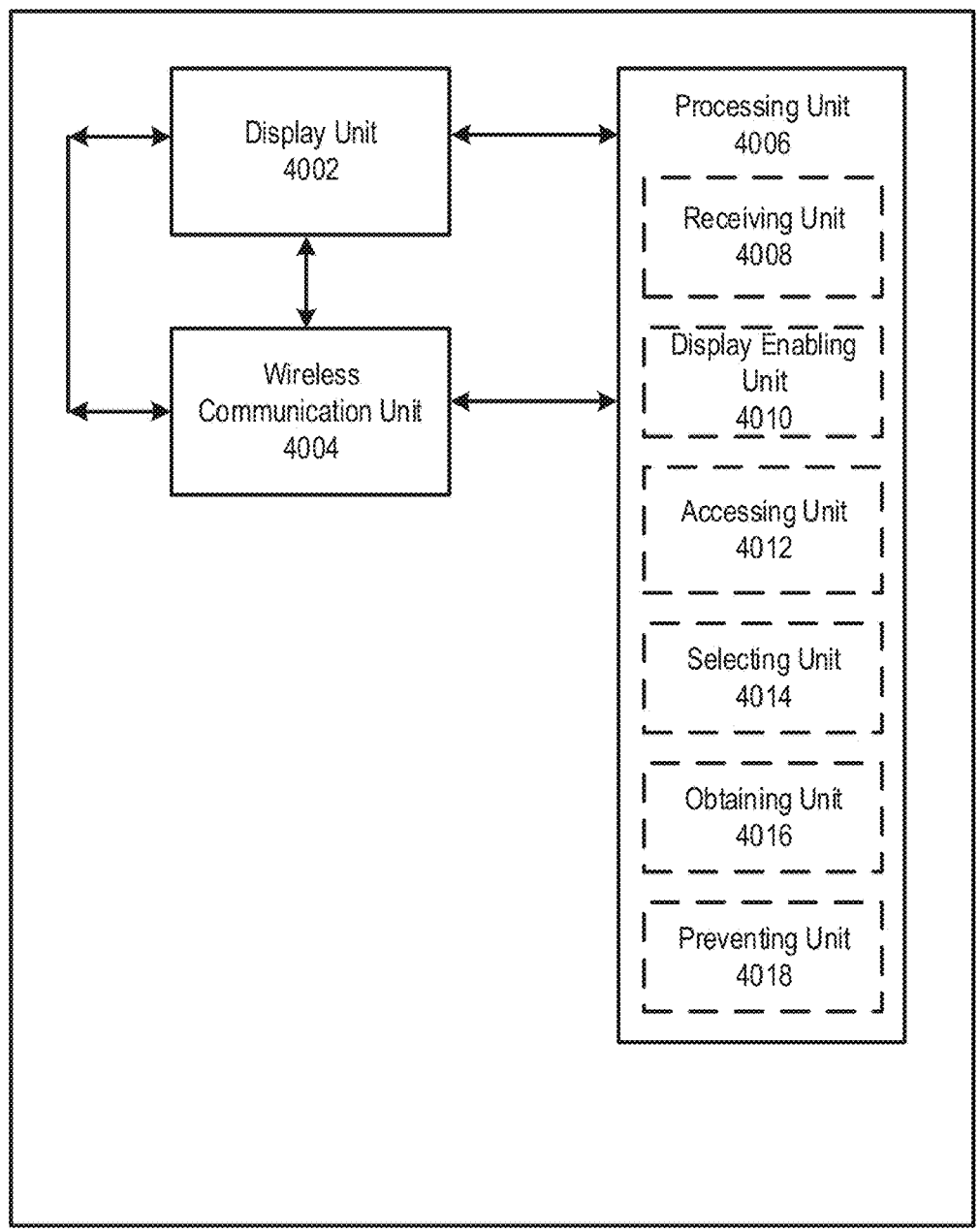
FIG. 40 is a functional block diagram of an electronic device in accordance with some embodiments.

In accordance with some embodiments, FIG. 40 shows an exemplary functional block diagram of an electronic device 4000 configured in accordance with the principles of the various described embodiments. In accordance with some embodiments, the functional blocks of electronic device 4000 are configured to perform the techniques described above. The functional blocks of the device 4000 are, optionally, implemented by hardware, software, or a combination of hardware and software to carry out the principles of the various described examples. It is understood by persons of skill in the art that the functional blocks described in FIG. 40 are, optional, combined or separated into sub-blocks to implement the principles of the various described examples. Therefore, the description herein optionally supports any possible combination or separation or further definition of the functional blocks described herein.

As shown in FIG. 40, an electronic device 4000 includes a display unit 4002 configured to display a graphic user interface, optionally, a wireless communication unit 4004 configured to send and/or receive wireless communications, and a processing unit 4006 coupled to the display unit 4002, and optionally, the wireless communication unit 4004. In some embodiments, device 4000 can optionally further include a touch-sensitive surface unit configured to receive contacts and coupled to the processing unit 4006. In some embodiments, the processing unit 4006 includes a receiving unit 4008, a display enabling unit 4010, an accessing unit 4012, a selecting unit 4014, an obtaining unit 4016, and a preventing unit 4018.

The processing unit 4006 is configured to access (e.g., with accessing unit 4012) a folder, the folder including two or more images; select (e.g., with selecting unit 4014) from the folder a first image; and enable display (e.g., with display enabling unit 4010), on the display unit (e.g., display unit 4002), of a user interface screen, the user interface screen comprising: a background based on the first image, the background comprising a plurality of pixels, wherein a subset of the pixels are modified in appearance relative to the image such that the subset of pixels represents one or more of: a first user interface object indicating a date; and a second user interface object indicating a time of day.

In some embodiments, the subset of the pixels is modified by color blending. In some embodiments, the subset of the pixels is modified by color blurring. In some embodiments, the subset of the pixels is modified in appearance relative to the image such that the subset of pixels represents the first user interface object indicating the date. In some embodiments, the subset of the pixels is modified in appearance relative to the image such that the subset of pixels represents the second user interface object indicating the time of day. In some embodiments, one of the first user interface object indicating the date and the second user interface object indicating the time of day is a first color independent of the background. In some embodiments, the processing unit 4006 is further configured to: receive (e.g., with receiving unit 4008) data representing a background color of the background at a position of the displayed first user interface object or the displayed second user interface object, wherein the first color is different from the background color at the position of the displayed first user interface object or the displayed second user interface object. In some embodiments, the processing unit 4006 is further configured to: after enabling display, on the display unit, of the first user interface screen, receive (e.g., with receiving unit 4008) first data representing a user input, and in response to receiving the first data representing the user input: obtain (e.g., with obtaining unit 4016) second data representing the displayed first background; select (e.g., with selecting unit 4014) a second image from the folder, wherein the second image is different from the first image; and enable display (e.g., with display enabling unit 4010), on the display unit (e.g., display unit 4002), of a second user interface screen, the second user interface screen comprising: a second background based on the second image, the second background comprising a second plurality of pixels, wherein a second subset of the pixels are modified in appearance relative to the second image such that the second subset of pixels represents one or more of: a third user interface object indicating a date; and a fourth user interface object indicating a time of day. In some embodiments, the processing unit 4006 is further configured to: receive (e.g., with receiving unit 4008) data representing a user prohibition of a third image from the folder; and in response to receiving the data: prevent (e.g., with preventing unit 4018) the display, on the display unit (e.g., display unit 4002), of the third image as a third background in response to a future user input. In some embodiments, at least one of the first background, the second background, and the third background is a photo. In some embodiments, the folder is stored on the electronic device 4000. In some embodiments, the electronic device 4000 further includes a wireless communication unit (e.g., wireless communication unit 4004), the processing unit 4006 is coupled to the wireless communication unit, and the folder is stored on an external device coupled to the electronic device 4000 via the wireless communication unit (e.g., wireless communication unit 4004). In some embodiments, accessing the folder comprises: receiving (e.g., with receiving unit 4008), via the wireless communication unit (e.g., wireless communication unit 4004), data representing at least one of the two or more backgrounds.

The operations described above with reference to FIG. 25 are, optionally, implemented by components depicted in FIGS. 1A-1B or FIG. 40. For example, accessing operation 2502, selecting operation 2504, and displaying operation 2506 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 41:
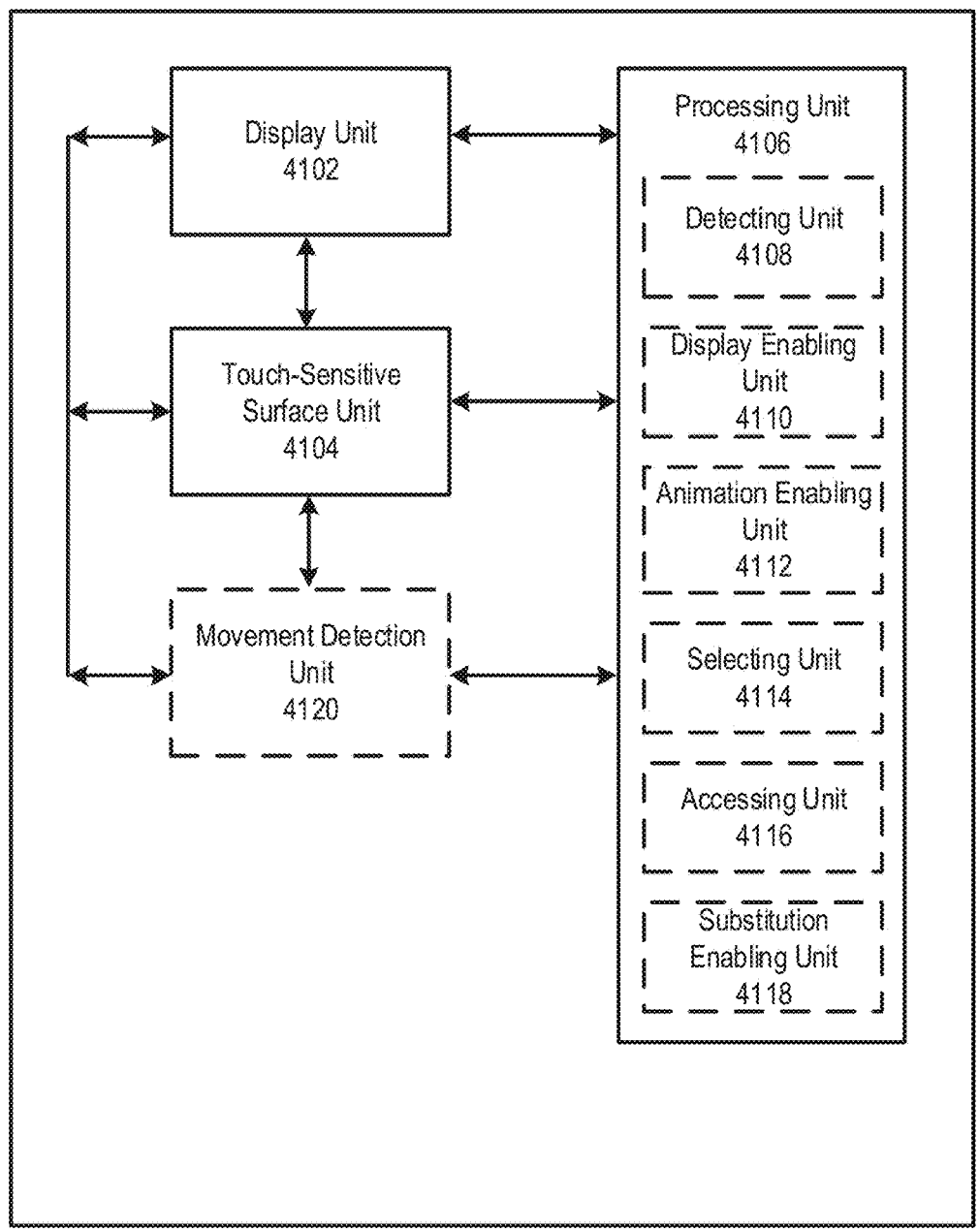
FIG. 41 is a functional block diagram of an electronic device in accordance with some embodiments.

In accordance with some embodiments, FIG. 41 shows an exemplary functional block diagram of an electronic device 4100 configured in accordance with the principles of the various described embodiments. In accordance with some embodiments, the functional blocks of electronic device 4100 are configured to perform the techniques described above. The functional blocks of the device 4100 are, optionally, implemented by hardware, software, or a combination of hardware and software to carry out the principles of the various described examples. It is understood by persons of skill in the art that the functional blocks described in FIG. 41 are, optionally, combined or separated into sub-blocks to implement the principles of the various described examples. Therefore, the description herein optionally supports any possible combination or separation or further definition of the functional blocks described herein.

As shown in FIG. 41, an electronic device 4100 includes a display unit 4102 configured to display a graphic user interface, optionally, a touch-sensitive surface unit 4104 configured to receive contacts, optionally, a movement detection unit 4120 configured to detect movement, and a processing unit 4106 coupled to the display unit 4102, optionally, the touch-sensitive surface unit 4104 and optionally, the movement detection unit 4120. In some embodiments, the processing unit 4106 includes a detecting unit 4108, a display enabling unit 4110, an animation enabling unit 4112, a selecting unit 4114, an accessing unit 4116, and a substitution enabling unit 4118.

The processing unit 4106 is configured to detect (e.g., with detecting unit 4108) a user input, wherein the user input is detected at a first time, and in response to detecting the user input: enable display (e.g., with display enabling unit 4110), on the display unit (e.g., display unit 4102), of a user interface screen, the user interface screen including: a first user interface object indicating the first time; and a second user interface object; and enable animation (e.g., with animation enabling unit 4112), on the display unit (e.g., display unit 4102), of the second user interface object, the animation comprising a sequential display of a first animated sequence, a second animated sequence after the first animated sequence, and a third animated sequence after the second animated sequence, wherein the first animated sequence, the second animated sequence, and the third animated sequence are different; after enabling animation of the second user interface object, detect (e.g., with detecting unit 4108) a second user input, wherein the second user input is detected at a second time, wherein the second time is after the first time, and in response to detecting the second user input: access (e.g., with accessing unit 4116) data representing the previously displayed second animated sequence; select (e.g., with selecting unit 4114) a fourth animated sequence, wherein the fourth animated sequence is different from the first animated sequence and the second animated sequence; enable display (e.g., with display enabling unit 4110), on the display unit (e.g., display unit 4102), of a second user interface screen, the second user interface screen including: the first user interface object, wherein the first user interface object is updated to indicate the second time; and a third user interface object related to the second user interface object; and enable animation (e.g., with animation enabling unit 4112), on the display unit (e.g., display unit 4102), of the third user interface object, the animation comprising a sequential display of the first animated sequence, the fourth animated sequence after the first animated sequence, and the third animated sequence after the fourth animated sequence.

In some embodiments, the third animated sequence is based on a reverse sequence of the first animated sequence. In some embodiments, the electronic device 4100 further comprises a movement detection unit (e.g., movement detection unit 4120), wherein the processing unit 4106 is coupled to the movement detection unit, and wherein the processing unit 4106 is further configured to enable detection of a movement of the electronic device via the movement detection unit (e.g., movement detection unit 4120), and wherein the user input represents a user movement of the electronic device 4100. In some embodiments, the electronic device 4100 further comprises a movement detection unit (e.g., movement detection unit 4120), wherein the processing unit 4106 is coupled to the movement detection unit, and wherein the processing unit 4106 is further configured to enable detection of a movement of the electronic device via the movement detection unit (e.g., movement detection unit 4120), and wherein the second user input represents a second user movement of the electronic device 4100. In some embodiments, the second user interface object and the third user interface object are the same. In some embodiments, the third user interface object is a reflection of the second user interface object. In some embodiments, the fourth animated sequence comprises a reflection of the second animated sequence about a horizontal axis. In some embodiments, the fourth animated sequence comprises a reflection of the second animated sequence about a vertical axis. In some embodiments, the processing unit 4106 is further configured to: detect (e.g., using detecting unit 4108) a contact on the touch-sensitive surface unit (e.g., touch-sensitive surface unit 4104), and in response to detecting the contact: enable substitution (e.g., with substitution enabling unit 4118), on the display unit (e.g., display unit 4102), of the second user interface object or the third user interface object with a display, on the display unit (e.g., display unit 4102), of a fourth user interface object, wherein the fourth user interface object is related to the second and the third user interface objects. In some embodiments, the first user interface object comprises a representation of a digital clock including a numerical indication of an hour and a numerical indication of a minute. In some embodiments, the first time is a current time.

The operations described above with reference to FIG. 26 are, optionally, implemented by components depicted in FIGS. 1A-1B or FIG. 41. For example, detecting operation 4102, displaying operation 4104, and animating operation 4106 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 42:
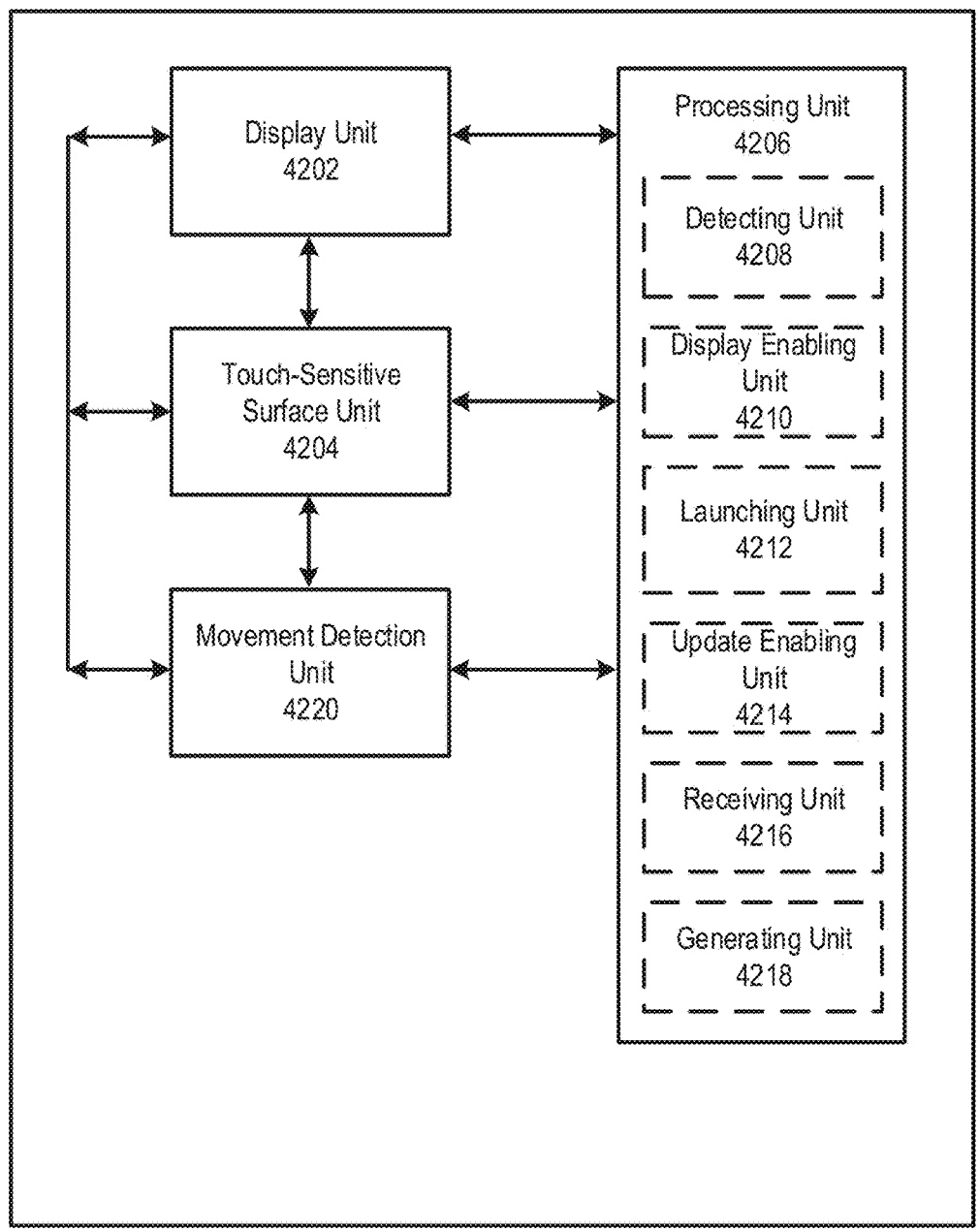
FIG. 42 is a functional block diagram of an electronic device in accordance with some embodiments.

In accordance with some embodiments, FIG. 42 shows an exemplary functional block diagram of an electronic device 4200 configured in accordance with the principles of the various described embodiments. In accordance with some embodiments, the functional blocks of electronic device 4200 are configured to perform the techniques described above. The functional blocks of the device 4200 are, optionally, implemented by hardware, software, or a combination of hardware and software to carry out the principles of the various described examples. It is understood by persons of skill in the art that the functional blocks described in FIG. 42 are, optionally, combined or separated into sub-blocks to implement the principles of the various described examples. Therefore, the description herein optionally supports any possible combination or separation or further definition of the functional blocks described herein.

As shown in FIG. 42, an electronic device 4200 includes a display unit 4202 configured to display a graphic user interface, optionally, a touch-sensitive surface unit 4204 configured to receive contacts, optionally, a movement detection unit 4220 configured to detect movement, and a processing unit 4206 coupled to the display unit 4202, optionally, the touch-sensitive surface unit 4204 and optionally, the movement detection unit 4220. In some embodiments, the processing unit 4206 includes a detecting unit 4208, a display enabling unit 4210, a launching unit 4212, an update enabling unit 4214, a receiving unit 4216, and a generating unit 4218.

The processing unit 4206 is configured to detect, by the movement detection unit (e.g., movement detection unit 4220), a user movement of the electronic device 4200; and, in response to detecting the movement: enable display (e.g., with display enabling unit 4210), on the display unit (e.g., display unit 4202), of an animated reveal of a clock face, wherein the animation comprises: enabling display (e.g., with display enabling unit 4210), on the display unit (e.g., display unit 4202), of an hour hand and a minute hand; and enabling display (e.g., with display enabling unit 4210), on the display unit (e.g., display unit 4202), of a first hour indication; and after displaying the first hour indication, enabling display (e.g., with display enabling unit 4210), on the display unit (e.g., display unit 4202), of a second hour indication, wherein the second hour indication is displayed on the clock face at a position after the first hour indication in a clockwise direction.

In some embodiments, the processing unit 4206 is further configured to: after enabling display (e.g., with display enabling unit 4210), on the display unit (e.g., display unit 4202), of the second hour indication, enable display (e.g., with display enabling unit 4210), on the display unit (e.g., display unit 4202), of a first minute indication; and enable display (e.g., with display enabling unit 4210); on the display unit (e.g., display unit 4202), of a second minute indication, wherein the second minute indication is displayed on the clock face at a position after the first minute indication in a clockwise direction. In some embodiments, the hour hand and the minute hand are displayed before the first hour indication. In some embodiments, the processing unit 4206 is further configured to: enable display (e.g., with display enabling unit 4210), on the display unit (e.g., display unit 4202), of an animated reveal of an outline of the clock face, wherein the outline of the clock face is animated to be displayed progressively in a clockwise direction. In some embodiments, after the animation, the clock face indicates a current time. In some embodiments, the processing unit 4206 is further configured to: enable display (e.g., with display enabling unit 4210), on the display unit (e.g., display unit 4202), of an affordance as a complication on the clock face, wherein the affordance represents an application; detect (e.g., with detecting unit 4208) a contact on the affordance on the touch-sensitive surface unit 4204), and in response to detecting the contact: launch (e.g., with launching unit 4212) the application represented by the affordance. In some embodiments, the processing unit 4206 is further configured to: enable update (e.g., with update enabling unit 4214), on the display unit (e.g., display unit 4202), of a color of the clock face, wherein updating the color comprises continuously changing the color of the clock face over time. In some embodiments, the color of the clock face is a background color of the clock face. In some embodiments, the clock face comprises a seconds hand, and the color of the clock face is a color of a seconds hand. In some embodiments, the processing unit 4206 is further configured to: detect (e.g., with detecting unit 4208), by the movement detection unit (e.g., movement detection unit 4220), a second user movement of the electronic device 4200; and, in response to detecting the second movement: enable display (e.g., with display enabling unit 4210), on the display unit (e.g., display unit 4202), of a second color of the clock face, wherein the second color is different from the first color: and enable update (e.g., with update enabling unit 4214), on the display unit (e.g., display unit 4202), of the second color of the clock face, wherein updating the second color comprises continuously changing the second color of the clock face over time. In some embodiments, the processing unit 4206 is further configured to: receive (e.g., with receiving unit 4216) data representing a name; and in response to receiving the data: generate (e.g., with generating unit 4218) a monogram; and enable display (e.g., with display enabling unit 4210), on the display unit (e.g., display unit 4202), of the monogram as a second affordance on the clock face.

The operations described above with reference to FIG. 27A are, optionally, implemented by components depicted in FIGS. 1A-1B or FIG. 42. For example, detecting operation 2702 and displaying operation 2704 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 43:
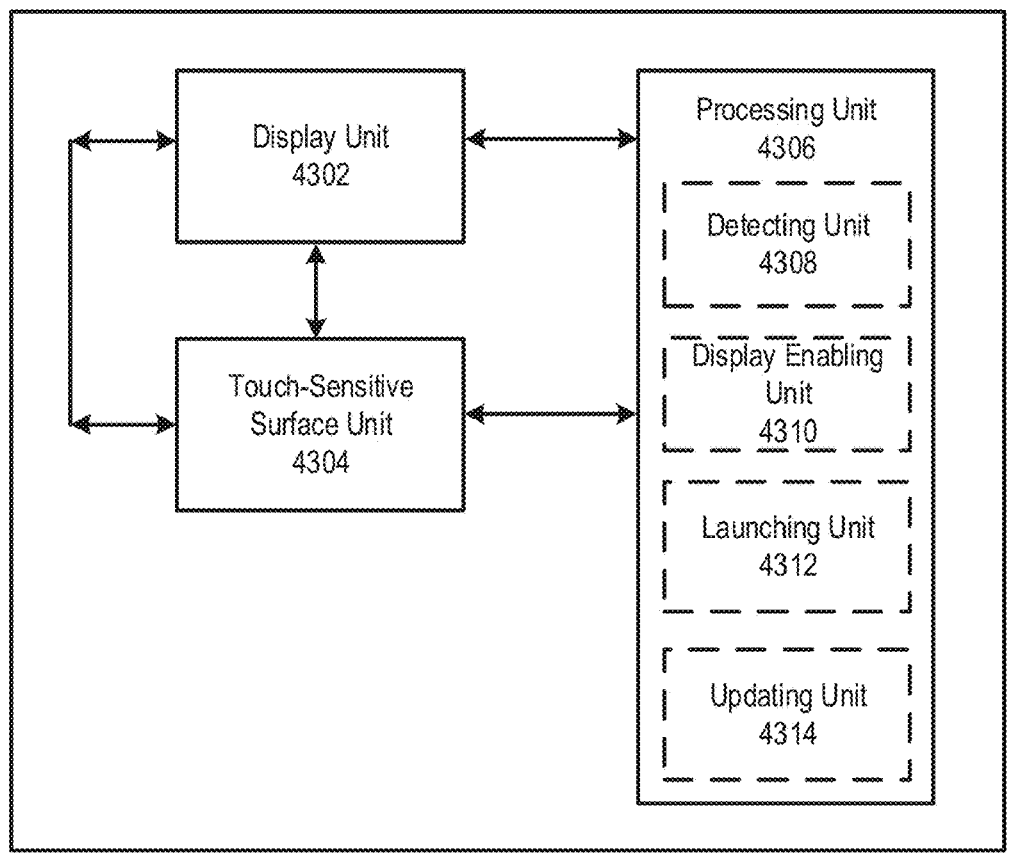
FIG. 43 is a functional block diagram of an electronic device in accordance with some embodiments.

In accordance with some embodiments, FIG. 43 shows an exemplary functional block diagram of an electronic device 4300 configured in accordance with the principles of the various described embodiments. In accordance with some embodiments, the functional blocks of electronic device 4300 are configured to perform the techniques described above. The functional blocks of the device 4300 are, optionally, implemented by hardware, software, or a combination of hardware and software to carry out the principles of the various described examples. It is understood by persons of skill in the art that the functional blocks described in FIG. 43 are, optionally, combined or separated into sub-blocks to implement the principles of the various described examples. Therefore, the description herein optionally supports any possible combination or separation or further definition of the functional blocks described herein.

As shown in FIG. 43, an electronic device 4300 includes a display unit 4302 configured to display a graphic user interface, optionally, a touch-sensitive surface unit 4304 configured to receive contacts, and a processing unit 4306 coupled to the display unit 4302, and optionally, the touch-sensitive surface unit 4304. In some embodiments, the processing unit 4306 includes a detecting unit 4308, a display enabling unit 4310, a launching unit 4312, and an updating unit 4314.

The processing unit 4306 is configured to enable display (e.g., with display enabling unit), on the display unit (e.g., display unit 4302), of a user interface screen, the user interface screen including: a clock face; and an affordance, wherein the affordance represents an application, wherein the affordance comprises a set of information obtained from the application, wherein the set of information is updated (e.g., with updating unit 4314) in accordance with data from the application, and wherein the affordance is displayed as a complication on the clock face; detect (e.g., with detecting unit 4308) a contact on the displayed affordance on the touch-sensitive surface unit (e.g., touch-sensitive surface 4304), and in response to detecting the contact: launch (e.g., with launching unit 4312) the application represented by the affordance.

The operations described above with reference to FIG. 32 are, optionally, implemented by components depicted in FIGS. 1A-1B or FIG. 43. For example, displaying operation 3202, detecting operation 3204, and launching operation 3206 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 44:
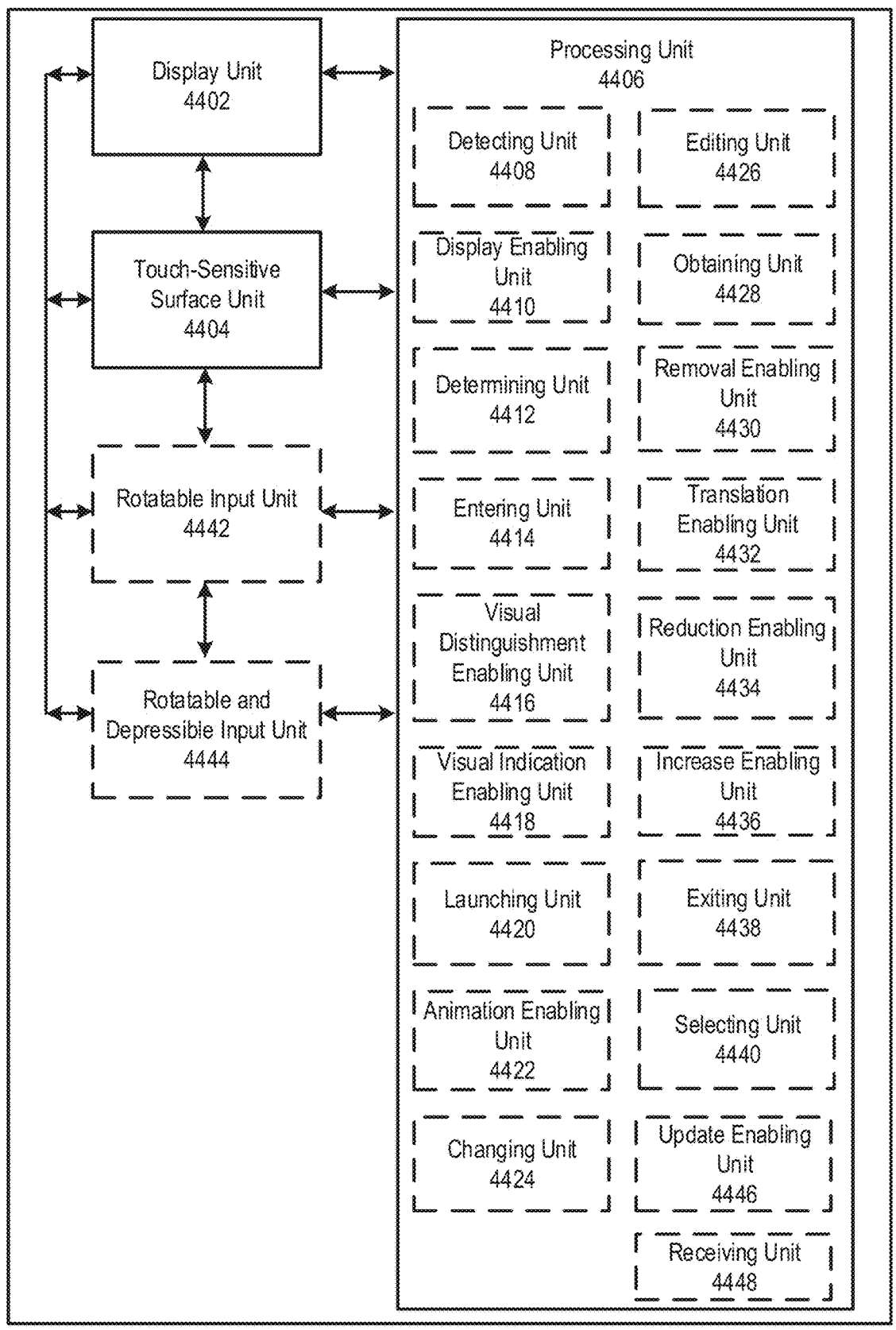
FIG. 44 is a functional block diagram of an electronic device in accordance with some embodiments.

In accordance with some embodiments, FIG. 44 shows an exemplary functional block diagram of an electronic device 4400 configured in accordance with the principles of the various described embodiments. In accordance with some embodiments, the functional blocks of electronic device 4400 are configured to perform the techniques described above. The functional blocks of the device 4400 are, optionally, implemented by hardware, software, or a combination of hardware and software to carry out the principles of the various described examples. It is understood by persons of skill in the art that the functional blocks described in FIG. 44 are, optionally, combined or separated into sub-blocks to implement the principles of the various described examples. Therefore, the description herein optionally supports any possible combination or separation or further definition of the functional blocks described herein.

As shown in FIG. 44, an electronic device 4400 includes a display unit 4402 configured to display a graphic user interface, optionally, a touch-sensitive surface unit 4404 configured to receive contacts and to detect intensity of contacts, optionally, a rotatable input unit 4442 configured to receive rotatable input (e.g., from a rotatable input mechanism), optionally, a rotatable and depressible input unit 4444 configured to receive rotatable and depressible input (e.g., from a rotatable and depressible input mechanism), and a processing unit 4206 coupled to the display unit 4202, optionally, the touch-sensitive surface unit 4204, optionally, the rotatable input unit 4442, and optionally, the rotatable and depressible input unit 4444. In some embodiments, the processing unit 4406 includes a detecting unit 4408, a display enabling unit 4410, a determining unit 4412, an entering unit 4414, a visual distinguishment enabling unit 4416, a visual indication enabling unit 4418, a launching unit 4420, an animation enabling unit 4422, a changing unit 4424, an editing unit 4426, an obtaining unit 4428, a removal enabling unit 4430, a translation enabling unit 4432, an exiting unit 4438, a reduction enabling unit 4434, an increase enabling unit 4436, a selecting unit 4440, an update enabling unit 4446, and a receiving unit 4448.

The processing unit 4406 is configured to enable display (e.g., with display enabling unit 4410), on the display unit (e.g., 4402), of a user interface screen including a clock face; detect (e.g., with detecting unit 4408) a contact on the touch-sensitive surface unit (e.g., 4404), the contact having a characteristic intensity, and in response to detecting the contact: determine (e.g., with determining unit 4412) whether the characteristic intensity is above an intensity threshold; and in accordance with a determination that the characteristic intensity is above the intensity threshold: enter (e.g., with entering unit 4414) a clock face edit mode of the electronic device; enable visual distinguishment (e.g., with visual distinguishment enabling unit 4416, on the display unit (e.g., display unit 4402), of the displayed clock face to indicate the clock face edit mode; and detect (e.g., with detecting unit 4408) a second contact on the touch-sensitive surface unit, wherein the second contact is on the visually distinguished displayed clock face, and in response to detecting the second contact: enable visual indication (e.g., with visual indication enabling unit 4418), on the display unit (e.g., display unit 4402), of an element of the clock face for editing.

In some embodiments, the clock face includes an affordance representing an application, wherein the contact is on the affordance representing the application on the touch-sensitive surface unit, and wherein the processing unit 4406 is further configured to: in accordance with a determination that the characteristic intensity is not above the intensity threshold: launch (e.g., with launching unit 4420) the application represented by the affordance. In some embodiments, enabling visual distinguishment (e.g., with visual distinguishment enabling unit 4416), on the display unit (e.g., display unit 4402), of the displayed clock face comprises reducing size of the displayed clock face. In some embodiments, enabling visual indication (e.g., with visual indication enabling unit 4418), on the display unit (e.g., display unit 4402), of the element of the clock face for editing comprises: enabling visual distinguishment enabling unit 4416), on the display unit (e.g., display unit 4402), of an outline around the element of the clock face. In some embodiments, the processing unit 4406 is further configured to: enable animation (e.g., with animation enabling unit 4422), on the display unit (e.g., 4402), of the outline around the element of the clock face to depict a rhythmic expansion and contraction of the outline. In some embodiments, visually indicating the element of the clock face for editing comprises: enabling animation (e.g., with animation enabling unit 4422), on the display unit (e.g., 4402), of the element of the clock face to depict a rhythmic expansion and contraction of the element of the clock face. In some embodiments, visually indicating the element of the clock face for editing comprises: enabling animation (e.g., with animation enabling unit 4422), on the display unit (e.g., 4402), of the element of the clock face to depict a flashing of the element of the clock face. In some embodiments, the processing unit 4406 is further configured to enable change (e.g., with changing unit 4424), on the display unit (e.g., 4402), of a color of the element of the clock face, and wherein visually indicating the element of the clock face for editing comprises: changing the color of the element of the clock face. In some embodiments, the electronic device further comprises a rotatable input unit (e.g., rotatable input unit 4442), wherein the processing unit 4406 is coupled to the rotatable input unit, and wherein the processing unit 4406 is further configured to: after entering the clock face edit mode: detect (e.g., with detecting unit 4408) a movement corresponding to a rotatable input from the rotatable input unit (e.g., rotatable input unit 4442), and in response to detecting the movement: edit (e.g., with editing unit 4426) an aspect of the visually indicated element of the clock face. In some embodiments, the processing unit 4406 is further configured to enable change (e.g., with changing unit 4424), on the display unit (e.g., 4402), of a color of the visually indicated element of the clock face, and wherein editing the aspect of the visually indicated element of the clock face comprises: enabling change (e.g., with changing unit 4424), on the display unit (e.g., display unit 4402), of the color of the visually indicated element of the clock face. In some embodiments, the processing unit 4406 is further configured to enable change (e.g., with changing unit 4424), on the display unit (e.g., 4402), of a color of the visually indicated element of the clock face, wherein the visually indicated element of the clock face is a clock face background, and wherein editing (e.g., with editing unit 4426) the aspect of the visually indicated element of the clock face comprises: enabling change (e.g., with changing unit 4424), on the display unit (e.g., display unit 4402), of the color of the clock face background. In some embodiments, the processing unit 4406 is further configured to enable change (e.g., with changing unit 4424), on the display unit (e.g., 4402), of a color of the visually indicated element of the clock face, wherein the clock face comprises a seconds hand, and wherein editing (e.g., with editing unit 4426) the aspect of the visually indicated element of the clock face comprises: enabling change (e.g., with changing unit 4424), on the display unit (e.g., display unit 4402) of a color of the seconds hand. In some embodiments, the clock face comprises an affordance representing an application, wherein the affordance is displayed, on the display unit (e.g., display unit 4402), as a complication on the clock face, wherein the affordance indicates a first set of information obtained from the application, and wherein editing (e.g., with changing unit 4424) the aspect of the visually indicated element of the clock face comprises enabling update (e.g., with updating unit 4446), on the display unit (e.g., display unit 4402), of the affordance to indicate a second set of information obtained from the application. In some embodiments, the clock face comprises an affordance representing an application, wherein the affordance is displayed as a complication on the clock face on the display unit, wherein the affordance indicates a set of information obtained from a first application, wherein editing the aspect of the visually indicated element of the clock face comprises enabling update (e.g., with updating unit 4446), on the display unit (e.g., display unit 4402), of the affordance to indicate a set of information obtained from a second application, and wherein the first and the second applications are different. In some embodiments, the clock face comprises a plurality of visible divisions of time, wherein the plurality comprises a first number of visible divisions of time, and wherein editing the aspect of the visually indicated element of the clock face comprises enabling change (e.g., with changing unit 4424), on the display unit, of the first number of visible divisions of time in the plurality to a second number of visible divisions of time in the plurality. In some embodiments, the second number is greater than the first number. In some embodiments, the second number is less than the first number. In some embodiments, the processing unit 4406 is further configured to: after entering the clock face edit mode: enable display (e.g., with display enabling unit 4410), on the display unit (e.g., 4402), of an indicator of position along a series of positions, the indicator indicating a first position along the series; and in response to receiving the data indicating the rotatable input of the rotatable input unit (e.g., rotatable input unit 4442): enable update (e.g., with update enabling unit 4446), on the display unit (e.g., display unit 4402), of the indicator of position to indicate a second position along the series. In some embodiments, the indicator of position along a series of positions indicates a position of a currently selected option for the editable aspect along a series of selectable options for the editable aspect of the visually indicated element of the clock face. In some embodiments, the indicator is displayed on the display at a position adjacent to the rotatable input unit. In some embodiments, the editable aspect of the visually indicated element of the clock face is color, and wherein the indicator comprises a series of colors, wherein each position in the series depicts a color, and wherein the color of the currently indicated position along the series is representative of the color of the visually indicated element. In some embodiments, the processing unit 4406 is further configured to: after visually indicating the element of the clock face for editing: detect (e.g., with detecting unit 4408) a third contact on the touch-sensitive surface unit (e.g., touch-sensitive surface unit 4404) at a second displayed element of the clock face, and in response to detecting the third contact: enable removal (e.g., with removal enabling unit 4430), on the display unit (e.g., display unit 4402), of the visual indication of the first element of the clock face for editing; and enable visual indication (e.g., with visual indication enabling unit 4418), on the display unit (e.g., display unit 4402), of the second element of the clock face for editing. In some embodiments, before detecting the third contact, the indicated first element of the clock face is indicated by an outline around the element, wherein enabling removal (e.g., with removal enabling unit 4430) of the visual indication of the first element comprises: enabling translation (e.g., with translation enabling unit 4432), on the display unit (e.g., display unit 4402), of the outline on-screen away from the first element. In some embodiments, enabling visual indication (e.g., with visual indication enabling unit 4418), on the display unit (e.g., display unit 4402), of the second element of the clock face for editing comprises: enabling translation (e.g., with translation enabling unit 4432), on the display unit (e.g., display unit 4402), of a visible outline on-screen towards from the second element; and enabling display (e.g., with display enabling unit 4410), on the display unit (e.g., 4402), of the visible outline around the second element, wherein the translating and the displaying comprise a continuous on-screen movement of the visible outline. In some embodiments, the processing unit 4406 is further configured to: after enabling visual indication (e.g., with visual indication enabling unit 4418), on the display (e.g., display unit 4402), of the first element of the clock face for editing, detect a swipe on the touch-sensitive surface unit, and in response to detecting the swipe: enable removal (e.g., with removal enabling unit 4430), on the display unit (e.g., display unit 4402), of the visual indication of the first element of the clock face for editing; enable visual indication (e.g., with visual indication enabling unit 4418), on the display unit (e.g., display unit 4402), of a second element of the clock face for editing; after visually indicating the second element of the clock face for editing, detect a user input, and in response to detecting the user input: edit (e.g., with editing unit 4426) a second aspect of the visually indicated second element of the clock face, wherein the second aspect of the second element is different from the first aspect of the first element of the clock face. In some embodiments, the processing unit 4406 is further configured to: enable display (e.g., with display enabling unit 4410), on the display unit (e.g., 4402), of a paging affordance on the user interface screen, wherein the paging affordance indicates an editable aspect of the currently indicated element of the clock face, a position of the editable aspect of the currently indicated element within a sequence of editable aspects, and a total number of editable aspects within the sequence of editable aspects. In some embodiments, the processing unit 4406 is further configured to: after entering the clock face edit mode of the electronic device: detect (e.g., with detecting unit 4408) a fourth contact on the touch-sensitive surface unit (e.g., touch-sensitive surface unit 4404), the fourth contact having a second characteristic intensity, and in response to detecting the fourth contact; determine (e.g., with determining unit 4412) whether the second characteristic intensity is above a second intensity threshold; and in accordance with a determination that the second characteristic intensity is above the second intensity threshold: exit (e.g., with exiting unit 4438) the clock face edit mode; and enable cessation, on the display unit (e.g., display unit 4402), of the visual distinguishment (e.g., enabling the cessation of the visual distinguishment with visual distinguishment unit 4416), on the display unit (e.g., display unit 4402), of the displayed clock face. In some embodiments, enabling visual distinguishment (e.g., with visual distinguishment unit 4416), on the display unit (e.g., display unit 4402), of the displayed clock face to indicate the clock face edit mode further comprises reducing a size of the displayed clock face, and wherein enabling cessation, on the display unit, of the visual distinguishment of the displayed clock face comprises enabling an increase (e.g., with increase enabling unit 4436), on the display unit (e.g., display unit 4402), of the size of the displayed clock face. In some embodiments, the electronic device further comprises a rotatable and depressible input unit (e.g., rotatable and depressible input unit 4444), wherein the processing unit 4406 is coupled to the rotatable and depressible input unit, and wherein the processing unit 4406 is further configured to: after entering the clock face edit mode of the electronic device: detect (e.g., with detecting unit 4408) a depression corresponding to a rotatable and depressible input from the rotatable and depressible input unit (e.g., rotatable and depressible input unit 4444), and in response to detecting the depression: exit (e.g., with exiting unit 4438) the clock face edit mode; and enable cessation, on the display unit, of the visual distinguishment (e.g., enabling the cessation of the visual distinguishment with visual distinguishment unit 4416), on the display unit (e.g., display unit 4402), of the displayed clock face. In some embodiments, enabling visual distinguishment, on the display unit, of the displayed clock face to indicate the clock face edit mode comprises: enabling a reduction (e.g., with reduction enabling unit 4434), on the display unit (e.g., display unit 4402), of a size of the displayed clock face, and wherein enabling cessation, on the display unit, of the visual distinguishment (e.g., enabling the cessation of the visual distinguishment with visual distinguishment unit 4416), on the display unit (e.g., display unit 4402), of the displayed clock face comprises: enabling an increase (e.g., with increase enabling unit 4436), on the display unit (e.g., display unit 4402), of the size of the displayed clock face. In some embodiments, the processing unit 4406 is further configured to: receive (e.g., with receiving unit 4448) a user input, and in response to receiving the user input: enter (e.g., with entering unit 4414) a color selection mode of the electronic device 4400; while in the color selection mode of the electronic device 4400, receive (e.g., with receiving unit 4448) data representing an image, and in response to receiving the data: select (e.g., with selecting unit 4440) a color of the image; and enable update (e.g., with update enabling unit 4446), on the display unit (e.g., display unit 4402), of the displayed clock face, wherein enabling update the displayed clock face comprises enabling change (e.g., with changing unit 4424), on the display unit (e.g., 4402), of a color of the clock face to the color of the image. In some embodiments, selecting the color of the image comprises selecting a color with greatest prevalence in the image.

The operations described above with reference to FIG. 28 are, optionally, implemented by components depicted in FIGS. 1A-1B or FIG. 44. For example, displaying operation 2802, detecting operation 2804, and determining operation 2806 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 45:
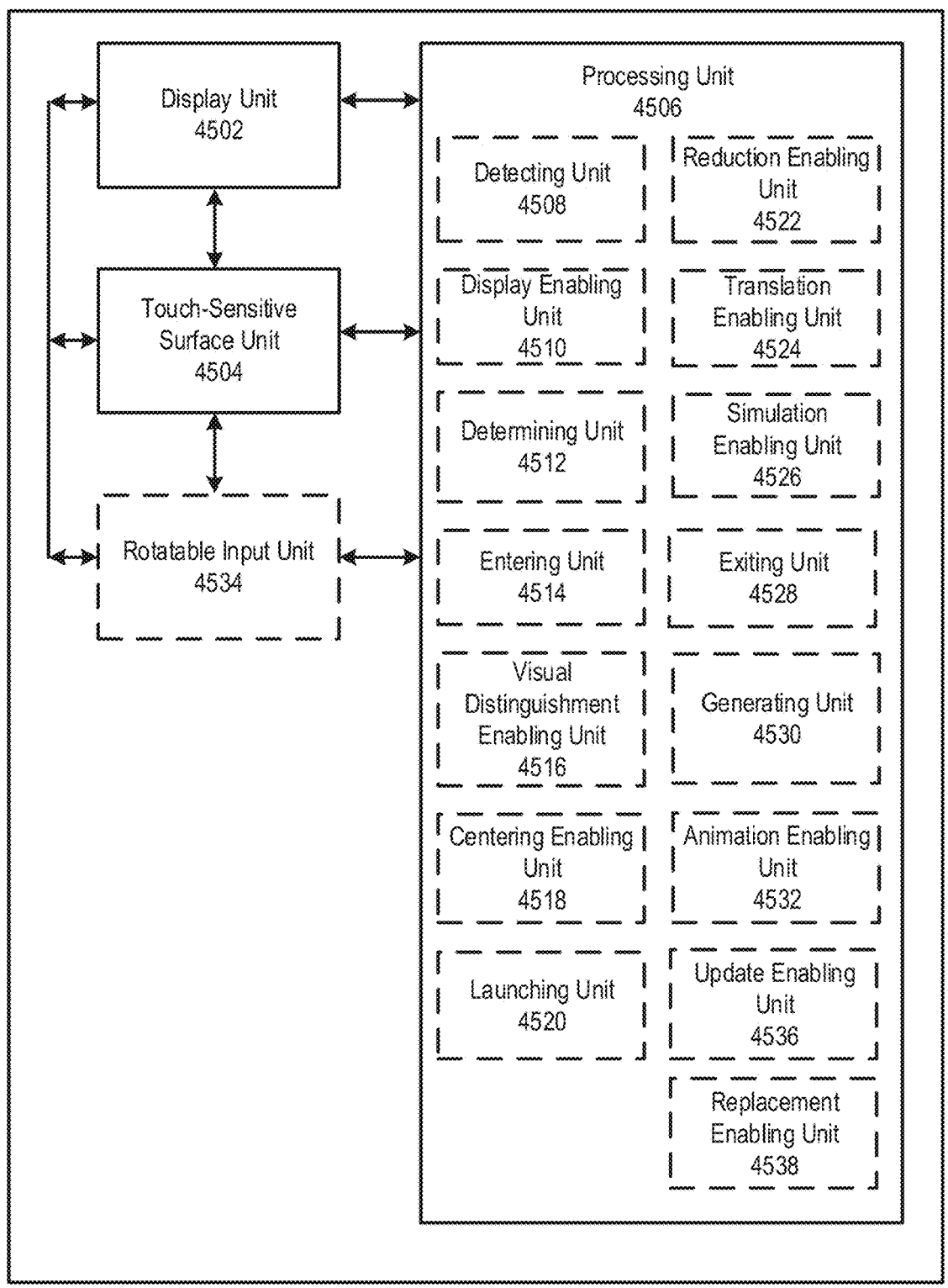
FIG. 45 is a functional block diagram of an electronic device in accordance with some embodiments.

In accordance with some embodiments, FIG. 45 shows an exemplary functional block diagram of an electronic device 4500 configured in accordance with the principles of the various described embodiments. In accordance with some embodiments, the functional blocks of electronic device 4500 are configured to perform the techniques described above. The functional blocks of the device 4500 are, optionally, implemented by hardware, software, or a combination of hardware and software to carry out the principles of the various described examples. It is understood by persons of skill in the art that the functional blocks described in FIG. 45 are, optionally, combined or separated into sub-blocks to implement the principles of the various described examples. Therefore, the description herein optionally supports any possible combination or separation or further definition of the functional blocks described herein.

As shown in FIG. 45, an electronic device 4500 includes a display unit 4502 configured to display a graphic user interface, optionally, a touch-sensitive surface unit 4504 configured to receive contacts and to detect intensity of contacts, and a processing unit 4506 coupled to the display unit 4502, and optionally, the touch-sensitive surface unit 4504. In some embodiments, the processing unit 4506 includes a detecting unit 4508, a display enabling unit 4510, a determining unit 4512, an entering unit 4514, a visual distinguishment enabling unit 4516, a centering enabling unit 4518, a launching unit 4520, a reduction enabling unit 4522, a translation enabling unit 4524, a simulation enabling unit 4526, an exiting unit 4528, a generating unit 4530, and an animation enabling unit 4532.

The processing unit 4506 is configured to enable display, on the display unit, on the touch-sensitive surface unit (e.g., touch-sensitive surface unit 4504) a user interface screen including a clock face; enable display (e.g., with display enabling unit 4510), on the display unit (e.g., display unit 4502), on the touch-sensitive surface unit (e.g., touch-sensitive surface unit 4504) (e.g., touch-sensitive surface unit 4504) a user interface screen including a clock face; detect a contact on the touch-sensitive surface unit (e.g., touch-sensitive surface unit 4504), the contact having a characteristic intensity, and in response to detecting the contact: determine (e.g., with determining unit 4512) whether the characteristic intensity is above an intensity threshold; and in accordance with a determination that the characteristic intensity is above the intensity threshold: enter (e.g., with entering unit 4514) a clock face selection mode of the electronic device; enable visual distinguishment (e.g, with visual distinguishment enabling unit 4516), on the display unit (e.g., display unit 4502), of the displayed clock face to indicate the clock face selection mode, wherein the displayed clock face is centered on the display; and detect (e.g., with detecting unit 4508) a swipe on the touch-sensitive surface unit (e.g., touch-sensitive surface unit 4504), and in response to detecting the swipe: enable centering (e.g., with centering enabling unit 4518), on the display unit (e.g., display unit 4502), of a second clock face.

In some embodiments, the clock face includes an affordance representing an application, wherein the contact is on the affordance representing the application on the touch-sensitive surface unit (e.g., touch-sensitive surface unit 4504), and the processing unit is further configured to: in accordance with a determination that the characteristic intensity is not above the intensity threshold: launch (e.g., with launching unit 4520) the application represented by the affordance. In some embodiments, visually distinguishing the displayed clock face to indicate the clock face selection mode comprises enabling reduction (e.g., with reduction enabling unit 4522), on the display unit (e.g., display unit 4502), of the size of the displayed clock face. In some embodiments, the first and the second clock faces are among a plurality of clock faces, the plurality including at least the first and the second clock face. In some embodiments, entering the clock face selection mode of the electronic device further comprises: enabling display (e.g., with display enabling unit 4510), on the display unit (e.g., display unit 4502), of at least the first and the second clock faces from the plurality of clock faces, wherein the displayed clock faces are shown at a reduced size and arranged in a sequence of clock faces, and wherein the clock faces in the sequence that are not currently centered are displayed in a partial view. In some embodiments, the second clock face is arranged after the first clock face in the sequence of clock faces, wherein enabling centering (e.g., with centering enabling unit 4518), on the display unit (e.g., display unit 4502), of the second clock face comprises: enabling translation (e.g., with translation enabling unit 4524), on the display unit (e.g., display unit 4502), of the first clock face on-screen; and enabling display (e.g., with display enabling unit 4510), on the display unit (e.g., display unit 4502), of a partial view of the first clock face. In some embodiments, centering the second clock face on the display comprises: enabling translation (e.g., with translation enabling unit 4524), on the display unit (e.g., display unit 4502), of the second clock face onto the displayed user interface screen; and enabling translation (e.g., with translation enabling unit 4524), on the display unit (e.g., display unit 4502), of the first clock face off of the displayed user interface screen. In some embodiments, enabling centering (e.g., with centering enabling unit 4518), on the display unit (e.g., display unit 4502), of the second clock face on the display comprises enabling simulation (e.g., with simulation enabling unit 4526), on the display unit (e.g., display unit 4502), of a movement of the second clock face towards the user on the display. In some embodiments, the processing unit is further configured to: after centering the second clock face on the display: detect (e.g., with detecting unit 4508) a contact on the displayed second clock face on the touch-sensitive surface unit (e.g., touch-sensitive surface unit 4504), and in response to detecting the contact: exit (e.g., with exiting unit 4528) the clock face selection mode; and enable display (e.g., with display enabling unit 4510), on the display unit (e.g., display unit 4502), of a second user interface screen including the second clock face. In some embodiments, the processing unit is further configured to: after entering the clock face selection mode: detect (e.g., with detecting unit 4508) a second swipe on the touch-sensitive surface unit (e.g., touch-sensitive surface unit 4504), and in response to detecting the second swipe: enable centering (e.g., with centering enabling unit 4518), on the display unit (e.g., display unit 4502), of a clock face generation affordance on the display; detect (e.g., with detecting unit 4508) a contact on the displayed clock face generation affordance, and in response to detecting the contact: generate (e.g., with generating unit 4530) a third clock face; and enable display (e.g., with display enabling unit 4510), on the display unit (e.g., display unit 4502), of the third clock face, wherein the third clock face is centered on the display. In some embodiments, the processing unit is further configured to: after entering the clock face selection mode, and before detecting the second swipe: enable display (e.g., with display enabling unit 4510), on the display unit (e.g., display unit 4502), of at least a partial view of the clock face generation affordance on the user interface screen. In some embodiments, the processing unit is further configured to: after entering the clock face selection mode: detect (e.g., with detecting unit 4508) a third swipe on the touch-sensitive surface unit (e.g., touch-sensitive surface unit 4504), and in response to detecting the third swipe: enable centering (e.g., with centering enabling unit 4518), on the display unit (e.g., display unit 4502), of a random clock face generation affordance on the display; detect (e.g., with detecting unit 4508) a contact on the displayed random clock face generation affordance on the touch-sensitive surface unit (e.g., touch-sensitive surface unit 4504), and in response to detecting the contact: generate (e.g., with generating unit 4530) a fourth clock face, wherein the fourth clock face is randomly generated; and enable display (e.g., with display enabling unit 4510), on the display unit (e.g., display unit 4502), of the fourth clock face, wherein the fourth clock face is centered on the display. In some embodiments, the fourth clock face is different from the first clock face, the second clock face, and the third clock face. In some embodiments, the processing unit is further configured to: after entering the clock face selection mode, and before detecting the third swipe: enable display (e.g., with display enabling unit 4510), on the display unit (e.g., display unit 4502), of at least a partial view of the random clock face generation affordance on the user interface screen. In some embodiments, enabling centering (e.g., with centering enabling unit 4518), on the display unit (e.g., display unit 4502), of the first clock face, the second clock face, the third clock face, or the fourth clock face further comprises: enabling visible distinguishment (e.g., with visual distinguishment enabling unit 4516), on the display unit (e.g., display unit 4502) of an outline around the centered clock face. In some embodiments, the processing unit is further configured to: enable animation (e.g., with animation enabling unit 4532), on the display unit (e.g., display unit 4502), of the outline around the centered clock face to depict a rhythmic expansion and contraction of the outline. In some embodiments, enabling centering (e.g., with centering enabling unit 4518), on the display unit (e.g., display unit 4502), of the first clock face, the second clock face, the third clock face, or the fourth clock face further comprises: enabling animation (e.g., with animation enabling unit 4532), on the display unit (e.g., display unit 4502), of the centered clock face to depict a rhythmic expansion and contraction of the centered clock face. In some embodiments, enabling centering (e.g., with centering enabling unit 4518), on the display unit (e.g., display unit 4502), of the first clock face, the second clock face, the third clock face, or the fourth clock face further comprises: enabling animation (e.g., with animation enabling unit 4532), on the display unit (e.g., display unit 4502), of the centered clock face to depict a flashing of the centered clock face. In some embodiments, the processing unit is further configured to: enable display (e.g., with display enabling unit 4510), on the display unit (e.g., display unit 4502), of a paging affordance on the user interface screen, wherein the paging affordance indicates the currently centered clock face, a position of the centered clock face within a sequence of clock faces, and a total number of clock faces within the sequence of clock faces.

The operations described above with reference to FIGS. 29-30 are, optionally, implemented by components depicted in FIGS. 1A-1B or FIG. 45. For example, displaying operation 2902, detecting operation 2904, and determining operation 2906 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 46:
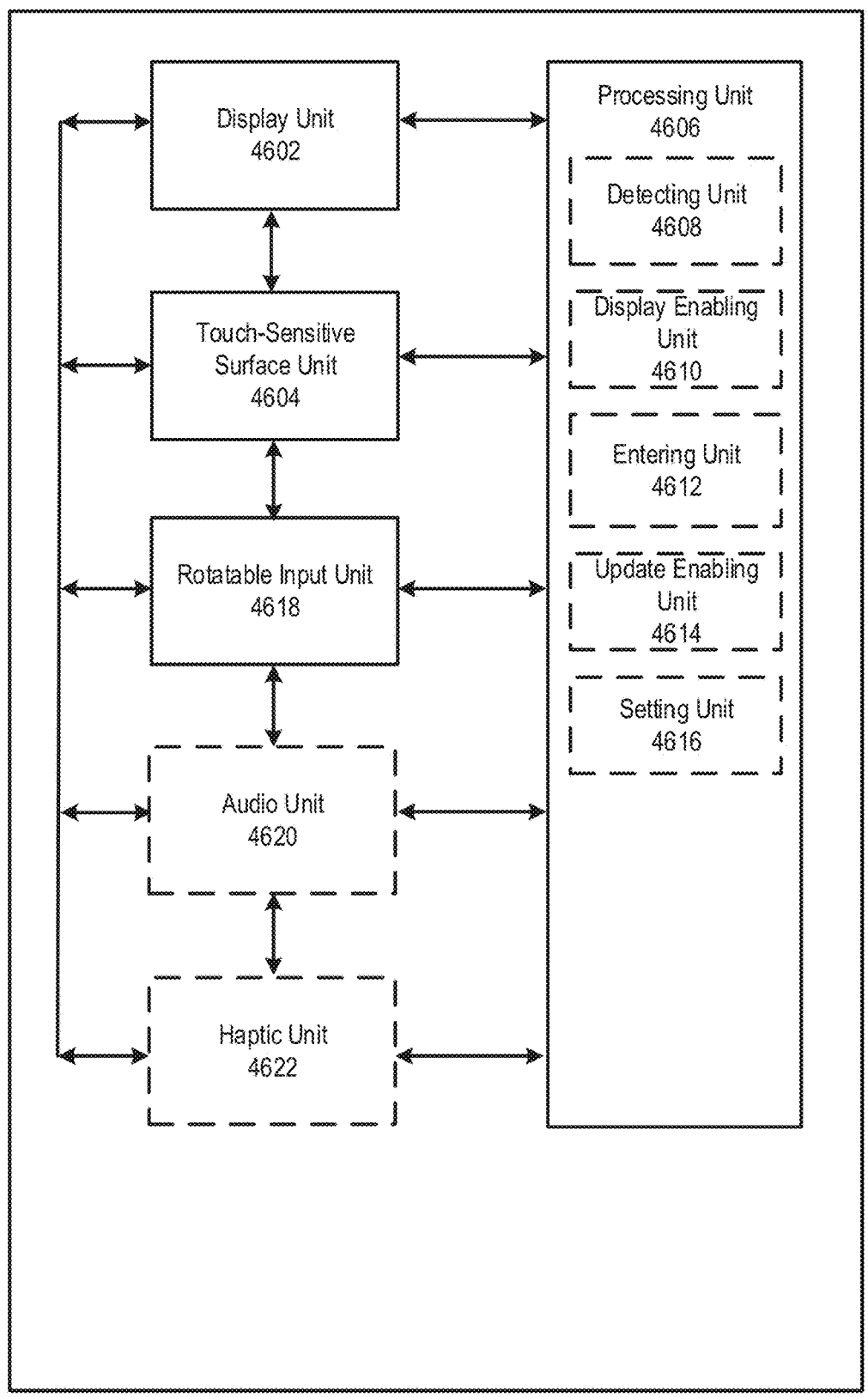
FIG. 46 is a functional block diagram of an electronic device in accordance with some embodiments.

In accordance with some embodiments, FIG. 46 shows an exemplary functional block diagram of an electronic device 4600 configured in accordance with the principles of the various described embodiments. In accordance with some embodiments, the functional blocks of electronic device 4600 are configured to perform the techniques described above. The functional blocks of the device 4600 are, optionally, implemented by hardware, software, or a combination of hardware and software to carry out the principles of the various described examples. It is understood by persons of skill in the art that the functional blocks described in FIG. 46 are, optionally, combined or separated into sub-blocks to implement the principles of the various described examples. Therefore, the description herein optionally supports any possible combination or separation or further definition of the functional blocks described herein.

As shown in FIG. 46, an electronic device 4600 includes a display unit 4602 configured to display a graphic user interface, optionally, a touch-sensitive surface unit 4604 configured to receive contacts, optionally, a rotatable input unit 4618 configured to receive rotatable input (e.g., from a rotatable input mechanism), optionally, an audio unit 4620 configured to generate audio, optionally, a haptic unit 4622 configured to generate haptic output, and a processing unit 4606 coupled to the display unit 4502, optionally, the touch-sensitive surface unit 4504, optionally, the rotatable input unit 4618, optionally, the audio unit 4620, and optionally, the haptic unit 4622. In some embodiments, the processing unit 4606 includes a detecting unit 4608, a display enabling unit 4610, an entering unit 4612, an update enabling unit 4614, and a setting unit 4616.

The processing unit 4606 is configured to enable display (e.g., with display enabling unit 4610), on the display unit (e.g., display unit 4602), of a user interface screen, the user interface screen including: a clock face; and an affordance on the clock face, the affordance indicating a first time of day; detect (e.g., with detecting unit 4608) a contact on the touch-sensitive surface unit (e.g., touch-sensitive surface unit 4604); and in response to detecting the contact: enter (e.g., with entering unit 4612) a user interaction mode of the electronic device; while the electronic device is in the user interaction mode, detect (e.g., with detecting unit 4608) a rotatable input from the rotatable input unit (e.g., rotatable input unit 4618), and in response to detecting the rotatable input: enable update (e.g., with update enabling unit 4614), on the display unit (e.g., display unit 4602), of the affordance to indicate a second time of day; detect (e.g., with detecting unit 4608) a second contact on the touch-sensitive surface unit (e.g., touch-sensitive surface unit 4604) at the affordance indicating the second time, and in response to detecting the second contact: set (e.g., with setting unit 4616) a user reminder for the second time of day.

In some embodiments, setting the user reminder for the second time of day comprises: enabling display (e.g., with display enabling unit 4610), on the display unit (e.g., display unit 4602), of a second affordance on the display, the second affordance representing a user prompt to set an alert for the second time of day. In some embodiments, the processing unit is further configured to enable display (e.g., with display enabling unit 4610), on the display unit (e.g., display unit 4602), of a visual alert for the second time of day, and wherein the user reminder for the third time of day comprises the visual alert for the second time of day. In some embodiments, the electronic device 4600 further comprises an audio unit (e.g., audio unit 4620), wherein the processing unit is coupled to the audio unit, and wherein the processing unit is further configured to enable an audio alert for the second time of day via the audio unit (e.g., with audio unit 4620), and wherein the user reminder for the third time of day comprises the audio alert for the second time of day. In some embodiments, the electronic device 4600 further comprises a haptic unit (e.g., haptic unit 4622), wherein the processing unit is coupled to the haptic unit, and wherein the processing unit is further configured to enable a haptic alert for the second time of day via the haptic unit (e.g., with haptic unit 4622), and wherein the user reminder for the second time of day comprises the haptic alert for the second time of day.

The operations described above with reference to FIG. 31 are, optionally, implemented by components depicted in FIGS. 1A-1B or FIG. 46. For example, displaying operation 3102, detecting operation 3104, and entering operation 3106 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 47:
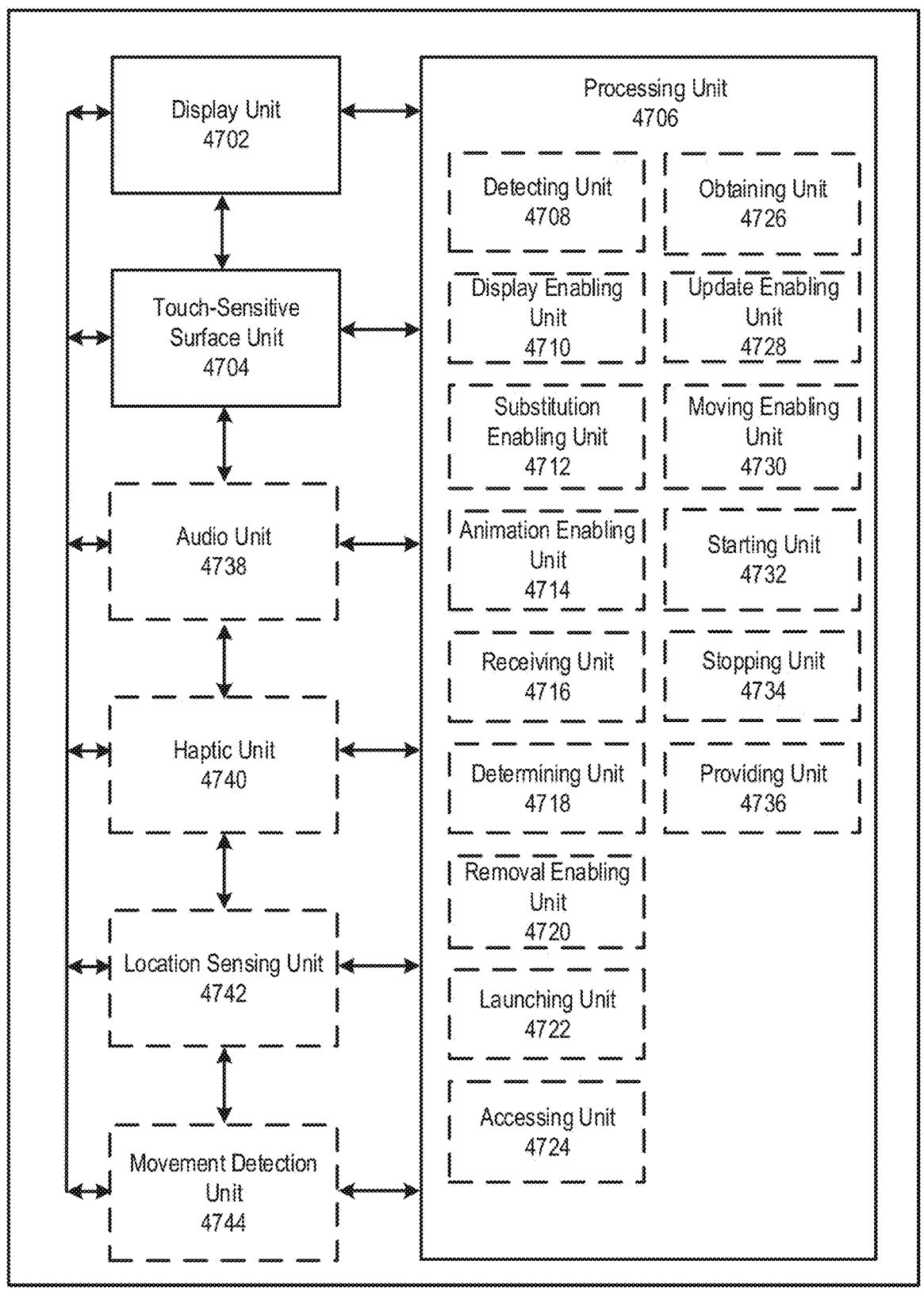
FIG. 47 is a functional block diagram of an electronic device in accordance with some embodiments.

In accordance with some embodiments, FIG. 47 shows an exemplary functional block diagram of an electronic device 4700 configured in accordance with the principles of the various described embodiments. In accordance with some embodiments, the functional blocks of electronic device 4700 are configured to perform the techniques described above. The functional blocks of the device 4700 are, optionally, implemented by hardware, software, or a combination of hardware and software to carry out the principles of the various described examples. It is understood by persons of skill in the art that the functional blocks described in FIG. 47 are, optionally, combined or separated into sub-blocks to implement the principles of the various described examples. Therefore, the description herein optionally supports any possible combination or separation or further definition of the functional blocks described herein.

As shown in FIG. 47, an electronic device 4700 includes a display unit 4702 configured to display a graphic user interface, optionally, a touch-sensitive surface unit 4704 configured to receive contacts, optionally, an audio unit 4738 configured to generate audio, optionally, a haptic unit 4740 configured to generate haptic output, optionally, a location sensing unit 4742 configured to sense location, optionally, a movement detection unit 4744, and a processing unit 4706 coupled to the display unit 4702, optionally, the touch-sensitive surface unit 4704, optionally, the audio unit 4738, optionally, the haptic unit 4740, optionally, the location sensing unit 4742, and optionally, the movement detection unit 4744. In some embodiments, the processing unit 4706 includes a detecting unit 4708, a display enabling unit 4710, a substitution enabling unit 4712, an animation enabling unit 4714, a receiving enabling unit 4716, a determining unit 4718, a removal enabling unit 4720, a launching unit 4722, an accessing unit 4724, an obtaining unit 4726, an update enabling unit 4728, a moving enabling unit 4730, a starting unit 4732, a stopping unit 4734, and a providing unit 4736.

The processing unit 4706 is configured to enable display (e.g., with display enabling unit 4710), on the display unit (e.g., display unit 4702), of a user interface screen, the user interface screen including a plurality of affordances, the plurality including a first affordance, wherein the first affordance indicates a clock face that includes: an indication of time; and an outline; detect (e.g., with detecting unit 4708) a contact on the displayed first affordance on the touch-sensitive surface unit (e.g., touch-sensitive surface unit 4704); and in response to detecting the contact: enable substitution (e.g., with substitution enabling unit 4712), on the display unit (e.g., display unit 4702), of the user interface screen with a second user interface screen, wherein the substitution comprises retaining one of the one or more of the indication of time and the outline, wherein the retained indication of time or outline is displayed on the second user interface screen at a size larger than on the first user interface screen.

In some embodiments, the processing unit 4706 is further configured to: enable animation (e.g., with animation enabling unit 4714), on the display unit (e.g., display unit 4702), of the one or more retained elements by progressively displaying the element on the second user interface screen. In some embodiments, the outline is retained, and wherein the outline is progressively displayed in a rotational motion.

In some embodiments, the processing unit 4706 is further configured to: receive (e.g., with receiving unit 4716) a notification; determine (e.g., with determining unit 4718) whether the notification has been missed; and in accordance with a determination that notification has been missed: enable display (e.g., with display enabling unit 4710), on the display unit (e.g., display unit 4702), of an affordance, the affordance indicating a missed notification. In some embodiments, an aspect of the displayed affordance represents a number of missed notifications received by the electronic device. In some embodiments, the processing unit 4706 is further configured to: receive data representing user viewing of the missed notification, and in response to receiving the data: enable removal (e.g., with removal enabling unit 4720), on the display unit (e.g., display unit 4702), of the affordance. In some embodiments, the processing unit 4706 is further configured to: enable display (e.g., with display enabling unit 4710), on the display unit (e.g., display unit 4702), of a stopwatch progress affordance, the stopwatch progress affordance indicating a currently running stopwatch application, wherein the stopwatch progress affordance comprises a representation of a digital stopwatch, and wherein the representation of the digital stopwatch is continuously updated (e.g., with update enabling unit 4728) to indicate a stopwatch time generated by the currently running stopwatch application; detect (e.g., with detecting unit 4708) a contact on the displayed stopwatch progress affordance, and in response to detecting the contact: launch (e.g., with launching unit 4722) the stopwatch application. In some embodiments, the electronic device comprises a location sensing unit (e.g., location sensing unit 4742), wherein the processing unit 4706 is coupled to the location sensing unit, and the processing unit 4706 is further configured to: while a clock face is displayed on the display unit, detect (e.g., with detecting unit 4708) a contact on the touch-sensitive surface unit (e.g., touch-sensitive surface unit 4704), and in response to detecting the contact: access (e.g., with accessing unit 4724) data representing a designated home location, the designated home location having an associated home time zone; obtain (e.g., with obtaining unit 4726) a current time zone of the electronic device from the location sensor; determine (e.g., with determining unit 4718) whether the current time zone is different from the home time zone; and in response to a determination that the current time zone is different from the home time zone: enable update (e.g., with update enabling unit 4728), on the display unit (e.g., display unit 4702), of the displayed clock face to indicate a current time at the home time zone. In some embodiments, the designated home location is user-designated. In some embodiments, the designated home location is a location designated by the system based on data representing one or more of: amount of time spent at the location; which times of day are spent at the location; and number of contact entries associated with the location stored on the electronic device. In some embodiments, the electronic device 4700 further includes a movement detection unit (e.g., movement detection unit 4744), the processing unit 4706 is coupled to the movement detection unit, and the processing unit 4706 is further configured to: enable display (e.g., with display enabling unit 4710), on the display unit (e.g., display unit 4702), of a clock face on the display, the displayed clock face comprising a plurality of pixels; detect (e.g., with detecting unit 4708) a movement of the electronic device 4700 via the movement detection unit (e.g., movement detection unit 4744); and in response to detecting the movement: enable moving (e.g., with moving enabling unit 4730), on the display unit (e.g., display unit 4702), of the displayed clock face on the display, wherein moving comprises modifying in appearance a subset of pixels in the plurality. In some embodiments, the processing unit 4706 is further configured to: enable display (e.g., with display enabling unit 4710), on the display unit (e.g., display unit 4702), of a tachymeter user interface object comprising a start/stop affordance; detect (e.g., with detecting unit 4708) a user input at a first time; in response to detecting the user input: start (e.g., with starting unit 4732) a virtual tachymeter; detect (e.g., with detecting unit 4708) a second user input at a second time, the second time separated from the first time by a tachymeter interval; in response to detecting the second user input: stop (e.g., with stopping unit 4734) the virtual tachymeter; and enable display (e.g., with display enabling unit 4710), on the display unit (e.g., display unit 4702), of a time value based on a number of units of time in a predetermined interval divided by the tachymeter interval. In some embodiments, the processing unit 4706 is further configured to: enable display (e.g., with display enabling unit 4710), on the display unit (e.g., display unit 4702), of a telemeter user interface object comprising a start/stop affordance; detect (e.g., with detecting unit 4708) a user input at a first time; in response to detecting the user input: start (e.g., with starting unit 4732) a virtual telemeter; detect (e.g., with detecting unit 4708) a second user input at a second time, the second time separated from the first time by a telemeter interval; in response to detecting the second contact: stop (e.g., with stopping unit 4734) the virtual telemeter; and enable display (e.g., with display enabling unit 4710), on the display unit (e.g., display unit 4702), of a distance based on the telemeter interval. In some embodiments, the processing unit 4706 is further configured to: enable display (e.g., with display enabling unit 4710), on the display unit (e.g., display unit 4702), of a repeated interval timer user interface; receive (e.g., with receiving unit 4716) data representing a user-designated time interval; and in response to receiving the data representing the user-designated time interval: provide (e.g., with providing unit 4736) a user alert, wherein the user alert is repeated at times based on the user-designated time interval. In some embodiments, the user alert comprises one or more of: a visual alert, enabled on the display unit (e.g., display unit 4702); an audio alert, wherein the electronic device further comprises an audio unit (e.g., audio unit 4738) coupled to the processing unit, and wherein the processing unit is further configured to enable an audio alert via the audio unit (e.g., audio unit 4738); and a haptic alert, wherein the electronic device further comprises a haptic unit (e.g., haptic unit 4740) coupled to the processing unit, and wherein the processing unit is further configured to enable a haptic alert via the haptic unit (e.g., haptic unit 4738).

The operations described above with reference to FIG. 33 are, optionally, implemented by components depicted in FIGS. 1A-1B or FIG. 47. For example, displaying operation 3302, detecting operation 3304, and substituting operation 3306 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 48:
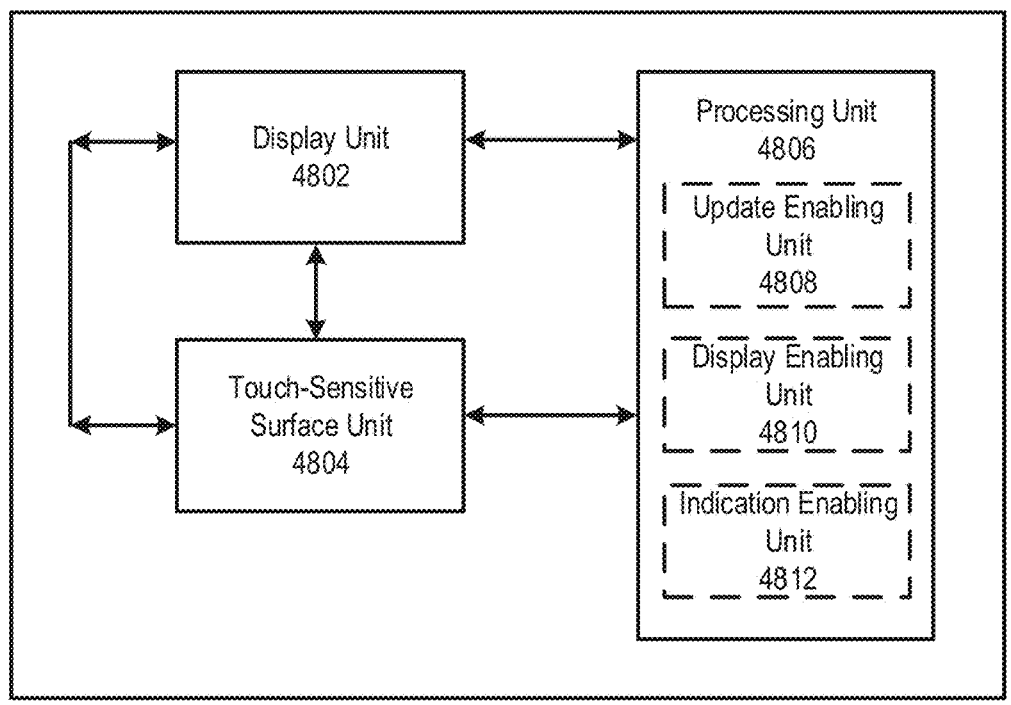
FIG. 48 is a functional block diagram of an electronic device in accordance with some embodiments.

In accordance with some embodiments, FIG. 48 shows an exemplary functional block diagram of an electronic device 4800 configured in accordance with the principles of the various described embodiments. In accordance with some embodiments, the functional blocks of electronic device 4800 are configured to perform the techniques described above. The functional blocks of the device 4800 are, optionally, implemented by hardware, software, or a combination of hardware and software to carry out the principles of the various described examples. It is understood by persons of skill in the art that the functional blocks described in FIG. 48 are, optionally, combined or separated into sub-blocks to implement the principles of the various described examples. Therefore, the description herein optionally supports any possible combination or separation or further definition of the functional blocks described herein.

As shown in FIG. 48, an electronic device 4800 includes a display unit 4802 configured to display a graphic user interface, optionally, a touch-sensitive surface unit 4804 configured to receive contacts, and a processing unit 4806 coupled to the display unit 4802, and optionally, the touch-sensitive surface unit 4804. In some embodiments, the processing unit 4806 includes an update enabling unit 4808, a display enabling unit 4810, and an indication enabling unit 4812.

The processing unit 4806 is configured to enable display (e.g., with display enabling unit 4810), on the display unit (e.g., display unit 4802), of a character user interface object, the character user interface object comprising representations of a first limb and a second limb, wherein the processing unit 4806 is configured to enable the character user interface object to indicate (e.g., with indication enabling unit 4812), on the display unit (e.g., display unit 4802), a first time by: enabling indication (e.g., with indication enabling unit 4812), on the display unit (e.g., display unit 4802), of a first hour with the first limb and a first minute with the second limb; and enable update (e.g., with update enabling unit 4808), on the display unit (e.g., display unit 4802), of the character user interface object to indicate a second time, wherein the processing unit is configured to enable the character user interface object to indicate (e.g., with indication enabling unit 4812), on the display unit (e.g., display unit 4802), the second time by: enabling indication (e.g., with indication enabling unit 4812), on the display unit (e.g., display unit 4802), of a second hour with the second limb and a second minute with the first limb.

In some embodiments, enabling update (e.g., with update enabling unit 4808), on the display unit (e.g., display unit 4802), of the character user interface object to indicate a second time comprises enabling an extension of the first limb and a retraction of the second limb on the display unit.

The operations described above with reference to FIG. 27B are, optionally, implemented by components depicted in FIGS. 1A-1B or FIG. 48. For example, displaying operation 2712, updating operation 2714, and the optional updating operation within block 2714 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 49:
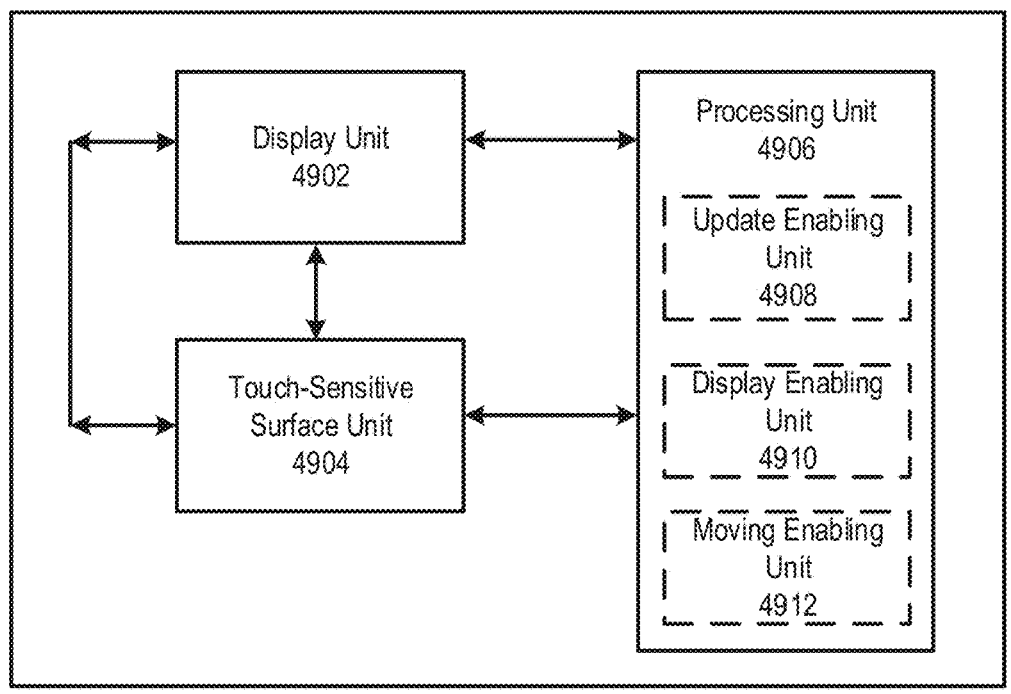
FIG. 49 is a functional block diagram of an electronic device in accordance with some embodiments.

In accordance with some embodiments, FIG. 49 shows an exemplary functional block diagram of an electronic device 4900 configured in accordance with the principles of the various described embodiments. In accordance with some embodiments, the functional blocks of electronic device 4900 are configured to perform the techniques described above. The functional blocks of the device 4900 are, optionally, implemented by hardware, software, or a combination of hardware and software to carry out the principles of the various described examples. It is understood by persons of skill in the art that the functional blocks described in FIG. 49 are, optionally, combined or separated into sub-blocks to implement the principles of the various described examples. Therefore, the description herein optionally supports any possible combination or separation or further definition of the functional blocks described herein.

As shown in FIG. 49, an electronic device 4900 includes a display unit 4902 configured to display a graphic user interface, optionally, a touch-sensitive surface unit 4904 configured to receive contacts, and a processing unit 4906 coupled to the display unit 4902, and optionally, the touch-sensitive surface unit 4904. In some embodiments, the processing unit 4906 includes an update enabling unit 4908, a display enabling unit 4910, and a moving enabling unit 4912.

The processing unit 4806 is configured to enable display (e.g., with display enabling unit 4910), on the display unit (e.g., display unit 4902), of a character user interface object on the display, the character user interface object comprising a representation of a limb, the limb including: a first endpoint of the limb having a first position, wherein the first endpoint of the limb is an axis of rotation for the limb, and a second endpoint of the limb having a second position, wherein the position of the second endpoint of the limb indicates a first time value; and enable update (e.g., with update enabling unit 4908), on the display unit (e.g., display unit 4902), of the character user interface object to indicate a second time value, wherein enabling update, on the display unit, of the character user interface object comprises enabling moving (e.g., with moving enabling unit 4912), on the display unit (e.g., display unit 4902), of the first endpoint of the limb to a third position, and moving the second endpoint of the limb to a fourth position to indicate the second time value.

In some embodiments, the character user interface object further comprises a representation of a second limb, the second limb including: a first endpoint of the second limb having a first position, wherein the first endpoint of the second limb is an axis of rotation for the second limb, and a second endpoint of the second limb having a second position, wherein the position of the second endpoint of the second limb indicates a third time value, and the processing unit is further configured to: enable update (e.g., with update enabling unit 4908), on the display unit (e.g., display unit 4902), of the character user interface object to indicate a fourth time value, wherein enabling update, on the display unit, of the character user interface object to indicate the fourth time value comprises enabling moving (e.g., with moving enabling unit 4912), on the display unit (e.g., display unit 4902), of the first endpoint of the second limb to a third position, and enabling moving (e.g., with moving enabling unit 4912), on the display unit (e.g., display unit 4902), of the second endpoint of the second limb to a fourth position to indicate the fourth value.

The operations described above with reference to FIG. 27C are, optionally, implemented by components depicted in FIGS. 1A-1B or FIG. 49. For example, displaying operation 2722 and updating operation 2724 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 50:
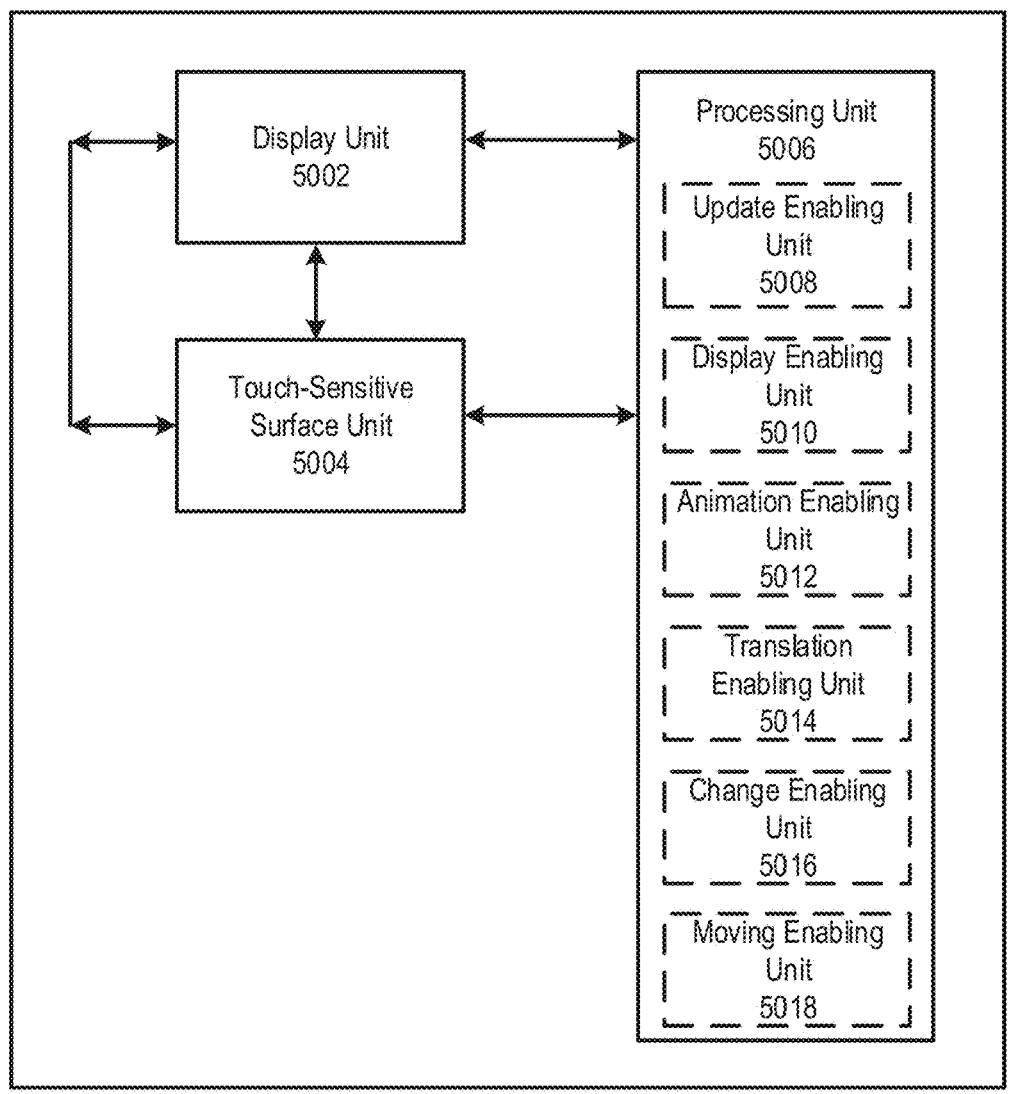
FIG. 50 is a functional block diagram of an electronic device in accordance with some embodiments.

In accordance with some embodiments, FIG. 50 shows an exemplary functional block diagram of an electronic device 5000 configured in accordance with the principles of the various described embodiments. In accordance with some embodiments, the functional blocks of electronic device 5000 are configured to perform the techniques described above. The functional blocks of the device 5000 are, optionally, implemented by hardware, software, or a combination of hardware and software to carry out the principles of the various described examples. It is understood by persons of skill in the art that the functional blocks described in FIG. 50 are, optionally, combined or separated into sub-blocks to implement the principles of the various described examples. Therefore, the description herein optionally supports any possible combination or separation or further definition of the functional blocks described herein.

As shown in FIG. 50, an electronic device 5000 includes a display unit 5002 configured to display a graphic user interface, optionally, a touch-sensitive surface unit 5004 configured to receive contacts, and a processing unit 5006 coupled to the display unit 5002, and optionally, the touch-sensitive surface unit 5004. In some embodiments, the processing unit 5006 includes an update enabling unit 5008, a display enabling unit 5010, an animation enabling unit 5012, a translation enabling unit 5014, a change enabling unit 5016, and a moving enabling unit 5018.

The processing unit 5006 is configured to enable display (e.g., with display enabling unit 5010), on the display unit (e.g., display unit 5002), of a character user interface object, the character user interface object comprising a representation of a limb, the limb including a first segment of the limb and a second segment of the limb, wherein the first segment of the limb connects a first endpoint of the limb to a joint of the limb, the first endpoint of the limb having a first position, and wherein the second segment of the limb connects a second endpoint of the limb to the joint of the limb, the second endpoint of the limb having a second position, wherein the joint of the limb is an axis of rotation for the second segment of the limb, and wherein the position of the second endpoint of the limb indicates a first time value; and enable update (e.g., with update enabling unit 5008), on the display unit (e.g., display unit 5002), of the character user interface object to indicate a second time value, wherein enabling update comprises enabling moving (e.g., with moving enabling unit 5018), on the display unit (e.g., display unit 5002), of the second endpoint of the limb along the axis of rotation for the second segment of the limb to a third position to indicate the second time.

In some embodiments, enabling update (e.g., with update enabling unit 5008), on the display unit (e.g., display unit 5002), of the character user interface object further comprises enabling moving (e.g., with moving enabling unit 5018), on the display unit (e.g., display unit 5002), of the first endpoint. In some embodiments, the character user interface object further comprises a representation of a second limb, the second limb including a first segment of the second limb and a second segment of the second limb, wherein the first segment of the second limb connects a first endpoint of the second limb to a joint of the second limb, the first endpoint of the second limb having a first position, wherein the second segment of the second limb connects a second endpoint of the second limb to the joint of the second limb, the second endpoint of the second limb having a second position, wherein the joint of the second limb is an axis of rotation for the second segment of the second limb, and wherein the position of the second endpoint of the second limb indicates a third time, and wherein the processing unit 5006 is further configured to: enable update (e.g., with update enabling unit 5008), on the display unit (e.g., display unit 5002), of the character user interface object to indicate a fourth time, wherein enabling update comprises enabling moving (e.g., with moving enabling unit 5018), on the display unit (e.g., display unit 5002), of the second endpoint of the second limb along the axis of rotation for the second segment of the second limb to a third position to indicate the fourth time value. In some embodiments, the first limb indicates an hour and the second limb indicates a minute. In some embodiments, the first limb indicates a minute and the second limb indicates an hour. In some embodiments, enabling update (e.g., with update enabling unit 5008), on the display unit (e.g., display unit 5002), of the character user interface object to indicate the second time further comprises: enabling animation (e.g., with animation enabling unit 5012), on the display unit (e.g., display unit 5002), of the character user interface object, wherein enabling animation, on the display unit, of the character user interface object comprises a motion of the first endpoint on-screen. In some embodiments, enabling update (e.g., with update enabling unit 5008), on the display unit (e.g., display unit 5002), of the character user interface object further comprises: enabling animation (e.g., with animation enabling unit 5012), on the display unit (e.g., display unit 5002), of the character user interface object, wherein enabling animation, on the display unit, of the character user interface object comprises a rotation of the second segment at the joint on-screen. In some embodiments, the processing unit is further configured to: enable translation (e.g., with translation enabling unit 5014), on the display unit (e.g., display unit 5002), of the character user interface object on-screen towards a center of the display. In some embodiments, enabling translation (e.g., with translation enabling unit 5014), on the display unit (e.g., display unit 5002), of the character user interface object comprises animating the character user interface object to represent walking. In some embodiments, the processing unit is further configured to: enable change (e.g., with change enabling unit 5016), on the display unit (e.g., display unit 5002), of a visual aspect of the display to highlight the character user interface object. In some embodiments, the processing unit is further configured to: enable animation (e.g., with animation enabling unit 5012), on the display unit (e.g., display unit 5002), of the character user interface object in response to being highlighted. In some embodiments, the character user interface object further comprises a representation of a foot. In some embodiments, the processing unit is further configured to: enable animation (e.g., with animation enabling unit 5012), on the display unit (e.g., display unit 5002), of the foot to indicate passage of time. In some embodiments, the first time and the second time are the same. In some embodiments, the processing unit is further configured to: enable display (e.g., with display enabling unit 5010), on the display unit (e.g., display unit 5002), of a numerical indication of a time value.

The operations described above with reference to FIG. 27D are, optionally, implemented by components depicted in FIGS. 1A-1B or FIG. 50. For example, displaying operation 2732 and updating operation 2734 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 51:
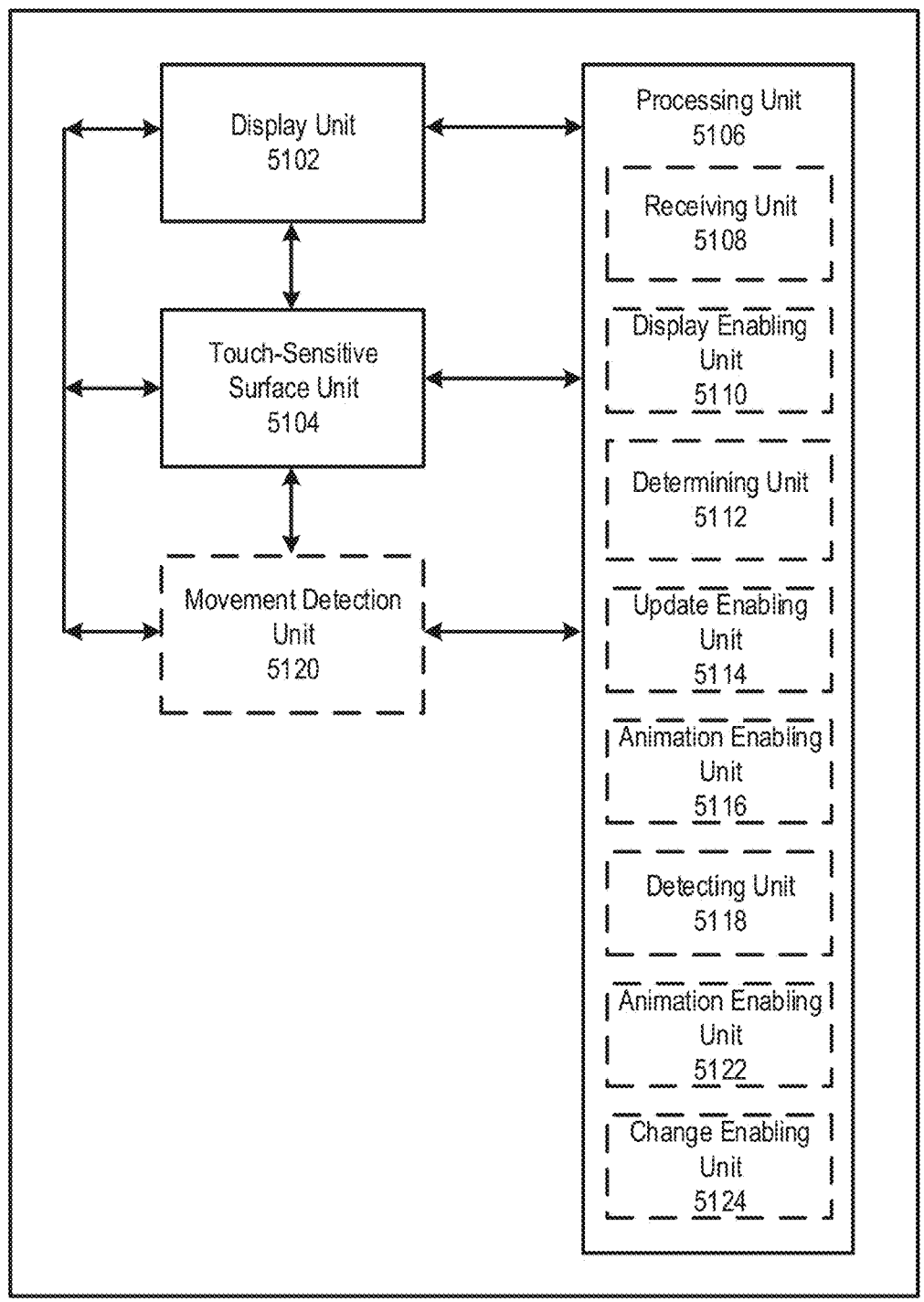
FIG. 51 is a functional block diagram of an electronic device in accordance with some embodiments.

In accordance with some embodiments, FIG. 51 shows an exemplary functional block diagram of an electronic device 5100 configured in accordance with the principles of the various described embodiments. In accordance with some embodiments, the functional blocks of electronic device 5100 are configured to perform the techniques described above. The functional blocks of the device 5100 are, optionally, implemented by hardware, software, or a combination of hardware and software to carry out the principles of the various described examples. It is understood by persons of skill in the art that the functional blocks described in FIG. 51 are, optionally, combined or separated into sub-blocks to implement the principles of the various described examples. Therefore, the description herein optionally supports any possible combination or separation or further definition of the functional blocks described herein.

As shown in FIG. 51, an electronic device 5100 includes a display unit 5102 configured to display a graphic user interface, optionally, a touch-sensitive surface unit 5104 configured to receive contacts, optionally, a movement detection unit 5120 configured to detect movement, and a processing unit 5106 coupled to the display unit 5102, optionally, the touch-sensitive surface unit 5104 and optionally, the movement detection unit 5120. In some embodiments, the processing unit 5106 includes a receiving unit 5108, a display enabling unit 5110, a determining unit 5112, an update enabling unit 5114, an animation enabling unit 5116, a detecting unit 5118, an animation enabling unit 5122, and a change enabling unit 5124.

The processing unit 5106 is configured to enable display (e.g., with display enabling unit 5110), on the display unit (e.g., display unit 5102), of a character user interface object, wherein the character user interface object indicates a current time; receive (e.g., with receiving unit 5108) first data indicative of an event; determine (e.g., with determining unit 5112) whether the event meets a condition; and in accordance with the determination that the event meets the condition: enable update (e.g., with update enabling unit 5114), on the display unit (e.g., display unit 5102), of the displayed character user interface object by changing (e.g., with change enabling unit 5124) a visual aspect of the character user interface object.

In some embodiments, after enabling update (e.g., with update enabling unit 5114), on the display unit (e.g., display unit 5102), of the displayed character user interface object, the character user interface object still indicates the current time. In some embodiments, after enabling update (e.g., with update enabling unit 5114), on the display unit (e.g., display unit 5102), of the displayed character user interface object, the character user interface object no longer indicates the current time. In some embodiments, the first data indicates a calendar event; the condition corresponds to a duration of the calendar event; and determining whether the event meets the condition comprises determining whether the current time is within the duration of the calendar event. In some embodiments, the calendar event is a birthday, and wherein enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to display a birthday greeting. In some embodiments, the calendar event is a holiday, and wherein updating the displayed character user interface object comprises enabling change (e.g., with change enabling unit 5124), on the display unit (e.g., display unit 5102), of a visual aspect of the character user interface object to reflect the holiday. In some embodiments, the first data indicates a notification, and wherein the processing unit is further configured to: enable display (e.g., with display enabling unit 5110), on the display unit (e.g., display unit 5102), of the notification on the display; and enable animation (e.g., with animation enabling unit 5122), on the display unit (e.g., display unit 5102), of the character user interface object to react to the displayed notification. In some embodiments, the first data indicates a time of day; the condition corresponds to a nighttime portion of the day; determining whether the event meets the condition comprises determining whether the time of day is within the nighttime portion of the day; and enabling update (e.g., with update enabling unit 5114), on the display unit (e.g., display unit 5102), of the displayed character user interface object comprises enabling change (e.g., with change enabling unit 5124), on the display unit (e.g., display unit 5102), of the visual aspect of the character user interface object to represent nighttime. In some embodiments, the first data indicates the current time; the condition corresponds to an hour on the hour; determining whether the event meets the condition comprises determining whether the current time is an hour on the hour; and enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to announce the hour on the hour for one or more hours. In some embodiments, the first data indicates current or forecasted weather; the condition corresponds to one or more designated weather conditions; determining whether the event meets the condition comprises determining whether the current or forecasted weather is one of the one or more designated weather conditions; and enabling update (e.g., with update enabling unit 5114), on the display unit (e.g., display unit 5102), of the displayed character user interface object comprises enabling change (e.g., with change enabling unit 5124), on the display unit (e.g., display unit 5102), of the visual aspect of the character user interface object to reflect the current or forecasted weather. In some embodiments, the first data indicates a second electronic device; the condition corresponds to a threshold proximity to the first electronic device; determining whether the event meets the condition comprises determining whether the second electronic device is within the threshold proximity to the first electronic device; and enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to react to the second electronic device. In some embodiments, the first data indicates user activity; the condition corresponds to a threshold interval after a previous user activity; determining whether the event meets the condition comprises determining whether the first data is received outside of the threshold interval after the previous user activity; and enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to reflect inactivity. In some embodiments, the first data indicates user activity; the condition corresponds to current user activity; determining whether the event meets the condition comprises determining whether the user activity is current user activity; and updating the displayed character user interface object comprises enabling animation (e.g., with animation enabling unit 5122), on the display unit (e.g., display unit 5102), of the character user interface object to represent exercise. In some embodiments, the first data indicates user movement of the device (e.g., from movement detection unit 5120); the condition corresponds to a threshold interval after a previous user movement of the device; determining whether the event meets the condition comprises determining whether the first data is received outside of the threshold interval after the previous user movement of the device (e.g., from movement detection unit 5120); and enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to represent fatigue. In some embodiments, the first data indicates user contact on the touch-sensitive surface unit (e.g., touch-sensitive surface unit 5104); the condition corresponds to a user contact on the displayed character user interface object; determining whether the event meets the condition comprises determining whether the user contact on the touch-sensitive surface unit is on the displayed character user interface object; and enabling update (e.g., with update enabling unit 5114), on the display unit (e.g., display unit 5102), of the displayed character user interface object comprises enabling animation (e.g., with animation enabling unit 5122), on the display unit (e.g., display unit 5102), of the character user interface object to react to the contact. In some embodiments, the processing unit 5106 is further configured to: detect (e.g., with detecting unit 5118) a user input; and in response to detecting the user input, enable display (e.g., with display enabling unit 5110), on the display unit (e.g., display unit 5102), of the character user interface object. In some embodiments, the user input comprises a user movement of the device, wherein the electronic device further comprises a movement detection unit (e.g., movement detection unit 5120), wherein the processing unit 5106 is coupled to the movement detection unit, and wherein the processing unit 5106 is further configured to: detect, by the movement detection unit (e.g., movement detection unit 5120), the user movement of the device 5100. In some embodiments, the user input comprises a contact on the touch-sensitive surface unit (e.g., touch-sensitive surface unit 5104), and wherein the processing unit 5106 is further configured to detect (e.g., with detecting unit 5118) the contact on the touch-sensitive surface unit.

The operations described above with reference to FIG. 27E are, optionally, implemented by components depicted in FIGS. 1A-1B or FIG. 51. For example, displaying operation 2742, receiving operation 2744, and determining operation 2746 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 52:
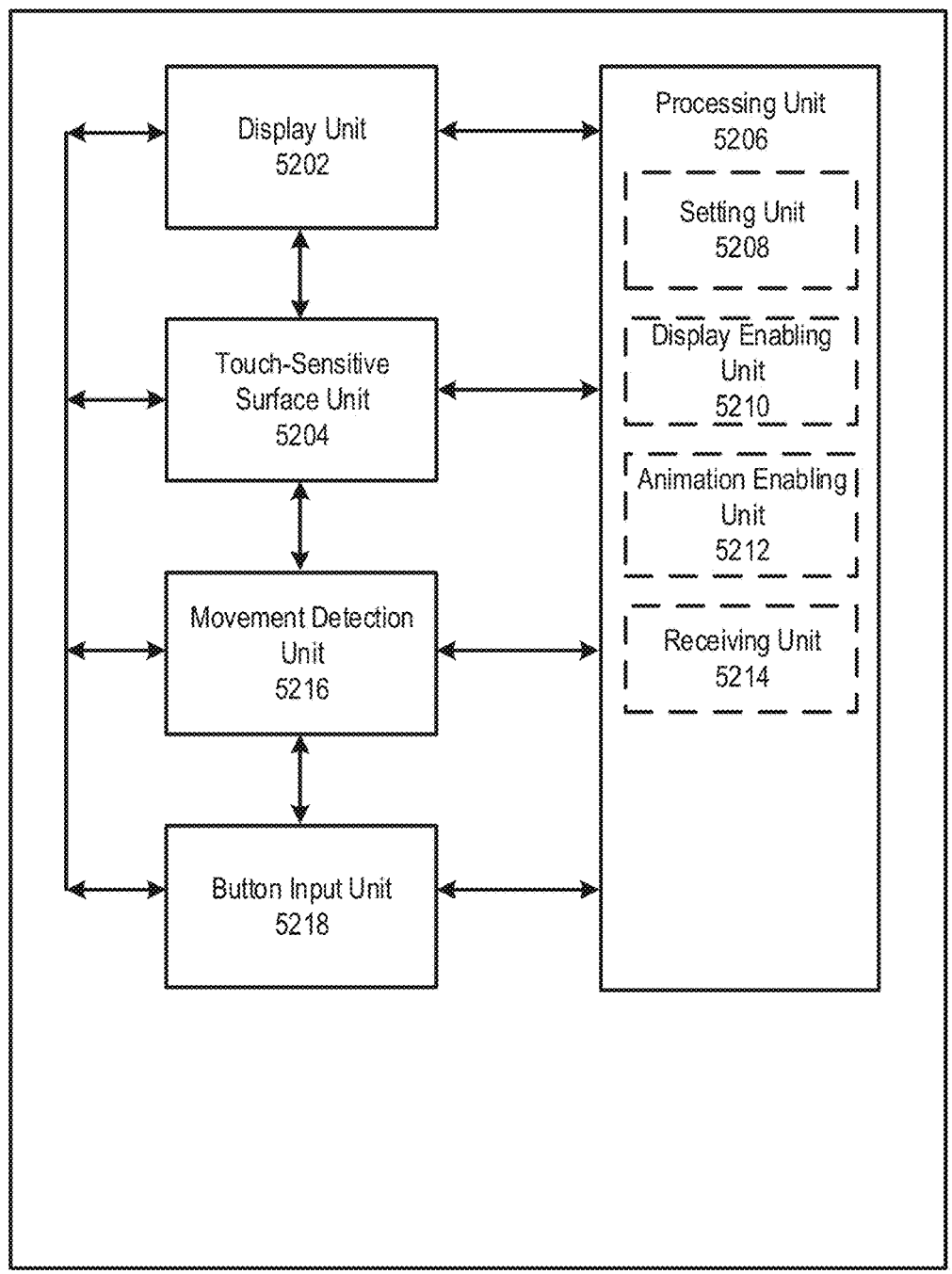
FIG. 52 is a functional block diagram of an electronic device in accordance with some embodiments.

In accordance with some embodiments, FIG. 52 shows an exemplary functional block diagram of an electronic device 5200 configured in accordance with the principles of the various described embodiments. In accordance with some embodiments, the functional blocks of electronic device 5200 are configured to perform the techniques described above. The functional blocks of the device 5200 are, optionally, implemented by hardware, software, or a combination of hardware and software to carry out the principles of the various described examples. It is understood by persons of skill in the art that the functional blocks described in FIG. 52 are, optionally, combined or separated into sub-blocks to implement the principles of the various described examples. Therefore, the description herein optionally supports any possible combination or separation or further definition of the functional blocks described herein.

As shown in FIG. 52, an electronic device 5200 includes a display unit 5202 configured to display a graphic user interface, optionally, a touch-sensitive surface unit 5204 configured to receive contacts, optionally, a movement detection unit 5216 configured to detect movement, optionally, a button input unit 5218 configured to receive input from a button, and a processing unit 5206 coupled to the display unit 5202, optionally, the touch-sensitive surface unit 5204, optionally, the movement detection unit 5216, and optionally, the button input unit 5218. In some embodiments, the processing unit 5206 includes a setting unit 5208, a display enabling unit 5210, an animation enabling unit 5212, and a receiving unit 5214.

The processing unit 5206 is configured to set (e.g., with setting unit 5208) the display unit (e.g., display unit 5202) to an inactive state; receive (e.g., with receiving unit 5214) first data indicative of an event; in response to receiving the first data: set (e.g., with setting unit 5208) the display unit (e.g., display unit 5202) to an active state; enable display (e.g., with display enabling unit 5210), on the display unit (e.g., display unit 5202), of a character user interface object on a side of the display; enable animation (e.g., with animation enabling unit 5212), on the display unit (e.g., display unit 5202), of the character user interface object towards a center of the display; and enable display (e.g., with display enabling unit 5210), on the display unit (e.g., display unit 5202), of the character user interface object at the center of the display in a position that indicates a current time.

In some embodiments, enabling animation (e.g., with animation enabling unit 5212), on the display unit (e.g., display unit 5202), of the character user interface object provides the impression of walking. In some embodiments, the electronic device 5200 includes a movement detection unit (e.g., movement detection unit 5216), wherein the movement detection unit is coupled to the processing unit 5206, and the processing unit 5206 is further configured to receive (e.g., with receiving unit 5214) input from the movement detection unit, and wherein the event includes a motion raising the electronic device 5200 into a viewing position. In some embodiments, the electronic device 5200 includes a button input unit (e.g., button input unit 5218), wherein the button input unit is coupled to the processing unit 5206, and the processing unit 5206 is further configured to receive input from the button input unit, and wherein the event includes a press on the button input unit on the device 5200. In some embodiments, the event includes a touch on the touch-sensitive surface (e.g., touch-sensitive surface unit 5204).

The operations described above with reference to FIG. 27F are, optionally, implemented by components depicted in FIGS. 1A-1B or FIG. 52. For example, setting operation 2752, receiving operation 2754, and setting operation 2756 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Attention is now directed toward embodiments of user interfaces and associated processes that can optionally be implemented on an electronic device, such as device 100, 300, or 500.

FIGS. 53A-53F illustrate exemplary user interfaces. FIGS. 54A-54E are flow diagrams illustrating exemplary methods. The user interfaces in FIGS. 53C-53F are used to illustrate the processes in FIGS. 54A-54E.

FIGS. 53A-53F depict device 5300, which in some embodiments includes some or all of the features described with respect to devices 100, 300, and/or 500. In some embodiments, device 5300 has touch-sensitive and pressure-sensitive display 5302 (sometimes simply called a touchscreen). In some embodiments, device 5300 has rotatable and depressible input mechanism 5304. In some embodiments, device 5300 has depressible input mechanism 5306. Display 5302 and input mechanisms 5304 and 5306 can optionally share some or all characteristics, respectively, with display 504 and input mechanisms 506 and 508.

In some embodiments, device 5300 includes an attachment mechanism for attaching, affixing, or connecting a device to a body part or to clothing of a user. In this manner, device 5300 can optionally be considered a "wearable device," sometimes simply referred to as a "wearable." In the examples of FIGS. 53A and 53B, device 5300 can optionally comprise a wrist strap (not pictured), which can optionally be used to affix the device to the wrist of a user. In some embodiments, device 5300 takes the form factor of a "smart watch," a portable electronic device configured to be affixed by a strap to the wrist of a user.

Attention is now directed toward techniques for accessing and presenting information corresponding to past times and future times. In some embodiments, a user interface is configured to present information in the form of complications, which can optionally be visually displayed user interface objects sharing any or all of the characteristics of complications discussed above in this disclosure.

In some embodiments, a user can optionally access a "time scrubbing" mode or a "time travel" mode, and associated user interfaces. In "time scrubbing" or "time travel" mode, a user can optionally advance or rewind a non-current time, also called a "scrubbing time." "Scrubbing" can optionally refer to the action of progressing through time forward, or progressing through time backward. A user can optionally "scrub forward" as he causes a scrubbing time to advance further into the future (as if fast-forwarding), and a user can optionally "scrub backward" as he causes a scrubbing time to move further into the past (as if rewinding). Rather than corresponding to the current time of day (or to a time somewhere else in the world), the scrubbing time can optionally be set in accordance with a user input. As the user sets and updates the scrubbing time (e.g., as the user scrubs), the information displayed in interfaces associated with time-scrubbing mode can optionally be updated in accordance with the scrubbing time. Namely, the scrubbing time can optionally be displayed on the time scrubbing interface, and a difference between the scrubbing time and the current time can optionally be displayed on the time scrubbing interface. In some embodiments, an indicator of the difference between the current time and the scrubbing time is displayed. In some embodiments, one or more complications can optionally be updated in accordance with the scrubbing time, such that the complications, while the device is in time-scrubbing mode, display information corresponding to the scrubbing time rather than information corresponding to the current time. In this way, the device can optionally appear to "travel" through time as the scrubbing time advances into the future or rewinds into the past, and the displayed complications are updated accordingly. In some embodiments, the complications can optionally display forecasted or predicted information corresponding to a scrubbing time in the future, and can optionally display recorded or historical information corresponding to a scrubbing time in the past.

Features described can allow a user to use time-scrubbing mode to quickly, easily, and intuitively access past and future information corresponding to a plurality of displayed complications; the user can optionally easily view information corresponding to more than one complication for the same point in the future or point in the past, and can optionally appreciate the manner in which the information corresponding to different complications did or will interrelate by virtue of corresponding to the same scrubbing time. For example, a user can optionally scrub forward in time to see that a calendar event later in the day corresponds to a forecasted thunderstorm; information which the user may not have appreciated if the user viewed the future event in a calendar application interface and the forecasted weather in a separate weather application interface.

Attention is now specifically directed to interfaces for time scrubbing a likeness of an analog clock face.

Figure 53A:
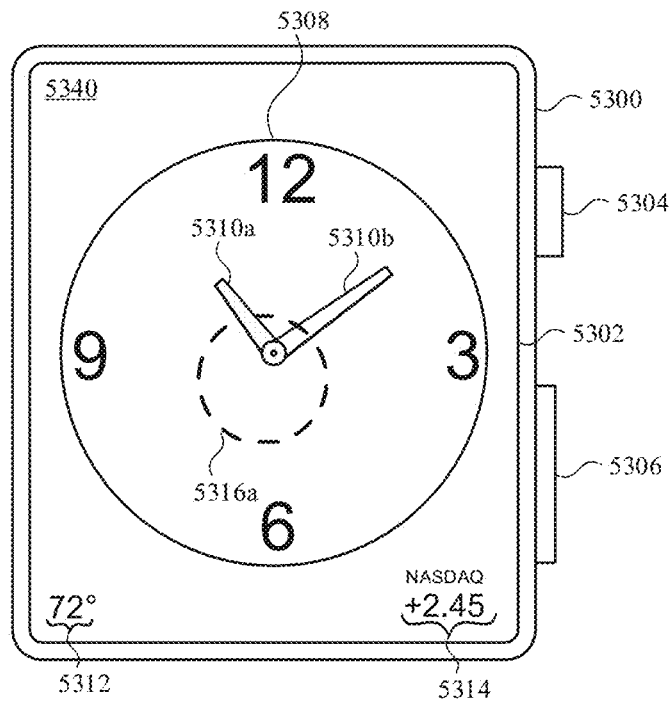
FIGS. 53A-53F illustrate exemplary user interfaces in accordance with some embodiments.

FIG. 53A depicts exemplary user interface 5340, displayed on display 5302 of device 5300. In some embodiments, user interface 5340 is a watch face interface screen, such as a home interface of a wearable smart-watch portable electronic device. Interface 5340 includes watch face 5308, which is a displayed likeness of an analog watch face. Watch face 5308 includes hour hand 5310a and minute hand 5310b. In some embodiments, watch face 5308 can optionally further include a second hand. In FIG. 53A, hour hand 5310a and minute hand 5310b indicate that the current time is 11:09.

Interface 5340 further includes weather complication 5312, which is a complication configured to indicate weather data for a user-selected location. In some embodiments, weather complication 5312 can optionally be associated with a weather application from which it draws weather data. In some embodiments, weather complication 5312 can optionally be a selectable affordance, such that detection of a user input at a location on display 5302 corresponding to weather complication 5312 can optionally cause an associated interface to be displayed, additional information to be displayed, or an associated application (e.g., a weather application) to be accessed or opened. In some embodiments, weather complication 5312 can optionally display information about the temperature, the precipitation, the wind speed, the cloud cover, or any other relevant or useful weather information.

In some embodiments, weather complication 5312 can optionally display information corresponding to present information, to future information (e.g., future scheduled events, predicted/forecasted information, etc.), or to past information (e.g., historical information, recorded events, past events, past predictions/forecasts, etc.). In the depicted example, weather complication 5312 is displaying current weather information, indicating that the current air temperature is 72°.

Interface 5340 further includes stock-market complication 5314, which is a complication configured to indicate stock-market data. In some embodiments, stock-market complication 5314 can optionally be associated with a stock-market application from which it draws stock-market data. In some embodiments, stock-market complication 5314 can optionally be a selectable affordance, such that detection of a user input at a location on display 5302 corresponding to stock-market complication 5314 can optionally cause an associated interface to be displayed, additional information to be displayed, or an associated application (e.g., a stock-market application) to be accessed or opened. In some embodiments, stock-market complication 5314 can optionally display information about one or more stocks, one or more markets or indexes, one or more portfolios, or any other relevant or useful stock-market information.

In some embodiments, stock-market complication 5314 can optionally display information corresponding to present information or to past information (e.g., historical information, recorded events, past events, or past predictions/forecasts). In some embodiments, stock-market complication 5314 may be incapable of displaying information corresponding to future information, as future stock-market information may be un-knowable. In some embodiments, stock-market complication 5314 can optionally be configured to display certain future information, such as scheduled future purchases or sales, scheduled future events (e.g., markets opening), or projected or predicted future stock market performances. In the depicted example, stock-market complication 5314 is displaying current stock-market information, indicating that the NASDAQ is up 2.45 points on the day.

FIG. 53A further depicts user input 5316a, which is a touch contact detected by touch-sensitive display 5302. Touch contact input 5316a can optionally be a single-touch input, a multi-touch input, a single-tap input, and/or a multi-tap input detected by touch- and/or pressure-sensitive elements in display 5302. In the displayed example, input 5316a is a single-finger, single-tap input detected at a location on display 5302 corresponding to displayed watch face 5308. Device 5300 can optionally be configured, in some embodiments, to, in response to detecting user input 5316a (or any other suitable predefined user input, including rotation of a rotatable input mechanism) activate a time-scrubbing mode.

Figure 53B:
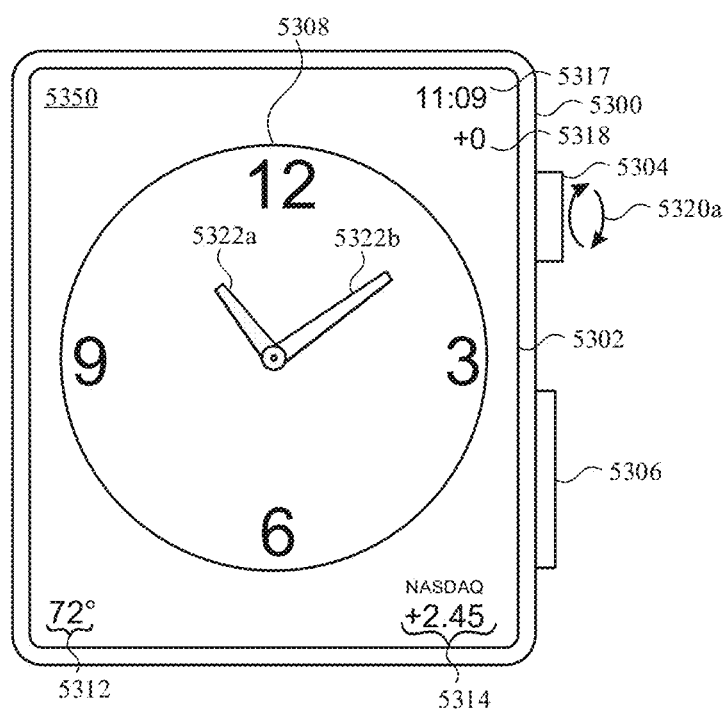

FIG. 53B depicts exemplary user interface 5350, displayed on display 5302 of device 5300. Exemplary user interface 5350 shows the manner in which, in some embodiments, device 5300 responds to the detection of input 5316a in FIG. 53A. Namely, user interface 5350 shows the activation, by device 5300, of a time-scrubbing mode and an associated time scrubbing interface in accordance with some embodiments.

In the depicted example, interface 5350 retains many of the same elements and features of interface 5340, including the same prominent watch face 5308, and the same complications 5312 and 5314. In some embodiments, the visual appearance of one or more of the elements of interface 5350 differs from the appearance of a corresponding or associated element in interface 5340, so as to indicate that time-scrubbing mode has been activated.

In some embodiments, time-scrubbing mode is a mode of operation of a device in which a user can optionally indicate, by one or more user inputs, a time other than a current time. In accordance with the user's indication of a past or future time, a device can optionally display an indication of the user's indicated time, and can optionally update one or more user interface objects in accordance with the user's indicated time. The updated user interface objects, such as complications, affordances, icons, or the like, can optionally be updated to show information that corresponds to the user's indicated time, which can optionally be called a scrubbing time. Thus, in some embodiments, as a user "scrubs" forward or backward in time, the scrubbing time is continuously updated, and other information displayed on an interface is correspondingly continuously updated, such that the information displayed on the display continuously corresponds to the scrubbing time. In the depicted example of activating and using a time-scrubbing mode of FIGS. 53A-53C, described in greater detail below, a user uses a rotational user input to scrub forward in time from 11:09 (the current time) to 11:34 (a future scrubbing time). In accordance with the forward scrubbing, complications 5312 and 5314 are updated to correspond to the future scrubbing time, with weather complication 5312 displaying a forecasted air temperature and stock-market complication 5314 ceasing to be displayed (to indicate that future information is unavailable).

In the depicted example, interface 5350 differs from interface 5340 in that, in the place of clock hands 5310a and 5310b, interface 5350 includes scrubbing hour hand 5322a and scrubbing minute hand 5322b. In some embodiments, scrubbing hands can optionally be displayed in place of or in addition to non-scrubbing hands (e.g., hands indicating the current time). In some embodiments, scrubbing hands can optionally have the same visual appearance as current-time hands, or can optionally have a different appearance from current-time hands. For example, scrubbing hands can optionally be displayed in a different size, shape, color, highlighting, or animation style as current-time hands. In some embodiments, for example, current-time hands (e.g., hands 5310a and 5310b in FIG. 53A) can optionally be displayed in white, while scrubbing hands (e.g., hands 5322a and 5322b) can optionally be displayed in green.

In the depicted example, interface 5350 further differs from interface 5340 by including digital clock face 5317, which displays the current time (11:09). Interface 5350 further differs from interface 5340 by including time difference indicator 5318, which displays an indication of the difference between the current time and the scrubbing time. In the example shown, the scrubbing time is 11:09 and the current time is also 11:09, as the scrubbing time has not yet been moved away from the current time. Therefore, time difference indicator 5318 indicates that there is no difference between the current time and the scrubbing time by indicating a difference of "+0" minutes.

FIG. 53B further depicts rotational input 5320a, which is a rotational user input detected by rotational input mechanism 5304 of device 5300. Rotational user input 5320a can optionally include one or more rotations of rotational input mechanism 5304, the one or more rotations each having one or more speeds, accelerations, directions, durations, and spacings relative to one another. The one or more rotations can optionally together form a predefined rotation pattern constituting an input. In the depicted example, rotational input 5320a is a single rotation of rotatable input mechanism 5304 in a clockwise direction as defined if looking at the face of the rotatable input mechanism from in the plane of the page to the left of the figure. (That is, the illustrated direction of rotation is such that rotatable input mechanism 5304 is being rotated into the plane of the page in the z-axis direction at the top of rotatable input mechanism 5304, while it is being rotated out of the plane of the page in the z-axis direction at the bottom of rotatable input mechanism 5304.) In some embodiments, rotational input 5320a is an input for scrubbing forward to a future time.

Figure 53C:
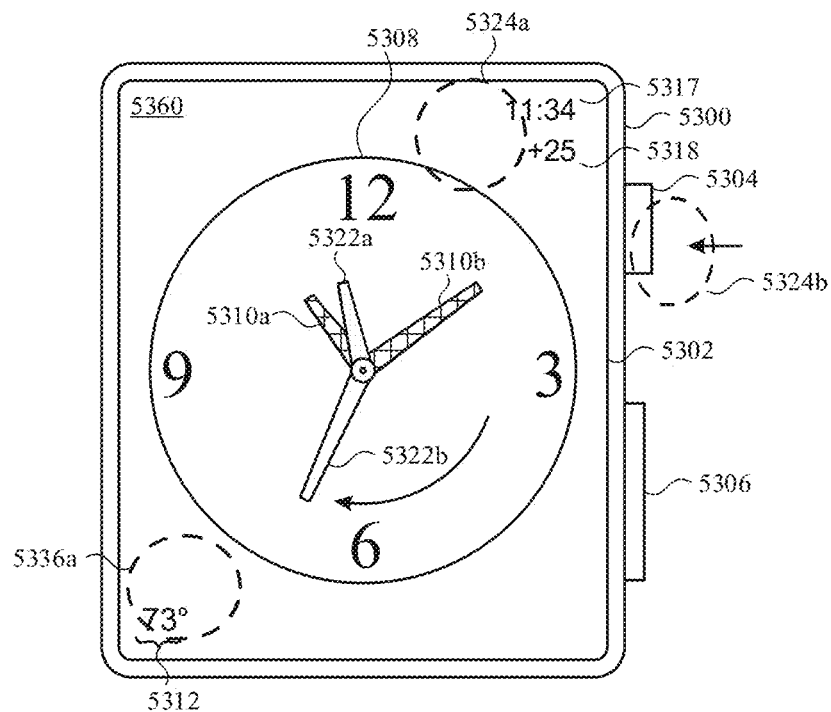

FIG. 53C depicts exemplary user interface 5360 displayed on display 5302 of device 5300. Exemplary user interface 5360 shows the manner in which, in some embodiments, device 5300 responds to the detection of input 5320a in FIG. 53B. Namely, user interface 5360 shows time scrubbing to a future time, by device 5300, and an associated interface in accordance with some embodiments. Specifically, interface 5360 depicts how watch face 5308 (and hands 5310a, 5310b, 5322a, and 5322b) and complications 5312 and 5314 are updated in accordance with time scrubbing.

First, in the depicted example, in accordance with user input 5320a, scrubbing hands 5322a and 5322b are moved forward to indicate the scrubbing time. In some embodiments, scrubbing hands can optionally be moved continuously, smoothly, or regularly to match a rotational user input, such that the further and faster a rotational input rotates, the further and faster scrubbing hands can optionally advance. In some embodiments, scrubbing hands can optionally sweep from a previous position into a current position, simulating the appearance of watch hands sweeping into a new position as the watch is set to a new time by rotating a watch crown. In the depicted example, scrubbing hour hand 5322a and scrubbing minute hand 5322b have swept from their previous position in interface 5350 to their new position in interface 5360 (as indicated by the arced arrow showing the movement of scrubbing hour hand 5322b) in accordance with the detection of rotational user input 5320a in FIG. 53B.

Further, in the depicted example, as scrubbing hands 5322a and 5322b sweep forward as the scrubbing time is advanced into the future, hands 5310a and 5310b, which are current-time hands, are revealed in their place. In some embodiments, hands 5310a and 5310b are identical in appearance as they were in interface 5340 in FIG. 53A. In some embodiments, hands 5310a and 5310b are displayed in a manner to visually indicate that time-scrubbing mode is active, such as by visually distinguishing the hands 5310a and 5310b from their appearance when time-scrubbing mode was not active, such as by being displayed in a different size, shape, color, highlighting, or animation style. In the depicted embodiment, hands 5310a and 5310b are displayed in a white color before the activation of time-scrubbing mode, while they are displayed in a gray, partially translucent color in time-scrubbing mode; this gray translucent color is indicated by the hash pattern on hands 5310a and 5310b in FIG. 53C. In the depicted example, hands 5310a and 5310b are displayed as being "behind" scrubbing hands 5322a and 5322b, as shown by hour scrubbing hand 5322a occluding hour hand 5310a where the two hands partially overlap; this arrangement can optionally help emphasize scrubbing hands while in time-scrubbing mode, as the scrubbing hands can optionally be central to the functionality of time scrubbing and can optionally correspond to other information displayed on a scrubbing interface.

Further, in the depicted example, digital clock face 5317 and time difference indicator 5318 have been updated in accordance with the scrubbing time. In the depicted example of interface 5360, digital clock face 5317 has been updated to indicate the new scrubbing time of 11:34, and time difference indicator has been updated to indicate the difference between the current time (11:09) and the scrubbing time (11:34) of "+25" minutes. In some embodiments, user interface objects such as digital clock face 5317 and time difference indicator 5318 can optionally be continuously or intermittently updated as a user scrubs forward or backward in time. Updates can optionally be displayed for each changing second, 15 seconds, minute, 5 minutes, hour, or the like. In some embodiments, one or more animations can optionally be used to depict text or numerals changing as the user scrubs forward or backward in time. In some embodiments, text, numerals, or other characters or elements of a user interface object can optionally be suddenly replaced by a new character as scrubbing is performed, such that the "09" in 11:09 would cease to be displayed and be immediately replaced by a "10." In some embodiments, one or more characters or other elements of a user interface object can optionally transition by way of an animation; for example, old elements or characters can optionally fade away by becoming increasingly translucent, can optionally shrink in size, can optionally translate in one or more directions, and/or can optionally be displayed as "flipping" out of view to simulate the appearance of a flap-display, split-flap display, or arrival/departure board; new elements or characters can optionally, for example, fade into view by becoming decreasingly translucent, can optionally grow in size, can optionally translate in one or more directions, and/or can optionally be displayed as "flipping" into view to simulate the appearance of a flap-display, split-flap display, or arrival/departure board. In some embodiments, any of the animations described above or elsewhere in this disclosure can optionally be reversed, such that an animation can optionally be displayed in a first order when a user is scrubbing in a first direction, and the animation can optionally be displayed in the opposite order (as if rewinding a video) when a user is scrubbing in the opposite direction.

Further, in the depicted example of FIG. 53C, complications 5312 and 5314 have been updated in accordance with the scrubbing to a future time, such that the displayed (or newly undisplayed) complications correspond to the displayed scrubbing time by displaying information related to the displayed scrubbing time. Complications can optionally be updated in time-scrubbing mode such that the information displayed by the complication corresponds to the currently displayed scrubbing time, rather than the current time. An update to a complication can optionally include, as compared to when the device was not in time-scrubbing mode or was scrubbed to a different scrubbing time, displaying different information, ceasing to display information, or beginning to display information after having ceased to display information.

For example, when a scrubbing time is a future time, displayed complications can optionally display future scheduled events such as future calendar events, can optionally display forecasted or projected information (such as a weather forecast) or can optionally indicate a lack of availability of information corresponding to the future time. In the case of a lack of availability of information corresponding to a future time, a complication can optionally affirmatively indicate that no information is available via displayed text or symbol, the complication can optionally cease to be displayed to indicate that no information is available, or the complication can optionally "freeze" and/or be displayed in a manner so as to indicate that the information displayed in the frozen state does not correspond to the future time (e.g., a complication can optionally be grayed out or faded out with the future-most available information displayed, if the complication is scrubbed so far into the future that no information for the scrubbing time is available).

When a scrubbing time is a past time, displayed complications can optionally display past scheduled events such as a past calendar event, can optionally display previously projected information such as a past weather forecast (e.g., in the absence of available historical data), or can optionally indicate a lack of availability of information corresponding to the past time. In the case of a lack of availability of information corresponding to a past time, a complication can optionally affirmatively indicate that no information is available via displayed text or symbol, the complication can optionally cease to be displayed to indicate that no information is available, or the complication can optionally "freeze" and/or be displayed in a manner so as to indicate that the information displayed in the frozen state does not correspond to the past time (e.g., a complication can optionally be grayed out or faded out with the oldest available information displayed, if the complication is scrubbed so far into the past that no information for the scrubbing time is available).

In some embodiments, a complication can optionally cease to display information when no information is available for or relevant to a certain period of time. For example, if a complication relates to a daily performance of a stock index, then, as a user scrubs backwards through time, the complication can optionally cease to display any information when the user scrubs to the early morning hours, or to a weekend, when the stock market was not open and no daily performance is considered relevant. As a user continues to scrub in the same direction, relevant information can optionally again be displayed as the user scrubs through additional scrubbing times, such as reaching another period when the stock market was open and beginning to display a daily performance for the stock index for that day and time.

In the example depicted in FIG. 53C, a user is scrubbing forward in time (the current time being 11:09, as indicated by hands 5310*a* and 5310*b*) and has reached 11:34 (as indicated by digital clock face 5317 and scrubbing hands 5322*a* and 5322*b*) with a time offset of plus 25 minutes (as indicated by time difference indicator 5318). As the user has scrubbed forward in time by 25 minutes, weather complication 5312 has been updated to reflect a weather forecast for 25 minutes in the future, when it is predicted to be one degree warmer, at 73° rather than the current 72° (as indicated in interface 5350 in FIG. 53B). As the user has scrubbed forward in time by 25 minutes, stock-market complication 5314 has been updated to reflect the fact that information about the future performance of the NASDAQ is unavailable; the lack of information is conveyed by the stock-market complication 5314, as shown in interface 5350 in FIG. 53B, ceasing to be displayed in interface 5360 in FIG. 53C.

FIG. 53C further depicts user input 5336*a*, which is a touch contact detected by touch-sensitive display 5302. Touch contact input 5336*a* can optionally be a single-touch input, a multi-touch input, a single-tap input, and/or a multi-tap input detected by touch- and/or pressure-sensitive elements in display 5302. In the displayed example, input 5336*a* is a single-finger, single-tap input detected at a location on display 5302 corresponding to displayed weather complication. In some embodiments, in response to detecting user input 5336*a*, device 5300 can optionally provide additional information, additional interfaces, or additional modes corresponding to weather complication 5312. For example, device 5300 can optionally launch a weather application associated with weather complication 5312. In some embodiments, device 5300 can optionally provide additional information, additional interfaces, or additional modes corresponding to a selected complication and to the scrubbing time. For example, in response to a user tapping a weather complication when the device is scrubbed to a past time, an interface of a weather application showing historical weather data for the scrubbed-to past time can optionally be displayed; in response to a user tapping a weather complication when the device is scrubbed to a future time, an interface of a weather application showing forecasted weather for the scrubbed-to future time can optionally be displayed. In the depicted example, in response to detecting user input 5336a, device 5300 can optionally provide current weather information (because the scrubbing time is so close to the present, e.g., below a predefined threshold amount of time into the future) in some embodiments, or it can optionally provide forecasted weather information associated with the scrubbing time of 11:34 in some embodiments.

FIG. 53C further depicts user inputs 5324a and 5324b, both of which are user inputs configured to cause device 5300 to exit time-scrubbing mode and return to a non-time-scrubbing interface. In some embodiments, any suitable user input can optionally be predetermined to cause a device to exit time-scrubbing mode. In the depicted example, user input 5324a is a touch contact detected on display 5302. In some embodiments, user input 5324a can optionally be a single-touch input, a multi-touch input, a single-tap input, and/or a multi-tap input detected by touch- and/or pressure-sensitive elements in display 5302. In some embodiments, user input 5324a is a single-tap input detected at a location corresponding to digital clock face 5317 and/or time difference indicator 5318. In the depicted example, user input 5324b is a depression input detected by rotatable and depressible input mechanism 5304. In some embodiments, user input 5324b can optionally be a single-press input or a multi-press input detected by a rotatable and depressible input mechanism. In some embodiments, user input 5324b is a single-press input detected by depressible and rotatable input mechanism 5304.

In response to detecting either user input 5324a or 5324b, or any other suitable predetermined user input, device 5300 can optionally cause time-scrubbing mode to be ceased and can optionally cease to display time scrubbing interfaces. In some embodiments, updated complications can optionally return to their original appearance before time-scrubbing mode was engaged, or can optionally change to an appearance corresponding to a new current time other than the current time that was current when time-scrubbing mode was engaged. In some embodiments, indications that time-scrubbing mode is active, such as digital clock face 5317, time difference indicator 5318, and scrubbing hands 5322a and 5322b can optionally cease to be displayed. In some embodiments, hands corresponding to a current time, such as hands 5310a and 5310b, can optionally return to their original visual appearance and style from before time-scrubbing mode was engaged. Any of these changes can optionally be made by way of any of the animations described above, including a reversed and/or accelerated version of any such animation. In the depicted example, in response to detecting user input 5324a or 5324b, device 5300 ceases to display user interface 5360 and displays user interface 5340 again; user interface 5340 indicates that the current time is still 11:09 and that the information corresponding to both weather complication 5312 (72°) and stock-market complication 5314 (NASDAQ+2.45) has not changed since time-scrubbing mode was activated.

Attention is now specifically directed to interfaces for time scrubbing a digital clock face. In the depicted example of activating and using a time-scrubbing mode of FIGS. 53D-53F, described in greater detail below, a user uses a rotational user input to scrub forward in time from 11:09 (the current time) to 11:34 (a future scrubbing time). In accordance with the forward scrubbing, complications 5312 and 5314 are updated to correspond to the future scrubbing time, with weather complication 5312 displaying a forecasted air temperature and stock-market complication 5314 ceasing to be displayed (to indicate that future information is unavailable).

Figure 53D:
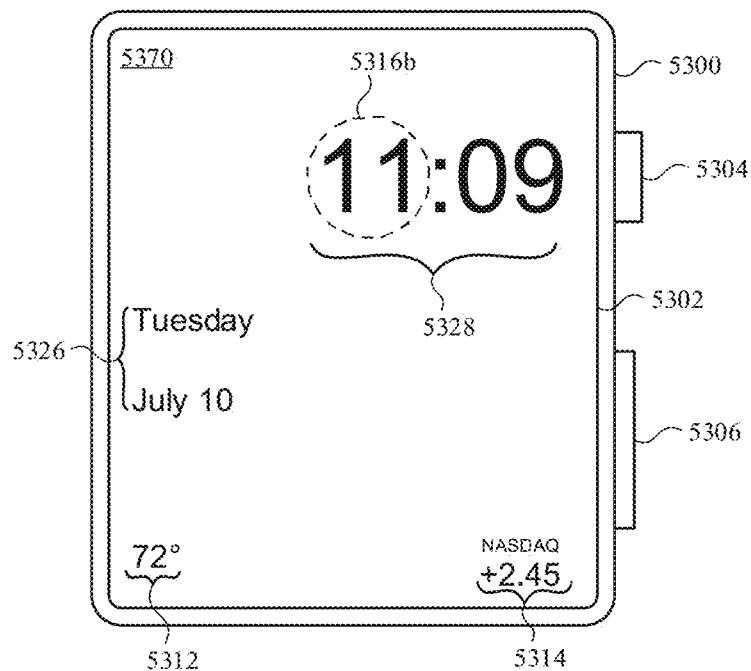

FIG. 53D depicts exemplary user interface 5370, displayed on display 5302 of device 5300. In some embodiments, user interface 5370 is a watch face interface screen, such as a home interface of a wearable smart-watch portable electronic device. In some embodiments, interface 5370 can optionally be displayed by device 5300 in response to a user (such as a user of a device displaying interface 5340 as described in FIG. 53A) selecting a different "face" for device 5300, for example causing interface 5340 to cease to be displayed and interface 5370 to begin to be displayed. Interface 5370 can optionally share some common elements with interface 5340, namely weather complication 5312 and stock-market complication 5314. In some embodiments, complications 5312 and 5314 in interface 5370 can optionally have some or all of the attributes as described above with reference to interface 5340 in FIG. 53A.

Interface 5370 includes digital watch face 5328, which is indicating that the current time is 11:09. Interface 5370 also includes day/date object 5326, which is indicating that the current day of the week is Tuesday and that the current date is July 10. In some embodiments, day/date object 5326 can optionally be considered a complication, and can optionally be referred to as a day/date complication.

FIG. 53D further depicts user input 5316b, which is a touch contact detected by touch-sensitive display 5302. Touch contact input 5316b can optionally be a single-touch input, a multi-touch input, a single-tap input, and/or a multi-tap input detected by touch- and/or pressure-sensitive elements in display 5302. In the displayed example, input 5316b is a single-finger, single-tap input detected at a location on display 5302 corresponding to digital clock face 5328. Device 5300 can optionally be configured, in some embodiments, to, in response to detecting user input 5316b (or any other suitable predefined user input, including rotation of a rotatable input mechanism), activate a time-scrubbing mode.

Figure 53E:
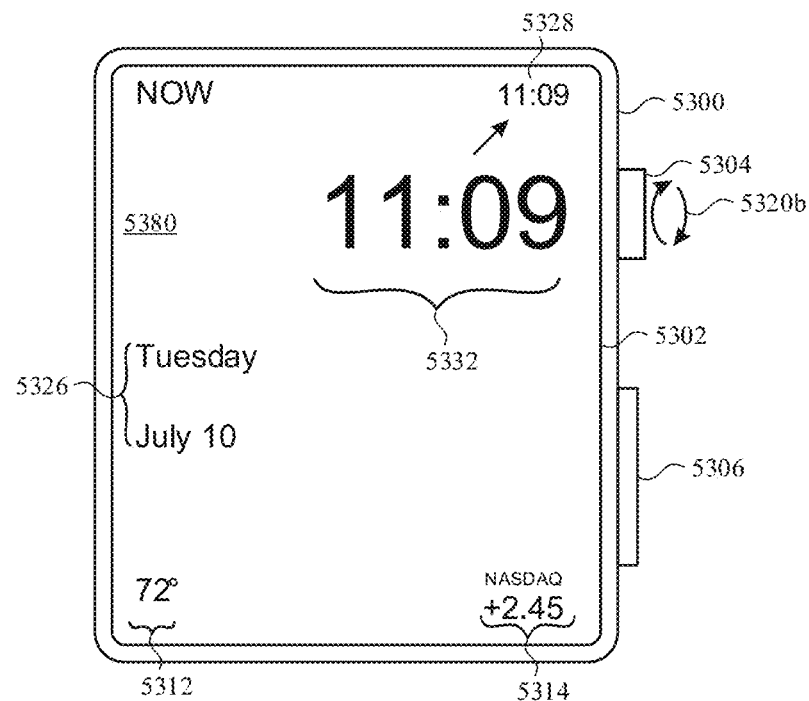

FIG. 53E depicts exemplary user interface 5380, displayed on display 5302 of device 5300. Exemplary user interface 5380 shows the manner in which, in some embodiments, device 5300 responds to the detection of input 5316b in FIG. 53D. Namely, user interface 5380 shows the activation, by device 5300, of a time-scrubbing mode and an associated time scrubbing interface in accordance with some embodiments.

In the depicted example, interface 5380 includes object 5326 and complications 5312 and 5314 in the same manner as described above with reference to interface 5370 in FIG. 53D. In some embodiments, object 5326 and complications 5312 and 5314 can optionally be visually distinguished in one or more ways from their respective appearances in interface 5370 in FIG. 53D to indicate that time-scrubbing mode is active.

In the depicted example, interface 5380 differs from interface 5370 in several ways that indicate that time-scrubbing mode has been activated. In the depicted example, interface 5380 differs from interface 5370 in that digital clock face 5328 has translated to the top right corner of display 5302 (as indicated by the diagonal arrow) and has decreased in size. In some embodiments, this transition can optionally include an animation of the translation and the resizing. In some embodiments, when digital clock face 5328 is moved from its position in interface 5370 to its position in interface 5380, it can optionally be displayed in a different size, shape, color, highlighting, or animation style. In some embodiments, the shape, color, highlighting, and/or animation style of digital clock face 5328 can optionally remain unchanged as digital clock face translates and is resized between interface 5370 in FIG. 53D and interface 5380 in FIG. 53E. In some embodiments, digital clock face 5328 can optionally appear in a white color in both interfaces 5370 and interface 5380.

In some embodiments, when digital clock face 5328 transitions to the top corner of display 5302 as time-scrubbing mode is activated, a visual indicator indicating that digital clock face 5328 indicates a current time can optionally be displayed. In the depicted example, the word "NOW" is displayed on display 5302 near the top left corner of display 5302. In some embodiments, the visual indicator, such as the word "NOW," can optionally be displayed in a similar or identical visual style as digital clock face 5328 following its transition into its position in interface 5380. For example, the word "NOW" can optionally be displayed in a similar size, font, color, highlighting, and/or animation style as digital clock face 5328 in interface 5380. In the depicted example, the word "NOW" or another indicator can optionally appear in a white color when digital clock face 5328 appears in a white color.

In the depicted example, interface 5380 further differs from interface 5370 by including digital clock face 5332, which is a second digital clock face that has appeared in the position on display 5302 that was previously occupied by digital clock face 5328 (before its transition and resizing) in interface 5370 in FIG. 53D. In some embodiments, digital clock face 5332 displays the scrubbing time of time-scrubbing mode, which currently is 11:09, the same as the current time, as the user has not entered any input causing the scrubbing time to advance into the future or rewind into the past. In some embodiments, digital clock face 5332 can optionally be displayed in the same or similar visual style as digital clock face 5328, including by being displayed in the same size, font, color, highlighting, and/or animation style. In some embodiments, digital clock face 5332 can optionally be displayed in a different visual style than digital clock face 5328 in interface 5370, to indicate to the user that digital clock face 5332 indicates a scrubbing time rather than a current time, such as by being displayed in a green color rather than a white color. In some embodiments, digital clock face 5332 can optionally appear on interface 5380 in response to the activation of time-scrubbing mode in accordance with any of the animations discussed above with reference to complications being updated during scrubbing. In some embodiments, the animation of digital clock face 5332 appearing in interface 5380 can optionally include digital clock face 5380 increasing in size and/or gradually becoming less translucent (e.g., fading in).

FIG. 53E further depicts rotational input 5320b, which is a rotational user input detected by rotational input mechanism 5304 of device 5300. In some embodiments, rotational user input 5320b can optionally have one or more characteristics in common with rotational input 5320a described above with reference to FIG. 53B. In some embodiments, rotational input 5320b is an input for scrubbing forward to a future time.

Figure 53F:
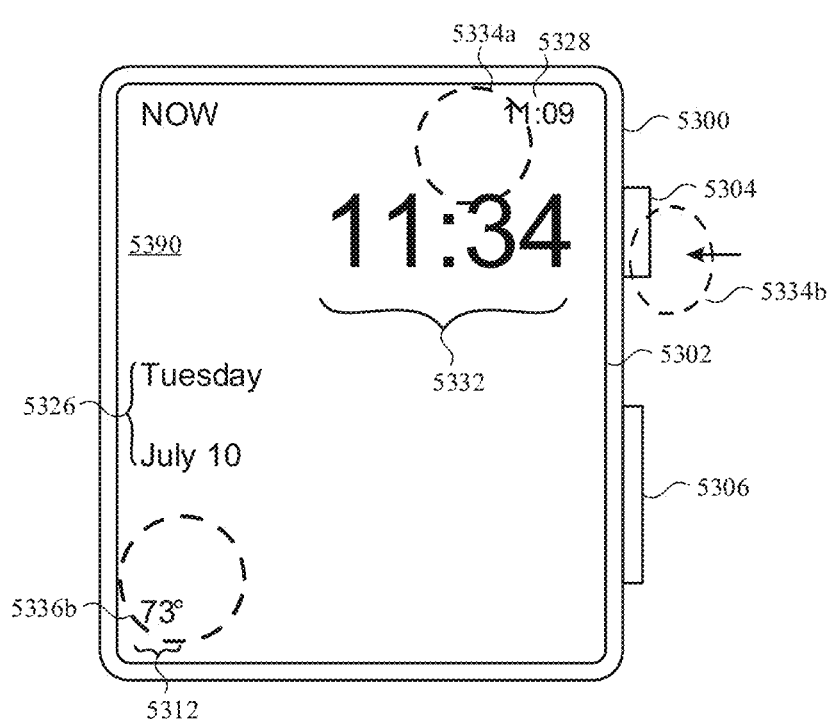

FIG. 53F depicts exemplary user interface 5390 displayed on display 5302 of device 5300. Exemplary user interface 5390 shows the manner in which, in some embodiments, device 5300 responds to the detection of input 5320b in FIG. 53E. Namely, user interface 5390 shows time scrubbing to a future time by device 5300 and an associated interface in accordance with some embodiments. Specifically, interface 5390 depicts how digital clock face 5332 and complications 5312 and 5314 are updated in accordance with time scrubbing.

First, in the depicted example, in accordance with user input 5320b, digital clock face 5332 has changed from displaying "11:09" to instead displaying "11:24," thereby indicating the scrubbing time. In some embodiments, a digital clock face can optionally be stepped forward in accordance with a rotational user input, such that the further and faster a rotational input rotates, the further and faster a digital clock face indicating a scrubbing time can optionally advance. In some embodiments, displayed numerals on a digital clock face can optionally change iteratively, such as once for every minute scrubbed, once for every five minutes scrubbed, or the like. Updates can optionally be displayed for each changing second, 15 seconds, minute, 5 minutes, hour, or the like. In some embodiments, displayed numerals on a digital clock face can optionally change gradually or smoothly, such as by fading into and out of view or translating into or out of view. In some embodiments, displayed numerals on a digital clock face can optionally be animated as changing individually (e.g., number by number), and in some embodiments displayed numerals on a digital clock face can optionally be animated as changing as a group (e.g., part of, or the entire, digital clock face changes together). In some embodiments, one or more of the numerals or other elements displayed as part of a digital clock face, including digital clock face 5332, can optionally change in any of the manners described above with reference to digital clock face 5317 and FIG. 53C, including by way of an animation simulating the appearance of a flap-display, split-flap display, or arrival/departure board.

Further, in the depicted example, as digital clock face 5332 advances further as the scrubbing time is advanced into the future, digital clock face 5328 can optionally remain fixed and continue to display the current time. (If the current time advances with the passage of time, digital clock face 5328 can optionally accordingly advance, and a scrubbing clock face such as digital clock face 5332 can optionally also accordingly advance to maintain the same offset between the current time and the scrubbing time.) In some embodiments, a time difference indicator can optionally be displayed as part of user interface 5390 (and/or 5380 in FIG. 53E), and the time difference indicator can optionally be updated (in accordance, in some embodiments, with any of the animations or display styles discussed above, including those discussed with reference to digital clock face 5332 and/or those discussed with reference to digital clock face 5317 and FIG. 53C) to display an updated time difference in accordance with the scrubbing time advancing further into the future. If user interface 5390 included a time difference indicator, for example, it would be updated in accordance with the time being scrubbed forward to indicate a positive 25 minute difference between the scrubbing time of 11:34 and the current time of 11:09.

Further, in the depicted example of FIG. 53F, complications 5312 and 5314 have been updated in the same manner as described above with reference to interface 5360 in FIG. 53C, so as to correspond to the scrubbing time of 11:34 rather than the current time of 11:09. In some embodiments, day/date object 5326 can optionally also be updated in accordance with a scrubbing time in time-scrubbing mode; for example, if a user scrubs far enough into the future or the past to reach a different day, then day/date object 5326 can optionally be updated in a same or similar manner as a complication can optionally be updated to reflect the change to the day and date.

FIG. 53F further depicts user input 5336*b*, which is a touch contact detected by touch-sensitive display 5302. Touch contact input 5336*b* can optionally be a single-touch input, a multi-touch input, a single-tap input, and/or a multi-tap input detected by touch- and/or pressure-sensitive elements in display 5302. In the displayed example, input 5336*b* is a single-finger, single-tap input detected at a location on display 5302 corresponding to displayed weather complication. In some embodiments, in response to detecting user input 5336*a*, device 5300 can optionally provide additional information, additional interfaces, or additional modes corresponding to weather complication 5312, including in any of the manners described above with respect to input 5336*a* and FIG. 53C.

FIG. 53F further depicts user inputs 5334*a* and 5334*b*, both of which are user inputs configured to cause device 5300 to exit time-scrubbing mode and return to a non-time-scrubbing interface. In some embodiments, any suitable user input can optionally be predetermined to cause a device to exit time-scrubbing mode. In some embodiments, user inputs 5334*a* and 5334*b* can optionally share some or all characteristics with user inputs 5324*a* and 5324*b* described above, respectively.

In response to detecting either user input 5334*a* or 5334*b*, or any other suitable predetermined user input, device 5300 can optionally cause time-scrubbing mode to be ceased and can optionally cease to display time scrubbing interfaces. In some embodiments, updated complications can optionally return to their original appearance before time-scrubbing mode was engaged, or can optionally change to an appearance corresponding to a new current time other than the current time that was current when time-scrubbing mode was engaged. In some embodiments, indications that time-scrubbing mode is active, such as digital clock face 5332, can optionally cease to be displayed, and user interface objects that moved position and/or changed appearance, such as digital clock face 5328, can optionally return to their original visual appearance and style from before time-scrubbing mode was activated. Any of these changes can optionally be made by way of any of the animations described above, including a reversed and/or accelerated version of any such animation. In the depicted example, in response to detecting user input 5334*a* or 5334*b*, device 5300 ceases to display user interface 5390 and displays user interface 5370 again; user interface 5370 indicates that the current time is still 11:09 and that the information corresponding to both weather complication 5312 (72°) and stock-market complication 5314 (NASDAQ+2.45) has not changed since time-scrubbing mode was activated.

FIGS. 54A-54E are flow diagrams illustrating a method for accessing and presenting information corresponding to past times and future times. Method 700 is performed at a device (e.g., 100, 300, 500, 5300) with a display and a rotatable input mechanism. Some operations in method 700 can optionally be combined, the order of some operations can optionally be changed, and some operations can optionally be omitted.

As described below, method 700 provides an intuitive way to access and present information corresponding to past times and future times. The method reduces the cognitive burden on a user for accessing and presenting information corresponding to past times and future times, thereby creating a more efficient human-machine interface. For battery-operated computing devices, enabling a user to access and present information corresponding to past times and future times, such as in a time-scrubbing mode in which displayed complications can optionally be scrubbed forward and/or backward in time, conserves power and increases the time between battery charges, by reducing the number of inputs required, reducing processing power used, and/or reducing the time of usage of the device.

In some embodiments, a device can optionally display a current-time indicator displaying a current time. In response to a user input (such as a tap on a touch-sensitive display on the current-time indicator), the device can optionally display, in addition to the current-time indicator, a non-current-time indicator. In response to and in accordance with a user input (such as a rotation of a rotatable input mechanism such as a crown of a smart watch), the time displayed by the non-current-time indicator can optionally be scrubbed forward or backward. In accordance with the scrubbing of the non-current time to a future or past time, one or more complications or other user interface objects can optionally be updated to correspond to the non-current time, by displaying information relating to the complication and correlating to the non-current time rather than the current time.

In FIG. 54A, at block 5402, method 700 is performed at an electronic device having a display and a rotatable input mechanism. An exemplary device is device 5300 of FIGS. 53A-53F, which has display 5302 and has a rotatable input mechanism 5304.

A block 5404, the device displays a first current-time indicator indicating a current time. In some embodiments, a current-time indicator is any watch face, clock face, or other indication of a time that is configured, designed, or understood to display a current time, such as the current time of day in the timezone in which a user is currently located. In some situations, a current-time indicator can optionally be displaying a non-current time, such as when the watch is not set for the correct time; however, in most situations, a current-time indicator will display the correct current time. In the example of interface 5340 in FIG. 53A, watch face 5308 and clock hands 5310*a* and 5310*b* together form a current-time indicator, indicating that the current time is 11:09. In the example of interface 5370 in FIG. 53D, digital clock face 5328 is a current-time indicator, indicating that the current time is 11:09.

At block 5406, the device displays a first user interface object configured to display information corresponding to the current time, wherein the information corresponding to the current time pertains to a first information source and is information other than a day, time, or date of the current time. In some embodiments, the first user interface object can optionally be a complication, as described above, and can optionally be configured to display information corresponding to a certain subject matter or a certain information source. In some embodiments, complications can optionally correspond to weather information, to stock market information, to calendar information, to day/date information, to time information, to world clock information, to social media information, to message information, to email information, to pedometer information, to health/fitness information, to exercise information, to alarm information, to stopwatch information, to information associated with third-party applications, or to any other suitable information that can optionally be visually presented as part of a complication or other user interface object. In the examples of interfaces 5340 and 5370 in FIGS. 53A and 53D, weather complication 5312 is a user interface object configured to display information corresponding to the current time (e.g., current information), the information pertaining to a weather application and/or a source of weather data in some embodiments. In some embodiments, weather complication 5312 can optionally be configured to display current weather information for the current time, such as a current air temperature (e.g., 72°). In the examples of interfaces 5340 and 5370 in FIGS. 53A and 53D, stock-market complication 5314 is a user interface object configured to display information corresponding to the current time (e.g., current information), the information pertaining to a stock-market application and/or a source of stock-market data, in some embodiments. In some embodiments, stock-market complication 5314 can optionally be configured to display a current performance of the NASDAQ, such as points gained or lost on the current day of trading (e.g., plus 2.45 points).

In some embodiments, user interface objects or complications can optionally be configured to display information that is the most current information available, such as a most recent temperature reading or a most recent stock score. In some embodiments, user interface objects or complications can optionally be configured to display information that explicitly relates to the current time, such as a calendar event that is occurring at the current time, or a proximate calendar event that is occurring at a time in the near future or a time in the near past with reference to the current time.

At block 5408, optionally, the device detects a first touch contact at a location corresponding to the first current-time indicator. In some embodiments, the input can optionally be one or more touch contacts detected by a touch-sensitive and/or pressure-sensitive surface, such as a touch-screen. In some embodiments, the first touch contact can optionally be detected at a location on a touch-screen at which the first current-time indicator is currently displayed. In some embodiments, a user can optionally tap a current-time indicator such as a displayed watch face or a digital clock face, and a device can optionally responsively activate a time-scrubbing mode and display associated time-scrubbing interfaces. In the example of interface 5340 in FIG. 53A, device 5300 detects user input 5316*a*, which is a touch contact detected by touch-sensitive display 5302. In some embodiments, user input 5316*a* is a single-finger single-tap gesture detected at a location of display 5302 at which watch face 5308 is currently displayed. In the example of interface 5370 in FIG. 53D, device 5300 detects user input 5316*b*, which is a touch contact detected by touch-sensitive display 5302. In some embodiments, user input 5316*b* is a single-finger single-tap gesture detected at a location of display 5302 at which digital clock face 5328 is currently displayed.

At block 5410, optionally, in response to detecting the first touch contact, the device displays a non-current-time indicator indicating the current time. In some embodiments, when time-scrubbing mode is activated, a non-current-time indicator is displayed. A non-current-time indicator can optionally be any watch face, clock face, or other indication of a time that is configured, designed, or understood to display a non-current time. In some embodiments, a non-current-time indicator can optionally indicate a "scrubbing time" that is displayed when time-scrubbing mode is activated; the scrubbing time can optionally be a time that is set in accordance with user inputs and is used to change what information is displayed by complications or other user interface objects during time-scrubbing mode. In some embodiments, the non-current-time indicator can optionally suddenly appear upon the activation of time-scrubbing mode, while in some embodiments the non-current-time indicator can optionally appear by way of animation such as translating into position or gradually becoming less transparent (e.g., fading in).

In some embodiments, a scrubbing time, such as one displayed on a scrubbing watch face or a scrubbing clock face, can optionally be set in accordance with user inputs, and can optionally also be set to the current time (such that the scrubbing time and the current time can optionally be the same time). In some embodiments, when a time-scrubbing mode is initially activated and a user input or instruction has not yet been received to set a scrubbing time, the scrubbing time is automatically set to the current time as a starting point. In this way, in some embodiments, a non-current-time indicator such as a scrubbing watch face or a scrubbing clock face can optionally sometimes display the current time. In such instances, despite the non-current-time indicator displaying a time that is the same as the current time, a user may understand that the non-current-time indicator is not an indication of the current time per se, but rather an indication that a scrubbing time is set to a time that is the same as the current time.

In the depicted example of interface 5350 of FIG. 53B, time-scrubbing mode has been activated and, accordingly, scrubbing hands 5322*a* and 5322*b* have been displayed in the same position that hands 5310*a* and 5310*b* were displayed prior to the activation of time-scrubbing mode. In some embodiments, scrubbing hands 5322*a* and 5322*b* are non-current-time indicators configured to indicate a scrubbing time, although in the example of interface 5350 of FIG. 53B, they are presently indicating a scrubbing time that is the same as the current time of 11:09.

In the depicted example of interface 5380 in FIG. 53E, time-scrubbing mode has been activated and, accordingly, digital clock face 5332 has been displayed in the same position that digital clock face 5328 was displayed prior to the activation of time-scrubbing mode. In some embodiments, digital clock face 5332 is a non-current-time indicator configured to indicate a scrubbing time, although in the example of interface 5380 in FIG. 53E, it is presently indicating a scrubbing time that is the same as the current time of 11:09.

In some embodiments, such as when a user executes multiple user inputs to scrub a scrubbing time forward and then backward, or backward and then forward, to return the scrubbing time to zero, a non-current-time indicator indicating the current time can optionally also be responsively displayed.

At block 5412, the device detects a first rotation of the rotatable input mechanism. In some embodiments, a first rotation of the rotatable input mechanism can optionally comprise one or more rotations in one or more directions, having one or more speeds, having one or more durations, and having one or more spacings relative to one another. In some embodiments, a first rotation of the rotatable input mechanism can optionally comprise a single rotation of a rotatable input mechanism in a predefined rotational direction. In some embodiments, a user can optionally rotate a rotatable input mechanism in a first direction, and a device can optionally responsively scrub a scrubbing time forward into the future (or, in some embodiments, backward into the past). In some embodiments, the first rotation of a rotatable input mechanism can optionally begin to be detected when a time-scrubbing mode is inactive, while in some embodiments it can optionally begin to be detected while a time-scrubbing mode is already activated. In the depicted examples of FIGS. 53B and 53E, rotational inputs 5320*a* and 5320*b* are detected by device 5300 when a user rotates rotatable input mechanism 5304 in a first direction.

In FIG. 54B, block 5402 is continued, such that the additional method blocks are also performed at an electronic device with a display and a rotatable input mechanism. In FIG. 54B, block 5414 follows from block 5412.

At block 5414, blocks 5416 to 5442 (some of which are optional), shown in FIGS. 54B and 54C, are performed in response to detecting the first rotation of the rotatable input mechanism. In discussing blocks 5416 to 5442 below, the phrase "in response to detecting the first rotation of the rotatable input mechanism" may or may not be repeated for clarity. In some embodiments, method steps are performed in response to detecting rotation of a rotatable input mechanism, which can optionally be the primary input mechanism for driving functionality in a time-scrubbing mode. That is, in some embodiments, rotation of a rotatable input mechanism can optionally be the core manner in which a user scrubs time forward or scrubs time backward, and various elements of the user interface objects can optionally react accordingly to the user's rotational input commands.

At block 5416, in response to detecting the first rotation of the rotatable input mechanism, the device displays a non-current-time indicator indicating a first non-current time determined in accordance with the first rotation. In some embodiments, the first non-current-time indicator can optionally be any of the non-current-time indicators described above with reference to block 5410, or can optionally share some or all of the characteristics of the non-current-time indicators described above. In some embodiments, in contrast to the non-current-time indicator in block 5410, the non-current-time indicator displayed in block 5414 (which can optionally be a different non-current-time indicator or the same non-current-time indicator) indicates a non-current time that is determined in accordance with the first rotation. In some embodiments, the indicated non-current time is a scrubbing time, and the scrubbing time is determined in accordance with a user's rotational scrubbing input.

In some embodiments, when the rotational input is detected before the activation of time-scrubbing mode, a non-current-time indicator, such as a scrubbing-time digital clock face or scrubbing hands on an analog clock face, can optionally begin to be displayed and display a user-selected scrubbing time. In some embodiments, when the rotational input is detected once a time-scrubbing mode has already been activated, then a previously displayed non-current-time indicator can optionally be modified to display a newly selected scrubbing time.

In some embodiments, a scrubbing time for a time-scrubbing mode can optionally be selected in accordance with a characteristic of the rotational input, and the selected scrubbing time can optionally be displayed by the non-current-time indicator. In some embodiments, the non-current-time indicator can optionally display an animation of the indicator changing to the newly selected scrubbing time, including any of the animation styles discussed above with reference to digital clock face 5317 and FIG. 53C. In some embodiments, an animation can optionally include displaying clock hands (e.g., a minute hand and an hour hand) sweeping into new positions.

In some embodiments, a rotation of a rotational input mechanism in one direction can optionally cause scrubbing forward, while a rotation of the rotational input mechanism in a direction substantially opposite to the one direction can optionally cause scrubbing backward. In some embodiments, the rate of scrubbing (forward or backward) can optionally be proportionally related to the rate of rotation; in some embodiments, the amount of time scrubbed can optionally be proportionally related to the distance (e.g., angular rotation) of rotation. In some embodiments, the scrubbing rate and amount of time scrubbed can optionally simulate the effect of a watch crown, where clock hands are physically connected to the crown by a series of gears, and accordingly the movement of the hands follows a user's twisting of the crown, reflecting a rotation of the crown by way of a predefined gear ratio. (In some embodiments, the rate and distance of scrubbing of a digital clock face can optionally be the same as the rate and distance of scrubbing of a displayed likeness of an analog clock face.)

In some embodiments, a device can optionally provide different "gearings" for different available faces. That is, a user can optionally select between more than one watch or clock interface, and, depending on the interface selected, the speed and distance of scrubbing in response to a given rotational input can optionally vary. For example, in some embodiments, an interface displaying (as a time indicator) a likeness of the globe can optionally display one rotation of the globe (approximately 24 hours) in response to a first rotation of the rotational input. Meanwhile, in some embodiments, an interface displaying (as a time indicator) a likeness of the solar system can optionally display one revolution of the Earth (approximately 365 days) in response to the same first rotation of the rotational input. Differences in the amount of time scrubbed in response to a given rotational input can optionally similarly be provided between other watch faces, such as an analog face like the one shown in interface 5340 in FIG. 53A, or a digital face such as the one shown in interface 5370 in FIG. 53D.

In some embodiments, the rate of time scrubbing and/or the amount of time scrubbed in response to a rotational input can optionally not have a fixed relationship to the angular magnitude of the rotational input. That is, in some embodiments, a rotational input of a given angular magnitude can optionally result in different amounts of time scrubbed, depending on various other factors. As discussed above, in some embodiments, different interfaces can optionally be associated with different default gearings. In some embodiments, a user can optionally manually select different gearings, for example by executing an input on a displayed user interface object or by executing an input by actuating a hardware button (e.g., executing one or more presses of a rotatable and depressible input mechanism).

In some embodiments, a gearing can optionally not be fixed, such that, during the course of an ongoing rotational input, the relative rate (e.g., instantaneous rate) of time scrubbing as compared to the rate (e.g., instantaneous rate) of rotation of the rotatable input mechanism can optionally be increased and/or decreased. For example, a variable gearing can optionally be configured such that rotation below a threshold speed (e.g., angular rotation per second) causes time scrubbing at a first rate or a first gearing, while rotation above the threshold speed causes time scrubbing at an accelerated rate or an accelerated fearing. In this way, when a user wishes to scrub by a large amount of time, the device can optionally recognize their rapid rotation of the rotational input mechanism and accordingly accelerate the time scrubbing rate, helping the user to more easily scrub by a large distance. In some embodiments, during an ongoing rotational input, if the speed of a rotational input drops below a predefined speed threshold after the time scrubbing rate has been accelerated, then the time scrubbing rate can optionally be decelerated and/or returned to its original rate; this deceleration can optionally aid a user who has used accelerated scrubbing to move the scrubbing time by a large amount, enabling the user to more precisely set the final desired scrubbing time as the user begins to slow his rotational input. In some embodiments, gearing can optionally be dynamically varied in accordance with any characteristic of a user input, such as a speed, a direction, a distance (e.g., angular distance), and/or a pressure.

In some embodiments in which a time scrubbing speed is accelerated, it should be noted that an animation of time scrubbing can optionally be different for accelerated scrubbing than for non-accelerated scrubbing. For example, in some embodiments, for non-accelerated scrubbing, a device can optionally provide a first animation of numbers on a digital clock face changing (with or without an accompanying animation such as a translation or a flipping effect) or a first animation of a minute hand and an hour hand sweeping around a clock face. Meanwhile, in some embodiments, for accelerated scrubbing, a device can optionally provide one or more different animations, such as blurring numbers on a digital clock face to signify that they are being changed rapidly, or by providing an animation of a blurred minute hand (or hiding a minute hand altogether) in order to avoid the minute hand appearing to "jump" from one position to another on a display without sweeping through intermediate positions. In some embodiments, such alternate animations for accelerated scrubbing can optionally be provided as part of an accelerated scrubbing mode, sometimes called a "turbo mode."

In some embodiments, a scrubbing time can optionally be set partially in accordance with a user's input and partially in accordance with predefined scrubbing times. For example, in some embodiments, predefined scrubbing times can optionally be configured such that, when a user executes an input that would set a scrubbing time to a predefined range of times, the actual scrubbing time is set to a predefined time. For example, if a predefined scrubbing time is 12:00 noon, and the user rotates a rotational input mechanism an appropriate distance and speed to set the scrubbing time to 11:58, then the scrubbing time can optionally be rounded to 12:00 noon and set to 12:00 noon. The range of scrubbing times that will "snap" to a predefined scrubbing time can optionally be set to any suitable length of time, such as one minute, five minutes, 15 minutes, 30 minutes, one hour, six hours, 12 hours, 24 hours, 2 days, one week, one month, one year, etc. In some embodiments, a device can optionally snap to different predefined scrubbing times depending on what interface a user is using; for example, in an interface featuring a likeness of the Earth or a representation of the sun, the device can optionally be configured to "snap" to scrubbing times to times corresponding to sunset, sunrise, or high noon. As another example, in interfaces featuring a likeness of the solar system, the device can optionally be configured to "snap" to scrubbing times corresponding to astronomical events such as planet alignments or eclipses.

In some embodiments, predefined scrubbing times can optionally be determined in accordance with user input. In some embodiments, a user can optionally manually set predefined scrubbing times, such as by setting "snap" times or selecting a "snap" interval. In some embodiments, predefined scrubbing times can optionally be set in accordance with data or information relating to one or more user interface objects or complications. For example, a device can optionally be configured to round a scrubbing time to the time at which a calendar event begins or ends. In some embodiments, a device can optionally be configured to round a scrubbing time to times at which data for a complication changes, becomes available, or ceases to be available. In some embodiments, a device can optionally be configured to slow or stop a scrubbing rate in accordance with a calendar event or other scheduled event being reached while scrubbing forward or backward, and a device can optionally be configured to snap or round a scrubbing time to a time corresponding to the calendar event or scheduled event.

In the depicted example of interface 5360 in FIG. 53C, scrubbing hands 5322*a* and 5322*b* have swept smoothly forward from their previous position in interface 5350 in FIG. 53B, moving forward in time in accordance with the speed and magnitude of user input 5320*a* in FIG. 53B, to indicate in user interface 5360 that the scrubbing time has been set to the non-current time of 11:34, which is 25 minutes ahead of the current time of 11:09. In the depicted example of interface 5390 in FIG. 53F, the numerals in digital clock face 5332 have changed in accordance with the speed and magnitude of user input 5320*b* in FIG. 53C to indicate in user interface 5390 that the scrubbing time has been set to the non-current time of 11:34, which is 25 minutes ahead of the current time of 11:09.

At block 5418, optionally, the first non-current time is a future time. In some embodiments, a non-current scrubbing time can optionally be a time that is in the future as compared to the current time. In some embodiments, a user can optionally scrub to a future time in a time-scrubbing mode by executing a rotation of a rotatable input mechanism in a predefined direction. A predefined direction of rotation for scrubbing into the future can optionally be substantially opposite to a predefined direction of rotation for scrubbing into the past. In the examples of interfaces 5360 and 5390 in FIGS. 53C and 53F, respectively, the scrubbing time is a future time of 11:34, which is 25 minutes ahead of the current time of 11:09.

At block 5420, optionally, the first non-current time is a past time. In some embodiments, a non-current scrubbing time can optionally be a time that is in the past as compared to the current time. In some embodiments, a user can optionally scrub to a past time in a time-scrubbing mode by executing a rotation of a rotatable input mechanism in a predefined direction. A predefined direction of rotation for scrubbing into the past can optionally be substantially opposite to a predefined direction of rotation for scrubbing into the future.

At block 5421, the non-current-time indicator is displayed at a location at which the first current-time indicator was displayed before the detection of the first rotation of the rotatable input mechanism. In some embodiments, a non-current-time indicator, such as one that is newly displayed upon the activation of time-scrubbing mode, can optionally be displayed at a location at which a current-time indicator was previously displayed before the activation of time-scrubbing mode. In some embodiments, the non-current-time indicator can optionally appear in its displayed position by way of any of the animations discussed above with reference to digital clock face 5317 and FIG. 53C. In some embodiments, a current-time indicator such as a digital clock face can optionally be animated as translating out of the way, and a non-current-time indicator, such as a different digital clock face with numerals displayed in a different color, can optionally be animated as increasing in size as if appearing from the distant z-axis and moving toward the viewer. In some embodiments, a scrubbing time indicator can optionally replace the current-time indicator on the display. In the example depicted in interfaces 5380 and 5390 of FIGS. 53E and 53F, digital clock face 5332 is displayed at the same location on display 5302 that digital clock face 5323 (which is reduced in size and translated to the upper corner upon the activation of time-scrubbing mode) was displayed in interface 5370 in FIG. 53D before the activation of time-scrubbing mode. In the example of interface 5350 in FIG. 53B, scrubbing hands 5322a and 5322b are displayed in the same position and same orientation as hands 5310a and 5310b were previously displayed, though scrubbing hands 5322a and 5322b can optionally be displayed in the depicted position in response to a touch contact activating time-scrubbing mode; after a rotational input while in time-scrubbing mode, scrubbing hands 5322a and 5322b can optionally be displayed at a different orientation (e.g., indicating a different time) though in the same general position (e.g., with the same center/anchor point) as hands 5310a and 5310b were previously displayed, as depicted in interface 5360 of FIG. 53C.

At block 5422, in response to detecting the first rotation of the rotatable input mechanism, the device updates the first user interface object to display information corresponding to the first non-current time, wherein the information corresponding to the first non-current time pertains to the first information source and is information other than a day, time, or date of the first non-current time. In some embodiments, when a user executes a rotational input as a command to scrub time forward or backward, one or more user interface objects displayed on a user interface, such as one or more complications, can optionally be updated in accordance with the newly selected scrubbing time. In some embodiments, a user interface object or a complication can optionally be predetermined to correspond to a first information source, subject matter, and/or a first application, and scrubbing time forward or backward will not change the information source, subject matter, or application to which a complication or user interface object pertains. For example, in some embodiments, when a complication is configured to display information pertaining to the weather obtained from a weather application, scrubbing the time forward or backward can optionally not change that the complication displays weather information obtained from a weather application—rather, the change can optionally be with respect to the time (rather than subject matter or information source) to which the displayed information pertains. That is, if the weather complication is configured to display current weather information (e.g., the most up-to-date temperature reading available) when a device is not in time-scrubbing mode, then scrubbing the time forward can optionally cause the weather complication to instead display forecasted or projected weather information, while scrubbing the time backward can optionally cause the device to display historical weather information (or past projected weather information) in some embodiments.

In some embodiments, information can optionally be considered to correspond to a time when the information is stored, linked, tagged, or associated with metadata indicating that the information corresponds to that time. For example, a piece of information (such as a weather forecast) can optionally be stored locally or remotely from the device, and can optionally be associated with a metadata or other tag that indicates a future time to which the weather forecast data corresponds (e.g., the time for the weather forecast). In some embodiments, as a user scrubs forward or backward through time, the device can optionally determine when to display the weather forecast data by comparing the displayed scrubbing time to the time associated with the tag or metadata of the stored weather forecast (or other stored data entry).

In some embodiments, a user interface object such as a complication can optionally be updated dynamically as a user scrubs time forward and/or scrubs time backward. In some embodiments, information displayed by a complication can optionally be updated with each displayed change to the non-current-time indicator, or it can optionally be updated in accordance with predefined periods of scrubbing time (e.g., 5 minutes, 15 minutes, 1 hour, 1 day, etc.). In some embodiments, information displayed by a complication can optionally be updated as frequently as new or different information from the currently displayed information is available; for example, if a weather forecast predicts a steady temperature for the next hour, and then an increase by one degree, then a complication displaying a weather temperature can optionally not display any change as the user scrubs through the first hour, then can optionally display the increased temperature when the scrubbing time reaches the time at which the forecasted temperature changes.

In some embodiments, a user interface object such as a complication can optionally be updated by way of an animation, including any of the animations described above with reference to digital clock face 5317 and FIG. 53C. In some embodiments, when a numeral displayed by an animation is changed, a sudden cut or a hard cut transition can optionally be used. In some embodiments, when a change other than a single numeral being changed is made to a complication, a transition animation can optionally be displayed in which a previous portion of (or all of) the complication is displayed as translating upwards (e.g., as if being flipped and rotated upward about a point of connection at the top of the complication, in the manner in which a page can optionally be flipped upward on a notepad), shrinking in size, and/or fading away (e.g., becoming increasingly transparent in time); while a new portion of (or all of) the complication can optionally be displayed as increasing in size (as if translating in from the distant z-axis and moving toward the viewer) and/or fading into view (e.g., becoming decreasingly transparent in time).

In the example of interfaces 5360 and 5390 in FIGS. 53C and 53F, respectively, weather complication 5312 has been updated in accordance with the time being scrubbed forward by 25 minutes to 11:34. Before the time was scrubbed forward, weather complication 5312 displayed a current weather temperature of 72°, while after the time has been scrubbed forward, weather complication 5312 has been updated to display a forecasted weather temperature of 73°, the forecasted weather temperature being a forecast corresponding to the future scrubbing time of 11:34.

At block 5424, optionally, the information corresponding to the first non-current time comprises projected data. In some embodiments, the information displayed by a user interface object or complication that has been updated in a time-scrubbing mode can optionally include projected or forecasted information, such as a weather forecast. In some embodiments, when forecasted or projected information (rather than known or scheduled information) is displayed, an indication (such as a visual symbol, a display stylization, etc.) can optionally be provided to alert the user that the information is a forecast or a projection. In the example of interfaces 5360 and 5390 in FIGS. 53C and 53F, respectively, the information displayed by weather complication 5312 is projected data in the form of a forecasted weather prediction for a future time.

In some embodiments, forecasted or projected information can optionally pertain to a future scrubbing time, in that the prediction or forecast was made about a future time, such that the user is provided with a forecast or a prediction for the future. In some embodiments, forecasted or projected information can optionally pertain to a past time, in that the prediction or forecast was made at a past time, such that the user is provided with a previous prediction or forecast.

At block 5426, optionally, the information corresponding to the first non-current time comprises a scheduled event. In some embodiments, information displayed by a complication can optionally include calendar information such as the name of a scheduled event, the time of a scheduled event, the place of a scheduled event, participants or invitees to a scheduled event, or other information about a scheduled event. For example, a complication can optionally be configured to display information from a user's personal calendar; in some embodiments, the complication can optionally display the name of a current calendar event, such as "Conference Call." In some embodiments, the complication can optionally display the name of a nearest upcoming calendar event. In some embodiments, when a user scrubs forward or backward in time, such a calendar complication can optionally change to display information corresponding to a calendar event scheduled for the scrubbing time, or to display information corresponding to a nearest upcoming calendar event with respect to the scrubbing time.

In some embodiments, when scrubbing into the future and/or the past, the device can optionally determine what information to display in a different manner than the device determines what information to display for the current time when time-scrubbing mode is not activated. For example, if a meeting is scheduled for 12:00 noon, then a calendar complication can optionally, in some embodiments, display information pertaining to the 12:00 noon meeting starting at a time before 12:00 noon, such as 11:00 a.m. or 9:00 a.m., or whenever a previous calendar event concludes. In this way, the user may see the calendar event regarding the 12:00 noon meeting before the time of the meeting, and is less likely to forget about the meeting and be late. Thus, information can optionally be displayed about the meeting for a period of time that extends beyond (e.g., before) the time of the calendar event in the user's calendar. In some embodiments, the same thing may not be true in time-scrubbing mode. For example, in some embodiments, when a user enters time-scrubbing mode, a calendar complication can optionally suppress display of information pertaining to calendar events when the scrubbing time is not set to a time for which the calendar event is actually scheduled. Thus, for a noon meeting, despite the device displaying the meeting, in some embodiments, outside time-scrubbing mode when the current time is 11:09, display of the meeting can optionally be suppressed in time-scrubbing mode when the scrubbing time is set to 11:09. In some embodiments, suppressing display of calendar events in time-scrubbing mode when the scrubbing time is not set to a time for which the calendar event is actually scheduled may aid a user's quick comprehension of the time for which calendar events are scheduled when a user is scrubbing through time quickly. (Note that, in other embodiments, time-scrubbing mode can optionally display calendar information when the scrubbing time is not set to a time for which the calendar event is scheduled; in some such embodiments, the device can optionally display a time for the calendar event to aid a user's understanding of the time of the calendar event as the user is scrubbing through time.)

At block 5428, optionally, the information corresponding to the first non-current time comprises historical data. In some embodiments, information displayed by a complication can optionally include historical information such as recorded data or other information. Recorded data or other information, in some embodiments, can optionally include recorded measurements, figures, readings, statistics, or events. Recorded data or other information, in some embodiments, can optionally include recorded forecasts or recorded predictions. Recorded data or other information, in some embodiments, can optionally include any information regarding the previous state of a device and/or of a user interface. In some embodiments, as a user scrubs through past times, a device can optionally display historical data that pertains to the past scrubbing time. In some embodiments, historical information can optionally pertain to a past scrubbing time in that the information itself concerns the past scrubbing time (e.g., a weather temperature reading at the time). In some embodiments, historical information can optionally pertain to a past scrubbing time in that the information was recorded or created at the past scrubbing time (e.g., a weather forecast made at the past scrubbing time).

Block 5430 optionally follows from blocks 5416-5420. At block 5430, optionally, in response to detecting the first rotation of the rotatable input mechanism, the device updates the first user interface object to indicate a lack of information corresponding to the first non-current time. In some embodiments, as a user is scrubbing forward or backward in time in a time-scrubbing mode, a user interface object or complication can optionally cease to be displayed to indicate that there is no information to be displayed corresponding to the selected scrubbing time. For example, when a user scrubs a stock-market complication to a future time, stock information can optionally not be available for the future time; accordingly, the complication (or part of the complication) can optionally cease to be displayed. A similar result could occur when a user scrubs so far forward in time that reliable projection or forecast data is not available; for example, a user can optionally scrub so far into the future that no weather forecast is available, and a weather complication could cease to be displayed. A similar result could occur when a user scrubs so far backward in time that historical data is no longer available; for example, a device (or an information source to which the device has access) can optionally only cache or otherwise store a limited amount of historical information, and when a user scrubs beyond that point, a complication can optionally cease to be displayed. A similar result could also occur when a user scrubs to a time to which no calendar data applies; for example, if a user scrubs to a time at which no events are scheduled on a calendar, then a device can optionally cease to display a calendar complication.

In some embodiments, when a user scrubs to a time for which no relevant information is available for display by a complication, a complication can optionally fade to a translucent appearance, can optionally be displayed in a faded or muted color scheme, or can optionally be displayed in a grayed-out color scheme, to indicate to the user that no information is available for the selected scrubbing time. In some such embodiments, the complication can optionally continue to display, in the altered (e.g., faded or grayed-out) manner, the information that was most recently displayed by the complication. This can optionally help the user to know that information pertaining to the selected scrubbing time is not available, while allowing the user to remain oriented to, and aware of, the complication's presence.

In FIG. 54C, block 5402 is continued, such that the additional method blocks are also performed at an electronic device with a display and a rotatable input mechanism. In FIG. 54C, block 5414 is continued, such that blocks 5432-5442 (some of which are optional) are performed "in response to detecting the first rotation of the rotatable input mechanism." In discussing blocks 5432 to 5442 below, the phrase "in response to detecting the first rotation of the rotatable input mechanism" may or may not be repeated for clarity.

Block 5432 follows from blocks 5422-5428, or optionally from block 5430. At block 5432, in response to detecting the first rotation of the rotatable input mechanism, the device displays one of the first current-time indicator and a second current-time indicator. In some embodiments, block 5432 can optionally be performed in response to detecting a user input that activates a time-scrubbing mode, such as the user input detected at block 5408. In some embodiments, when a time-scrubbing mode is activated (whether by a touch contact detected on a touch-sensitive surface or by a rotation of a rotatable input mechanism), in addition to displaying a non-current-time indicator indicating a scrubbing time, the device can optionally also display a current-time indicator. In some embodiments, the current-time indicator displayed in time-scrubbing mode can optionally be the same current-time indicator that was displayed before the activation of time-scrubbing mode, such as the current-time indicator displayed at block 5404, such that the same current-time indicator continues to be displayed. In some embodiments, the current-time indicator displayed in time-scrubbing mode can optionally be a second current-time indicator different from the current-time indicator that was displayed before the activation of time-scrubbing mode.

At block 5434, optionally, displaying the first current-time indicator in response to detecting the first rotation comprises displaying the first current-time indicator with a modified visual appearance. In some embodiments, upon the activation of time-scrubbing mode, the visual appearance of the first current-time indicator can optionally be altered in such a way so as to signal to the user that time-scrubbing mode has been activated and to direct the user's focus to the non-current-time indicator rather than the current-time indicator. For example, a size, shape, color, highlighting, and/or animation style of a current-time indicator can optionally be altered upon the activation of time-scrubbing mode.

In some embodiments, a current-time indicator can optionally be displayed in a faded, muted, partially transparent, or grayed-out color scheme while time-scrubbing mode is active. In the depicted example of interface 5360 in FIG. 53C, clock hands 5310a and 5310b are displayed in a grayed-out color scheme, as indicated by the hashing shown in the figure. This grayed-out color scheme can optionally signal to a user that time-scrubbing mode is active, and can optionally direct a user's attention to scrubbing hands 5322a and 5322b instead, which can optionally be displayed in a brighter or more noticeable color, such as green.

In the example of interface 5380 in FIG. 53E, digital clock face 5328 can optionally be displayed in green when time-scrubbing mode is activated, whereas it can optionally have been displayed in white before time-scrubbing mode was activated. In some embodiments, displaying more user interface objects, including current-time indicators, in a bright color such as green can optionally signal to a user that the device is in a time-scrubbing mode of operation.

In some embodiments, a current-time indicator can optionally be displayed in a smaller size than it was displayed before the activation of a time-scrubbing mode. In the depicted example of interface 5380 in FIG. 53E, digital clock face 5328 has been translated to the top corner of display 5302 (as indicated by the diagonal arrow) and is displayed in a smaller size than the size at which it was displayed (in interface 5370 in FIG. 53D) before the activation of time-scrubbing mode. The smaller display size of the current-time indicator can optionally signal to a user that time-scrubbing mode is active, and can optionally direct a user's attention to digital clock face 5332, which can optionally be displayed in a larger size and can optionally display a scrubbing time.

At block 5436, optionally, displaying the first current-time indicator in response to detecting the first rotation comprises displaying the first current-time indicator in a different position on the display than a position at which it was displayed prior to detecting the first rotation. In some embodiments, upon the activation of time-scrubbing mode, a current-time indicator can optionally cease to be displayed in one position and instead be displayed in another position. The position at which the current-time indicator is displayed during time-scrubbing mode can optionally be a less prominent position than the prior position, such as a position closer to an edge or corner of the display. In the example of interface 5390 in FIG. 53F, digital clock face 5328 is displayed at a different position than the position at which it was displayed (in interface 5370 in FIG. 53D) prior to the activation of time-scrubbing mode, having been moved closer to the upper right-hand corner of display 5302.

At block 5438, optionally, displaying the first current-time indicator in response to detecting the first rotation comprises animating the first current-time indicator from its initial position to the different position on the display. In some embodiments, the animation can optionally comprise the indicator fading away (e.g., becoming more transparent) from its old position and/or fading into (e.g., becoming less transparent) its new position. In some embodiments, the animation can optionally include translating the object across the display. In some embodiments, the animation can optionally include displaying the object increasing or decreasing in size. In some embodiments, the animation can optionally include any of the animations described above with respect to digital clock face 5317 and FIG. 53C or with respect to block 5422. In some embodiments, the current-time indicator can optionally suddenly cease to be displayed at its initial position and immediately begin to be displayed at the different position.

At block 5440, optionally, in response to detecting the first rotation of the rotatable input mechanism, the device displays a time difference indicator indicating a time difference between the current time and the first non-current time. In some embodiments, a time difference indicator can optionally be any user interface object that indicates a difference between one time and another time, such as the difference between a current time and a scrubbing time. In some embodiments, a time difference indicator can optionally indicate a number of seconds, minutes, hours, days, weeks, months, years, etc. In some embodiments, a time difference indicator can optionally indicate whether a scrubbing time is in the future or in the past relative to a current time. In some embodiments, a time difference indicator is automatically displayed upon activation of time-scrubbing mode. In some embodiments, explicitly displaying the difference between the scrubbing time and the current time can optionally help a user to more easily understand and contextualize how far away from the current time the scrubbing time (and the corresponding information displayed in the complications) is. In the example of interfaces 5350 and 5360 in FIGS. 53B and 53C, respectively, time difference indicator 5318 uses numerals to indicate the number of minutes difference between the current time and the scrubbing time, which is zero minutes in FIG. 53B and 25 minutes in FIG. 53C. In the example depicted, time difference indicator 5318 uses a "+" symbol to indicate that the scrubbing time is in the future as compared to the current time (and defaults to using a "+" symbol when the scrubbing time is equal to the current time). In some embodiments, if the scrubbing time is in the past as compared to the current time, then time difference indicator 5318 can optionally display a "−" symbol to indicate that the scrubbing time is a past time.

In some embodiments, when time-scrubbing mode is activated, elements previously displayed on the display can optionally be removed from the display. For example, in some embodiments, complications or other user interface objects displayed at a portion of the display where a time difference indicator is displayed can optionally be removed from the display (e.g., the device can optionally cease to display them) during time-scrubbing mode. In some embodiments, the same can optionally be true of interface objects or complications that are displayed at a location on the display where a current-time indicator (or an accompanying object such as the displayed word "NOW") is displayed when time-scrubbing mode is active. In some embodiments, complications can optionally be removed from the display upon the activation of time-scrubbing mode without regard for whether any other object will be displayed at the same location on the display during time-scrubbing mode. In some embodiments, when a current-time indicator or a time-difference indicator is displayed at or moved to a location of a display at which numbers on a likeness of an analog clock face were displayed, the numbers on the likeness of the analog clock face can optionally be hidden; for example, if a current-time indicator or time-difference indicator is displayed near the bottom of a clock interface in a time-scrubbing mode, then the numbers "5," "6," and "7" can optionally be hidden on the clock face. In some embodiments, dials or sub-dials displayed in a device interface (such as any dial described elsewhere in this disclosure) can optionally cease to be displayed upon the activation of time-scrubbing mode when a time-difference indicator or a current-time indicator is displayed at a portion of the display at which the dial or sub-dial was previously displayed.

In some embodiments, user interface elements displayed before the activation of a time-scrubbing mode can optionally change in size or appearance in order to make room for the display of a time-difference indicator or a current-time indicator in time-scrubbing mode. For example, in some embodiments, previously-displayed tick marks can optionally be replaced by or animated as transitioning into dots, which can optionally be smaller in size and/or can optionally have more empty space between them on the display. In some embodiments, any suitable user interface object can optionally shrink in size and/or change locations on the display upon the activation of time-scrubbing mode, including to create space on the display for the display of a time-difference indicator and/or a current-time indicator or associated user interface objects.

In FIG. 54D, block 5402 is continued, such that the additional method blocks are also performed at an electronic device with a display and a rotatable input mechanism.

Blocks 5442, 5444-5446, and 5448 each follow, optionally, from blocks 5414-5440.

At block 5442, optionally, in response to a passage of time, the device updates the non-current-time indicator to indicate a second non-current time in accordance with the passage of time, such that a time difference between the current time and a presently indicated non-current time remains fixed. In some embodiments, as time passes, the current time is accordingly updated to keep time. Additionally to updating the current time, the device, in some embodiments, also updates a non-current time, such as a scrubbing time for time-scrubbing mode, in accordance with the passage of time. In this way, in some embodiments, once a user has set a scrubbing time, the difference between the scrubbing time and the current time can optionally remain fixed even as time passes. Thus, in some embodiments, when a scrubbing time is set to the future, the current time will not "catch up" to the scrubbing time, because the scrubbing time will advance in time in parallel to the current time.

In some embodiments, as the scrubbing time is advanced in accordance with the passage of time, complications and other user interface objects can optionally be accordingly updated, in accordance with any of the methods explained above, to reflect the newly updated scrubbing time. Thus, a complication in time-scrubbing mode can optionally be updated, in some embodiments, both in accordance with the scrubbing time being altered by user input and in accordance with the scrubbing time being altered by the passage of time.

At block 5444, optionally, while displaying the updated first user interface object displaying information corresponding to the first non-current time, the device detects a second touch contact at a location corresponding to the updated first user interface object, and in response to detecting the second touch contact, displays a user interface corresponding to the first user interface object. The touch contact detected can optionally be a single-touch input, a multi-touch input, a single-tap input, and/or a multi-tap input detected by touch- and/or pressure-sensitive elements in any touch- and/or pressure-sensitive surface, including a touchscreen. In some embodiments, complications or other user interface objects that are updated in accordance with a scrubbing time in time-scrubbing mode can optionally be selectable affordances, such that if a device detects an input at a location corresponding to the complication, then an interface or application associated with the complication can optionally be accessed. For example, a user can optionally tap on a weather complication, in some embodiments, such as weather complication 5312, to cause an associated weather application to be opened. In another example, a user can optionally tap on a stock-market complication such as stock-market complication 5314, and, in some embodiments, a stock-market application can optionally be opened. In the depicted example of FIGS. 53C and 53F, user inputs 5336*a* and 5336*b* are detected on display 5302 at a location at which weather complication 5312 is displayed; in some embodiments, in response to detecting user input 5336*a* or 5336*b*, a weather application can optionally be accessed and a weather interface can optionally be displayed.

At block 5446, optionally, the user interface displayed in accordance with the detection of a second touch contact at a location corresponding to the updated first user interface object corresponds to the first non-current time. In some embodiments, the functionality of tapping or otherwise selecting complications or other user interface objects can optionally vary in accordance with the displayed scrubbing time, such that a different application or interface can optionally be provided depending on what the scrubbing time is set to at the moment of the user's selection. For example, in response to a user tapping a weather complication when the device is scrubbed to a past time, an interface of a weather application showing historical weather data for the scrubbed-to past time can optionally be displayed; in response to a user tapping a weather complication when the device is scrubbed to a future time, an interface of a weather application showing forecasted weather for the scrubbed-to future time can optionally be displayed. In another example, in response to a user tapping a calendar complication, a calendar event that is scheduled for the scrubbed-to time can optionally be opened, and an interface for that specific event can optionally be displayed. In the depicted example of FIGS. 53C and 53F, in response to detecting user input 5336a or 5336b, device 5300 can optionally provide an interface corresponding to forecasted weather information associated with the scrubbing time of 11:34 in some embodiments.

In some embodiments, a displayed complication can optionally correspond to an interface of the device that is configured to display a likeness of the Earth, the moon, and/or the solar system. In some embodiments, if a user scrubs time forward or backward on a scrubbing interface that contains such a complication, and then taps the complication to select it, then a corresponding Earth, moon, and/or solar system interface can optionally be displayed, wherein the Earth, moon, and/or solar system interface is itself scrubbed forward to the scrubbing time of the previous interface. In some embodiments, a user can optionally select complications corresponding to Earth, moon, and/or solar system interfaces to cause an animation to be displayed of the interface "flying" (e.g., smoothly zooming and panning) between views of the Earth, views of the moon, and/or views of the solar system. As the user flies between these various interfaces, in some embodiments, time scrubbing can optionally be maintained, and the scrubbing time can optionally be reflected in the complications displayed in each interface and/or in the displayed likenesses of the Earth, the moon, and/or the solar system.

At block 5448, optionally, the device detects a third touch contact at a location corresponding to the first current-time indicator, and in response to detecting the third touch contact, ceases to display the non-current-time indicator and updates the first user interface object to display information corresponding to the current time. The touch contact detected can optionally be a single-touch input, a multi-touch input, a single-tap input, and/or a multi-tap input detected by touch- and/or pressure-sensitive elements in any touch- and/or pressure-sensitive surface, including a touchscreen. In some embodiments, when a user taps on the current-time indicator, the device can optionally responsively exit time-scrubbing mode. Upon exiting time-scrubbing mode, in some embodiments, the device can optionally cease to display the scrubbing time. Upon exiting time-scrubbing mode, in some embodiments, display of the current time can optionally return to an original visual appearance (e.g., position, size, color, style, etc.) that was displayed before time-scrubbing mode was activated. Upon exiting time-scrubbing mode, in some embodiments, complications or other user interface object that were updated, in accordance with any of the above methods, to correspond to a scrubbing time, can optionally be again updated to correspond to the current time. In some embodiments, this can optionally involve returning to their original appearance from before time-scrubbing mode was activated, while in some embodiments it can optionally involve displaying new and/or different information (such as information corresponding to a new current time that is different from when time-scrubbing mode was activated, or information that is newly available or has been updated since time-scrubbing mode was activated). The displayed complications or user interface objects can optionally be updated, upon deactivating time-scrubbing mode, in accordance with any of the animations discussed above with reference to digital clock face 5317 in FIG. 53C. In the depicted example of FIGS. 53C and 53F, touch contacts 5324a and 5334a are each detected at a location on display 5302 at which a current-time indicator is displayed; in response to detecting either input, device 5300 can optionally cause time-scrubbing mode to be deactivated, and the displayed time indicators and complications can optionally be accordingly updated. In the depicted example, if no information has changed and the time has not changed since the activation of time-scrubbing mode, exiting time-scrubbing mode in FIGS. 53C and 53F can optionally cause the display, respectively, of interface 5340 in FIG. 53A and of interface 5370 in FIG. 53C.

In some embodiments, other user inputs can optionally be operable to cause the device to exit a time-scrubbing mode. In some embodiments, alternate user inputs that can optionally cause a device to exit a time-scrubbing mode can optionally include a depression of a rotatable and depressible input mechanism, such as user inputs 5324b and 5334b in FIGS. 53C and 53F, respectively. Allowing a user to exit a time-scrubbing mode by depressing a rotatable and depressible input mechanism can optionally increase the ease of scrubbing time forward or backward and then easily exiting time-scrubbing mode when a user is finished with time-scrubbing mode, as commands to execute both functions can be entered with a single input mechanism. In some embodiments, a device can optionally exit a time-scrubbing mode after a predefined period of time of inactivity, such as when a device times out and a display is darkened.

At block 5450, optionally, the device detects a second rotation of the rotatable input mechanism, and, in response to detecting the second rotation of the rotatable input mechanism, the device updates the non-current-time indicator to indicate a third non-current time, determined in accordance with the second rotation, and updates the first user interface object to display information corresponding to the third non-current time, wherein the information corresponding to the third non-current time pertains to the first information source and is information other than a day, a time, or a date of the first non-current time; and displays one of the first current-time indicator and the second current-time indicator. In some embodiments, after detecting a first rotation and setting a first scrubbing time, as described above, a device can optionally then detect another rotation of the same rotational input mechanism, and can optionally set another scrubbing time in accordance with the second rotation. The device can optionally set a second scrubbing time in accordance with any of the methods described above, and can optionally update the displayed user interface object and complications to correspond to the second scrubbing time in accordance with any of the methods described above. In some embodiments, a user can optionally scrub forward or backward in time, pause, and then scrub forward or backward in time again, with or without leaving time-scrubbing mode. In some embodiments, displayed complications can optionally be dynamically updated throughout the process to always reflect the displayed scrubbing time as the user scrubs, pauses, and then scrubs again. In some embodiments, this process can optionally be wholly or partially repeated or iterated any number of times.

In FIG. 54E, block 5402 is continued, such that the additional method blocks are also performed at an electronic device with a display and a rotatable input mechanism.

Blocks 5452 and 5454 follow, optionally, from blocks 5414-5440.

At block 5452, optionally, the device displays a second user interface object configured to display second information corresponding to the current time, wherein the second information corresponding to the current time pertains to a second information source and is information other than a day, time, or date of the current time; and, in response to detecting the first rotation of the rotatable input mechanism: updates the second user interface object to display second information corresponding to the first non-current time, wherein the second information corresponding to the first non-current time pertains to the second information source and is information other than a day, time, or date of the first non-current time.

At block 5454, optionally, the first and second information sources are separate applications.

In some embodiments, a device can optionally display more than one complication or other user interface object, wherein the complications or other user interface objects pertain to separate subject matters, separate information sources, or separate applications of the device. For example, in some embodiments, an interface of a device such as a watch face interface or a home screen interface can optionally display two distinct complications, each complication being associated with a distinct application of the device and each complication drawing information from the respective associated application and displaying the information on the interface. In the depicted example of FIG. 53A, weather complication 5312 and stock-market complication 5314 are distinct complications that can optionally each be associated with a distinct information source and/or application (e.g., a weather application and a stock-market complication, respectively).

In some embodiments, when a user scrubs time forward or backward in any of the manners described above, not just one but both (and, in some embodiments, more than two) of the displayed complications or other user interface objects are simultaneously updated in accordance with the time scrubbing. A second displayed complication or user interface object (in addition to a third, fourth, etc.) can optionally be updated in accordance with scrubbing by any of the methods described above. In some embodiments, all of the complications displayed on an interface can optionally be simultaneously updated in accordance with the displayed non-current time as a user scrubs through time. This may be advantageous because, in some embodiments, a user can optionally be able to observe past information and/or future information of more than one information source or of more than one application without having to separately open each application; this can optionally allow a user to observe and recognize contextual relationships between temporally-related data provided by different applications or different information sources by being able to see information from all applications at once, the information displayed all corresponding to the same past time or to the same future time.

In the depicted example of FIG. 53C, in response to the user scrubbing forward in time by 25 minutes to a scrubbing time of 11:34, weather complication 5312 has been updated in accordance with the scrubbing time to display a forecasted weather temperature of 73° for the scrubbing time of 11:34. At the same time, stock-market complication 5314 has been updated by being removed from interface 5360, in accordance with the fact that no information is available from the stock-market application or information source associated with stock-market complication 5314. (In some embodiments, a second complication having access to information, from an associated application or information source, corresponding to the scrubbing time of 11:34, could display the information alongside the information displayed by weather complication 5312.) Thus, in some embodiments, in order to view future information (or to be informed of a lack of future information) from the distinct and separate applications that are associated with complications 5312 and 5314, a user can optionally not need to separately access each application or separately instruct each application to access and/or display future information; rather, simply by scrubbing to a future time, both complications can optionally be caused to simultaneously access and display future information corresponding to the selected scrubbing time.

It should be understood that the particular order in which the operations in FIG. 54 have been described is merely exemplary and is not intended to indicate that the described order is the only order in which the operations could be performed. One of ordinary skill in the art would recognize various ways to reorder the operations described herein.

Note that details of the processes described above with respect to method 5400 (e.g., FIG. 54) are also applicable in an analogous manner to the methods and techniques described elsewhere in this application. For example, other methods described in this application can optionally include one or more of the characteristics of method 5400. For example, the devices, hardware elements, inputs, interfaces, modes of operation, faces, time indicators, and complications described above with respect to method 5400 can optionally share one or more of the characteristics of the devices, hardware elements, inputs, interfaces, modes of operation, faces, time indicators, and complications described elsewhere in this application with respect to other methods. Moreover, the techniques described above with respect to method 5400 can optionally be used in combination with any of the interfaces, faces, or complications described elsewhere in this application. For brevity, these details are not repeated elsewhere in this application.

Figure 55:
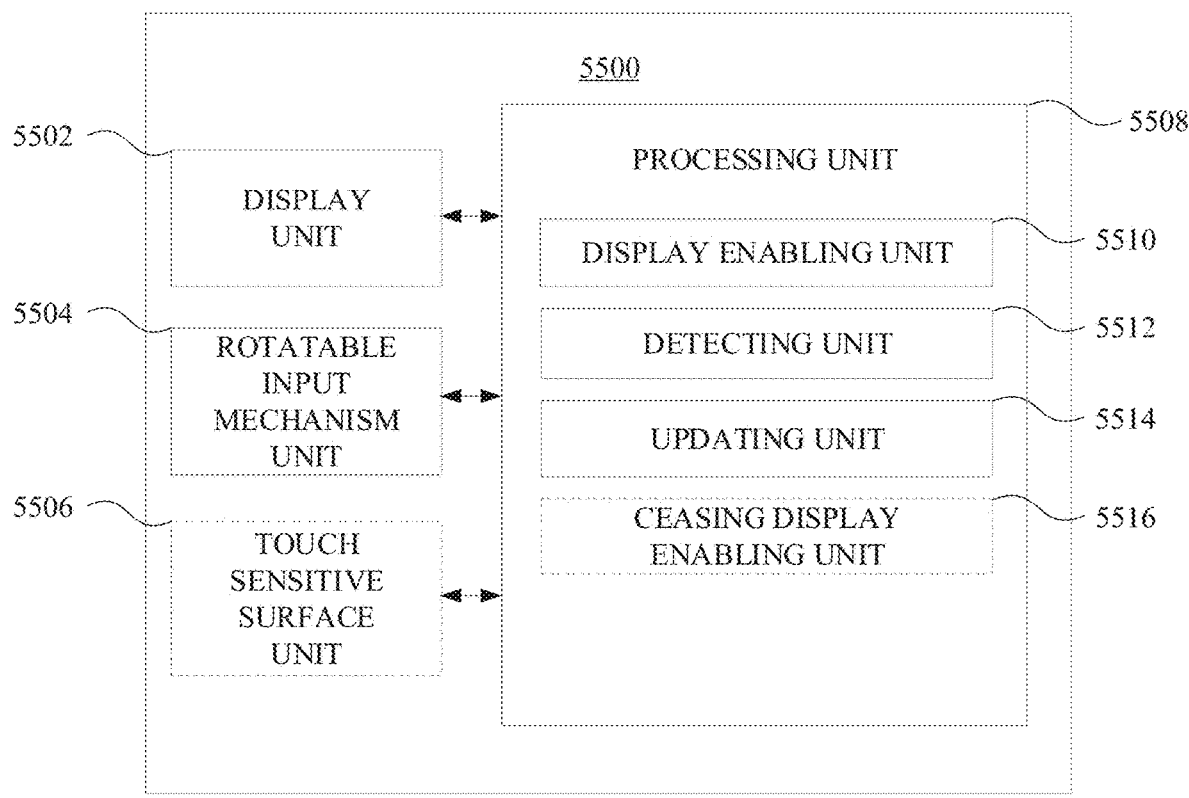
FIG. 55 is a functional block diagram of an electronic device in accordance with some embodiments.

In accordance with some embodiments, FIG. 55 shows an exemplary functional block diagram of an electronic device 5500 configured in accordance with the principles of the various described embodiments. In accordance with some embodiments, the functional blocks of electronic device 5500 are configured to perform the techniques described above. The functional blocks of the device 5500 are, optionally, implemented by hardware, software, or a combination of hardware and software to carry out the principles of the various described examples. It is understood by persons of skill in the art that the functional blocks described in FIG. 55 are, optionally, combined or separated into sub-blocks to implement the principles of the various described examples. Therefore, the description herein optionally supports any possible combination or separation or further definition of the functional blocks described herein.

As shown in FIG. 55, electronic device 5500 includes a display unit 5502 configured to display a graphic user interface including complications, current-time indicators, and non-current-time indicators; electronic device 5500 further includes a rotatable input mechanism unit 5504 configured to receive rotational inputs. Optionally, device 5500 also includes a touch-sensitive surface unit 5506 configured to receive contacts. Device 5500 further includes processing unit 5508 coupled to display unit 5502, rotatable input mechanism unit 5504, and, optionally, touch-sensitive surface unit 5506. Processing unit 5508 contains display enabling unit 5510, detecting unit 5512, and updating unit 5514. Optionally, processing unit 5508 further ceasing display enabling unit 5516.

Processing unit 5512 is configured to: enable display (e.g., with display enabling unit 5510) on display unit 5502 of a first current-time indicator indicating a current time; enable display (e.g., with display enabling unit 5510) on display unit 5502 of a first user interface object configured to display information corresponding to the current time, wherein the information corresponding to the current time pertains to a first information source and is information other than a day, time, or date of the current time; detect (e.g., with detecting unit 5512) a first rotation of rotatable input mechanism unit 5504; in response to detecting the first rotation of rotatable input mechanism unit 5504: enable display (e.g., with display enabling unit 5510) on display unit 5502 of a non-current-time indicator indicating a first non-current time determined in accordance with the first rotation; update (e.g., with updating unit 5514) the first user interface object to display information corresponding to the first non-current time, wherein the information corresponding to the first non-current time pertains to the first information source and is information other than a day, time, or date of the first non-current time; and enable display (e.g., with display enabling unit 5510) on display unit 5502 of one of the first current-time indicator and a second current-time indicator.

In some embodiments, processing unit 5508 is further configured to: in response to detecting the first rotation of the rotatable input mechanism unit 5504: update (e.g., with updating unit 5514) the first user interface object to indicate a lack of information corresponding to the first non-current time.

In some embodiments, the first non-current time is a future time.

In some embodiments, the information corresponding to the first non-current time comprises projected data.

In some embodiments, the information corresponding to the first non-current time comprises a scheduled event.

In some embodiments, the first non-current time is a past time.

In some embodiments, the information corresponding to the first non-current time comprises historical data.

In some embodiments, enabling display (e.g., with display enabling unit 5510) on display unit 5502 of the first current-time indicator in response to detecting the first rotation comprises enabling display on display unit 5502 of the first current-time indicator with a modified visual appearance.

In some embodiments, enabling display (e.g., with display enabling unit 5510) on display unit 5502 of the first current-time indicator in response to detecting the first rotation comprises enabling display on display unit 5502 of the first current-time indicator in a different position on the display than a position at which it was displayed prior to detecting the first rotation.

In some embodiments, enabling display (e.g., with display enabling unit 5510) on display unit 5502 of the first current-time indicator in response to detecting the first rotation comprises animating the first current-time indicator from its initial position to the different position on the display.

In some embodiments, the non-current-time indicator is displayed at a location at which the first current-time indicator was displayed before the detection of the first rotation of rotatable input mechanism unit 5504.

In some embodiments, processing unit 5508 is further configured to: in response to detecting the first rotation of rotatable input mechanism unit 5504, enable display (e.g., with display enabling unit 5510) on display unit 5502 of a time difference indicator indicating a time difference between the current time and the first non-current time.

In some embodiments, processing unit 5508 is further configured to: before detecting the first rotation of rotatable input mechanism unit 5504, detect (e.g., with detecting unit 5512) a first touch contact at a location corresponding to the first current-time indicator; and in response to detecting the first touch contact: enable display (e.g., with display enabling unit 5510) on display unit 5502 of the non-current-time indicator indicating the current time.

In some embodiments, processing unit 5508 is further configured to: in response to a passage of time, update (e.g., with updating unit 5514) the non-current-time indicator to indicate a second non-current time in accordance with the passage of time, such that a time difference between the current time and a presently indicated non-current time remains fixed.

In some embodiments, processing unit 5508 is further configured to: while enabling display on display unit 5502 of the updated first user interface object displaying information corresponding to the first non-current time, detect (e.g., with detecting unit 5512) a second touch contact at a location corresponding to the updated first user interface object; and in response to detecting the second touch contact, enable display (e.g., with display enabling unit 5510) on display unit 5502 of a user interface corresponding to the first user interface object.

In some embodiments, the user interface corresponds to the first non-current time.

In some embodiments, processing unit 5508 is further configured to: after detecting the first rotation of rotatable input mechanism unit 5504, detect (e.g., with detecting unit 5512) a third touch contact at a location corresponding to the first current-time indicator; and in response to detecting the third touch contact: cease to enable display (e.g., with ceasing display enabling unit 5518) on display unit 5502 of the non-current-time indicator; and update (e.g., with updating unit 5514) the first user interface object to display information corresponding to the current time.

In some embodiments, processing unit 5508 is further configured to: detect (e.g., with detecting unit 5512) a second rotation of rotatable input mechanism unit 5504; in response to detecting the second rotation of rotatable input mechanism unit 5504: update (e.g., with updating unit 5514) the non-current-time indicator to indicate a third non-current time determined in accordance with the second rotation; update (e.g., with updating unit 5514) the first user interface object to display information corresponding to the third non-current time, wherein the information corresponding to the third non-current time pertains to the first information source and is information other than a day, time, or date of the first non-current time; and enable display (e.g., with display enabling unit 5510) on display unit 5502 of one of the first current-time indicator and the second current-time indicator.

In some embodiments, processing unit 5508 is further configured to: enable display (e.g., with display enabling unit 5510) on display unit 5502 of a second user interface object configured to display second information corresponding to the current time, wherein the second information corresponding to the current time pertains to a second information source and is information other than a day, time, or date of the current time; and in response to detecting the first rotation of rotatable input mechanism unit 5504: update (e.g., with updating unit 5514) the second user interface object to display second information corresponding to the first non-current time, wherein the second information corresponding to the first non-current time pertains to the second information source and is information other than a day, time, or date of the first non-current time.

In some embodiments, the first and second information sources are separate applications.

The operations described above with reference to FIGS. 54A-54E are, optionally, implemented by components depicted in FIG. 1A, 1B, 2, 3, 4A, 4B, 5A, 5B, 53A, 53B or 55. For example, displaying operations 5404, 5406, 5416, and 5432; detecting operation 5412; and updating operation 5422 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A, 1B, 2, 3, 4A, 4B, 5A, 5B.

4. Exercise-Based Watch Faces and Complications

Attention is now directed towards embodiments of exercise-based watch faces and complications, as well as user interfaces ("UI") and associated processes related thereto, that can optionally be implemented on a multifunction device with a display and a touch-sensitive surface, such as devices 100, 300, and/or 500 (FIGS. 1A, 3A, and/or 5A).

The following examples illustrate exemplary embodiments of exercise-based watch faces and complications. It is to be noted that any of the aspects described above in relation to context-specific user interfaces (e.g., editing or selecting context-specific user interfaces, optional context-specific user interface features or aspects, etc.) can optionally be implemented with any of the exercise-based watch faces and complications described below. For example, one or more of the complications or complication features described above can optionally find use in the exercise-based watch faces, complications, and user interfaces described below. Specific description of all possible context-specific user interfaces or configuration of optional context-specific user interface aspects described herein is not practical given the sheer number of permutations. Therefore, exemplary embodiments are provided below to illustrate the techniques provided herein, but a skilled artisan will recognize that numerous other embodiments are contemplated within the scope of the present disclosure.

As discussed above, it is desirable to provide user interfaces that help integrate exercise into a user's daily routine. Such user interfaces allow a user to seamlessly access exercise-related information and functionalities along with other day-to-day tasks such as timekeeping, notifications, emails, scheduling, and so forth. For example, a user may wish to maintain an exercise schedule, track and record a user workout, and/or receive exercise-related information using the same device by which the user schedules their meetings, reads emails, receives notifications, and the like. Advantageously, this provides a more streamlined and efficient human-machine interface, particularly for users that engage in regular exercise and/or have an interest in personal fitness. For example, this allows the user to access day-to-day functionalities and exercise-related information and functionalities from the same user interface, thus reducing the number of user inputs required to access these functionalities and thereby allowing for, inter alia, greater battery life, reduced processing power, and reduced battery usage by the display.

FIGS. 56A and 56B show exemplary context-specific user interfaces including exercise-based watch faces and complications that can optionally be operated on device 5600. Device 5600 can optionally be device 100, 300, or 500 in some embodiments. The electronic device has a display (e.g., 504).

A user may wish to view a watch face that displays exercise-related information and/or provides one or more exercise-related functionalities. FIGS. 56A and 56B illustrate examples of such exercise-based watch faces. Exercise-based watch faces can optionally include one or more indications of time along with one or more exercise-related complications, affordances, and/or user interface objects, which can optionally display exercise-related information or represent an exercise-related application or functionality. Optionally, one or more of these exercise-related affordances and/or user interface objects can optionally be displayed as a complication associated with the indication(s) of time (e.g., within or adjacent to the indication(s) of time on the display). In some embodiments, these exercise-based watch faces can optionally further include any other displayed complication(s), such as those described above, which can optionally include exercise-related information or functionality.

FIG. 56A shows exemplary user interface screen 5602 that can optionally be displayed by device 5600. Screen 5602 includes user interface object 5604 that indicates the time of day. In this example, user interface object 5604 is a representation of an analog clock, with an hour hand and minute hand. Any user interface object that indicates a time of day can optionally be used, such as a representation of an analog or digital clock, or any of the other indications of time described herein. As described above, the clock faces of the present disclosure are not in any way limited to a traditional notion of a clock face (e.g., a circular display with hour indications and one or more hands to indicate time, or a representation of a digital clock).

Screen 5602 also includes affordances 5606, 5608, 5610, 5612, and 5614, which are displayed as complications associated with user interface object 5604 (e.g., within user interface object 5604 itself, or adjacent to user interface object 5604 on the display). Affordance 5608 is an exercise-based complication that represents a workout application. A workout application can optionally include, for example and without limitation, an application for monitoring, scheduling, tracking, and/or planning a user workout, as described in greater detail below. Affordance 5606 is an exercise-based complication that represents an exercise information application, which can optionally, e.g., allow a user to access exercise-related information, track their own exercise-related information (e.g., using exercise-tracking data obtained by device 5600), and so forth. Affordance 5610 is an exercise-based complication that represents a pedometer application, which can optionally allow a user to access pedometer data. Affordance 5612 is a complication that represents a weather application. This weather application can optionally be a general weather application, or it can optionally be a weather application that provides information relevant to user exercise (e.g., an exercise-based complication that represents an exercise-related weather application). Affordances 5606, 5608, 5610, and 5612 are further exemplified and described infra. Affordance 5614 can optionally be a complication that displays calendar information, such as the date or any other calendar-related information described herein. In some embodiments, the calendar information can optionally be obtained from a calendar application. Any of the complications described herein, or any complication representing an application described herein (e.g., a calendar application, a world clock application, a stopwatch application, and the like) can optionally be displayed in addition to, or in place of, one or more of the complications illustrated in FIG. 56A or 56B.

FIG. 56B shows another exemplary user interface screen 5620 that can optionally be displayed by device 5600. Screen 5620 contains similar content as compared with screen 5602 but in a different configuration. Screen 5620 includes user interface object 5622 that indicates the time of day, but in contrast to the representation of the analog clock depicted by 5604, 5622 is a representation of a digital clock. Screen 5620 also includes affordance 5624, which displays calendar information similar to 5614 but additionally includes the date, month, and day of the week. Like screen 5602, screen 5620 displays affordances 5606, 5608, 5610, and 5612 displayed as complications associated with object 5622 (e.g., within user interface object 5622 itself, or adjacent to user interface object 5622 on the display).

A user may wish to use a portable multifunction device such as those described herein to begin or monitor a workout routine. A user may wish to access such exercise-related functionalities directly from, e.g., a user interface for keeping time and using complication(s) of interest. It is advantageous to provide the user the ability to access these exercise-related functionalities with minimal navigation or user input steps, thereby providing a more efficient user interface with while conserving battery life and battery usage by the display.

FIGS. 57A-57D show exemplary context-specific user interfaces including exercise-based watch faces and complications that can optionally be operated on device 5700. Device 5700 can optionally be device 100, 300, or 500 in some embodiments. The electronic device has a display (e.g., 504).

Figure 57A:
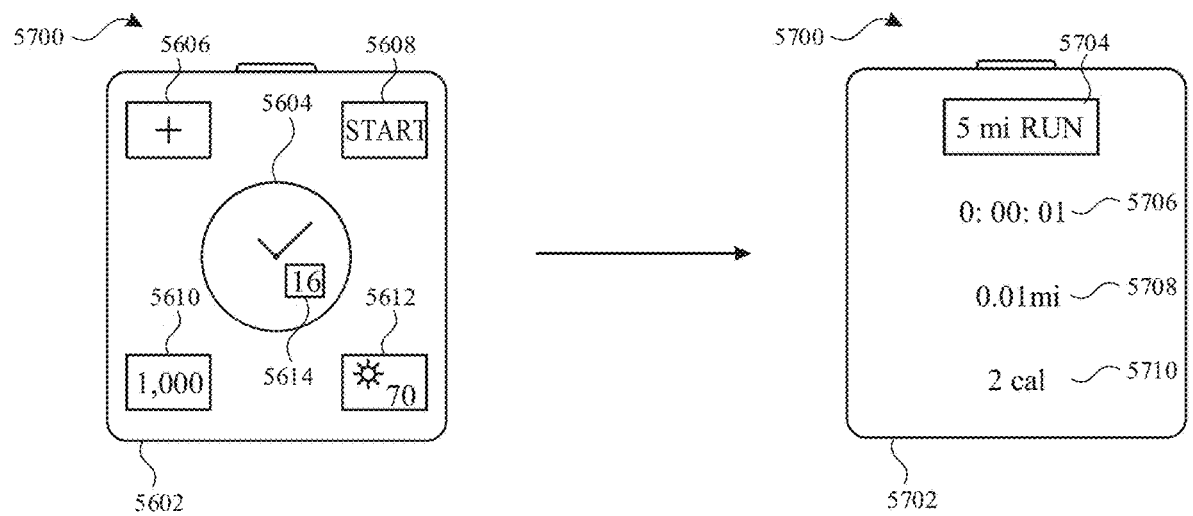
FIGS. 57A-57D illustrate exemplary exercise-based watch faces and complications.

As shown on FIG. 57A, device 5700 displays screen 5602, as described above. Device 5700 can optionally detect a user input (e.g., as described in greater detail below) and, in response to detecting a user input, begin a workout routine. A workout routine can optionally include any routine that includes one or more parameters of a user workout, including but not limited to duration (e.g., elapsed time); number repetitions of a physical activity (e.g., weightlifting, circuit training, swinging a golf club or tennis racket, jumping rope, laps, etc.); time(s) of a day when the user performs physical activity; amount of Calories burned by a user of the device while performing physical activity; distance travelled by a user of the device while performing physical activity (e.g., running, jogging, walking, swimming, etc.); steps taken by a user of the device while performing physical activity; elevation climbed by a user of the device while performing physical activity; highest/lowest/average velocity of a user of the device while performing physical activity; highest/lowest/average heart rate of a user of the device while performing physical activity; highest/lowest/average body temperature of a user of the device while performing physical activity; or the like. In some embodiments, a workout routine can optionally be based on one or more of these workout parameters, or any combination of these workout parameters.

In FIG. 57A, in response to detecting the user input, device 5700 begins a workout routine by displaying screen 5702, which includes affordance 5704 indicating the type of workout (e.g., a 5-mile run), affordance 5706 representing a workout timer, affordance 5708 indicating a distance tracker, and affordance 5710 indicating a Calorie tracker (e.g., a number of Calories burned during the workout routine). Any value corresponding to one or more workout parameters (e.g., as described above) can optionally be represented.

In some embodiments, one or more of these affordances can optionally be updated (e.g., in designated intervals, or continuously) to reflect a user's progress in one or more workout parameters. Exemplary affordances can optionally include, without limitation, a timer, lap or repetition counter, pedometer or other distance indicator, heart rate monitor, calorie tracker, speed indicator, and so forth. One or more of these affordances can optionally be updated using data obtained by one or more of activity sensors 520, e.g., GPS sensor 532, accelerometer 534, directional sensor 540 (e.g., compass), gyroscope 536, motion sensor 538, and/or other sensor(s) 541 (e.g., a biometric sensor).

In some embodiments, the workout routine can optionally be a workout routine from a set of workout routines, which can optionally be stored on device 5700 (e.g., in a memory such as memory 102, 370, or 518), or stored on an external device coupled to device 5700 via wireless communication (e.g., using RF circuitry 108 or communication unit 530). In some embodiments, the workout routine can optionally correspond to a latest workout routine that is not currently begun or displayed, e.g., the user's last started, or last completed, workout routine. In some embodiments, the workout routine can optionally correspond to a next workout routine, e.g., according to a list or schedule of workout routines. For example, the user or system can optionally designate an ordered list of workout routines (optionally, scheduled for particular times), and in response to detecting the user input, device 5700 can optionally begin the next workout routine on the list (e.g., after obtaining data representing the last scheduled, started, or completed workout routine on the list). In some embodiments, the workout routine can optionally be a randomly selected or randomly generated workout routine.

In some embodiments, the workout routine can optionally be designated by the user. For example, the user can optionally designate one or more workout routines, which can optionally be saved by device 5700 or an external device coupled to device 5700 via wireless communication (e.g., using RF circuitry 108 or communication unit 530). This allows the user to set their own workout schedule, so that when they begin a workout routine, it corresponds to the next workout according to the schedule. In some embodiments, the user can optionally designate a preference (e.g., through the workout application) as to which workout routine is begun, such as a particular or favorite workout routine, the previous started or completed workout routine, the next scheduled workout routine, a random workout routine, or the like.

In other embodiments, the workout routine can optionally be designated by the system (e.g., device 5700). For example, the user can optionally select a predetermined goal, such as running a marathon, and the system can optionally designate a workout or training schedule that corresponds to the user goal. Alternatively, the system can optionally use a heuristic method or other algorithm to designate a workout routine, e.g., based on previous and/or current user performance. For example, the system can optionally adapt the workout routine during the routine itself based on user progress in one or more workout parameters, which can optionally in some embodiments be based on data obtained by one or more of activity sensors 520, e.g., GPS sensor 532, accelerometer 534, directional sensor 540 (e.g., compass), gyroscope 536, motion sensor 538, and/or other sensor(s) 541 (e.g., a biometric sensor for tracking user heart rate); GPS module 135; or workout support module 142. Alternatively, the user can optionally input information such as user height, weight, age, fitness level, or the like, and the system can optionally designate a workout routine based on one or more of these user parameters. This allows device 5700 to act as a virtual trainer that helps the user to reach a fitness goal.

Figure 57B:
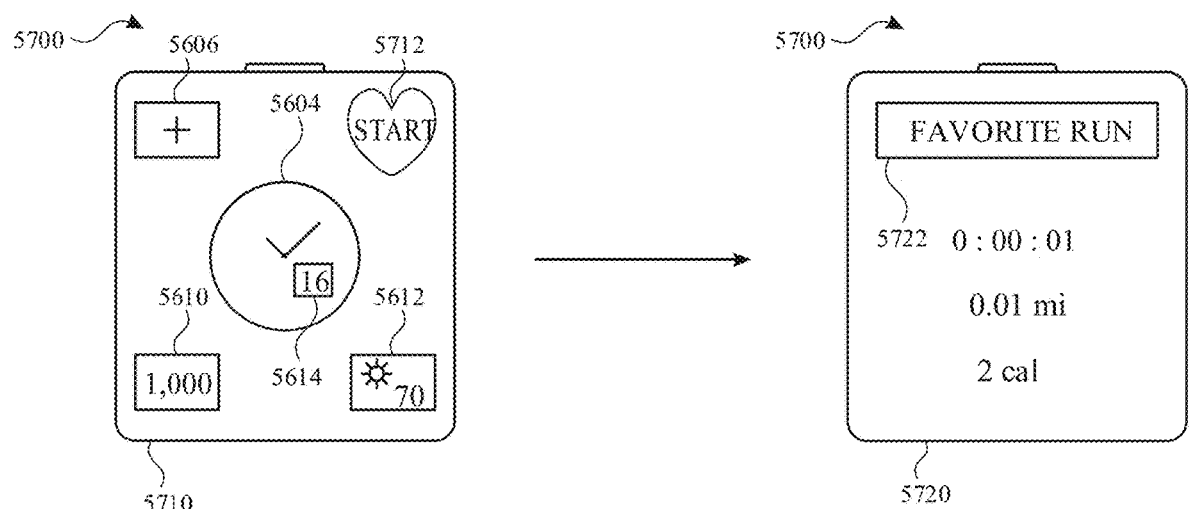

In FIG. 57B, device 5700 displays user interface screen 5710, which, like screen 5602, includes affordances 5606, 5610, 5612, and 5614. Screen 5710 also includes affordance 5712, which like 5608 represents a workout application. However, the appearance of 5712 indicates to the user what type of workout routine is begun upon detecting the user input. In this case, affordance 5712 indicates the workout routine is a user favorite routine, as depicted by the heart shape. In response to detecting the user input, device 5700 displays user interface screen 5720, which displays one or more workout parameters, as well as affordance 5722, which indicates the workout routine that is currently begun (in this case, the user's favorite run).

As illustrated in FIG. 57B, in some embodiments, a visual aspect or appearance of the affordance representing the workout application can optionally indicate the type of workout routine. For example, the affordance can optionally indicate whether the workout routine corresponds to a latest workout routine that is not currently begun, corresponds to a next workout routine according to a list of workout routines, is randomly selected or randomly generated, is user-designated, and/or is system-designated. Any visual aspect of the affordance can optionally indicate what type of workout routine is available. For example, the affordance can optionally include one or more graphical or text elements indicative of the workout routine. In some embodiments, a descriptive text can optionally indicate the workout routine, such as "Workout 1." In some embodiments, a graphical depiction of a type of exercise or exercise-related apparatus or apparel can optionally be displayed, such as running shoes, a bicycle, a weight, stairs, a figure engaged in some form of exercise, a symbol depicting a cardio workout, and so forth.

In some embodiments, in response to detecting the user input, device 5700 further launches a workout application, e.g., a workout application represented by affordance 5608 or 5712. This can optionally be advantageous if, for example, the workout application includes a workout tracking functionality. In other embodiments, in response to detecting the user input, device 5700 can optionally forego launching the workout application. For example, if the workout application does not track a user workout and instead displays information that a user may wish to access at times other than during an actual workout (e.g., information related to completed user workouts, or aspects related to workout planning rather than workout tracking), the user may wish to forego launching the application during a workout.

Figure 57C:
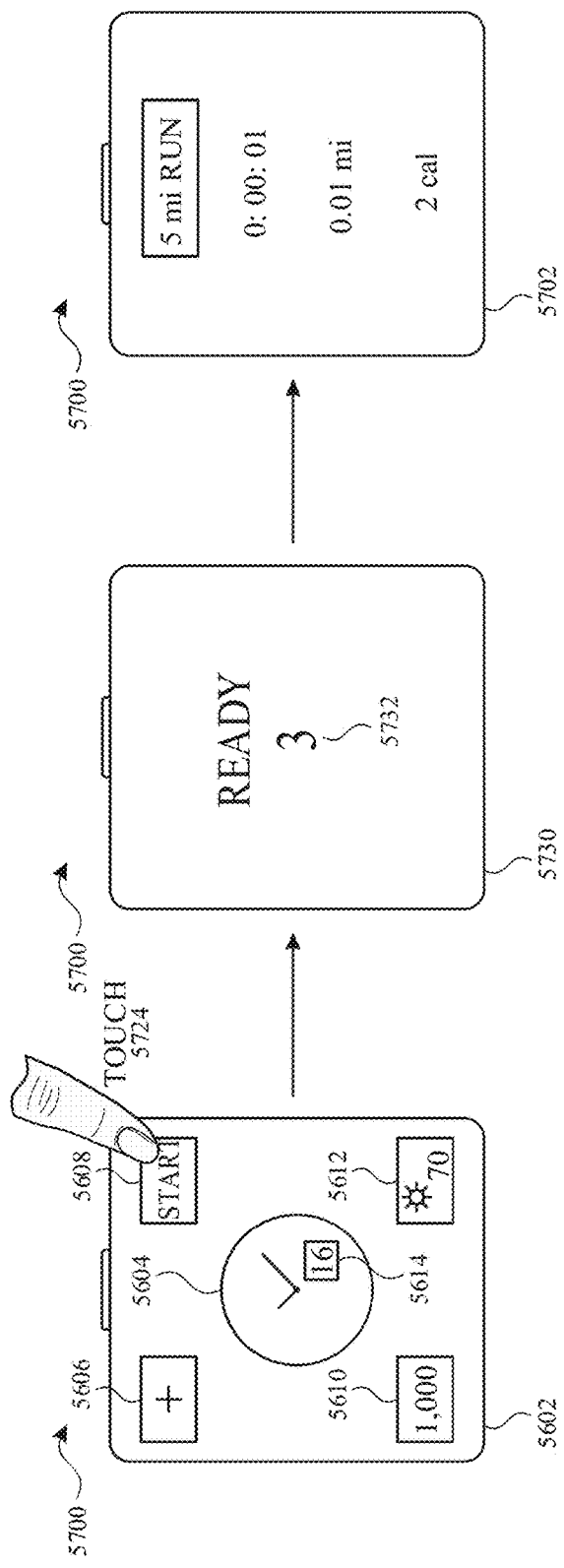
Figure 57D:
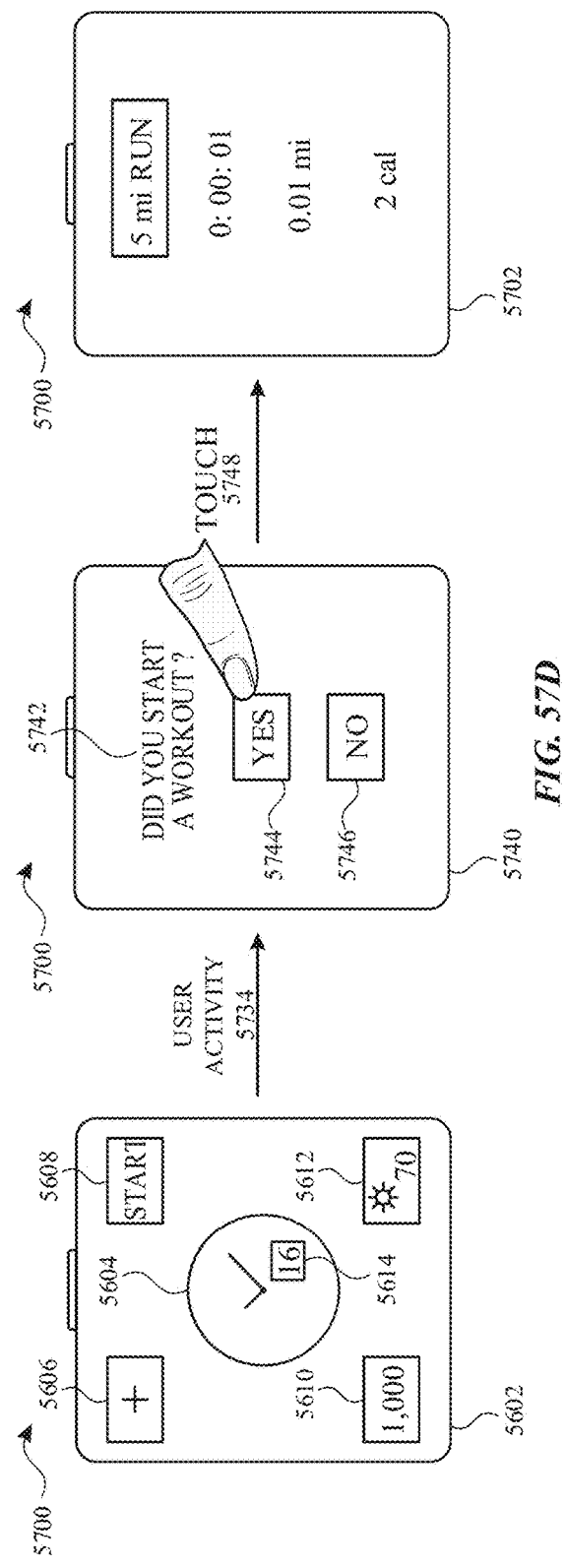

Several types of user inputs are contemplated as user inputs to begin a workout routine, as described above. Two exemplary types of user input are illustrated in FIGS. 57C-57D. These exemplary user inputs are provided without limitation, as other types of user input, such as other touch gestures or verbal inputs (e.g., a verbal command to start a workout) can optionally alternatively or additionally be used.

In some embodiments, the user input to begin a workout routine can optionally be a touch on a touch-sensitive display (e.g., touch-sensitive display 112 or touchscreen 504) at or near the location of a displayed affordance representing a workout application. In FIG. 57C, the user input is touch 5724 on affordance 5608. In response to detecting touch 5724, device 5700 begins a workout routine.

FIG. 57C also illustrates an optional feature for beginning a workout routine. In response to detecting touch 5724, device 5700 displays screen 5730, which includes a countdown timer 5732 for beginning the workout routine. This allows the user to provide the user input to start the workout routine and then coordinate the start of their exercise with the start of the workout routine. After finishing the countdown, device 5700 displays screen 5702, as described above.

FIG. 57C illustrates how, in some embodiments, device 5700 can optionally begin a workout routine in response to detecting the user input without prompting the user to start a workout. Advantageously, this allows the user to provide an input and immediately begin a workout routine using device 5700 without requiring any additional user inputs, thereby providing a more efficient user interface while conserving battery life.

In some embodiments, the user input to begin a workout routine can optionally be a user activity, e.g., an indication of user physical activity that meets an activity criterion based on activity data generated by an activity sensor. As shown in FIG. 57D, the user input can optionally be a user physical activity, such as user activity 5734. In some embodiments, device 5700 can optionally include one or more activity sensors (e.g., activity sensor 520), which can optionally include, e.g., one or more of a GPS sensor 532, accelerometer 534, directional sensor 540 (e.g., compass), gyroscope 536, motion sensor 538, and/or other sensor(s) 541, such as a pedometer, a passive infrared sensor, an ultrasonic sensor, a microwave sensor, a tomographic motion detector, a camera, a biometric sensor, a light sensor, a timer, or the like, and/or a combination thereof, all of which can be operatively connected to I/O section 514.

Based on activity data generated by the activity sensor (e.g., 520), device 5700 detects an indication of user physical activity. In order to detect an indication of user physical activity, device 5700, or any of the devices described herein, can optionally include one or more processors (e.g., 516) that can be configured to process activity data (e.g., from activity sensor(s) 520) to determine if the physical activity data represents a physical activity or a gesture being performed by the user, where a physical activity can generally refer to any bodily motion that can enhance or maintain physical fitness and overall health and wellness. For example, processors 516 can be coupled to provide instructions to activity sensors 520 via I/O section 514 and can be coupled to receive activity data from activity sensors 520 via I/O section 514. Additionally, processors 516 can determine, based on the physical activity data received from the sensors, various attributes or parameters of the detected physical activity. Techniques for monitoring a user physical activity and/or distinguish user physical activity from a gesture are provided, for example, in U.S. Provisional Application Ser. No. 62/129,828, filed Mar. 7, 2015, which is hereby incorporated by reference in its entirety.

In some embodiments, the user physical activity meets one or more activity criteria, e.g., a physical activity threshold. For example, processors 516 can be configured to identify the type or intensity of physical activity represented by the activity data, such as whether the detected activity is standing, bicycling, jogging, walking, running, swimming, jumping, going up stairs, a rapid movement (such as from wrestling or other martial arts), or the like. In some examples, processor 516 can determine a physical activity of a user based on one or more physical activity recognition algorithms. Some algorithms can instruct processor 516 to recognize movement of device 500 as being associated with a gesture if the detected movement does not meet an activity criterion, e.g., it does not have an intensity level greater than or equal to a physical activity threshold. The physical activity threshold can be represented as a distance traveled, a speed, a number of Calories burned, a number of steps taken, any one or more of these attributes calculated per unit time, or the like.

In some embodiments, the physical activity threshold can optionally comprise an increase in user heart rate (e.g., an increase above a threshold heart rate, an increase of a threshold amount within a designated time interval, etc.), which can optionally be detected by a biometric sensor as described above. The algorithms for storing such instructions for the one or more processors 516 can be stored in memory section 518. In some embodiments, the activity criterion does not include a user gesture. Examples of gestures recognizable by device 500 include, but are not limited to, waving hands, moving fingers, such as typing, or the like.

FIG. 57D also illustrates another optional feature for beginning a workout routine. In response to detecting user activity 5734, device 5700 displays screen 5740, which includes user prompt 5742 for confirming a workout, e.g., displayed as a user interface object. Screen 5740 also includes "yes" affordance 5744 for confirming a workout and "no" affordance 5746 for not confirming a workout. Other user prompts can optionally be used, such as an audible question to the user that can optionally be answered by a voice input. The user can optionally then confirm the workout, for example, by touch 5748 on "yes" affordance 5744. In response to detecting the user confirmation, device 5700 displays screen 5702. Providing a user prompt to begin a workout can optionally help to avoid unwanted initiations of a workout routine.

While FIGS. 57C and 57D illustrate particular combinations of optional exercise-related features, other combinations are contemplated. For example, optional countdown timer 5732 can optionally be displayed after displaying screen 5740 and detecting touch 5748. Further, the features illustrated on screens 5730 and 5740 are optional; device 5700 can optionally display screen 5702 after detecting a user input such as user activity 5734 or touch 5724.

A user may wish to limit notifications received by a device during a workout. In some embodiments, in response to detecting a user input to start a workout routine (as described above), device 5700 can optionally enter a "do not disturb" (DND) mode of the device. While in the DND mode, the electronic device can cease to output some or all notifications. In some examples, while in the DND mode, the one or more processors can cease to present a notification in response to any notification triggering event, such as the receipt of a text message, receipt of an email, receipt of a phone call, the occurrence of an event associated with an application running on the electronic device, an event scheduled in the user's calendar, or the like. In other examples, while in the DND mode, the one or more processors can cease to present a notification in response to certain types of notification triggering events, such as the receipt of a text message, receipt of an email, receipt of a phone call, the occurrence of an event associated with an application running on the electronic device, an event scheduled in the user's calendar, or the like, but can present a notification in response to other types of notification triggering events, such as the receipt of a high-priority text message, receipt of a high-priority email, or receipt of a high-priority phone call. In yet other examples, while in the DND mode, the one or more processors can cease to present all types of notifications, such as a display of text or an image, an audible noise, or a haptic output. In other examples, while in the DND mode, the one or more processors can cease to present some types of notifications, such as an audible noise or a haptic output, but can continue to present other types of notification, such as the display of text or an image.

In some embodiments, device 5700 can optionally remain in the DND mode for a predetermined amount of time. In other embodiments, device 5700 can optionally remain in the DND mode until the user provides a user input corresponding to a cessation of a workout. This user input can optionally include selection of an "end workout" affordance, or cessation of a user physical activity, e.g., one that meets one or more activity criteria, based on data generated by the activity sensor 520, as described above.

A user may wish to set an auto-reply for when the user is engaged in a workout. In some embodiments, in response to detecting a user input to start a workout routine (as described above), device 5700 can optionally enter an auto-reply mode of the device. While in the auto-reply mode, the electronic device can optionally automatically generate a reply to a received notification, text, email, and/or call from a sender. The reply can optionally in some examples comprise a text, graphic, or other notification to the sender, for example a simple "busy," or a graphical or text-based indication that the user is exercising/in a workout. In some embodiments, the form of the reply can optionally be designated by the system. In other embodiments, the user can optionally customize the reply, e.g., through a workout or notifications application.

In some embodiments, device 5700 can optionally remain in the auto-reply mode for a predetermined amount of time. In other embodiments, device 5700 can optionally remain in the auto-reply mode until the user provides a user input corresponding to a cessation of a workout. This user input can optionally include selection of an "end workout" affordance, or cessation of a user physical activity, e.g., one that meets one or more activity criteria, based on data generated by the activity sensor 520, as described above.

A user may wish to modify one or more haptic outputs (e.g., using haptic feedback module 133 and tactile output generator 167) during exercise. In some embodiments, after beginning a workout routine, device 5700 can optionally cease to produce a haptic output in response to an incoming message or received notification. For example, the user may wish to forego receiving haptic outputs during a workout.

In some embodiments, device 5700 can optionally remain in a state with haptic output ceased for a predetermined amount of time. In other embodiments, device 5700 can optionally remain in a state with haptic output ceased until the user provides a user input corresponding to a cessation of a workout. This user input can optionally include selection of an "end workout" affordance, or cessation of a user physical activity, e.g., one that meets one or more activity criteria, based on data generated by the activity sensor 520, as described above.

In response to detecting the user input corresponding to a cessation of a workout, device 5700 can optionally subsequently produce a haptic output in response to an incoming electronic message or notification received after detecting the cessation of the workout. In some embodiments, in response to detecting the cessation of a workout, device

5700 can optionally subsequently produce a haptic output in response to an incoming electronic message or notification received while the device was in the state with haptic output ceased. This notifies the user that an incoming electronic message or notification can optionally have been missed.

In other embodiments, a user may wish to receive enhanced haptic output(s) during a workout. For example, the user may wish for a different type of haptic output during a workout (e.g., more intense, a different pattern, a different duration, and so forth), which can optionally result in enhanced perceptibility. In some embodiments, after beginning the workout routine, device 5700 can optionally produce an enhanced haptic output in response to an incoming electronic message. An enhanced haptic output can optionally refer to a haptic output with a greater intensity, frequency, and/or number, e.g., as compared to a haptic output produced before beginning the workout routine.

In some embodiments, an enhanced haptic output can optionally include a first haptic output and a subsequent second haptic output, where the first and second haptic outputs are distinct. For example, in order to increase the saliency with which a user perceives a haptic alert, the user may wish to receive a "pre-alert" haptic output. The first haptic alert can optionally "prime" the user for receiving a second haptic alert, which in some embodiments can optionally indicate specific information (e.g., the source of the alert) or be associated with a second output (e.g., an audible or visible output), as described below. For example, it may be difficult for the user to perceive a haptic alert while moving or paying attention to something else during a workout. Therefore, a first haptic alert that "primes" the user to perceive a second haptic alert (and optionally, an associated second output) may be advantageous. In some embodiments, the first haptic output has a greater intensity and/or duration, as compared to the second haptic output. This may be advantageous, for example, by providing a stronger haptic signal to the user, drawing their attention to device 5700 in preparation for a second haptic signal (e.g., one with a distinctive aspect based on the source of the alert, or one associated with an audible or visible output). In some embodiments, device 5700 can optionally include a user interface (not shown) for configuring whether issuing the haptic alert includes issuing a first, "priming" haptic alert. In such embodiments, if device 5700 is configured to not issue a "priming" haptic alert, issuing the haptic alert can optionally include issuing only one haptic alert.

In some embodiments, device 5700 can optionally use a haptic output to communicate one or more workout parameters to the user during a workout. For example, device 5700 can optionally produce a haptic output after completion of a particular workout goal (e.g., a designated number of steps, a designated duration of time, etc.), after the completion of a subroutine as part of a circuit training workout, and/or after completion of a designated number of repetitions. In some embodiments, device 5700 can optionally use a haptic output as feedback during a user's workout. For example, device 5700 can optionally guide the user by providing a haptic feedback in response to successful, or unsuccessful, completion of an exercise, such as a golf club or racket swing (e.g., based on swing velocity, acceleration, direction, and so forth), swimming stroke, and the like. In some embodiments, the success of the completed exercise can optionally be based on data obtained by one or more activity sensors such as gyroscope/accelerometer data as described above.

A user may wish to send a notification regarding exercise to another user, such as a friend or other contact. For example, members of a running club may wish to send notifications to other members when they have completed a run, or a user may wish to notify a coach or fellow member about completed exercise. In some embodiments, device 5700 can optionally send a notification indicating a workout to an external device. For example, device 5700 can optionally send a notification upon beginning a workout, during a workout, or after user completion of a workout. A notification can optionally include, e.g., a text indicating that the user is exercising or has completed exercise. In some embodiments, the notification can optionally indicate one or more parameters of a user's workout, such as duration, number of repetitions, speed, heart rate, calories burned, a geographical indication of a user run, and so forth, or any combination thereof.

A user may wish to broadcast an exercise-related status to another user. For example, the user may wish to notify one or more friends or other contacts that the user is exercising. The user can optionally be part of an exercise group, e.g., a running club, and wish to let the rest of the club know that the user is exercising. Techniques for facilitating these interactions can optionally help to reinforce a user's exercise routine through social interactions.

Figure 58:
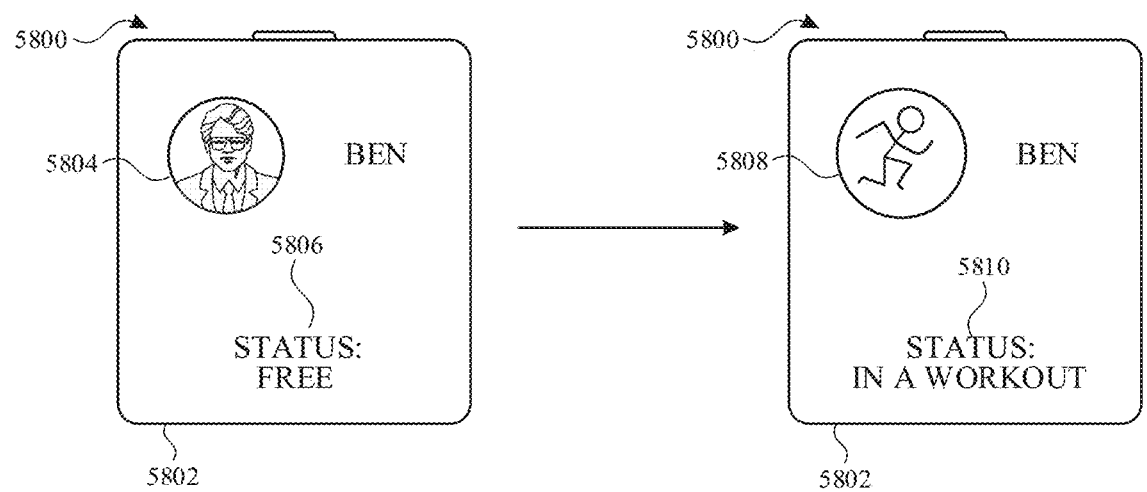
FIG. 58 illustrates exemplary exercise-based watch faces and complications.

FIG. 58 shows exemplary context-specific user interfaces that can optionally be operated on device 5800. Device 5800 can optionally be device 100, 300, or 500 in some embodiments. The electronic device has a display (e.g., 504).

Device 5800 displays screen 5802, which includes the name of a contact ("Ben"), the contact's avatar or profile picture 5804, and the contact's status 5806. Thus, screen 5802 notifies the user of device 5800 of Ben's status. Screen 5802 indicates that Ben is free and displays a non-exercise-related avatar or profile picture. Ben's status can optionally be obtained, e.g., via wireless communication (e.g., using RF circuitry 108 or communication unit 530) from an external device (such as those described herein) operated by Ben, or from a network or server to which Ben's external device is or was connected.

When device 5800 receives an indication from a device associated with Ben (e.g., data received via wireless communication as described above) that Ben has started a workout, device 5800 updates screen 5802 to display an exercise-related user avatar or profile picture 5808 and/or display an exercise-related user status 5810. In some embodiments, Ben's device can optionally send the indication of a workout in response to Ben's selection of a "start workout" affordance or an indication of Ben's physical activity (as described above). As shown on updated screen 5802, Ben's updated avatar or profile picture 5808 indicates a workout by displaying a graphical indication of exercise, such as a picture of Ben running, or a graphical representation of a runner. In other examples, the avatar or profile picture's appearance can optionally be altered to represent current or just-completed exercise through other means, such as depicting sweating, a flushed appearance, athletic apparel, and the like. In some embodiments, Ben's device can optionally send data representing a designated picture, such as a photo of Ben engaged in exercise, that serves as the avatar or profile picture indicating a workout. User status 5810 also indicates that Ben is in a workout. In some embodiments, 5808 and 5810 are displayed until device 5800 receives an indication of cessation of Ben's workout (e.g., data received via wireless communication from Ben's device as described above), at which point screen 5802 resumes displaying 5804 and 5806. In some embodiments, Ben's device can optionally send the indication of workout cessation in response to Ben's selection of an "end workout" affordance or a cessation of Ben's physical activity (as described above).

A user may wish to use a pedometer application to access and track pedometer information and/or pedometer-related goals. As described above, another exemplary exercise-based complication described herein is a complication that represents a pedometer application, as illustrated by affordance 5610.

Figure 59:
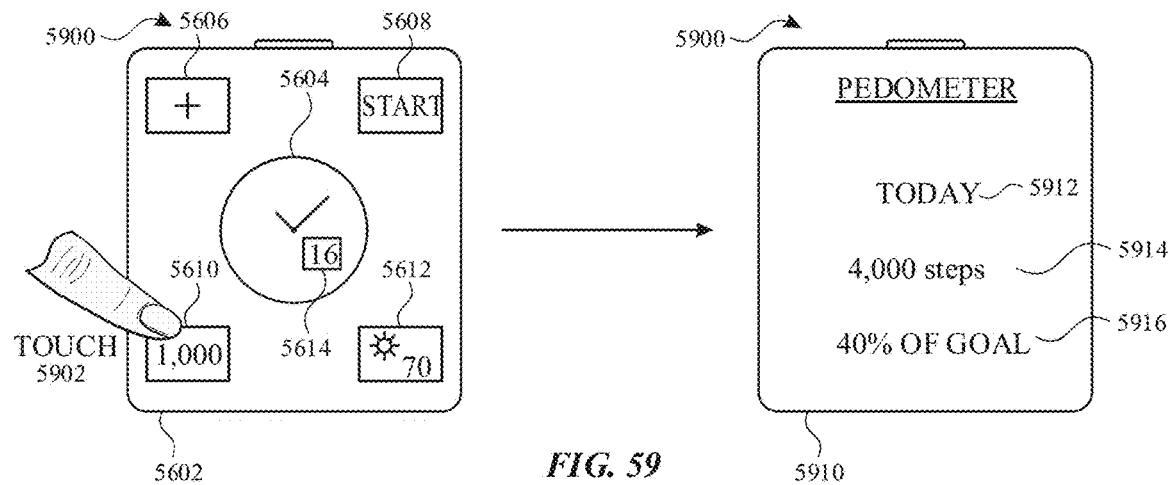
FIG. 59 illustrates exemplary exercise-based watch faces and complications.

FIG. 59 shows exemplary context-specific user interfaces that can optionally be operated on device 5900. Device 5900 can optionally be device 100, 300, or 500 in some embodiments. The electronic device has a display (e.g., 504).

In FIG. 59, device 5900 displays screen 5602, as described above. Screen 5602 includes affordance 5610 that represents a pedometer application. Affordance 5610 displays a set of information obtained from the pedometer application. This set of information, as displayed by affordance 5610, can optionally be updated (e.g., continuously, or at a designated interval) in accordance with data obtained from the pedometer application. For example, the pedometer application can optionally track a user's steps, e.g., using data obtained from one or more of the activity sensors described herein. As shown in FIG. 59, affordance 5610 displays "1,000" corresponding to the number of steps the user has taken in a designated interval (e.g., today).

In some embodiments, a set of information displayed by affordance 5610 includes one or more indications of distanced traveled, number of steps taken, energy expended, or a combination thereof. In some embodiments, one or more of these indications can optionally reflect a unit of measurement (e.g., a unit of length, such as miles or kilometers, or a unit of energy, such as a calorie). In some embodiments, one or more of these indications can optionally reflect a fraction of a predetermined goal. For example, the user can optionally select a goal (e.g., number of steps taken in a day, week, month, year, etc.), and the affordance can optionally reflect the fraction of the user's progress toward that goal in a designated period of time. In some embodiments, the goal can optionally be system-designated. In some embodiments, the goal can optionally be user-designated. In some embodiments, the displayed set of information can optionally indicate a number or attained fraction of a predetermined goal that increases as the user progresses. In other embodiments, the displayed set of information can optionally indicate a remaining number or fraction of a predetermined goal that decreases as the user progresses (e.g., a countdown).

In some embodiments, device 5900 can optionally detect a user input corresponding to a selection of affordance 5610. As illustrated in FIG. 59, in some embodiments, the user input can optionally include a touch on displayed affordance 5610 (e.g., on a touch-sensitive display), such as touch 5902.

In some embodiments, in response to detecting the user input corresponding to a selection of the affordance 5610 (e.g., touch 5902), device 5900 can optionally launch the pedometer application. As illustrated in FIG. 59, in response to detecting touch 5902, device 5900 displays user interface screen 5910, which represents the pedometer application. In this example, screen 5910 displays user interface objects 5912 (depicting a designated interval of time), 5914 (depicting a unit of measurement reflecting a user's steps taken in the interval), and 5916 (depicting a fraction of a predetermined goal attained during the interval).

A user may wish to use an exercise information application to access exercise-related information, track their own exercise-related information, designate exercise or exercise-related application preferences (e.g., related to workout selection, pedometer characteristics and designated goals, etc. as described above), and so forth. As described above, another exemplary exercise-based complication described herein is a complication that represents an exercise information application, as illustrated by affordance 5606.

Figure 60:
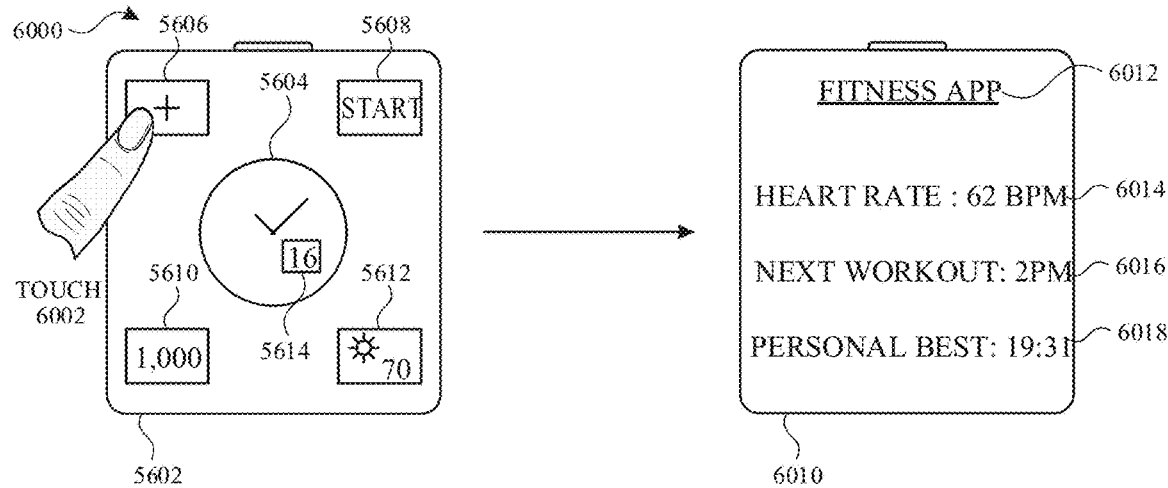
FIG. 60 illustrates exemplary exercise-based watch faces and complications.

FIG. 60 shows exemplary context-specific user interfaces that can optionally be operated on device 6000. Device 6000 can optionally be device 100, 300, or 500 in some embodiments. The electronic device has a display (e.g., 504).

In FIG. 60, device 6000 displays screen 5602, as described above. Screen 5602 includes affordance 5606 that represents an exercise information application. In some embodiments, affordance 5606 can optionally depict a symbol and/or text indicating to the user that it represents an exercise information application (e.g., a third-party or branded symbol). In some embodiments, affordance 5606 can optionally indicate exercise-related information.

To launch the exercise information application, the user can optionally provide a user input. As illustrated in FIG. 60, in some embodiments, the user input can optionally include a touch on displayed affordance 5606 (e.g., on a touch-sensitive display), such as touch 6002. In response to detecting touch 6002, device 6000 displays user interface screen 6010, which represents the exercise information application. Screen 6010 displays exemplary exercise information, such as user interface object 6012 indicating that the user is viewing the exercise information application, user interface object 6014 indicating user heart rate, user interface object 6016 indicating an upcoming scheduled user workout, and user interface object 6018 indicating a user workout goal or previous workout information (e.g., a previous user performance in a previous workout). In some embodiments, one or more items of exercise information can optionally be updated to reflect a user progress; e.g., affordance 6014 can optionally be updated to reflect a user's current heart rate (e.g., based on data obtained from a biometric sensor as described above).

A user may wish to access weather information in order to plan a workout. For example, the user can optionally engage in an outdoor workout and wish to know what type of apparel is best suited for the weather at the time of the workout, and/or wish to know what time of day will have weather suitable for a workout. As described above, another exemplary exercise-based complication described herein is a complication that represents a weather application, as illustrated by affordance 5612.

Figure 61:
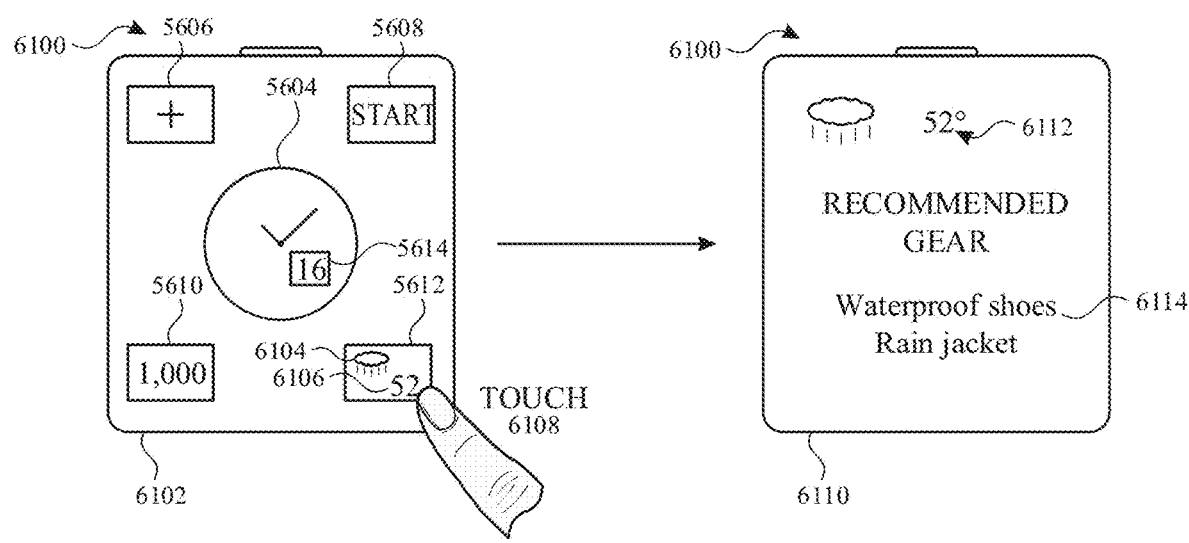
FIG. 61 illustrates exemplary exercise-based watch faces and complications.

FIG. 61 shows exemplary context-specific user interfaces that can optionally be operated on device 6100. Device 6100 can optionally be device 100, 300, or 500 in some embodiments. The electronic device has a display (e.g., 504).

In FIG. 61, device 6100 displays screen 6102. Screen 6102, like 5602 as described above, includes user interface object 5604 and affordances 5606, 5608, 5610, 5612, and 5614. Affordance 5612 represents an application that includes one or more weather-related data and is displayed as a complication associated with user interface object 5604.

In some embodiments, the appearance of affordance 5612 is updated to indicate a weather condition. In FIG. 61, affordance 5612 is indicating a rainy weather condition by displaying user interface object 6104, representing a rain cloud. Affordance 5612 is also indicating a temperature (52° F.) through user interface object 6106. Examples of displayed weather conditions include without limitation indications (via text and/or graphical elements) of temperature, sunlight (or cloud cover), precipitation (or the likelihood thereof), humidity, and/or wind. Weather condition(s) can optionally represent current or forecasted weather condition(s), e.g., based on weather information obtained via wireless communication (e.g., using RF circuitry 108 or communication unit 530). For example, in some embodiments, the weather information can optionally be obtained from an external device coupled to device 6100 via wireless communication. In some embodiments, weather information can optionally be accessed by device 6100, or an external device coupled to device 6100 via wireless communication, by retrieving the weather information from an external server, such as from a weather service, e.g., The Weather Channel, Accuweather, The National Weather Service, Yahoo!™ Weather, Weather Underground, and the like.

As shown in FIG. 61, the user can optionally provide a user input (e.g., touch 6108 on displayed affordance 5612). In response to detecting touch 6108, device 6100 launches the weather application. In some embodiments, the application can optionally be a general weather application. In other embodiments, the application can optionally be an exercise-specific weather application (e.g., an application that displays weather information relevant for planning a workout, and/or an application that makes workout recommendations based on weather information). For example, in some embodiments, affordance 5612 can optionally display general weather information, and in order to view weather information tailored to exercise (e.g., a workout recommendation based on the weather information), the user can optionally launch the application.

Further in response to detecting touch 6108, device 6100 displays user interface screen 6110, which displays workout recommendations based on weather information (e.g., as described above). Screen 6110 shows user interface object 6112, which depicts a weather condition (in this example, a temperature, an indication of precipitation, and an indication of cloud cover).

Screen 6110 also shows user interface object 6114, which depicts a workout recommendation based on the weather information. In this example, user interface object 6114 is providing recommended apparel (e.g., waterproof shoes and a rain jacket) based on weather information (e.g., the weather information depicted by user interface object 6112 and/or affordance 5612). A variety of workout recommendations based on the weather information are contemplated and apparent to one of skill in the art. For example, for windy or cold weather (e.g., having a temperature below a user- or system-designated threshold), a thermal shell, long sleeves, long pants, hat, gloves, and/or the like can optionally be recommended. For warm, humid, or sunny weather, a lightweight/breathable or no shell, shorts, short sleeves, and/or the like can optionally be recommended. If the conditions are dark (e.g., based on daylight hours and/or cloud cover), one or more reflectors and/or articles of clothing with a reflective element can optionally be recommended. If the conditions include precipitation, one or waterproof articles of clothing can optionally be recommended, e.g., waterproof shoes (optionally with more grip than other shoes), a waterproof shell or rain jacket, a hat, and the like.

In some embodiments, the recommended apparel can optionally be branded apparel. In certain embodiments, the recommended apparel can optionally include apparel from a user purchase history. For example, the application that includes one or more weather-related data can optionally be linked to a user's purchase history (e.g., from a third-party retail site or application). The application can optionally then select one or more recommended articles of apparel from the user's purchase history, such that the application recommends apparel based on the weather information and based on a user's purchased item(s).

A user may wish to receive a recommendation of apparel related to a scheduled workout, based on current and/or forecasted weather. Alternatively, or in addition to an apparel-related recommendation based on the weather information, a user may wish to receive a recommendation as to when to exercise, e.g., based on the weather information. For example, a user may wish to know the best time of day to schedule a workout, based on current and/or forecasted weather information. Providing a user interface for easily accessing such recommendations saves user inputs and usage of battery power by the display by allowing the user to quickly access these types of information, rather than having to scroll through a weather application not tailored to exercise and have to come up with an optimal workout time or workout apparel.

Figure 62A:
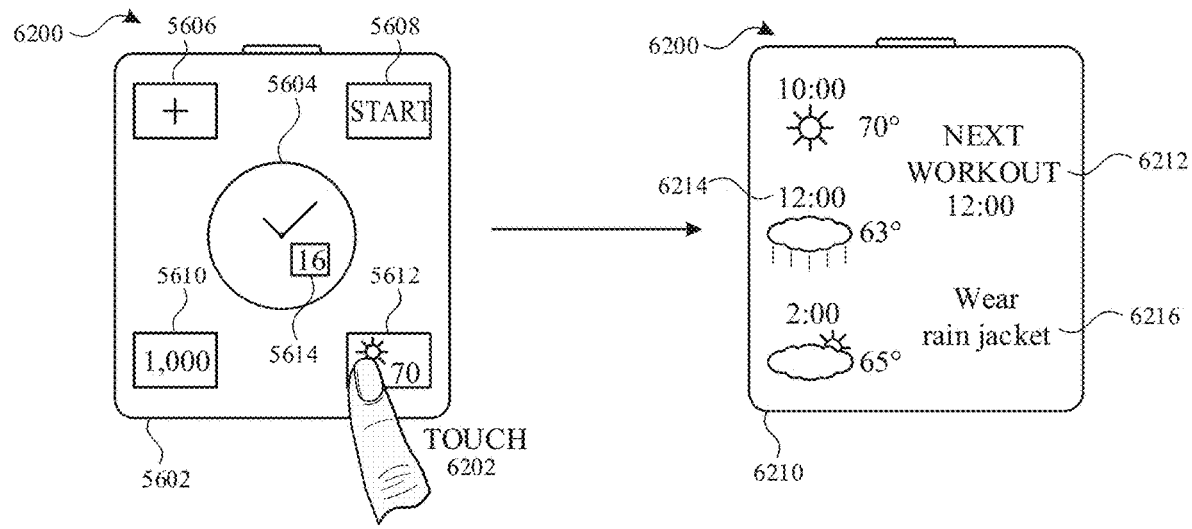
FIGS. 62A and 62B illustrate exemplary exercise-based watch faces and complications.
Figure 62B:
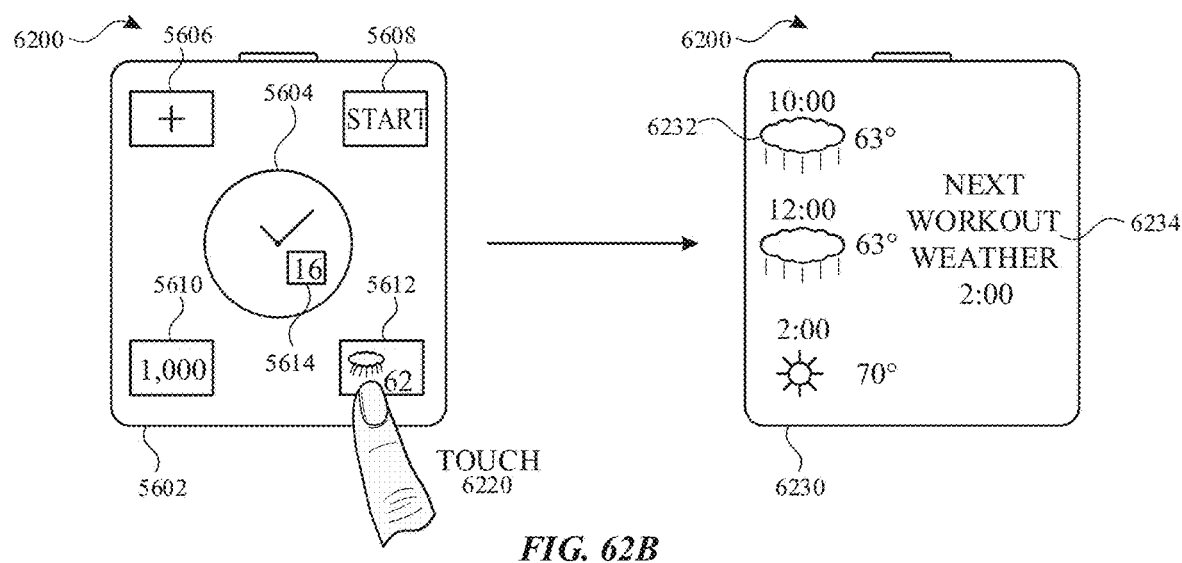

FIGS. 62A and 62B show exemplary context-specific user interfaces that can optionally be operated on device 6200. Device 6200 can optionally be device 100, 300, or 500 in some embodiments. The electronic device has a display (e.g., 504).

In FIGS. 62A and 62B, device 6200 displays screen 5602, which, as described above, includes user interface object 5604 and affordances 5606, 5608, 5610, 5612, and 5614. Affordance 5612 represents an application that includes one or more weather-related data and is displayed as a complication associated with user interface object 5604.

In some embodiments, a user may wish to receive a recommendation of apparel based on the time of a scheduled workout (e.g., the user's next scheduled workout). In FIG. 62A, affordance 5612 indicates sunny weather. To access a recommendation, the user provides a user input (e.g., touch 6202 on affordance 5612) to launch the application and view the recommendation. In response to detecting touch 6202, device 6200 displays user interface screen 6210. Screen 6210 includes user interface object 6212, which gives the time of the user's next scheduled workout. Screen 6210 also includes user interface object 6214, which provides one or more weather conditions (e.g., current and/or forecasted). In this example, object 6214 indicates that the weather is sunny at 10:00, will be rainy at 12:00, and will be partly cloudy at 2:00, along with temperatures associated with each time. Screen 6210 also includes user interface object 6216, which provides a recommendation of apparel (using text and/or graphical elements) based on the weather information associated with the user's next scheduled workout. In this example, object 6216 is recommending a rain jacket based on the forecasted weather condition (as shown by object 6214) associated with the time of the next scheduled workout (as shown by object 6212). In some embodiments, the recommendation of apparel can optionally be associated with the user's next scheduled workout. In some embodiments, the recommendation of apparel can optionally be associated with the current time.

In some embodiments, a user may wish to receive a recommended time of day for a workout based on the weather information. In FIG. 62B, affordance 5612 indicates rainy weather. To access a recommendation, the user provides a user input (e.g., touch 6220 on affordance 5612) to launch the application and view the recommendation. In response to detecting touch 6220, device 6200 displays user interface screen 6230. Screen 6230 includes user interface object 6232, which provides one or more weather conditions (e.g., current and/or forecasted). In this example, object 6232 indicates that the weather is rainy at 10:00, will be rainy at 12:00, and will be sunny at 2:00, along with temperatures associated with each time. Screen 6230 includes user interface object 6234, which includes a recommended time of day for a workout (using text and/or graphical elements) based on the weather information (see, e.g., object 6232). In this example, object 6234 is displaying a recommended time for a workout of 2:00, which corresponds to the next forecasted sunny weather.

Similar to recommended apparel as described above, a recommended time of day for a workout can optionally be based on weather information including without limitation one or more of precipitation, cloud cover/sunlight, humidity, light/dark conditions, temperature, and wind. Weather condition(s) can optionally represent current or forecasted weather condition(s), e.g., based on weather information obtained via wireless communication (e.g., using RF circuitry 108 or communication unit 530). In some embodiments, the weather information can optionally be obtained from an external device coupled to device 6200 via wireless communication. In some embodiments, weather information can optionally be accessed by device 6200, or an external device coupled to device 6200 via wireless communication, by retrieving the weather information from an external server, such as from a weather service, e.g., The Weather Channel, Accuweather, The National Weather Service, Yahoo!™ Weather, Weather Underground, and the like.

FIGS. 63-66 illustrate additional optional features and aspects of the exercise-based watch faces and complications described herein. These optional features can optionally be combined with any of the context-specific user interfaces and complications described above.

A user may wish to view additional exercise-related information and complications. For example, a user may wish to view an indication of user heart rate, or user progress toward one or more designated exercise or fitness goals.

Figure 63:
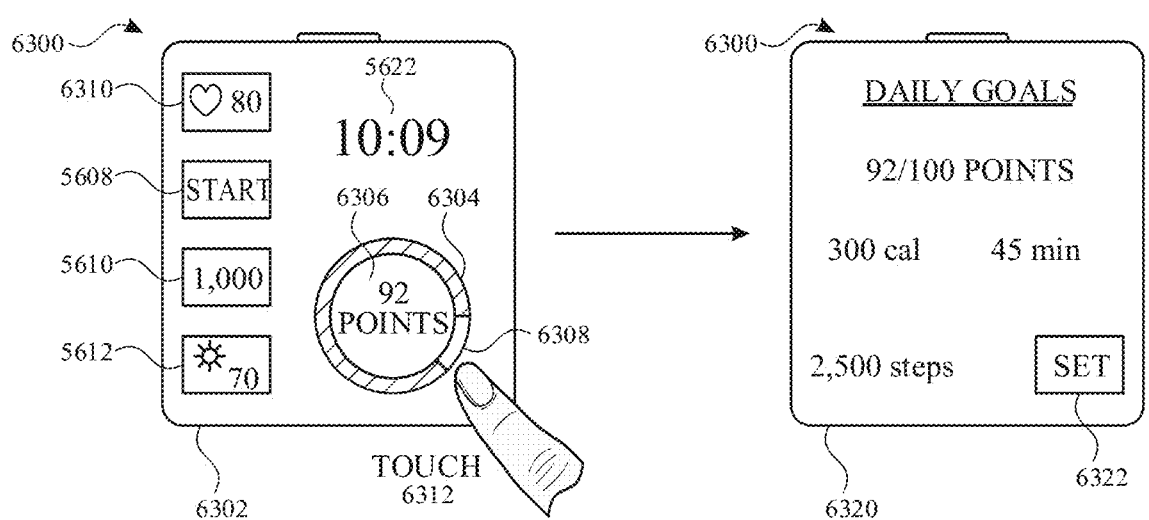
FIG. 63 illustrates exemplary exercise-based watch faces and complications.

FIG. 63 shows exemplary context-specific user interfaces that can optionally be operated on device 6300. Device 6300 can optionally be device 100, 300, or 500 in some embodiments. The electronic device has a display (e.g., 504).

In FIG. 63, device 6300 displays screen 6302, which includes user interface object 5622 and affordances 5608, 5610, and 5612, as described above. Screen 6302 also includes affordance 6310. Affordance 6310 displays an indication of user heart rate. In some embodiments, affordance 6310 is updated (e.g., continuously, or at predetermined intervals) to reflect user heart rate. Affordance 6310 can optionally be updated, e.g., using biometric data on user heart rate generated by a biometric sensor (e.g., as part of activity sensors 520 as described herein). It will be appreciated that an indication of user heart rate, as illustrated by affordance 6310, can optionally be displayed on any of the user interfaces described and/or illustrated herein and is merely presented in combination with the specific features shown in FIG. 63 for convenience of description.

Screen 6302 also includes affordance 6304, which indicates user progress toward one or more fitness goals. Affordance 6304 can optionally represent the one or more fitness goals through text and/or graphical elements. In this example, affordance 6304 displays a user's progress toward the fitness goal(s) using both text (e.g., affordance 6306, indicating a user progress of 92 points) and graphical elements (e.g., affordance 6308, which includes both filled and non-filled segments of a ring to represent a user's progress toward the fitness goal(s)).

In some embodiments, the one or more fitness goals can optionally include without limitation number of steps taken, number of Calories burned, number of repetitions completed, number of workouts completed, duration of time the user is engaged in exercise (e.g., total amount of time a user is engaged in exercise, or the amount of time a user is engaged in exercise of a threshold intensity, which can optionally be based for example on user heart rate, or number/frequency/intensity of user movements), and any combination thereof. For example, user progress can optionally be tracked using an algorithm that encompasses one or more of the above aspects, optionally with each aspect having an associated weight assigned in the algorithm. In some embodiments, the fitness goal(s) can optionally be user-designated (e.g., a goal preset by the user). In other embodiments, the fitness goal(s) can optionally be system-designated.

As shown in FIG. 63, the user can optionally provide a user input (e.g., touch 6312 on affordance 6304) and, in response to detecting the user input, device 6300 can optionally launch an application with additional exercise information. In this example, in response to detecting touch 6312, device 6300 displays screen 6320, which displays one or more user fitness goals and/or user progress towards the goal(s). In this case, screen 6320 displays the user's progress towards the fitness goal(s) in terms of fractional completion ("92/100 points"), calories burned ("300 cal"), duration of exercise completed ("45 min"), and number of steps taken ("2,500 steps"). In addition, screen 6320 includes affordance 6322, which allows the user to set one or more of these fitness goal(s), add another fitness goal, remove a fitness goal, and so forth. These functionalities can optionally be accessed, e.g., by detecting a user touch on affordance 6322.

A user may wish to view the time of one or more future scheduled workouts, the time of one or more previous workouts, and/or a recommended preparation based on a scheduled or previous workout.

Figure 64A:
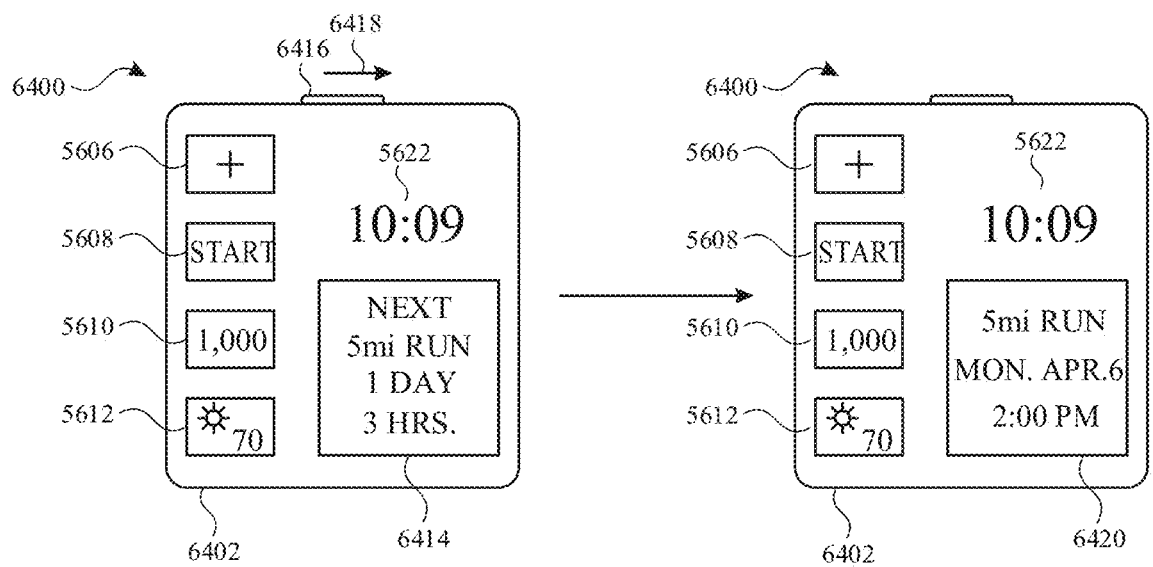
FIGS. 64A-64C illustrate exemplary exercise-based watch faces and complications.
Figure 64B:
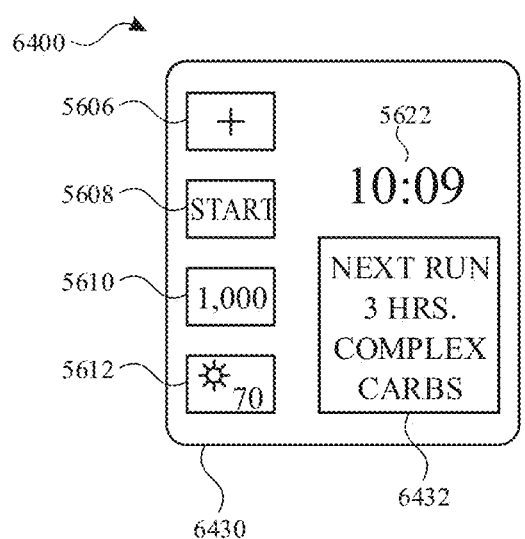
Figure 64C:
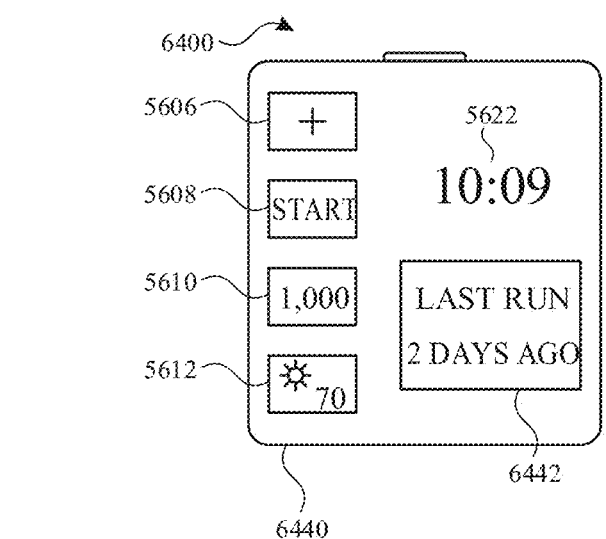

FIGS. 64A-64C show exemplary context-specific user interfaces that can optionally be operated on device 6400. Device 6400 can optionally be device 100, 300, or 500 in some embodiments. The electronic device has a display (e.g., 504).

In FIG. 64A, device 6400 displays screen 6402, which includes user interface object 5622 and affordances 5606, 5608, 5610, and 5612, as described above. Screen 6402 also includes user interface object 6414. User interface object 6414 displays an indication of time until a next workout routine according to a list of workout routines, e.g., the user's next scheduled workout. In this example, 6414 indicates that the user's next scheduled workout is a 5 mile run scheduled for 1 day and 3 hours from, e.g., the current time.

In some embodiments, the next workout refers to the next upcoming workout according to a designated or predetermined schedule of workouts. In some embodiments, the schedule of workouts can optionally be user-designated. In other embodiments, the schedule of workouts can optionally be system-designated. For example, the user can optionally input a fitness goal, such as an achievement (e.g., running a marathon), performance milestone (e.g., a particular time on a type of run), fitness parameter (e.g., heart rate, weight, amount of exercise in a duration of time, etc.), and the like, and the system can optionally generate a workout schedule to achieve the fitness goal. In some embodiments, the user interface object can optionally be linked to a calendar application (e.g., a general calendar application in which the user has stored exercise-related events such as scheduled workouts, or an exercise-based calendar application such as a running schedule) and obtain data representing the next scheduled workout from the calendar application.

In some embodiments, the user can optionally scroll through past and/or future scheduled workouts by providing a user input. As shown in FIG. 64A, the user can optionally use the movement of a rotatable input mechanism (e.g., 506) to view past and/or future scheduled workouts. The user can optionally rotate rotatable input mechanism 6416 through rotation 6418, and, in response to detecting rotation 6418, device 6400 can optionally update screen 6402 to replace object 6414 with user interface object 6420. In this example, object 6420 displays an indication of a future workout scheduled after the workout shown in 6414, i.e., a 5 mile run scheduled for 2 pm on Monday, April 6. As described above, the scheduled workouts can optionally be obtained from a general or exercise-specific calendar application. In some embodiments, the user can optionally provide a movement of 6416 in a direction opposite that of 6418 and, in response to detecting the movement, device 6400 can optionally display an indication of a past workout (e.g., a workout completed or started in the past, or a workout scheduled for a past date). Exemplary techniques for providing a "time scrubbing" or "time travel" functionality such as this are described supra (e.g., with respect to FIGS. 53A-55).

FIG. 64B illustrates an exemplary user interface for providing a workout-related training or preparation recommendation(s). As shown in FIG. 64B, device 6400 is displaying screen 6430, which includes user interface object 5622 and affordances 5606, 5608, 5610, and 5612, as described above. Screen 6430 also includes user interface object 6432. User interface object 6432 displays a preparation recommendation for the user to eat a meal with complex carbohydrates in preparation for a next scheduled run in 3 hours.

In some embodiments, the preparation recommendation(s) can optionally be based on a next scheduled workout (e.g., based on one or more parameters of the workout, including workout length, type of exercise, workout intensity, time until next workout, time between the next workout and the previous workout, time between the next workout and a future workout, and the like). In some embodiments, preparation recommendations can optionally refer to one or more of a type of food to consume (e.g., carbohydrate, protein, fats, vitamins, supplements, or other nutrients, etc.), an amount of food to consume (e.g., by weight, or by caloric content), an amount of sleep, an amount of rest, a type or amount of stretching or warmup exercise, and so forth.

A user may wish to be reminded of an amount of time since previous exercise (e.g., the last workout). As shown in FIG. 64C, device 6400 is displaying screen 6440, which includes user interface object 5622 and affordances 5606, 5608, 5610, and 5612, as described above. Screen 6440 also includes user interface object 6442. User interface object 6442 displays an indication of time since a latest workout routine that is not currently begun (e.g., the last workout). In this example, 6442 indicates that the user's last workout was a run 2 days ago.

In some embodiments, the previous workout can optionally be determined based on a user input indicating the start or the completion of exercise. This user input can optionally include selection of an "end workout" affordance, or cessation of a user physical activity, e.g., one that meets one or more activity criteria, based on data generated by the activity sensor 520, as described above. In some embodiments, the previous workout can optionally be determined based on a schedule of user workouts, e.g., based on data obtained from a general or exercise-based calendar application as described above.

A user may wish to view a graphical indication of an amount of time they have engaged in physical activity or inactivity, or of an amount of time since they have engaged in physical activity.

Figure 65:
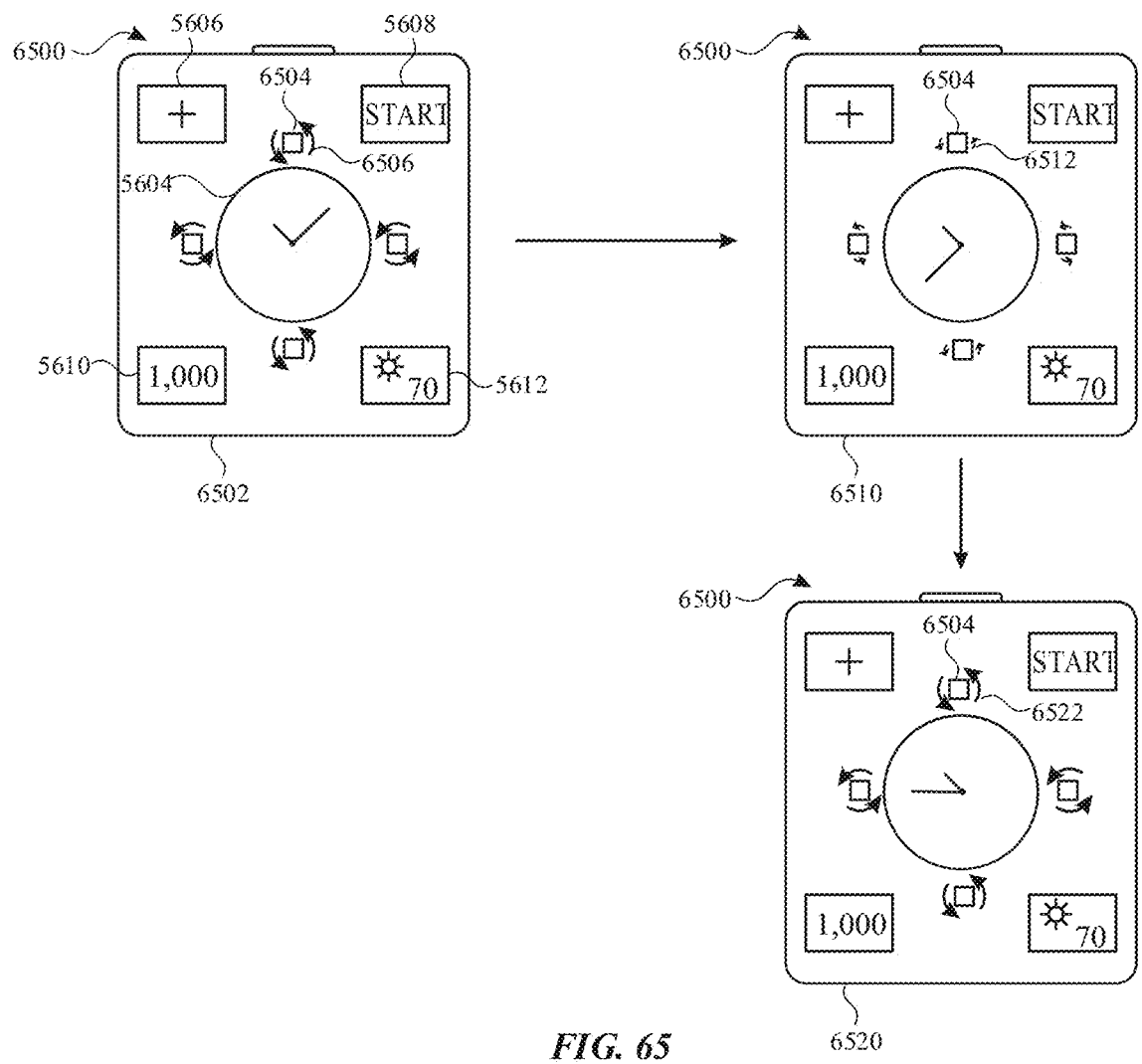
FIG. 65 illustrates exemplary exercise-based watch faces and complications.

FIG. 65 shows exemplary context-specific user interfaces that can optionally be operated on device 6500. Device 6500 can optionally be device 100, 300, or 500 in some embodiments. The electronic device has a display (e.g., 504).

In FIG. 65, device 6500 displays screen 6502, which includes user interface object 5604 and affordances 5606, 5608, 5610, and 5612, as described above. Screen 6502 also includes user interface objects, in this case depicted as squares (e.g., user interface object 6504), that move (e.g., as depicted by arrows such as 6506). In this example, the movement (e.g., the rate, degree, and/or direction of rotation) of object 6504 is based on a user's physical activity. For example, as shown on screen 6510, if the user engages in half an hour of physical inactivity (e.g., if the user does not stand up, or if the user does not walk) the rotation of 6504 slows down, as indicated by arrows such as 6512. As shown on screen 6520, if the user subsequently engages in physical activity (e.g., if the user stands up and/or walks), the rotation of 6504 accelerates again, as indicated by arrows such as 6522. These techniques provide the user with a simple visual indication that provides an inactivity tracking functionality. It will be appreciated with one of skill in the art that other aspects of a user interface object can optionally be used to depict physical activity or inactivity, including without limitation other movements, size, shape, and color, as described in greater detail below.

Figure 66:
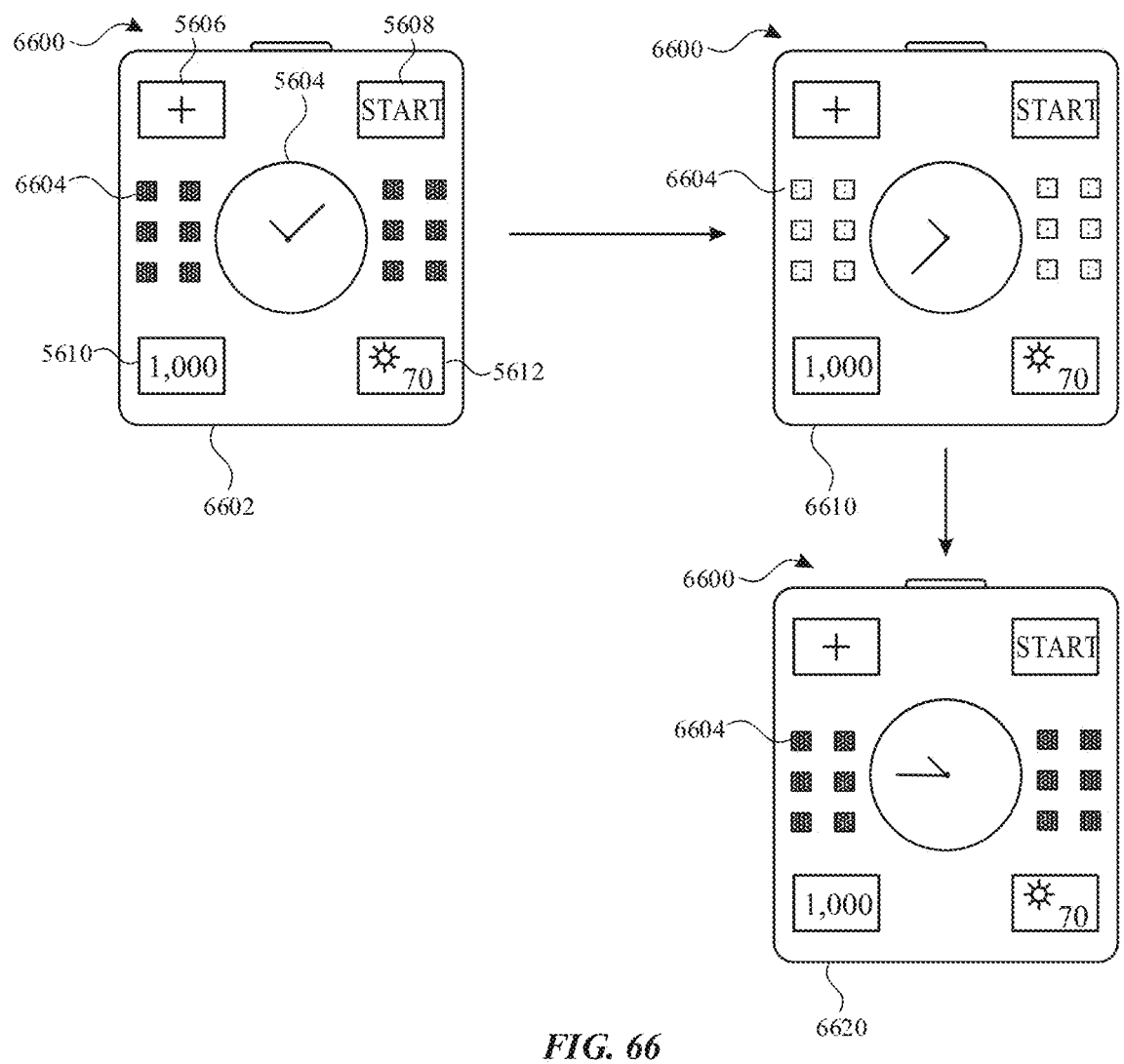
FIG. 66 illustrates exemplary exercise-based watch faces and complications.

Another exemplary embodiment for indicating physical activity/inactivity is illustrated in FIG. 66. FIG. 66 shows exemplary context-specific user interfaces that can optionally be operated on device 6600. Device 6600 can optionally be device 100, 300, or 500 in some embodiments. The electronic device has a display (e.g., 504).

In FIG. 66, device 6600 displays screen 6602, which includes user interface object 5604 and affordances 5606, 5608, 5610, and 5612, as described above. Screen 6602 also includes user interface objects, in this case depicted as squares (e.g., user interface object 6604), that have a particular color, hue, or brightness. In this example, the color, hue, or brightness of object 6604 is based on a user's physical activity. For example, if the user engages in half an hour of physical inactivity (e.g., if the user does not stand up, or if the user does not walk) the color, hue, and/or brightness of 6604 fades or lessens, as depicted on screen 6610. As shown on screen 6620, if the user subsequently engages in physical activity (e.g., if the user stands up and/or walks), the color, hue, and/or brightness of 6604 is restored. These techniques illustrate another exemplary visual indication for providing inactivity tracking.

The techniques illustrated in FIGS. 65 and 66 provide the user with simple visual indications, suitable for use in any of the exemplary user interfaces provided herein, of physical activity or inactivity. In some embodiments, a user interface object (e.g., 6504 or 6604) that provides inactivity tracking can be used to track the number of hour-long segments (or segments of other lengths) that a user is inactive and prompt users to be active before the hour (or other length of time) elapses, e.g., by depicting a visual change in the user interface object, such as a rotation rate or color/hue/brightness as described above. To do so, the inactivity tracking can include a visual representation of an amount of a user's inactivity (e.g., a length of time the user is inactive as measured by an inactivity timer), an amount of detected user activity (e.g., a length of time the user is active, a number of steps taken by the user, a number of Calories expended, or the like), or a combination thereof. The user can be categorized as being inactive when the device detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a distance per unit time threshold, or the like), the absence of the user engaging in specified type of activity (e.g., standing, walking, running, swimming, climbing stairs, or the like), or a combination thereof. Techniques and interfaces for monitoring user physical activity/inactivity are provided, for example, in U.S. Provisional Application Ser. No. 62,129,828, filed Mar. 7, 2015, which is hereby incorporated by reference in its entirety.

A user may wish to use any of the portable multifunction devices described herein to track and/or guide a user's physical activity. For example, a user can optionally run a particular course or race and wish to "check in" at particular locations on the course for the purpose of timing or mapping the user's progress, navigating the course, and so forth. In another example, a user may wish to check in at a golf course (e.g., at the beginning of a course, or at each hole of a golf course) to obtain information about a particular hole, club selection, range-finding, and the like. In either example, the user may wish to broadcast the user's progress to one or more contacts (e.g., other members of a running or country club, other golfers or race participants, spectators, friends, etc.). In some embodiments, any of the portable multifunction devices described herein can optionally allow the user to check in at a particular location, e.g., using RF circuitry 108 and/or communication unit 530 for send or receive over Wi-Fi, Bluetooth, near field communication (NFC), cellular, and/or other wireless communication techniques. For example, a user may use the device to check in at an NFC sticker posted at a location (e.g., a station along a running course or a golf tee). In some embodiments, the device can optionally display a map of the golf course, golf course hole, race route, etc. (e.g., obtained in advance of or during the race or golf outing from, e.g., an NFC sticker, QR code, website, external server, and the like) to allow the user to track their progress and/or check in at designated location(s), as described above.

FIG. 67 is a flow diagram illustrating process 6700 for providing one or more exercise-based watch faces and complications. In some embodiments, process 6700 can optionally be performed at an electronic device with a touch-sensitive display, such as devices 100 (FIG. 1A), 300 (FIG. 3), 500 (FIG. 5) or 5600-6600 (FIGS. 56A-66). Some operations in process 6700 can optionally be combined, the order of some operations can optionally be changed, and some operations can optionally be omitted. Process 6700 provides exercise-based watch faces and complications that allow a user to keep time and access a workout routine from the same interface, making these interfaces less confusing and, thus, conserving power and increasing battery life.

At block 6702, the device displays a user interface screen that includes a user interface object indicating a time of day and an affordance (e.g., 5608) representing a workout application, the affordance displayed as a complication associated with the user interface object. Optionally, at block 6702, the device displays a second affordance on the user interface screen, the second affordance representing a second application different from the workout application and being displayed as a complication associated with the user interface object. At block 6704, the device detects a user input corresponding to a selection of the affordance (e.g., touch 5724 or user activity 5734). At block 6706, responsive at least in part to detecting the user input, the device begins a workout routine (e.g., as illustrated in FIGS. 57A-57D).

Note that details of the processes described above with respect to process 6700 (FIG. 67) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and/or process 6800 (FIG. 68) can optionally include one or more of the characteristics of the various methods described above with reference to process 6700. For brevity, these details are not repeated below.

It should be understood that the particular order in which the operations in FIG. 67 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and process 6800 (FIG. 68) can optionally be incorporated with one another. Thus, the techniques described with respect to process 6700 can optionally be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and/or process 6800 (FIG. 68).

FIG. 68 is a flow diagram illustrating process 6800 for providing one or more exercise-based watch faces and complications. In some embodiments, process 6800 can optionally be performed at an electronic device with a touch-sensitive display, such as devices 100 (FIG. 1A), 300 (FIG. 3), 500 (FIG. 5) or 5600-6600 (FIGS. 56A-66). Some operations in process 6800 can optionally be combined, the order of some operations can optionally be changed, and some operations can optionally be omitted. Process 6800 provides exercise-based watch faces and complications that allow a user to keep time and access one or more workout recommendations (e.g., based on weather information) from the same interface, making these interfaces less confusing and, thus, conserving power and increasing battery life.

At block 6802, the device displays a user interface screen that includes a user interface object indicating a time of day and an affordance (e.g., 5612) representing an application that includes one or more weather-related data, the affordance displayed as a complication associated with the user interface object. At block 6804, the device detects a user input corresponding to a selection of the affordance (e.g., touch 6108, 6202, or 6220). At block 6706, responsive at least in part to detecting the user input, the device launches the application (e.g., as illustrated in FIGS. 61, 62A, and 62B). At block 6808, responsive at least in part to detecting the user input, the device displays one or more workout recommendations based on weather information. Optionally, at block 6808, the device obtains the weather information via wireless communication (e.g., using RF circuitry 108 or communication unit 530).

Note that details of the processes described above with respect to process 6800 (FIG. 68) are also applicable in an analogous manner to the methods described below. For example, process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and/or process 6700 (FIG. 67) can optionally include one or more of the characteristics of the various methods described above with reference to process 6800. For brevity, these details are not repeated below.

It should be understood that the particular order in which the operations in FIG. 68 have been described is exemplary and not intended to indicate that the described order is the only order in which the operations could be performed. One of ordinary skill in the art would recognize various ways to reorder the operations described herein, as well as excluding certain operations. For brevity, these details are not repeated here. Additionally, it should be noted that aspects of process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and process 6700 (FIG. 67) can optionally be incorporated with one another. Thus, the techniques described with respect to process 6800 can optionally be relevant to process 2000 (FIG. 20), process 2100 (FIG. 21), process 2200 (FIG. 22), process 2300 (FIG. 23), process 2400 (FIG. 24), process 2500 (FIG. 25), process 2600 (FIG. 26), process 2700 (FIG. 27A), process 2710 (FIG. 27B), process 2720 (FIG. 27C), process 2730 (FIG. 27D), process 2740 (FIG. 27E), process 2750 (FIG. 27F), process 2800 (FIG. 28), process 2900 (FIG. 29), process 3000 (FIG. 30), process 3100 (FIG. 31), process 3200 (FIG. 32), process 3300 (FIG. 33), and/or process 6700 (FIG. 67).

Figure 69:
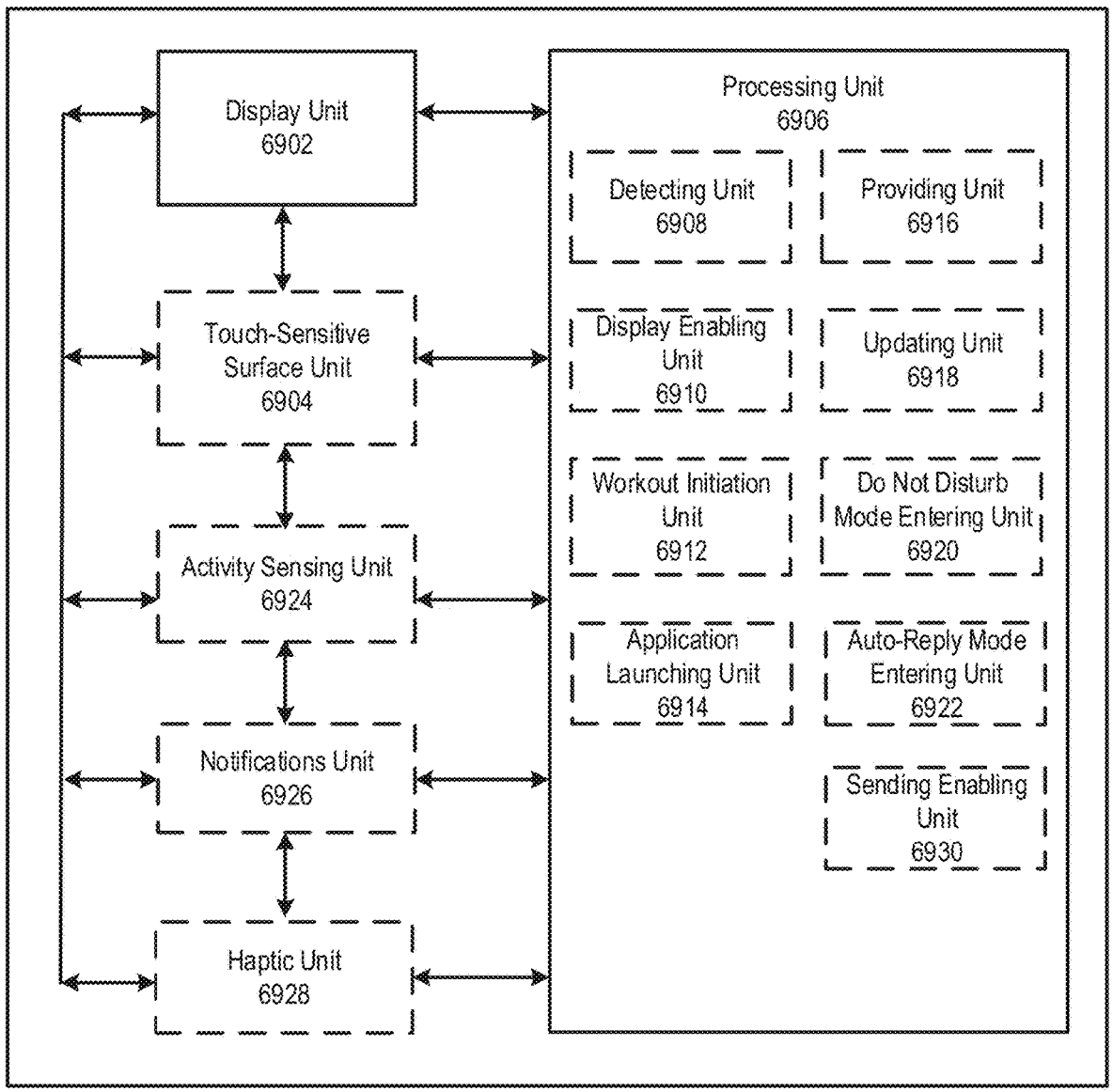
FIG. 69 is a functional block diagram of an electronic device in accordance with some embodiments.

In accordance with some embodiments, FIG. 69 shows an exemplary functional block diagram of an electronic device 6900 configured in accordance with the principles of the various described embodiments. In accordance with some embodiments, the functional blocks of electronic device 6900 are configured to perform the techniques described above. The functional blocks of the device 6900 are, optionally, implemented by hardware, software, or a combination of hardware and software to carry out the principles of the various described examples. It is understood by persons of skill in the art that the functional blocks described in FIG. 69 are, optionally, combined or separated into sub-blocks to implement the principles of the various described examples. Therefore, the description herein optionally supports any possible combination or separation or further definition of the functional blocks described herein.

As shown in FIG. 69, an electronic device 6900 includes a display unit 6902 configured to display a graphic user interface, optionally, a touch-sensitive surface unit 6904 configured to receive contacts, optionally, an activity sensing unit 6924 configured to detect an activity of a user of device 6900, optionally, notifications unit 6926 configured to send and/or receive notifications, optionally, haptic unit 6928 configured to produce haptic outputs, and a processing unit 6906 coupled to the display unit 6902, optionally, the touch-sensitive surface unit 6904, optionally, the activity sensing unit 6924, optionally, the notifications unit 6926, and optionally, the haptic unit 6928. In some embodiments, the processing unit 6906 includes a detecting unit 6908, a display enabling unit 6910, a workout initiation unit 6912, an application launching unit 6914, a providing unit 6916, an updating unit 6918, a do not disturb mode entering unit 6920, an auto-reply mode entering unit 6922, and a sending enabling unit 6930.

The processing unit 6906 is configured to enable display (e.g., with display enabling unit 6910), on the display unit (e.g., display unit 6902), of a user interface screen, the user interface screen including: a user interface object indicating a time of day; and an affordance representing a workout application, wherein the affordance is displayed as a complication associated with the user interface object; detect a user input (e.g., with detecting unit 6908) corresponding to a selection of the affordance; and in response to detecting the user input: begin a workout routine (e.g., with workout initiation unit 6912).

In some embodiments, in response to detecting the user input (e.g., with detecting unit 6908), the processing unit 6906 is further configured to: launch (e.g., with application launching unit 6914) the workout application.

In some embodiments, the processing unit 6906 is further configured to: enable display (e.g., with display enabling unit 6910), on the display unit (e.g., display unit 6902), of a second affordance, wherein the second affordance represents a second application, the second application being different from the workout application, and wherein the second affordance is displayed as a complication associated with the user interface object.

In some embodiments, the second affordance represents a second application selected from a weather application, a calendar application, a pedometer application, a stopwatch application, and a world clock application.

In some embodiments, the second affordance represents a pedometer application, the second affordance comprises a set of information obtained from the pedometer application, and the set of information is updated (e.g., with updating unit 6918) in accordance with data from the pedometer application.

In some embodiments, the processing unit 6906 is further configured to: detect (e.g., with detecting unit 6908) a second user input corresponding to a selection of the second affordance; and in response to detecting the second user input: launch (e.g., with application launching unit 6914) the pedometer application.

In some embodiments, the set of information comprises one or more indications of distanced traveled, number of steps taken, energy expended, or a combination thereof.

In some embodiments, at least a first indication of the one or more indications reflects a unit of measurement.

In some embodiments, at least a first indication of the one or more indications reflects a fraction of a predetermined goal.

In some embodiments, the display unit (e.g., display unit 6902) is a touch-sensitive display unit (e.g., it can optionally include or be coupled to touch-sensitive surface unit 6904), and detecting (e.g., with detecting unit 6908) the user input corresponding to a selection of the affordance comprises: detecting (e.g., with detecting unit 6908) a contact on the displayed affordance.

In some embodiments, electronic device 6900 further comprises an activity sensing unit (e.g., activity sensing unit 6924), the processing unit 6906 is coupled to the activity sensing unit 6924, and detecting the user input corresponding to a selection of the affordance comprises: detecting (e.g., with detecting unit 6908) an indication of user physical activity that meets an activity criterion based on activity data generated by the activity sensing unit (e.g., activity sensing unit 6924).

In some embodiments, the activity sensor 6924 is configured to detect one or more types of physical activity, the one or more types of physical activity comprising walking, running, going up stairs, or jumping.

In some embodiments, the activity criterion comprises one or more of a minimum number of steps taken per unit time, an amount of Calories burned per unit time, or a speed.

In some embodiments, the activity criterion comprises an increase in user heart rate.

In some embodiments, detecting (e.g., with detecting unit 6908) the user input corresponding to a selection of the affordance further comprises: after detecting the indication of user physical activity that meets the activity criterion: providing (e.g., with providing unit 6916) a user prompt for confirming a user workout; and detecting (e.g., with detecting unit 6908) a user input corresponding to a confirmation of the user workout.

In some embodiments, the workout routine is based on one or more workout parameters comprising duration of time, distance, number of steps, heart rate, number of Calories burned, or a combination thereof.

In some embodiments, in response to detecting (e.g., with detecting unit 6908) the user input, the processing unit 6906 is further configured to: enable display (e.g., with display enabling unit 6910), on the display unit (e.g., display unit 6902), of a value corresponding to the one or more workout parameters.

In some embodiments, after enabling display (e.g., with display enabling unit 6910), on the display unit (e.g., display unit 6902), of the value corresponding to the first workout parameter, the processing unit 6906 is further configured to: enable update (e.g., with updating unit 6918), on the display unit (e.g., display unit 6902), of the displayed value to reflect user progress with respect to the one or more workout parameters.

In some embodiments, the workout routine corresponds to a latest workout routine that is not currently begun.

In some embodiments, the workout routine corresponds to a next workout routine according to a list of workout routines.

In some embodiments, the workout routine is user-designated.

In some embodiments, the workout routine is system-designated.

In some embodiments, a visual aspect of the affordance (e.g., as displayed on display unit 6902) indicates whether the workout routine corresponds to a latest workout routine that is not currently begun, corresponds to a next workout routine according to a list of workout routines, is user-designated, or is system-designated.

In some embodiments, in response to detecting (e.g., with detecting unit 6908) the user input, the processing unit 6906 is further configured to: enter (e.g., with do not disturb mode entering unit 6920) a do not disturb (DND) mode of electronic device 6900.

In some embodiments, in response to detecting (e.g., with detecting unit 6908) the user input, the processing unit 6906 is further configured to: enter (e.g., with auto-reply mode entering unit 6922) an auto-reply mode of electronic device 6900.

In some embodiments, in response to detecting (e.g., with detecting unit 6908) the user input, the processing unit 6906 is further configured to: update (e.g., with updating unit 6918) a user avatar or user profile picture to indicate a workout.

In some embodiments, electronic device 6900 further comprises a notifications unit (e.g., notifications unit 6926), the processing unit 6906 is coupled to the notifications unit, and, in response to detecting (e.g., with detecting unit 6908) the user input, the processing unit 6906 is further configured to: enable sending (e.g., using sending enabling unit 6930), by the notifications unit (e.g., notifications unit 6926), a notification indicating a workout to an external device.

In some embodiments, electronic device 6900 further comprises a haptic unit (e.g., haptic unit 6928), the processing unit 6906 is coupled to the haptic unit, and the processing unit 6906 is further configured to: after beginning the workout routine (e.g., with workout initiation unit 6912), cease to produce a haptic output via the haptic unit (e.g., haptic unit 6928) in response to an incoming electronic message; detect (e.g., with detecting unit 6908) a cessation of the workout routine; and in response to detecting the cessation: produce, via the haptic unit (e.g., with haptic unit 6928), a haptic output in response to a second incoming electronic message received after detecting the cessation.

In some embodiments, in response to detecting (e.g., with detecting unit 6908) the cessation, the processing unit 6906 is further configured to: produce, via the haptic unit (e.g., haptic unit 6928), a haptic output corresponding to the first incoming electronic message.

In some embodiments, electronic device 6900 further comprises an activity sensing unit (e.g., activity sensing unit 6924), the processing unit 6906 is coupled to the activity sensing unit, and detecting (e.g., with detecting unit 6908) the cessation is based on a cessation of user physical activity that meets an activity criterion based on data generated by the activity sensing unit (e.g., activity sensing unit 6924).

In some embodiments, detecting (e.g., with detecting unit 6908) the cessation is based on a user input indicating a cessation of the workout routine.

In some embodiments, electronic device 6900 further comprises a haptic unit (e.g., haptic unit 6928), the processing unit 6906 is coupled to the haptic unit, and the processing unit 6906 is further configured to: after beginning the workout routine, produce, via the haptic unit (e.g., haptic unit 6928), an enhanced haptic output in response to an incoming electronic message.

In some embodiments, the enhanced haptic output comprises a more intense haptic output as compared to a haptic output produced via the haptic unit (e.g., haptic unit 6928) before beginning the workout routine.

In some embodiments, the enhanced haptic output comprises a first haptic output and a second haptic output, and the second haptic output is produced via the haptic unit (e.g., haptic unit 6928) after the first haptic output and is distinct from the second haptic output.

The operations described above with reference to FIG. 67 are, optionally, implemented by components depicted in FIGS. 1A-1B or FIG. 69. For example, displaying operation 6702, detecting operation 6704, and beginning operation 6706 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

Figure 70:
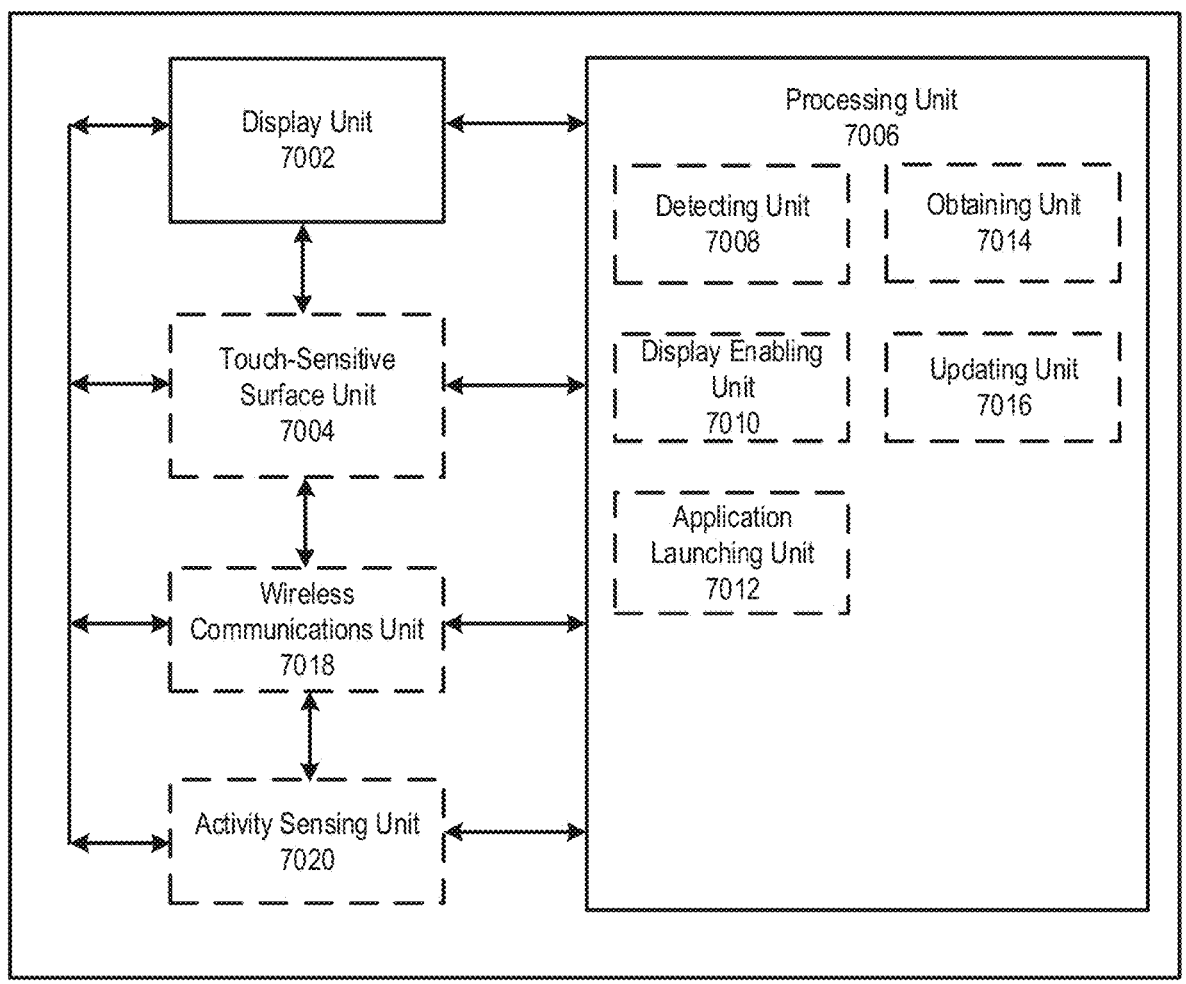
FIG. 70 is a functional block diagram of an electronic device in accordance with some embodiments.

In accordance with some embodiments, FIG. 70 shows an exemplary functional block diagram of an electronic device 7000 configured in accordance with the principles of the various described embodiments. In accordance with some embodiments, the functional blocks of electronic device 7000 are configured to perform the techniques described above. The functional blocks of the device 7000 are, optionally, implemented by hardware, software, or a combination of hardware and software to carry out the principles of the various described examples. It is understood by persons of skill in the art that the functional blocks described in FIG. 70 are, optionally, combined or separated into sub-blocks to implement the principles of the various described examples. Therefore, the description herein optionally supports any possible combination or separation or further definition of the functional blocks described herein.

As shown in FIG. 70, an electronic device 7000 includes a display unit 7002 configured to display a graphic user interface, optionally, a touch-sensitive surface unit 7004 configured to receive contacts, optionally, a wireless communications unit 7018 configured to send and/or receive wireless communications, optionally, activity sensing unit 7020 configured to detect an activity of a user of device 7000, and a processing unit 7006 coupled to the display unit 7002, optionally, the touch-sensitive surface unit 7004, optionally, the wireless communications unit 7018, and optionally, the activity sensing unit 7020. In some embodiments, the processing unit 7006 includes a detecting unit 7008, a display enabling unit 7010, an application launching unit 7012, an obtaining unit 7014, and an updating unit 7016.

The processing unit 7006 is configured to enable display (e.g., with display enabling unit 7010), on the display unit (e.g., display unit 7002), of a user interface screen, the user interface screen including: a user interface object indicating a time of day; and an affordance representing an application that includes one or more weather-related data, wherein the affordance is displayed as a complication associated with the user interface object; detect a user input (e.g., with detecting unit 7008) corresponding to a selection of the affordance; and in response to detecting the user input: launch (e.g., with application launching unit 7012) the application; and enable display (e.g., with display enabling unit 7010), on the display unit (e.g., display unit 7002), of one or more workout recommendations based on weather information.

In some embodiments, electronic device 7000 further comprises a wireless communications unit (e.g., wireless communications unit 7018), the processing unit 7006 is coupled to the wireless communications unit, and the processing unit 7006 is further configured to: obtain (e.g., with obtaining unit 7014), via the wireless communications unit (e.g., wireless communications unit 7018), the weather information.

In some embodiments, the processing unit 7006 is further configured to: enable update (e.g., with updating unit 7016), on the display unit (e.g., display unit 7002), of the displayed affordance to indicate a weather condition based on the obtained weather information.

In some embodiments, the display unit (e.g., display unit 7002) is a touch-sensitive display unit (e.g., it can optionally include or be coupled to touch-sensitive surface unit 7004), and detecting (e.g., with detecting unit 7008) the user input corresponding to a selection of the affordance comprises: detecting (e.g., with detecting unit 7008) a contact on the displayed affordance.

In some embodiments, the one or more workout recommendations comprise recommended apparel based on the weather information.

In some embodiments, the recommended apparel comprises branded apparel.

In some embodiments, the recommended apparel comprises apparel from a user purchase history.

In some embodiments, the one or more workout recommendations comprise a recommended time of day based on the weather information.

In some embodiments, the weather information comprises information on one or more of temperature, sunlight, precipitation, humidity, or wind.

In some embodiments, the weather information comprises current weather information.

In some embodiments, the weather information comprises forecasted weather information.

In some embodiments, the processing unit 6906 and/or 7006 is further configured to: enable display (e.g., with display enabling unit 6910 and/or 7010), on the display unit (e.g., display unit 6902 and/or 7002), of an indication of time since a latest workout routine that is not currently begun.

In some embodiments, the processing unit 6906 and/or 7006 is further configured to: enable display (e.g., with display enabling unit 6910 and/or 7010), on the display unit (e.g., display unit 6902 and/or 7002), of an indication of time until a next workout routine according to a list of workout routines.

In some embodiments, the processing unit 6906 and/or 7006 is further configured to: enable display (e.g., with display enabling unit 6910 and/or 7010), on the display unit (e.g., display unit 6902 and/or 7002), of one or more preparation recommendations based on the time until the next workout routine.

In some embodiments, electronic device 6900 and/or 7000 further comprises an activity sensing unit (e.g., activity sensing unit 6924 and/or 7020), the processing unit 6906 and/or 7006 is coupled to the activity sensing unit, the activity sensing unit is a biometric sensing unit, and the processing unit 6906 and/or 7006 is further configured to: enable display (e.g., with display enabling unit 6910 and/or 7010), on the display unit (e.g., display unit 6902 and/or 7002), of an indication of user heart rate based on biometric data generated by the biometric sensing unit.

The operations described above with reference to FIG. 68 are, optionally, implemented by components depicted in FIGS. 1A-1B or FIG. 70. For example, displaying operation 6802, detecting operation 6804, and launching operation 6806 can optionally be implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface corresponds to a predefined event or sub event, such as activation of an affordance on a user interface. When a respective predefined event or sub-event is detected, event recognizer 180 activates an event handler 190 associated with the detection of the event or sub-event. Event handler 190 can optionally utilize or call data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

What is claimed is:

1. An electronic device, comprising:
a display;
one or more processors;
one or more sensors; and
a memory storing one or more programs configured to be executed by the one or more processors, the one or more programs including instructions for:
 detecting, via the one or more sensors, activity data;
 in response to detecting the activity data:
  in accordance with a determination that the activity data satisfies activity criteria, displaying an alert, wherein the alert includes a first affordance and a prompt to begin a workout; and
  in accordance with a determination that the activity data does not satisfy the activity criteria, forgoing display of the alert;
 receiving a first user input corresponding to a selection of the first affordance; and
 in response to receiving the first user input, initiating a workout tracking functionality corresponding to a determined type of workout.

2. The electronic device of claim 1, wherein the one or more sensors include an accelerometer, a global positioning system (GPS) sensor, a heart rate monitor, a timer, a gyroscope, a camera, or any combination thereof.

3. The electronic device of claim 1, wherein the activity data is detected before a workout tracking functionality is active.

4. The electronic device of claim 1, wherein the activity data was detected via a first sensor of the one or more sensors, the one or more programs further including instructions for:
 initiating the workout tracking functionality corresponding to the determined type of physical activity corresponding to the alert by detecting second activity data via a second sensor, different from the first sensor, of the one or more sensors.

5. The electronic device of claim 1, wherein the activity data is detected while an existing workout tracking functionality is active, and wherein the alert includes a second affordance, the one or more programs further including instructions for:
 receiving a second user input corresponding to a selection of the second affordance and
 in response to receiving the second user input:
  ending a current workout tracking functionality; and
  storing activity data detected prior to receiving the second user input as a previous workout.

6. The electronic device of claim 1, wherein the alert includes a third affordance, and wherein a workout tracking functionality corresponding to the alert is a first workout tracking functionality, the one or more programs further including instructions for:
 receiving a user input corresponding to a selection of the third affordance; and
 in response to receiving the user input, initiating a second workout tracking functionality corresponding to the alert, wherein the second workout tracking functionality is different from the first workout tracking functionality.

7. The electronic device of claim 1, wherein the alert is a first alert including first content, the one or more programs further including instructions for:
 after displaying the first alert, displaying a second alert including second content erein the second content is different from the first content.

8. A non-transitory computer-readable storage medium storing one or more programs configured to be executed by one or more processors of an electronic device with a display and one or more sensors, the one or more programs including instructions for:
 detecting, via the one or more sensors, activity data;
 in response to detecting the activity data:
  in accordance with a determination that the activity data satisfies activity criteria, displaying an alert, wherein the alert includes a first affordance and a prompt to begin a workout; and
  in accordance with a determination that the activity data does not satisfy the activity criteria, forgoing display of the alert;
 receiving a first user input corresponding to a selection of the first affordance; and
 in response to receiving the first user input, initiating a workout tracking functionality corresponding to a determined type of workout.

9. The non-transitory computer-readable storage medium of claim 8, wherein the one or more sensors include an accelerometer, a global positioning system (GPS) sensor, a heart rate monitor, a timer, a gyroscope, a camera, or any combination thereof.

10. The non-transitory computer-readable storage medium of claim 8, wherein the activity data is detected before a workout tracking functionality is active.

11. The non-transitory computer-readable storage medium of claim 8, wherein the activity data was detected via a first sensor of the one or more sensors, the one or more programs further including instructions for:
   initiating the workout tracking functionality corresponding to the determined type of physical activity corresponding to the alert by detecting second activity data via a second sensor, different from the first sensor, of the one or more sensors.

12. The non-transitory computer-readable storage medium of claim 8, wherein the activity data is detected while an existing workout tracking functionality is active, and wherein the alert includes a second affordance, the one or more programs further including instructions for:
   receiving a second user input corresponding to a selection of the second affordance; and
   in response to receiving the second user input:
      ending a current workout tracking functionality; and
      storing activity data detected prior to receiving the second user input as a previous workout.

13. The non-transitory computer-readable storage medium of claim 8, wherein the alert includes a third affordance, and wherein a workout tracking functionality corresponding to the alert is a first workout tracking functionality, the one or more programs further including instructions for:
   receiving a user input corresponding to a selection of the third affordance; and
   in response to receiving the user input, initiating a second workout tracking functionality corresponding to the alert, wherein the second workout tracking functionality is different from the first workout tracking functionality.

14. The non-transitory computer-readable storage medium of claim 8, wherein the alert is a first alert including first content, the one or more programs further including instructions for:
   after displaying the first alert, displaying a second alert including second content, wherein the second content is different from the first content.

15. A method, comprising:
   at an electronic device including a display and one or more sensors:
      detecting, via the one or more sensors, activity data;
      in response to detecting the activity data:
         in accordance with a determination that the activity data satisfies activity criteria, displaying an alert, wherein the alert includes a first affordance and a prompt to begin a workout; and
         in accordance with a determination that the activity data does not satisfy the activity criteria, forgoing display of the alert;
      receiving a first user input corresponding to a selection of the first affordance; and
      in response to receiving the first user input, initiating a workout tracking functionality corresponding to a determined type of workout.

16. The method of claim 15, wherein the one or more sensors include an accelerometer, a global positioning system (GPS) sensor, a heart rate monitor, a timer, a gyroscope, a camera, or any combination thereof.

17. The method of claim 15, wherein the activity data is detected before a workout tracking functionality is active.

18. The method of claim 15, wherein the activity data was detected via a first sensor of the one or more sensors, the method further comprising:
   initiating the workout tracking functionality corresponding to the determined type of physical activity corresponding to the alert by detecting second activity data via a second sensor, different from the first sensor, of the one or more sensors.

19. The method of claim 15, wherein the activity data is detected while an existing workout tracking functionality is active, and wherein the alert includes a second affordance, the method further comprising:
   receiving a second user input corresponding to a selection of the second affordance; and
   in response to receiving the second user input:
      ending a current workout tracking functionality; and
      storing activity data detected prior to receiving the second user input as a previous workout.

20. The method of claim 15, wherein the alert includes a third affordance, and wherein a workout tracking functionality corresponding to the alert is a first workout tracking functionality, the method further comprising:
   receiving a user input corresponding to a selection of the third affordance; and
   in response to receiving the user input, initiating a second workout tracking functionality corresponding to the alert, wherein the second workout tracking functionality is different from the first tracking functionality.

21. The method of claim 15, wherein the alert is a first alert including first content, the method further comprising:
   after displaying the first alert, displaying a second alert including second content, wherein the second content is different from the first content.

* * * * *

UNITED STATES PATENT AND TRADEMARK OFFICE
CERTIFICATE OF CORRECTION

Page 1 of 1

PATENT NO. : 11,580,867 B2
APPLICATION NO. : 16/418786
DATED : February 14, 2023
INVENTOR(S) : Christopher Wilson et al.

It is certified that error appears in the above-identified patent and that said Letters Patent is hereby corrected as shown below:

In the Claims

Column 226, Line 21, Claim 5, delete "affordance" and insert --affordance;--.

Column 226, Line 42, Claim 7, delete "content erein" and insert --content, wherein--.

Column 228, Line 44, Claim 20, after "first" insert --workout--.

Signed and Sealed this
Twentieth Day of August, 2024

Katherine Kelly Vidal
*Director of the United States Patent and Trademark Office*